(12) United States Patent
Nishi et al.

(10) Patent No.: US 6,964,976 B2
(45) Date of Patent: Nov. 15, 2005

(54) AMINO ALCOHOL DERIVATIVES

(75) Inventors: Takahide Nishi, Tokyo (JP); Toshiyasu Takemoto, Tokyo (JP); Takaichi Shimozato, Miura (JP); Futoshi Nara, Yachiyo (JP)

(73) Assignee: Sankyo Company, Limited, Tokyo (JP)

( * ) Notice: Subject to any disclaimer, the term of this patent is extended or adjusted under 35 U.S.C. 154(b) by 62 days.

(21) Appl. No.: 10/718,858

(22) Filed: Nov. 20, 2003

(65) Prior Publication Data
US 2004/0132784 A1 Jul. 8, 2004

Related U.S. Application Data

(60) Division of application No. 10/337,702, filed on Jan. 7, 2003, now Pat. No. 6,723,745, which is a continuation-in-part of application No. PCT/JP01/05988, filed on Jul. 10, 2001.

(30) Foreign Application Priority Data

| Jul. 13, 2000 | (JP) | 2000-212246 |
| Aug. 9, 2000 | (JP) | 2000-241744 |
| Sep. 19, 2000 | (JP) | 2000-283218 |

(51) Int. Cl.⁷ .................. A61K 31/42; A61K 31/135; C07D 263/04; C07C 215/00
(52) U.S. Cl. .............. 514/376; 514/653; 548/228; 564/355
(58) Field of Search .............. 514/376, 653; 548/228; 564/355

(56) References Cited

U.S. PATENT DOCUMENTS

| 4,450,115 A | * | 5/1984 | Takizawa et al. ........... 558/422 |
| 4,474,977 A | * | 10/1984 | Lambelin et al. .............. 560/1 |
| 4,613,619 A | * | 9/1986 | Sleigh et al. ................ 514/546 |
| 4,638,070 A | * | 1/1987 | Lambelin et al. ............. 549/23 |
| 4,840,935 A | * | 6/1989 | Wagnon et al. ............... 514/18 |
| 5,089,529 A | * | 2/1992 | Kimura et al. .............. 514/648 |
| 5,250,546 A | * | 10/1993 | Masaki et al. .............. 514/331 |
| 5,604,229 A | | 2/1997 | Fujita et al. |
| 5,616,726 A | * | 4/1997 | Mitsuda et al. ............. 548/475 |
| 5,635,534 A | * | 6/1997 | Fujita et al. ................ 514/539 |
| 5,907,039 A | * | 5/1999 | Jinbo et al. ................. 540/609 |
| RE36,718 E | * | 5/2000 | Mitsuda et al. ............. 548/475 |
| 6,214,873 B1 | | 4/2001 | Adachi et al. |
| 6,355,444 B1 | * | 3/2002 | Glassy et al. .............. 435/7.23 |
| 6,368,850 B1 | * | 4/2002 | Bernegger-Egli et al. ... 435/280 |
| 6,723,745 B2 | | 4/2004 | Nishi et al. |
| 2002/0091105 A1 | | 7/2002 | Mandala et al. |
| 2004/0058894 A1 | | 3/2004 | Doherty et al. |

FOREIGN PATENT DOCUMENTS

| EP | 0 297 782 | 1/1989 |
| EP | 0 492 497 A2 | 7/1992 |
| EP | 0 778 263 A1 | 6/1997 |
| EP | 1 002 792 A1 | 5/2000 |
| JP | 2-256612 | 10/1990 |
| JP | 04-104796 | 4/1992 |
| JP | 9-124564 | 5/1997 |

OTHER PUBLICATIONS

Huang, et al., Kidney International, "Th1 responsiveness to nephritogenic antigens determines susceptibility to crescentic glomerulonephritis in mice", 51, pp. 94–103 (1997).

Berman, et al., J. Immunology, "Decreased Il–4 Production in New Onset Type I Insulin–Dependent Diabetes Mellitus[1]", 157, pp. 4690–4696 (1996).

Cativiela, et al., "Stereoselective synthesis of quaternary α–amino acids. Part 1:Acyclic compounds", Tetrahedron: Asymmetry, 9, pp. 3517–3599 (1998).

Gander, et al., "Synthesis of Enantiomerically Pure, α–Alkylated Lysine, Ornithine, and Tryptophan–Derivatives", Helvetica Chimica Acta, 71, pp. 224–236, (1988) (English language Abstract).

Sano, et al., "Lewis Acid– and Cationic Lithium–Mediated Diastereoselective Aldol–Type Reaction Based on a Double Chiral. Recognition manner for the Asymmetric Synthesis of α–Substituted Serines", Tetrahedron Letters, 36, No. 23, pp. 4101–4104 (1995).

Nagao, et al., "Efficient Preparation of New Chiral Synthons Useful for (+)–Carbacyclin Synthesis by Utilizing Enzymatic Hydrolysis" Chemistry Letters, pp. 239–242 (1989).

Tamai et al., Enzymatic Hydrolyses of the δ–Symmetric Dicarboxylic Diesters Bearing a Sulfinyl Group as the Prochiral Center, Chemistry Letters, pp. 2381–2384 (1994).

Casarrubio, et al., "On the Syntheses of Thiophene Analogs of Practolol and 'Reversed' Practolol", J. Heterocyclic Chem, 20, 1557–1560 (1983).

(Continued)

Primary Examiner—Deborah C. Lambkin
(74) Attorney, Agent, or Firm—Frishauf, Holtz, Goodman & Chick, P.C.

(57) ABSTRACT

Compounds of formula (I) which exhibit excellent immune suppression activity, pharmacologically acceptable salts thereof, esters thereof or other derivatives:

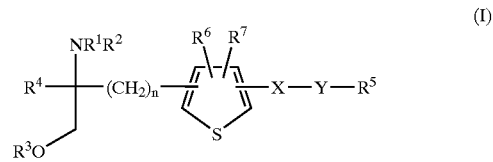

wherein $R^1$ and $R^2$ are a hydrogen atom, an amino protecting group; $R^3$ is a hydrogen atom, a hydroxy protecting group; $R^4$ is a lower alkyl group; n is an integer from 1 to 6; X is an ethylene group; Y is a $C_1$–$C_{10}$ alkylene group, a $C_1$–$C_{10}$ alkylene group substituted with 1 to 3 substituents selected from substituent group a and b; $R^5$ is an aryl group; $R^6$ and $R^7$ are a hydrogen atom, a group selected from substituent group a; with the proviso when $R^5$ is a hydrogen atom, Y is not a single bond or a straight chain $C_1$–$C_{10}$ alkylene group.

28 Claims, No Drawings

OTHER PUBLICATIONS

Charette et al., "Synthesis of α,α–Disubstituted–α–Amino Acids by Double Nucleophilic Addition to Cyanohydrins", Tetrahedron Letters 39, 5147–5150 (1998).

Hatakeyama et al., "Et₂AlCl–Catalyzed Cyclization of Epoxytrichloroacetimidates for the Synthesis of α–Substituted Serines", J. Org. Chem., 62, 2275–2279 (1997).

Hatakeyama, et al., "Total Synthesis of (+)–Conagenin", Tetrahedron Letters, 37, No. 23, pp. 4047–4050 (1996).

Avenoza, et al., "Preparation and Synthetic Applications of (S)– and (R)–N–Boc–N,O–isopropylidene–α–methylserinals: Asymmetric Synthesis of (S)– and (R)–2–Amino–2–methylbutanoic Acids (Iva)", J. Org. Chem., 64, 8220–8225 (1999).

Kiuchi et al., "Synthesis and Immunosuppressive Activity of 2–Substituted 2–Aminopropane–1,3–diols and 2–Aminoethanols"; Journal of Medicinal Chemistry, vol. 43, 2000, pp. 2946–2961, XP002271142.

Kiuchi et al., "Synthesis and Biological Evaluation of 2,2–Disubstituted 2–Aminoethanols: Analogues of FTY720" Bioorganic and Medicinal Chemistry Letters, vol. 8, 1998, pp. 101–106 XP002271143.

Wermuth et al., "The Practice of Medicinal Chemistry", Practice of Medicinal Chemistry, XX, XX, 1996, pp. 203–237, XP002190259.

* cited by examiner

AMINO ALCOHOL DERIVATIVES

This application is a divisional application of Ser. No. 10/337,702 filed Jan. 7, 2003, now U.S. Pat. No. 6,723,745, which is a continuation-in-part of International Application PCT/JP01/05988 filed Jul. 10, 2001 (not published in English).

BACKGROUND OF THE INVENTION

The present invention relates to amino alcohol derivatives having excellent immune suppression activity, pharmacologically acceptable salts thereof, esters thereof or other derivatives thereof; to pharmaceutical compositions containing said compounds as an active ingredient; to the use of said compounds in the preparation of said pharmaceutical compositions; and to methods for prevention or treatment of autoimmune diseases, which comprise administering a pharmacologically effective amount of said compound to warm blooded animals in need of such prevention or treatment.

In another aspect, the present invention relates to optically active novel amino alcohol derivatives (particularly, optically active 4,4-disubstituted oxazolidin-2-one derivatives), which are useful synthetic intermediates for the preparation of said amino alcohol derivatives or other medicaments.

In yet another aspect, the present invention relates to a novel processes for the excellent selective preparation of optically active 2-substituted 2-amino-1,3-propanediol mono-ester derivatives, which are useful synthetic intermediates for the preparation of said amino alcohol derivatives in optically active form.

Steroids or antiinflammatory drugs have been used as therapeutic agents for inflammatory responses caused by abnormal immunological responses in diseases related to the immune system such as rheumatoid arthritis and other autoimmune diseases. However, these agents are agents that improve the symptoms, but they do not provide treatment of the causes.

Although abnormal immunological responses have also been reported to contribute to the pathogenesis of diabetes mellitus and nephritis [Kidney International, 51, 94 (1997); Journal of Immunology, 157, 4691 (1996)], no agents have ever been developed to improve the abnormal immunological responses.

On the other hand, development of immune suppressors is important for prevention of immunological rejection occurring in organ transplantation or for the prevention or therapy of autoimmune diseases. Nevertheless, well known immunosuppressors such as cyclosporin A (CsA) and tacrolimus (TRL) are known to cause renal toxicity or hepatotoxicity. Although steroids have been administered together with immunosuppressors in order to decrease such adverse effects of the immunosuppressors, the immunosuppressing effects could not be satisfactorily elicited without the adverse events.

From these backgrounds, many attempts have been made to find compounds exerting excellent immunosuppressing effects with low toxicity.

The following compounds are known as immunosuppressive agents:

(1) In the specification of WO94/08943 (EP627406) compounds of formula (a) are disclosed as immunosuppressive agents,

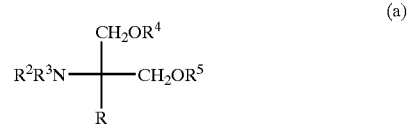

wherein R is a straight or branched carbon chain which may have, in the chain, a group selected from the group consisting of a double bond, a triple bond, oxygen atom, sulfur atom, —N($R^6$)—(wherein $R^6$ is a hydrogen atom), optionally substituted arylene, optionally substituted heteroarylene or the like, and which may be substituted, at the chain end thereof, by optionally substituted aryl, optionally substituted cycloalkyl, optionally substituted heteroaryl or the like; and $R^2$, $R^3$, $R^4$, $R^5$ are the same or different and each represent a hydrogen atom, an alkyl group or the like.

The compounds of formula (a) have two oxymethyl groups (—$CH_2OR^4$ and —$CH_2OR^5$) as essential groups. The compounds of the present invention, however, have a —$CH_2OR^3$ group and a lower alkyl group and are different from the compounds of formula (a) in these substituents.

In said specification no typical compounds similar to the compounds of formula (I) in the present invention are disclosed at all. Only the following two compounds of the compounds of formula (a) are highly similar in chemical structure to the compounds of formula (I) in the present invention:

Example 29

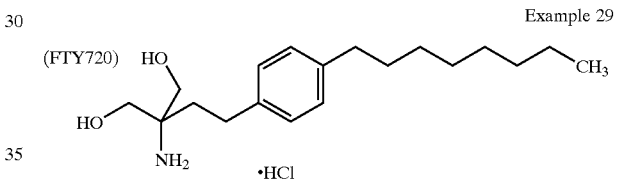

Example 293

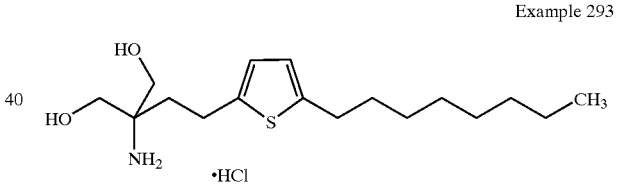

(2) In the specification of WO96/06068 compounds of formula (b) are disclosed as immunosuppressive agents,

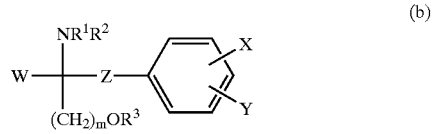

wherein $R^1$, $R^2$ and $R^3$ each are a hydrogen atom or the like; W is a hydrogen atom, an alkyl group or the like; Z is a single bond or an alkylene group; X is a hydrogen atom or an alkoxy group; Y is a hydrogen atom, an alkyl, alkoxy, acyl, acyloxy, amino, acylamino group or the like.

The compounds of formula (b) essentially have a phenyl group as a basic skeleton. The compounds of formula (I) in the present invention have a thiophene group instead of the phenyl group of compounds of formula (b) and are different from the compounds of formula (b) in the basic skeleton.

In said specification no typical compounds similar to the compounds of formula (I) in the present invention are disclosed at all. Only the following three compounds of the compounds of formula (b) are highly similar in chemical structure to the compounds of formula (I) in the present invention:

Example 26

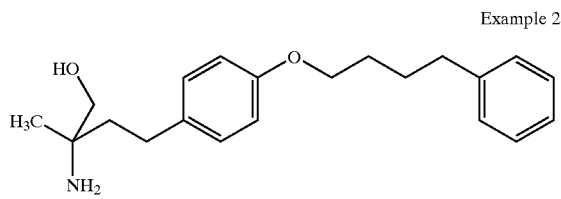

Example 57

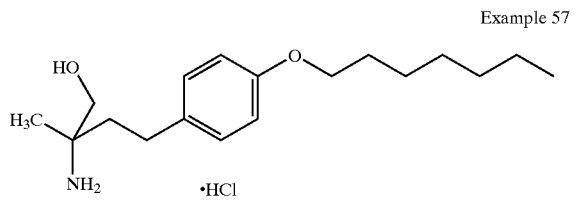

Example 87

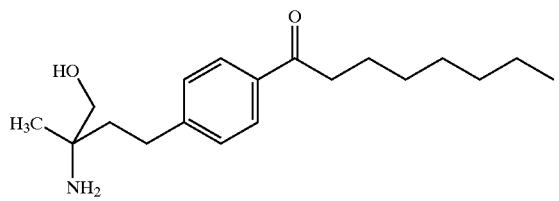

(3) In the specification of WO98/45249 compounds of formula (c) are disclosed as immunosuppressive agents, (c)

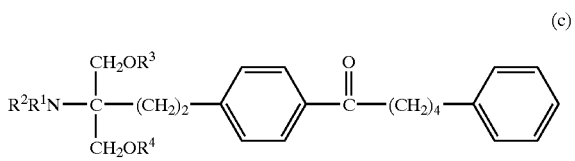

wherein $R^1$, $R^2$, $R^3$, $R^4$ are the same or different and each represent a hydrogen atom or an acyl group.

The compounds of formula (c) have two oxymethyl groups (—$CH_2OR^3$ and —$CH_2OR^4$) as essential substituent groups. The compounds of the present invention have a —$CH_2OR^3$ group and a lower alkyl group and are different from the compounds of formula (a) in these substituents. The compounds of formula (c) have a phenyl group between —$(CH_2)_2$— and —$CO(CH_2)_4$— as a basic skeleton. The compounds of formula (I) in the present invention have a thiophene group instead of the phenyl group of the compounds of formula (c). The present compounds of formula (I) are also different from the compounds of formula (c) in the basic skeleton. The compounds of formula (c) have only a phenyl group at the end of —CO—$(CH_2)_4$— group. The compounds of formula (I) in the present invention may have a phenyl group, a cycloalkyl group or a heterocyclic group at the end of the molecule.

In said specification no typical compounds similar in chemical structure to the compounds of formula (I) in the present invention are disclosed at all. Only the following three compounds of the compounds of formula (c) are highly similar in chemical structure to the compounds of formula (I) in the present invention:

Example 1

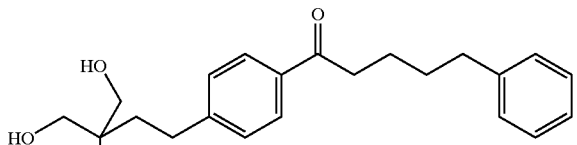

Example 3

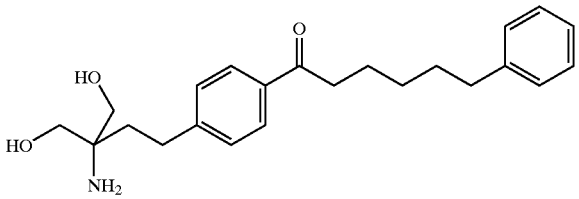

On the other hand, various optically active substituted amino acid and substituted amino alcohol derivatives (particularly α-substituted amino acid and α-substituted amino alcohol derivatives) exhibit biological activity; are partial components of natural products and pharmaceutical agents; and are important synthetic intermediates. For example, α-methyl-α-vinyl amino acids are useful as an amino acid decarboxylase inhibitor; α-ethynyl-α-methyl amino acids are useful as a glutamic acid decarboxylase inhibitor; ISP-1 (Myriocin), which is isolated from metabolites of *Isalia sinclairii*, has immune suppression activity; and Conagenine and the like participate in the regulation of immune response through T-cells. From these results, α-substituted amino acid and amino alcohol derivatives are very interesting compounds as a partial component of natural products having biological activity, in the field of biochemistry and in the field of organic synthesis.

These α-substituted amino acid and amino alcohol derivatives have an asymmetric center(s) and an efficient process for the preparation of one enantiomer thereof has been expected.

There are a few reports of processes for the preparation of optically active substituted amino acid and amino alcohol derivatives and a few reports of synthetic examples of optically active amino alcohol derivatives such as optically active 4,4-disubstituted oxazolizin-2-one derivatives, which are useful synthetic intermediates of optically active substituted amino acid and amino alcohol derivatives described hereinbefore. For example, there are reports by C. Cativiela et al., Tetrahedron: Asymmetry, 9, 3517 (1998) and Synthesis of Optically active α-amino acids (Pergamon Press) R. M. Williams et al and the methods are largely classified into two groups for preparation of them. The one is a diasteroselective alkylation method using an assisting group for asymmetric synthesis, a typical example being a method described by Seebach in Helv. Chim. Acta., 71, 224 (1988) or the synthesis of α-substituted serine derivatives which are obtained by a highly diastereoselective aldol reaction using chiral bis-lactam ether carboxylic acid esters and Mg(II) and Sn(II) type Lewis acids described by Nagao and Sano et al. in Tetrahedron Lett., 36, 2097 (1995) and Tetrahedron Lett., 36, 4101 (1995). The other one is a synthesis of α-substituted serine derivatives which are obtained by enantioselective enzymatic hydrolysis of prochiral σ-symmetry diester compounds (α-substituted-α-protected malonic acid diesters) and is described by Nagao, Tamai et al., in Chemistry Lett., 239 (1989) and Chemistry Lett., 2381 (1994).

The former method has multi-step reactions and needs a stoichiometric asymmetric source. The latter method has a reduction step and cannot be used when a compound has a group unstable under reduction conditions.

There are some reports described hereinbefore but, however the practically useful methods are limited. In general, one enantiomer is optically resolved from a racemic mixture. In this case there is a problem that the total yield of the desired compound is low.

BRIEF SUMMARY OF THE INVENTION

The present inventors have performed painstaking research to complete these objectives, and found that the amino alcohol derivatives (I) of the present invention exert an excellent immunosuppressive effect with low toxicity and are useful as therapeutic agents for autoimmune diseases such as systemic lupus erythematosus, rheumatoid arthritis, polymyositis, dermatomyositis, Behcet's syndrome, Chron disease, ulcerative colitis, autoimmune hepatitis, aplastic anemia, scleoderma, idiopathic thrombocytopenic purpura, autoimmune hemolytic anemia, multiple sclerosis, autoimmune bullosis, vulgarity psoriasis, vasculitis syndrome, Wegener's granuloma, uveitis, cryptogenic fibrosing alveolitis, Goodpasture's syndrome, sarcoidosis, allergic granulomatous angitis, bronchial asthma, myocarditis, cardiomyopathy, aortic arch syndrome, myocardial postinfarction syndrome, primary pulmonary hypertension, minimal change nephrotic syndrome, membranous nephropathy, membranoproliferative glomerulonephritis, focal glomerular sclerosis, crescent glomerulonephritis, myasthenia gravis, inflammatory neuropathy, atopic dermatitis, chronic actinic dermatitis, acute polyarthritis, Sydenhan chorea disease, progressive systemic sclerosis, adult onset type diabetes mellitus, insulin dependent diabetes mellitus, juvenile diabetes, atherosclerosis, glomerular nephritis, tubu-rointerstitial nephritis, primary biliary cirrhosis, primary sclerosing cholangitis, fulminant hepatic failure, viral hepatitis, GVHD, immunological rejection following organ transplantation, contact dermatitis, sepsis or other immunology related diseases, and completed the present invention.

The present invention provides amino alcohol derivatives which exhibit low toxicity and excellent immune suppression activity, pharmacologically acceptable salts thereof, esters thereof or other derivatives thereof.

In another aspect, the present invention provides pharmaceutical compositions containing said amino alcohol derivatives, a pharmacologically acceptable salt thereof, an ester thereof, or other derivative thereof as an active ingredient; the use of said compounds in the preparation of said pharmaceutical compositions; or methods for prevention or treatment of the diseases described hereinbefore such as autoimmune diseases and the like, which comprise administering a pharmacologically effective amount of said compound to warm blooded animals (e.g. humans) in need of such prevention or treatment.

The inventors have made a great effort to solve the problems described hereinbefore about a process for the preparation of optically active amino alcohol derivatives and intermediates thereof. They have found that optically active novel amino alcohol derivatives of formulae (La) and (Lb) (especially 4,4-disubstituted oxazolizin-2-one derivatives) can be obtained more easily than by conventional methods and said derivatives are useful synthetic intermediates for the preparation of optically active substituted amino acid and substituted amino alcohol derivatives and medicaments.

In addition they have also made a great effort to find a process for the selective preparation of the optically active amino alcohol compounds of formulae (La) and (Lb). They found that optically active 2-substituted 2-amino-1,3-propanediol mono-ester derivatives of formulae (XLIVa) or (XLIVb) are useful intermediate for the preparation and said compounds of formulae (XLIVa) and (XLIVb) can easily be obtained from 2-substituted 2-amino-1,3-propanediol derivatives of formula (XLII) using carboxylic acid vinyl esters of formula (XLIII) in the presence of lipase through selective acylation of one hydroxyl group in good yield.

DETAILED DESCRIPTION OF THE INVENTION (1) The present invention comprises amino alcohol derivatives of the following formula (I), pharmacologically acceptable salts thereof, esters thereof or other derivatives thereof:

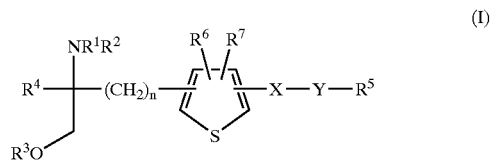

wherein
$R^1$ and $R^2$ are the same or different and each represents a hydrogen atom or an amino protecting group;
$R^3$ represents a hydrogen atom or a hydroxy protecting group;
$R^4$ represents a lower alkyl group;
n represents an integer from 1 to 6;
X represents an ethylene group, a vinylene group, an ethynylene group, a group of formula -D-CH$_2$— (wherein D represents a carbonyl group, a group of formula —CH(OH)—, an oxygen atom, a sulfur atom, or a nitrogen atom), an aryl group, or an aryl group substituted with 1 to 3 substituents selected from substituent group a;
Y represent a single bond, a $C_1$–$C_{10}$ alkylene group, a $C_1$–$C_{10}$ alkylene group substituted with 1 to 3 substituents selected from substituent groups a and b, a $C_1$–$C_{10}$ alkylene group which has an oxygen atom or a sulfur atom in said carbon chain or at the end of said carbon chain, or a $C_1$–$C_{10}$ alkylene group which is substituted with 1 to 3 substituents selected from substituent groups a and b and has an oxygen atom or a sulfur atom in said carbon chain or at the end of said carbon chain;
$R^5$ represents a hydrogen atom, a cycloalkyl group, an aryl group, a heterocyclic group, a cycloalkyl group substituted with 1 to 3 substituents selected from substituent groups a and b, an aryl group substituted with 1 to 3 substituents selected from substituent groups a and b, or a heterocyclic group substituted with 1 to 3 substituents selected from substituent groups a and b;
$R^6$ and $R^7$ are the same or different and each represents a hydrogen atom or a group selected from substituent group a;
with the proviso that when $R^5$ is a hydrogen atom, Y is not a single bond or a straight $C_1$–$C_{10}$ alkylene group;
substituent group a consists of a halogen atom, a lower alkyl group, a halognated lower alkyl group, a lower alkoxy group, a lower alkylthio group, a carboxyl group, a lower alkoxycarbonyl group,.a hydroxyl group, a lower aliphatic acyl group, an amino group, a mono lower alkylamino group, a di lower alkylamino group, a lower aliphatic acylamino group, a cyano group, and a nitro group;
substituent group b consists of a cycloalkyl group, an aryl group, a heterocyclic group, a cycloalkyl group substituted with 1 to 3 substituents selected from substituent group a, an aryl group substituted with 1 to 3 substituents selected from substituent group a, and a heterocyclic group substituted with 1 to 3 substituents selected from substituent group a.

Among these compounds described in (1), preferred compounds include:

(2) a compound according to (1) wherein said compound has a formula (Ia), a pharmacologically acceptable salt thereof, an ester thereof or other derivative thereof;

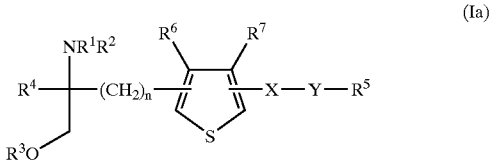

(3) a compound according to (1) wherein said compound has a formula (Ib), a pharmacologically acceptable salt thereof, an ester thereof or other derivative thereof,

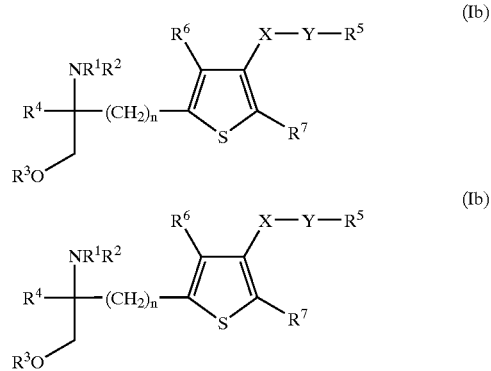

(4) a compound according to any one of (1) to (3) wherein $R^1$ and $R^2$ are the same or different and each is a hydrogen atom, a lower alkoxycarbonyl group, an aralkyloxycarbonyl group, or an arakyloxycarbonyl group substituted with 1 to 3 substituents selected from substituent group a, or a pharmacologically acceptable salt thereof;

(5) a compound according to any one of (1) to (3) wherein each of $R^1$ and $R^2$ is a hydrogen atom, or a pharmacologically acceptable salt thereof;

(6) a compound according to any one of (1) to (5) wherein $R^3$ is a hydrogen atom, a lower alkyl group, a lower aliphatic acyl group, an aromatic acyl group or an aromatic acyl group substituted with 1 to 3 substituents selected from substituent group a, or a pharmacologically acceptable salt thereof;

(7) a compound according to any one of (1) to (5) wherein $R^3$ is a hydrogen atom, or a pharmacologically acceptable salt thereof;

(8) a compound according to any one of (1) to (7) wherein $R^4$ is a $C_1$–$C_4$ alkyl group, or a pharmacologically acceptable salt thereof;

(9) a compound according to any one of (1) to (7) wherein $R^4$ is a $C_1$–$C_2$ alkyl group, or a pharmacologically acceptable salt thereof;

(10) a compound according to any one of (1) to (7) wherein $R^4$ is a methyl group, or a pharmacologically acceptable salt thereof;

(11) a compound according to any one of (1) to (10) wherein n is 2 or 3, or a pharmacologically acceptable salt thereof;

(12) a compound according to any one of (1) to (10) wherein n is 2, or a pharmacologically acceptable salt thereof;

(13) a compound according to any one of (1) to (12) wherein X is an ethylene group, an ethynylene group, an aryl group, or an aryl group substituted with 1 to 3 substituents selected from substituent group a, or a pharmacologically acceptable salt thereof;

(14) a compound according to any one of (1) to (12) wherein X is an ethylene group, or a pharmacologically acceptable salt thereof;

(15) a compound according to any one of (1) to (12) wherein X is an ethynylene group, or a pharmacologically acceptable salt thereof;

(16) a compound according to any one of (1) to (12) wherein X is a group of formula -D-$CH_2$—, or a pharmacologically acceptable salt thereof;

(17) a compound according to any one of (1) to (12) wherein X is a group of formula -D-$CH_2$— (wherein D represents a carbonyl group or a group of formula —CH(OH)—), or a pharmacologically acceptable salt thereof;

(18) a compound according to any one of (1) to (17) wherein Y is a $C_1$–$C_{10}$ alkylene group, or a $C_1$–$C_{10}$ alkylene group substituted with 1 to 3 substituents selected from substituent groups a and b, or a pharmacologically acceptable salt thereof;

(19) a compound according to any one of (1) to (17) wherein Y is a $C_1$–$C_6$ alkylene group, or a $C_1$–$C_6$ alkylene group substituted with 1 to 3 substituents selected from substituent groups a and b, or a pharmacologically acceptable salt thereof;

(20) a compound according to any one of (1) to (17) wherein Y is an ethylene group, a trimethylene group, a tetramethylene group, an ethylene group substituted with 1 to 3 substituents selected from substituent groups a and b, a trimethylene group substituted with 1 to 3 substituents selected from substituent groups a and b, or a tetramethylene group substituted with 1 to 3 substituents selected from substituent groups a and b, or a pharmacologically acceptable salt thereof;

(21) a compound according to any one of (1) to (17) wherein Y is an ethylene group, a trimethylene group, or a tetramethylene group, or a pharmacologically acceptable salt thereof;

(22) a compound according to any one of (1) to (17) wherein Y is an ethylene group or a trimethylene group, or a pharmacologically acceptable salt thereof;

(23) a compound according to any one of (1) to (17) wherein Y is a $C_1$–$C_{10}$ alkylene group which has an oxygen atom or a sulfur atom in said carbon chain or at the end of said carbon chain, or a $C_1$–$C_{10}$ alkylene group which is substituted with 1 to 3 substituents selected from substituent groups a and b and has an oxygen atom or a sulfur atom in said carbon chain or at the end of said carbon chain, or a pharmacologically acceptable salt thereof;

(24) a compound according to any one of (1) to (17) wherein Y is a $C_1$–$C_{10}$ alkylene group which has an oxygen atom or a sulfur atom in said carbon chain or at the end of said carbon chain, or a pharmacologically acceptable salt thereof;

(25) a compound according to any one of (1) to (17) wherein Y is a $C_1$–$C_{10}$ alkylene group which has an oxygen atom in said carbon chain or at the end of said carbon chain, or a pharmacologically acceptable salt thereof;

(26) a compound according to any one of (1) to (17) wherein Y is a $C_1$–$C_6$ alkylene group which has an oxygen atom in said carbon chain or at the end of said carbon chain, or a pharmacologically acceptable salt thereof,

(27) a compound according to any one of (1) to (17) wherein Y is a group of formula —O—CH$_2$—, —O—(CH$_2$)$_2$—, —O—(CH$_2$)$_3$—, —CH$_2$—O—, —(CH$_2$)$_2$—O—, or —(CH$_2$)$_3$—O—, or a pharmacologically acceptable salt thereof;

(28) a compound according to any one of (1) to (17) wherein Y is a group of formula —CH$_2$—O—, or a pharmacologically acceptable salt thereof;

(29) a compound according to any one of (1) to (17) wherein Y is a group of formula —O—(CH$_2$)$_2$— or —(CH$_2$)$_2$—O—, or a pharmacologically acceptable salt thereof;

(30) a compound according to any one of (1) to (29) wherein R$^5$ is a hydrogen atom, or a pharmacologically acceptable salt thereof;

(31) a compound according to any one of (1) to (29) wherein R$^5$ is a cycloalkyl group, a heterocyclic group, a cycloalkyl group substituted with 1 to 3 substituents selected from substituent groups a and b, or a heterocyclic group substituted with 1 to 3 substituents selected from substituent groups a and b, or a pharmacologically acceptable salt thereof;

(32) a compound according to any one of (1) to (29) wherein R$^5$ is a cycloalkyl group or a cycloalkyl group substituted with 1 to 3 substituents selected from substituent groups a and b, or a pharmacologically acceptable salt thereof;

(33) a compound according to any one of (1) to (29) wherein R$^5$ is a cycloalkyl group, or a pharmacologically acceptable salt thereof;

(34) a compound according to any one of (1) to (29) wherein R$^5$ is a cyclohexyl group, or a pharmacologically acceptable salt thereof;

(35) a compound according to any one of (1) to (29) wherein R$^5$ is an aryl group or an aryl group substituted with 1 to 3 substituents selected from substituent groups a and b, or a pharmacologically acceptable salt thereof;

(36) a compound according to any one of (1) to (29) wherein R$^5$ is an aryl group or an aryl group substituted with 1 to 3 substituents (said substituent is selected from the group consisting of a halogen atom, a lower alkyl group, a halogenated lower alkyl group, a lower alkoxy group, a lower alkylthio group and a lower aliphatic acyl group), or a pharmacologically acceptable salt thereof;

(37) a compound according to any one of (1) to (29) wherein R$^5$ is an aryl group or an aryl group substituted with 1 to 3 substituents (said substituent is selected from the group consisting of a halogen atom, a lower alkyl group, a halogenated lower alkyl group, a lower alkoxy group, and a lower aliphatic acyl group), or a pharmacologically acceptable salt thereof;

(38) a compound according to any one of (1) to (29) wherein R$^5$ is a phenyl group or a phenyl group substituted with 1 to 3 substituents (said substituent is selected from the group consisting of a halogen atom, a lower alkyl group, a halogenated lower alkyl group, a lower alkoxy group, and a lower aliphatic acyl group), or a pharmacologically acceptable salt thereof;

(39) a compound according to any one of (1) to (29) wherein R$^5$ is a phenyl group or a phenyl group substituted with 1 to 3 substituents (said substituent is selected from the group consisting of a fluorine atom, a chlorine atom, a methyl, trifluoromethyl, methoxy, and acetyl group), or a pharmacologically acceptable salt thereof;

(40) a compound according to any one of (1) to (29) wherein R$^5$ is a phenyl, 3-fluorophenyl, 4-fluorophenyl, 3,4-difluorophenyl, 3,5-difluorophenyl, 3-chlorophenyl, 4-chlorophenyl, 3,4-dichlorophenyl, 3,5-dichlorophenyl, 3-methylphenyl, 4-methylphenyl, 3,4-dimethylphenyl, 3,5-dimethylphenyl, 3-trifluoromethylphenyl, 4-trifluoromethylphenyl, 3,4-ditrifluoromethylphenyl, 3,5-ditrifluoromethylphenyl, 3-methoxyphenyl, 4-methoxyphenyl, 3,4-dimethoxyphenyl, 3,5-dimethoxyphenyl, 3,4,5-trimethoxyphenyl, 3-acetylphenyl, or 4-acetylphenyl, or a pharmacologically acceptable salt thereof;

(41) a compound according to any one of (1) to (40) wherein R$^6$ and R$^7$ are the same or different and each is a hydrogen atom, a halogen atom, a lower alkyl group, a halogenated lower alkyl group, a lower alkoxy group or a lower alkylthio group, or a pharmacologically acceptable salt thereof;

(42) a compound according to any one of (1) to (40) wherein each of R$^6$ and R$^7$ is a hydrogen atom, or a pharmacologically acceptable salt thereof;

(43) a compound according to (1) wherein said compound is selected the following compounds, a pharmacologically acceptable salt thereof, an ester thereof or other derivative thereof:

2-amino-2-methyl-4-[5-(6-cyclohexylhexyl)thiophen-2-yl]butan-1-ol,
2-amino-2-methyl-4-[5-(5-cyclohexylpentyl)thiophen-2-yl]butan-1-ol,
2-amino-2-methyl-4-[5-(4-cyclohexylbutyl)thiophen-2-yl]butan-1-ol,
2-amino-2-methyl-4-[5-(6-cyclohexylhex-1-ynyl)thiophen-2-yl]butan-1-ol,
2-amino-2-methyl-4-[5-(5-cyclohexylpent-1-ynyl)thiophen-2-yl]butan-1-ol,
2-amino-2-methyl-4-[5-(4-cyclohexylbut-1-ynyl)thiophen-2-yl]butan-1-ol,
2-amino-2-methyl-4-[5-(6-cyclohexylhexanoyl)thiophen-2-yl]butan-1-ol,
2-amino-2-methyl-4-[5-(5-cyclohexylpentanoyl)thiophen-2-yl]butan-1-ol,
2-amino-2-methyl-4-[5-(4-cyclohexylbutanoyl)thiophen-2-yl]butan-1-ol,
2-amino-2-ethyl-4-[5-(6-cyclohexylhexyl)thiophen-2-yl]butan-1-ol,
2-amino-2-ethyl-4-[5-(5-cyclohexylpentyl)thiophen-2-yl]butan-1-ol,
2-amino-2-ethyl-4-[5-(4-cyclohexylbutyl)thiophen-2-yl]butan-1-ol,
2-amino-2-ethyl-4-[5-(6-cyclohexylhex-1-ynyl)thiophen-2-yl]butan-1-ol,
2-amino-2-ethyl-4-[5-(5-cyclohexylpent-1-ynyl)thiophen-2-yl]butan-1-ol,
2-amino-2-ethyl-4-[5-(4-cyclohexylbut-1-ynyl)thiophen-2-yl]butan-1-ol,
2-amino-2-ethyl-4-[5-(6-cyclohexylhexanoyl)thiophen-2-yl]butan-1-ol,
2-amino-2-ethyl-4-[5-(5-cyclohexylpentanoyl)thiophen-2-yl]butan-1-ol,
2-amino-2-ethyl-4-[5-(4-cyclohexylbutanoyl)thiophen-2-yl]butan-1-ol,
2-amino-2-methyl-4-[5-(6-phenylhexyl)thiophen-2-yl]butan-1-ol,
2-amino-2-methyl-4-[5-(5-phenylpentyl)thiophen-2-yl]butan-1-ol,
2-amino-2-methyl-4-[5-(4-phenylbutyl)thiophen-2-yl]butan-1-ol,
2-amino-2-methyl-4-[5-(6-phenylhex-1-ynyl)thiophen-2-yl]butan-1-ol,
2-amino-2-methyl-4-[5-(5-phenylpent-1-ynyl)thiophen-2-yl]butan-1-ol,
2-amino-2-methyl-4-[5-(4-phenylbut-1-ynyl)thiophen-2-yl]butan-1-ol, 2-amino-2-methyl-4-[5-(6-phenylhexanoyl)thiophen-2-yl]butan-1-ol,
2-amino-2-methyl-4-[5-(5-phenylpentanoyl)thiophen-2-yl]butan-1-ol,
2-amino-2-methyl-4-[5-(4-phenylbutanoyl)thiophen-2-yl]butan-1-ol,
2-amino-2-methyl-4-[5-(5-cyclohexyloxypent-1-ynyl)thiophen-2-yl]butan-1-ol,
2-amino-2-methyl-4-[5-(4-cyclohexyloxybut-1-ynyl)thiophen-2-yl]butan-1-ol,
2-amino-2-methyl-4-[5-(3-cyclohexyloxypropynyl)thiophen-2-yl]butan-1-ol,
2-amino-2-methyl-4-[5-(5-cyclohexyloxypentyl)thiophen-2-yl]butan-1-ol,
2-amino-2-methyl-4-[5-(4-cyclohexyloxybutyl)thiophen-2-yl]butan-1-ol,
2-amino-2-methyl-4-[5-(3-cyclohexyloxypropyl)thiophen-2-yl]butan-1-ol,
2-amino-2-methyl-4-[5-(5-cyclohexyloxypentanoyl)thiophen-2-yl]butan-1-ol,
2-amino-2-methyl-4-[5-(4-cyclohexyloxybutanoyl)thiophen-2-yl]butan-1-ol,
2-amino-2-methyl-4-[5-(3-cyclohexyloxypropanoyl)thiophen-2-yl]butan-1-ol,
2-amino-2-methyl-4-[5-(5-phenoxypent-1-ynyl)thiophen-2-yl]butan-1-ol,
2-amino-2-methyl-4-[5-(4-phenoxybut-1-ynyl)thiophen-2-yl]butan-1-ol,
2-amino-2-methyl-4-[5-(3-phenoxypropynyl)thiophen-2-yl]butan-1-ol,
2-amino-2-methyl-4-[5-(5-phenoxypentyl)thiophen-2-yl]butan-1-ol,
2-amino-2-methyl-4-[5-(4-phenoxybutyl)thiophen-2-yl]butan-1-ol,
2-amino-2-methyl-4-[5-(3-phenoxypropyl)thiophen-2-yl]butan-1-ol,
2-amino-2-methyl-4-[5-(5-phenoxypentanoyl)thiophen-2-yl]butan-1-ol,
2-amino-2-methyl-4-[5-(4-phenoxybutanoyl)thiophen-2-yl]butan-1-ol,
2-amino-2-methyl-4-[5-(3-phenoxypropanoyl)thiophen-2-yl]butane-1-ol,
2-amino-2-methyl-4-[5-(4-benzyloxyphenyl)thiophen-2-yl]butan-1-ol,
2-amino-2-methyl-4-[5-(4-cyclohexylmethoxyphenyl)thiophen-2-yl]butan-1-ol,
2-amino-2-methyl-4-[5-(4-cyclohexylethoxyphenyl)thiophen-2-yl]butan-1-ol,
2-amino-2-methyl-4-[5-(3-cyclohexylmethoxypropynyl)thiophen-2-yl]butan-1-ol,
2-amino-2-methyl-4-[5-(3-cyclohexylmethoxypropyl)thiophen-2-yl]butan-1-ol, and
2-amino-2-methyl-4-[5-(3-cyclohexylmethoxypropanoyl)thiophen-2-yl]butan-1-ol.

(44) a compound according to (1) wherein said compound is selected the following compounds, a pharmacologically acceptable salt thereof, an ester thereof or other derivative thereof:
2-amino-2-methyl-4-[5-(4-cyclohexylbutyl)thiophen-2-yl]butan-1-ol,
2-amino-2-methyl-4-[5-(5-cyclohexylpentyl)thiophen-2-yl]butan-1-ol,
2-amino-2-methyl-4-[5-(5-phenylpentyl)thiophen-2-yl]butan-1-ol,
2-amino-2-methyl-4-[5-(4-cyclohexyloxybutyl)thiophen-2-yl]butan-1-ol,
2-amino-2-methyl-4-{5-[4-(4-fluorophenoxy)butyl]thiophen-2-yl}butan-1-ol,
2-amino-2-methyl-4-{5-[4-(4-methoxyphenoxy)butyl]thiophen-2-yl}butan-1-ol,
2-amino-2-methyl-4-[5-(4-benzyloxybutyl)thiophen-2-yl]butan-1-ol,
2-amino-2-methyl-4-[5-(4-cyclohexylbut-1-ynyl)thiophen-2-yl]butan-1-ol,
2-amino-2-methyl-4-[5-(4-phenylbut-1-ynyl)thiophen-2-yl]butan-1-ol,
2-amino-2-methyl-4-[5-(5-cyclohexylpent-1-ynyl)thiophen-2-yl]butan-1-ol,
2-amino-2-methyl-4-[5-(5-phenylpent-1-ynyl)thiophen-2-yl]butan-1-ol,
2-amino-2-methyl-4-{5-[5-(4-fluorophenyl)pent-1-ynyl]thiophen-2-yl}butan-1-ol,
2-amino-2-methyl-4-{5-[5-(4-methoxyphenyl)pent-1-ynyl]thiophen-2-yl}butan-1-ol,
2-amino-2-methyl-4-{5-[3-(4-methylcyclohexyloxy)propynyl]thiophen-2-yl}butan-1-ol,
2-amino-2-methyl-4-{5-[3-(4-methylphenoxy)propynyl]thiophen-2-yl}butan-1-ol,
2-amino-2-methyl-4-{5-[3-(4-ethylphenoxy)propynyl]thiophen-2-yl}butan-1-ol,
2-amino-2-methyl-4-{5-[3-(4-methylthiophenoxy)propynyl]thiophen-2-yl}butan-1-ol,
2-amino-2-methyl-4-[5-(4-cyclohexyloxybut-1-ynyl)thiophen-2-yl]butan-1-ol,
2-amino-2-methyl-4-{5-[4-(4-fluorophenoxy)but-1-ynyl]thiophen-2-yl}butan-1-ol,
2-amino-2-methyl-4-{5-[4-(4-methylphenoxy)but-1-ynyl]thiophen-2-yl}butan-1-ol,
2-amino-2-methyl-4-[5-(3-cyclohexylmethoxypropynyl)thiophen-2-yl]butan-1-ol,
2-amino-2-methyl-4-[5-(4-phenylmethoxybut-1-ynyl)thiophen-2-yl]butan-1-ol,
2-amino-2-methyl-4-[5-(4-cyclohexylbutanoyl)thiophen-2-yl]butan-1-ol,
2-amino-2-methyl-4-[5-(4-phenylbutanoyl)thiophen-2-yl]butan-1-ol,
2-amino-2-methyl-4-[5-(5-cyclohexylpentanoyl)thiophen-2-yl]butan-1-ol,
2-amino-2-methyl-4-[5-(5-phenylpentanoyl)thiophen-2-yl]butan-1-ol,
2-amino-2-methyl-4-{5-[5-(4-fluorophenyl)pentanoyl]thiophen-2-yl}butan-1-ol,
2-amino-2-ethyl-4-[5-(5-cyclohexylpentyl)thiophen-2-yl]butan-1-ol,
2-amino-2-ethyl-4-[5-(5-cyclohexylpent-1-ynyl)thiophen-2-yl]butan-1-ol,
2-amino-2-ethyl-4-[5-(5-cyclohexylpentanoyl)thiophen-2-yl]butan-1-ol,
2-amino-2-methyl-4-{5-[3-(4-chlorophenoxy)propynyl]thiophen-2-yl}butan-1-ol,
2-amino-2-methyl-4-{5-[3-(3-methylphenoxy)propynyl]thiophen-2-yl}butan-1-ol,
2-amino-2-methyl-4-{5-[3-(3,4-dimethylphenoxy)propynyl]thiophen-2-yl}butan-1-ol,
2-amino-2-methyl-4-{5-[3-(3-methoxyphenoxy)propynyl]thiophen-2-yl}butan-1-ol,
2-amino-2-methyl-4-{5-[3-(3,4-dimethoxyphenoxy)propynyl]thiophen-2-yl}butan-1-ol,
2-amino-2-methyl-4-{5-[3-(3,5-dimethoxyphenoxy)propynyl]thiophen-2-yl}butan-1-ol,
2-amino-2-methyl-4-{5-[3-(3-acetylphenoxy)propynyl]thiophen-2-yl}butan-1-ol, and
2-amino-2-methyl-4-{5-[3-(4-acetylphenoxy)propynyl]thiophen-2-yl}butan-1-ol.

Preferred compounds of formula (I) also include ones comprising a combination of one group selected from each of the groups consisting of (2) and (3); (4) and (5); (6) and (7); (8) to (10); (11) and (12); (13) to (17); (18) to (29); (30) to (40); and (41) and (42).

(45) The present invention includes an optically active amino alcohol derivative of formula (La) or (Lb):

$$\text{(La)} \quad R^{3a}O\underset{NR^1R^2}{\overset{R^{4a}}{\diagup\!\!\!\diagdown}}(CH_2)_m-Ar$$

or $$\text{(Lb)} \quad R^{3a}O\underset{NR^1R^2}{\overset{R^{4a}}{\diagup\!\!\!\diagdown}}(CH_2)_m-Ar$$

wherein
$R^1$ and $R^2$ are the same or different and each represents a hydrogen atom or an amino protecting group;
$R^{3a}$ represents a hydrogen atom or a hydroxy protecting group or when $R^1$ is a hydrogen atom, $R^2$ and $R^{3a}$ taken together form a group of formula —(C=O)—;
$R^{4a}$ represents a $C_1$–$C_{20}$ alkyl group, a $C_2$–$C_{20}$ alkyl group interrupted with a heteroatom(s), a $C_1$–$C_{20}$ alkyl group substituted with an aryl group(s) or a heteroaryl group(s), a $C_2$–$C_{20}$ alkynyl group, a $C_3$–$C_{20}$ alkynyl group interrupted with a heteroatom(s), a $C_2$–$C_{20}$ alkynyl group substituted with an aryl group(s) or a heteroaryl group(s), a $C_2$–$C_{20}$ alkenyl group, a $C_3$–$C_{20}$ alkenyl group interrupted with a heteroatom(s), a $C_2$–$C_{20}$ alkenyl group substituted with an aryl group(s) or a heteroaryl group(s), a $C_2$–$C_{20}$ alkyl group which is substituted with an aryl group(s) or a heteroaryl group(s) and interrupted with a heteroatom(s), or a cycloalkyl group;
m represent an integer from 0 to 4;
Ar represents an aryl group, a heteroaryl group, an aryl group substituted with 1 to 5 substituents selected from substituent group a, a heteroaryl group substituted with 1 to 5 substituents selected from substituent group a, with the proviso that when Ar is an aryl group, $R^1$ is not a hydrogen atom and $R^2$ and/or $R^{3a}$ do not represent a hydrogen atom;
substituent group a represents a halogen atom, a lower alkyl group, a halogenated lower alkyl group, a lower alkoxy group, a lower alkylthio group, a carboxyl group, a lower alkoxycarbonyl group, a hydroxyl group, a lower aliphatic acyl group, an amino group, a lower mono-alkylamino group, a lower di-alkylamino group, a lower aliphatic acylamino group, a cyano group, and a nitro group.

Preferred compounds of formula (La) or (Lb) include the following compounds:

(46) a compound according to (45) wherein said compound has formula (La);
(47) a compound according to (45) or (46) wherein $R^1$ is a hydrogen atom;
(48) a compound according to any one of (45) to (47) wherein $R^2$ and $R^{3a}$ taken together form a group of formula —(C=O)—;
(49) a compound according to any one of (45) to (47) wherein $R^{3a}$ is a hydrogen atom;
(50) a compound according to any one of (45) to (49) wherein $R^{4a}$ is a $C_1$–$C_{10}$ alkyl group, a $C_2$–$C_{10}$ alkyl group interrupted with a heteroatom(s), a $C_1$–$C_{10}$ alkyl group substituted with an aryl group(s) or a heteroaryl group(s), a $C_2$–$C_{10}$ alkynyl group, a $C_3$–$C_{10}$ alkynyl group interrupted with a heteroatom(s), a $C_2$–$C_{10}$ alkynyl group substituted with an aryl group(s) or a heteroaryl group(s), a $C_2$–$C_{10}$ alkenyl group, a $C_3$–$C_{10}$ alkenyl group interrupted with a heteroatom(s), a $C_2$–$C_{10}$ alkenyl group substituted with an aryl group(s) or a heteroaryl group(s), a $C_2$–$C_{10}$ alkyl group which is substituted with an aryl group(s) or a heteroaryl group(s) and interrupted with a heteroatom(s), or a $C_5$–$C_{10}$ cycloalkyl group;
(51) a compound according to any one of (45) to (49) wherein $R^{4a}$ is a $C_1$–$C_{10}$ alkyl group, a $C_2$–$C_{10}$ alkyl group interrupted with a heteroatom(s), a $C_1$–$C_{10}$ alkyl group substituted with an aryl group(s) or a heteroaryl group(s), a $C_2$–$C_{10}$ alkynyl group, a $C_2$–$C_{10}$ alkenyl group, or a $C_5$–$C_{10}$ cycloalkyl group;
(52) a compound according to any one of (45) to (49) wherein $R^{4a}$ is a $C_1$–$C_{10}$ alkyl group;
(53) a compound according to any one of (45) to (49) wherein $R^{4a}$ is a $C_1$–$C_6$ alkyl group;
(54) a compound according to any one of (45) to (49) wherein $R^{4a}$ is a methyl group or an ethyl group;
(55) a compound according to any one of (45) to (54) wherein Ar is a phenyl, furyl, thienyl or benzothienyl group, said groups optionally being substituted with 1 to 4 substituents selected from substituent group a;
(56) a compound according to any one of (45) to (54) wherein Ar is a thienyl group or a thienyl group substituted with 1 to 4 substituents selected from substituent group a;
(57) a compound according to any one of (45) to (54) wherein Ar is a benzothienyl group or a benzothienyl group substituted with 1 to 4 substituents selected from substituent group a;
(58) a compound according to (45) to (57) wherein m is 0;
(59) a compound according to any one of (45) to (57) wherein substituent group a is a halogen atom, a hydroxyl group, a lower alkyl group, a halogenated lower alkyl group, a lower alkoxy group, a carboxyl group, a lower aliphatic acyl group, a lower aliphatic acylamino group, an amino group, a cyano group, or a nitro group;
(60) The present invention relates to a process for the preparation of a compound of a formula (XLIVa) or (XLIVb)

$$\text{(XLIVa)} \quad R^{11}\underset{O}{\overset{O}{\diagup\!\!\!\diagdown}}O\underset{NR^1R^2}{\overset{R^{4a}}{\diagup\!\!\!\diagdown}}OH$$

or $$\text{(XLIVb)} \quad R^{11}\underset{O}{\overset{O}{\diagup\!\!\!\diagdown}}O\underset{NR^1R^2}{\overset{R^{4a}}{\diagup\!\!\!\diagdown}}OH$$

[wherein:
$R^1$ and $R^2$ are the same or different and each represents a hydrogen atom or an amino protecting group;
$R^{4a}$ represents a $C_1$–$C_{20}$ alkyl group, a $C_2$–$C_{20}$ alkyl group interrupted with a heteroatom(s), a $C_1$–$C_{20}$ alkyl group substituted with an aryl group(s) or a heteroaryl group(s), a $C_2$–$C_{20}$ alkynyl group, a $C_3$–$C_{20}$ alkynyl group interrupted with a heteroatom(s), a $C_2$–$C_{20}$ alkynyl group substituted with an aryl group(s) or a heteroaryl group(s), a $C_2$–$C_{20}$ alkenyl group, a $C_3$–$C_{20}$ alkenyl group interrupted with a heteroatom(s), a $C_2$–$C_{20}$ alkenyl group substituted with an aryl group(s) or a heteroaryl group(s), a $C_2$–$C_{20}$ alkyl group which is substituted with an aryl group(s) or a heteroaryl group(s) and interrupted with a heteroatom(s), or a cycloalkyl group; and
$R^{11}$ has the same meaning as that indicated above for $R^{4a}$.].
The process comprises a selective acylation reaction-of one hydroxyl group of a 2-substituted 2-amino-1,3-propanediol derivative of formula (XLII)

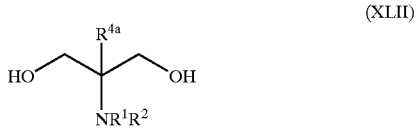
(XLII)

[wherein $R^1$, $R^2$ and $R^{4a}$ are defined in above.]
with a carboxylic acid ester derivative of formula (XLIII)

(XLIII)

[wherein $R^{11}$ is defined in above.]
in the presence of a lipase to afford a 2-substituted 2-amino-1,3-propanediol mono-ester derivative of formula (XLIVa) or (XLIVb).

(61) a process for preparation according to (60) wherein one of $R^1$ and $R^2$ is a hydrogen atom and the other one is an amino protecting group;

(62) a process for preparation according to (60) or (61) wherein $R^{4a}$ is a $C_1$–$C_{10}$ alkyl group, a $C_2$–$C_{10}$ alkyl group interrupted with a heteroatom(s), a $C_1$–$C_{10}$ alkyl group substituted with an aryl group(s) or a heteroaryl group(s), a $C_2$–$C_{10}$ alkynyl group, a $C_3$–$C_{10}$ alkynyl group interrupted with a heteroatom(s), a $C_2$–$C_{10}$ alkynyl group substituted with an aryl group(s) or a heteroaryl group(s), a $C_2$–$C_{10}$ alkenyl group, a $C_3$–$C_{10}$ alkenyl group interrupted with a heteroatom(s), a $C_2$–$C_{10}$ alkenyl group substituted with an aryl group(s) or a heteroaryl group(s), a $C_2$–$C_{10}$ alkyl group which is substituted with an aryl group(s) or a heteroaryl group(s) and interrupted with a heteroatom(s), or a $C_5$–$C_{10}$ cycloalkyl group;

(63) a process for preparation according to (60) or (61) wherein $R^{4a}$ is a $C_1$–$C_{10}$ alkyl group, a $C_2$–$C_{10}$ alkyl group interrupted with a heteroatom(s), a $C_1$–$C_{10}$ alkyl group substituted with an aryl group(s) or a heteroaryl group(s), a $C_2$–$C_{10}$ alkynyl group, a $C_2$–$C_{10}$ alkenyl group, or a $C_5$–$C_{10}$ cycloalkyl group;

(64) a process for preparation according to (60) or (63) wherein $R^{11}$ is a $C_1$–$C_{20}$ alkyl group, or a $C_1$–$C_{20}$ alkyl group substituted with an aryl group(s) or a heteroaryl group(s).

In the above formulae, an "aryl group" and an "aryl moiety" of an aryl group substituted with 1 to 3 substituents selected from substituent group a; an aryl group substituted with 1 to 3 substituents selected from substituent groups a and b; and an aryl group substituted with 1 to 5 substituents selected from substituent group a in the definition of X, $R^5$, Ar and substituent group b each are, for example, an aromatic hydrocarbon having 6 to 10 carbons such as phenyl, indenyl and naphthyl; preferably a phenyl or naphthyl group and most preferably a phenyl group.

In the above formulae, an "alkylene group" and an "alkylene moiety" of a $C_1$–$C_{10}$ alkylene group substituted with 1 to 3 substituents selected from substituent group a and b in the definition of Y each are a straight or branched chain alkylene having 1 to 10 carbons such as methylene, methylmethylene, ethylene, propylene, trimethylene, 1-methylethylene, tetramethylene, 1-methyltrimethylene, 2-methyltrimethylene, 3-methyltrimethylene, 1-methylpropylene, 1,1-dimethylethylene, pentamethylene, 1-methyltetramethylene, 2-methyltetramethylene, 3-methyltetramethylene, 4-methyltetramethylene, 1,1-dimethytrimethylene, 2,2-dimethytrimethylene, 3,3-dimethytrimethylene, hexamethylene, 1-methylpentamethylene, 2-methylpentamethylene, 3-methylpentamethylene, 4-methylpentamethylene, 5-methylpentamethylene, 1,1-dimlethyltetramethylene, 2,2-dimethyltetramethylene, 3,3-dimethyltetramethylene, 4,4-dimethyltetramethylene, heptamethylene, 1-methylhexamethylene, 2-methylhexamethylene, 5-methylhexamethylene, 3-ethylpentamethylene, octamethylene, 2-methylheptamethylene, 5-methylheptamethylene, 2-ethylhexamethylene, 2-ethyl-3-methylpentamethylene, 3-ethyl-2-methylpentamethylene, nonamethylene, 2-methyloctamethylene, 7-methyloctamethylene, 4-ethylheptamethylene, 3-ethyl-2-methylhexamethylene, 2-ethyl-1-methylhexamethylene, decamethylene group; preferably a $C_1$–$C_6$ alkylene; more preferably a $C_1$–$C_5$ alkylene; still more preferably an ethylene, trimethylene or tetramethylene group; and most preferably an ethylene or trimethylene group.

In the above formulae, a "$C_1$–$C_{10}$ alkylene group which has an oxygen atom or a sulfur atom in said carbon chain or at the end of said carbon chain" and a "$C_1$–$C_{10}$ alkylene moiety which has an oxygen atom or a sulfur atom in said carbon chain or at the end of said carbon chain" of a $C_1$–$C_{10}$ alkylene group which is substituted with 1 to 3 substituents selected from substituent groups a and b and has an oxygen atom or a sulfur atom in said carbon chain or at the end of said carbon chain in the definition of Y is a $C_1$–$C_{10}$ alkylene group indicated above which has an oxygen atom or a sulfur atom in said carbon chain or at the end of said carbon chain, for example, a group of formula —O—$CH_2$—, —O—$(CH_2)_2$—, —O—$(CH_2)_3$—, —O—$(CH_2)_4$—, —O—$(CH_2)_5$—, —O—$(CH_2)_6$—, —O—$(CH_2)_7$—, —O—$(CH_2)_8$—, —O—$(CH_2)_9$—, —O—$(CH_2)_{10}$—, —$CH_2$—O—$CH_2$—, —$CH_2$—O—$(CH_2)_2$—, —$CH_2$—O—$(CH_2)_3$—, —$CH_2$—O—$(CH_2)_4$—, —$(CH_2)_2$—O—$CH_2$—, —$(CH_2)_2$—O—$(CH_2)_2$—, —$(CH_2)_2$—O—$(CH_2)_3$—, —$(CH_2)_2$—O—$(CH_2)_4$—, —$(CH_2)_3$—O—$CH_2$—, —$(CH_2)_3$—O—$(CH_2)_2$—, —$(CH_2)_3$—O—$(CH_2)_3$—, —$(CH_2)_4$—O—$CH_2$—, —$(CH_2)_4$—O—$(CH_2)_2$—, —$(CH_2)_5$—O—$CH_2$—, —$CH_2$—O—, —$(CH_2)_2$—O—, —$(CH_2)_3$—O—, —$(CH_2)_4$—O—, —$(CH_2)_5$—O—, —$(CH_2)_6$—O—, —$(CH_2)_7$—O—, —$(CH_2)_8$—O—, —$(CH_2)_9$—O—, —$(CH_2)_{10}$—O—, —S—$CH_2$—, —S—$(CH_2)_2$—, —S—$(CH_2)_3$—, —S—$(CH_2)_4$—, —S—$(CH_2)_5$—, —S—$(CH_2)_6$—, —S—$(CH_2)_7$—, —S—$(CH_2)_8$—, —S—$(CH_2)_9$—, —S—$(CH_2)_{10}$—, —$CH_2$—S—$CH_2$—, —$CH_2$—S—$(CH_2)_2$—, —$CH_2$—S—$(CH_2)_3$—, —$CH_2$—S—$(CH_2)_4$—, —$(CH_2)_2$—S—$CH_2$—, —$(CH_2)_2$—S—$(CH_2)_2$—, —$(CH_2)_2$—S—$(CH_2)_3$—, —$(CH_2)_2$—S—$(CH_2)_4$—, —$(CH_2)_3$—S—$CH_2$—, —$(CH_2)_3$—S—$(CH_2)_2$—, —$(CH_2)_3$—S—$(CH_2)_3$—, —$(CH_2)_4$—S—$CH_2$—, —$(CH_2)_4$—S—$(CH_2)_2$—, —$(CH_2)_5$—S—$CH_2$—, —$CH_2$—S—$(CH_2)_2$—S, —$(CH_2)_3$—S—, —$(CH_2)_4$—S—, —$(CH_2)_5$—S—, —$(CH_2)_6$—S—, —$(CH_2)_7$—S—, —$(CH_2)_8$—S—, —$(CH_2)_9$—S—, —$(CH_2)_{10}$—S—; preferably a $C_1$–$C_6$ alkylene group which has an oxygen atom in said carbon chain or at the end of carbon chain; more preferably —O—$CH_2$—, —O—$(CH_2)_2$—, —O—$(CH_2)_3$—, —$CH_2$—O—, —$(CH_2)_2$—O—, or —$(CH_2)_3$—O—; and most preferably —$CH_2$—O—, —O—$(CH_2)_2$—, or —$(CH_2)_2$—O—.

In the above formulae the "cycloalkyl groups" in substituent groups b and the "cycloalkyl moieties" of the cycloalkyl group substituted with 1 to 3 substituents selected from substituent group a and the cycloalkyl group substituted with 1 to 3 substituents selected from substituent groups a and b in the definitions of $R^{4a}$, $R^5$ and $R^{11}$, each comprise a saturated carbon ring having 3 to 10 carbons, which is optionally fused with a cyclic group(s) such as a benzene ring, for example, cyclopropyl, cyclobutyl, cyclopentyl, cyclohexyl, cycloheptyl, norbornyl, adamantyl and indanyl. A preferred cycloalkyl group in the definition of $R^5$ and substituent group b is a $C_5$–$C_6$ cycloalkyl group and the most preferred one is a cyclohexyl group. On the other hand a preferred cycloalkyl group in the definition of $R^{4a}$ and $R^{11}$ is a $C_5$–$C_{10}$ cycloalkyl group.

In the above formulae the "heteroaryl group" and the "heteroaryl moiety" of the heteroaryl group substituted with 1 to 5 substituents selected from substituent group a in the definition of Ar each comprise a 5- to 7-membered heterocyclic group having 1 to 3 of a sulfur atom(s), an oxygen atom(s) and/or a nitrogen atom(s), for example, furyl, thienyl, pyrrolyl, azepinyl, pyrazolyl, imidazolyl, oxazolyl, isoxazolyl, thiazolyl, isothiazolyl, 1,2,3-oxadiazolyl, triazolyl, tetrazolyl, thiadiazolyl, pyranyl, pyridyl, pyridazinyl, pyrimidinyl and pyrazinyl.

In addition, the heteroaryl group indicated above optionally may be fused with a cyclic group. Examples of such a group include, for example, benzothienyl, isobenzofuranyl, chromenyl, xanthenyl, phenoxathiinyl, indolizinyl, isoindolyl, indolyl, indazolyl, purinyl, quinolizinyl, isoquinolyl, quinolyl, phthalazinyl, naphthylizinyl, quinoxalinyl, quinazolinyl, carbazolyl, carbolinyl, acridinyl and isoindolinyl. Preferred heteroaryl groups are a furyl, thienyl or benzothienyl group and the most preferred heteroaryl group is a thienyl or a benzothienyl group.

In the above formulae the "heterocyclic groups" in the definition of $R^5$ and substituent group b and the "heterocyclic moiety" of the heterocyclic group substituted with 1 to 3 substituents selected from substituent group a and the heterocyclic group substituted with 1 to 3 substituents selected from substituent groups a and b each represent a 5- to 7 membered heterocyclic group having 1 to 3 of a sulfur atom(s), an oxygen atom and/or a nitrogen atom, and examples of such heterocyclic groups include the heteroaryl groups indicated above, and heterocyclic compounds corresponding to partially or completely hydrogenated heteroaryl groups indicated above such as tetrahydropyranyl, morpholinyl, thiomorpholinyl, pyrrolidinyl, pyrrolyl, imidazolidinyl, pyrazolidinyl, piperidinyl, piperazinyl, oxazolidinyl, isoxazolidinyl, thiazolidinyl and pyrazolidinyl. Preferred heterocyclic groups are 5- or 6-membered heteroaryl groups and the most preferred heteocyclic group is a morpholinyl, thiomorpholinyl or piperidinyl group.

In the above formulae the "halogen atom" in the definition of substituent group a is a fluorine, chlorine, bromine or iodine atom; preferably a fluorine atom or chlorine atom and most preferably a fluorine atom.

In the above formulae the "lower alkyl groups" in the definition of $R^4$ and substituent group a each represent, for example, a straight or branched chain alkyl group having 1 to 6 carbons such as a methyl, ethyl, propyl, isopropyl, butyl, isobutyl, s-butyl, t-butyl, pentyl, isopentyl, 2-methylbutyl, neopentyl, 1-ethylpropyl, hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 1-ethylbutyl or 2-ethylbutyl group; preferably a $C_1$–$C_4$ alkyl group; more preferably a $C_1$–$C_2$ alkyl group and most preferably a methyl group.

In the above formulae the "halogenated lower alkyl group" in the definition of substituent group a represents the lower alkyl group, which is described hereinbefore which is substituted with a haologen atom(s), for example, a halogenated $C_1$–$C_6$ alkyl group such as a trifluoromethyl, trichloromethyl, difluoromethyl, dichloromethyl, dibromomethyl, fluoromethyl, 2,2,2-trifluoroethyl, 2,2,2-trichloroethyl, 2-bromoethyl, 2-chloroethyl, 2-fluoroethyl, 2-iodoethyl, 3-chloropropyl, 4-fluorobutyl, 6-iodohexyl or 2,2-dibromoethyl group; preferably a halogenated $C_1$–$C_4$ alkyl group; more preferably a halogenated $C_1$–$C_2$ alkyl group; and most preferably a trifluoromethyl group.

In the above formulae the "lower alkoxy group" in the definition of substituent group a represents an oxygen atom which is attached to the lower alkyl group described hereinbefore, for example, a straight or branched chain alkoxy group having 1 to 6 carbons such as a methoxy, ethoxy, propoxy, isopropoxy, butoxy, isobutoxy, s-butoxy, t-butoxy, pentoxy, isopentoxy, 2-methylbutoxy, 1-ethylpropoxy, 2-ethylpropoxy, neopentoxy, hexyloxy, 4-methylpentoxy, 3-methylpentoxy, 2-methylpentoxy, 3,3-dimethylbutoxy, 2,2-dimethylbutoxy, 1,1-dimethylbutoxy, 1,2-dimethylbutoxy, 1,3-dimethylbutoxy or 2,3-dimethylbutoxy group; preferably a $C_1$–$C_4$ alkoxy group; more preferably a $C_1$–$C_2$ alkoxy group; and most preferably a methoxy group.

In the above formulae the "lower alkylthio group" in the definition of substituent group a represents a sulfur atom which is attached to a lower alkyl group described hereinbefore, for example, an alkylthio group having 1 to 6 carbons such as a methylthio, ethylthio, propylthio, isopropylthio, butylthio, isobutylthio, s-butylthio, t-butylthio, pentylthio, isopentylthio, 2-methylbutylthio, neopentylthio, hexylthio, 4-methylpentylthio, 3-methylpentylthio, 2-methylpentylthio, 3,3-dimethylbutylthio, 2,2-dimethylbutylthio, 1,1-dimethylbutylthio, 1,2-dimethylbutylthio, 1,3-dimethylbutylthio or 2,3-dimethylbutylthio group; preferably a $C_1$–$C_4$ alkylthio group; more preferably a $C_1$–$C_2$ alkylthio group; and most preferably a methylthio group.

In the above formulae the "lower alkoxycarbonyl group" in the definition of substituent group a represents a carbonyl group which is attached to the lower alkoxy group described hereinbefore, for example, a straight or branched chain alkoxycarbonyl group having 1 to 6 carbons such as a methoxycarbonyl, ethoxycarbonyl, propoxycarbonyl, isopropoxycarbonyl, butoxycarbonyl, isobutoxycarbonyl, s-butoxycarbonyl, t-butoxycarbonyl, pentoxycarbonyl, isopentoxycarbonyl, 2-methylbutoxycarbonyl, neopentoxycarbonyl, hexyloxycarbonyl, 4-methylpentoxycarbonyl, 3-methylpentoxycarbonyl, 2-methylpentoxycarbonyl, 3,3-dimethylbutoxycarbonyl, 2,2-dimethylbutoxycarbonyl, 1,1-dimethylbutoxycarbonyl, 1,2-dimethylbutoxycarbonyl, 1,3-dimethylbutoxycarbonyl or 2,3-dimethylbutoxycarbonyl group; preferably a $C_1$–$C_4$ alkoxycarbonyl group; more preferably a $C_1$–$C_2$ alkoxycarbonyl group; and most preferably a methoxycarbonyl group.

In the above formulae the "lower aliphatic acyl group" in the definition of substituent group a represents a carbonyl group which is attached to a hydrogen atom or a saturated or unsaturated chain hydrocarbon, for example, a straight or branched chain lower aliphatic acyl group having 1 to 7 carbons such as a formyl, acetyl, propionyl, butyryl, isobutyryl, valeryl, isovaleryl, pivaloyl, hexanoyl, acryloyl, methacryloyl or crotonoyl group; preferably a $C_1$–$C_4$ lower aliphatic acyl group; more preferably an acetyl or propionyl group; and most preferably an acetyl group.

In the above formulae the "mono lower alkylamino group" in the definition of substituent group a represents an amino group which is attached to one alkyl group described hereinbefore, for example, a mono $C_1$–$C_6$ alkylamino group such as a methylamino, ethylamino, propylamino, isopropylamino, butylamino, isobutylamino, s-butylamino, t-butylamino, pentylamino, isopentylamino, 2-methylbutylamino, neopentylamino, 1-ethylpropylamino, hexylamino, isohexylamino, 4-methylpentylamino, 3-methylpentylamino, 2-methylpentylamino, 1-methylpentylamino, 3,3-dimethylbutylamino, 2,2-dimethylbutylamino, 1,1-dimethylbutylamino, 1,2-dimethylbutylamino, 1,3-dimethylbutylamino, 2,3-dimethylbutylamino or 2-ethylbutylamino group; preferably a $C_1$–$C_4$ alkylamino group; more preferably a $C_1$–$C_2$ alkyl amino group; and most preferably a methylamino group.

In the above formulae the "di lower alkylamino group" in the definition of substituent group a represents an amino group which is attached to two alkyl groups described hereinbefore, for example, a di $C_1$–$C_6$ alkylamino group such as a dimethylamino, diethylamino, N-ethyl-N-methylamino, dipropylamino, dibutylamino, dipentylamino or dihexylamino group; preferably a di $C_1$–$C_4$ alkylamino group; more preferably a di $C_1$–$C_2$ alkyl amino group; and most preferably a dimethylamino group.

In the above formulae the "lower aliphatic acylamino group" in the definition of substituent group a represents, for example, a straight or branched chain aliphatic acylamino group having 1 to 7 carbons such as a formylamino, acetylamino, propionylamino, butyrylamino, isobutyrylamino, valerylamino, isovalerylamino, pivaloylamino, hexanoylamino, acryloylamino, methacryloylamino or crotonoylamino group; preferably an acetylamino or propionylamino group; and most preferably an acetylamino group.

In the above formulae the "amino protecting groups" in the definition of $R^1$ and $R^2$ each represent an amino protecting group known to those skilled in organic synthesis, for example:

the lower alkyl group described hereinbefore; an aliphatic acyl group, for example, the lower aliphatic acyl group described hereinbefore, a halogenated lower aliphatic acyl group such as chloroacetyl, dichloroacetyl, trichloroacetyl or trifluoroacetyl or a lower aliphatic acyl group substituted with a lower alkoxy group such as methoxyacetyl; an aromatic acyl group, for example, an aromatic acyl group such as benzoyl, 1-indancarbonyl, 2-indancarbonyl or 1- or 2-naphthoyl, or an aromatic acyl group substituted with 1 to 3 substituents selected from substituent group a such as 4-chlorobenzoyl, 4-fluorobenzoyl, 2,4,6-trimethylbenzoyl, 4-toluoyl, 4-anisoyl, 4-nitrobenzoyl, 2-nitrobenzoyl, 2-(methoxycarbonyl)benzoyl or 4-phenylbenzoyl; an alkoxycarbonyl group, for example, the lower alkoxycarbonyl described hereinbefore or a lower alkoxycarbonyl group substituted with a halogen atom(s) or a tri lower alkylsilyl group(s) such as 2,2,2-trichloroethoxycarbonyl or 2-trimethylsilylethoxycarbonyl; an alkenyloxycarbonyl group such as vinyloxycarbonyl or allyloxycarbonyl; an aralkyloxycarbonyl group, for example, an aralkyloxycarbonyl group such as a benzyloxycarbonyl group or an aralkyloxycarbonyl group substituted with 1 to 3 substituents selected from substituent group a such as 4-methoxybenzyloxycarbonyl, 3,4-dimethoxybenzyloxycarbonyl, 2-nitrobenzyloxycarbonyl or 4-nitrobenzyloxycarbonyl; a silyl group, for example, a lower alkylsilyl group such as trimethylsilyl, triethylsilyl, isopropyldimethylsilyl, t-butyldimethylsilyl, methyldiisopropylsilyl, methyl-di-t-butylsilyl or triisopropylsilyl, a silyl group tri substituted with an aryl group(s) or with an aryl(s) and a lower alkyl group(s) such as diphenylmethylsilyl or diphenylbutylsilyl, diphenylisopropylsilyl, phenyldiisopropylsilyl; an aralkyl group, for example a lower alkyl group substituted with 1 to 3 aryl groups such as benzyl, phenethyl, 3-phenylpropyl, α-naphthylmethyl, β-naphthylmethyl, diphenylmethyl, triphenylmethyl, α-naphthyldiphenylmethyl or 9-anthrylmethyl or a lower alkyl group substituted with 1 to 3 substituted aryl groups wherein said aryl group is substituted with lower alkyl, lower alkoxy, nitro, halo or cyano, such as 4-methylbenzyl, 2,4,6-trimethylbenzyl, 3,4,5-trimethylbenzyl, 4-methoxybenzyl, 4-methoxyphenyldiphenylmethyl, 2-nitrobenzyl, 4-nitrobenzyl, 4-chlorobenzyl, 4-bromobenzyl, 4-cyanobenzyl, 4-cyanobenzyldiphenylmethyl, bis(2-nitrophenyl)methyl or piperonyl; and a substituted methylene group which forms a Schiff base such as N,N-dimethylaminomethylene, benzylidene, 4-methoxybenzylidene, 4-nitrobenzylidene, salicylidene, 5-chlorosalicylidene, diphenylmethylene or (5-chloro-2-hydroxyphenyl)phenylmethylene;

preferably a lower alkoxycarbonyl group, an aralkyloxycarbonyl group or an aralkyloxycarbonyl group substituted with 1 to 3 substituents selected from substituent group a.

The "hydroxy protecting group" in the definition $R^3$ and $R^{3a}$ represents a general protecting group which can be deprotected by a chemical process such as hydrogenolysis, hydrolysis, electrolysis, photolysis and a protecting group which can be deprotected by a biological process such as hydrolysis in vivo.

Examples of general protecting groups includes the lower alkyl groups described hereinbefore; the aliphatic acyl groups described hereinbefore; the aromatic acyl groups described hereinbefore; a tetrahydropyranyl or tetrahydrothiopyranyl group such as tetrahydropyran-2-yl, 3-bromotetrahydropyran-2-yl or 4-methoxytetrahydropyran-4-yl, tetrahydrothiopyran-2-yl or 4-methoxytetrahydrothiopyran-4-yl; a tetrahydrofuranyl or tetrahydrothiofuranyl group such as tetrahydrofuran-2-yl or tetrahydrothiofuran-2-yl; the silyl groups described hereinbefore; an alkoxymethyl group, for example, a lower alkoxylated lower alkoxymethyl group such as methoxymethyl, 1,1-dimethyl-1-methoxymethyl, ethoxymethyl, propoxymethyl, isopropoxymethyl, butoxymethyl or t-butoxymethyl; a lower alkoxylated alkoxymethyl group such as 2-methoxyethoxymethyl or a halogenated lower alkoxymethyl group such as 2,2,2-trichloroethoxymethyl or bis(2-chloroethoxy)methyl; a substituted ethyl group, for example a lower alkoxylated ethyl group such as 1-ethoxyethyl or 1-(isopropoxy)ethyl or a halogenated ethyl group such as 2,2,2-trichloroethyl; the aralkyl groups described hereinbefore; the alkoxycarbonyl groups described hereinbefore; and the alkenyloxycarbonyl group described hereinbefore; the aralkyloxycarbonyl group described hereinbefore.

On the other hand examples of a protecting group which can be deprotected by a biological process such as hydrolysis in vivo, include an acyloxyalkyl group such as ethylcarbonyloxymethyl, pivaloyloxymethyl, dimethylaminoacetyloxymethyl or 1-acetoxyethyl; a 1-(alkoxycarbonyloxy)alkyl group such as 1-(methoxycarbonyloxy)ethyl, 1-(ethoxycarbonyloxy)ethyl, ethoxycarbonyloxymethyl, 1-(isopropoxycarbonyloxy)ethyl, 1-(t-butoxycarbonyloxy)ethyl, 1-(ethoxycarbonyloxy)propyl or 1-(cyclohexyloxycarbonyloxy)ethyl; a phthalidyl group; a carbonyloxyalkyl group, for example, an oxodioxolenylmethyl group such as 4-methyloxodioxolenylmethyl or 4-phenyloxodioxolenylmethyl; the aliphatic acyl groups described hereinbefore; the aromatic acyl groups described hereinbefore; a residual group of a half ester of succinic acid; a residual group of an ester of phosphoric acid; a residual group of an ester formation of an amino acid; a carbamoyl group; an alkylidene group such as benzylidene; an alkoxyethylidene group such as methoxyethylidene or ethoxyethylidene; a protecting group of two hydroxyl groups such as oxomethylene or oxoethylene; and a carbonyloxyalkyloxycarbonyl group such as pivaloyloxymethyloxycarbonyl.

Whether a compound of formula (I) has such a group can be determined as follows. The derivative under investigation is intravenously administered to a test animal such as a rat or mouse and the body fluids of the test animal are thereafter studied. If the parent compound of said derivative or a pharmaceutically acceptable salt of the parent compound is detected in said body fluid, said derivative under investigation is judged to have a protecting group which can be deprotected by biological process. Examples of such a hydroxy protecting group are preferably a lower alkyl group, a lower aliphatic acyl group, an aromatic acyl group or an aromatic acyl group substituted with 1 to 3 substituents selected from substituent group a.

In the above formulae typical examples of the "cycloalkyl group substituted with 1 to 3 substituents selected from substituent groups a and b" in the definition of $R^5$ are, for example, a 2-fluorocyclopropyl, 2-chlorocyclopropyl, 2- or 3-fluorocyclopentyl, 2- or 3-chlorocyclopentyl, 2-, 3- or 4-fluorocyclohexyl, 2-, 3- or 4-chlorocyclohexyl, 2-, 3- or 4-bromocyclohexyl, 2-, 3- or 4-iodocyclohexyl, 2-methylcyclopropyl, 2-ethylcyclopropyl, 2- or 3-methylcyclopentyl, 2- or 3-ethylcyclopentyl, 2-, 3- or 4-methylcyclohexyl, 2-, 3- or 4-ethylcyclohexyl, 2-trifluoromethylcyclopropyl, 2- or 3-trifluoromethylcyclobutyl, 2- or 3-trifluoromethylcyclopentyl, 2-, 3- or 4-trifluoromethylcyclohexyl, 2-methoxycyclopropyl, 2- or 3-methoxycyclobutyl, 2- or 3-methoxycyclopentyl, 2-, 3- or 4-methoxycyclohexyl, 2-, 3- or 4-ethoxycyclohexyl, 2-, 3- or 4-propoxycyclohexyl, 2-, 3- or 4-isopropoxycyclohexyl, 2-, 3- or 4-(1-ethylpropoxy)cyclohexyl, 2-, 3- or 4-(2-ethylpropoxy)cyclohexyl, 2-carboxycyclopropyl, 2- or 3-carboxycyclopentyl, 2-, 3- or 4-carboxycyclohexyl, 2-methoxycarbonylcyclopropyl, 2- or 3-methoxycarbonylcyclopentyl, 2-, 3- or 4-methoxycarbonylcyclohexyl, 2-hydroxycyclopropyl, 2- or 3-hydroxycyclopentyl, 2-, 3- or 4-hydroxycyclohexyl, 2-formylcyclopropyl, 2- or 3-formylcyclopentyl, 2-, 3- or 4-formylcyclohexyl, 2-acetylcyclopropyl, 2- or 3-acetylcyclopentyl, 2-, 3- or 4-acetylcyclohexyl, 2-aminocyclopropyl, 2- or 3-aminocyclopentyl, 2-, 3- or 4-aminocyclohexyl, 2-methylaminocyclopropyl, 2- or 3-methylaminocyclobutyl, 2- or 3-methylaminocyclopentyl, 2-, 3- or 4-methylaminocyclohexyl, 2-dimethylaminocyclopropyl, 2- or 3-dimethylaminocyclobutyl, 2- or 3-dimethylaminocyclopentyl, 2-, 3- or 4-dimethylaminocyclohexyl, 2-cyanocyclopropyl, 2- or 3-cyanocyclopentyl, 2-, 3- or 4-cyanocyclohexyl, 2- or 3-cyclohexylcyclopentyl, 2-, 3- or 4-cyclohexylcyclohexyl, 2-phenylcyclopropyl, 2- or 3-phenylcyclopentyl, 2-, 3- or 4-phenylcyclohexyl, 3,4-difluorocyclohexyl, 3,4-dichlorocyclohexyl, 2,3-dimethoxycyclohexyl, 3,4-dimethoxycyclohexyl, 3,5-dimethoxycyclohexyl, or 3,4,5-trimethoxycyclohexyl group; preferably a cycloalkyl group substituted with 1 to 3 substituents (said substituent is selected from the group consisting of a halogen atom, a lower alkyl group, a halogenated lower alkyl group, a lower alkoxy group, a lower alkylthio group, and a lower aliphatic acyl group); more preferably a cycloalkyl group substituted with 1 to 3 substituents (said substituent is selected from the group consisting of a halogen atom, a lower alkyl group, a halogenated lower alkyl group, a lower alkoxy group, and a lower aliphatic acyl group); still more preferably a cyclohexyl group substituted with 1 to 3 substituents (said substituent is selected from the group consisting of a halogen atom, a lower alkyl group, a halogenated lower alkyl group, a lower alkoxy group, and a lower aliphatic acyl group); most preferably a cyclohexyl group substituted with 1 to 3 substituents (said substituent is selected from the group consisting of a fluorine atom, a chlorine atom, and methyl, trifluoromethyl, methoxy and acetyl groups).

In the above formulae typical examples of the "aryl group substituted with 1 to 3 substituents selected from substituent groups a and b" in the definition of $R^5$ are, for example, a 2-, 3- or 4-fluorophenyl, 2-, 3- or 4-chlorophenyl, 2-, 3- or 4-bromophenyl, 2-, 3- or 4-iodophenyl, 2-, 3- or 4-methylphenyl, 2-, 3- or 4-ethylphenyl, 2-, 3-, 4-propylphenyl, 2-, 3- or 4-butylphenyl, 2-, 3- or 4-pentylphenyl, 2-, 3- or 4-trifluoromethylpheynyl, 2-, 3- or 4-methoxyphenyl, 2-, 3- or 4-ethoxyphenyl, 2-, 3- or 4-propoxyphenyl, 2-, 3- or 4-isopropoxyphenyl, 2-, 3- or 4-butoxyphenyl, 2-, 3- or 4-(1-ethylpropoxy)phenyl, 2-, 3- or 4-(2-ethylpropoxy)phenyl, 2-, 3- or 4-methylthiophenyl, 2-, 3- or 4-ethylthiophenyl, 2-, 3- or 4-carboxyphenyl, 2-, 3- or 4-methoxycarbonylphenyl, 2-, 3- or 4-ethoxycarbonylphenyl, 2-, 3- or 4-hydroxyphenyl, 2-, 3- or 4-formylphenyl, 2-, 3- or 4-acetylphenyl, 2-, 3- or 4-aminophenyl, 2-, 3-, or 4-methylaminophenyl, 2-, 3- or 4-dimethylaminophenyl, 2-, 3- or 4-cyanophenyl, 2-, 3- or 4-cyclopentylphenyl, 2-, 3- or 4-cyclohexylphenyl, 2-, 3- or 4-biphenyl, 2,4-difluorophenyl, 3,4-difluorophenyl, 3,5-difluorophenyl, 2,4-dichlorophenyl, 3,4-dichlorophenyl, 3,5-dichlorophenyl, 3,4-dibromophenyl, 2,3-dimethylphenyl, 3,4-dimethylphenyl, 3,5-dimethylphenyl, 2,3-dimethoxyphenyl, 3,4-dimethoxyphenyl, 3,5-dimethoxyphenyl, 3,4,5-trimethoxyphenyl, 3-fluoro-4-methoxyphenyl, 4-methyl-2-methoxyphenyl, 6-fluoro-4-methyl-2-methoxyphenyl, 5-fluoroinden-3-yl, 5-fluoroinden-3-yl, 5-methylinden-3-yl, 5-methoxyinden-3-yl, 5-fluoroinden-2-yl, 5-chloroinden-2-yl, 5-methylinden-2-yl, 5-methoxyinden-2-yl, 5-hydroxyinden-3-yl, 5-nitroinden-3-yl, 5-cyclohexylinden-3-yl, 5-phenylinden-3-yl, 5-phenoxyinden-3-yl, 5-benzyloxyinden-3-yl, 5-phenylthioinden-3-yl, 5-hydroxyinden-2-yl, 5-nitroinden-2-yl, 5-cyclohexylinden-2-yl, 5-phenylinden-2-yl, 5-fluoronaphthalen-2-yl, 5-methylnaphthalen-2-yl, 5-methoxynaphthalen-2-yl, 5-fluoronaphthalen-1-yl, 5-methylnaphthalen-1-yl, 5-methoxynaphthalen-1-yl, 5-hydroxynaphthalen-2-yl, 5-nitronaphthalen-2-yl, 5-cyclohexylnaphthalen-2-yl, 5-phenylnaphthalen-2-yl, 5-phenoxynaphthalen-2-yl, 5-benzyloxynaphthalen-2-yl, 5-phenylthionaphthalen-2-yl, 5-hydroxynaphthalen-1 -yl, 5-nitronaphthalen-1-yl, 5-cyclohexylnaphthalen-1-yl or 5-phenylnaphthalen-1-yl group; preferably an aryl group substituted with 1 to 3 substituents (said substituent is selected from the group consisting of a halogen atom, a lower alkyl group, a halogenated lower alkyl group, a lower alkoxy group, a lower alkylthio group and a lower aliphatic acyl group); more preferably an aryl group substituted with 1 to 3 substituents (said substituent is selected from the group consisting of a halogen atom, a lower alkyl group, a halogenated lower alkyl group, a lower alkoxy group, and a lower aliphatic acyl group); more preferably a phenyl group substituted with 1 to 3 substituents (said substituent is selected from the group consisting of a halogen atom, a lower alkyl group, a halogenated lower alkyl group, a lower alkoxy group, and a lower aliphatic acyl group); still more preferably a phenyl group substituted with 1 to 3 substituents (said substituent is selected from the group consisting of a fluorine atom, a chlorine atom and methyl, trifluoromethyl, methoxy and acetyl groups); and most preferably a 3-fluorophenyl, 4-fluorophenyl, 3,4-difluorophenyl, 3,5-difluorophenyl, 3-chlorophenyl, 4-chlorophenyl, 3,4-dichlorophenyl, 3,5-dichlorophenyl, 3-methylphenyl, 4-methylphenyl, 3,4-dimethylphenyl, 3,5-dimethylphenyl, 3-trifluoromethylphenyl, 4-trifluoromethylphenyl, 3,4-ditrifluoromethylphenyl, 3,5-ditrifluoromethylphenyl, 3-methoxyphenyl, 4-methoxyphenyl, 3,4-dimethoxyphenyl, 3,5-dimethoxyphenyl, 3,4,5-trimethoxyphenyl, 3-acetylphenyl, or 4-acetylphenyl group.

In the above formulae typical examples of the "heterocyclic group substituted with 1 to 3 substituents selected from substituent groups a and b" in the definition of $R^5$ are, for example, a 3-, 4- or 5-methylfuran-2-yl, 2-, 4- or 5-methylfuran-3-yl, 3-, 4- or 5-fluorothiophen-2yl, 2-, 4- or 5-fluorofuran-3-yl, 3-, 4- or 5-bromothiophen-2-yl, 2-, 4- or 5-bromofuran-3-yl, 3-, 4- or 5-methylthiophen-2-yl, 2-, 4- or 5-methylthiophen-3-yl, 3-, 4- or 5-ethylthiophen-2yl, 2-, 4- or 5-ethylthiophen-3-yl, 3-, 4- or 5-methoxythiophen-2-yl, 2-, 4- or 5-methoxythiophen-3-yl, 3- or 4-methylthiazol-5-yl, 3-, 4- or 5-fluorobenzothiophen-2-yl, 3-, 4- or 5-bromobenzothiophen-2-yl, 3-, 4- or 5-methylbenzothiophen-2-yl, 3-, 4- or 5-methoxybenzothiophen-2-yl, 2-, 4- or 5-fluorobenzothiophen-3-yl, 2-, 4- or 5-bromobenzothiophen-3-yl, 2-, 4- or 5methylbenzothiophen-3-yl, 2-, 4- or 5-methoxybenzothiophen-3-yl, 4-, 5-, 6- or 7-methylbenzothiophen-2-yl, 3-, 4- or 5-hydroxyfuran-2-yl, 2-, 4- or 5-hydroxyfuran-3-yl, 3-, 4- or 5-hydroxythiophen-2-yl, 3-, 4- or 5-nitrothiophen-2-yl, 3-, 4- or 5-phenylthiophen-2-yl, 2-, 4- or 5-hydroxythiophen-3-yl, 2-, 4- or 5-cyanothiophen-3-yl, 1-, 2- or 3-hydroxypyridin-4-yl, 1-, 2- or 3-cyanopyridin-4-yl or 1-, 2- or 3-phenylpyridin-4-yl group; and preferably a 3-, 4- or 5-fluorothiophen-2-yl or 3-, 4-, or 5-fluorofuran-3-yl group.

In the above formulae examples of the "$C_1$–$C_{20}$ alkyl groups" in the definition of $R^{4a}$ and $R^{11}$ are, for example, a straight or branched chain alkyl group having 1 to 20 carbons such as the lower alkyl groups described hereinbefore, heptyl, 1-methylhexyl, 2-methylhexyl, 3-methylhexyl, 4-methylhexyl, 5-methylhexyl, 1-propylbutyl, 4,4-dimethylpentyl, octyl, 1-methylheptyl, 2-methylheptyl, 3-methylheptyl, 4-methylheptyl, 5-methylheptyl, 6-methylheptyl, 1-propylpentyl, 2-ethylhexyl, 5,5-dimethylhexyl, nonyl, 3-methyloctyl, 4-methyloctyl, 5-methyloctyl, 6-methyloctyl, 1-propylhexyl, 2-ethylheptyl, 6,6-dimethylheptyl, decyl, 1-methylnonyl, 3-methylnonyl, 8-methylnonyl, 3-ethyloctyl, 3,7-dimethyloctyl, 7,7-dimethyloctyl, undecyl, 4,8-dimethylnonyl, dodecyl, tridecyl, tetradecyl, pentadecyl, 3,7,11-trimethyldodecyl, hexadecyl, 4,8,12-trimethyltridecyl, 1-methylpentadecyl, 14-methylpentadecyl, 13,13-dimethyltetradecyl, heptadecyl, 15-methylhexadecyl, octadecyl, 1-methylheptadecyl, nonadecyl, icosyl and 3,7,11,15-tetramethylhexadecyl group; preferably a $C_1$–$C_{10}$ alkyl group; more preferably a $C_1$–$C_6$ alkyl group; and most preferably a methyl or ethyl group.

In the above formulae the "$C_2$–$C_{20}$ alkyl group interrupted with a hetero atom(s)" in the definition of $R^{4a}$ and $R^{11}$ represents the $C_2$–$C_{20}$ alkyl groups which are described hereinbefore and which are interrupted with 1 or 2 of the same or different heteroatoms such as a sulfur atom, an oxygen atom or a nitrogen atom. Examples of such group include an alkyl group, which has 2 to 20 carbons and is interrupted with one or two sulfur atoms, such as methylthiomethyl, 1-methylthioethyl, 2-methylthioethyl, ethylthiomethyl, 1-methylthiopropyl, 2-methylthiopropyl, 3-methylthiopropyl, 2-ethylthioethyl, 2-methyl-2-methylthioethyl, 1-methylthiobutyl, 2-methylthiobutyl, 3-methylthiobutyl, 2-ethylthiopropyl, 3-methyl-3-methylthiopropyl, 4-methylthiopentyl, 3-methylthiopentyl, 2-methylthiopentyl, 1-methylthiopentyl, 3,3-dimethylthiobutyl, 2,2-dimethylthiobutyl, 1,1-dimethylthiobutyl, 1-methyl-2-methylthiobutyl, 1,3-dimethylthiobutyl, 2,3-dimethylthiobutyl, 2-ethylthiobutyl, 1-methylthiohexyl, 2-methylthiohexyl, 3-methylthiohexyl, 4-methylthiohexyl, 5-methylthiohexyl, 1-propylthiobutyl, 4-methyl-4-methylthiopentyl, 1-methylthioheptyl, 2-methylthioheptyl, 3-methylthioheptyl, 4-methylthioheptyl, 5-methylthioheptyl, 6-methylthioheptyl, 1-propylthiopentyl, 2-ethylthiohexyl, 5-methyl-5-methylthiohexyl, 3-methylthiooctyl, 4-methylthiooctyl, 5-methylthiooctyl, 6-methylthiooctyl, 1-propylthiohexyl, 2-ethylthioheptyl, 6-methyl-6-methylthioheptyl, 1-methylthiononyl, 3-methylthiononyl, 8-methylthiononyl, 3-ethylthiooctyl, 3-methyl-7-methylthiooctyl, 7,7-dimethylthiooctyl, 4-methyl-8-methythiononyl, 3,7-dimethyl-11-methylthiododecyl, 4,8-dimethyl-12-methylthiotridecyl, 1-methylthiopentadecyl, 14-methylthiopentadecyl, 13-methyl-13-methylthiotetradecyl, 15-methylthiohexadecyl, 1-methylthioheptadecyl, and 3,7,11-trimethyl-15-methylthiohexadecyl; an alkyl group, which has 2 to 20 carbons and is interrupted with one or two oxygen atoms, such as methyloxymethyl, 1-methyloxyethyl, 2-methyloxyethyl, ethyloxymethyl, 1-methyloxypropyl, 2-methyloxypropyl, 3-methyloxypropyl, 2-ethyloxyethyl, 2-methyl-2-methyloxyethyl, 1-methyloxybutyl, 2-methyloxybutyl, 3-methyloxybutyl, 2-ethyloxypropyl, 3-methyl-3-methyloxypropyl, 4-methyloxypentyl, 3-methyloxypentyl, 2-methyloxypentyl, 1-methyloxypentyl, 3,3-dimethyloxybutyl, 2,2-dimethyloxybutyl, 1,1-dimethyloxybutyl, 1-methyl-2-methyloxybutyl, 1,3-dimethyloxybutyl, 2,3-dimethyloxybutyl, 2-ethyloxybutyl, 1-methyloxyhexyl, 2-methyloxyhexyl, 3-methyloxyhexyl, 4-methyloxyhexyl, 5-methyloxyhexyl, 1-propyloxybutyl, 4-methyl-4-methyloxypentyl, 1-methyloxyheptyl, 2-methyloxyheptyl, 3-methyloxyheptyl, 4-methyloxyheptyl, 5-methyloxyheptyl, 6-methyloxyheptyl, 1-propyloxypentyl, 2-ethyloxyhexyl, 5-methyl-5-methyloxyhexyl, 3-methyloxyoctyl, 4-methyloxyoctyl, 5-methyloxyoctyl, 6-methyloxyoctyl, 1-propyloxyhexyl, 2-ethyloxyheptyl, 6-methyl-6-methyloxyheptyl, 1-methyloxynonyl, 3-methyloxynonyl, 8-methyloxynonyl, 3-ethyloxyoctyl, 3-methyl-7-methyloxyoctyl, 7,7-dimethyloxyoctyl, 4-methyl-8-methyoxynonyl, 3,7-dimethyl-11-methyloxydodecyl, 4,8-dimethyl-12-methyloxytridecyl, 1-methyloxypentadecyl, 14-methyloxypentadecyl, 13-methyl-13-methyloxytetradecyl, 15-methyloxyhexadecyl, 1-methyloxyheptadecyl, and 3,7, 11-trimethyl-15-methyloxyhexadecyl; an alkyl group, which has 1 to 20 carbons and is interrupted with one or two nitrogen atoms, such as N-methylaminomethyl, 1-(N-methylamino)ethyl, 2-(N-methylamio)ethyl, N-ethylaminomethyl, 1-(N-methylamino)propyl, 2-(N-methylamino)propyl, 3-(N-methylamino)propyl, 2-(N-ethylamino)ethyl, 2-(N,N-dimethylamino)ethyl, 1-(N-methylamino)butyl, 2-(N-methylamino)butyl, 3-(N-methylamino)butyl, 2-(N-ethylamino)propyl, 3-(N,N-dimethylamino)propyl, 4-(N-methylamino)pentyl, 3-(N-methylamino)pentyl, 2-(N-methylamino)pentyl, 1-(N-methylamino)pentyl, 3-(N,N-dimethylamino)butyl, 2-(N,N-dimethylamino)butyl, 1-(N,N-dimethylamino)butyl, 1-methyl-2-(N-methylamino)butyl, 1,3-di(N-methylamino) butyl, 2,3-di(N-methylamino)butyl, 2-(N-ethylamino)butyl, 1-(N-methylamino)hexyl, 2-(N-methylamino)hexyl, 3-(N-methylamino)hexyl, 4-(N-methylamino)hexyl, 5-(N-methylamino)hexyl, 1-(N-propylamino)butyl, 4-methyl-4-(N-methylamino)pentyl, 1-(N-methylamino)heptyl, 2-(N-methylamino)heptyl, 3-(N-methylamino)heptyl, 4-(N-methylamino)heptyl, 5-(N-methylamino)heptyl, 6-(N-methylamino)heptyl, 1-(N-propylamino)pentyl, 2-(N-ethylamino)hexyl, 5-methyl-5-(N-methylamino)hexyl, 3-(N-methylamino)octyl, 4-(N-methylamino)octyl, 5-(N-methylamino)octyl, 6-(N-methylamino)octyl, 1-(N-propylamino)hexyl, 2-(N-ethylamino)heptyl, 6-methyl-6-(N-methylamino)heptyl, 1-(N-methylamino)nonyl, 3-(N-methylamino)nonyl, 8-(N-methylamino)nonyl, 3-(N-ethylamino)octyl, 3-methyl-7-(N-methylamino)octyl, 7,7-di(N-methylamino)octyl, 4-methyl-8-(N-methylamino)nonyl, 3,7-dimethyl-11-(N-methylamino)dodecyl, 4,8-dimethyl-12-(N-methylamino)dodecyl, 1-(N-methylamino)pentadecyl, 14-(N-methylamino)pentadecyl, 13-methyl-13-(N-methylamino)tetradecyl, 15-(N-methylamino)hexadecyl, 1-(N-methylamino)heptadecyl, and 3,7,11-trimethyl-15-(N-methylamino)hexadecyl; and preferably a $C_2$–$C_{10}$ alkyl group interrupted with a heteroatom(s).

In the above formulae the "$C_1$–$C_{20}$ alkyl group substituted with an aryl group(s) or a heteroaryl group(s)" in the definition of $R^{4a}$ and $R^{11}$ represents the $C_1$–$C_{20}$ alkyl groups described hereinbefore substituted with 1 to 3 of the same or different aryl groups described hereinbefore or the same or different heteroaryl groups described hereinbefore.

In the above formulae the "$C_2$–$C_{20}$ alkynyl group" in the definition of $R^{4a}$ and $R^{11}$ comprises, for example, a straight or branched chain alkynyl group having 2 to 20 carbons such as an ethynyl, 2-propynyl, 1-methyl-2-propynyl, 2-butynyl, 1-methyl-2-butynyl, 1-ethyl-2-butynyl, 3-butynyl, 1-methyl-3-butynyl, 2-methyl-3-butynyl, 1-ethyl-3-butynyl, 2-pentynyl, 1-methyl-2-pentynyl, 3-pentynyl, 1-methyl-3-pentynyl, 2-methyl-3-pentynyl, 4-pentynyl, 1-methyl-4-pentynyl, 2-methyl-4-pentynyl, 2-hexynyl, 3-hexynyl, 4-hexynyl, 5-hexynyl, heptynyl, 1-methylhexynyl, 2-methylhexynyl, 3-methylhexynyl, 4-methylhexynyl, 5-methylhexynyl, 1-propylbutynyl, 4,4-dimethylpentynyl, octynyl, 1-methylheptynyl, 2-methylheptynyl, 3-methylheptynyl, 4-methylheptynyl, 5-methylheptynyl, 6-methylheptynyl, 1-propylpentynyl, 2-ethylhexynyl, 5,5-dimethylhexynyl, nonynyl, 3-methyloctynyl, 4-methyloctynyl, 5-methyloctynyl, 6-methyloctynyl, 1-propylhexynyl, 2-ethylheptynyl, 6,6-dimethylheptynyl, decynyl, 1-methylnonynyl, 3-methylnonynyl, 8-methylnonynyl, 3-ethyloctynyl, 3,7-dimethyloctynyl, 7,7-dimethyloctynyl, undecynyl, 4,8-dimethylnonynyl, dodecynyl, tridecynyl, tetradecynyl, pentadecynyl, 3,7,11-trimethyldodecynyl, hexadecynyl, 4,8,12-trimethyltridecynyl, 1-methylpentadecynyl, 14-methylpentadecynyl, 13,13-dimethyltetradecynyl, heptadecynyl, 15-methylhexadecynyl, octadecynyl, 1-methylheptadecynyl, nonadecynyl, icosynyl or 3,7,11,15-tetramethylhexadecynyl group; preferably a $C_2$–$C_{10}$ alkynyl group.

In the above formulae the "$C_3$–$C_{20}$ alkynyl group interrupted with a hetero atom(s)" in the definition of $R^{4a}$ and $R^{11}$ represents the $C_3$–$C_{20}$ alkynyl groups which are described hereinbefore and which are interrupted with 1 or 2 of the same or different heteroatoms such as a sulfur atom, an oxygen atom or a nitrogen atom. Examples of such groups include an alkynyl group which has 3 to 20 carbons and is interrupted with one or two sulfur atoms, such as 1-methylthioethynyl, 2-methylthioethynyl, 1-methylthiopropynyl, 2-methylthiopropynyl, 3-methylthiopropynyl, 2-ethylthioethynyl, 2-methyl-2-methylthioethynyl, 1-methylthiobutynyl, 2-methylthiobutynyl, 3-methylthiobutynyl, 2-ethylthiopropynyl, 3-methyl-3-methylthiopropynyl, 4-methylthiopentynyl, 3-methylthiopentynyl, 2-methylthiopentynyl, 1-methylthiopentynyl, 3,3-dimethylthiobutynyl, 2,2-dimethylthiobutynyl, 1,1-dimethylthiobutynyl, 1-methyl-2-methylthiobutynyl, 1,3-dimethylthiobutynyl, 2,3-dimethylthiobutynyl, 2-ethylthiobutynyl, 1-methylthiohexynyl, 2-methylthiohexynyl, 3-methylthiohexynyl, 4-methylthiohexynyl, 5-methylthiohexynyl, 1-propylthiobutynyl, 4-methyl-4-methylthiopentynyl, 1-methylthioheptynyl, 2-methylthioheptynyl, 3-methylthioheptynyl, 4-methylthioheptynyl, 5-methylthioheptynyl, 6-methylthioheptynyl, 1-propylthiopentynyl, 2-ethylthiohexynyl, 5-methyl-5-methylthiohexynyl, 3-methylthiooctynyl, 4-methylthiooctynyl, 5-methylthiooctynyl, 6-methylthiooctynyl, 1-propylthiohexynyl, 2-ethylthioheptynyl, 6-methyl-6-methylthioheptynyl, 1-methylthiononynyl, 3-methylthiononynyl, 8-methylthiononynyl, 3-ethylthiooctynyl, 3-methyl-7-methylthiooctynyl, 7,7-dimethylthiooctynyl, 4-methyl-8-methythiononynyl, 3,7-dimethyl-11-methylthiododecynyl, 4,8-dimethyl-12-methylthiotridecynyl, 1-methylthiopentadecynyl, 14-methylthiopentadecynyl, 13-methyl-13-methylthiotetradecynyl, 15-methylthiohexadecynyl, 1-methylthioheptadecynyl, and 3,7,11-trimethyl-15-methylthiohexadecynyl; an alkynyl group, which has 3 to 20 carbons and is interrupted with one or two oxygen atoms, such as 1-methyloxyethynyl, 2-methyloxyethynyl, 11-methyloxypropynyl, 2-methyloxypropynyl, 3-methyloxypropynyl, 2-ethyloxyethynyl, 2-methyl-2-methyloxyethynyl, 1-methyloxybutynyl, 2-methyloxybutynyl, 3-methyloxybutynyl, 2-ethyloxypropynyl, 3-methyl-3-methyloxypropynyl, 4-methyloxypentynyl, 3-methyloxypentynyl, 2-methyloxypentynyl, 1-methyloxypentynyl, 3,3-dimethyloxybutynyl, 2,2-dimethyloxybutynyl, 1,1-dimethyloxybutynyl, 1-methyl-2-methyloxybutynyl, 1,3-dimethyloxybutynyl, 2,3-dimethyloxybutynyl, 2-ethyloxybutynyl, 1-methyloxyhexynyl, 2-methyloxyhexynyl, 3-methyloxyhexynyl, 4-methyloxyhexynyl, 5-methyloxyhexynyl, 1-propyloxybutynyl, 4-methyl-4-methyloxypentynyl, 1-methyloxyheptynyl, 2-methyloxyheptynyl, 3-methyloxyheptynyl, 4-methyloxyheptynyl, 5-methyloxyheptynyl, 6-methyloxyheptynyl, 1-propyloxypentynyl, 2-ethyloxyhexynyl, 5-methyl-5-methyloxyhexynyl, 3-methyloxyoctynyl, 4-methyloxyoctynyl, 5-methyloxyoctynyl, 6-methyloxyoctynyl, 1-propyloxyhexynyl, 2-ethyloxyheptynyl, 6-methyl-6-methyloxyheptynyl, 1-methyloxynonynyl, 3-methyloxynonynyl, 8-methyloxynonynyl, 3-ethyloxyoctynyl, 3-methyl-7-methyloxyoctynyl, 7,7- dimethyloxyoctynyl, 4-methyl-8-methoxynonynyl, 3,7-dimethyl-11-methyloxydodecynyl, 4,8-dimethyl-12-methyloxytridecynyl, 1-methyloxypentadecynyl, 14-methyloxypentadecynyl, 13-methyl-13-methyloxytetradecynyl, 15-methyloxyhexadecynyl, 1-methyloxyheptadecynyl, and 3,7,11-trimethyl-15-methyloxyhexadecynyl; an alkynyl group, which has 3 to 20 carbons and is interrupted with one or two nitrogen atoms, such as 1-(N-methylamino)ethynyl, 2-(N-methylamio)ethynyl, 1-(N-methylamino)propynyl, 2-(N-methylamino)propynyl, 3-(N-methylamino)propynyl, 2-(N-ethylamino)ethynyl, 2-(N,N-dimethylamino)ethynyl, 1-(N-methylamino)butynyl, 2-(N-methylamino)butynyl, 3-(N-methylamino)butynyl, 2-(N-ethylamino)propynyl, 3-(N,N-dimethylamino)propynyl, 4-(N-methylamino)pentynyl, 3-(N-methylamino)pentynyl, 2-(N-methylamino)pentynyl, 1-(N-methylamino)pentynyl, 3-(N,N-dimethylamino)butynyl, 2-(N,N-dimethylamino)butynyl, 1-(N,N-dimethylamino)butynyl, 1-methyl-2-(N-methylamino)butynyl, 1,3-di(N-methylamino)butynyl, 2,3-di(N-methylamino)butynyl, 2-(N-ethylamino)butynyl, 1-(N-methylamino)hexynyl, 2-(N-methylamino)hexynyl, 3-(N-methylamino)hexynyl, 4-(N-methylamino)hexynyl, 5-(N-methylamino)hexynyl, 1-(N-propylamino)butynyl, 4-methyl-4-(N-methylamino)pentynyl, 1-(N-methylamino)heptynyl, 2-(N-methylamino)heptynyl, 3-(N-methylamino)heptynyl, 4-(N-methylamino)heptynyl, 5-(N-methylamino)heptynyl, 6-(N-methylamino)heptynyl, 1-(N-propylamino)pentynyl, 2-(N-ethylamino)hexynyl, 5-methyl-5-(N-methylamino)hexynyl, 3-(N-methylamino)octynyl, 4-(N-methylamino)octynyl, 5-(N-methylamino)octynyl, 6-(N-methylamino)octynyl, 1-(N-propylamino)hexynyl, 2-(N-ethylamino)heptynyl, 6-methyl-6-(N-methylamino)heptynyl, 1-(N-methylamino)nonynyl, 3-(N-methylamino)nonynyl, 8-(N-methylamino)nonynyl, 3-(N-ethylamino)octynyl, 3-methyl-7-(N-methylamino)octynyl, 7,7-di(N-methylamino)octynyl, 4-methyl-8-(N-methylamino)nonynyl, 3,7-dimethyl-11-(N-methylamino)dodecynyl, 4,8-dimethyl-12-(N-methylamino)tridecynyl, 1-(N-methylamino)pentadecynyl, 14-(N-methylamino)pentadecynyl, 13-methyl-13-(N-methylamino)tetradecynyl, 15-(N-methylamino)hexadecynyl, 1-(N-methylamino)heptadecynyl, and 3,7,11-trimethyl-15-(N-methylamino)hexadecynyl; and preferably a $C_3$–$C_{10}$ alkynyl group interrupted with a heteroatom(s).

In the above formulae the "$C_2$–$C_{20}$ alkynyl group substituted with an aryl group(s) or a heteroaryl group(s)" in the definition of $R^{4a}$ and $R^{11}$ represents the $C_2$–$C_{20}$ alkynyl groups described hereinbefore substituted with the same or different 1 to 3 of the aryl groups described hereinbefore or the heteroaryl groups described hereinbefore.

In the above formulae the "$C_2$–$C_{20}$ alkenyl group" in the definition of $R^{4a}$ and $R^{11}$ includes, for example, a straight or branched chain alkenyl group having 2 to 20 carbons such as an ethenyl, 2-propenyl, 1-methyl-2-propenyl, 2-methyl-2-propenyl, 2-ethyl-2-propenyl, 2-butenyl, 1-methyl-2-butenyl, 2-methyl-2-butenyl, 1-ethyl-2-butenyl, 3-butenyl, 1-methyl-3-butenyl, 2-methyl-3-butenyl, 1-ethyl-3-butenyl, 2-pentenyl, 1-methyl-2-pentenyl, 2-methyl-2-pentenyl, 3-pentenyl, 1-methyl-3-pentenyl, 2-methyl-3-pentenyl, 4-pentenyl, 1-methyl-4-pentenyl, 2-methyl-4-pentenyl, 2-hexenyl, 3-hexenyl, 4-hexenyl, 5-hexenyl, heptenyl, 1-methylhexenyl, 2-methylhexenyl, 3-methylhexenyl, 4-methylhexenyl, 5-methylhexenyl, 1-propylbutenyl, 4,4-dimethylpentenyl, octenyl, 1-methylheptenyl, 2-methylheptenyl, 3-methylheptenyl, 4-methylheptenyl, 5-methylheptenyl, 6-methylheptenyl, 1-propylpentenyl, 2-ethylhexenyl, 5,5-dimethylhexenyl, nonenyl, 3-methyloctenyl, 4-methyloctenyl, 5-methyloctenyl, 6-methyloctenyl, 1-propylhexenyl, 2-ethylheptenyl, 6,6-dimethylheptenyl, decenyl, 1-methylnonenyl, 3-methylnonenyl, 8-methylnonenyl, 3-ethyloctenyl, 3,7-dimethyloctenyl, 7,7-dimethyloctenyl, undecenyl, 4,8-dimethylnonenyl, dodecenyl, tridecenyl, tetradecenyl, pentadecenyl, 3,7,11-trimethyldodecenyl, hexadecenyl, 4,8,12-trimethyltridecenyl, 1-methylpentadecenyl, 14-methylpentadecenyl, 13,13-dimethyltetradecenyl, heptadecenyl, 15-methylhexadecenyl, octadecenyl, 1-methylheptadecenyl, nonadecenyl, icosenyl and 3,7,11,15-tetramethylhexadecenyl group; preferably a $C_2$–$C_{10}$ alkenyl group.

In the above formulae the "$C_3$–$C_{20}$ alkenyl group interrupted with a hetero atom(s)" in the definition of $R^{4a}$ and $R^{11}$ represents the $C_3$–$C_{20}$ alkenyl groups which are described hereinbefore and interrupted with the same or different 1 or 2 of heteroatoms such as a sulfur atom, an oxygen atom or a nitrogen atom. Examples of such a group include an alkenyl group which has 3 to 20 carbons and is interrupted with one or two sulfur atoms, such as 1-methylthioethenyl, 2-methylthioethenyl, 1-methylthiopropenyl, 2-methylthiopropenyl, 3-methylthiopropenyl, 2-ethylthioethenyl, 2-methyl-2-methylthioethenyl, 1-methylthiobutenyl, 2-methylthiobutenyl, 3-methylthiobutenyl, 2-ethylthiopropenyl, 3-methyl-3-methylthiopropenyl, 4-methylthiopentenyl, 3-methylthiopentenyl, 2-methylthiopentenyl, 1-methylthiopentenyl, 3,3-dimethylthiobutenyl, 2,2-dimethylthiobutenyl, 1,1-dimethylthiobutenyl, 1-methyl-2-methylthiobutenyl, 1,3-dimethylthiobutenyl, 2,3-dimethylthiobutenyl, 2-ethylthiobutenyl, 1-methylthiohexenyl, 2-methylthiohexenyl, 3-methylthiohexenyl, 4-methylthiohexenyl, 5-methylthiohexenyl, 1-propylthiobutenyl, 4-methyl-4-methylthiopentenyl, 1-methylthioheptenyl, 2-methylthioheptenyl, 3-methylthioheptenyl, 4-methylthioheptenyl, 5-methylthioheptenyl, 6-methylthioheptenyl, 1-propylthiopentenyl, 2-ethylthiohexenyl, 5-methyl-5-methylthiohexenyl, 3-methylthiooctenyl, 4-methylthiooctenyl, 5-methylthiooctenyl, 6-methylthiooctenyl, 1-propylthiohexenyl, 2-ethylthioheptenyl, 6-methyl-6-methylthioheptenyl, 1-methylthiononenyl, 3-methylthiononenyl, 8-methylthiononenyl, 3-ethylthiooctenyl, 3-methyl-7-methylthiooctenyl, 7,7-dimethylthiooctenyl, 4-methyl-8-methythiononenyl, 3,7-dimethyl-11-methylthiododecenyl, 4,8-dimethyl-12-methylthiotridecenyl, 1-methylthiopentadecenyl, 14-methylthiopentadecenyl, 13-methyl-13-methylthiotetradecenyl, 15-methylthiohexadecenyl, 1-methylthioheptadecenyl, and 3,7,11-trimethyl-15-methylthiohexadecenyl; an alkenyl group, which has 3 to 20 carbons and interrupted with one or two oxygen atoms, such as 1-methyloxyethenyl, 2-methyloxyethenyl, 1-methyloxypropenyl, 2-methyloxypropenyl, 3-methyloxypropenyl, 2-ethyloxyethenyl, 2-methyl-2-methyloxyethenyl, 1-methyloxybutenyl, 2-methyloxybutenyl, 3-methyloxybutenyl, 2-ethyloxypropenyl, 3-methyl-3-methyloxypropenyl, 4-methyloxypentenyl, 3-methyloxypentenyl, 2-methyloxypentenyl, 1-methyloxypentenyl, 3,3-dimethyloxybutenyl, 2,2-dimethyloxybutenyl, 1,1-dimethyloxybutenyl, 1-methyl-2-methyloxybutenyl, 1,3-dimethyloxybutenyl, 2,3-dimethyloxybutenyl, 2-ethyloxybutenyl, 1-methyloxyhexenyl, 2-methyloxyhexenyl, 3-methyloxyhexenyl, 4-methyloxyhexenyl, 5-methyloxyhexenyl, 1-propyloxybutenyl, 4-methyl-4-methyloxypentenyl, 1-methyloxyheptenyl, 2-methyloxyheptenyl, 3-methyloxyheptenyl, 4-methyloxyheptenyl, 5-methyloxyheptenyl, 6-methyloxyheptenyl, 1-propyloxypentenyl, 2-ethyloxyhexenyl, 5-methyl-5-methyloxyhexenyl, 3-methyloxyoctenyl, 4-methyloxyoctenyl, 5-methyloxyoctenyl, 6-methyloxyoctenyl, 1-propyloxyhexenyl, 2-ethyloxyheptenyl, 6-methyl-6-methyloxyheptenyl, 1-methyloxynonenyl, 3-methyloxynonenyl, 8-methyloxynonenyl, 3-ethyloxyoctenyl, 3-methyl-7-methyloxyoctenyl, 7,7-dimethyloxyoctenyl, 4-methyl-8-methyloxynonenyl, 3,7-dimethyl-11-methyloxydodecenyl, 4,8-dimethyl-12-methyloxytridecenyl, 1-methyloxypentadecenyl, 14-methyloxypentadecenyl, 13-methyl-13-methyloxytetradecenyl, 15-methyloxyhexadecenyl, 1-methyloxyheptadecenyl, and 3,7,11-trimethyl-15-methyloxyhexadecenyl; an alkenyl group which has 3 to 20 carbons and is interrupted with one or two nitrogen atoms, such as 1-(N-methylamino)ethenyl, 2-(N-methylamio)ethenyl, 1-(N-methylamino)propenyl, 2-(N-methylamino)propenyl, 3-(N-methylamino)propenyl, 2-(N-ethylamino)ethenyl, 2-(N,N-dimethylamino)ethenyl, 1-(N-methylamino)butenyl, 2-(N-methylamino)butenyl, 3-(N-methylamino)butenyl, 2-(N-ethylamino)propenyl, 3-(N,N-dimethylamino)propenyl, 4-(N-methylamino)pentenyl, 3-(N-methylamino)pentenyl, 2-(N-methylamino)pentenyl, 1-(N-methylamino)pentenyl, 3-(N,N-dimethylamino)butenyl, 2-(N,N-dimethylamino)butenyl, 1-(N,N-dimethylamino)butenyl, 1-methyl-2-(N-methylamino)butenyl, 1,3-di(N-methylamino)butenyl, 2,3-di(N-methylamino)butenyl, 2-(N-ethylamino)butenyl, 1-(N-methylamino)hexenyl, 2-(N-methylamino)hexenyl, 3-(N-methylamino)hexenyl, 4-(N-methylamino)hexenyl, 5-(N-methylamino)hexenyl, 1-(N-propylamino)butenyl, 4-methyl-4-(N-methylamino)pentenyl, 1-(N-methylamino)heptenyl, 2-(N-methylamino)heptenyl, 3-(N-methylamino)heptenyl, 4-(N-methylamino)heptenyl, 5-(N-methylamino)heptenyl, 6-(N-methylamino)heptenyl, 1-(N-propylamino)pentenyl, 2-(N-ethylamino)hexenyl, 5-methyl-5-(N-methylamino)hexenyl, 3-(N-methylamino)octenyl, 4-(N-methylamino)octenyl, 5-(N-methylamino)octenyl, 6-(N-methylamino)octenyl, 1-(N-propylamino)hexenyl, 2-(N-ethylamino)heptenyl, 6-methyl-6-(N-methylamino)heptenyl, 1-(N-methylamino)nonenyl, 3-(N-methylamino)nonenyl, 8-(N-methylamino)nonenyl, 3-(N-ethylamino)octenyl, 3-methyl-7-(N-methylamino)octenyl, 7,7-di(N-methylamino)octenyl, 4-methyl-8-(N-methylamino)nonenyl, 3,7-dimethyl-11-(N-methylamino)dodecenyl, 4,8-dimethyl-12-(N-methylamino)tridecenyl, 1-(N-methylamino)pentadecenyl, 14-(N-methylamino)pentadecenyl, 13-methyl-13-(N-methylamino)tetradecenyl, 15-(N-methylamino)hexadecenyl, 1-(N-methylamino)heptadecenyl, and 3,7,11-trimethyl-15-(N-methylamino)hexadecenyl; and preferably a $C_3$–$C_{10}$ alkenyl group interrupted with a heteroatom(s).

In the above formulae the "$C_2$–$C_{20}$ alkenyl group substituted with an aryl group(s) or a heteroaryl group(s)" in the definition of $R^{4a}$ and $R^{11}$ represents the $C_2$–$C_{20}$ alkenyl groups described hereinbefore substituted with the same or different 1 to 3 of the aryl groups described hereinbefore or the heteroaryl groups described hereinbefore.

In the above formulae the "$C_2$–$C_{20}$ alkyl group which is substituted with an aryl group(s) or a heteroaryl group(s) and interrupted with a heteroatom(s)" in the definition of $R^{4a}$ and $R^{11}$ represents the $C_2$–$C_{20}$ alkyl groups interrupted with a heteroatom(s), described hereinbefore and substituted with the same or different 1 to 3 of the aryl groups described hereinbefore or the heteroaryl groups described hereinbefore.

The lipase employed in this invention is not particularly limited and the preferred lipase is different depending on the starting material, however, is typically obtained from *Pseudomonas* sp., *Pseudomonas fluorescens*, *Pseudomonas cepacia*, *Chromobacterium viscosum*, *Aspergillus niger*, *Aspergillus oryzae*, *Candida antarctica*, *Candida cylindracea*, *Candida lipolytica*, *Candida rugosa*, *Candida utilis*, *Penicillium roqueforti*, *Rhizopus arrhizus*, *Rhizopus delemar*, *Rhizopus javanicus*, *Rhizomucor miehei*, *Rhizopus niveus*, *Humicola lanuginosa*, *Mucor Javanicus*, *Mucor miehei*, *Thermus aquaticus*, *Thermus flavus*, *Thermus thermophilus* or the like; or human pancreas, hog pancreas, porcine pancreas or wheat germ. Partially or completely purified enzyme moiety and fixed enzyme can be employed and the most preferred lipase is fixed *Pseudomonas* sp. [for example, immobilized lipase from *Pseudomonas* sp. (TOYOBO Kabusiki Kaisya)].

Preferred vinyl ester derivatives of the carboxylic acid of formula (XLIII, $R^{11}COOCH=CH_2$) employed in this invention are different depending on the starting material, however they are typically a vinyl ester of a straight chain aliphatic acid such as the vinyl ester of n-hexanoic acid, vinyl ester of n-heptanoic acid, vinyl ester of n-pentanoic acid, vinyl ester of acetic acid or the like; and the most preferred one is the vinyl ester of n-hexanoic acid.

When the compound of formula (I) has a basic group such as amino group, the pharmaceutically acceptable salt can be prepared by the reaction of compound (I) with an acid. When the compound of formula (I) has a carboxy group the pharmaceutically acceptable salt can be prepared by the reaction of compound (I) with a base.

The preferred salts based on a basic group include a hydrohalogenic acid salt such as a hydrofluoride, hydrochloride, hydrobromide or hydroiodide; an inorganic acid salt such as a nitrate, perchlorate, sulfate or phosphate; a lower alkanesulfonic acid salt such as a methanesulfonate, trifluoromethanesulfonate or ethanesulfonate; an aryl sulfonic acid salt such as a benzenesulfonate or p-toluenesulfonate; an organic acid salt such as an acetate, maleate, fumarate, succinate, citrate, ascorbate, tartrate, oxalate, maleate or the like; an amino acid salt such as a glycine salt, lysine salt, arginine salt, ornithine salt, glutamic acid salt or aspartic acid salt and most preferably an organic acid salt.

On the other hand the preferred salts based on an acid group includes an alkali metal salt such as a sodium salt, potassium salt or lithium salt; an alkaline earth metal salt such as a calcium salt or magnesium salt; a metal salt such as an aluminum salt or iron salt; an inorganic salt such as an ammonium salt; an amine salt such as a t-octylamine salt, benzylamine salt, morpholine salt, glucosamine salt, phenylglycine alkyl ester salt, ethylenediamine salt, N-methylglucamine salt, guanidine salt, diethylamine salt, triethylamine salt, dicyclohexylamine salt, N,N'-dibenzylethylenediamine salt, chloroprocaine salt, procaine salt, diethanolamine salt, N-benzylphenethylamine salt, piperazine salt, tetramethylammonium salt or tris (hydroxymethyl)aminomethane salt; and an amino acid salt such as a glycine salt, lysine salt, arginine salt, ornithine salt, glutamic acid salt or aspartic acid salt.

When the Compound (I), a pharmaceutically acceptable salt thereof, an ester thereof or other derivative thereof are allowed to stand so that they are opened to the atmosphere or are recrystallized, they may absorb water and water may be attached to them to form a hydrate.

The salts of the present invention encompass such hydrates.

The compounds of formula (I), pharmaceutically acceptable salts thereof, esters thereof or other derivatives thereof have an asymmetric carbon (s) and can exist as optical isomer(s). In this invention a single optical isomer and a mixture of optical isomers are represented by the single chemical formula (I). The present invention encompasses the optical isomers individually and mixtures thereof in optional ratios. For example, the compounds of formula (I), pharmaceutically acceptable salts thereof, esters thereof or other derivatives thereof have the following partial chemical formula wherein the —NR$^1$R$^2$ group is attached to an asymmetric carbon and the preferred absolute configuration at this asymmetric carbon is the R configuration.

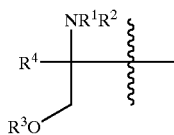

In the above formulae the "ester" refers to an ester of a compound of formula (I) which has a group capable of being esterified. The ester includes the ester of a hydroxyl group and the ester of a carboxy group. Each ester residual group belongs to a general protecting group in chemical reactions or a protecting group capable of being removed by a biological process such as hydrolysis in vivo.

The "general protecting group in chemical reaction" can be cleaved by a chemical process such as hydrogenolysis, hydrolysis, electrolysis or photolysis.

The "general protecting group in chemical reactions" and the "protecting group capable of being removed by a biological process such as hydrolysis in vivo" in the esters of a hydroxyl group have the same meaning as that described above for a hydroxyl protecting group.

The "general protecting group in chemical reactions" in the ester of a carboxyl group preferably includes a lower alkyl group described hereinbefore; a lower alkenyl group such as ethenyl, 1-propenyl, 2-propenyl, 1-methyl-2-propenyl, 1-methyl-1-propenyl, 2-methyl-1-propenyl, 1-butenyl, 2-butenyl, 1-methyl-2-butenyl, 1-methyl-1-butenyl, 3-methyl-2-butenyl, 1-ethyl-2-butenyl, 3-butenyl, 1-methyl-3-butenyl, 2-methyl-3-butenyl, 1-ethyl-3-butenyl, 1-pentenyl, 2-pentenyl, 1-methyl-2-pentenyl, 2-methyl-2-pentenyl, 3-pentenyl, 1-methyl-3-pentenyl, 2-methyl-3-pentenyl, 4-pentenyl, 1-methyl-4-pentenyl, 2-methyl-4-pentenyl, 1-hexenyl, 2-hexenyl, 3-hexenyl, 4-hexenyl or 5-hexenyl; a lower alkynyl group such as ethynyl, 2-propynyl, 1-methyl-2-propynyl, 2-butynyl, 1-methyl-2-butynyl, 1-ethyl-2-butynyl, 3-butynyl, 1-methyl-3-butynyl, 2-methyl-3-butynyl, 1-ethyl-3-butynyl, 2-pentynyl, 1-methyl-2-pentynyl, 3-pentynyl, 1-methyl-3-pentynyl, 2-methyl-3-pentynyl, 4-pentynyl, 1-methyl-4-pentynyl, 2-methyl-4-pentynyl, 2-hexynyl, 3-hexynyl, 4-hexynyl or 5-hexynyl; a halogenated lower alkyl group described hereinbefore; a hydroxy lower alkyl group such as 2-hydroxyethyl, 2,3-dihydroxypropyl, 3-hydroxypropyl, 3,4-dihydroxybutyl or 4-hydroxybutyl; a lower aliphatic acyl-lower alkyl group such as acetylmethyl; an aralkyl group described hereinbefore; or a silyl group described hereinbefore.

The "protecting group capable of being removed by a biological process such as hydrolysis in vivo" can be cleaved by a biological process such as hydrolysis in the human body to afford a free acid or a salt thereof. Whether a derivative of formula (I) has such a protecting group can be easily determined. The derivative under investigation is administered intravenously to a test animal such as a mouse or a rat and the body fluids of the test animal are thereafter studied. If the parent compound or a pharmacologically acceptable salt thereof is detected in the body fluids of the test animal, the derivative under investigation is judged to have such a group. The "protecting group capable of being removed by a biological process such as hydrolysis in vivo" preferably includes a lower alkoxy lower alkyl group such as methoxyethyl, 1-ethoxyethyl, 1-methyl-1-methoxyethyl, 1-(isopropoxy)ethyl, 2-methoxyethyl, 2-ethoxyethyl, 1,1-dimethyl-1-methoxyethyl, ethoxymethyl, n-propoxymethyl, isopropoxymethyl, n-butoxymethyl or t-butoxymethyl; a lower alkoxy lower alkoxy lower alkyl group such as 2-methoxyethoxymethyl; an aryloxy lower alkyl group such as phenoxymethyl; a halogenated lower alkoxy lower alkyl group such as 2,2,2-trichloroethoxymethyl or bis(2-chloroethoxy)methyl; a lower alkoxycarbonyl lower alkyl group such as methoxycarbonylmethyl; a cyano lower alkyl group such as cyanomethyl or 2-cyanoethyl; a lower alkylthiomethyl group such as methylthiomethyl or ethylthiomethyl; an arylthiomethyl group such as phenylthiomethyl or naphthylthiomethyl; a lower alkyl optionally substituted with a halogen atom(s) sulfonyl lower alkyl group such as 2-methanesulfonylethyl or 2-trifluoromethanesulfonylethyl; an arylsulfonyl lower alkyl group such as 2-benzenesulfonylethyl or 2-toluenesulfonylethyl; a 1-(acyloxy) lower alkyl group described hereinbefore; a phthalidyl group described hereinbefore; an aryl group described hereinbefore; a lower alkyl group described hereinbefore; a carboxyalkyl group such as carboxymethyl; and an amide-formation residual group of an amino acid such as phenylalanine.

When the compound of formula (I) in this invention has an amino group and/or a carboxyl group, such a compound can be converted to a derivative other than a pharmacologically acceptable salt or an ester described hereinbefore. The "other derivative" refers to such a derivative, for example, an amide derivative such as an acyl group.

Typical examples of compounds of formula (I) in this invention are listed in the following Table 1 and 2. Typical examples of compound of formula (La) and (La-1) in this invention are listed in Table 3 and 4. The present invention is not limited to these examples.

The following abbreviation are used in these lists:

Ac: acetyl group; Boc: t-butoxycarbonyl group; Bpyrr: benzopyrrolyl group; Bu: butyl group; iBu: isobutyl group; Bz: benzyl group; Bzt: benzothienyl group; Et: ethyl group; Fur: furyl group; cHx: cyclohexyl group; Me: methyl group; Np(1): naphthalen-1-yl group; Np(2): naphthalen-2-yl group; Ph: phenyl group; cPn: cyclopentyl group; Pr: propyl group; iPr: isopropyl group; Pyr: pyridyl group; TBDMS: t-butyldimethylsilyl group; and The: thienyl group.

TABLE 1

(Ia)

$$\text{structure: thiophene ring with NR}^1\text{R}^2\text{, R}^4\text{, R}^3\text{O-CH}_2\text{ substituents on one side via (CH}_2)_n\text{, and X-Y-R}^5 \text{ on other side, with R}^6 \text{ and R}^7 \text{ on ring}$$

| Exemp. Compd. No. | $R^1$ | $R^2$ | $R^3$ | $R^4$ | n | —X—Y—$R^5$ | $R^6$ | $R^7$ |
|---|---|---|---|---|---|---|---|---|
| 1-1 | H | H | H | Me | 1 | —(CH$_2$)$_5$—cHx | H | H |
| 1-2 | H | H | H | Me | 1 | —(CH$_2$)$_6$—cHx | H | H |
| 1-3 | H | H | H | Me | 1 | —CH=CH—(CH$_2$)$_3$—cHx | H | H |
| 1-4 | H | H | H | Me | 1 | —CH=CH—(CH$_2$)$_4$—cHx | H | H |
| 1-5 | H | H | H | Me | 1 | —C≡C—(CH$_2$)$_3$—cHx | H | H |
| 1-6 | H | H | H | Me | 1 | —C≡C—(CH$_2$)$_4$—cHx | H | H |
| 1-7 | H | H | H | Me | 1 | —CO—(CH$_2$)$_4$—cHx | H | H |
| 1-8 | H | H | H | Me | 1 | —CO—(CH$_2$)$_5$—cHx | H | H |
| 1-9 | H | H | H | Me | 1 | —CH(OH)—(CH$_2$)$_4$—cHx | H | H |
| 1-10 | H | H | H | Me | 1 | —CH(OH)—(CH$_2$)$_5$—cHx | H | H |
| 1-11 | H | H | H | Me | 1 | -4-(cHx—CH$_2$O)Ph | H | H |
| 1-12 | H | H | H | Me | 1 | -(4-BzO—Ph) | H | H |
| 1-13 | H | H | H | Me | 1 | —C≡C—CH$_2$O—cPn | H | H |
| 1-14 | H | H | H | Me | 1 | —C≡C—(CH$_2$)$_2$O—cPn | H | H |
| 1-15 | H | H | H | Me | 1 | —C≡C—CH$_2$O—cHx | H | H |
| 1-16 | H | H | H | Me | 1 | —C≡C—(CH$_2$)$_2$O—cHx | H | H |
| 1-17 | H | H | H | Me | 1 | —C≡C—CH$_2$O—Ph | H | H |
| 1-18 | H | H | H | Me | 1 | —C≡C—(CH$_2$)$_2$O—Ph | H | H |
| 1-19 | H | H | H | Me | 2 | —(CH$_2$)$_2$—cHx | H | H |
| 1-20 | H | H | Me | Me | 2 | —(CH$_2$)$_2$—cHx | H | H |
| 1-21 | Me | H | H | Me | 2 | —(CH$_2$)$_2$—cHx | H | H |
| 1-22 | CO$_2$Me | H | H | Me | 2 | —(CH$_2$)$_2$—cHx | H | H |
| 1-23 | H | H | H | Me | 2 | —(CH$_2$)$_2$—(4-F—cHx) | H | H |
| 1-24 | H | H | H | Me | 2 | —(CH$_2$)$_2$—(4-Me—cHx) | H | H |
| 1-25 | H | H | H | Me | 2 | —(CH$_2$)$_2$—(4-Et—cHx) | H | H |
| 1-26 | H | H | H | Me | 2 | —(CH$_2$)$_2$—(4-CF$_3$—cHx) | H | H |
| 1-27 | H | H | H | Me | 2 | —(CH$_2$)$_2$—(4-MeO—cHx) | H | H |
| 1-28 | H | H | H | Me | 2 | —(CH$_2$)$_2$—(4-EtO—cHx) | H | H |
| 1-29 | H | H | H | Me | 2 | —(CH$_2$)$_2$—(4-MeS—cHx) | H | H |
| 1-30 | H | H | H | Me | 2 | —(CH$_2$)$_2$—(4-cHx—cHx) | H | H |
| 1-31 | H | H | H | Me | 2 | —(CH$_2$)$_2$—(4-Ph—cHx) | H | H |
| 1-32 | H | H | H | Me | 2 | —(CH$_2$)$_2$—Ph | H | H |
| 1-33 | H | H | Me | Me | 2 | —(CH$_2$)$_2$—Ph | H | H |
| 1-34 | Me | H | H | Me | 2 | —(CH$_2$)$_2$—Ph | H | H |
| 1-35 | CO$_2$Me | H | H | Me | 2 | —(CH$_2$)$_2$—Ph | H | H |
| 1-36 | H | H | H | Me | 2 | —(CH$_2$)$_2$—(4-F—Ph) | H | H |
| 1-37 | H | H | H | Me | 2 | —(CH$_2$)$_2$—(4-Me—Ph) | H | H |
| 1-38 | H | H | H | Me | 2 | —(CH$_2$)$_2$—(4-Et—Ph) | H | H |
| 1-39 | H | H | H | Me | 2 | —(CH$_2$)$_2$—(4-CF$_3$—Ph) | H | H |
| 1-40 | H | H | H | Me | 2 | —(CH$_2$)$_2$—(4-MeO—Ph) | H | H |
| 1-41 | H | H | H | Me | 2 | —(CH$_2$)$_2$—(4-EtO—Ph) | H | H |
| 1-42 | H | H | H | Me | 2 | —(CH$_2$)$_2$—(4-MeS—Ph) | H | H |
| 1-43 | H | H | H | Me | 2 | —(CH$_2$)$_2$—(4-cHx—Ph) | H | H |
| 1-44 | H | H | H | Me | 2 | —(CH$_2$)$_2$—(4-Ph—Ph) | H | H |
| 1-45 | H | H | H | Me | 2 | —(CH$_2$)$_3$—cHx | H | H |
| 1-46 | H | H | Me | Me | 2 | —(CH$_2$)$_3$—cHx | H | H |
| 1-47 | Me | H | H | Me | 2 | —(CH$_2$)$_3$—cHx | H | H |
| 1-48 | CO$_2$Me | H | H | Me | 2 | —(CH$_2$)$_3$—cHx | H | H |
| 1-49 | H | H | H | Me | 2 | —(CH$_2$)$_3$—(4-F—cHx) | H | H |
| 1-50 | H | H | H | Me | 2 | —(CH$_2$)$_3$—(4-Me—cHx) | H | H |
| 1-51 | H | H | H | Me | 2 | —(CH$_2$)$_3$—(4-Et—cHx) | H | H |
| 1-52 | H | H | H | Me | 2 | —(CH$_2$)$_3$—(4-CF$_3$—cHx) | H | H |
| 1-53 | H | H | H | Me | 2 | —(CH$_2$)$_3$—(4-MeO—cHx) | H | H |
| 1-54 | H | H | H | Me | 2 | —(CH$_2$)$_3$—(4-EtO—cHx) | H | H |
| 1-55 | H | H | H | Me | 2 | —(CH$_2$)$_3$—(4-MeS—cHx) | H | H |
| 1-56 | H | H | H | Me | 2 | —(CH$_2$)$_3$—(4-cHx—cHx) | H | H |
| 1-57 | H | H | H | Me | 2 | —(CH$_2$)$_3$—(4-Ph—cHx) | H | H |
| 1-58 | H | H | H | Me | 2 | —(CH$_2$)$_3$—Ph | H | H |
| 1-59 | H | H | Me | Me | 2 | —(CH$_2$)$_3$—Ph | H | H |
| 1-60 | Me | H | H | Me | 2 | —(CH$_2$)$_3$—Ph | H | H |
| 1-61 | CO$_2$Me | H | H | Me | 2 | —(CH$_2$)$_3$—Ph | H | H |
| 1-62 | H | H | H | Me | 2 | —(CH$_2$)$_3$—(4-F—Ph) | H | H |
| 1-63 | H | H | H | Me | 2 | —(CH$_2$)$_3$—(4-Me—Ph) | H | H |
| 1-64 | H | H | H | Me | 2 | —(CH$_2$)$_3$—(4-Et—Ph) | H | H |
| 1-65 | H | H | H | Me | 2 | —(CH$_2$)$_3$—(4-CF$_3$—Ph) | H | H |

TABLE 1-continued (Ia)

$$\text{R}^4\underset{\text{R}^3\text{O}}{\overset{\text{NR}^1\text{R}^2}{-}}(\text{CH}_2)_n-\underset{\text{S}}{\overset{\text{R}^6\quad\text{R}^7}{\text{thiophene}}}-\text{X}-\text{Y}-\text{R}^5$$

| Exemp. Compd. No. | R¹ | R² | R³ | R⁴ | n | —X—Y—R⁵ | R⁶ | R⁷ |
|---|---|---|---|---|---|---|---|---|
| 1-66 | H | H | H | Me | 2 | —(CH₂)₃—(4-MeO—Ph) | H | H |
| 1-67 | H | H | H | Me | 2 | —(CH₂)₃—(4-EtO—Ph) | H | H |
| 1-68 | H | H | H | Me | 2 | —(CH₂)₃—(4-MeS—Ph) | H | H |
| 1-69 | H | H | H | Me | 2 | —(CH₂)₃—(4-cHx—Ph) | H | H |
| 1-70 | H | H | H | Me | 2 | —(CH₂)₃—(4-Ph—Ph) | H | H |
| 1-71 | H | H | H | Me | 2 | —(CH₂)₄—cHx | H | H |
| 1-72 | H | H | Me | Me | 2 | —(CH₂)₄—cHx | H | H |
| 1-73 | Me | H | H | Me | 2 | —(CH₂)₄—cHx | H | H |
| 1-74 | CO₂Me | H | H | Me | 2 | —(CH₂)₄—cHx | H | H |
| 1-75 | H | H | H | Me | 2 | —(CH₂)₄—(4-F—cHx) | H | H |
| 1-76 | H | H | H | Me | 2 | —(CH₂)₄—(4-Me—cHx) | H | H |
| 1-77 | H | H | H | Me | 2 | —(CH₂)₄—(4-Et—cHx) | H | H |
| 1-78 | H | H | H | Me | 2 | —(CH₂)₄—(4-CF₃—cHx) | H | H |
| 1-79 | H | H | H | Me | 2 | —(CH₂)₄—(4-MeO—cHx) | H | H |
| 1-80 | H | H | H | Me | 2 | —(CH₂)₄—(4-EtO—cHx) | H | H |
| 1-81 | H | H | H | Me | 2 | —(CH₂)₄—(4-MeS—cHx) | H | H |
| 1-82 | H | H | H | Me | 2 | —(CH₂)₄—(4-cHx—cHx) | H | H |
| 1-83 | H | H | H | Me | 2 | —(CH₂)₄—(4-Ph—cHx) | H | H |
| 1-84 | H | H | H | Me | 2 | —(CH₂)₄—Ph | H | H |
| 1-85 | H | H | Me | Me | 2 | —(CH₂)₄—Ph | H | H |
| 1-86 | Me | H | H | Me | 2 | —(CH₂)₄—Ph | H | H |
| 1-87 | CO₂Me | H | H | Me | 2 | —(CH₂)₄—Ph | H | H |
| 1-88 | H | H | H | Me | 2 | —(CH₂)₄—(4-F—Ph) | H | H |
| 1-89 | H | H | H | Me | 2 | —(CH₂)₄—(4-Me—Ph) | H | H |
| 1-90 | H | H | H | Me | 2 | —(CH₂)₄—(4-Et—Ph) | H | H |
| 1-91 | H | H | H | Me | 2 | —(CH₂)₄—(4-CF₃—Ph) | H | H |
| 1-92 | H | H | H | Me | 2 | —(CH₂)₄—(4-MeO—Ph) | H | H |
| 1-93 | H | H | H | Me | 2 | —(CH₂)₄—(4-EtO—Ph) | H | H |
| 1-94 | H | H | H | Me | 2 | —(CH₂)₄—(4-MeS—Ph) | H | H |
| 1-95 | H | H | H | Me | 2 | —(CH₂)₄—(4-cHx—Ph) | H | H |
| 1-96 | H | H | H | Me | 2 | —(CH₂)₄—(4-Ph—Ph) | H | H |
| 1-97 | H | H | H | Me | 2 | —(CH₂)₅—cPn | H | H |
| 1-98 | H | H | H | Me | 2 | —(CH₂)₅—cHx | H | H |
| 1-99 | H | H | H | Me | 2 | —(CH₂)₅—cHx | Me | H |
| 1-100 | H | H | H | Me | 2 | —(CH₂)₅—cHx | H | Me |
| 1-101 | H | H | H | Me | 2 | —(CH₂)₅—cHx | F | H |
| 1-102 | H | H | H | Me | 2 | —(CH₂)₅—cHx | H | F |
| 1-103 | H | H | Me | Me | 2 | —(CH₂)₅—cHx | H | H |
| 1-104 | Me | H | H | Me | 2 | —(CH₂)₅—cHx | H | H |
| 1-105 | CO₂Me | H | H | Me | 2 | —(CH₂)₅—cHx | H | H |
| 1-106 | H | H | H | Me | 2 | —(CH₂)₅—(3-F—cHx) | H | H |
| 1-107 | H | H | H | Me | 2 | —(CH₂)₅—(4-F—cHx) | H | H |
| 1-108 | H | H | H | Me | 2 | —(CH₂)₅—(4-Cl—cHx) | H | H |
| 1-109 | H | H | H | Me | 2 | —(CH₂)₅—(4-Br—cHx) | H | H |
| 1-110 | H | H | H | Me | 2 | —(CH₂)₅—(3-Me—cHx) | H | H |
| 1-111 | H | H | H | Me | 2 | —(CH₂)₅—(4-Me—cHx) | H | H |
| 1-112 | H | H | H | Me | 2 | —(CH₂)₅—(3-Et—cHx) | H | H |
| 1-113 | H | H | H | Me | 2 | —(CH₂)₅—(4-Et—cHx) | H | H |
| 1-114 | H | H | H | Me | 2 | —(CH₂)₅—(3-Pr—cHx) | H | H |
| 1-115 | H | H | H | Me | 2 | —(CH₂)₅—(4-Pr—cHx) | H | H |
| 1-116 | H | H | H | Me | 2 | —(CH₂)₅—(4-iPr—cHx) | H | H |
| 1-117 | H | H | H | Me | 2 | —(CH₂)₅—(3-Bu—cHx) | H | H |
| 1-118 | H | H | H | Me | 2 | —(CH₂)₅—(4-Bu—cHx) | H | H |
| 1-119 | H | H | H | Me | 2 | —(CH₂)₅—(3-CF₃—cHx) | H | H |
| 1-120 | H | H | H | Me | 2 | —(CH₂)₅—(4-CF₃—cHx) | H | H |
| 1-121 | H | H | H | Me | 2 | —(CH₂)₅—(3-MeO—cHx) | H | H |
| 1-122 | H | H | H | Me | 2 | —(CH₂)₅—(4-MeO—cHx) | H | H |
| 1-123 | H | H | H | Me | 2 | —(CH₂)₅—(3-EtO—cHx) | H | H |
| 1-124 | H | H | H | Me | 2 | —(CH₂)₅—(4-EtO—cHx) | H | H |
| 1-125 | H | H | H | Me | 2 | —(CH₂)₅—(3-PrO—cHx) | H | H |
| 1-126 | H | H | H | Me | 2 | —(CH₂)₅—(4-PrO—cHx) | H | H |
| 1-127 | H | H | H | Me | 2 | —(CH₂)₅—(3-iPrO—cHx) | H | H |
| 1-128 | H | H | H | Me | 2 | —(CH₂)₅—(4-iPrO—cHx) | H | H |
| 1-129 | H | H | H | Me | 2 | —(CH₂)₅—[3-(2-Et—PrO)—cHx] | H | H |
| 1-130 | H | H | H | Me | 2 | —(CH₂)₅—[4-(2-Et—PrO)—cHx] | H | H |

TABLE 1-continued (Ia)

$$\text{structure with } R^4, R^3O, NR^1R^2, (CH_2)_n, \text{ thiophene ring with } R^6, R^7, X-Y-R^5$$

| Exemp. Compd. No. | R¹ | R² | R³ | R⁴ | n | —X—Y—R⁵ | R⁶ | R⁷ |
|---|---|---|---|---|---|---|---|---|
| 1-131 | H | H | H | Me | 2 | —(CH₂)₅—(3-iBuO—cHx) | H | H |
| 1-132 | H | H | H | Me | 2 | —(CH₂)₅—(4-iBuO—cHx) | H | H |
| 1-133 | H | H | H | Me | 2 | —(CH₂)₅—(3-MeS—cHx) | H | H |
| 1-134 | H | H | H | Me | 2 | —(CH₂)₅—(4-MeS—cHx) | H | H |
| 1-135 | H | H | H | Me | 2 | —(CH₂)₅—(3-EtS—cHx) | H | H |
| 1-136 | H | H | H | Me | 2 | —(CH₂)₅—(4-EtS—cHx) | H | H |
| 1-137 | H | H | H | Me | 2 | —(CH₂)₅—(3-PrS—cHx) | H | H |
| 1-138 | H | H | H | Me | 2 | —(CH₂)₅—(4-PrS—cHx) | H | H |
| 1-139 | H | H | H | Me | 2 | —(CH₂)₅—(3-iPrS—cHx) | H | H |
| 1-140 | H | H | H | Me | 2 | —(CH₂)₅—(4-iPrS—cHx) | H | H |
| 1-141 | H | H | H | Me | 2 | —(CH₂)₅—[3-(2-Et—PrS)—cHx] | H | H |
| 1-142 | H | H | H | Me | 2 | —(CH₂)₅—[4-(2-Et—PrS)—cHx] | H | H |
| 1-143 | H | H | H | Me | 2 | —(CH₂)₅—(3-iBuS—cHx) | H | H |
| 1-144 | H | H | H | Me | 2 | —(CH₂)₅—(4-iBuS—cHx) | H | H |
| 1-145 | H | H | H | Me | 2 | —(CH₂)₅—(3-cHx—cHx) | H | H |
| 1-146 | H | H | H | Me | 2 | —(CH₂)₅—(4-cHx—cHx) | H | H |
| 1-147 | H | H | H | Me | 2 | —(CH₂)₅—(3-Ph—cHx) | H | H |
| 1-148 | H | H | H | Me | 2 | —(CH₂)₅—(4-Ph—cHx) | H | H |
| 1-149 | H | H | H | Me | 2 | —(CH₂)₅—(2,4-diMe—cHx) | H | H |
| 1-150 | H | H | H | Me | 2 | —(CH₂)₅—(3,4-diMe—cHx) | H | H |
| 1-151 | H | H | H | Me | 2 | —(CH₂)₅—(3,5-diMe—cHx) | H | H |
| 1-152 | H | H | H | Me | 2 | —(CH₂)₅—Ph | H | H |
| 1-153 | H | H | H | Me | 2 | —(CH₂)₅—Ph | Me | H |
| 1-154 | H | H | H | Me | 2 | —(CH₂)₅—Ph | H | Me |
| 1-155 | H | H | H | Me | 2 | —(CH₂)₅—Ph | F | H |
| 1-156 | H | H | H | Me | 2 | —(CH₂)₅—Ph | H | F |
| 1-157 | H | H | Me | Me | 2 | —(CH₂)₅—Ph | H | H |
| 1-158 | Me | H | H | Me | 2 | —(CH₂)₅—Ph | H | H |
| 1-159 | CO₂Me | H | H | Me | 2 | —(CH₂)₅—Ph | H | H |
| 1-160 | H | H | H | Me | 2 | —(CH₂)₅—(3-F—Ph) | H | H |
| 1-161 | H | H | H | Me | 2 | —(CH₂)₅—(4-F—Ph) | H | H |
| 1-162 | H | H | H | Me | 2 | —(CH₂)₅—(4-Cl—Ph) | H | H |
| 1-163 | H | H | H | Me | 2 | —(CH₂)₅—(4-Br—Ph) | H | H |
| 1-164 | H | H | H | Me | 2 | —(CH₂)₅—(3-Me—Ph) | H | H |
| 1-165 | H | H | H | Me | 2 | —(CH₂)₅—(4-Me—Ph) | H | H |
| 1-166 | H | H | H | Me | 2 | —(CH₂)₅—(3-Et—Ph) | H | H |
| 1-167 | H | H | H | Me | 2 | —(CH₂)₅—(4-Et—Ph) | H | H |
| 1-168 | H | H | H | Me | 2 | —(CH₂)₅—(3-Pr—Ph) | H | H |
| 1-169 | H | H | H | Me | 2 | —(CH₂)₅—(4-Pr—Ph) | H | H |
| 1-170 | H | H | H | Me | 2 | —(CH₂)₅—(3-iPr—Ph) | H | H |
| 1-171 | H | H | H | Me | 2 | —(CH₂)₅—(4-iPr—Ph) | H | H |
| 1-172 | H | H | H | Me | 2 | —(CH₂)₅—(3-Bu—Ph) | H | H |
| 1-173 | H | H | H | Me | 2 | —(CH₂)₅—(4-Bu—Ph) | H | H |
| 1-174 | H | H | H | Me | 2 | —(CH₂)₅—(3-CF₃—Ph) | H | H |
| 1-175 | H | H | H | Me | 2 | —(CH₂)₅—(4-CF₃—Ph) | H | H |
| 1-176 | H | H | H | Me | 2 | —(CH₂)₅—(3-MeO—Ph) | H | H |
| 1-177 | H | H | H | Me | 2 | —(CH₂)₅—(4-MeO—Ph) | H | H |
| 1-178 | H | H | H | Me | 2 | —(CH₂)₅—(3-EtO—Ph) | H | H |
| 1-179 | H | H | H | Me | 2 | —(CH₂)₅—(4-EtO—Ph) | H | H |
| 1-180 | H | H | H | Me | 2 | —(CH₂)₅—(3-PrO—Ph) | H | H |
| 1-181 | H | H | H | Me | 2 | —(CH₂)₅—(4-PrO—Ph) | H | H |
| 1-182 | H | H | H | Me | 2 | —(CH₂)₅—(3-iPrO—Ph) | H | H |
| 1-183 | H | H | H | Me | 2 | —(CH₂)₅—(4-iPrO—Ph) | H | H |
| 1-184 | H | H | H | Me | 2 | —(CH₂)₅—[3-(2-Et—PrO)—Ph] | H | H |
| 1-185 | H | H | H | Me | 2 | —(CH₂)₅—[4-(2-Et—PrO)—Ph] | H | H |
| 1-186 | H | H | H | Me | 2 | —(CH₂)₅—(3-iBuO—Ph) | H | H |
| 1-187 | H | H | H | Me | 2 | —(CH₂)₅—(4-iBuO—Ph) | H | H |
| 1-188 | H | H | H | Me | 2 | —(CH₂)₅—(3-MeS—Ph) | H | H |
| 1-189 | H | H | H | Me | 2 | —(CH₂)₅—(4-MeS—Ph) | H | H |
| 1-190 | H | H | H | Me | 2 | —(CH₂)₅—(3-EtS—Ph) | H | H |
| 1-191 | H | H | H | Me | 2 | —(CH₂)₅—(4-EtS—Ph) | H | H |
| 1-192 | H | H | H | Me | 2 | —(CH₂)₅—(3-PrS—Ph) | H | H |
| 1-193 | H | H | H | Me | 2 | —(CH₂)₅—(4-PrS—Ph) | H | H |
| 1-194 | H | H | H | Me | 2 | —(CH₂)₅—(3-iPrS—Ph) | H | H |
| 1-195 | H | H | H | Me | 2 | —(CH₂)₅—(4-iPrS—Ph) | H | H |

TABLE 1-continued (Ia)

Structure: thiophene with NR¹R² and R⁴ and R³O-CH₂ substituents via (CH₂)ₙ at one position, and X—Y—R⁵ at the other, with R⁶ and R⁷ on the thiophene ring.

| Exemp. Compd. No. | R¹ | R² | R³ | R⁴ | n | —X—Y—R⁵ | R⁶ | R⁷ |
|---|---|---|---|---|---|---|---|---|
| 1-196 | H | H | H | Me | 2 | —(CH$_2$)$_5$—[3-(2-Et—PrS)—Ph] | H | H |
| 1-197 | H | H | H | Me | 2 | —(CH$_2$)$_5$—[4-(2-Et—PrS)—Ph] | H | H |
| 1-198 | H | H | H | Me | 2 | —(CH$_2$)$_5$—(3-iBuS—Ph) | H | H |
| 1-199 | H | H | H | Me | 2 | —(CH$_2$)$_5$—(4-iBuS—Ph) | H | H |
| 1-200 | H | H | H | Me | 2 | —(CH$_2$)$_5$—(3-cHx—Ph) | H | H |
| 1-201 | H | H | H | Me | 2 | —(CH$_2$)$_5$—(4-cHx—Ph) | H | H |
| 1-202 | H | H | H | Me | 2 | —(CH$_2$)$_5$—(3-Ph—Ph) | H | H |
| 1-203 | H | H | H | Me | 2 | —(CH$_2$)$_5$—(4-Ph—Ph) | H | H |
| 1-204 | H | H | H | Me | 2 | —(CH$_2$)$_5$—(2,4-diMe—Ph) | H | H |
| 1-205 | H | H | H | Me | 2 | —(CH$_2$)$_5$—(3,4-diMe—Ph) | H | H |
| 1-206 | H | H | H | Me | 2 | —(CH$_2$)$_5$—(3,5-diMe—Ph) | H | H |
| 1-207 | H | H | H | Me | 2 | —(CH$_2$)$_5$—Np(1) | H | H |
| 1-208 | H | H | H | Me | 2 | —(CH$_2$)$_5$—Np(2) | H | H |
| 1-209 | H | H | H | Me | 2 | —(CH$_2$)$_6$—cPn | H | H |
| 1-210 | H | H | H | Me | 2 | —(CH$_2$)$_6$—cHx | H | H |
| 1-211 | H | H | H | Me | 2 | —(CH$_2$)$_6$—cHx | Me | H |
| 1-212 | H | H | H | Me | 2 | —(CH$_2$)$_6$—cHx | H | Me |
| 1-213 | H | H | H | Me | 2 | —(CH$_2$)$_6$—cHx | F | H |
| 1-214 | H | H | H | Me | 2 | —(CH$_2$)$_6$—cHx | H | F |
| 1-215 | H | H | Me | Me | 2 | —(CH$_2$)$_6$—cHx | H | H |
| 1-216 | Me | H | H | Me | 2 | —(CH$_2$)$_6$—cHx | H | H |
| 1-217 | CO$_2$Me | H | H | Me | 2 | —(CH$_2$)$_6$—cHx | H | H |
| 1-218 | H | H | H | Me | 2 | —(CH$_2$)$_6$—(3-F—cHx) | H | H |
| 1-219 | H | H | H | Me | 2 | —(CH$_2$)$_6$—(4-F—cHx) | H | H |
| 1-220 | H | H | H | Me | 2 | —(CH$_2$)$_6$—(4-Cl—cHx) | H | H |
| 1-221 | H | H | H | Me | 2 | —(CH$_2$)$_6$—(4-Br—cHx) | H | H |
| 1-222 | H | H | H | Me | 2 | —(CH$_2$)$_6$—(3-Me—cHx) | H | H |
| 1-223 | H | H | H | Me | 2 | —(CH$_2$)$_6$—(4-Me—cHx) | H | H |
| 1-224 | H | H | H | Me | 2 | —(CH$_2$)$_6$—(3-Et—cHx) | H | H |
| 1-225 | H | H | H | Me | 2 | —(CH$_2$)$_6$—(4-Et—cHx) | H | H |
| 1-226 | H | H | H | Me | 2 | —(CH$_2$)$_6$—(3-Pr—cHx) | H | H |
| 1-227 | H | H | H | Me | 2 | —(CH$_2$)$_6$—(4-Pr—cHx) | H | H |
| 1-228 | H | H | H | Me | 2 | —(CH$_2$)$_6$—(4-iPr—cHx) | H | H |
| 1-229 | H | H | H | Me | 2 | —(CH$_2$)$_6$—(3-Bu—cHx) | H | H |
| 1-230 | H | H | H | Me | 2 | —(CH$_2$)$_6$—(4-Bu—cHx) | H | H |
| 1-231 | H | H | H | Me | 2 | —(CH$_2$)$_6$—(3-CF$_3$—cHx) | H | H |
| 1-232 | H | H | H | Me | 2 | —(CH$_2$)$_6$—(4-CF$_3$—cHx) | H | H |
| 1-233 | H | H | H | Me | 2 | —(CH$_2$)$_6$—(3-MeO—cHx) | H | H |
| 1-234 | H | H | H | Me | 2 | —(CH$_2$)$_6$—(4-MeO—cHx) | H | H |
| 1-235 | H | H | H | Me | 2 | —(CH$_2$)$_6$—(3-EtO—cHx) | H | H |
| 1-236 | H | H | H | Me | 2 | —(CH$_2$)$_6$—(4-EtO—cHx) | H | H |
| 1-237 | H | H | H | Me | 2 | —(CH$_2$)$_6$—(3-PrO—cHx) | H | H |
| 1-238 | H | H | H | Me | 2 | —(CH$_2$)$_6$—(4-PrO—cHx) | H | H |
| 1-239 | H | H | H | Me | 2 | —(CH$_2$)$_6$—(3-iPrO—cHx) | H | H |
| 1-240 | H | H | H | Me | 2 | —(CH$_2$)$_6$—(4-iPrO—cHx) | H | H |
| 1-241 | H | H | H | Me | 2 | —(CH$_2$)$_6$—[3-(2-Et—PrO)—cHx] | H | H |
| 1-242 | H | H | H | Me | 2 | —(CH$_2$)$_6$—[4-(2-Et—PrO)—cHx] | H | H |
| 1-243 | H | H | H | Me | 2 | —(CH$_2$)$_6$—(3-iBuO—cHx) | H | H |
| 1-244 | H | H | H | Me | 2 | —(CH$_2$)$_6$—(4-iBuO—cHx) | H | H |
| 1-245 | H | H | H | Me | 2 | —(CH$_2$)$_6$—(3-MeS—cHx) | H | H |
| 1-246 | H | H | H | Me | 2 | —(CH$_2$)$_6$—(4-MeS—cHx) | H | H |
| 1-247 | H | H | H | Me | 2 | —(CH$_2$)$_6$—(3-EtS—cHx) | H | H |
| 1-248 | H | H | H | Me | 2 | —(CH$_2$)$_6$—(4-EtS—cHx) | H | H |
| 1-249 | H | H | H | Me | 2 | —(CH$_2$)$_6$—(3-PrS—cHx) | H | H |
| 1-250 | H | H | H | Me | 2 | —(CH$_2$)$_6$—(4-PrS—cHx) | H | H |
| 1-251 | H | H | H | Me | 2 | —(CH$_2$)$_6$—(3-iPrS—cHx) | H | H |
| 1-252 | H | H | H | Me | 2 | —(CH$_2$)$_6$—(4-iPrS—cHx) | H | H |
| 1-253 | H | H | H | Me | 2 | —(CH$_2$)$_6$—[3-(2-Et—PrS)—cHx] | H | H |
| 1-254 | H | H | H | Me | 2 | —(CH$_2$)$_6$—[4-(2-Et—PrS)—cHx] | H | H |
| 1-255 | H | H | H | Me | 2 | —(CH$_2$)$_6$—(3-iBuS—cHx) | H | H |
| 1-256 | H | H | H | Me | 2 | —(CH$_2$)$_6$—(4-iBuS—cHx) | H | H |
| 1-257 | H | H | H | Me | 2 | —(CH$_2$)$_6$—(3-cHx—cHx) | H | H |
| 1-258 | H | H | H | Me | 2 | —(CH$_2$)$_6$—(4-cHx—cHx) | H | H |
| 1-259 | H | H | H | Me | 2 | —(CH$_2$)$_6$—(3-Ph—cHx) | H | H |
| 1-260 | H | H | H | Me | 2 | —(CH$_2$)$_6$—(4-Ph—cHx) | H | H |

TABLE 1-continued (Ia)

Structure: R⁴, R³O, NR¹R² attached to carbon with (CH₂)ₙ linked to thiophene ring (with R⁶, R⁷) and X—Y—R⁵

| Exemp. Compd. No. | R¹ | R² | R³ | R⁴ | n | —X—Y—R⁵ | R⁶ | R⁷ |
|---|---|---|---|---|---|---|---|---|
| 1-261 | H | H | H | Me | 2 | —(CH₂)₆—(2,4-diMe—cHx) | H | H |
| 1-262 | H | H | H | Me | 2 | —(CH₂)₆—(3,4-diMe—cHx) | H | H |
| 1-263 | H | H | H | Me | 2 | —(CH₂)₆—(3,5-diMe—cHx) | H | H |
| 1-264 | H | H | H | Me | 2 | —(CH₂)₆—Ph | H | H |
| 1-265 | H | H | H | Me | 2 | —(CH₂)₆—Ph | Me | H |
| 1-266 | H | H | H | Me | 2 | —(CH₂)₆—Ph | H | Me |
| 1-267 | H | H | H | Me | 2 | —(CH₂)₆—Ph | F | H |
| 1-268 | H | H | H | Me | 2 | —(CH₂)₆—Ph | H | F |
| 1-269 | H | H | Me | Me | 2 | —(CH₂)₆—Ph | H | H |
| 1-270 | Me | H | H | Me | 2 | —(CH₂)₆—Ph | H | H |
| 1-271 | CO₂Me | H | H | Me | 2 | —(CH₂)₆—Ph | H | H |
| 1-272 | H | H | H | Me | 2 | —(CH₂)₆—(3-F—Ph) | H | H |
| 1-273 | H | H | H | Me | 2 | —(CH₂)₆—(4-F—Ph) | H | H |
| 1-274 | H | H | H | Me | 2 | —(CH₂)₆—(4-Cl—Ph) | H | H |
| 1-275 | H | H | H | Me | 2 | —(CH₂)₆—(4-Br—Ph) | H | H |
| 1-276 | H | H | H | Me | 2 | —(CH₂)₆—(3-Me—Ph) | H | H |
| 1-277 | H | H | H | Me | 2 | —(CH₂)₆—(4-Me—Ph) | H | H |
| 1-278 | H | H | H | Me | 2 | —(CH₂)₆—(3-Et—Ph) | H | H |
| 1-279 | H | H | H | Me | 2 | —(CH₂)₆—(4-Et—Ph) | H | H |
| 1-280 | H | H | H | Me | 2 | —(CH₂)₆—(3-Pr—Ph) | H | H |
| 1-281 | H | H | H | Me | 2 | —(CH₂)₆—(4-Pr—Ph) | H | H |
| 1-282 | H | H | H | Me | 2 | —(CH₂)₆—(3-iPr—Ph) | H | H |
| 1-283 | H | H | H | Me | 2 | —(CH₂)₆—(4-iPr—Ph) | H | H |
| 1-284 | H | H | H | Me | 2 | —(CH₂)₆—(3-Bu—Ph) | H | H |
| 1-285 | H | H | H | Me | 2 | —(CH₂)₆—(4-Bu—Ph) | H | H |
| 1-286 | H | H | H | Me | 2 | —(CH₂)₆—(3-CF₃—Ph) | H | H |
| 1-287 | H | H | H | Me | 2 | —(CH₂)₆—(4-CF₃—Ph) | H | H |
| 1-288 | H | H | H | Me | 2 | —(CH₂)₆—(3-MeO—Ph) | H | H |
| 1-289 | H | H | H | Me | 2 | —(CH₂)₆—(4-MeO—Ph) | H | H |
| 1-290 | H | H | H | Me | 2 | —(CH₂)₆—(3-EtO—Ph) | H | H |
| 1-291 | H | H | H | Me | 2 | —(CH₂)₆—(4-EtO—Ph) | H | H |
| 1-292 | H | H | H | Me | 2 | —(CH₂)₆—(3-PrO—Ph) | H | H |
| 1-293 | H | H | H | Me | 2 | —(CH₂)₆—(4-PrO—Ph) | H | H |
| 1-294 | H | H | H | Me | 2 | —(CH₂)₆—(3-iPrO—Ph) | H | H |
| 1-295 | H | H | H | Me | 2 | —(CH₂)₆—(4-iPrO—Ph) | H | H |
| 1-296 | H | H | H | Me | 2 | —(CH₂)₆—[3-(2-Et—PrO)—Ph] | H | H |
| 1-297 | H | H | H | Me | 2 | —(CH₂)₆—[4-(2-Et—PrO)—Ph] | H | H |
| 1-298 | H | H | H | Me | 2 | —(CH₂)₆—(3-iBuO—Ph) | H | H |
| 1-299 | H | H | H | Me | 2 | —(CH₂)₆—(4-iBuO—Ph) | H | H |
| 1-300 | H | H | H | Me | 2 | —(CH₂)₆—(3-MeS—Ph) | H | H |
| 1-301 | H | H | H | Me | 2 | —(CH₂)₆—(4-MeS—Ph) | H | H |
| 1-302 | H | H | H | Me | 2 | —(CH₂)₆—(3-EtS—Ph) | H | H |
| 1-303 | H | H | H | Me | 2 | —(CH₂)₆—(4-EtS—Ph) | H | H |
| 1-304 | H | H | H | Me | 2 | —(CH₂)₆—(3-PrS—Ph) | H | H |
| 1-305 | H | H | H | Me | 2 | —(CH₂)₆—(4-PrS—Ph) | H | H |
| 1-306 | H | H | H | Me | 2 | —(CH₂)₆—(3-iPrS—Ph) | H | H |
| 1-307 | H | H | H | Me | 2 | —(CH₂)₆—(4-iPrS—Ph) | H | H |
| 1-308 | H | H | H | Me | 2 | —(CH₂)₆—[3-(2-Et—PrS)—Ph] | H | H |
| 1-309 | H | H | H | Me | 2 | —(CH₂)₆—[4-(2-Et—PrS)—Ph] | H | H |
| 1-310 | H | H | H | Me | 2 | —(CH₂)₆—(3-iBuS—Ph) | H | H |
| 1-311 | H | H | H | Me | 2 | —(CH₂)₆—(4-iBuS—Ph) | H | H |
| 1-312 | H | H | H | Me | 2 | —(CH₂)₆—(3-cHx—Ph) | H | H |
| 1-313 | H | H | H | Me | 2 | —(CH₂)₆—(4-cHx—Ph) | H | H |
| 1-314 | H | H | H | Me | 2 | —(CH₂)₆—(3-Ph—Ph) | H | H |
| 1-315 | H | H | H | Me | 2 | —(CH₂)₆—(4-Ph—Ph) | H | H |
| 1-316 | H | H | H | Me | 2 | —(CH₂)₆—(2,4-diMe—Ph) | H | H |
| 1-317 | H | H | H | Me | 2 | —(CH₂)₆—(3,4-diMe—Ph) | H | H |
| 1-318 | H | H | H | Me | 2 | —(CH₂)₆—(3,5-diMe—Ph) | H | H |
| 1-319 | H | H | H | Me | 2 | —(CH₂)₆—Np(1) | H | H |
| 1-320 | H | H | H | Me | 2 | —(CH₂)₆—Np(2) | H | H |
| 1-321 | H | H | H | Me | 2 | —(CH₂)₇—cHx | H | H |
| 1-322 | H | H | Me | Me | 2 | —(CH₂)₇—cHx | H | H |
| 1-323 | Me | H | H | Me | 2 | —(CH₂)₇—cHx | H | H |
| 1-324 | CO₂Me | H | H | Me | 2 | —(CH₂)₇—cHx | H | H |
| 1-325 | H | H | H | Me | 2 | —(CH₂)₇—(4-F—cHx) | H | H |

TABLE 1-continued (Ia)

$$\text{structure: } R^3O-CH_2-C(R^4)(NR^1R^2)-(CH_2)_n-\text{[thiophene with } R^6, R^7\text{]}-X-Y-R^5$$

| Exemp. Compd. No. | $R^1$ | $R^2$ | $R^3$ | $R^4$ | n | —X—Y—$R^5$ | $R^6$ | $R^7$ |
|---|---|---|---|---|---|---|---|---|
| 1-326 | H | H | H | Me | 2 | —(CH$_2$)$_7$—(4-Me—cHx) | H | H |
| 1-327 | H | H | H | Me | 2 | —(CH$_2$)$_7$—(4-Et—cHx) | H | H |
| 1-328 | H | H | H | Me | 2 | —(CH$_2$)$_7$—(4-CF$_3$—cHx) | H | H |
| 1-329 | H | H | H | Me | 2 | —(CH$_2$)$_7$—(4-MeO—cHx) | H | H |
| 1-330 | H | H | H | Me | 2 | —(CH$_2$)$_7$—(4-EtO—cHx) | H | H |
| 1-331 | H | H | H | Me | 2 | —(CH$_2$)$_7$—(4-MeS—cHx) | H | H |
| 1-332 | H | H | H | Me | 2 | —(CH$_2$)$_7$—(4-cHx—cHx) | H | H |
| 1-333 | H | H | H | Me | 2 | —(CH$_2$)$_7$—(4-Ph—cHx) | H | H |
| 1-334 | H | H | H | Me | 2 | —(CH$_2$)$_7$—Ph | H | H |
| 1-335 | H | H | Me | Me | 2 | —(CH$_2$)$_7$—Ph | H | H |
| 1-336 | Me | H | H | Me | 2 | —(CH$_2$)$_7$—Ph | H | H |
| 1-337 | CO$_2$Me | H | H | Me | 2 | —(CH$_2$)$_7$—Ph | H | H |
| 1-338 | H | H | H | Me | 2 | —(CH$_2$)$_7$—(4-F—Ph) | H | H |
| 1-339 | H | H | H | Me | 2 | —(CH$_2$)$_7$—(4-Me—Ph) | H | H |
| 1-340 | H | H | H | Me | 2 | —(CH$_2$)$_7$—(4-Et—Ph) | H | H |
| 1-341 | H | H | H | Me | 2 | —(CH$_2$)$_7$—(4-CF$_3$—Ph) | H | H |
| 1-342 | H | H | H | Me | 2 | —(CH$_2$)$_7$—(4-MeO—Ph) | H | H |
| 1-343 | H | H | H | Me | 2 | —(CH$_2$)$_7$—(4-EtO—Ph) | H | H |
| 1-344 | H | H | H | Me | 2 | —(CH$_2$)$_7$—(4-MeS—Ph) | H | H |
| 1-345 | H | H | H | Me | 2 | —(CH$_2$)$_7$—(4-cHx—Ph) | H | H |
| 1-346 | H | H | H | Me | 2 | —(CH$_2$)$_7$—(4-Ph—Ph) | H | H |
| 1-347 | H | H | H | Me | 2 | —(CH$_2$)$_5$—cHx | H | H |
| 1-348 | H | H | Me | Me | 2 | —(CH$_2$)$_8$—cHx | H | H |
| 1-349 | Me | H | H | Me | 2 | —(CH$_2$)$_8$—cHx | H | H |
| 1-350 | CO$_2$Me | H | H | Me | 2 | —(CH$_2$)$_8$—cHx | H | H |
| 1-351 | H | H | H | Me | 2 | —(CH$_2$)$_8$—(4-F—cHx) | H | H |
| 1-352 | H | H | H | Me | 2 | —(CH$_2$)$_8$—(4-Me—cHx) | H | H |
| 1-353 | H | H | H | Me | 2 | —(CH$_2$)$_8$—(4-Et—cHx) | H | H |
| 1-354 | H | H | H | Me | 2 | —(CH$_2$)$_8$—(4-CF$_3$—cHx) | H | H |
| 1-355 | H | H | H | Me | 2 | —(CH$_2$)$_8$—(4-MeO—cHx) | H | H |
| 1-356 | H | H | H | Me | 2 | —(CH$_2$)$_8$—(4-EtO—cHx) | H | H |
| 1-357 | H | H | H | Me | 2 | —(CH$_2$)$_8$—(4-MeS—cHx) | H | H |
| 1-358 | H | H | H | Me | 2 | —(CH$_2$)$_8$—(4-cHx—cHx) | H | H |
| 1-359 | H | H | H | Me | 2 | —(CH$_2$)$_8$—(4-Ph—cHx) | H | H |
| 1-360 | H | H | H | Me | 2 | —(CH$_2$)$_8$—Ph | H | H |
| 1-361 | H | H | Me | Me | 2 | —(CH$_2$)$_8$—Ph | H | H |
| 1-362 | Me | H | H | Me | 2 | —(CH$_2$)$_8$—Ph | H | H |
| 1-363 | CO$_2$Me | H | H | Me | 2 | —(CH$_2$)$_8$—Ph | H | H |
| 1-364 | H | H | H | Me | 2 | —(CH$_2$)$_8$—(4-F—Ph) | H | H |
| 1-365 | H | H | H | Me | 2 | —(CH$_2$)$_8$—(4-Me—Ph) | H | H |
| 1-366 | H | H | H | Me | 2 | —(CH$_2$)$_8$—(4-Et—Ph) | H | H |
| 1-367 | H | H | H | Me | 2 | —(CH$_2$)$_8$—(4-CF$_3$—Ph) | H | H |
| 1-368 | H | H | H | Me | 2 | —(CH$_2$)$_8$—(4-MeO—Ph) | H | H |
| 1-369 | H | H | H | Me | 2 | —(CH$_2$)$_8$—(4-EtO—Ph) | H | H |
| 1-370 | H | H | H | Me | 2 | —(CH$_2$)$_8$—(4-MeS—Ph) | H | H |
| 1-371 | H | H | H | Me | 2 | —(CH$_2$)$_8$—(4-cHx—Ph) | H | H |
| 1-372 | H | H | H | Me | 2 | —(CH$_2$)$_8$—(4-Ph—Ph) | H | H |
| 1-373 | H | H | H | Me | 2 | —(CH$_2$)$_3$—O—cHx | H | H |
| 1-374 | H | H | Me | Me | 2 | —(CH$_2$)$_3$—O—cHx | H | H |
| 1-375 | Me | H | H | Me | 2 | —(CH$_2$)$_3$—O—cHx | H | H |
| 1-376 | CO$_2$Me | H | H | Me | 2 | —(CH$_2$)$_3$—O—cHx | H | H |
| 1-377 | H | H | H | Me | 2 | —(CH$_2$)$_3$—O—(4-F—cHx) | H | H |
| 1-378 | H | H | H | Me | 2 | —(CH$_2$)$_3$—O—(4-Me—cHx) | H | H |
| 1-379 | H | H | H | Me | 2 | —(CH$_2$)$_3$—O—(4-Et—cHx) | H | H |
| 1-380 | H | H | H | Me | 2 | —(CH$_2$)$_3$—O—(4-CF$_3$—cHx) | H | H |
| 1-381 | H | H | H | Me | 2 | —(CH$_2$)$_3$—O—(4-MeO—cHx) | H | H |
| 1-382 | H | H | H | Me | 2 | —(CH$_2$)$_3$—O—(4-EtO—cHx) | H | H |
| 1-383 | H | H | H | Me | 2 | —(CH$_2$)$_3$—O—(4-MeS—cHx) | H | H |
| 1-384 | H | H | H | Me | 2 | —(CH$_2$)$_3$—O—(4-cHx—cHx) | H | H |
| 1-385 | H | H | H | Me | 2 | —(CH$_2$)$_3$—O—(4-Ph—cHx) | H | H |
| 1-386 | H | H | H | Me | 2 | —(CH$_2$)$_3$—O—Ph | H | H |
| 1-387 | H | H | Me | Me | 2 | —(CH$_2$)$_3$—O—Ph | H | H |
| 1-388 | Me | H | H | Me | 2 | —(CH$_2$)$_3$—O—Ph | H | H |
| 1-389 | CO$_2$Me | H | H | Me | 2 | —(CH$_2$)$_3$—O—Ph | H | H |
| 1-390 | H | H | H | Me | 2 | —(CH$_2$)$_3$—O—(4-F—Ph) | H | H |

TABLE 1-continued (Ia)

$$\text{Structure with } NR^1R^2, R^4, R^3O, (CH_2)_n, \text{ thiophene ring with } R^6, R^7, \text{ and } X-Y-R^5$$

| Exemp. Compd. No. | R¹ | R² | R³ | R⁴ | n | —X—Y—R⁵ | R⁶ | R⁷ |
|---|---|---|---|---|---|---|---|---|
| 1-391 | H | H | H | Me | 2 | —(CH₂)₃—O—(4-Me—Ph) | H | H |
| 1-392 | H | H | H | Me | 2 | —(CH₂)₃—O—(4-Et—Ph) | H | H |
| 1-393 | H | H | H | Me | 2 | —(CH₂)₃—O—(4-CF₃—Ph) | H | H |
| 1-394 | H | H | H | Me | 2 | —(CH₂)₃—O—(4-MeO—Ph) | H | H |
| 1-395 | H | H | H | Me | 2 | —(CH₂)₃—O—(4-EtO—Ph) | H | H |
| 1-396 | H | H | H | Me | 2 | —(CH₂)₃—O—(4-MeS—Ph) | H | H |
| 1-397 | H | H | H | Me | 2 | —(CH₂)₃—O—(4-cHx—Ph) | H | H |
| 1-398 | H | H | H | Me | 2 | —(CH₂)₃—O—(4-Ph—Ph) | H | H |
| 1-399 | H | H | H | Me | 2 | —(CH₂)₄—O—cPn | H | H |
| 1-400 | H | H | H | Me | 2 | —(CH₂)₄—O—cHx | H | H |
| 1-401 | H | H | H | Me | 2 | —(CH₂)₄—O—cHx | Me | H |
| 1-402 | H | H | H | Me | 2 | —(CH₂)₄—O—cHx | H | Me |
| 1-403 | H | H | H | Me | 2 | —(CH₂)₄—O—cHx | F | H |
| 1-404 | H | H | H | Me | 2 | —(CH₂)₄—O—cHx | F | F |
| 1-405 | H | H | Me | Me | 2 | —(CH₂)₄—O—cHx | H | H |
| 1-406 | Me | H | H | Me | 2 | —(CH₂)₄—O—cHx | H | H |
| 1-407 | CO₂Me | H | H | Me | 2 | —(CH₂)₄—O—cHx | H | H |
| 1-408 | H | H | H | Me | 2 | —(CH₂)₄—O—(3-F—cHx) | H | H |
| 1-409 | H | H | H | Me | 2 | —(CH₂)₄—O—(4-F—cHx) | H | H |
| 1-410 | H | H | H | Me | 2 | —(CH₂)₄—O—(4-Cl—cHx) | H | H |
| 1-411 | H | H | H | Me | 2 | —(CH₂)₄—O—(4-Br—cHx) | H | H |
| 1-412 | H | H | H | Me | 2 | —(CH₂)₄—O—(3-Me—cHx) | H | H |
| 1-413 | H | H | H | Me | 2 | —(CH₂)₄—O—(4-Me—cHx) | H | H |
| 1-414 | H | H | H | Me | 2 | —(CH₂)₄—O—(3-Et—cHx) | H | H |
| 1-415 | H | H | H | Me | 2 | —(CH₂)₄—O—(4-Et—cHx) | H | H |
| 1-416 | H | H | H | Me | 2 | —(CH₂)₄—O—(3-Pr—cHx) | H | H |
| 1-417 | H | H | H | Me | 2 | —(CH₂)₄—O—(4-Pr—cHx) | H | H |
| 1-418 | H | H | H | Me | 2 | —(CH₂)₄—O—(4-iPr—cHx) | H | H |
| 1-419 | H | H | H | Me | 2 | —(CH₂)₄—O—(3-Bu—cHx) | H | H |
| 1-420 | H | H | H | Me | 2 | —(CH₂)₄—O—(4-Bu—cHx) | H | H |
| 1-421 | H | H | H | Me | 2 | —(CH₂)₄—O—(3-CF₃—cHx) | H | H |
| 1-422 | H | H | H | Me | 2 | —(CH₂)₄—O—(4-CF₃—cHx) | H | H |
| 1-423 | H | H | H | Me | 2 | —(CH₂)₄—O—(3-MeO—cHx) | H | H |
| 1-424 | H | H | H | Me | 2 | —(CH₂)₄—O—(4-MeO—cHx) | H | H |
| 1-425 | H | H | H | Me | 2 | —(CH₂)₄—O—(3-EtO—cHx) | H | H |
| 1-426 | H | H | H | Me | 2 | —(CH₂)₄—O—(4-EtO—cHx) | H | H |
| 1-427 | H | H | H | Me | 2 | —(CH₂)₄—O—(3-PrO—cHx) | H | H |
| 1-428 | H | H | H | Me | 2 | —(CH₂)₄—O—(4-PrO—cHx) | H | H |
| 1-429 | H | H | H | Me | 2 | —(CH₂)₄—O—(3-iPrO—cHx) | H | H |
| 1-430 | H | H | H | Me | 2 | —(CH₂)₄—O—(4-iPrO—cHx) | H | H |
| 1-431 | H | H | H | Me | 2 | —(CH₂)₄—O—[3-(2-Et—PrO)—cHx] | H | H |
| 1-432 | H | H | H | Me | 2 | —(CH₂)₄—O—[4-(2-Et—PrO)—cHx] | H | H |
| 1-433 | H | H | H | Me | 2 | —(CH₂)₄—O—(3-iBuO—cHx) | H | H |
| 1-434 | H | H | H | Me | 2 | —(CH₂)₄—O—(4-iBuO—cHx) | H | H |
| 1-435 | H | H | H | Me | 2 | —(CH₂)₄—O—(3-MeS—cHx) | H | H |
| 1-436 | H | H | H | Me | 2 | —(CH₂)₄—O—(4-MeS—cHx) | H | H |
| 1-437 | H | H | H | Me | 2 | —(CH₂)₄—O—(3-EtS—cHx) | H | H |
| 1-438 | H | H | H | Me | 2 | —(CH₂)₄—O—(4-EtS—cHx) | H | H |
| 1-439 | H | H | H | Me | 2 | —(CH₂)₄—O—(3-PrS—cHx) | H | H |
| 1-440 | H | H | H | Me | 2 | —(CH₂)₄—O—(4-PrS—cHx) | H | H |
| 1-441 | H | H | H | Me | 2 | —(CH₂)₄—O—(3-iPrS—cHx) | H | H |
| 1-442 | H | H | H | Me | 2 | —(CH₂)₄—O—(4-iPrS—cHx) | H | H |
| 1-443 | H | H | H | Me | 2 | —(CH₂)₄—O—[3-(2-Et—PrS)—cHx] | H | H |
| 1-444 | H | H | H | Me | 2 | —(CH₂)₄—O—[4-(2-Et—PrS)—cHx] | H | H |
| 1-445 | H | H | H | Me | 2 | —(CH₂)₄—O—(3-iBuS—cHx) | H | H |
| 1-446 | H | H | H | Me | 2 | —(CH₂)₄—O—(4-iBuS—cHx) | H | H |
| 1-447 | H | H | H | Me | 2 | —(CH₂)₄—O—(3-cHx—cHx) | H | H |
| 1-448 | H | H | H | Me | 2 | —(CH₂)₄—O—(4-cHx—cHx) | H | H |
| 1-449 | H | H | H | Me | 2 | —(CH₂)₄—O—(3-Ph—cHx) | H | H |
| 1-450 | H | H | H | Me | 2 | —(CH₂)₄—O—(4-Ph—cHx) | H | H |
| 1-451 | H | H | H | Me | 2 | —(CH₂)₄—O—(2,4-diMe—cHx) | H | H |
| 1-452 | H | H | H | Me | 2 | —(CH₂)₄—O—(3,4-diMe—cHx) | H | H |
| 1-453 | H | H | H | Me | 2 | —(CH₂)₄—O—(3,5-diMe—cHx) | H | H |
| 1-454 | H | H | H | Me | 2 | —(CH₂)₄—O—Ph | H | H |
| 1-455 | H | H | H | Me | 2 | —(CH₂)₄—O—Ph | Me | H |

TABLE 1-continued (Ia)

$$\text{structure with } NR^1R^2, R^4, R^3O, (CH_2)_n, \text{thiophene ring with } R^6, R^7, \text{and } X-Y-R^5$$

| Exemp. Compd. No. | $R^1$ | $R^2$ | $R^3$ | $R^4$ | n | —X—Y—$R^5$ | $R^6$ | $R^7$ |
|---|---|---|---|---|---|---|---|---|
| 1-456 | H | H | H | Me | 2 | —(CH$_2$)$_4$—O—Ph | H | Me |
| 1-457 | H | H | H | Me | 2 | —(CH$_2$)$_4$—O—Ph | F | H |
| 1-458 | H | H | H | Me | 2 | —(CH$_2$)$_4$—O—Ph | H | F |
| 1-459 | H | H | Me | Me | 2 | —(CH$_2$)$_4$—O—Ph | H | H |
| 1-460 | Me | H | H | Me | 2 | —(CH$_2$)$_4$—O—Ph | H | H |
| 1-461 | CO$_2$Me | H | H | Me | 2 | —(CH$_2$)$_4$—O—Ph | H | H |
| 1-462 | H | H | H | Me | 2 | —(CH$_2$)$_4$—O—(3-F—Ph) | H | H |
| 1-463 | H | H | H | Me | 2 | —(CH$_2$)$_4$—O—(4-F—Ph) | H | H |
| 1-464 | H | H | H | Me | 2 | —(CH$_2$)$_4$—O—(4-Cl—Ph) | H | H |
| 1-465 | H | H | H | Me | 2 | —(CH$_2$)$_4$—O—(4-Br—Ph) | H | H |
| 1-466 | H | H | H | Me | 2 | —(CH$_2$)$_4$—O—(3-Me—Ph) | H | H |
| 1-467 | H | H | H | Me | 2 | —(CH$_2$)$_4$—O—(4-Me—Ph) | H | H |
| 1-468 | H | H | H | Me | 2 | —(CH$_2$)$_4$—O—(3-Et—Ph) | H | H |
| 1-469 | H | H | H | Me | 2 | —(CH$_2$)$_4$—O—(4-Et—Ph) | H | H |
| 1-470 | H | H | H | Me | 2 | —(CH$_2$)$_4$—O—(3-Pr—Ph) | R | H |
| 1-471 | H | H | H | Me | 2 | —(CH$_2$)$_4$—O—(4-Pr—Ph) | H | H |
| 1-472 | H | H | H | Me | 2 | —(CH$_2$)$_4$—O—(3-iPr—Ph) | H | H |
| 1-473 | H | H | H | Me | 2 | —(CH$_2$)$_4$—O—(4-iPr—Ph) | H | H |
| 1-474 | H | H | H | Me | 2 | —(CH$_2$)$_4$—O—(3-Bu—Ph) | H | H |
| 1-475 | H | H | H | Me | 2 | —(CH$_2$)$_4$—O—(4-Bu—Ph) | H | H |
| 1-476 | H | H | H | Me | 2 | —(CH$_2$)$_4$—O—(3-CF$_3$—Ph) | H | H |
| 1-477 | H | H | H | Me | 2 | —(CH$_2$)$_4$—O—(4-CF$_3$—Ph) | H | H |
| 1-478 | H | H | H | Me | 2 | —(CH$_2$)$_4$—O—(3-MeO—Ph) | H | H |
| 1-479 | H | H | H | Me | 2 | —(CH$_2$)$_4$—O—(4-MeO—Ph) | H | H |
| 1-480 | H | H | H | Me | 2 | —(CH$_2$)$_4$—O—(3-EtO—Ph) | H | H |
| 1-481 | H | H | H | Me | 2 | —(CH$_2$)$_4$—O—(4-EtO—Ph) | H | H |
| 1-482 | H | H | H | Me | 2 | —(CH$_2$)$_4$—O—(3-PrO—Ph) | H | H |
| 1-483 | H | H | H | Me | 2 | —(CH$_2$)$_4$—O—(4-PrO—Ph) | H | H |
| 1-484 | H | H | H | Me | 2 | —(CH$_2$)$_4$—O—(3-iPrO—Ph) | H | H |
| 1-485 | H | H | H | Me | 2 | —(CH$_2$)$_4$—O—(4-iPrO—Ph) | H | H |
| 1-486 | H | H | H | Me | 2 | —(CH$_2$)$_4$—O—[3-(2-Et—PrO)—Ph] | H | H |
| 1-487 | H | H | H | Me | 2 | —(CH$_2$)$_4$—O—[4-(2-Et—PrO)—Ph] | H | H |
| 1-488 | H | H | H | Me | 2 | —(CH$_2$)$_4$—O—(3-iBuO—Ph) | H | H |
| 1-489 | H | H | H | Me | 2 | —(CH$_2$)$_4$—O—(4-iBuO—Ph) | H | H |
| 1-490 | H | H | H | Me | 2 | —(CH$_2$)$_4$—O—(3-MeS—Ph) | H | H |
| 1-491 | H | H | H | Me | 2 | —(CH$_2$)$_4$—O—(4-MeS—Ph) | H | H |
| 1-492 | H | H | H | Me | 2 | —(CH$_2$)$_4$—O—(3-EtS—Ph) | H | H |
| 1-493 | H | H | H | Me | 2 | —(CH$_2$)$_4$—O—(4-EtS—Ph) | H | H |
| 1-494 | H | H | H | Me | 2 | —(CH$_2$)$_4$—O—(3-PrS—Ph) | H | H |
| 1-495 | H | H | H | Me | 2 | —(CH$_2$)$_4$—O—(4-PrS—Ph) | H | H |
| 1-496 | H | H | H | Me | 2 | —(CH$_2$)$_4$—O—(3-iPrS—Ph) | H | H |
| 1-497 | H | H | H | Me | 2 | —(CH$_2$)$_4$—O—(4-iPrS—Ph) | H | H |
| 1-498 | H | H | H | Me | 2 | —(CH$_2$)$_4$—O—[3-(2-Et—PrS)—Ph] | H | H |
| 1-499 | H | H | H | Me | 2 | —(CH$_2$)$_4$—O—[4-(2-Et—PrS)—Ph] | H | H |
| 1-500 | H | H | H | Me | 2 | —(CH$_2$)$_4$—O—(3-iBuS—Ph) | H | H |
| 1-501 | H | H | H | Me | 2 | —(CH$_2$)$_4$—O—(4-iBuS—Ph) | H | H |
| 1-502 | H | H | H | Me | 2 | —(CH$_2$)$_4$—O—(3-cHx—Ph) | H | H |
| 1-503 | H | H | H | Me | 2 | —(CH$_2$)$_4$—O—(4-cHx—Ph) | H | H |
| 1-504 | H | H | H | Me | 2 | —(CH$_2$)$_4$—O—(3-Ph—Ph) | H | H |
| 1-505 | H | H | H | Me | 2 | —(CH$_2$)$_4$—O—(4-Ph—Ph) | H | H |
| 1-506 | H | H | H | Me | 2 | —(CH$_2$)$_4$—O—(2,4-diMe—Ph) | H | H |
| 1-507 | H | H | H | Me | 2 | —(CH$_2$)$_4$—O—(3,4-diMe—Ph) | H | H |
| 1-508 | H | H | H | Me | 2 | —(CH$_2$)$_4$—O—(3,5-diMe—Ph) | H | H |
| 1-509 | H | H | H | Me | 2 | —(CH$_2$)$_5$—O—cHx | H | H |
| 1-510 | H | H | H | Me | 2 | —(CH$_2$)$_5$—O—Ph | H | H |
| 1-511 | H | H | H | Me | 2 | —(CH$_2$)$_6$—O—cHx | H | H |
| 1-512 | H | H | H | Me | 2 | —(CH$_2$)$_6$—O—Ph | H | H |
| 1-513 | H | H | H | Me | 2 | —(CH$_2$)$_3$—OCH$_2$—cHx | H | H |
| 1-514 | H | H | Me | Me | 2 | —(CH$_2$)$_3$—OCH$_2$—cHx | H | H |
| 1-515 | Me | H | H | Me | 2 | —(CH$_2$)$_3$—OCH$_2$—cHx | H | H |
| 1-516 | CO$_2$Me | H | H | Me | 2 | —(CH$_2$)$_3$—OCH$_2$—cHx | H | H |
| 1-517 | H | H | H | Me | 2 | —(CH$_2$)$_3$—OCH$_2$—(4-F—cHx) | H | H |
| 1-518 | H | H | H | Me | 2 | —(CH$_2$)$_3$—OCH$_2$—(4-Me—cHx) | H | H |
| 1-519 | H | H | H | Me | 2 | —(CH$_2$)$_3$—OCH$_2$—(4-Et—cHx) | H | H |
| 1-520 | H | H | H | Me | 2 | —(CH$_2$)$_3$—OCH$_2$—(4-CF$_3$—cHx) | H | H |

TABLE 1-continued (Ia)

Structure: R⁴, R³O, (CH₂)ₙ, NR¹R², thiophene with R⁶, R⁷, and X—Y—R⁵

| Exemp. Compd. No. | R¹ | R² | R³ | R⁴ | n | —X—Y—R⁵ | R⁶ | R⁷ |
|---|---|---|---|---|---|---|---|---|
| 1-521 | H | H | H | Me | 2 | —(CH₂)₃—OCH₂—(4-MeO—cHx) | H | H |
| 1-522 | H | H | H | Me | 2 | —(CH₂)₃—OCH₂—(4-EtO—cHx) | H | H |
| 1-523 | H | H | H | Me | 2 | —(CH₂)₃—OCH₂—(4-MeS—cHx) | H | H |
| 1-524 | H | H | H | Me | 2 | —(CH₂)₃—OCH₂—(4-cHx—cHx) | H | H |
| 1-525 | H | H | H | Me | 2 | —(CH₂)₃—OCH₂—(4-Ph—cHx) | H | H |
| 1-526 | H | H | H | Me | 2 | —(CH₂)₃—OCH₂—Ph | H | H |
| 1-527 | H | H | Me | Me | 2 | —(CH₂)₃—OCH₂—Ph | H | H |
| 1-528 | Me | H | H | Me | 2 | —(CH₂)₃—OCH₂—Ph | H | H |
| 1-529 | CO₂Me | H | H | Me | 2 | —(CH₂)₃—OCH₂—Ph | H | H |
| 1-530 | H | H | H | Me | 2 | —(CH₂)₃—OCH₂—(4-F—Ph) | H | H |
| 1-531 | H | H | H | Me | 2 | —(CH₂)₃—OCH₂—(4-Me—Ph) | H | H |
| 1-532 | H | H | H | Me | 2 | —(CH₂)₃—OCH₂—(4-Et—Ph) | H | H |
| 1-533 | H | H | H | Me | 2 | —(CH₂)₃—OCH₂—(4-CF₃—Ph) | H | H |
| 1-534 | H | H | H | Me | 2 | —(CH₂)₃—OCH₂—(4-MeO—Ph) | H | H |
| 1-535 | H | H | H | Me | 2 | —(CH₂)₃—OCH₂—(4-EtO—Ph) | H | H |
| 1-536 | H | H | H | Me | 2 | —(CH₂)₃—OCH₂—(4-MeS—Ph) | H | H |
| 1-537 | H | H | H | Me | 2 | —(CH₂)₃—OCH₂—(4-cHx—Ph) | H | H |
| 1-538 | H | H | H | Me | 2 | —(CH₂)₃—OCH₂—(4-Ph—Ph) | H | H |
| 1-539 | H | H | H | Me | 2 | —(CH₂)₄—OCH₂—cPn | H | H |
| 1-540 | H | H | H | Me | 2 | —(CH₂)₄—OCH₂—cHx | H | H |
| 1-541 | H | H | H | Me | 2 | —(CH₂)₄—OCH₂—cHx | Me | H |
| 1-542 | H | H | H | Me | 2 | —(CH₂)₄—OCH₂—cHx | H | Me |
| 1-543 | H | H | H | Me | 2 | —(CH₂)₄—OCH₂—cHx | F | H |
| 1-544 | H | H | H | Me | 2 | —(CH₂)₄—OCH₂—cHx | H | F |
| 1-545 | H | H | Me | Me | 2 | —(CH₂)₄—OCH₂—cHx | H | H |
| 1-546 | Me | H | H | Me | 2 | —(CH₂)₄—OCH₂—cHx | H | H |
| 1-547 | CO₂Me | H | H | Me | 2 | —(CH₂)₄—OCH₂—cHx | H | H |
| 1-548 | H | H | H | Me | 2 | —(CH₂)₄—OCH₂—(3-F—cHx) | H | H |
| 1-549 | H | H | H | Me | 2 | —(CH₂)₄—OCH₂—(4-F—cHx) | H | H |
| 1-550 | H | H | H | Me | 2 | —(CH₂)₄—OCH₂—(4-Cl—cHx) | H | H |
| 1-551 | H | H | H | Me | 2 | —(CH₂)₄—OCH₂—(4-Br—cHx) | H | H |
| 1-552 | H | H | H | Me | 2 | —(CH₂)₄—OCH₂—(3-Me—cHx) | H | H |
| 1-553 | H | H | H | Me | 2 | —(CH₂)₄—OCH₂—(4-Me—cHx) | H | H |
| 1-554 | H | H | H | Me | 2 | —(CH₂)₄—OCH₂—(3-Et—cHx) | H | H |
| 1-555 | H | H | H | Me | 2 | —(CH₂)₄—OCH₂—(4-Et—cHx) | H | H |
| 1-556 | H | H | H | Me | 2 | —(CH₂)₄—OCH₂—(3-Pr—cHx) | H | H |
| 1-557 | H | H | H | Me | 2 | —(CH₂)₄—OCH₂—(4-Pr—cHx) | H | H |
| 1-558 | H | H | H | Me | 2 | —(CH₂)₄—OCH₂—(4-iPr—cHx) | H | H |
| 1-559 | H | H | H | Me | 2 | —(CH₂)₄—OCH₂—(3-Bu—cHx) | H | H |
| 1-560 | H | H | H | Me | 2 | —(CH₂)₄—OCH₂—(4-Bu—cHx) | H | H |
| 1-561 | H | H | H | Me | 2 | —(CH₂)₄—OCH₂—(3-CF₃—cHx) | H | H |
| 1-562 | H | H | H | Me | 2 | —(CH₂)₄—OCH₂—(4-CF₃—cHx) | H | H |
| 1-563 | H | H | H | Me | 2 | —(CH₂)₄—OCH₂—(3-MeO—cHx) | H | H |
| 1-564 | H | H | H | Me | 2 | —(CH₂)₄—OCH₂—(4-MeO—cHx) | H | H |
| 1-565 | H | H | H | Me | 2 | —(CH₂)₄—OCH₂—(3-EtO—cHx) | H | H |
| 1-566 | H | H | H | Me | 2 | —(CH₂)₄—OCH₂—(4-EtO—cHx) | H | H |
| 1-567 | H | H | H | Me | 2 | —(CH₂)₄—OCH₂—(3-PrO—cHx) | H | H |
| 1-568 | H | H | H | Me | 2 | —(CH₂)₄—OCH₂—(4-PrO—cHx) | H | H |
| 1-569 | H | H | H | Me | 2 | —(CH₂)₄—OCH₂—(3-iPrO—cHx) | H | H |
| 1-570 | H | H | H | Me | 2 | —(CH₂)₄—OCH₂—(4-iPrO—cHx) | H | H |
| 1-571 | H | H | H | Me | 2 | —(CH₂)₄—OCH₂—[3-(2-Et—PrO)—cHx] | H | H |
| 1-572 | H | H | H | Me | 2 | —(CH₂)₄—OCH₂—[4-(2-Et—PrO)—cHx] | H | H |
| 1-573 | H | H | H | Me | 2 | —(CH₂)₄—OCH₂—(3-iBuO—cHx) | H | H |
| 1-574 | H | H | H | Me | 2 | —(CH₂)₄—OCH₂—(4-iBuO—cHx) | H | H |
| 1-575 | H | H | H | Me | 2 | —(CH₂)₄—OCH₂—(3-MeS—cHx) | H | H |
| 1-576 | H | H | H | Me | 2 | —(CH₂)₄—OCH₂—(4-MeS—cHx) | H | H |
| 1-577 | H | H | H | Me | 2 | —(CH₂)₄—OCH₂—(3-EtS—cHx) | H | H |
| 1-578 | H | H | H | Me | 2 | —(CH₂)₄—OCH₂—(4-EtS—cHx) | H | H |
| 1-579 | H | H | H | Me | 2 | —(CH₂)₄—OCH₂—(3-PrS—cHx) | H | H |
| 1-580 | H | H | H | Me | 2 | —(CH₂)₄—OCH₂—(4-PrS—cHx) | H | H |
| 1-581 | H | H | H | Me | 2 | —(CH₂)₄—OCH₂—(3-iPrS—cHx) | H | H |
| 1-582 | H | H | H | Me | 2 | —(CH₂)₄—OCH₂—(4-iPrS—cHx) | H | H |
| 1-583 | H | H | H | Me | 2 | —(CH₂)₄—OCH₂—[3-(2-Et—PrS)—cHx] | H | H |
| 1-584 | H | H | H | Me | 2 | —(CH₂)₄—OCH₂—[4-(2-Et—PrS)—cHx] | H | H |
| 1-585 | H | H | H | Me | 2 | —(CH₂)₄—OCH₂—(3-iBuS—cHx) | H | H |

TABLE 1-continued (Ia)

$$\text{structure with } NR^1R^2, R^4, R^3O, (CH_2)_n, \text{thiophene ring with } R^6, R^7, \text{ and } X-Y-R^5$$

| Exemp. Compd. No. | R¹ | R² | R³ | R⁴ | n | —X—Y—R⁵ | R⁶ | R⁷ |
|---|---|---|---|---|---|---|---|---|
| 1-586 | H | H | H | Me | 2 | —(CH₂)₄—OCH₂—(4-iBuS—cHx) | H | H |
| 1-587 | H | H | H | Me | 2 | —(CH₂)₄—OCH₂—(3-cHx—cHx) | H | H |
| 1-588 | H | H | H | Me | 2 | —(CH₂)₄—OCH₂—(4-cHx—cHx) | H | H |
| 1-589 | H | H | H | Me | 2 | —(CH₂)₄—OCH₂—(3-Ph—cHx) | H | H |
| 1-590 | H | H | H | Me | 2 | —(CH₂)₄—OCH₂—(4-Ph—cHx) | H | H |
| 1-591 | H | H | H | Me | 2 | —(CH₂)₄—OCH₂—(2,4-diMe—cHx) | H | H |
| 1-592 | H | H | H | Me | 2 | —(CH₂)₄—OCH₂—(3,4-diMe—cHx) | H | H |
| 1-593 | H | H | H | Me | 2 | —(CH₂)₄—OCH₂—(3,5-diMe—cHx) | H | H |
| 1-594 | H | H | H | Me | 2 | —(CH₂)₄—OCH₂—Ph | H | H |
| 1-595 | H | H | H | Me | 2 | —(CH₂)₄—OCH₂—Ph | Me | H |
| 1-596 | H | H | H | Me | 2 | —(CH₂)₄—OCH₂—Ph | H | Me |
| 1-597 | H | H | H | Me | 2 | —(CH₂)₄—OCH₂—Ph | F | H |
| 1-598 | H | H | H | Me | 2 | —(CH₂)₄—OCH₂—Ph | H | F |
| 1-599 | H | H | Me | Me | 2 | —(CH₂)₄—OCH₂—Ph | H | H |
| 1-600 | Me | H | H | Me | 2 | —(CH₂)₄—OCH₂—Ph | H | H |
| 1-601 | CO₂Me | H | H | Me | 2 | —(CH₂)₄—OCH₂—Ph | H | H |
| 1-602 | H | H | H | Me | 2 | —(CH₂)₄—OCH₂—(3-F—Ph) | H | H |
| 1-603 | H | H | H | Me | 2 | —(CH₂)₄—OCH₂—(4-F—Ph) | H | H |
| 1-604 | H | H | H | Me | 2 | —(CH₂)₄—OCH₂—(4-Cl—Ph) | H | H |
| 1-605 | H | H | H | Me | 2 | —(CH₂)₄—OCH₂—(4-Br—Ph) | H | H |
| 1-606 | H | H | H | Me | 2 | —(CH₂)₄—OCH₂—(3-Me—Ph) | H | H |
| 1-607 | H | H | H | Me | 2 | —(CH₂)₄—OCH₂—(4-Me—Ph) | H | H |
| 1-608 | H | H | H | Me | 2 | —(CH₂)₄—OCH₂—(3-Et—Ph) | H | H |
| 1-609 | H | H | H | Me | 2 | —(CH₂)₄—OCH₂—(4-Et—Ph) | H | H |
| 1-610 | H | H | H | Me | 2 | —(CH₂)₄—OCH₂—(3-Pr—Ph) | H | H |
| 1-611 | H | H | H | Me | 2 | —(CH₂)₄—OCH₂—(4-Pr—Ph) | H | H |
| 1-612 | H | H | H | Me | 2 | —(CH₂)₄—OCH₂—(3-iPr—Ph) | H | H |
| 1-613 | H | H | H | Me | 2 | —(CH₂)₄—OCH₂—(4-iPr—Ph) | H | H |
| 1-614 | H | H | H | Me | 2 | —(CH₂)₄—OCH₂—(3-Bu—Ph) | H | H |
| 1-615 | H | H | H | Me | 2 | —(CH₂)₄—OCH₂—(4-Bu—Ph) | H | H |
| 1-616 | H | H | H | Me | 2 | —(CH₂)₄—OCH₂—(3-CF₃—Ph) | H | H |
| 1-617 | H | H | H | Me | 2 | —(CH₂)₄—OCH₂—(4-CF₃—Ph) | H | H |
| 1-618 | H | H | H | Me | 2 | —(CH₂)₄—OCH₂—(3-MeO—Ph) | H | H |
| 1-619 | H | H | H | Me | 2 | —(CH₂)₄—OCH₂—(4-MeO—Ph) | H | H |
| 1-620 | H | H | H | Me | 2 | —(CH₂)₄—OCH₂—(3-EtO—Ph) | H | H |
| 1-621 | H | H | H | Me | 2 | —(CH₂)₄—OCH₂—(4-EtO—Ph) | H | H |
| 1-622 | H | H | H | Me | 2 | —(CH₂)₄—OCH₂—(3-PrO—Ph) | H | H |
| 1-623 | H | H | H | Me | 2 | —(CH₂)₄—OCH₂—(4-PrO—Ph) | H | H |
| 1-624 | H | H | H | Me | 2 | —(CH₂)₄—OCH₂—(3-iPrO—Ph) | H | H |
| 1-625 | H | H | H | Me | 2 | —(CH₂)₄—OCH₂—(4-iPrO—Ph) | H | H |
| 1-626 | H | H | H | Me | 2 | —(CH₂)₄—OCH₂—[3-(2-Et—PrO)—Ph] | H | H |
| 1-627 | H | H | H | Me | 2 | —(CH₂)₄—OCH₂—[4-(2-Et—PrO)—Ph] | H | H |
| 1-628 | H | H | H | Me | 2 | —(CH₂)₄—OCH₂—(3-iBuO—Ph) | H | H |
| 1-629 | H | H | H | Me | 2 | —(CH₂)₄—OCH₂—(4-iBuO—Ph) | H | H |
| 1-630 | H | H | H | Me | 2 | —(CH₂)₄—OCH₂—(3-MeS—Ph) | H | H |
| 1-631 | H | H | H | Me | 2 | —(CH₂)₄—OCH₂—(4-MeS—Ph) | H | H |
| 1-632 | H | H | H | Me | 2 | —(CH₂)₄—OCH₂—(3-EtS—Ph) | H | H |
| 1-633 | H | H | H | Me | 2 | —(CH₂)₄—OCH₂—(4-EtS—Ph) | H | H |
| 1-634 | H | H | H | Me | 2 | —(CH₂)₄—OCH₂—(3-PrS—Ph) | H | H |
| 1-635 | H | H | H | Me | 2 | —(CH₂)₄—OCH₂—(4-PrS—Ph) | H | H |
| 1-636 | H | H | H | Me | 2 | —(CH₂)₄—OCH₂—(3-iPrS—Ph) | H | H |
| 1-637 | H | H | H | Me | 2 | —(CH₂)₄—OCH₂—(4-iPrS—Ph) | H | H |
| 1-638 | H | H | H | Me | 2 | —(CH₂)₄—OCH₂—[3-(2-Et—PrS)—Ph] | H | H |
| 1-639 | H | H | H | Me | 2 | —(CH₂)₄—OCH₂—[4-(2-Et—PrS)—Ph] | H | H |
| 1-640 | H | H | H | Me | 2 | —(CH₂)₄—OCH₂—(3-iBuS—Ph) | H | H |
| 1-641 | H | H | H | Me | 2 | —(CH₂)₄—OCH₂—(4-iBuS—Ph) | H | H |
| 1-642 | H | H | H | Me | 2 | —(CH₂)₄—OCH₂—(3-cHx—Ph) | H | H |
| 1-643 | H | H | H | Me | 2 | —(CH₂)₄—OCH₂—(4-cHx—Ph) | H | H |
| 1-644 | H | H | H | Me | 2 | —(CH₂)₄—OCH₂—(3-Ph—Ph) | H | H |
| 1-645 | H | H | H | Me | 2 | —(CH₂)₄—OCH₂—(4-Ph—Ph) | H | H |
| 1-646 | H | H | H | Me | 2 | —(CH₂)₄—OCH₂—(2,4-diMe—Ph) | H | H |
| 1-647 | H | H | H | Me | 2 | —(CH₂)₄—OCH₂—(3,4-diMe—Ph) | H | H |
| 1-648 | H | H | H | Me | 2 | —(CH₂)₄—OCH₂—(3,5-diMe—Ph) | H | H |
| 1-649 | H | H | H | Me | 2 | —(CH₂)₅—OCH₂—cHx | H | H |
| 1-650 | H | H | H | Me | 2 | —(CH₂)₅—OCH₂—Ph | H | H |

TABLE 1-continued (Ia)

Structure: R⁴, R³O—CH₂, NR¹R², attached to C, then (CH₂)ₙ—thiophene (with R⁶, R⁷ on ring)—X—Y—R⁵

| Exemp. Compd. No. | R¹ | R² | R³ | R⁴ | n | —X—Y—R⁵ | R⁶ | R⁷ |
|---|---|---|---|---|---|---|---|---|
| 1-651 | H | H | H | Me | 2 | —(CH₂)₆—OCH₂—cHx | H | H |
| 1-652 | H | H | H | Me | 2 | —(CH₂)₆—OCH₂—Ph | H | H |
| 1-653 | H | H | H | Me | 2 | —CH=CH—cHx | H | H |
| 1-654 | H | H | H | Me | 2 | —CH=CH—Ph | H | H |
| 1-655 | H | H | H | Me | 2 | —CH=CH—(CH₂)₂—cHx | H | H |
| 1-656 | H | H | H | Me | 2 | —CH=CH—(CH₂)₂—Ph | H | H |
| 1-657 | H | H | H | Me | 2 | —CH=CH—(CH₂)₃—cHx | H | H |
| 1-658 | H | H | Me | Me | 2 | —CH=CH—(CH₂)₃—cHx | H | H |
| 1-659 | Me | H | H | Me | 2 | —CH=CH—(CH₂)₃—cHx | H | H |
| 1-660 | CO₂Me | H | H | Me | 2 | —CH=CH—(CH₂)₃—cHx | H | H |
| 1-661 | H | H | H | Me | 2 | —CH=CH—(CH₂)₃—(4-F—cHx) | H | H |
| 1-662 | H | H | H | Me | 2 | —CH=CH—(CH₂)₃—(4-Me—cHx) | H | H |
| 1-663 | H | H | H | Me | 2 | —CH=CH—(CH₂)₃—(4-Et—cHx) | H | H |
| 1-664 | H | H | H | Me | 2 | —CH=CH—(CH₂)₃—(4-CF₃—cHx) | H | H |
| 1-665 | H | H | H | Me | 2 | —CH=CH—(CH₂)₃—(4-MeO—cHx) | H | H |
| 1-666 | H | H | H | Me | 2 | —CH=CH—(CH₂)₃—(4-EtO—cHx) | H | H |
| 1-667 | H | H | H | Me | 2 | —CH=CH—(CH₂)₃—(4-MeS—cHx) | H | H |
| 1-668 | H | H | H | Me | 2 | —CH=CH—(CH₂)₃—(4-cHx—cHx) | H | H |
| 1-669 | H | H | H | Me | 2 | —CH=CH—(CH₂)₃—(4-Ph—cHx) | H | H |
| 1-670 | H | H | H | Me | 2 | —CH=CH—(CH₂)₃—Ph | H | H |
| 1-671 | H | H | Me | Me | 2 | —CH=CH—(CH₂)₃—Ph | H | H |
| 1-672 | Me | H | H | Me | 2 | —CH=CH—(CH₂)₃—Ph | H | H |
| 1-673 | CO₂Me | H | H | Me | 2 | —CH=CH—(CH₂)₃—Ph | H | H |
| 1-674 | H | H | H | Me | 2 | —CH=CH—(CH₂)₃—(4-F—Ph) | H | H |
| 1-675 | H | H | H | Me | 2 | —CH=CH—(CH₂)₃—(4-Me—Ph) | H | H |
| 1-676 | H | H | H | Me | 2 | —CH=CH—(CH₂)₃—(4-Et—Ph) | H | H |
| 1-677 | H | H | H | Me | 2 | —CH=CH—(CH₂)₃—(4-CF₃—Ph) | H | H |
| 1-678 | H | H | H | Me | 2 | —CH=CH—(CH₂)₃—(4-MeO—Ph) | H | H |
| 1-679 | H | H | H | Me | 2 | —CH=CH—(CH₂)₃—(4-EtO—Ph) | H | H |
| 1-680 | H | H | H | Me | 2 | —CH=CH—(CH₂)₃—(4-MeS—Ph) | H | H |
| 1-681 | H | H | H | Me | 2 | —CH=CH—(CH₂)₃—(4-cHx—Ph) | H | H |
| 1-682 | H | H | H | Me | 2 | —CH=CH—(CH₂)₃—(4-Ph—Ph) | H | H |
| 1-683 | H | H | H | Me | 2 | —CH=CH—(CH₂)₄—cHx | H | H |
| 1-684 | H | H | Me | Me | 2 | —CH=CH—(CH₂)₄—cHx | H | H |
| 1-685 | Me | H | H | Me | 2 | —CH=CH—(CH₂)₄—cHx | H | H |
| 1-686 | CO₂Me | H | H | Me | 2 | —CH=CH—(CH₂)₄—cHx | H | H |
| 1-687 | H | H | H | Me | 2 | —CH=CH—(CH₂)₄—(4-F—cHx) | H | H |
| 1-688 | H | H | H | Me | 2 | —CH=CH—(CH₂)₄—(4-Me—cHx) | H | H |
| 1-689 | H | H | H | Me | 2 | —CH=CH—(CH₂)₄—(4-Et—cHx) | H | H |
| 1-690 | H | H | H | Me | 2 | —CH=CH—(CH₂)₄—(4-CF₃—cHx) | H | H |
| 1-691 | H | H | H | Me | 2 | —CH=CH—(CH₂)₄—(4-MeO—cHx) | H | H |
| 1-692 | H | H | H | Me | 2 | —CH=CH—(CH₂)₄—(4-EtO—cHx) | H | H |
| 1-693 | H | H | H | Me | 2 | —CH=CH—(CH₂)₄—(4-MeS—cHx) | H | H |
| 1-694 | H | H | H | Me | 2 | —CH=CH—(CH₂)₄—(4-cHx—cHx) | H | H |
| 1-695 | H | H | H | Me | 2 | —CH=CH—(CH₂)₄—(4-Ph—cHx) | H | H |
| 1-696 | H | H | H | Me | 2 | —CH=CH—(CH₂)₄—Ph | H | H |
| 1-697 | H | H | Me | Me | 2 | —CH=CH—(CH₂)₄—Ph | H | H |
| 1-698 | Me | H | H | Me | 2 | —CH=CH—(CH₂)₄—Ph | H | H |
| 1-699 | CO₂Me | H | H | Me | 2 | —CH=CH—(CH₂)₄—Ph | H | H |
| 1-700 | H | H | H | Me | 2 | —CH=CH—(CH₂)₄—(4-F—Ph) | H | H |
| 1-701 | H | H | H | Me | 2 | —CH=CH—(CH₂)₄—(4-Me—Ph) | H | H |
| 1-702 | H | H | H | Me | 2 | —CH=CH—(CH₂)₄—(4-Et—Ph) | H | H |
| 1-703 | H | H | H | Me | 2 | —CH=CH—(CH₂)₄—(4-CF₃—Ph) | H | H |
| 1-704 | H | H | H | Me | 2 | —CH=CH—(CH₂)₄—(4-MeO—Ph) | H | H |
| 1-705 | H | H | H | Me | 2 | —CH=CH—(CH₂)₄—(4-EtO—Ph) | H | H |
| 1-706 | H | H | H | Me | 2 | —CH=CH—(CH₂)₄—(4-MeS—Ph) | H | H |
| 1-707 | H | H | H | Me | 2 | —CH=CH—(CH₂)₄—(4-cHx—Ph) | H | H |
| 1-708 | H | H | H | Me | 2 | —CH=CH—(CH₂)₄—(4-Ph—Ph) | H | H |
| 1-709 | H | H | H | Me | 2 | —CH=CH—(CH₂)₅—cHx | H | H |
| 1-710 | H | H | H | Me | 2 | —CH=CH—(CH₂)₅—Ph | H | H |
| 1-711 | H | H | H | Me | 2 | —CH=CH—(CH₂)₆—cHx | H | H |
| 1-712 | H | H | H | Me | 2 | —CH=CH—(CH₂)₆—Ph | H | H |
| 1-713 | H | H | H | Me | 2 | —C≡C—CH₂O—cHx | H | H |
| 1-714 | H | H | H | Me | 2 | —C≡C—CH₂O—Ph | H | H |
| 1-715 | H | H | H | Me | 2 | —C≡C—(CH₂)₂O—cHx | H | H |

TABLE 1-continued (Ia)

| Exemp. Compd. No. | R¹ | R² | R³ | R⁴ | n | —X—Y—R⁵ | R⁶ | R⁷ |
|---|---|---|---|---|---|---|---|---|
| 1-716 | H | H | H | Me | 2 | —C≡C—(CH$_2$)$_2$O—Ph | H | H |
| 1-717 | H | H | H | Me | 2 | —C≡C—cHx | H | H |
| 1-718 | H | H | Me | Me | 2 | —C≡C—cHx | H | H |
| 1-719 | Me | H | H | Me | 2 | —C≡C—cHx | H | H |
| 1-720 | CO$_2$Me | H | H | Me | 2 | —C≡C—cHx | H | H |
| 1-721 | H | H | H | Me | 2 | —C≡C—(4-F—cHx) | H | H |
| 1-722 | H | H | H | Me | 2 | —C≡C—(4-Me—cHx) | H | H |
| 1-723 | H | H | H | Me | 2 | —C≡C—(4-Et—cHx) | H | H |
| 1-724 | H | H | H | Me | 2 | —C≡C—(4-CF$_3$—cHx) | H | H |
| 1-725 | H | H | H | Me | 2 | —C≡C—(4-MeO—cHx) | H | H |
| 1-726 | H | H | H | Me | 2 | —C≡C—(4-EtO—cHx) | H | H |
| 1-727 | H | H | H | Me | 2 | —C≡C—(4-MeS—cHx) | H | H |
| 1-728 | H | H | H | Me | 2 | —C≡C—(4-cHx—cHx) | H | H |
| 1-729 | H | H | H | Me | 2 | —C≡C—(4-Ph—cHx) | H | H |
| 1-730 | H | H | H | Me | 2 | —C≡C—Ph | H | H |
| 1-731 | H | H | Me | Me | 2 | —C≡C—Ph | H | H |
| 1-732 | Me | H | H | Me | 2 | —C≡C—Ph | H | H |
| 1-733 | CO$_2$Me | H | H | Me | 2 | —C≡C—Ph | H | H |
| 1-734 | H | H | H | Me | 2 | —C≡C—(4-F—Ph) | H | H |
| 1-735 | H | H | H | Me | 2 | —C≡C—(4-Me—Ph) | H | H |
| 1-736 | H | H | H | Me | 2 | —C≡C—(4-Pr—Ph) | H | H |
| 1-737 | H | H | H | Me | 2 | —C≡C—(4-Bu—Ph) | H | H |
| 1-738 | H | H | H | Me | 2 | —C≡C—(4-MeO—Ph) | H | H |
| 1-739 | H | H | H | Me | 2 | —C≡C—(4-EtO—Ph) | H | H |
| 1-740 | H | H | H | Me | 2 | —C≡C—(4-PrO—Ph) | H | H |
| 1-741 | H | H | H | Me | 2 | —C≡C—(4-cHx—Ph) | H | H |
| 1-742 | H | H | H | Me | 2 | —C≡C—(4-Ph—Ph) | H | H |
| 1-743 | H | H | H | Me | 2 | —C≡C—(CH$_2$)$_2$—cHx | H | H |
| 1-744 | H | H | Me | Me | 2 | —C≡C—(CH$_2$)$_2$—cHx | H | H |
| 1-745 | Me | H | H | Me | 2 | —C≡C—(CH$_2$)$_2$—cHx | H | H |
| 1-746 | CO$_2$Me | H | H | Me | 2 | —C≡C—(CH$_2$)$_2$—cHx | H | H |
| 1-747 | H | H | H | Me | 2 | —C≡C—(CH$_2$)$_2$—(4-F—cHx) | H | H |
| 1-748 | H | H | H | Me | 2 | —C≡C—(CH$_2$)$_2$—(4-Me—cHx) | H | H |
| 1-749 | H | H | H | Me | 2 | —C≡C—(CH$_2$)$_2$—(4-Et—cHx) | H | H |
| 1-750 | H | H | H | Me | 2 | —C≡C—(CH$_2$)$_2$—(4-CF$_3$—cHx) | H | H |
| 1-751 | H | H | H | Me | 2 | —C≡C—(CH$_2$)$_2$—(4-MeO—cHx) | H | H |
| 1-752 | H | H | H | Me | 2 | —C≡C—(CH$_2$)$_2$—(4-EtO—cHx) | H | H |
| 1-753 | H | H | H | Me | 2 | —C≡C—(CH$_2$)$_2$—(4-MeS—cHx) | H | H |
| 1-754 | H | H | H | Me | 2 | —C≡C—(CH$_2$)$_2$—(4-cHx—cHx) | H | H |
| 1-755 | H | H | H | Me | 2 | —C≡C—(CH$_2$)$_2$—(4-Ph—cHx) | H | H |
| 1-756 | H | H | H | Me | 2 | —C≡C—(CH$_2$)$_2$—Ph | H | H |
| 1-757 | H | H | Me | Me | 2 | —C≡C—(CH$_2$)$_2$—Ph | H | H |
| 1-758 | Me | H | H | Me | 2 | —C≡C—(CH$_2$)$_2$—Ph | H | H |
| 1-759 | CO$_2$Me | H | H | Me | 2 | —C≡C—(CH$_2$)$_2$—Ph | H | H |
| 1-760 | H | H | H | Me | 2 | —C≡C—(CH$_2$)$_2$—(4-F—Ph) | H | H |
| 1-761 | H | H | H | Me | 2 | —C≡C—(CH$_2$)$_2$—(4-Me—Ph) | H | H |
| 1-762 | H | H | H | Me | 2 | —C≡C—(CH$_2$)$_2$—(4-Et—Ph) | H | H |
| 1-763 | H | H | H | Me | 2 | —C≡C—(CH$_2$)$_2$—(4-CF$_3$—Ph) | H | H |
| 1-764 | H | H | H | Me | 2 | —C≡C—(CH$_2$)$_2$—(4-MeO—Ph) | H | H |
| 1-765 | H | H | H | Me | 2 | —C≡C—(CH$_2$)$_2$—(4-EtO—Ph) | H | H |
| 1-766 | H | H | H | Me | 2 | —C≡C—(CH$_2$)$_2$—(4-MeS—Ph) | H | H |
| 1-767 | H | H | H | Me | 2 | —C≡C—(CH$_2$)$_2$—(4-cHx—Ph) | H | H |
| 1-768 | H | H | H | Me | 2 | —C≡C—(CH$_2$)$_2$—(4-Ph—Ph) | H | H |
| 1-769 | H | H | H | Me | 2 | —C≡C—(CH$_2$)$_3$—cPn | H | H |
| 1-770 | H | H | H | Me | 2 | —C≡C—(CH$_2$)$_3$—cHx | H | H |
| 1-771 | H | H | H | Me | 2 | —C≡C—(CH$_2$)$_3$—cHx | Me | H |
| 1-772 | H | H | H | Me | 2 | —C≡C—(CH$_2$)$_3$—cHx | H | Me |
| 1-773 | H | H | H | Me | 2 | —C≡C—(CH$_2$)$_3$—cHx | F | H |
| 1-774 | H | H | H | Me | 2 | —C≡C—(CH$_2$)$_3$—cHx | H | F |
| 1-775 | H | H | Me | Me | 2 | —C≡C—(CH$_2$)$_3$—cHx | H | H |
| 1-776 | Me | H | H | Me | 2 | —C≡C—(CH$_2$)$_3$—cHx | H | H |
| 1-777 | CO$_2$Me | H | H | Me | 2 | —C≡C—(CH$_2$)$_3$—cHx | H | H |
| 1-778 | H | H | H | Me | 2 | —C≡C—(CH$_2$)$_3$—(3-F—cHx) | H | H |
| 1-779 | H | H | H | Me | 2 | —C≡C—(CH$_2$)$_3$—(4-F—cHx) | H | H |
| 1-780 | H | H | H | Me | 2 | —C≡C—(CH$_2$)$_3$—(4-Cl—cHx) | H | H |

TABLE 1-continued (Ia)

$$\text{structure: } R^4, R^3O, NR^1R^2 \text{ on carbon with } (CH_2)_n \text{ linked to thiophene bearing } R^6, R^7 \text{ and } X-Y-R^5$$

| Exemp. Compd. No. | $R^1$ | $R^2$ | $R^3$ | $R^4$ | n | —X—Y—$R^5$ | $R^6$ | $R^7$ |
|---|---|---|---|---|---|---|---|---|
| 1-781 | H | H | H | Me | 2 | —C≡C—$(CH_2)_3$—(4-Br—cHx) | H | H |
| 1-782 | H | H | H | Me | 2 | —C≡C—$(CH_2)_3$—(3-Me—cHx) | H | H |
| 1-783 | H | H | H | Me | 2 | —C≡C—$(CH_2)_3$—(4-Me—cHx) | H | H |
| 1-784 | H | H | H | Me | 2 | —C≡C—$(CH_2)_3$—(3-Et—cHx) | H | H |
| 1-785 | H | H | H | Me | 2 | —C≡C—$(CH_2)_3$—(4-Et—cHx) | H | H |
| 1-786 | H | H | H | Me | 2 | —C≡C—$(CH_2)_3$—(3-Pr—cHx) | H | H |
| 1-787 | H | H | H | Me | 2 | —C≡C—$(CH_2)_3$—(4-Pr—cHx) | H | H |
| 1-788 | H | H | H | Me | 2 | —C≡C—$(CH_2)_3$—(4-iPr—cHx) | H | H |
| 1-789 | H | H | H | Me | 2 | —C≡C—$(CH_2)_3$—(3-Bu—cHx) | H | H |
| 1-790 | H | H | H | Me | 2 | —C≡C—$(CH_2)_3$—(4-Bu—cHx) | H | H |
| 1-791 | H | H | H | Me | 2 | —C≡C—$(CH_2)_3$—(3-$CF_3$—cHx) | H | H |
| 1-792 | H | H | H | Me | 2 | —C≡C—$(CH_2)_3$—(4-$CF_3$—cHx) | H | H |
| 1-793 | H | H | H | Me | 2 | —C≡C—$(CH_2)_3$—(3-MeO—cHx) | H | H |
| 1-794 | H | H | H | Me | 2 | —C≡C—$(CH_2)_3$—(4-MeO—cHx) | H | H |
| 1-795 | H | H | H | Me | 2 | —C≡C—$(CH_2)_3$—(3-EtO—cHx) | H | H |
| 1-796 | H | H | H | Me | 2 | —C≡C—$(CH_2)_3$—(4-EtO—cHx) | H | H |
| 1-797 | H | H | H | Me | 2 | —C≡C—$(CH_2)_3$—(3-PrO—cHx) | H | H |
| 1-798 | H | H | H | Me | 2 | —C≡C—$(CH_2)_3$—(4-PrO—cHx) | H | H |
| 1-799 | H | H | H | Me | 2 | —C≡C—$(CH_2)_3$—(3-iPrO—cHx) | H | H |
| 1-800 | H | H | H | Me | 2 | —C≡C—$(CH_2)_3$—(4-iPrO—cHx) | H | H |
| 1-801 | H | H | H | Me | 2 | —C≡C—$(CH_2)_3$—[3-(2-Et—PrO)—cHx] | H | H |
| 1-802 | H | H | H | Me | 2 | —C≡C—$(CH_2)_3$—[4-(2-Et—PrO)—cHx] | H | H |
| 1-803 | H | H | H | Me | 2 | —C≡C—$(CH_2)_3$—(3-iBuO—cHx) | H | H |
| 1-804 | H | H | H | Me | 2 | —C≡C—$(CH_2)_3$—(4-iBuO—cHx) | H | H |
| 1-805 | H | H | H | Me | 2 | —C≡C—$(CH_2)_3$—(3-MeS—cHx) | H | H |
| 1-806 | H | H | H | Me | 2 | —C≡C—$(CH_2)_3$—(4-MeS—cHx) | H | H |
| 1-807 | H | H | H | Me | 2 | —C≡C—$(CH_2)_3$—(3-EtS—cHx) | H | H |
| 1-808 | H | H | H | Me | 2 | —C≡C—$(CH_2)_3$—(4-EtS—cHx) | H | H |
| 1-809 | H | H | H | Me | 2 | —C≡C—$(CH_2)_3$—(3-PrS—cHx) | H | H |
| 1-810 | H | H | H | Me | 2 | —C≡C—$(CH_2)_3$—(4-PrS—cHx) | H | H |
| 1-811 | H | H | H | Me | 2 | —C≡C—$(CH_2)_3$—(3-iPrS—cHx) | H | H |
| 1-812 | H | H | H | Me | 2 | —C≡C—$(CH_2)_3$—(4-iPrS—cHx) | H | H |
| 1-813 | H | H | H | Me | 2 | —C≡C—$(CH_2)_3$—[3-(2-Et—PrS)—cHx] | H | H |
| 1-814 | H | H | H | Me | 2 | —C≡C—$(CH_2)_3$—[4-(2-Et—PrS)—cHx] | H | H |
| 1-815 | H | H | H | Me | 2 | —C≡C—$(CH_2)_3$—(3-iBuS—cHx) | H | H |
| 1-816 | H | H | H | Me | 2 | —C≡C—$(CH_2)_3$—(4-iBuS—cHx) | H | H |
| 1-817 | H | H | H | Me | 2 | —C≡C—$(CH_2)_3$—(3-cHx—cHx) | H | H |
| 1-818 | H | H | H | Me | 2 | —C≡C—$(CH_2)_3$—(4-cHx—cHx) | H | H |
| 1-819 | H | H | H | Me | 2 | —C≡C—$(CH_2)_3$—(3-Ph—cHx) | H | H |
| 1-820 | H | H | H | Me | 2 | —C≡C—$(CH_2)_3$—(4-Ph—cHx) | H | H |
| 1-821 | H | H | H | Me | 2 | —C≡C—$(CH_2)_3$—(2,4-diMe—cHx) | H | H |
| 1-822 | H | H | H | Me | 2 | —C≡C—$(CH_2)_3$—(3,4-diMe—cHx) | H | H |
| 1-823 | H | H | H | Me | 2 | —C≡C—$(CH_2)_3$—(3,5-diMe—cHx) | H | H |
| 1-824 | H | H | H | Me | 2 | —C≡C—$(CH_2)_3$—Ph | H | H |
| 1-825 | H | H | H | Me | 2 | —C≡C—$(CH_2)_3$—Ph | Me | H |
| 1-826 | H | H | H | Me | 2 | —C≡C—$(CH_2)_3$—Ph | H | Me |
| 1-827 | H | H | H | Me | 2 | —C≡C—$(CH_2)_3$—Ph | F | H |
| 1-828 | H | H | H | Me | 2 | —C≡C—$(CH_2)_3$—Ph | H | F |
| 1-829 | H | H | Me | Me | 2 | —C≡C—$(CH_2)_3$—Ph | H | H |
| 1-830 | Me | H | H | Me | 2 | —C≡C—$(CH_2)_3$—Ph | H | H |
| 1-831 | $CO_2Me$ | H | H | Me | 2 | —C≡C—$(CH_2)_3$—Ph | H | H |
| 1-832 | H | H | H | Me | 2 | —C≡C—$(CH_2)_3$—(3-F—Ph) | H | H |
| 1-833 | H | H | H | Me | 2 | —C≡C—$(CH_2)_3$—(4-F—Ph) | H | H |
| 1-834 | H | H | H | Me | 2 | —C≡C—$(CH_2)_3$—(4-Cl—Ph) | H | H |
| 1-835 | H | H | H | Me | 2 | —C≡C—$(CH_2)_3$—(4-Br—Ph) | H | H |
| 1-836 | H | H | H | Me | 2 | —C≡C—$(CH_2)_3$—(3-Me—Ph) | H | H |
| 1-837 | H | H | H | Me | 2 | —C≡C—$(CH_2)_3$—(4-Me—Ph) | H | H |
| 1-838 | H | H | H | Me | 2 | —C≡C—$(CH_2)_3$—(3-Et—Ph) | H | H |
| 1-839 | H | H | H | Me | 2 | —C≡C—$(CH_2)_3$—(4-Et—Ph) | H | H |
| 1-840 | H | H | H | Me | 2 | —C≡C—$(CH_2)_3$—(3-Pr—Ph) | H | H |
| 1-841 | H | H | H | Me | 2 | —C≡C—$(CH_2)_3$—(4-Pr—Ph) | H | H |
| 1-842 | H | H | H | Me | 2 | —C≡C—$(CH_2)_3$—(3-iPr—Ph) | H | H |
| 1-843 | H | H | H | Me | 2 | —C≡C—$(CH_2)_3$—(4-iPr—Ph) | H | H |
| 1-844 | H | H | H | Me | 2 | —C≡C—$(CH_2)_3$—(3-Bu—Ph) | H | H |
| 1-845 | H | H | H | Me | 2 | —C≡C—$(CH_2)_3$—(4-Bu—Ph) | H | H |

TABLE 1-continued

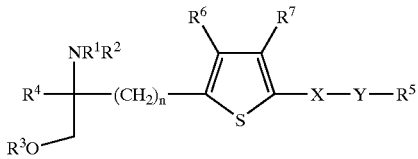
(Ia)

| Exemp. Compd. No. | $R^1$ | $R^2$ | $R^3$ | $R^4$ | n | —X—Y—$R^5$ | $R^6$ | $R^7$ |
|---|---|---|---|---|---|---|---|---|
| 1-846 | H | H | H | Me | 2 | —C≡C—(CH$_2$)$_3$—(3-CF$_3$—Ph) | H | H |
| 1-847 | H | H | H | Me | 2 | —C≡C—(CH$_2$)$_3$—(4-CF$_3$—Ph) | H | H |
| 1-848 | H | H | H | Me | 2 | —C≡C—(CH$_2$)$_3$—(3-MeO—Ph) | H | H |
| 1-849 | H | H | H | Me | 2 | —C≡C—(CH$_2$)$_3$—(4-MeO—Ph) | H | H |
| 1-850 | H | H | H | Me | 2 | —C≡C—(CH$_2$)$_3$—(3-EtO—Ph) | H | H |
| 1-851 | H | H | H | Me | 2 | —C≡C—(CH$_2$)$_3$—(4-EtO—Ph) | H | H |
| 1-852 | H | H | H | Me | 2 | —C≡C—(CH$_2$)$_3$—(3-PrO—Ph) | H | H |
| 1-853 | H | H | H | Me | 2 | —C≡C—(CH$_2$)$_3$—(4-PrO—Ph) | H | H |
| 1-854 | H | H | H | Me | 2 | —C≡C—(CH$_2$)$_3$—(3-iPrO—Ph) | H | H |
| 1-855 | H | H | H | Me | 2 | —C≡C—(CH$_2$)$_3$—(4-iPrO—Ph) | H | H |
| 1-856 | H | H | H | Me | 2 | —C≡C—(CH$_2$)$_3$—[3-(2-Et—PrO)—Ph] | H | H |
| 1-857 | H | H | H | Me | 2 | —C≡C—(CH$_2$)$_3$—[4-(2-Et—PrO)—Ph] | H | H |
| 1-858 | H | H | H | Me | 2 | —C≡C—(CH$_2$)$_3$—(3-iBuO—Ph) | H | H |
| 1-859 | H | H | H | Me | 2 | —C≡C—(CH$_2$)$_3$—(4-iBuO—Ph) | H | H |
| 1-860 | H | H | H | Me | 2 | —C≡C—(CH$_2$)$_3$—(3-MeS—Ph) | H | H |
| 1-861 | H | H | H | Me | 2 | —C≡C—(CH$_2$)$_3$—(4-MeS—Ph) | H | H |
| 1-862 | H | H | H | Me | 2 | —C≡C—(CH$_2$)$_3$—(3-EtS—Ph) | H | H |
| 1-863 | H | H | H | Me | 2 | —C≡C—(CH$_2$)$_3$—(4-EtS—Ph) | H | H |
| 1-864 | H | H | H | Me | 2 | —C≡C—(CH$_2$)$_3$—(3-PrS—Ph) | H | H |
| 1-865 | H | H | H | Me | 2 | —C≡C—(CH$_2$)$_3$—(4-PrS—Ph) | H | H |
| 1-866 | H | H | H | Me | 2 | —C≡C—(CH$_2$)$_3$—(3-iPrS—Ph) | H | H |
| 1-867 | H | H | H | Me | 2 | —C≡C—(CH$_2$)$_3$—(4-iPrS—Ph) | H | H |
| 1-868 | H | H | H | Me | 2 | —C≡C—(CH$_2$)$_3$—[3-(2-Et—PrS)—Ph] | H | H |
| 1-869 | H | H | H | Me | 2 | —C≡C—(CH$_2$)$_3$—[4-(2-Et—PrS)—Ph] | H | H |
| 1-870 | H | H | H | Me | 2 | —C≡C—(CH$_2$)$_3$—(3-iBuS—Ph) | H | H |
| 1-871 | H | H | H | Me | 2 | —C≡C—(CH$_2$)$_3$—(4-iBuS—Ph) | H | H |
| 1-872 | H | H | H | Me | 2 | —C≡C—(CH$_2$)$_3$—(3-cHx—Ph) | H | H |
| 1-873 | H | H | H | Me | 2 | —C≡C—(CH$_2$)$_3$—(4-cHx—Ph) | H | H |
| 1-874 | H | H | H | Me | 2 | —C≡C—(CH$_2$)$_3$—(3-Ph—Ph) | H | H |
| 1-875 | H | H | H | Me | 2 | —C≡C—(CH$_2$)$_3$—(4-Ph—Ph) | H | H |
| 1-876 | H | H | H | Me | 2 | —C≡C—(CH$_2$)$_3$—(2,4-diMe—Ph) | H | H |
| 1-877 | H | H | H | Me | 2 | —C≡C—(CH$_2$)$_3$—(3,4-diMe—Ph) | H | H |
| 1-878 | H | H | H | Me | 2 | —C≡C—(CH$_2$)$_3$—(3,5-diMe—Ph) | H | H |
| 1-879 | H | H | H | Me | 2 | —C≡C—(CH$_2$)$_3$—Np(1) | H | H |
| 1-880 | H | H | H | Me | 2 | —C≡C—(CH$_2$)$_3$—Np(2) | H | H |
| 1-881 | H | H | H | Me | 2 | —C≡C—(CH$_2$)$_4$—cPn | H | H |
| 1-882 | H | H | H | Me | 2 | —C≡C—(CH$_2$)$_4$—cHx | H | H |
| 1-883 | H | H | H | Me | 2 | —C≡C—(CH$_2$)$_4$—cHx | Me | H |
| 1-884 | H | H | H | Me | 2 | —C≡C—(CH$_2$)$_4$—cHx | H | Me |
| 1-885 | H | H | H | Me | 2 | —C≡C—(CH$_2$)$_4$—cHx | F | H |
| 1-886 | H | H | H | Me | 2 | —C≡C—(CH$_2$)$_4$—cHx | H | F |
| 1-887 | H | H | Me | Me | 2 | —C≡C—(CH$_2$)$_4$—cHx | H | H |
| 1-888 | Me | H | H | Me | 2 | —C≡C—(CH$_2$)$_4$—cHx | H | H |
| 1-889 | CO$_2$Me | H | H | Me | 2 | —C≡C—(CH$_2$)$_4$—cHx | H | H |
| 1-890 | H | H | H | Me | 2 | —C≡C—(CH$_2$)$_4$—(3-F—cHx) | H | H |
| 1-891 | H | H | H | Me | 2 | —C≡C—(CH$_2$)$_4$—(4-F—cHx) | H | H |
| 1-892 | H | H | H | Me | 2 | —C≡C—(CH$_2$)$_4$—(4-Cl—cHx) | H | H |
| 1-893 | H | H | H | Me | 2 | —C≡C—(CH$_2$)$_4$—(4-Br—cHx) | H | H |
| 1-894 | H | H | H | Me | 2 | —C≡C—(CH$_2$)$_4$—(3-Me—cHx) | H | H |
| 1-895 | H | H | H | Me | 2 | —C≡C—(CH$_2$)$_4$—(4-Me—cHx) | H | H |
| 1-896 | H | H | H | Me | 2 | —C≡C—(CH$_2$)$_4$—(3-Et—cHx) | H | H |
| 1-897 | H | H | H | Me | 2 | —C≡C—(CH$_2$)$_4$—(4-Et—cHx) | H | H |
| 1-898 | H | H | H | Me | 2 | —C≡C—(CH$_2$)$_4$—(3-Pr—cHx) | H | H |
| 1-899 | H | H | H | Me | 2 | —C≡C—(CH$_2$)$_4$—(4-Pr—cHx) | H | H |
| 1-900 | H | H | H | Me | 2 | —C≡C—(CH$_2$)$_4$—(4-iPr—cHx) | H | H |
| 1-901 | H | H | H | Me | 2 | —C≡C—(CH$_2$)$_4$—(3-Bu—cHx) | H | H |
| 1-902 | H | H | H | Me | 2 | —C≡C—(CH$_2$)$_4$—(4-Bu—cHx) | H | H |
| 1-903 | H | H | H | Me | 2 | —C≡C—(CH$_2$)$_4$—(3-CF$_3$—cHx) | H | H |
| 1-904 | H | H | H | Me | 2 | —C≡C—(CH$_2$)$_4$—(4-CF$_3$—cHx) | H | H |
| 1-905 | H | H | H | Me | 2 | —C≡C—(CH$_2$)$_4$—(3-MeO—cHx) | H | H |
| 1-906 | H | H | H | Me | 2 | —C≡C—(CH$_2$)$_4$—(4-MeO—cHx) | H | H |
| 1-907 | H | H | H | Me | 2 | —C≡C—(CH$_2$)$_4$—(3-EtO—cHx) | H | H |
| 1-908 | H | H | H | Me | 2 | —C≡C—(CH$_2$)$_4$—(4-EtO—cHx) | H | H |
| 1-909 | H | H | H | Me | 2 | —C≡C—(CH$_2$)$_4$—(3-PrO—cHx) | H | H |
| 1-910 | H | H | H | Me | 2 | —C≡C—(CH$_2$)$_4$—(4-PrO—cHx) | H | H |

TABLE 1-continued (Ia)

Structure: R⁴, R³O, NR¹R² attached to carbon with (CH₂)ₙ linked to thiophene ring bearing R⁶, R⁷ and X—Y—R⁵

| Exemp. Compd. No. | R¹ | R² | R³ | R⁴ | n | —X—Y—R⁵ | R⁶ | R⁷ |
|---|---|---|---|---|---|---|---|---|
| 1-911 | H | H | H | Me | 2 | —C≡C—(CH₂)₄—(3-iPrO—cHx) | H | H |
| 1-912 | H | H | H | Me | 2 | —C≡C—(CH₂)₄—(4-iPrO—cHx) | H | H |
| 1-913 | H | H | H | Me | 2 | —C≡C—(CH₂)₄—[3-(2-Et—PrO)—cHx] | H | H |
| 1-914 | H | H | H | Me | 2 | —C≡C—(CH₂)₄—[4-(2-Et—PrO)—cHx] | H | H |
| 1-915 | H | H | H | Me | 2 | —C≡C—(CH₂)₄—(3-iBuO—cHx) | H | H |
| 1-916 | H | H | H | Me | 2 | —C≡C—(CH₂)₄—(4-iBuO—cHx) | H | H |
| 1-917 | H | H | H | Me | 2 | —C≡C—(CH₂)₄—(3-MeS—cHx) | H | H |
| 1-918 | H | H | H | Me | 2 | —C≡C—(CH₂)₄—(4-MeS—cHx) | H | H |
| 1-919 | H | H | H | Me | 2 | —C≡C—(CH₂)₄—(3-EtS—cHx) | H | H |
| 1-920 | H | H | H | Me | 2 | —C≡C—(CH₂)₄—(4-EtS—cHx) | H | H |
| 1-921 | H | H | H | Me | 2 | —C≡C—(CH₂)₄—(3-PrS—cHx) | H | H |
| 1-922 | H | H | H | Me | 2 | —C≡C—(CH₂)₄—(4-PrS—cHx) | H | H |
| 1-923 | H | H | H | Me | 2 | —C≡C—(CH₂)₄—(3-iPrS—cHx) | H | H |
| 1-924 | H | H | H | Me | 2 | —C≡C—(CH₂)₄—(4-iPrS—cHx) | H | H |
| 1-925 | H | H | H | Me | 2 | —C≡C—(CH₂)₄—[3-(2-Et—PrS)—cHx] | H | H |
| 1-926 | H | H | H | Me | 2 | —C≡C—(CH₂)₄—[4-(2-Et—PrS)—cHx] | H | H |
| 1-927 | H | H | H | Me | 2 | —C≡C—(CH₂)₄—(3-iBuS—cHx) | H | H |
| 1-928 | H | H | H | Me | 2 | —C≡C—(CH₂)₄—(4-iBuS—cHx) | H | H |
| 1-929 | H | H | H | Me | 2 | —C≡C—(CH₂)₄—(3-cHx—cHx) | H | H |
| 1-930 | H | H | H | Me | 2 | —C≡C—(CH₂)₄—(4-cHx—cHx) | H | H |
| 1-931 | H | H | H | Me | 2 | —C≡C—(CH₂)₄—(3-Ph—cHx) | H | H |
| 1-932 | H | H | H | Me | 2 | —C≡C—(CH₂)₄—(4-Ph—cHx) | H | H |
| 1-933 | H | H | H | Me | 2 | —C≡C—(CH₂)₄—(2,4-diMe—cHx) | H | H |
| 1-934 | H | H | H | Me | 2 | —C≡C—(CH₂)₄—(3,4-diMe—cHx) | H | H |
| 1-935 | H | H | H | Me | 2 | —C≡C—(CH₂)₄—(3,5-diMe—cHx) | H | H |
| 1-936 | H | H | H | Me | 2 | —C≡C—(CH₂)₄—Ph | H | H |
| 1-937 | H | H | H | Me | 2 | —C≡C—(CH₂)₄—Ph | Me | H |
| 1-938 | H | H | H | Me | 2 | —C≡C—(CH₂)₄—Ph | H | Me |
| 1-939 | H | H | H | Me | 2 | —C≡C—(CH₂)₄—Ph | F | H |
| 1-940 | H | H | H | Me | 2 | —C≡C—(CH₂)₄—Ph | H | F |
| 1-941 | H | H | Me | Me | 2 | —C≡C—(CH₂)₄—Ph | H | H |
| 1-942 | Me | H | H | Me | 2 | —C≡C—(CH₂)₄—Ph | H | H |
| 1-943 | CO₂Me | H | H | Me | 2 | —C≡C—(CH₂)₄—Ph | H | H |
| 1-944 | H | H | H | Me | 2 | —C≡C—(CH₂)₄—(3-F—Ph) | H | H |
| 1-945 | H | H | H | Me | 2 | —C≡C—(CH₂)₄—(4-F—Ph) | H | H |
| 1-946 | H | H | H | Me | 2 | —C≡C—(CH₂)₄—(4-Cl—Ph) | H | H |
| 1-947 | H | H | H | Me | 2 | —C≡C—(CH₂)₄—(4-Br—Ph) | H | H |
| 1-948 | H | H | H | Me | 2 | —C≡C—(CH₂)₄—(3-Me—Ph) | H | H |
| 1-949 | H | H | H | Me | 2 | —C≡C—(CH₂)₄—(4-Me—Ph) | H | H |
| 1-950 | H | H | H | Me | 2 | —C≡C—(CH₂)₄—(3-Et—Ph) | H | H |
| 1-951 | H | H | H | Me | 2 | —C≡C—(CH₂)₄—(4-Et—Ph) | H | H |
| 1-952 | H | H | H | Me | 2 | —C≡C—(CH₂)₄—(3-Pr—Ph) | H | H |
| 1-953 | H | H | H | Me | 2 | —C≡C—(CH₂)₄—(4-Pr—Ph) | H | H |
| 1-954 | H | H | H | Me | 2 | —C≡C—(CH₂)₄—(3-iPr—Ph) | H | H |
| 1-955 | H | H | H | Me | 2 | —C≡C—(CH₂)₄—(4-iPr—Ph) | H | H |
| 1-956 | H | H | H | Me | 2 | —C≡C—(CH₂)₄—(3-Bu—Ph) | H | H |
| 1-957 | H | H | H | Me | 2 | —C≡C—(CH₂)₄—(4-Bu—Ph) | H | H |
| 1-958 | H | H | H | Me | 2 | —C≡C—(CH₂)₄—(3-CF₃—Ph) | H | H |
| 1-959 | H | H | H | Me | 2 | —C≡C—(CH₂)₄—(4-CF₃—Ph) | H | H |
| 1-960 | H | H | H | Me | 2 | —C≡C—(CH₂)₄—(3-MeO—Ph) | H | H |
| 1-961 | H | H | H | Me | 2 | —C≡C—(CH₂)₄—(4-MeO—Ph) | H | H |
| 1-962 | H | H | H | Me | 2 | —C≡C—(CH₂)₄—(3-EtO—Ph) | H | H |
| 1-963 | H | H | H | Me | 2 | —C≡C—(CH₂)₄—(4-EtO—Ph) | H | H |
| 1-964 | H | H | H | Me | 2 | —C≡C—(CH₂)₄—(3-PrO—Ph) | H | H |
| 1-965 | H | H | H | Me | 2 | —C≡C—(CH₂)₄—(4-PrO—Ph) | H | H |
| 1-966 | H | H | H | Me | 2 | —C≡C—(CH₂)₄—(3-iPrOPh) | H | H |
| 1-967 | H | H | H | Me | 2 | —C≡C—(CH₂)₄—(4-iPrO—Ph) | H | H |
| 1-968 | H | H | H | Me | 2 | —C≡C—(CH₂)₄—[3-(2-Et—PrO)—Ph] | H | H |
| 1-969 | H | H | H | Me | 2 | —C≡C—(CH₂)₄—[4-(2-Et—PrO)—Ph] | H | H |
| 1-970 | H | H | H | Me | 2 | —C≡C—(CH₂)₄—(3-iBuO—Ph) | H | H |
| 1-971 | H | H | H | Me | 2 | —C≡C—(CH₂)₄—(4-iBuO—Ph) | H | H |
| 1-972 | H | H | H | Me | 2 | —C≡C—(CH₂)₄—(3-MeS—Ph) | H | H |
| 1-973 | H | H | H | Me | 2 | —C≡C—(CH₂)₄—(4-MeS—Ph) | H | H |
| 1-974 | H | H | H | Me | 2 | —C≡C—(CH₂)₄—(3-EtS—Ph) | H | H |
| 1-975 | H | H | H | Me | 2 | —C≡C—(CH₂)₄—(4-EtS—Ph) | H | H |

TABLE 1-continued (Ia)

| Exemp. Compd. No. | $R^1$ | $R^2$ | $R^3$ | $R^4$ | n | —X—Y—$R^5$ | $R^6$ | $R^7$ |
|---|---|---|---|---|---|---|---|---|
| 1-976 | H | H | H | Me | 2 | —C≡C—(CH$_2$)$_4$—(3-PrS—Ph) | H | H |
| 1-977 | H | H | H | Me | 2 | —C≡C—(CH$_2$)$_4$—(4-PrS—Ph) | H | H |
| 1-978 | H | H | H | Me | 2 | —C≡C—(CH$_2$)$_4$—(3-iPrS—Ph) | H | H |
| 1-979 | H | H | H | Me | 2 | —C≡C—(CH$_2$)$_4$—(4-iPrS—Ph) | H | H |
| 1-980 | H | H | H | Me | 2 | —C≡C—(CH$_2$)$_4$—[3-(2-Et—PrS)—Ph] | H | H |
| 1-981 | H | H | H | Me | 2 | —C≡C—(CH$_2$)$_4$—[4-(2-Et—PrS)—Ph] | H | H |
| 1-982 | H | H | H | Me | 2 | —C≡C—(CH$_2$)$_4$—(3-iBuS—Ph) | H | H |
| 1-983 | H | H | H | Me | 2 | —C≡C—(CH$_2$)$_4$—(4-iBuS—Ph) | H | H |
| 1-984 | H | H | H | Me | 2 | —C≡C—(CH$_2$)$_4$—(3-cHx—Ph) | H | H |
| 1-985 | H | H | H | Me | 2 | —C≡C—(CH$_2$)$_4$—(4-cHx—Ph) | H | H |
| 1-986 | H | H | H | Me | 2 | —C≡C—(CH$_2$)$_4$—(3-Ph—Ph) | H | H |
| 1-987 | H | H | H | Me | 2 | —C≡C—(CH$_2$)$_4$—(4-Ph—Ph) | H | H |
| 1-988 | H | H | H | Me | 2 | —C≡C—(CH$_2$)$_4$—(2,4-diMe—Ph) | H | H |
| 1-989 | H | H | H | Me | 2 | —C≡C—(CH$_2$)$_4$—(3,4-diMe—Ph) | H | H |
| 1-990 | H | H | H | Me | 2 | —C≡C—(CH$_2$)$_4$—(3,5-diMe—Ph) | H | H |
| 1-991 | H | H | H | Me | 2 | —C≡C—(CH$_2$)$_4$—Np(1) | H | H |
| 1-992 | H | H | H | Me | 2 | —C≡C—(CH$_2$)$_4$—Np(2) | H | H |
| 1-993 | H | H | H | Me | 2 | —C≡C—(CH$_2$)$_5$—cHx | H | H |
| 1-994 | H | H | Me | Me | 2 | —C≡C—(CH$_2$)$_5$—cHx | H | H |
| 1-995 | Me | H | H | Me | 2 | —C≡C—(CH$_2$)$_5$—cHx | H | H |
| 1-996 | CO$_2$Me | H | H | Me | 2 | —C≡C—(CH$_2$)$_5$—cHx | H | H |
| 1-997 | H | H | H | Me | 2 | —C≡C—(CH$_2$)$_5$—(4-F—cHx) | H | H |
| 1-998 | H | H | H | Me | 2 | —C≡C—(CH$_2$)$_5$—(4-Me—cHx) | H | H |
| 1-999 | H | H | H | Me | 2 | —C≡C—(CH$_2$)$_5$—(4-Et—cHx) | H | H |
| 1-1000 | H | H | H | Me | 2 | —C≡C—(CH$_2$)$_5$—(4-CF$_3$—cHx) | H | H |
| 1-1001 | H | H | H | Me | 2 | —C≡C—(CH$_2$)$_5$—(4-MeO—cHx) | H | H |
| 1-1002 | H | H | H | Me | 2 | —C≡C—(CH$_2$)$_5$—(4-EtO—cHx) | H | H |
| 1-1003 | H | H | H | Me | 2 | —C≡C—(CH$_2$)$_5$—(4-MeS—cHx) | H | H |
| 1-1004 | H | H | H | Me | 2 | —C≡C—(CH$_2$)$_5$—(4-cHx—cHx) | H | H |
| 1-1005 | H | H | H | Me | 2 | —C≡C—(CH$_2$)$_5$—(4-Ph—cHx) | H | H |
| 1-1006 | H | H | H | Me | 2 | —C≡C—(CH$_2$)$_5$—Ph | H | H |
| 1-1007 | H | H | Me | Me | 2 | —C≡C—(CH$_2$)$_5$—Ph | H | H |
| 1-1008 | Me | H | H | Me | 2 | —C≡C—(CH$_2$)$_5$—Ph | H | H |
| 1-1009 | CO$_2$Me | H | H | Me | 2 | —C≡C—(CH$_2$)$_5$—Ph | H | H |
| 1-1010 | H | H | H | Me | 2 | —C≡C—(CH$_2$)$_5$—(4-F—Ph) | H | H |
| 1-1011 | H | H | H | Me | 2 | —C≡C—(CH$_2$)$_5$—(4-Me—Ph) | H | H |
| 1-1012 | H | H | H | Me | 2 | —C≡C—(CH$_2$)$_5$—(4-Et—Ph) | H | H |
| 1-1013 | H | H | H | Me | 2 | —C≡C—(CH$_2$)$_5$—(4-CF$_3$—Ph) | H | H |
| 1-1014 | H | H | H | Me | 2 | —C≡C—(CH$_2$)$_5$—(4-MeO—Ph) | H | H |
| 1-1015 | H | H | H | Me | 2 | —C≡C—(CH$_2$)$_5$—(4-EtO—Ph) | H | H |
| 1-1016 | H | H | H | Me | 2 | —C≡C—(CH$_2$)$_5$—(4-MeS—Ph) | H | H |
| 1-1017 | H | H | H | Me | 2 | —C≡C—(CH$_2$)$_5$—(4-cHx—Ph) | H | H |
| 1-1018 | H | H | H | Me | 2 | —C≡C—(CH$_2$)$_5$—(4-Ph—Ph) | H | H |
| 1-1019 | H | H | H | Me | 2 | —C≡C—(CH$_2$)$_6$—cHx | H | H |
| 1-1020 | H | H | Me | Me | 2 | —C≡C—(CH$_2$)$_6$—cHx | H | H |
| 1-1021 | Me | H | H | Me | 2 | —C≡C—(CH$_2$)$_6$—cHx | H | H |
| 1-1022 | CO$_2$Me | H | H | Me | 2 | —C≡C—(CH$_2$)$_6$—cHx | H | H |
| 1-1023 | H | H | H | Me | 2 | —C≡C—(CH$_2$)$_6$—(4-F—cHx) | H | H |
| 1-1024 | H | H | H | Me | 2 | —C≡C—(CH$_2$)$_6$—(4-Me—cHx) | H | H |
| 1-1025 | H | H | H | Me | 2 | —C≡C—(CH$_2$)$_6$—(4-Et—cHx) | H | H |
| 1-1026 | H | H | H | Me | 2 | —C≡C—(CH$_2$)$_6$—(4-CF$_3$—cHx) | H | H |
| 1-1027 | H | H | H | Me | 2 | —C≡C—(CH$_2$)$_6$—(4-MeO—cHx) | H | H |
| 1-1028 | H | H | H | Me | 2 | —C≡C—(CH$_2$)$_6$—(4-EtO—cHx) | H | H |
| 1-1029 | H | H | H. | Me | 2 | —C≡C—(CH$_2$)$_6$—(4-MeS—cHx) | H | H |
| 1-1030 | H | H | H | Me | 2 | —C≡C—(CH$_2$)$_6$—(4-cHx—cHx) | H | H |
| 1-1031 | H | H | H | Me | 2 | —C≡C—(CH$_2$)$_6$—(4-Ph—cHx) | H | H |
| 1-1032 | H | H | H | Me | 2 | —C≡C—(CH$_2$)$_6$—Ph | H | H |
| 1-1033 | H | H | Me | Me | 2 | —C≡C—(CH$_2$)$_6$—Ph | H | H |
| 1-1034 | Me | H | H | Me | 2 | —C≡C—(CH$_2$)$_6$—Ph | H | H |
| 1-1035 | CO$_2$Me | H | H | Me | 2 | —C≡C—(CH$_2$)$_6$—Ph | H | H |
| 1-1036 | H | H | H | Me | 2 | —C≡C—(CH$_2$)$_6$—(4-F—Ph) | H | H |
| 1-1037 | H | H | H | Me | 2 | —C≡C—(CH$_2$)$_6$—(4-Me—Ph) | H | H |
| 1-1038 | H | H | H | Me | 2 | —C≡C—(CH$_2$)$_6$—(4-Et—Ph) | H | H |
| 1-1039 | H | H | H | Me | 2 | —C≡C—(CH$_2$)$_6$—(4-CF$_3$—Ph) | H | H |
| 1-1040 | H | H | H | Me | 2 | —C≡C—(CH$_2$)$_6$—(4-MeO—Ph) | H | H |

TABLE 1-continued (Ia)

Structure: R⁴, R³O–CH₂, (CH₂)n, NR¹R², thiophene ring with R⁶, R⁷, and X—Y—R⁵ substituent.

| Exemp. Compd. No. | R¹ | R² | R³ | R⁴ | n | —X—Y—R⁵ | R⁶ | R⁷ |
|---|---|---|---|---|---|---|---|---|
| 1-1041 | H | H | H | Me | 2 | —C≡C—(CH₂)₆—(4-EtO—Ph) | H | H |
| 1-1042 | H | H | H | Me | 2 | —C≡C—(CH₂)₆—(4-MeS—Ph) | H | H |
| 1-1043 | H | H | H | Me | 2 | —C≡C—(CH₂)₆—(4-cHx—Ph) | H | H |
| 1-1044 | H | H | H | Me | 2 | —C≡C—(CH₂)₆—(4-Ph—Ph) | H | H |
| 1-1045 | H | H | H | Me | 2 | —C≡C—CH₂—O—cHx | H | H |
| 1-1046 | H | H | Me | Me | 2 | —C≡C—CH₂—O—cHx | H | H |
| 1-1047 | Me | H | H | Me | 2 | —C≡C—CH₂—O—cHx | H | H |
| 1-1048 | CO₂Me | H | H | Me | 2 | —C≡C—CH₂—O—cHx | H | H |
| 1-1049 | H | H | H | Me | 2 | —C≡C—CH₂—O—(4-F—cHx) | H | H |
| 1-1050 | H | H | H | Me | 2 | —C≡C—CH₂—O—(4-Me—cHx) | H | H |
| 1-1051 | H | H | H | Me | 2 | —C≡C—CH₂—O—(4-Et—cHx) | H | H |
| 1-1052 | H | H | H | Me | 2 | —C≡C—CH₂—O—(4-CF₃—cHx) | H | H |
| 1-1053 | H | H | H | Me | 2 | —C≡C—CH₂—O—(4-MeO—cHx) | H | H |
| 1-1054 | H | H | H | Me | 2 | —C≡C—CH₂—O—(4-EtO—cHx) | H | H |
| 1-1055 | H | H | H | Me | 2 | —C≡C—CH₂—O—(4-MeS—cHx) | H | H |
| 1-1056 | H | H | H | Me | 2 | —C≡C—CH₂—O—(4-cHx—cHx) | H | H |
| 1-1057 | H | H | H | Me | 2 | —C≡C—CH₂—O—(4-Ph—cHx) | H | H |
| 1-1058 | H | H | H | Me | 2 | —C≡C—CH₂—O—Ph | H | H |
| 1-1059 | H | H | Me | Me | 2 | —C≡C—CH₂—O—Ph | H | H |
| 1-1060 | Me | H | H | Me | 2 | —C≡C—CH₂—O—Ph | H | H |
| 1-1061 | CO₂Me | H | H | Me | 2 | —C≡C—CH₂—O—Ph | H | H |
| 1-1062 | H | H | H | Me | 2 | —C≡C—CH₂—O—(4-F—Ph) | H | H |
| 1-1063 | H | H | H | Me | 2 | —C≡C—CH₂—O—(4-Me—Ph) | H | H |
| 1-1064 | H | H | H | Me | 2 | —C≡C—CH₂—O—(4-Et—Ph) | H | H |
| 1-1065 | H | H | H | Me | 2 | —C≡C—CH₂—O—(4-CF₃—Ph) | H | H |
| 1-1066 | H | H | H | Me | 2 | —C≡C—CH₂—O—(4-MeO—Ph) | H | H |
| 1-1067 | H | H | H | Me | 2 | —C≡C—CH₂—O—(4-EtO—Ph) | H | H |
| 1-1068 | H | H | H | Me | 2 | —C≡C—CH₂—O—(4-MeS—Ph) | H | H |
| 1-1069 | H | H | H | Me | 2 | —C≡C—CH₂—O—(4-cHx—Ph) | H | H |
| 1-1070 | H | H | H | Me | 2 | —C≡C—CH₂—O—(4-Ph—Ph) | H | H |
| 1-1071 | H | H | H | Me | 2 | —C≡C—(CH₂)₂O—cPn | H | H |
| 1-1072 | H | H | H | Me | 2 | —C≡C—(CH₂)₂O—cHx | H | H |
| 1-1073 | H | H | H | Me | 2 | —C≡C—(CH₂)₂O—cHx | Me | H |
| 1-1074 | H | H | H | Me | 2 | —C≡C—(CH₂)₂O—cHx | H | Me |
| 1-1075 | H | H | H | Me | 2 | —C≡C—(CH₂)₂O—cHx | F | H |
| 1-1076 | H | H | H | Me | 2 | —C≡C—(CH₂)₂O—cHx | H | F |
| 1-1077 | H | H | Me | Me | 2 | —C≡C—(CH₂)₂O—cHx | H | H |
| 1-1078 | Me | H | H | Me | 2 | —C≡C—(CH₂)₂O—cHx | H | H |
| 1-1079 | CO₂Me | H | H | Me | 2 | —C≡C—(CH₂)₂O—cHx | H | H |
| 1-1080 | H | H | H | Me | 2 | —C≡C—(CH₂)₂O—(3-F—cHx) | H | H |
| 1-1081 | H | H | H | Me | 2 | —C≡C—(CH₂)₂O—(4-F—cHx) | H | H |
| 1-1082 | H | H | H | Me | 2 | —C≡C—(CH₂)₂O—(4-Cl—cHx) | H | H |
| 1-1083 | H | H | H | Me | 2 | —C≡C—(CH₂)₂O—(4-Br—cHx) | H | H |
| 1-1084 | H | H | H | Me | 2 | —C≡C—(CH₂)₂O—(3-Me—cHx) | H | H |
| 1-1085 | H | H | H | Me | 2 | —C≡C—(CH₂)₂O—(4-Me—cHx) | H | H |
| 1-1086 | H | H | H | Me | 2 | —C≡C—(CH₂)₂O—(3-Et—cHx) | H | H |
| 1-1087 | H | H | H | Me | 2 | —C≡C—(CH₂)₂O—(4-Et—cHx) | H | H |
| 1-1088 | H | H | H | Me | 2 | —C≡C—(CH₂)₂O—(3-Pr—cHx) | H | H |
| 1-1089 | H | H | H | Me | 2 | —C≡C—(CH₂)₂O—(4-Pr—cHx) | H | H |
| 1-1090 | H | H | H | Me | 2 | —C≡C—(CH₂)₂O—(4-iPr—cHx) | H | H |
| 1-1091 | H | H | H | Me | 2 | —C≡C—(CH₂)₂O—(3-Bu—cHx) | H | H |
| 1-1092 | H | H | H | Me | 2 | —C≡C—(CH₂)₂O—(4-Bu—cHx) | H | H |
| 1-1093 | H | H | H | Me | 2 | —C≡C—(CH₂)₂O—(3-CF₃—cHx) | H | H |
| 1-1094 | H | H | H | Me | 2 | —C≡C—(CH₂)₂O—(4-CF₃—cHx) | H | H |
| 1-1095 | H | H | H | Me | 2 | —C≡C—(CH₂)₂O—(3-MeO—cHx) | H | H |
| 1-1096 | H | H | H | Me | 2 | —C≡C—(CH₂)₂O—(4-MeO—cHx) | H | H |
| 1-1097 | H | H | H | Me | 2 | —C≡C—(CH₂)₂O—(3-EtO—cHx) | H | H |
| 1-1098 | H | H | H | Me | 2 | —C≡C—(CH₂)₂O—(4-EtO—cHx) | H | H |
| 1-1099 | H | H | H | Me | 2 | —C≡C—(CH₂)₂O—(3-PrO—cHx) | H | H |
| 1-1100 | H | H | H | Me | 2 | —C≡C—(CH₂)₂O—(4-PrO—cHx) | H | H |
| 1-1101 | H | H | H | Me | 2 | —C≡C—(CH₂)₂O—(3-iPrO—cHx) | H | H |
| 1-1102 | H | H | H | Me | 2 | —C≡C—(CH₂)₂O—(4-iPrO—cHx) | H | H |
| 1-1103 | H | H | H | Me | 2 | —C≡C—(CH₂)₂O—[3-(2-Et—PrO)—cHx] | H | H |
| 1-1104 | H | H | H | Me | 2 | —C≡C—(CH₂)₂O—[4-(2-Et—PrO)—cHx] | H | H |
| 1-1105 | H | H | H | Me | 2 | —C≡C—(CH₂)₂O—(3-iBuO—cHx) | H | H |

TABLE 1-continued

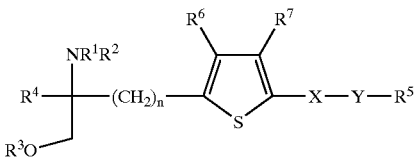

(Ia)

| Exemp. Compd. No. | $R^1$ | $R^2$ | $R^3$ | $R^4$ | n | —X—Y—$R^5$ | $R^6$ | $R^7$ |
|---|---|---|---|---|---|---|---|---|
| 1-1106 | H | H | H | Me | 2 | —C≡C—(CH$_2$)$_2$O—(4-iBuO—cHx) | H | H |
| 1-1107 | H | H | H | Me | 2 | —C≡C—(CH$_2$)$_2$O—(3-MeS—cHx) | H | H |
| 1-1108 | H | H | H | Me | 2 | —C≡C—(CH$_2$)$_2$O—(4-MeS—cHx) | H | H |
| 1-1109 | H | H | H | Me | 2 | —C≡C—(CH$_2$)$_2$O—(3-EtS—cHx) | H | H |
| 1-1110 | H | H | H | Me | 2 | —C≡C—(CH$_2$)$_2$O—(4-EtS—cHx) | H | H |
| 1-1111 | H | H | H | Me | 2 | —C≡C—(CH$_2$)$_2$O—(3-PrS—cHx) | H | H |
| 1-1112 | H | H | H | Me | 2 | —C≡C—(CH$_2$)$_2$O—(4-PrS—cHx) | H | H |
| 1-1113 | H | H | H | Me | 2 | —C≡C—(CH$_2$)$_2$O—(3-iPrS—cHx) | H | H |
| 1-1114 | H | H | H | Me | 2 | —C≡C—(CH$_2$)$_2$O—(4-iPrS—cHx) | H | H |
| 1-1115 | H | H | H | Me | 2 | —C≡C—(CH$_2$)$_2$O—[3-(2-Et—PrS)—cHx] | H | H |
| 1-1116 | H | H | H | Me | 2 | —C≡C—(CH$_2$)$_2$O—[4-(2-Et—PrS)—cHx] | H | H |
| 1-1117 | H | H | H | Me | 2 | —C≡C—(CH$_2$)$_2$O—(3-iBuS—cHx) | H | H |
| 1-1118 | H | H | H | Me | 2 | —C≡C—(CH$_2$)$_2$O—(4-iBuS—cHx) | H | H |
| 1-1119 | H | H | H | Me | 2 | —C≡C—(CH$_2$)$_2$O—(3-cHx—cHx) | H | H |
| 1-1120 | H | H | H | Me | 2 | —C≡C—(CH$_2$)$_2$O—(4-cHx—cHx) | H | H |
| 1-1121 | H | H | H | Me | 2 | —C≡C—(CH$_2$)$_2$O—(3-Ph—cHx) | H | H |
| 1-1122 | H | H | H | Me | 2 | —C≡C—(CH$_2$)$_2$O—(4-Ph—cHx) | H | H |
| 1-1123 | H | H | H | Me | 2 | —C≡C—(CH$_2$)$_2$O—(2,4-diMe—cHx) | H | H |
| 1-1124 | H | H | H | Me | 2 | —C≡C—(CH$_2$)$_2$O—(3,4-diMe—cHx) | H | H |
| 1-1125 | H | H | H | Me | 2 | —C≡C—(CH$_2$)$_2$O—(3,5-diMe—cHx) | H | H |
| 1-1126 | H | H | H | Me | 2 | —C≡C—(CH$_2$)$_2$O—Ph | H | H |
| 1-1127 | H | H | H | Me | 2 | —C≡C—(CH$_2$)$_2$O—Ph | Me | H |
| 1-1128 | H | H | H | Me | 2 | —C≡C—(CH$_2$)$_2$O—Ph | H | Me |
| 1-1129 | H | H | H | Me | 2 | —C≡C—(CH$_2$)$_2$O—Ph | F | H |
| 1-1130 | H | H | H | Me | 2 | —C≡C—(CH$_2$)$_2$O—Ph | H | F |
| 1-1131 | H | H | Me | Me | 2 | —C≡C—(CH$_2$)$_2$O—Ph | H | H |
| 1-1132 | Me | H | H | Me | 2 | —C≡C—(CH$_2$)$_2$O—Ph | H | H |
| 1-1133 | CO$_2$Me | H | H | Me | 2 | —C≡C—(CH$_2$)$_2$O—Ph | H | H |
| 1-1134 | H | H | H | Me | 2 | —C≡C—(CH$_2$)$_2$O—(3-F—Ph) | H | H |
| 1-1135 | H | H | H | Me | 2 | —C≡C—(CH$_2$)$_2$O—(4-F—Ph) | H | H |
| 1-1136 | H | H | H | Me | 2 | —C≡C—(CH$_2$)$_2$O—(4-Cl—Ph) | H | H |
| 1-1137 | H | H | H | Me | 2 | —C≡C—(CH$_2$)$_2$O—(4-Br—Ph) | H | H |
| 1-1138 | H | H | H | Me | 2 | —C≡C—(CH$_2$)$_2$O—(3-Me—Ph) | H | H |
| 1-1139 | H | H | H | Me | 2 | —C≡C—(CH$_2$)$_2$O—(4-Me—Ph) | H | H |
| 1-1140 | H | H | H | Me | 2 | —C≡C—(CH$_2$)$_2$O—(3-Et—Ph) | H | H |
| 1-1141 | H | H | H | Me | 2 | —C≡C—(CH$_2$)$_2$O—(4-Et—Ph) | H | H |
| 1-1142 | H | H | H | Me | 2 | —C≡C—(CH$_2$)$_2$O—(3-Pr—Ph) | H | H |
| 1-1143 | H | H | H | Me | 2 | —C≡C—(CH$_2$)$_2$O—(4-Pr—Ph) | H | H |
| 1-1144 | H | H | H | Me | 2 | —C≡C—(CH$_2$)$_2$O—(3-iPr—Ph) | H | H |
| 1-1145 | H | H | H | Me | 2 | —C≡C—(CH$_2$)$_2$O—(4-iPr—Ph) | H | H |
| 1-1146 | H | H | H | Me | 2 | —C≡C—(CH$_2$)$_2$O—(3-Bu—Ph) | H | H |
| 1-1147 | H | H | H | Me | 2 | —C≡C—(CH$_2$)$_2$O—(4-Bu—Ph) | H | H |
| 1-1148 | H | H | H | Me | 2 | —C≡C—(CH$_2$)$_2$O—(3-CF$_3$—Ph) | H | H |
| 1-1149 | H | H | H | Me | 2 | —C≡C—(CH$_2$)$_2$O—(4-CF$_3$—Ph) | H | H |
| 1-1150 | H | H | H | Me | 2 | —C≡C—(CH$_2$)$_2$O—(3-MeO—Ph) | H | H |
| 1-1151 | H | H | H | Me | 2 | —C≡C—(CH$_2$)$_2$O—(4-MeO—Ph) | H | H |
| 1-1152 | H | H | H | Me | 2 | —C≡C—(CH$_2$)$_2$O—(3-EtO—Ph) | H | H |
| 1-1153 | H | H | H | Me | 2 | —C≡C—(CH$_2$)$_2$O—(4-EtO—Ph) | H | H |
| 1-1154 | H | H | H | Me | 2 | —C≡C—(CH$_2$)$_2$O—(3-PrO—Ph) | H | H |
| 1-1155 | H | H | H | Me | 2 | —C≡C—(CH$_2$)$_2$O—(4-PrO—Ph) | H | H |
| 1-1156 | H | H | H | Me | 2 | —C≡C—(CH$_2$)$_2$O—(3-iPrO—Ph) | H | H |
| 1-1157 | H | H | H | Me | 2 | —C≡C—(CH$_2$)$_2$O—(4-iPrO—Ph) | H | H |
| 1-1158 | H | H | H | Me | 2 | —C≡C—(CH$_2$)$_2$O—[3-(2-Et—PrO)—Ph] | H | H |
| 1-1159 | H | H | H | Me | 2 | —C≡C—(CH$_2$)$_2$O—[4-(2-Et—PrO)—Ph] | H | H |
| 1-1160 | H | H | H | Me | 2 | —C≡C—(CH$_2$)$_2$O—(3-iBuO—Ph) | H | H |
| 1-1161 | H | H | H | Me | 2 | —C≡C—(CH$_2$)$_2$O—(4-iBuO—Ph) | H | H |
| 1-1162 | H | H | H | Me | 2 | —C≡C—(CH$_2$)$_2$O—(3-MeS—Ph) | H | H |
| 1-1163 | H | H | H | Me | 2 | —C≡C—(CH$_2$)$_2$O—(4-MeS—Ph) | H | H |
| 1-1164 | H | H | H | Me | 2 | —C≡C—(CH$_2$)$_2$O—(3-EtS—Ph) | H | H |
| 1-1165 | H | H | H | Me | 2 | —C≡C—(CH$_2$)$_2$O—(4-EtS—Ph) | H | H |
| 1-1166 | H | H | H | Me | 2 | —C≡C—(CH$_2$)$_2$O—(3-PrS—Ph) | H | H |
| 1-1167 | H | H | H | Me | 2 | —C≡C—(CH$_2$)$_2$O—(4-PrS—Ph) | H | H |
| 1-1168 | H | H | H | Me | 2 | —C≡C—(CH$_2$)$_2$O—(3-iPrS—Ph) | H | H |
| 1-1169 | H | H | H | Me | 2 | —C≡C—(CH$_2$)$_2$O—(4-iPrS—Ph) | H | H |
| 1-1170 | H | H | H | Me | 2 | —C≡C—(CH$_2$)$_2$O—[3-(2-Et—PrS)—Ph] | H | H |

TABLE 1-continued

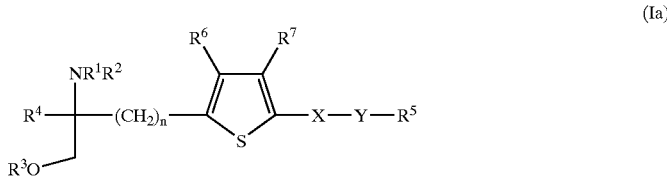

(Ia)

| Exemp. Compd. No. | R¹ | R² | R³ | R⁴ | n | —X—Y—R⁵ | R⁶ | R⁷ |
|---|---|---|---|---|---|---|---|---|
| 1-1171 | H | H | H | Me | 2 | —C≡C—(CH$_2$)$_2$O—[4-(2-Et—PrS)—Ph] | H | H |
| 1-1172 | H | H | H | Me | 2 | —C≡C—(CH$_2$)$_2$O—(3-iBuS—Ph) | H | H |
| 1-1173 | H | H | H | Me | 2 | —C≡C—(CH$_2$)$_2$O—(4-iBuS—Ph) | H | H |
| 1-1174 | H | H | H | Me | 2 | —C≡C—(CH$_2$)$_2$O—(3-cHx—Ph) | H | H |
| 1-1175 | H | H | H | Me | 2 | —C≡C—(CH$_2$)$_2$O—(4-cHx—Ph) | H | H |
| 1-1176 | H | H | H | Me | 2 | —C≡C—(CH$_2$)$_2$O—(3-Ph—Ph) | H | H |
| 1-1177 | H | H | H | Me | 2 | —C≡C—(CH$_2$)$_2$O—(4-Ph—Ph) | H | H |
| 1-1178 | H | H | H | Me | 2 | —C≡C—(CH$_2$)$_2$O—(2,4-diMe—Ph) | H | H |
| 1-1179 | H | H | H | Me | 2 | —C≡C—(CH$_2$)$_2$O—(3,4-diMe—Ph) | H | H |
| 1-1180 | H | H | H | Me | 2 | —C≡C—(CH$_2$)$_2$O—(3,5-diMe—Ph) | H | H |
| 1-1181 | H | H | H | Me | 2 | —C≡C—(CH$_2$)$_3$O—cHx | H | H |
| 1-1182 | H | H | H | Me | 2 | —C≡C—(CH$_2$)$_3$O—Ph | H | H |
| 1-1183 | H | H | H | Me | 2 | —C≡C—(CH$_2$)$_4$O—cHx | H | H |
| 1-1184 | H | H | H | Me | 2 | —C≡C—(CH$_2$)$_4$O—Ph | H | H |
| 1-1185 | H | H | H | Me | 2 | —C≡C—CH$_2$—OCH$_2$—cHx | H | H |
| 1-1186 | H | H | Me | Me | 2 | —C≡C—CH$_2$—OCH$_2$—cHx | H | H |
| 1-1187 | Me | H | H | Me | 2 | —C≡C—CH$_2$—OCH$_2$—cHx | H | H |
| 1-1188 | CO$_2$Me | H | H | Me | 2 | —C≡C—CH$_2$—OCH$_2$—cHx | H | H |
| 1-1189 | H | H | H | Me | 2 | —C≡C—CH$_2$—OCH$_2$—(4-F—cHx) | H | H |
| 1-1190 | H | H | H | Me | 2 | —C≡C—CH$_2$—OCH$_2$—(4-Me—cHx) | H | H |
| 1-1191 | H | H | H | Me | 2 | —C≡C—CH$_2$—OCH$_2$—(4-Et—cHx) | H | H |
| 1-1192 | H | H | H | Me | 2 | —C≡C—CH$_2$—OCH$_2$—(4-CF$_3$—cHx) | H | H |
| 1-1193 | H | H | H | Me | 2 | —C≡C—CH$_2$—OCH$_2$—(4-MeO—cHx) | H | H |
| 1-1194 | H | H | H | Me | 2 | —C≡C—CH$_2$—OCH$_2$—(4-EtO—cHx) | H | H |
| 1-1195 | H | H | H | Me | 2 | —C≡C—CH$_2$—OCH$_2$—(4-MeS—cHx) | H | H |
| 1-1196 | H | H | H | Me | 2 | —C≡C—CH$_2$—OCH$_2$—(4-cHx—cHx) | H | H |
| 1-1197 | H | H | H | Me | 2 | —C≡C—CH$_2$—OCH$_2$—(4-Ph—cHx) | H | H |
| 1-1198 | H | H | H | Me | 2 | —C≡C—CH$_2$—OCH$_2$—Ph | H | H |
| 1-1199 | H | H | Me | Me | 2 | —C≡C—CH$_2$—OCH$_2$—Ph | H | H |
| 1-1200 | Me | H | H | Me | 2 | —C≡C—CH$_2$—OCH$_2$—Ph | H | H |
| 1-1201 | CO$_2$Me | H | H | Me | 2 | —C≡C—CH$_2$—OCH$_2$—Ph | H | H |
| 1-1202 | H | H | H | Me | 2 | —C≡C—CH$_2$—OCH$_2$—(4-F—Ph) | H | H |
| 1-1203 | H | H | H | Me | 2 | —C≡C—CH$_2$—OCH$_2$—(4-Me—Ph) | H | H |
| 1-1204 | H | H | H | Me | 2 | —C≡C—CH$_2$—OCH$_2$—(4-Et—Ph) | H | H |
| 1-1205 | H | H | H | Me | 2 | —C≡C—CH$_2$—OCH$_2$—(4-CF$_3$—Ph) | H | H |
| 1-1206 | H | H | H | Me | 2 | —C≡C—CH$_2$—OCH$_2$—(4-MeO—Ph) | H | H |
| 1-1207 | H | H | H | Me | 2 | —C≡C—CH$_2$—OCH$_2$—(4-EtO—Ph) | H | H |
| 1-1208 | H | H | H | Me | 2 | —C≡C—CH$_2$—OCH$_2$—(4-MeS—Ph) | H | H |
| 1-1209 | H | H | H | Me | 2 | —C≡C—CH$_2$—OCH$_2$—(4-cHx—Ph) | H | H |
| 1-1210 | H | H | H | Me | 2 | —C≡C—CH$_2$—OCH$_2$—(4-Ph—Ph) | H | H |
| 1-1211 | H | H | H | Me | 2 | —C≡C—(CH$_2$)$_2$—OCH$_2$—cPn | H | H |
| 1-1212 | H | H | H | Me | 2 | —C≡C—(CH$_2$)$_2$—OCH$_2$—cHx | H | H |
| 1-1213 | H | H | H | Me | 2 | —C≡C—(CH$_2$)$_2$—OCH$_2$—cHx | Me | H |
| 1-1214 | H | H | H | Me | 2 | —C≡C—(CH$_2$)$_2$—OCH$_2$—cHx | H | Me |
| 1-1215 | H | H | H | Me | 2 | —C≡C—(CH$_2$)$_2$—OCH$_2$—cHx | F | H |
| 1-1216 | H | H | H | Me | 2 | —C≡C—(CH$_2$)$_2$—OCH$_2$—cHx | H | F |
| 1-1217 | H | H | Me | Me | 2 | —C≡C—(CH$_2$)$_2$—OCH$_2$—CH$_2$—cHx | H | H |
| 1-1218 | Me | H | H | Me | 2 | —C≡C—(CH$_2$)$_2$—OCH$_2$—cHx | H | H |
| 1-1219 | CO$_2$Me | H | H | Me | 2 | —C≡C—(CH$_2$)$_2$—OCH$_2$—cHx | H | H |
| 1-1220 | H | H | H | Me | 2 | —C≡C—(CH$_2$)$_2$—OCH$_2$—(3-F—cHx) | H | H |
| 1-1221 | H | H | H | Me | 2 | —C≡C—(CH$_2$)$_2$—OCH$_2$—(4-F—cHx) | H | H |
| 1-1222 | H | H | H | Me | 2 | —C≡C—(CH$_2$)$_2$—OCH$_2$—(4-Cl—cHx) | H | H |
| 1-1223 | H | H | H | Me | 2 | —C≡C—(CH$_2$)$_2$—OCH$_2$—(4-Br—cHx) | H | H |
| 1-1224 | H | H | H | Me | 2 | —C≡C—(CH$_2$)$_2$—OCH$_2$—(3-Me—cHx) | H | H |
| 1-1225 | H | H | H | Me | 2 | —C≡C—(CH$_2$)$_2$—OCH$_2$—(4-Me—cHx) | H | H |
| 1-1226 | H | H | H | Me | 2 | —C≡C—(CH$_2$)$_2$—OCH$_2$—(3-Et—cHx) | H | H |
| 1-1227 | H | H | H | Me | 2 | —C≡C—(CH$_2$)$_2$—OCH$_2$—(4-Et—cHx) | H | H |
| 1-1228 | H | H | H | Me | 2 | —C≡C—(CH$_2$)$_2$—OCH$_2$—(3-Pr—cHx) | H | H |
| 1-1229 | H | H | H | Me | 2 | —C≡C—(CH$_2$)$_2$—OCH$_2$—(4-Pr—cHx) | H | H |
| 1-1230 | H | H | H | Me | 2 | —C≡C—(CH$_2$)$_2$—OCH$_2$—(4-iPr—cHx) | H | H |
| 1-1231 | H | H | H | Me | 2 | —C≡C—(CH$_2$)$_2$—OCH$_2$—(3-Bu—cHx) | H | H |
| 1-1232 | H | H | H | Me | 2 | —C≡C—(CH$_2$)$_2$—OCH$_2$—(4-Bu—cHx) | H | H |
| 1-1233 | H | H | H | Me | 2 | —C≡C—(CH$_2$)$_2$—OCH$_2$—(3-CF$_3$—cHx) | H | H |
| 1-1234 | H | H | H | Me | 2 | —C≡C—(CH$_2$)$_2$—OCH$_2$—(4-CF$_3$—cHx) | H | H |
| 1-1235 | H | H | H | Me | 2 | —C≡C—(CH$_2$)$_2$—OCH$_2$—(3-MeO—cHx) | H | H |

TABLE 1-continued (Ia)

| Exemp. Compd. No. | R¹ | R² | R³ | R⁴ | n | —X—Y—R⁵ | R⁶ | R⁷ |
|---|---|---|---|---|---|---|---|---|
| 1-1236 | H | H | H | Me | 2 | —C≡C—(CH$_2$)$_2$—OCH$_2$—(4-MeO—cHx) | H | H |
| 1-1237 | H | H | H | Me | 2 | —C≡C—(CH$_2$)$_2$—OCH$_2$—(3-EtO—cHx) | H | H |
| 1-1238 | H | H | H | Me | 2 | —C≡C—(CH$_2$)$_2$—OCH$_2$—(4-EtO—cHx) | H | H |
| 1-1239 | H | H | H | Me | 2 | —C≡C—(CH$_2$)$_2$—OCH$_2$—(3-PrO—cHx) | H | H |
| 1-1240 | H | H | H | Me | 2 | —C≡C—(CH$_2$)$_2$—OCH$_2$—(4-PrO—cHx) | H | H |
| 1-1241 | H | H | H | Me | 2 | —C≡C—(CH$_2$)$_2$—OCH$_2$—(3-iPrO—cHx) | H | H |
| 1-1242 | H | H | H | Me | 2 | —C≡C—(CH$_2$)$_2$—OCH$_2$—(4-iPrO—cHx) | H | H |
| 1-1243 | H | H | H | Me | 2 | —C≡C—(CH$_2$)$_2$—OCH$_2$—[3-(2-Et—PrO)cHx] | H | H |
| 1-1244 | H | H | H | Me | 2 | —C≡C—(CH$_2$)$_2$—OCH$_2$—[4-(2-Et—PrO)cHx] | H | H |
| 1-1245 | H | H | H | Me | 2 | —C≡C—(CH$_2$)$_2$—OCH$_2$—(3-iBuO—cHx) | H | H |
| 1-1246 | H | H | H | Me | 2 | —C≡C—(CH$_2$)$_2$—OCH$_2$—(4-iBuO—cHx) | H | H |
| 1-1247 | H | H | H | Me | 2 | —C≡C—(CH$_2$)$_2$—OCH$_2$—(3-MeS—cHx) | H | H |
| 1-1248 | H | H | H | Me | 2 | —C≡C—(CH$_2$)$_2$—OCH$_2$—(4-MeS—cHx) | H | H |
| 1-1249 | H | H | H | Me | 2 | —C≡C—(CH$_2$)$_2$—OCH$_2$—(3-EtS—cHx) | H | H |
| 1-1250 | H | H | H | Me | 2 | —C≡C—(CH$_2$)$_2$—OCH$_2$—(4-EtS—cHx) | H | H |
| 1-1251 | H | H | H | Me | 2 | —C≡C—(CH$_2$)$_2$—OCH$_2$—(3-PrS—cHx) | H | H |
| 1-1252 | H | H | H | Me | 2 | —C≡C—(CH$_2$)$_2$—OCH$_2$—(4-PrS—cHx) | H | H |
| 1-1253 | H | H | H | Me | 2 | —C≡C—(CH$_2$)$_2$—OCH$_2$—(3-iPrS—cHx) | H | H |
| 1-1254 | H | H | H | Me | 2 | —C≡C—(CH$_2$)$_2$—OCH$_2$—(4-iPrS—cHx) | H | H |
| 1-1255 | H | H | H | Me | 2 | —C≡C—(CH$_2$)$_2$—OCH$_2$—[3-(2-Et—PrS)cHx] | H | H |
| 1-1256 | H | H | H | Me | 2 | —C≡C—(CH$_2$)$_2$—OCH$_2$—[4-(2-Et—PrS)cHx] | H | H |
| 1-1257 | H | H | H | Me | 2 | —C≡C—(CH$_2$)$_2$—OCH$_2$—(3-iBuS—cHx) | H | H |
| 1-1258 | H | H | H | Me | 2 | —C≡C—(CH$_2$)$_2$—OCH$_2$—(4-iBuS—cHx) | H | H |
| 1-1259 | H | H | H | Me | 2 | —C≡C—(CH$_2$)$_2$—OCH$_2$—(3-cHx—cHx) | H | H |
| 1-1260 | H | H | H | Me | 2 | —C≡C—(CH$_2$)$_2$—OCH$_2$—(4-cHx—cHx) | H | H |
| 1-1261 | H | H | H | Me | 2 | —C≡C—(CH$_2$)$_2$—OCH$_2$—(3-Ph—cHx) | H | H |
| 1-1262 | H | H | H | Me | 2 | —C≡C—(CH$_2$)$_2$—OCH$_2$—(4-Ph—cHx) | H | H |
| 1-1263 | H | H | H | Me | 2 | —C≡C—(CH$_2$)$_2$—OCH$_2$—(2,4-diMe—cHx) | H | H |
| 1-1264 | H | H | H | Me | 2 | —C≡C—(CH$_2$)$_2$—OCH$_2$—(3,4-diMe—cHx) | H | H |
| 1-1265 | H | H | H | Me | 2 | —C≡C—(CH$_2$)$_2$—OCH$_2$—(3,5-diMe—cHx) | H | H |
| 1-1266 | H | H | H | Me | 2 | —C≡C—(CH$_2$)$_2$—OCH$_2$—Ph | H | H |
| 1-1267 | H | H | H | Me | 2 | —C≡C—(CH$_2$)$_2$—OCH$_2$—Ph | Me | H |
| 1-1268 | H | H | H | Me | 2 | —C≡C—(CH$_2$)$_2$—OCH$_2$—Ph | H | Me |
| 1-1269 | H | H | H | Me | 2 | —C≡C—(CH$_2$)$_2$—OCH$_2$—Ph | F | H |
| 1-1270 | H | H | H | Me | 2 | —C≡C—(CH$_2$)$_2$—OCH$_2$—Ph | H | F |
| 1-1271 | H | H | Me | Me | 2 | —C≡C—(CH$_2$)$_2$—OCH$_2$—CH$_2$—Ph | H | H |
| 1-1272 | Me | H | H | Me | 2 | —C≡C—(CH$_2$)$_2$—OCH$_2$—Ph | H | H |
| 1-1273 | CO$_2$Me | H | H | Me | 2 | —C≡C—(CH$_2$)$_2$—OCH$_2$—Ph | H | H |
| 1-1274 | H | H | H | Me | 2 | —C≡C—(CH$_2$)$_2$—OCH$_2$—(3-F—Ph) | H | H |
| 1-1275 | H | H | H | Me | 2 | —C≡C—(CH$_2$)$_2$—OCH$_2$—(4-F—Ph) | H | H |
| 1-1276 | H | H | H | Me | 2 | —C≡C—(CH$_2$)$_2$—OCH$_2$—(4-Cl—Ph) | H | H |
| 1-1277 | H | H | H | Me | 2 | —C≡C—(CH$_2$)$_2$—OCH$_2$—(4-Br—Ph) | H | H |
| 1-1278 | H | H | H | Me | 2 | —C≡C—(CH$_2$)$_2$—OCH$_2$—(3-Me—Ph) | H | H |
| 1-1279 | H | H | H | Me | 2 | —C≡C—(CH$_2$)$_2$—OCH$_2$—(4-Me—Ph) | H | H |
| 1-1280 | H | H | H | Me | 2 | —C≡C—(CH$_2$)$_2$—OCH$_2$—(3-Et—Ph) | H | H |
| 1-1281 | H | H | H | Me | 2 | —C≡C—(CH$_2$)$_2$—OCH$_2$—(4-Et—Ph) | H | H |
| 1-1282 | H | H | H | Me | 2 | —C≡C—(CH$_2$)$_2$—OCH$_2$—(3-Pr—Ph) | H | H |
| 1-1283 | H | H | H | Me | 2 | —C≡C—(CH$_2$)$_2$—OCH$_2$—(4-Pr—Ph) | H | H |
| 1-1284 | H | H | H | Me | 2 | —C≡C—(CH$_2$)$_2$—OCH$_2$—(3-iPr—Ph) | H | H |
| 1-1285 | H | H | H | Me | 2 | —C≡C—(CH$_2$)$_2$—OCH$_2$—(4-iPr—Ph) | H | H |
| 1-1286 | H | H | H | Me | 2 | —C≡C—(CH$_2$)$_2$—OCH$_2$—(3-Bu—Ph) | H | H |
| 1-1287 | H | H | H | Me | 2 | —C≡C—(CH$_2$)$_2$—OCH$_2$—(4-Bu—Ph) | H | H |
| 1-1288 | H | H | H | Me | 2 | —C≡C—(CH$_2$)$_2$—OCH$_2$—(3-CF$_3$—Ph) | H | H |
| 1-1289 | H | H | H | Me | 2 | —C≡C—(CH$_2$)$_2$—OCH$_2$—(4-CF$_3$—Ph) | H | H |
| 1-1290 | H | H | H | Me | 2 | —C≡C—(CH$_2$)$_2$—OCH$_2$—(3-MeO—Ph) | H | H |
| 1-1291 | H | H | H | Me | 2 | —C≡C—(CH$_2$)$_2$—OCH$_2$—(4-MeO—Ph) | H | H |
| 1-1292 | H | H | H | Me | 2 | —C≡C—(CH$_2$)$_2$—OCH$_2$—(3-EtO—Ph) | H | H |
| 1-1293 | H | H | H | Me | 2 | —C≡C—(CH$_2$)$_2$—OCH$_2$—(4-EtO—Ph) | H | H |
| 1-1294 | H | H | H | Me | 2 | —C≡C—(CH$_2$)$_2$—OCH$_2$—(3-PrO—Ph) | H | H |
| 1-1295 | H | H | H | Me | 2 | —C≡C—(CH$_2$)$_2$—OCH$_2$—(4-PrO—Ph) | H | H |
| 1-1296 | H | H | H | Me | 2 | —C≡C—(CH$_2$)$_2$—OCH$_2$—(3-iPrO—Ph) | H | H |
| 1-1297 | H | H | H | Me | 2 | —C≡C—(CH$_2$)$_2$—OCH$_2$—(4-iPrO—Ph) | H | H |
| 1-1298 | H | H | H | Me | 2 | —C≡C—(CH$_2$)$_2$—OCH$_2$—[3-(2-Et—PrO)Ph] | H | H |
| 1-1299 | H | H | H | Me | 2 | —C≡C—(CH$_2$)$_2$—OCH$_2$—[4-(2-Et—PrO)Ph] | H | H |
| 1-1300 | H | H | H | Me | 2 | —C≡C—(CH$_2$)$_2$—OCH$_2$—(3-iBuO—Ph) | H | H |

TABLE 1-continued (Ia)

Structure: R⁴, NR¹R², R³O— attached to carbon with (CH₂)ₙ linked to thiophene bearing R⁶, R⁷ and X—Y—R⁵

| Exemp. Compd. No. | R¹ | R² | R³ | R⁴ | n | —X—Y—R⁵ | R⁶ | R⁷ |
|---|---|---|---|---|---|---|---|---|
| 1-1301 | H | H | H | Me | 2 | —C≡C—(CH₂)₂—OCH₂—(4-iBuO—Ph) | H | H |
| 1-1302 | H | H | H | Me | 2 | —C≡C—(CH₂)₂—OCH₂—(3-MeS—Ph) | H | H |
| 1-1303 | H | H | H | Me | 2 | —C≡C—(CH₂)₂—OCH₂—(4-MeS—Ph) | H | H |
| 1-1304 | H | H | H | Me | 2 | —C≡C—(CH₂)₂—OCH₂—(3-EtS—Ph) | H | H |
| 1-1305 | H | H | H | Me | 2 | —C≡C—(CH₂)₂—OCH₂—(4-EtS—Ph) | H | H |
| 1-1306 | H | H | H | Me | 2 | —C≡C—(CH₂)₂—OCH₂—(3-PrS—Ph) | H | H |
| 1-1307 | H | H | H | Me | 2 | —C≡C—(CH₂)₂—OCH₂—(4-PrS—Ph) | H | H |
| 1-1308 | H | H | H | Me | 2 | —C≡C—(CH₂)₂—OCH₂—(3-iPrS—Ph) | H | H |
| 1-1309 | H | H | H | Me | 2 | —C≡C—(CH₂)₂—OCH₂—(4-iPrS—Ph) | H | H |
| 1-1310 | H | H | H | Me | 2 | —C≡C—(CH₂)₂—OCH₂—[3-(2-Et—PrS)Ph] | H | H |
| 1-1311 | H | H | H | Me | 2 | —C≡C—(CH₂)₂—OCH₂—[4-(2-Et—PrS)Ph] | H | H |
| 1-1312 | H | H | H | Me | 2 | —C≡C—(CH₂)₂—OCH₂—(3-iBuS—Ph) | H | H |
| 1-1313 | H | H | H | Me | 2 | —C≡C—(CH₂)₂—OCH₂—(4-iBuS—Ph) | H | H |
| 1-1314 | H | H | H | Me | 2 | —C≡C—(CH₂)₂—OCH₂—(3-cHx—Ph) | H | H |
| 1-1315 | H | H | H | Me | 2 | —C≡C—(CH₂)₂—OCH₂—(4-cHx—Ph) | H | H |
| 1-1316 | H | H | H | Me | 2 | —C≡C—(CH₂)₂—OCH₂—(3-Ph—Ph) | H | H |
| 1-1317 | H | H | H | Me | 2 | —C≡C—(CH₂)₂—OCH₂—(4-Ph—Ph) | H | H |
| 1-1318 | H | H | H | Me | 2 | —C≡C—(CH₂)₂—OCH₂—(2,4-diMe—Ph) | H | H |
| 1-1319 | H | H | H | Me | 2 | —C≡C—(CH₂)₂—OCH₂—(3,4-diMe—Ph) | H | H |
| 1-1320 | H | H | H | Me | 2 | —C≡C—(CH₂)₂—OCH₂—(3,5-diMe—Ph) | H | H |
| 1-1321 | H | H | H | Me | 2 | —C≡C—(CH₂)₃—OCH₂—cHx | H | H |
| 1-1322 | H | H | H | Me | 2 | —C≡C—(CH₂)₃—OCH₂—Ph | H | H |
| 1-1323 | H | H | H | Me | 2 | —C≡C—(CH₂)₄—OCH₂—cHx | H | H |
| 1-1324 | H | H | H | Me | 2 | —C≡C—(CH₂)₄—OCH₂—Ph | H | H |
| 1-1325 | H | H | H | Me | 2 | —CO—CH₂—(4-cHx—Ph) | H | H |
| 1-1326 | H | H | H | Me | 2 | —CO—CH₂—(4-Ph—Ph) | H | H |
| 1-1327 | H | H | H | Me | 2 | —CO—(CH₂)₂—cHx | H | H |
| 1-1328 | H | H | H | Me | 2 | —CO—(CH₂)₂—Ph | H | H |
| 1-1329 | H | H | H | Me | 2 | —CO—(CH₂)₃—cHx | H | H |
| 1-1330 | H | H | H | Me | 2 | —CO—(CH₂)₃—Ph | H | H |
| 1-1331 | H | H | H | Me | 2 | —CO—(CH₂)₄—cHx | H | H |
| 1-1332 | H | H | Me | Me | 2 | —CO—(CH₂)₄—cHx | H | H |
| 1-1333 | Me | H | H | Me | 2 | —CO—(CH₂)₄—cHx | H | H |
| 1-1334 | CO₂Me | H | H | Me | 2 | —CO—(CH₂)₄—cHx | H | H |
| 1-1335 | H | H | H | Me | 2 | —CO—(CH₂)₄—(4-F—cHx) | H | H |
| 1-1336 | H | H | H | Me | 2 | —CO—(CH₂)₄—(4-Me—cHx) | H | H |
| 1-1337 | H | H | H | Me | 2 | —CO—(CH₂)₄—(4-Et—cHx) | H | H |
| 1-1338 | H | H | H | Me | 2 | —CO—(CH₂)₄—(4-CF₃—cHx) | H | H |
| 1-1339 | H | H | H | Me | 2 | —CO—(CH₂)₄—(4-MeO—cHx) | H | H |
| 1-1340 | H | H | H | Me | 2 | —CO—(CH₂)₄—(4-EtO—cHx) | H | H |
| 1-1341 | H | H | H | Me | 2 | —CO—(CH₂)₄—(4-MeS—cHx) | H | H |
| 1-1342 | H | H | H | Me | 2 | —CO—(CH₂)₄—(4-cHx—cHx) | H | H |
| 1-1343 | H | H | H | Me | 2 | —CO—(CH₂)₄—(4-Ph—cHx) | H | H |
| 1-1344 | H | H | H | Me | 2 | —CO—(CH₂)₄—Ph | H | H |
| 1-1345 | H | H | Me | Me | 2 | —CO—(CH₂)₄—Ph | H | H |
| 1-1346 | Me | H | H | Me | 2 | —CO—(CH₂)₄—Ph | H | H |
| 1-1347 | CO₂Me | H | H | Me | 2 | —CO—(CH₂)₄—Ph | H | H |
| 1-1348 | H | H | H | Me | 2 | —CO—(CH₂)₄—(4-F—Ph) | H | H |
| 1-1349 | H | H | H | Me | 2 | —CO—(CH₂)₄—(4-Me—Ph) | H | H |
| 1-1350 | H | H | H | Me | 2 | —CO—(CH₂)₄—(4-Et—Ph) | H | H |
| 1-1351 | H | H | H | Me | 2 | —CO—(CH₂)₄—(4-CF₃—Ph) | H | H |
| 1-1352 | H | H | H | Me | 2 | —CO—(CH₂)₄—(4-MeO—Ph) | H | H |
| 1-1353 | H | H | H | Me | 2 | —CO—(CH₂)₄—(4-EtO—Ph) | H | H |
| 1-1354 | H | H | H | Me | 2 | —CO—(CH₂)₄—(4-MeS—Ph) | H | H |
| 1-1355 | H | H | H | Me | 2 | —CO—(CH₂)₄—(4-cHx—Ph) | H | H |
| 1-1356 | H | H | H | Me | 2 | —CO—(CH₂)₄—(4-Ph—Ph) | H | H |
| 1-1357 | H | H | H | Me | 2 | —CO—(CH₂)₅—cHx | H | H |
| 1-1358 | H | H | Me | Me | 2 | —CO—(CH₂)₅—cHx | H | H |
| 1-1359 | Me | H | H | Me | 2 | —CO—(CH₂)₅—cHx | H | H |
| 1-1360 | CO₂Me | H | H | Me | 2 | —CO—(CH₂)₅—cHx | H | H |
| 1-1361 | H | H | H | Me | 2 | —CO—(CH₂)₅—(4-F—cHx) | H | H |
| 1-1362 | H | H | H | Me | 2 | —CO—(CH₂)₅—(4-Me—cHx) | H | H |
| 1-1363 | H | H | H | Me | 2 | —CO—(CH₂)₅—(4-Et—cHx) | H | H |
| 1-1364 | H | H | H | Me | 2 | —CO—(CH₂)₅—(4-CF₃—cHx) | H | H |
| 1-1365 | H | H | H | Me | 2 | —CO—(CH₂)₅—(4-MeO—cHx) | H | H |

TABLE 1-continued (Ia)

Structure: $R^4$, $NR^1R^2$, $R^3O$—CH2— attached to carbon with $(CH_2)_n$ linker to thiophene ring bearing $R^6$, $R^7$ and X—Y—$R^5$

| Exemp. Compd. No. | R¹ | R² | R³ | R⁴ | n | —X—Y—R⁵ | R⁶ | R⁷ |
|---|---|---|---|---|---|---|---|---|
| 1-1366 | H | H | H | Me | 2 | —CO—(CH₂)₅—(4-EtO—cHx) | H | H |
| 1-1367 | H | H | H | Me | 2 | —CO—(CH₂)₅—(4-MeS—cHx) | H | H |
| 1-1368 | H | H | H | Me | 2 | —CO—(CH₂)₅—(4-cHx—cHx) | H | H |
| 1-1369 | H | H | H | Me | 2 | —CO—(CH₂)₅—(4-Ph—cHx) | H | H |
| 1-1370 | H | H | H | Me | 2 | —CO—(CH₂)₅—Ph | H | H |
| 1-1371 | H | H | Me | Me | 2 | —CO—(CH₂)₅—Ph | H | H |
| 1-1372 | Me | H | H | Me | 2 | —CO—(CH₂)₅—Ph | H | H |
| 1-1373 | CO₂Me | H | H | Me | 2 | —CO—(CH₂)₅—Ph | H | H |
| 1-1374 | H | H | H | Me | 2 | —CO—(CH₂)₅—(4-F—Ph) | H | H |
| 1-1375 | H | H | H | Me | 2 | —CO—(CH₂)₅—(4-Me—Ph) | H | H |
| 1-1376 | H | H | H | Me | 2 | —CO—(CH₂)₅—(4-Et—Ph) | H | H |
| 1-1377 | H | H | H | Me | 2 | —CO—(CH₂)₅—(4-CF₃—Ph) | H | H |
| 1-1378 | H | H | H | Me | 2 | —CO—(CH₂)₅—(4-MeO—Ph) | H | H |
| 1-1379 | H | H | H | Me | 2 | —CO—(CH₂)₅—(4-EtO—Ph) | H | H |
| 1-1380 | H | H | H | Me | 2 | —CO—(CH₂)₅—(4-MeS—Ph) | H | H |
| 1-1381 | H | H | H | Me | 2 | —CO—(CH₂)₅—(4-cHx—Ph) | H | H |
| 1-1382 | H | H | H | Me | 2 | —CO—(CH₂)₅—(4-Ph—Ph) | H | H |
| 1-1383 | H | H | H | Me | 2 | —CO—(CH₂)₆—cHx | H | H |
| 1-1384 | H | H | H | Me | 2 | —CO—(CH₂)₆—Ph | H | H |
| 1-1385 | H | H | H | Me | 2 | —CO—(CH₂)₇—cHx | H | H |
| 1-1386 | H | H | H | Me | 2 | —CO—(CH₂)₇—Ph | H | H |
| 1-1387 | H | H | H | Me | 2 | —CO—(CH₂)₂—O—cHx | H | H |
| 1-1388 | H | H | Me | Me | 2 | —CO—(CH₂)₂—O—cHx | H | H |
| 1-1389 | Me | H | H | Me | 2 | —CO—(CH₂)₂—O—cHx | H | H |
| 1-1390 | CO₂Me | H | H | Me | 2 | —CO—(CH₂)₂—O—cHx | H | H |
| 1-1391 | H | H | H | Me | 2 | —CO—(CH₂)₂—O—(4-F—cHx) | H | H |
| 1-1392 | H | H | H | Me | 2 | —CO—(CH₂)₂—O—(4-Me—cHx) | H | H |
| 1-1393 | H | H | H | Me | 2 | —CO—(CH₂)₂—O—(4-Et—cHx) | H | H |
| 1-1394 | H | H | H | Me | 2 | —CO—(CH₂)₂—O—(4-CF₃—cHx) | H | H |
| 1-1395 | H | H | H | Me | 2 | —CO—(CH₂)₂—O—(4-MeO—cHx) | H | H |
| 1-1396 | H | H | H | Me | 2 | —CO—(CH₂)₂—O—(4-EtO—cHx) | H | H |
| 1-1397 | H | H | H | Me | 2 | —CO—(CH₂)₂—O—(4-MeS—cHx) | H | H |
| 1-1398 | H | H | H | Me | 2 | —CO—(CH₂)₂—O—(4-cHx—cHx) | H | H |
| 1-1399 | H | H | H | Me | 2 | —CO—(CH₂)₂—O—(4-Ph—cHx) | H | H |
| 1-1400 | H | H | H | Me | 2 | —CO—(CH₂)₂—O—Ph | H | H |
| 1-1401 | H | H | Me | Me | 2 | —CO—(CH₂)₂—O—Ph | H | H |
| 1-1402 | Me | H | H | Me | 2 | —CO—(CH₂)₂—O—Ph | H | H |
| 1-1403 | CO₂Me | H | H | Me | 2 | —CO—(CH₂)₂—O—Ph | H | H |
| 1-1404 | H | H | H | Me | 2 | —CO—(CH₂)₂—O—(4-F—Ph) | H | H |
| 1-1405 | H | H | H | Me | 2 | —CO—(CH₂)₂—O—(4-Me—Ph) | H | H |
| 1-1406 | H | H | H | Me | 2 | —CO—(CH₂)₂—O—(4-Et—Ph) | H | H |
| 1-1407 | H | H | H | Me | 2 | —CO—(CH₂)₂—O—(4-CF₃—Ph) | H | H |
| 1-1408 | H | H | H | Me | 2 | —CO—(CH₂)₂—O—(4-MeO—Ph) | H | H |
| 1-1409 | H | H | H | Me | 2 | —CO—(CH₂)₂—O—(4-EtO—Ph) | H | H |
| 1-1410 | H | H | H | Me | 2 | —CO—(CH₂)₂—O—(4-MeS—Ph) | H | H |
| 1-1411 | H | H | H | Me | 2 | —CO—(CH₂)₂—O—(4-cHx—Ph) | H | H |
| 1-1412 | H | H | H | Me | 2 | —CO—(CH₂)₂—O—(4-Ph—Ph) | H | H |
| 1-1413 | H | H | H | Me | 2 | —CO—(CH₂)₃—O—cPn | H | H |
| 1-1414 | H | H | H | Me | 2 | —CO—(CH₂)₃—O—cHx | H | H |
| 1-1415 | H | H | H | Me | 2 | —CO—(CH₂)₃—O—cHx | Me | H |
| 1-1416 | H | H | H | Me | 2 | —CO—(CH₂)₃—O—cHx | H | Me |
| 1-1417 | H | H | H | Me | 2 | —CO—(CH₂)₃—O—cHx | F | H |
| 1-1418 | H | H | H | Me | 2 | —CO—(CH₂)₃—O—cHx | H | F |
| 1-1419 | H | H | Me | Me | 2 | —CO—(CH₂)₃—O—cHx | H | H |
| 1-1420 | Me | H | H | Me | 2 | —CO—(CH₂)₃—O—cHx | H | H |
| 1-1421 | CO₂Me | H | H | Me | 2 | —CO—(CH₂)₃—O—cHx | H | H |
| 1-1422 | H | H | H | Me | 2 | —CO—(CH₂)₃—O—(3-F—cHx) | H | H |
| 1-1423 | H | H | H | Me | 2 | —CO—(CH₂)₃—O—(4-F—cHx) | H | H |
| 1-1424 | H | H | H | Me | 2 | —CO—(CH₂)₃—O—(4-Cl—cHx) | H | H |
| 1-1425 | H | H | H | Me | 2 | —CO—(CH₂)₃—O—(4-Br—cHx) | H | H |
| 1-1426 | H | H | H | Me | 2 | —CO—(CH₂)₃—O—(3-Me—cHx) | H | H |
| 1-1427 | H | H | H | Me | 2 | —CO—(CH₂)₃—O—(4-Me—cHx) | H | H |
| 1-1428 | H | H | H | Me | 2 | —CO—(CH₂)₃—O—(3-Et—cHx) | H | H |
| 1-1429 | H | H | H | Me | 2 | —CO—(CH₂)₃—O—(4-Et—cHx) | H | H |
| 1-1430 | H | H | H | Me | 2 | —CO—(CH₂)₃—O—(3-Pr—cHx) | H | H |

TABLE 1-continued

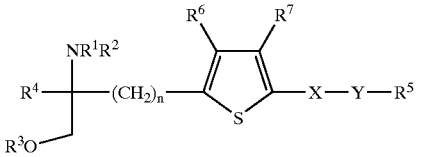

(Ia)

| Exemp. Compd. No. | $R^1$ | $R^2$ | $R^3$ | $R^4$ | n | —X—Y—$R^5$ | $R^6$ | $R^7$ |
|---|---|---|---|---|---|---|---|---|
| 1-1431 | H | H | H | Me | 2 | —CO—$(CH_2)_3$—O—(4-Pr—cHx) | H | H |
| 1-1432 | H | H | H | Me | 2 | —CO—$(CH_2)_3$—O—(4-iPr—cHx) | H | H |
| 1-1433 | H | H | H | Me | 2 | —CO—$(CH_2)_3$—O—(3-Bu—cHx) | H | H |
| 1-1434 | H | H | H | Me | 2 | —CO—$(CH_2)_3$—O—(4-Bu—cHx) | H | H |
| 1-1435 | H | H | H | Me | 2 | —CO—$(CH_2)_3$—O—(3-$CF_3$—cHx) | H | H |
| 1-1436 | H | H | H | Me | 2 | —CO—$(CH_2)_3$—O—(4-$CF_3$—cHx) | H | H |
| 1-1437 | H | H | H | Me | 2 | —CO—$(CH_2)_3$—O—(3-MeO—cHx) | H | H |
| 1-1438 | H | H | H | Me | 2 | —CO—$(CH_2)_3$—O—(4-MeO—cHx) | H | H |
| 1-1439 | H | H | H | Me | 2 | —CO—$(CH_2)_3$—O—(3-EtO—cHx) | H | H |
| 1-1440 | H | H | H | Me | 2 | —CO—$(CH_2)_3$—O—(4-EtO—cHx) | H | H |
| 1-1441 | H | H | H | Me | 2 | —CO—$(CH_2)_3$—O—(3-PrO—cHx) | H | H |
| 1-1442 | H | H | H | Me | 2 | —CO—$(CH_2)_3$—O—(4-PrO—cHx) | H | H |
| 1-1443 | H | H | H | Me | 2 | —CO—$(CH_2)_3$—O—(3-iPrO—cHx) | H | H |
| 1-1444 | H | H | H | Me | 2 | —CO—$(CH_2)_3$—O—(4-iPrO—cHx) | H | H |
| 1-1445 | H | H | H | Me | 2 | —CO—$(CH_2)_3$—O—[3-(2-Et—PrO)cHx] | H | H |
| 1-1446 | H | H | H | Me | 2 | —CO—$(CH_2)_3$—O—[4-(2-Et—PrO)cHx] | H | H |
| 1-1447 | H | H | H | Me | 2 | —CO—$(CH_2)_3$—O—(3-iBuO—cHx) | H | H |
| 1-1448 | H | H | H | Me | 2 | —CO—$(CH_2)_3$—O—(4-iBuO—cHx) | H | H |
| 1-1449 | H | H | H | Me | 2 | —CO—$(CH_2)_3$—O—(3-MeS—cHx) | H | H |
| 1-1450 | H | H | H | Me | 2 | —CO—$(CH_2)_3$—O—(4-MeS—cHx) | H | H |
| 1-1451 | H | H | H | Me | 2 | —CO—$(CH_2)_3$—O—(3-EtS—cHx) | H | H |
| 1-1452 | H | H | H | Me | 2 | —CO—$(CH_2)_3$—O—(4-EtS—cHx) | H | H |
| 1-1453 | H | H | H | Me | 2 | —CO—$(CH_2)_3$—O—(3-PrS—cHx) | H | H |
| 1-1454 | H | H | H | Me | 2 | —CO—$(CH_2)_3$—O—(4-PrS—cHx) | H | H |
| 1-1455 | H | H | H | Me | 2 | —CO—$(CH_2)_3$—O—(3-iPrS—cHx) | H | H |
| 1-1456 | H | H | H | Me | 2 | —CO—$(CH_2)_3$—O—(4-iPrS—cHx) | H | H |
| 1-1457 | H | H | H | Me | 2 | —CO—$(CH_2)_3$—O—[3-(2-Et—PrS)cHx] | H | H |
| 1-1458 | H | H | H | Me | 2 | —CO—$(CH_2)_3$—O—[4-(2-Et—PrS)cHx] | H | H |
| 1-1459 | H | H | H | Me | 2 | —CO—$(CH_2)_3$—O—(3-iBuS—cHx) | H | H |
| 1-1460 | H | H | H | Me | 2 | —CO—$(CH_2)_3$—O—(4-iBuS—cHx) | H | H |
| 1-1461 | H | H | H | Me | 2 | —CO—$(CH_2)_3$—O—(3-cHx—cHx) | H | H |
| 1-1462 | H | H | H | Me | 2 | —CO—$(CH_2)_3$—O—(4-cHx—cHx) | H | H |
| 1-1463 | H | H | H | Me | 2 | —CO—$(CH_2)_3$—O—(3-Ph—cHx) | H | H |
| 1-1464 | H | H | H | Me | 2 | —CO—$(CH_2)_3$—O—(4-Ph—cHx) | H | H |
| 1-1465 | H | H | H | Me | 2 | —CO—$(CH_2)_3$—O—(2,4-diMe—cHx) | H | H |
| 1-1466 | H | H | H | Me | 2 | —CO—$(CH_2)_3$—O—(3,4-diMe—cHx) | H | H |
| 1-1467 | H | H | H | Me | 2 | —CO—$(CH_2)_3$—O—(3,5-diMe—cHx) | H | H |
| 1-1468 | H | H | H | Me | 2 | —CO—$(CH_2)_3$—O—Ph | H | H |
| 1-1469 | H | H | H | Me | 2 | —CO—$(CH_2)_3$—O—Ph | Me | H |
| 1-1470 | H | H | H | Me | 2 | —CO—$(CH_2)_3$—O—Ph | H | Me |
| 1-1471 | H | H | H | Me | 2 | —CO—$(CH_2)_3$—O—Ph | F | H |
| 1-1472 | H | H | H | Me | 2 | —CO—$(CH_2)_3$—O—Ph | H | F |
| 1-1473 | H | H | Me | Me | 2 | —CO—$(CH_2)_3$—O—Ph | H | H |
| 1-1474 | Me | H | H | Me | 2 | —CO—$(CH_2)_3$—O—Ph | H | H |
| 1-1475 | $CO_2Me$ | H | H | Me | 2 | —CO—$(CH_2)_3$—O—Ph | H | H |
| 1-1476 | H | H | H | Me | 2 | —CO—$(CH_2)_3$—O—(3-F—Ph) | H | H |
| 1-1477 | H | H | H | Me | 2 | —CO—$(CH_2)_3$—O—(4-F—Ph) | H | H |
| 1-1478 | H | H | H | Me | 2 | —CO—$(CH_2)_3$—O—(4-Cl—Ph) | H | H |
| 1-1479 | H | H | H | Me | 2 | —CO—$(CH_2)_3$—O—(4-Br—Ph) | H | H |
| 1-1480 | H | H | H | Me | 2 | —CO—$(CH_2)_3$—O—(3-Me—Ph) | H | H |
| 1-1481 | H | H | H | Me | 2 | —CO—$(CH_2)_3$—O—(4-Me—Ph) | H | H |
| 1-1482 | H | H | H | Me | 2 | —CO—$(CH_2)_3$—O—(3-Et—Ph) | H | H |
| 1-1483 | H | H | H | Me | 2 | —CO—$(CH_2)_3$—O—(4-Et—Ph) | H | H |
| 1-1484 | H | H | H | Me | 2 | —CO—$(CH_2)_3$—O—(3-Pr—Ph) | H | H |
| 1-1485 | H | H | H | Me | 2 | —CO—$(CH_2)_3$—O—(4-Pr—Ph) | H | H |
| 1-1486 | H | H | H | Me | 2 | —CO—$(CH_2)_3$—O—(3-iPr—Ph) | H | H |
| 1-1487 | H | H | H | Me | 2 | —CO—$(CH_2)_3$—O—(4-iPr—Ph) | H | H |
| 1-1488 | H | H | H | Me | 2 | —CO—$(CH_2)_3$—O—(3-Bu—Ph) | H | H |
| 1-1489 | H | H | H | Me | 2 | —CO—$(CH_2)_3$—O—(4-Bu—Ph) | H | H |
| 1-1490 | H | H | H | Me | 2 | —CO—$(CH_2)_3$—O—(3-$CF_3$—Ph) | H | H |
| 1-1491 | H | H | H | Me | 2 | —CO—$(CH_2)_3$—O—(4-$CF_3$—Ph) | H | H |
| 1-1492 | H | H | H | Me | 2 | —CO—$(CH_2)_3$—O—(3-MeO—Ph) | H | H |
| 1-1493 | H | H | H | Me | 2 | —CO—$(CH_2)_3$—O—(4-MeO—Ph) | H | H |
| 1-1494 | H | H | H | Me | 2 | —CO—$(CH_2)_3$—O—(3-EtO—Ph) | H | H |
| 1-1495 | H | H | H | Me | 2 | —CO—$(CH_2)_3$—O—(4-EtO—Ph) | H | H |

TABLE 1-continued (Ia)

$$\text{structure: } R^4, NR^1R^2, R^3O-CH_2-, (CH_2)_n \text{ attached to thiophene ring with } R^6, R^7 \text{ substituents and } X-Y-R^5$$

| Exemp. Compd. No. | R¹ | R² | R³ | R⁴ | n | —X—Y—R⁵ | R⁶ | R⁷ |
|---|---|---|---|---|---|---|---|---|
| 1-1496 | H | H | H | Me | 2 | —CO—(CH₂)₃—O—(3-PrO—Ph) | H | H |
| 1-1497 | H | H | H | Me | 2 | —CO—(CH₂)₃—O—(4-PrO—Ph) | H | H |
| 1-1498 | H | H | H | Me | 2 | —CO—(CH₂)₃—O—(3-iPrO—Ph) | H | H |
| 1-1499 | H | H | H | Me | 2 | —CO—(CH₂)₃—O—(4-iPrO—Ph) | H | H |
| 1-1500 | H | H | H | Me | 2 | —CO—(CH₂)₃—O—[3-(2-Et—PrO)—Ph] | H | H |
| 1-1501 | H | H | H | Me | 2 | —CO—(CH₂)₃—O—[4-(2-Et—PrO)—Ph] | H | H |
| 1-1502 | H | H | H | Me | 2 | —CO—(CH₂)₃—O—(3-iBuO—Ph) | H | H |
| 1-1503 | H | H | H | Me | 2 | —CO—(CH₂)₃—O—(4-iBuO—Ph) | H | H |
| 1-1504 | H | H | H | Me | 2 | —CO—(CH₂)₃—O—(3-MeS—Ph) | H | H |
| 1-1505 | H | H | H | Me | 2 | —CO—(CH₂)₃—O—(4-MeS—Ph) | H | H |
| 1-1506 | H | H | H | Me | 2 | —CO—(CH₂)₃—O—(3-EtS—Ph) | H | H |
| 1-1507 | H | H | H | Me | 2 | —CO—(CH₂)₃—O—(4-EtS—Ph) | H | H |
| 1-1508 | H | H | H | Me | 2 | —CO—(CH₂)₃—O—(3-PrS—Ph) | H | H |
| 1-1509 | H | H | H | Me | 2 | —CO—(CH₂)₃—O—(4-PrS—Ph) | H | H |
| 1-1510 | H | H | H | Me | 2 | —CO—(CH₂)₃—O—(3-iPrS—Ph) | H | H |
| 1-1511 | H | H | H | Me | 2 | —CO—(CH₂)₃—O—(4-iPrS—Ph) | H | H |
| 1-1512 | H | H | H | Me | 2 | —CO—(CH₂)₃—O—[3-(2-Et—PrS)—Ph] | H | H |
| 1-1513 | H | H | H | Me | 2 | —CO—(CH₂)₃—O—[4-(2-Et—PrS)—Ph] | H | H |
| 1-1514 | H | H | H | Me | 2 | —CO—(CH₂)₃—O—(3-iBuS—Ph) | H | H |
| 1-1515 | H | H | H | Me | 2 | —CO—(CH₂)₃—O—(4-iBuS—Ph) | H | H |
| 1-1516 | H | H | H | Me | 2 | —CO—(CH₂)₃—O—(3-cHx—Ph) | H | H |
| 1-1517 | H | H | H | Me | 2 | —CO—(CH₂)₃—O—(4-cHx—Ph) | H | H |
| 1-1518 | H | H | H | Me | 2 | —CO—(CH₂)₃—O—(3-Ph—Ph) | H | H |
| 1-1519 | H | H | H | Me | 2 | —CO—(CH₂)₃—O—(4-Ph—Ph) | H | H |
| 1-1520 | H | H | H | Me | 2 | —CO—(CH₂)₃—O—(2,4-diMe—Ph) | H | H |
| 1-1521 | H | H | H | Me | 2 | —CO—(CH₂)₃—O—(3,4-diMe—Ph) | H | H |
| 1-1522 | H | H | H | Me | 2 | —CO—(CH₂)₃—O—(3,5-diMe—Ph) | H | H |
| 1-1523 | H | H | H | Me | 2 | —CO—(CH₂)₄—O—cHx | H | H |
| 1-1524 | H | H | H | Me | 2 | —CO—(CH₂)₄—O—Ph | H | H |
| 1-1525 | H | H | H | Me | 2 | —CO—(CH₂)₅—O—cHx | H | H |
| 1-1526 | H | H | H | Me | 2 | —CO—(CH₂)₅—O—Ph | H | H |
| 1-1527 | H | H | H | Me | 2 | —CO—(CH₂)₂—OCH₂—cHx | H | H |
| 1-1528 | H | H | Me | Me | 2 | —CO—(CH₂)₂—OCH₂—cHx | H | H |
| 1-1529 | Me | H | H | Me | 2 | —CO—(CH₂)₂—OCH₂—cHx | H | H |
| 1-1530 | CO₂Me | H | H | Me | 2 | —CO—(CH₂)₂—OCH₂—cHx | H | H |
| 1-1531 | H | H | H | Me | 2 | —CO—(CH₂)₂—OCH₂—(4-F—cHx) | H | H |
| 1-1532 | H | H | H | Me | 2 | —CO—(CH₂)₂—OCH₂—(4-Me—cHx) | H | H |
| 1-1533 | H | H | H | Me | 2 | —CO—(CH₂)₂—OCH₂—(4-Et—cHx). | H | H |
| 1-1534 | H | H | H | Me | 2 | —CO—(CH₂)₂—OCH₂—(4-CF₃—cHx) | H | H |
| 1-1535 | H | H | H | Me | 2 | —CO—(CH₂)₂—OCH₂—(4-MeO—cHx) | H | H |
| 1-1536 | H | H | H | Me | 2 | —CO—(CH₂)₂—OCH₂—(4-EtO—cHx) | H | H |
| 1-1537 | H | H | H | Me | 2 | —CO—(CH₂)₂—OCH₂—(4-MeS—cHx) | H | H |
| 1-1538 | H | H | H | Me | 2 | —CO—(CH₂)₂—OCH₂—(4-cHx—cHx) | H | H |
| 1-1539 | H | H | H | Me | 2 | —CO—(CH₂)₂—OCH₂—(4-Ph—cHx) | H | H |
| 1-1540 | H | H | H | Me | 2 | —CO—(CH₂)₂—OCH₂—Ph | H | H |
| 1-1541 | H | H | Me | Me | 2 | —CO—(CH₂)₂—OCH₂—Ph | H | H |
| 1-1542 | Me | H | H | Me | 2 | —CO—(CH₂)₂—OCH₂—Ph | H | H |
| 1-1543 | CO₂Me | H | H | Me | 2 | —CO—(CH₂)₂—OCH₂—Ph | H | H |
| 1-1544 | H | H | H | Me | 2 | —CO—(CH₂)₂—OCH₂—(4-F—Ph) | H | H |
| 1-1545 | H | H | H | Me | 2 | —CO—(CH₂)₂—OCH₂—(4-Me—Ph) | H | H |
| 1-1546 | H | H | H | Me | 2 | —CO—(CH₂)₂—OCH₂—(4-Et—Ph) | H | H |
| 1-1547 | H | H | H | Me | 2 | —CO—(CH₂)₂—OCH₂—(4-CF₃—Ph) | H | H |
| 1-1548 | H | H | H | Me | 2 | —CO—(CH₂)₂—OCH₂—(4-MeO—Ph) | H | H |
| 1-1549 | H | H | H | Me | 2 | —CO—(CH₂)₂—OCH₂—(4-EtO—Ph) | H | H |
| 1-1550 | H | H | H | Me | 2 | —CO—(CH₂)₂—OCH₂—(4-MeS—Ph) | H | H |
| 1-1551 | H | H | H | Me | 2 | —CO—(CH₂)₂—OCH₂—(4-cHx—Ph) | H | H |
| 1-1552 | H | H | H | Me | 2 | —CO—(CH₂)₂—OCH₂—(4-Ph—Ph) | H | H |
| 1-1553 | H | H | H | Me | 2 | —CO—(CH₂)₃—OCH₂—CH₂—cPn | H | H |
| 1-1554 | H | H | H | Me | 2 | —CO—(CH₂)₃—OCH₂—cHx | H | H |
| 1-1555 | H | H | H | Me | 2 | —CO—(CH₂)₃—OCH₂—cHx | Me | H |
| 1-1556 | H | H | H | Me | 2 | —CO—(CH₂)₃—OCH₂—cHx | H | Me |
| 1-1557 | H | H | H | Me | 2 | —CO—(CH₂)₃—OCH₂—cHx | F | H |
| 1-1558 | H | H | H | Me | 2 | —CO—(CH₂)₃—OCH₂—cHx | H | F |
| 1-1559 | H | H | Me | Me | 2 | —CO—(CH₂)₃—OCH₂—cHx | H | H |
| 1-1560 | Me | H | H | Me | 2 | —CO—(CH₂)₃—OCH₂—cHx | H | H |

TABLE 1-continued

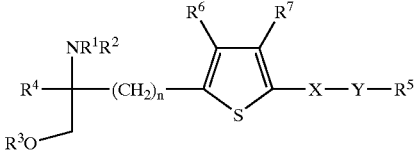

(Ia)

| Exemp. Compd. No. | $R^1$ | $R^2$ | $R^3$ | $R^4$ | n | —X—Y—$R^5$ | $R^6$ | $R^7$ |
|---|---|---|---|---|---|---|---|---|
| 1-1561 | $CO_2Me$ | H | H | Me | 2 | —CO—$(CH_2)_3$—$OCH_2$—cHx | H | H |
| 1-1562 | H | H | H | Me | 2 | —CO—$(CH_2)_3$—$OCH_2$—(3-F—cHx) | H | H |
| 1-1563 | H | H | H | Me | 2 | —CO—$(CH_2)_3$—$OCH_2$—(4-F—cHx) | H | H |
| 1-1564 | H | H | H | Me | 2 | —CO—$(CH_2)_3$—$OCH_2$—(4-Cl—cHx) | H | H |
| 1-1565 | H | H | H | Me | 2 | —CO—$(CH_2)_3$—$OCH_2$—(4-Br—cHx) | H | H |
| 1-1566 | H | H | H | Me | 2 | —CO—$(CH_2)_3$—$OCH_2$—(3-Me—cHx) | H | H |
| 1-1567 | H | H | H | Me | 2 | —CO—$(CH_2)_3$—$OCH_2$—(4-Me—cHx) | H | H |
| 1-1568 | H | H | H | Me | 2 | —CO—$(CH_2)_3$—$OCH_2$—(3-Et—cHx) | H | H |
| 1-1569 | H | H | H | Me | 2 | —CO—$(CH_2)_3$—$OCH_2$—(4-Et—cHx) | H | H |
| 1-1570 | H | H | H | Me | 2 | —CO—$(CH_2)_3$—$OCH_2$—(3-Pr—cHx) | H | H |
| 1-1571 | H | H | H | Me | 2 | —CO—$(CH_2)_3$—$OCH_2$—(4-Pr—cHx) | H | H |
| 1-1572 | H | H | H | Me | 2 | —CO—$(CH_2)_3$—$OCH_2$—(4-iPr—cHx) | H | H |
| 1-1573 | H | H | H | Me | 2 | —CO—$(CH_2)_3$—$OCH_2$—(3-Bu—cHx) | H | H |
| 1-1574 | H | H | H | Me | 2 | —CO—$(CH_2)_3$—$OCH_2$—(4-Bu—cHx) | H | H |
| 1-1575 | H | H | H | Me | 2 | —CO—$(CH_2)_3$—$OCH_2$—(3-$CF_3$—cHx) | H | H |
| 1-1576 | H | H | H | Me | 2 | —CO—$(CH_2)_3$—$OCH_2$—(4-$CF_3$—cHx) | H | H |
| 1-1577 | H | H | H | Me | 2 | —CO—$(CH_2)_3$—$OCH_2$—(3-MeO—cHx) | H | H |
| 1-1578 | H | H | H | Me | 2 | —CO—$(CH_2)_3$—$OCH_2$—(4-MeO—cHx) | H | H |
| 1-1579 | H | H | H | Me | 2 | —CO—$(CH_2)_3$—$OCH_2$—(3-EtO—cHx) | H | H |
| 1-1580 | H | H | H | Me | 2 | —CO—$(CH_2)_3$—$OCH_2$—(4-EtO—cHx) | H | H |
| 1-1581 | H | H | H | Me | 2 | —CO—$(CH_2)_3$—$OCH_2$—(3-PrO—cHx) | H | H |
| 1-1582 | H | H | H | Me | 2 | —CO—$(CH_2)_3$—$OCH_2$—(4-PrO—cHx) | H | H |
| 1-1583 | H | H | H | Me | 2 | —CO—$(CH_2)_3$—$OCH_2$—(3-iPrO—cHx) | H | H |
| 1-1584 | H | H | H | Me | 2 | —CO—$(CH_2)_3$—$OCH_2$—(4-iPrO—cHx) | H | H |
| 1-1585 | H | H | H | Me | 2 | —CO—$(CH_2)_3$—$OCH_2$—[3-(2-Et—PrO)cHx] | H | H |
| 1-1586 | H | H | H | Me | 2 | —CO—$(CH_2)_3$—$OCH_2$—[4-(2-Et—PrO)cHx] | H | H |
| 1-1587 | H | H | H | Me | 2 | —CO—$(CH_2)_3$—$OCH_2$—(3-iBuO—cHx) | H | H |
| 1-1588 | H | H | H | Me | 2 | —CO—$(CH_2)_3$—$OCH_2$—(4-iBuO—cHx) | H | H |
| 1-1589 | H | H | H | Me | 2 | —CO—$(CH_2)_3$—$OCH_2$—(3-MeS—cHx) | H | H |
| 1-1590 | H | H | H | Me | 2 | —CO—$(CH_2)_3$—$OCH_2$—(4-MeS—cHx) | H | H |
| 1-1591 | H | H | H | Me | 2 | —CO—$(CH_2)_3$—$OCH_2$—(3-EtS—cHx) | H | H |
| 1-1592 | H | H | H | Me | 2 | —CO—$(CH_2)_3$—$OCH_2$—(4-EtS—cHx) | H | H |
| 1-1593 | H | H | H | Me | 2 | —CO—$(CH_2)_3$—$OCH_2$—(3-PrS—cHx) | H | H |
| 1-1594 | H | H | H | Me | 2 | —CO—$(CH_2)_3$—$OCH_2$—(4-PrS—cHx) | H | H |
| 1-1595 | H | H | H | Me | 2 | —CO—$(CH_2)_3$—$OCH_2$—(3-iPrS—cHx) | H | H |
| 1-1596 | H | H | H | Me | 2 | —CO—$(CH_2)_3$—$OCH_2$—(4-iPrS—cHx) | H | H |
| 1-1597 | H | H | H | Me | 2 | —CO—$(CH_2)_3$—$OCH_2$—[3-(2-Et—PrS)cHx] | H | H |
| 1-1598 | H | H | H | Me | 2 | —CO—$(CH_2)_3$—$OCH_2$—[4-(2-Et—PrS)cHx] | H | H |
| 1-1599 | H | H | H | Me | 2 | —CO—$(CH_2)_3$—$OCH_2$—(3-iBuS—cHx) | H | H |
| 1-1600 | H | H | H | Me | 2 | —CO—$(CH_2)_3$—$OCH_2$—(4-iBuS—cHx) | H | H |
| 1-1601 | H | H | H | Me | 2 | —CO—$(CH_2)_3$—$OCH_2$—(3-cHx—cHx) | H | H |
| 1-1602 | H | H | H | Me | 2 | —CO—$(CH_2)_3$—$OCH_2$—(4-cHx—cHx) | H | H |
| 1-1603 | H | H | H | Me | 2 | —CO—$(CH_2)_3$—$OCH_2$—(3-Ph—cHx) | H | H |
| 1-1604 | H | H | H | Me | 2 | —CO—$(CH_2)_3$—$OCH_2$—(4-Ph—cHx) | H | H |
| 1-1605 | H | H | H | Me | 2 | —CO—$(CH_2)_3$—$OCH_2$—(2,4-diMe—cHx) | H | H |
| 1-1606 | H | H | H | Me | 2 | —CO—$(CH_2)_3$—$OCH_2$—(3,4-diMe—cHx) | H | H |
| 1-1607 | H | H | H | Me | 2 | —CO—$(CH_2)_3$—$OCH_2$—(3,5-diMe—cHx) | H | H |
| 1-1608 | H | H | H | Me | 2 | —CO—$(CH_2)_3$—$OCH_2$—Ph | H | H |
| 1-1609 | H | H | H | Me | 2 | —CO—$(CH_2)_3$—$OCH_2$—Ph | Me | H |
| 1-1610 | H | H | H | Me | 2 | —CO—$(CH_2)_3$—$OCH_2$—Ph | H | Me |
| 1-1611 | H | H | H | Me | 2 | —CO—$(CH_2)_3$—$OCH_2$—Ph | F | H |
| 1-1612 | H | H | H | Me | 2 | —CO—$(CH_2)_3$—$OCH_2$—Ph | H | F |
| 1-1613 | H | H | Me | Me | 2 | —CO—$(CH_2)_3$—$OCH_2$—Ph | H | H |
| 1-1614 | Me | H | H | Me | 2 | —CO—$(CH_2)_3$—$OCH_2$—Ph | H | H |
| 1-1615 | $CO_2Me$ | H | H | Me | 2 | —CO—$(CH_2)_3$—$OCH_2$—Ph | H | H |
| 1-1616 | H | H | H | Me | 2 | —CO—$(CH_2)_3$—$OCH_2$—(3-F—Ph) | H | H |
| 1-1617 | H | H | H | Me | 2 | —CO—$(CH_2)_3$—$OCH_2$—(4-F—Ph) | H | H |
| 1-1618 | H | H | H | Me | 2 | —CO—$(CH_2)_3$—$OCH_2$—(4-Cl—Ph) | H | H |
| 1-1619 | H | H | H | Me | 2 | —CO—$(CH_2)_3$—$OCH_2$—(4-Br—Ph) | H | H |
| 1-1620 | H | H | H | Me | 2 | —CO—$(CH_2)_3$—$OCH_2$—(3-Me—Ph) | H | H |
| 1-1621 | H | H | H | Me | 2 | —CO—$(CH_2)_3$—$OCH_2$—(4-Me—Ph) | H | H |
| 1-1622 | H | H | H | Me | 2 | —CO—$(CH_2)_3$—$OCH_2$—(3-Et—Ph) | H | H |
| 1-1623 | H | H | H | Me | 2 | —CO—$(CH_2)_3$—$OCH_2$—(4-Et—Ph) | H | H |
| 1-1624 | H | H | H | Me | 2 | —CO—$(CH_2)_3$—$OCH_2$—(3-Pr—Ph) | H | H |
| 1-1625 | H | H | H | Me | 2 | —CO—$(CH_2)_3$—$OCH_2$—(4-Pr—Ph) | H | H |

TABLE 1-continued (Ia)

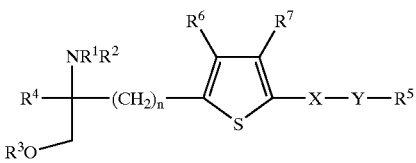

| Exemp. Compd. No. | $R^1$ | $R^2$ | $R^3$ | $R^4$ | n | —X—Y—$R^5$ | $R^6$ | $R^7$ |
|---|---|---|---|---|---|---|---|---|
| 1-1626 | H | H | H | Me | 2 | —CO—$(CH_2)_3$—$OCH_2$—(3-iPr—Ph) | H | H |
| 1-1627 | H | H | H | Me | 2 | —CO—$(CH_2)_3$—$OCH_2$—(4-iPr—Ph) | H | H |
| 1-1628 | H | H | H | Me | 2 | —CO—$(CH_2)_3$—$OCH_2$—(3-Bu—Ph) | H | H |
| 1-1629 | H | H | H | Me | 2 | —CO—$(CH_2)_3$—$OCH_2$—(4-Bu—Ph) | H | H |
| 1-1630 | H | H | H | Me | 2 | —CO—$(CH_2)_3$—$OCH_2$—(3-$CF_3$—Ph) | H | H |
| 1-1631 | H | H | H | Me | 2 | —CO—$(CH_2)_3$—$OCH_2$—(4-$CF_3$—Ph) | H | H |
| 1-1632 | H | H | H | Me | 2 | —CO—$(CH_2)_3$—$OCH_2$—(3-MeO—Ph) | H | H |
| 1-1633 | H | H | H | Me | 2 | —CO—$(CH_2)_3$—$OCH_2$—(4-MeO—Ph) | H | H |
| 1-1634 | H | H | H | Me | 2 | —CO—$(CH_2)_3$—$OCH_2$—(3-EtO—Ph) | H | H |
| 1-1635 | H | H | H | Me | 2 | —CO—$(CH_2)_3$—$OCH_2$—(4-EtO—Ph) | H | H |
| 1-1636 | H | H | H | Me | 2 | —CO—$(CH_2)_3$—$OCH_2$—(3-PrO—Ph) | H | H |
| 1-1637 | H | H | H | Me | 2 | —CO—$(CH_2)_3$—$OCH_2$—(4-PrO—Ph) | H | H |
| 1-1638 | H | H | H | Me | 2 | —CO—$(CH_2)_3$—$OCH_2$—(3-iPrO—Ph) | H | H |
| 1-1639 | H | H | H | Me | 2 | —CO—$(CH_2)_3$—$OCH_2$—(4-iPrO—Ph) | H | H |
| 1-1640 | H | H | H | Me | 2 | —CO—$(CH_2)_3$—$OCH_2$—[3-(2-Et—PrO)Ph] | H | H |
| 1-1641 | H | H | H | Me | 2 | —CO—$(CH_2)_3$—$OCH_2$—[4-(2-Et—PrO)Ph] | H | H |
| 1-1642 | H | H | H | Me | 2 | —CO—$(CH_2)_3$—$OCH_2$—(3-iBuO—Ph) | H | H |
| 1-1643 | H | H | H | Me | 2 | —CO—$(CH_2)_3$—$OCH_2$—(4-iBuO—Ph) | H | H |
| 1-1644 | H | H | H | Me | 2 | —CO—$(CH_2)_3$—$OCH_2$—(3-MeS—Ph) | H | H |
| 1-1645 | H | H | H | Me | 2 | —CO—$(CH_2)_3$—$OCH_2$—(4-MeS—Ph) | H | H |
| 1-1646 | H | H | H | Me | 2 | —CO—$(CH_2)_3$—$OCH_2$—(3-EtS—Ph) | H | H |
| 1-1647 | H | H | H | Me | 2 | —CO—$(CH_2)_3$—$OCH_2$—(4-EtS—Ph) | H | H |
| 1-1648 | H | H | H | Me | 2 | —CO—$(CH_2)_3$—$OCH_2$—(3-PrS—Ph) | H | H |
| 1-1649 | H | H | H | Me | 2 | —CO—$(CH_2)_3$—$OCH_2$—(4-PrS—Ph) | H | H |
| 1-1650 | H | H | H | Me | 2 | —CO—$(CH_2)_3$—$OCH_2$—(3-iPrS—Ph) | H | H |
| 1-1651 | H | H | H | Me | 2 | —CO—$(CH_2)_3$—$OCH_2$—(4-iPrS—Ph) | H | H |
| 1-1652 | H | H | H | Me | 2 | —CO—$(CH_2)_3$—$OCH_2$—[3-(2-Et—PrS)Ph] | H | H |
| 1-1653 | H | H | H | Me | 2 | —CO—$(CH_2)_3$—$OCH_2$—[4-(2-Et—PrS)Ph] | H | H |
| 1-1654 | H | H | H | Me | 2 | —CO—$(CH_2)_3$—$OCH_2$—(3-iBuS—Ph) | H | H |
| 1-1655 | H | H | H | Me | 2 | —CO—$(CH_2)_3$—$OCH_2$—(4-iBuS—Ph) | H | H |
| 1-1656 | H | H | H | Me | 2 | —CO—$(CH_2)_3$—$OCH_2$—(3-cHx—Ph) | H | H |
| 1-1657 | H | H | H | Me | 2 | —CO—$(CH_2)_3$—$OCH_2$—(4-cHx—Ph) | H | H |
| 1-1658 | H | H | H | Me | 2 | —CO—$(CH_2)_3$—$OCH_2$—(3-Ph—Ph) | H | H |
| 1-1659 | H | H | H | Me | 2 | —CO—$(CH_2)_3$—$OCH_2$—(4-Ph—Ph) | H | H |
| 1-1660 | H | H | H | Me | 2 | —CO—$(CH_2)_3$—$OCH_2$—(2,4-diMe—Ph) | H | H |
| 1-1661 | H | H | H | Me | 2 | —CO—$(CH_2)_3$—$OCH_2$—(3,4-diMe—Ph) | H | H |
| 1-1662 | H | H | H | Me | 2 | —CO—$(CH_2)_3$—$OCH_2$—(3,5-diMe—Ph) | H | H |
| 1-1663 | H | H | H | Me | 2 | —CO—$(CH_2)_4$—$OCH_2$—cHx | H | H |
| 1-1664 | H | H | H | Me | 2 | —CO—$(CH_2)_4$—$OCH_2$—Ph | H | H |
| 1-1665 | H | H | H | Me | 2 | —CO—$(CH_2)_5$—$OCH_2$—cHx | H | H |
| 1-1666 | H | H | H | Me | 2 | —CO—$(CH_2)_5$—$OCH_2$—Ph | H | H |
| 1-1667 | H | H | H | Me | 2 | —CH(OH)—$CH_2$—cHx | H | H |
| 1-1668 | H | H | H | Me | 2 | —CH(OH)—$CH_2$—Ph | H | H |
| 1-1669 | H | H | H | Me | 2 | —CH(OH)—$(CH_2)_2$—cHx | H | H |
| 1-1670 | H | H | H | Me | 2 | —CH(OH)—$(CH_2)_2$—Ph | H | H |
| 1-1671 | H | H | H | Me | 2 | —CH(OH)—$(CH_2)_3$—cHx | H | H |
| 1-1672 | H | H | H | Me | 2 | —CH(OH)—$(CH_2)_3$—Ph | H | H |
| 1-1673 | H | H | H | Me | 2 | —CH(OH)—$(CH_2)_4$—cHx | H | H |
| 1-1674 | H | H | Me | Me | 2 | —CH(OH)—$(CH_2)_4$—cHx | H | H |
| 1-1675 | Me | H | H | Me | 2 | —CH(OH)—$(CH_2)_4$—cHx | H | H |
| 1-1676 | $CO_2Me$ | H | H | Me | 2 | —CH(OH)—$(CH_2)_4$—cHx | H | H |
| 1-1677 | H | H | H | Me | 2 | —CH(OH)—$(CH_2)_4$—(4-F—cHx) | H | H |
| 1-1678 | H | H | H | Me | 2 | —CH(OH)—$(CH_2)_4$—(4-Me—cHx) | H | H |
| 1-1679 | H | H | H | Me | 2 | —CH(OH)—$(CH_2)_4$—(4-Et—cHx) | H | H |
| 1-1680 | H | H | H | Me | 2 | —CH(OH)—$(CH_2)_4$—(4-$CF_3$—cHx) | H | H |
| 1-1681 | H | H | H | Me | 2 | —CH(OH)—$(CH_2)_4$—(4-MeO—cHx) | H | H |
| 1-1682 | H | H | H | Me | 2 | —CH(OH)—$(CH_2)_4$—(4-EtO—cHx) | H | H |
| 1-1683 | H | H | H | Me | 2 | —CH(OH)—$(CH_2)_4$—(4-MeS—cHx) | H | H |
| 1-1684 | H | H | H | Me | 2 | —CH(OH)—$(CH_2)_4$—(4-cHx—cHx) | H | H |
| 1-1685 | H | H | H | Me | 2 | —CH(OH)—$(CH_2)_4$—(4-Ph—cHx) | H | H |
| 1-1686 | H | H | H | Me | 2 | —CH(OH)—$(CH_2)_4$—Ph | H | H |
| 1-1687 | H | H | Me | Me | 2 | —CH(OH)—$(CH_2)_4$—Ph | H | H |
| 1-1688 | Me | H | H | Me | 2 | —CH(OH)—$(CH_2)_4$—Ph | H | H |
| 1-1689 | $CO_2Me$ | H | H | Me | 2 | —CH(OH)—$(CH_2)_4$—Ph | H | H |
| 1-1690 | H | H | H | Me | 2 | —CH(OH)—$(CH_2)_4$—(4-F—Ph) | H | H |

TABLE 1-continued (Ia)

Structure: thiophene with substituents $R^6$, $R^7$ on positions 3,4; $NR^1R^2$, $R^4$, $R^3O$ on a carbon attached via $(CH_2)_n$; and $X-Y-R^5$ on the other side.

| Exemp. Compd. No. | $R^1$ | $R^2$ | $R^3$ | $R^4$ | n | —X—Y—$R^5$ | $R^6$ | $R^7$ |
| --- | --- | --- | --- | --- | --- | --- | --- | --- |
| 1-1691 | H | H | H | Me | 2 | —CH(OH)—(CH$_2$)$_4$—(4-Me—Ph) | H | H |
| 1-1692 | H | H | H | Me | 2 | —CH(OH)—(CH$_2$)$_4$—(4-Et—Ph) | H | H |
| 1-1693 | H | H | H | Me | 2 | —CH(OH)—(CH$_2$)$_4$—(4-CF$_3$—Ph) | H | H |
| 1-1694 | H | H | H | Me | 2 | —CH(OH)—(CH$_2$)$_4$—(4-MeO—Ph) | H | H |
| 1-1695 | H | H | H | Me | 2 | —CH(OH)—(CH$_2$)$_4$—(4-EtO—Ph) | H | H |
| 1-1696 | H | H | H | Me | 2 | —CH(OH)—(CH$_2$)$_4$—(4-MeS—Ph) | H | H |
| 1-1697 | H | H | H | Me | 2 | —CH(OH)—(CH$_2$)$_4$—(4-cHx—Ph) | H | H |
| 1-1698 | H | H | H | Me | 2 | —CH(OH)—(CH$_2$)$_4$—(4-Ph—Ph) | H | H |
| 1-1699 | H | H | H | Me | 2 | —CH(OH)—(CH$_2$)$_5$—cHx | H | H |
| 1-1700 | H | H | Me | Me | 2 | —CH(OH)—(CH$_2$)$_5$—cHx | H | H |
| 1-1701 | Me | H | H | Me | 2 | —CH(OH)—(CH$_2$)$_5$—cHx | H | H |
| 1-1702 | CO$_2$Me | H | H | Me | 2 | —CH(OH)—(CH$_2$)$_5$—cHx | H | H |
| 1-1703 | H | H | H | Me | 2 | —CH(OH)—(CH$_2$)$_5$—(4-F—cHx) | H | H |
| 1-1704 | H | H | H | Me | 2 | —CH(OH)—(CH$_2$)$_5$—(4-Me—cHx) | H | H |
| 1-1705 | H | H | H | Me | 2 | —CH(OH)—(CH$_2$)$_5$—(4-Et—cHx) | H | H |
| 1-1706 | H | H | H | Me | 2 | —CH(OH)—(CH$_2$)$_5$—(4-CF$_3$—cHx) | H | H |
| 1-1707 | H | H | H | Me | 2 | —CH(OH)—(CH$_2$)$_5$—(4-MeO—cHx) | H | H |
| 1-1708 | H | H | H | Me | 2 | —CH(OH)—(CH$_2$)$_5$—(4-EtO—cHx) | H | H |
| 1-1709 | H | H | H | Me | 2 | —CH(OH)—(CH$_2$)$_5$—(4-MeS—cHx) | H | H |
| 1-1710 | H | H | H | Me | 2 | —CH(OH)—(CH$_2$)$_5$—(4-cHx—cHx) | H | H |
| 1-1711 | H | H | H | Me | 2 | —CH(OH)—(CH$_2$)$_5$—(4-Ph—cHx) | H | H |
| 1-1712 | H | H | H | Me | 2 | —CH(OH)—(CH$_2$)$_5$—Ph | H | H |
| 1-1713 | H | H | Me | Me | 2 | —CH(OH)—(CH$_2$)$_5$—Ph | H | H |
| 1-1714 | Me | H | H | Me | 2 | —CH(OH)—(CH$_2$)$_5$—Ph | H | H |
| 1-1715 | CO$_2$Me | H | H | Me | 2 | —CH(OH)—(CH$_2$)$_5$—Ph | H | H |
| 1-1716 | H | H | H | Me | 2 | —CH(OH)—(CH$_2$)$_5$—(4-F—Ph) | H | H |
| 1-1717 | H | H | H | Me | 2 | —CH(OH)—(CH$_2$)$_5$—(4-Me—Ph) | H | H |
| 1-1718 | H | H | H | Me | 2 | —CH(OH)—(CH$_2$)$_5$—(4-Et—Ph) | H | H |
| 1-1719 | H | H | H | Me | 2 | —CH(OH)—(CH$_2$)$_5$—(4-CF$_3$—Ph) | H | H |
| 1-1720 | H | H | H | Me | 2 | —CH(OH)—(CH$_2$)$_5$—(4-MeO—Ph) | H | H |
| 1-1721 | H | H | H | Me | 2 | —CH(OH)—(CH$_2$)$_5$—(4-EtO—Ph) | H | H |
| 1-1722 | H | H | H | Me | 2 | —CH(OH)—(CH$_2$)$_5$—(4-MeS—Ph) | H | H |
| 1-1723 | H | H | H | Me | 2 | —CH(OH)—(CH$_2$)$_5$—(4-cHx—Ph) | H | H |
| 1-1724 | H | H | H | Me | 2 | —CH(OH)—(CH$_2$)$_5$—(4-Ph—Ph) | H | H |
| 1-1725 | H | H | H | Me | 2 | —CH(OH)—(CH$_2$)$_6$—cHx | H | H |
| 1-1726 | H | H | H | Me | 2 | —CH(OH)—(CH$_2$)$_6$—Ph | H | H |
| 1-1727 | H | H | H | Me | 2 | —CH(OH)—(CH$_2$)$_7$—cHx | H | H |
| 1-1728 | H | H | H | Me | 2 | —CH(OH)—(CH$_2$)$_7$—Ph | H | H |
| 1-1729 | H | H | H | Me | 2 | -4-(cHx—CH$_2$O)Ph | H | H |
| 1-1730 | H | H | Me | Me | 2 | -4-(cHx—CH$_2$O)Ph | H | H |
| 1-1731 | Me | H | H | Me | 2 | -4-(cHx—CH$_2$O)Ph | H | H |
| 1-1732 | CO$_2$Me | H | H | Me | 2 | -4-(cHx—CH$_2$O)Ph | H | H |
| 1-1733 | H | H | H | Me | 2 | -4-(cHx—CH$_2$O)-2-F—Ph | H | H |
| 1-1734 | H | H | H | Me | 2 | -4-(cHx—CH$_2$O)-3-F—Ph | H | H |
| 1-1735 | H | H | H | Me | 2 | -4-(cHx—CH$_2$O)-2,3-diF—Ph | H | H |
| 1-1736 | H | H | H | Me | 2 | -4-(cHx—CH$_2$O)-2-Cl—Ph | H | H |
| 1-1737 | H | H | H | Me | 2 | -4-(cHx—CH$_2$O)-3-Cl—Ph | H | H |
| 1-1738 | H | H | H | Me | 2 | -4-(cHx—CH$_2$O)-2,3-diCl—Ph | H | H |
| 1-1739 | H | H | H | Me | 2 | -4-(cHx—CH$_2$O)-2-Me—Ph | H | H |
| 1-1740 | H | H | H | Me | 2 | -4-(cHx—CH$_2$O)-3-Me—Ph | H | H |
| 1-1741 | H | H | H | Me | 2 | -4-(cHx—CH$_2$O)-2,3-diMe—Ph | H | H |
| 1-1742 | H | H | H | Me | 2 | -4-[cHx—(CH$_2$)$_2$O]Ph | H | H |
| 1-1743 | H | H | H | Me | 2 | -4-[cHx—(CH$_2$)$_3$O]Ph | H | H |
| 1-1744 | H | H | H | Me | 2 | -(4-BzO—Ph) | H | H |
| 1-1745 | H | H | Me | Me | 2 | -(4-BzO—Ph) | H | H |
| 1-1746 | Me | H | H | Me | 2 | -(4-BzO—Ph) | H | H |
| 1-1747 | CO$_2$Me | H | H | Me | 2 | -(4-BzO—Ph) | H | H |
| 1-1748 | H | H | H | Me | 2 | -(4-BzO-2-F—Ph) | H | H |
| 1-1749 | H | H | H | Me | 2 | -(4-BzO-3-F—Ph) | H | H |
| 1-1750 | H | H | H | Me | 2 | -(4-BzO-2,3-diF—Ph) | H | H |
| 1-1751 | H | H | H | Me | 2 | -(4-BzO-2-Cl—Ph) | H | H |
| 1-1752 | H | H | H | Me | 2 | -(4-BzO-3-Cl—Ph) | H | H |
| 1-1753 | H | H | H | Me | 2 | -(4-BzO-2,3-diCl—Ph) | H | H |
| 1-1754 | H | H | H | Me | 2 | -(4-BzO-2-Me—Ph) | H | H |
| 1-1755 | H | H | H | Me | 2 | -(4-BzO-3-Me—Ph) | H | H |

TABLE 1-continued (Ia)

[Structure: thiophene ring with NR¹R², R⁴, R³O-CH₂, (CH₂)ₙ, R⁶, R⁷, X—Y—R⁵ substituents]

| Exemp. Compd. No. | R¹ | R² | R³ | R⁴ | n | —X—Y—R⁵ | R⁶ | R⁷ |
|---|---|---|---|---|---|---|---|---|
| 1-1756 | H | H | H | Me | 2 | -(4-BzO-2,3-diMe—Ph) | H | H |
| 1-1757 | H | H | H | Me | 2 | -4-[Ph—(CH₂)₂O]—Ph | H | H |
| 1-1758 | H | H | H | Me | 2 | -4-[Ph—(CH₂)₃O]—Ph | H | H |
| 1-1759 | H | H | H | Et | 2 | —(CH₂)₃—cHx | H | H |
| 1-1760 | H | H | H | Et | 2 | —(CH₂)₃—Ph | H | H |
| 1-1761 | H | H | H | Et | 2 | —(CH₂)₄—cHx | H | H |
| 1-1762 | H | H | H | Et | 2 | —(CH₂)₄—Ph | H | H |
| 1-1763 | H | H | H | Et | 2 | —(CH₂)₅—cPn | H | H |
| 1-1764 | H | H | H | Et | 2 | —(CH₂)₅—cHx | H | H |
| 1-1765 | H | H | H | Et | 2 | —(CH₂)₅—cHx | Me | H |
| 1-1766 | H | H | H | Et | 2 | —(CH₂)₅—cHx | H | Me |
| 1-1767 | H | H | H | Et | 2 | —(CH₂)₅—cHx | F | H |
| 1-1768 | H | H | H | Et | 2 | —(CH₂)₅—cHx | H | F |
| 1-1769 | H | H | Me | Et | 2 | —(CH₂)₅—cHx | H | H |
| 1-1770 | Me | H | H | Et | 2 | —(CH₂)₅—cHx | H | H |
| 1-1771 | CO₂Me | H | H | Et | 2 | —(CH₂)₅—cHx | H | H |
| 1-1772 | H | H | H | Et | 2 | —(CH₂)₅—(4-F—cHx) | H | H |
| 1-1773 | H | H | H | Et | 2 | —(CH₂)₅—(4-Cl—cHx) | H | H |
| 1-1774 | H | H | H | Et | 2 | —(CH₂)₅—(4-Br—cHx) | H | H |
| 1-1775 | H | H | H | Et | 2 | —(CH₂)₅—(4-Me—cHx) | H | H |
| 1-1776 | H | H | H | Et | 2 | —(CH₂)₅—(4-Et—cHx) | H | H |
| 1-1777 | H | H | H | Et | 2 | —(CH₂)₅—(4-Pr—cHx) | H | H |
| 1-1778 | H | H | H | Et | 2 | —(CH₂)₅—(4-iPr—cHx) | H | H |
| 1-1779 | H | H | H | Et | 2 | —(CH₂)₅—(4-CF₃—cHx) | H | H |
| 1-1780 | H | H | H | Et | 2 | —(CH₂)₅—(4-MeO—cHx) | H | H |
| 1-1781 | H | H | H | Et | 2 | —(CH₂)₅—(4-EtO—cHx) | H | H |
| 1-1782 | H | H | H | Et | 2 | —(CH₂)₅—(4-PrO—cHx) | H | H |
| 1-1783 | H | H | H | Et | 2 | —(CH₂)₅—(4-iPrO—cHx) | H | H |
| 1-1784 | H | H | H | Et | 2 | —(CH₂)₅—(3-MeS—cHx) | H | H |
| 1-1785 | H | H | H | Et | 2 | —(CH₂)₅—(4-MeS—cHx) | H | H |
| 1-1786 | H | H | H | Et | 2 | —(CH₂)₅—(2,4-diMe—cHx) | H | H |
| 1-1787 | H | H | H | Et | 2 | —(CH₂)₅—(3,4-diMe—cHx) | H | H |
| 1-1788 | H | H | H | Et | 2 | —(CH₂)₅—(3,5-diMe—cHx) | H | H |
| 1-1789 | H | H | H | Et | 2 | —(CH₂)₅—Ph | H | H |
| 1-1790 | H | H | H | Et | 2 | —(CH₂)₅—Ph | Me | H |
| 1-1791 | H | H | H | Et | 2 | —(CH₂)₅—Ph | H | Me |
| 1-1792 | H | H | H | Et | 2 | —(CH₂)₅—Ph | F | H |
| 1-1793 | H | H | H | Et | 2 | —(CH₂)₅—Ph | H | F |
| 1-1794 | H | H | Me | Et | 2 | —(CH₂)₅—Ph | H | H |
| 1-1795 | Me | H | H | Et | 2 | —(CH₂)₅—Ph | H | H |
| 1-1796 | CO₂Me | H | H | Et | 2 | —(CH₂)₅—Ph | H | H |
| 1-1797 | H | H | H | Et | 2 | —(CH₂)₅—(4-F—Ph) | H | H |
| 1-1798 | H | H | H | Et | 2 | —(CH₂)₅—(4-Cl—Ph) | H | H |
| 1-1799 | H | H | H | Et | 2 | —(CH₂)₅—(4-Br—Ph) | H | H |
| 1-1800 | H | H | H | Et | 2 | —(CH₂)₅—(4-Me—Ph) | H | H |
| 1-1801 | H | H | H | Et | 2 | —(CH₂)₅—(4-Et—Ph) | H | H |
| 1-1802 | H | H | H | Et | 2 | —(CH₂)₅—(4-Pr—Ph) | H | H |
| 1-1803 | H | H | H | Et | 2 | —(CH₂)₅—(4-iPr—Ph) | H | H |
| 1-1804 | H | H | H | Et | 2 | —(CH₂)₅—(4-Bu—Ph) | H | H |
| 1-1805 | H | H | H | Et | 2 | —(CH₂)₅—(4-CF₃—Ph) | H | H |
| 1-1806 | H | H | H | Et | 2 | —(CH₂)₅—(4-MeO—Ph) | H | H |
| 1-1807 | H | H | H | Et | 2 | —(CH₂)₅—(4-EtO—Ph) | H | H |
| 1-1808 | H | H | H | Et | 2 | —(CH₂)₅—(4-PrO—Ph) | H | H |
| 1-1809 | H | H | H | Et | 2 | —(CH₂)₅—(4-iPrO—Ph) | H | H |
| 1-1810 | H | H | H | Et | 2 | —(CH₂)₅—(3-MeS—Ph) | H | H |
| 1-1811 | H | H | H | Et | 2 | —(CH₂)₅—(4-MeS—Ph) | H | H |
| 1-1812 | H | H | H | Et | 2 | —(CH₂)₅—(2,4-diMe—Ph) | H | H |
| 1-1813 | H | H | H | Et | 2 | —(CH₂)₅—(3,4-diMe—Ph) | H | H |
| 1-1814 | H | H | H | Et | 2 | —(CH₂)₅—(3,5-diMe—Ph) | H | H |
| 1-1815 | H | H | H | Et | 2 | —(CH₂)₆—cPn | H | H |
| 1-1816 | H | H | H | Et | 2 | —(CH₂)₆—cHx | H | H |
| 1-1817 | H | H | H | Et | 2 | —(CH₂)₆—cHx | Me | H |
| 1-1818 | H | H | H | Et | 2 | —(CH₂)₆—cHx | H | Me |
| 1-1819 | H | H | H | Et | 2 | —(CH₂)₆—cHx | F | H |
| 1-1820 | H | H | H | Et | 2 | —(CH₂)₆—cHx | H | F |

TABLE 1-continued (Ia)

Structure: R⁴, R³O, (CH₂)ₙ, NR¹R², thiophene ring with R⁶ and R⁷, X—Y—R⁵

| Exemp. Compd. No. | R¹ | R² | R³ | R⁴ | n | —X—Y—R⁵ | R⁶ | R⁷ |
|---|---|---|---|---|---|---|---|---|
| 1-1821 | H | H | Me | Et | 2 | —(CH$_2$)$_6$—cHx | H | H |
| 1-1822 | Me | H | H | Et | 2 | —(CH$_2$)$_6$—cHx | H | H |
| 1-1823 | CO$_2$Me | H | H | Et | 2 | —(CH$_2$)$_6$—cHx | H | H |
| 1-1824 | H | H | H | Et | 2 | —(CH$_2$)$_6$—(4-F—cHx) | H | H |
| 1-1825 | H | H | H | Et | 2 | —(CH$_2$)$_6$—(4-Cl—cHx) | H | H |
| 1-1826 | H | H | H | Et | 2 | —(CH$_2$)$_6$—(4-Br—cHx) | H | H |
| 1-1827 | H | H | H | Et | 2 | —(CH$_2$)$_6$—(4-Me—cHx) | H | H |
| 1-1828 | H | H | H | Et | 2 | —(CH$_2$)$_6$—(4-Et—cHx) | H | H |
| 1-1829 | H | H | H | Et | 2 | —(CH$_2$)$_6$—(4-Pr—cHx) | H | H |
| 1-1830 | H | H | H | Et | 2 | —(CH$_2$)$_6$—(4-iPr—cHx) | H | H |
| 1-1831 | H | H | H | Et | 2 | —(CH$_2$)$_6$—(4-Bu—cHx) | H | H |
| 1-1832 | H | H | H | Et | 2 | —(CH$_2$)$_6$—(4-CF$_3$—cHx) | H | H |
| 1-1833 | H | H | H | Et | 2 | —(CH$_2$)$_6$—(4-MeO—cHx) | H | H |
| 1-1834 | H | H | H | Et | 2 | —(CH$_2$)$_6$—(4-EtO—cHx) | H | H |
| 1-1835 | H | H | H | Et | 2 | —(CH$_2$)$_6$—(4-PrO—cHx) | H | H |
| 1-1836 | H | H | H | Et | 2 | —(CH$_2$)$_6$—(4-iPrO—cHx) | H | H |
| 1-1837 | H | H | H | Et | 2 | —(CH$_2$)$_6$—(3-MeS—cHx) | H | H |
| 1-1838 | H | H | H | Et | 2 | —(CH$_2$)$_6$—(4-MeS—cHx) | H | H |
| 1-1839 | H | H | H | Et | 2 | —(CH$_2$)$_6$—(2,4-diMe—cHx) | H | H |
| 1-1840 | H | H | H | Et | 2 | —(CH$_2$)$_6$—(3,4-diMe—cHx) | H | H |
| 1-1841 | H | H | H | Et | 2 | —(CH$_2$)$_6$—(3,5-diMe—cHx) | H | H |
| 1-1842 | H | H | H | Et | 2 | —(CH$_2$)$_6$—Ph | H | H |
| 1-1843 | H | H | H | Et | 2 | —(CH$_2$)$_6$—Ph | Me | H |
| 1-1844 | H | H | H | Et | 2 | —(CH$_2$)$_6$—Ph | H | Me |
| 1-1845 | H | H | H | Et | 2 | —(CH$_2$)$_6$—Ph | F | H |
| 1-1846 | H | H | H | Et | 2 | —(CH$_2$)$_6$—Ph | H | F |
| 1-1847 | H | H | Me | Et | 2 | —(CH$_2$)$_6$—Ph | H | H |
| 1-1848 | Me | H | H | Et | 2 | —(CH$_2$)$_6$—Ph | H | H |
| 1-1849 | CO$_2$Me | H | H | Et | 2 | —(CH$_2$)$_6$—Ph | H | H |
| 1-1850 | H | H | H | Et | 2 | —(CH$_2$)$_6$—(4-F—Ph) | H | H |
| 1-1851 | H | H | H | Et | 2 | —(CH$_2$)$_6$—(4-Cl—Ph) | H | H |
| 1-1852 | H | H | H | Et | 2 | —(CH$_2$)$_6$—(4-Br—Ph) | H | H |
| 1-1853 | H | H | H | Et | 2 | —(CH$_2$)$_6$—(4-Me—Ph) | H | H |
| 1-1854 | H | H | H | Et | 2 | —(CH$_2$)$_6$—(4-Et—Ph) | H | H |
| 1-1855 | H | H | H | Et | 2 | —(CH$_2$)$_6$—(4-Pr—Ph) | H | H |
| 1-1856 | H | H | H | Et | 2 | —(CH$_2$)$_6$—(4-iPr—Ph) | H | H |
| 1-1857 | H | H | H | Et | 2 | —(CH$_2$)$_6$—(4-Bu—Ph) | H | H |
| 1-1858 | H | H | H | Et | 2 | —(CH$_2$)$_6$—(4-CF$_3$—Ph) | H | H |
| 1-1859 | H | H | H | Et | 2 | —(CH$_2$)$_6$—(4-MeO—Ph) | H | H |
| 1-1860 | H | H | H | Et | 2 | —(CH$_2$)$_6$—(4-EtO—Ph) | H | H |
| 1-1861 | H | H | H | Et | 2 | —(CH$_2$)$_6$—(4-PrO—Ph) | H | H |
| 1-1862 | H | H | H | Et | 2 | —(CH$_2$)$_6$—(4-iPrO—Ph) | H | H |
| 1-1863 | H | H | H | Et | 2 | —(CH$_2$)$_6$—(3-MeS—Ph) | H | H |
| 1-1864 | H | H | H | Et | 2 | —(CH$_2$)$_6$—(4-MeS—Ph) | H | H |
| 1-1865 | H | H | H | Et | 2 | —(CH$_2$)$_6$—(2,4-diMe—Ph) | H | H |
| 1-1866 | H | H | H | Et | 2 | —(CH$_2$)$_6$—(3,4-diMe—Ph) | H | H |
| 1-1867 | H | H | H | Et | 2 | —(CH$_2$)$_6$—(3,5-diMe—Ph) | H | H |
| 1-1868 | H | H | H | Et | 2 | —(CH$_2$)$_7$—cHx | H | H |
| 1-1869 | H | H | H | Et | 2 | —(CH$_2$)$_7$—Ph | H | H |
| 1-1870 | H | H | H | Et | 2 | —CH=CH—cHx | H | H |
| 1-1871 | H | H | H | Et | 2 | —CH=CH—Ph | H | H |
| 1-1872 | H | H | H | Et | 2 | —CH=CH—(CH$_2$)$_3$—cHx | H | H |
| 1-1873 | H | H | Me | Et | 2 | —CH=CH—(CH$_2$)$_3$—cHx | H | H |
| 1-1874 | Me | H | H | Et | 2 | —CH=CH—(CH$_2$)$_3$—cHx | H | H |
| 1-1875 | CO$_2$Me | H | H | Et | 2 | —CH=CH—(CH$_2$)$_3$—cHx | H | H |
| 1-1876 | H | H | H | Et | 2 | —CH=CH—(CH$_2$)$_3$—Ph | H | H |
| 1-1877 | H | H | Me | Et | 2 | —CH=CH—(CH$_2$)$_3$—Ph | H | H |
| 1-1878 | Me | H | H | Et | 2 | —CH=CH—(CH$_2$)$_3$—Ph | H | H |
| 1-1879 | CO$_2$Me | H | H | Et | 2 | —CH=CH—(CH$_2$)$_3$—Ph | H | H |
| 1-1880 | H | H | H | Et | 2 | —CH=CH—(CH$_2$)$_4$—cHx | H | H |
| 1-1881 | H | H | Me | Et | 2 | —CH=CH—(CH$_2$)$_4$—cHx | H | H |
| 1-1882 | Me | H | H | Et | 2 | —CH=CH—(CH$_2$)$_4$—cHx | H | H |
| 1-1883 | CO$_2$Me | H | H | Et | 2 | —CH=CH—(CH$_2$)$_4$—cHx | H | H |
| 1-1884 | H | H | H | Et | 2 | —CH=CH—(CH$_2$)$_4$—Ph | H | H |
| 1-1885 | H | H | Me | Et | 2 | —CH=CH—(CH$_2$)$_4$—Ph | H | H |

TABLE 1-continued

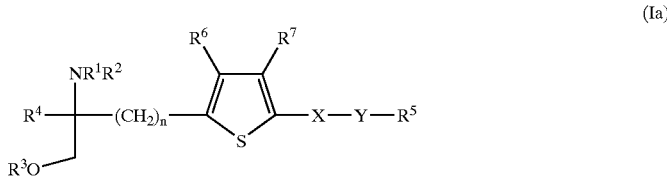

(Ia)

| Exemp. Compd. No. | $R^1$ | $R^2$ | $R^3$ | $R^4$ | n | —X—Y—$R^5$ | $R^6$ | $R^7$ |
|---|---|---|---|---|---|---|---|---|
| 1-1886 | Me | H | H | Et | 2 | —CH=CH—$(CH_2)_4$—Ph | H | H |
| 1-1887 | $CO_2Me$ | H | H | Et | 2 | —CH=CH—$(CH_2)_4$—Ph | H | H |
| 1-1888 | H | H | H | Et | 2 | —CH=CH—$CH_2O$—cHx | H | H |
| 1-1889 | H | H | H | Et | 2 | —CH=CH—$CH_2O$—Ph | H | H |
| 1-1890 | H | H | H | Et | 2 | —CH=CH—$(CH_2)_2O$—cHx | H | H |
| 1-1891 | H | H | H | Et | 2 | —CH=CH—$(CH_2)_2O$—Ph | H | H |
| 1-1892 | H | H | H | Et | 2 | —C≡C—$CH_2$—cHx | H | H |
| 1-1893 | H | H | Me | Et | 2 | —C≡C—$CH_2$—cHx | H | H |
| 1-1894 | Me | H | H | Et | 2 | —C≡C—$CH_2$—cHx | H | H |
| 1-1895 | $CO_2Me$ | H | H | Et | 2 | —C≡C—$CH_2$—cHx | H | H |
| 1-1896 | H | H | H | Et | 2 | —C≡C—$CH_2$—Ph | H | H |
| 1-1897 | H | H | Me | Et | 2 | —C≡C—$CH_2$—Ph | H | H |
| 1-1898 | Me | H | H | Et | 2 | —C≡C—$CH_2$—Ph | H | H |
| 1-1899 | $CO_2Me$ | H | H | Et | 2 | —C≡C—$CH_2$—Ph | H | H |
| 1-1900 | H | H | H | Et | 2 | —C≡C—$(CH_2)_2$—cHx | H | H |
| 1-1901 | H | H | Me | Et | 2 | —C≡C—$(CH_2)_2$—cHx | H | H |
| 1-1902 | Me | H | H | Et | 2 | —C≡C—$(CH_2)_2$—cHx | H | H |
| 1-1903 | $CO_2Me$ | H | H | Et | 2 | —C≡C—$(CH_2)_2$—cHx | H | H |
| 1-1904 | H | H | H | Et | 2 | —C≡C—$(CH_2)_2$—Ph | H | H |
| 1-1905 | H | H | Me | Et | 2 | —C≡C—$(CH_2)_2$—Ph | H | H |
| 1-1906 | Me | H | H | Et | 2 | —C≡C—$(CH_2)_2$—Ph | H | H |
| 1-1907 | $CO_2Me$ | H | H | Et | 2 | —C≡C—$(CH_2)_2$—Ph | H | H |
| 1-1908 | H | H | H | Et | 2 | —C≡C—$(CH_2)_3$—cPn | H | H |
| 1-1909 | H | H | H | Et | 2 | —C≡C—$(CH_2)_3$—cHx | H | H |
| 1-1910 | H | H | H | Et | 2 | —C≡C—$(CH_2)_3$—cHx | Me | H |
| 1-1911 | H | H | H | Et | 2 | —C≡C—$(CH_2)_3$—cHx | H | Me |
| 1-1912 | H | H | H | Et | 2 | —C≡C—$(CH_2)_3$—cHx | F | H |
| 1-1913 | H | H | H | Et | 2 | —C≡C—$(CH_2)_3$—cHx | H | F |
| 1-1914 | H | H | Me | Et | 2 | —C≡C—$(CH_2)_3$—cHx | H | H |
| 1-1915 | Me | H | H | Et | 2 | —C≡C—$(CH_2)_3$—cHx | H | H |
| 1-1916 | $CO_2Me$ | H | H | Et | 2 | —C≡C—$(CH_2)_3$—cHx | H | H |
| 1-1917 | H | H | H | Et | 2 | —C≡C—$(CH_2)_3$—(4-F—cHx) | H | H |
| 1-1918 | H | H | H | Et | 2 | —C≡C—$(CH_2)_3$—(4-Cl—cHx) | H | H |
| 1-1919 | H | H | H | Et | 2 | —C≡C—$(CH_2)_3$—(4-Br—cHx) | H | H |
| 1-1920 | H | H | H | Et | 2 | —C≡C—$(CH_2)_3$—(4-Me—cHx) | H | H |
| 1-1921 | H | H | H | Et | 2 | —C≡C—$(CH_2)_3$—(4-Et—cHx) | H | H |
| 1-1922 | H | H | H | Et | 2 | —C≡C—$(CH_2)_3$—(4-Pr—cHx) | H | H |
| 1-1923 | H | H | H | Et | 2 | —C≡C—$(CH_2)_3$—(4-iPr—cHx) | H | H |
| 1-1924 | H | H | H | Et | 2 | —C≡C—$(CH_2)_3$—(4-Bu—cHx) | H | H |
| 1-1925 | H | H | H | Et | 2 | —C≡C—$(CH_2)_3$—(4-$CF_3$—cHx) | H | H |
| 1-1926 | H | H | H | Et | 2 | —C≡C—$(CH_2)_3$—(4-MeO—cHx) | H | H |
| 1-1927 | H | H | H | Et | 2 | —C≡C—$(CH_2)_3$—(4-EtO—cHx) | H | H |
| 1-1928 | H | H | H | Et | 2 | —C≡C—$(CH_2)_3$—(4-PrO—cHx) | H | H |
| 1-1929 | H | H | H | Et | 2 | —C≡C—$(CH_2)_3$—(4-iPrO—cHx) | H | H |
| 1-1930 | H | H | H | Et | 2 | —C≡C—$(CH_2)_3$—(3-MeS—cHx) | H | H |
| 1-1931 | H | H | H | Et | 2 | —C≡C—$(CH_2)_3$—(4-MeS—cHx) | H | H |
| 1-1932 | H | H | H | Et | 2 | —C≡C—$(CH_2)_3$—(2,4-diMe—cHx) | H | H |
| 1-1933 | H | H | H | Et | 2 | —C≡C—$(CH_2)_3$—(3,4-diMe—cHx) | H | H |
| 1-1934 | H | H | H | Et | 2 | —C≡C—$(CH_2)_3$—(3,5-diMe—cHx) | H | H |
| 1-1935 | H | H | H | Et | 2 | —C≡C—$(CH_2)_3$—Ph | H | H |
| 1-1936 | H | H | H | Et | 2 | —C≡C—$(CH_2)_3$—Ph | Me | H |
| 1-1937 | H | H | H | Et | 2 | —C≡C—$(CH_2)_3$—Ph | H | Me |
| 1-1938 | H | H | H | Et | 2 | —C≡C—$(CH_2)_3$—Ph | F | H |
| 1-1939 | H | H | H | Et | 2 | —C≡C—$(CH_2)_3$—Ph | H | F |
| 1-1940 | H | H | Me | Et | 2 | —C≡C—$(CH_2)_3$—Ph | H | H |
| 1-1941 | Me | H | H | Et | 2 | —C≡C—$(CH_2)_3$—Ph | H | H |
| 1-1942 | $CO_2Me$ | H | H | Et | 2 | —C≡C—$(CH_2)_3$—Ph | H | H |
| 1-1943 | H | H | H | Et | 2 | —C≡C—$(CH_2)_3$—(4-F—Ph) | H | H |
| 1-1944 | H | H | H | Et | 2 | —C≡C—$(CH_2)_3$—(4-Cl—Ph) | H | H |
| 1-1945 | H | H | H | Et | 2 | —C≡C—$(CH_2)_3$—(4-Br—Ph) | H | H |
| 1-1946 | H | H | H | Et | 2 | —C≡C—$(CH_2)_3$—(4-Me—Ph) | H | H |
| 1-1947 | H | H | H | Et | 2 | —C≡C—$(CH_2)_3$—(4-Et—Ph) | H | H |
| 1-1948 | H | H | H | Et | 2 | —C≡C—$(CH_2)_3$—(4-Pr—Ph) | H | H |
| 1-1949 | H | H | H | Et | 2 | —C≡C—$(CH_2)_3$—(4-iPr—Ph) | H | H |
| 1-1950 | H | H | H | Et | 2 | —C≡C—$(CH_2)_3$—(4-Bu—Ph) | H | H |

TABLE 1-continued (Ia)

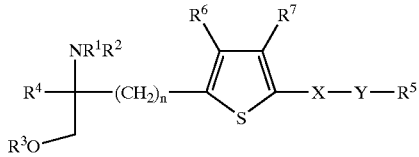

| Exemp. Compd. No. | R¹ | R² | R³ | R⁴ | n | —X—Y—R⁵ | R⁶ | R⁷ |
|---|---|---|---|---|---|---|---|---|
| 1-1951 | H | H | H | Et | 2 | —C≡C—(CH₂)₃—(4-CF₃—Ph) | H | H |
| 1-1952 | H | H | H | Et | 2 | —C≡C—(CH₂)₃—(4-MeO—Ph) | H | H |
| 1-1953 | H | H | H | Et | 2 | —C≡C—(CH₂)₃—(4-EtO—Ph) | H | H |
| 1-1954 | H | H | H | Et | 2 | —C≡C—(CH₂)₃—(4-PrO—Ph) | H | H |
| 1-1955 | H | H | H | Et | 2 | —C≡C—(CH₂)₃—(4-iPrO—Ph) | H | H |
| 1-1956 | H | H | H | Et | 2 | —C≡C—(CH₂)₃—(3-MeS—Ph) | H | H |
| 1-1957 | H | H | H | Et | 2 | —C≡C—(CH₂)₃—(4-MeS—Ph) | H | H |
| 1-1958 | H | H | H | Et | 2 | —C≡C—(CH₂)₃—(2,4-diMe—Ph) | H | H |
| 1-1959 | H | H | H | Et | 2 | —C≡C—(CH₂)₃—(3,4-diMe—Ph) | H | H |
| 1-1960 | H | H | H | Et | 2 | —C≡C—(CH₂)₃—(3,5-diMe—Ph) | H | H |
| 1-1961 | H | H | H | Et | 2 | —C≡C—(CH₂)₄—cPn | H | H |
| 1-1962 | H | H | H | Et | 2 | —C≡C—(CH₂)₄—cHx | H | H |
| 1-1963 | H | H | H | Et | 2 | —C≡C—(CH₂)₄—cHx | Me | H |
| 1-1964 | H | H | H | Et | 2 | —C≡C—(CH₂)₄—cHx | H | Me |
| 1-1965 | H | H | H | Et | 2 | —C≡C—(CH₂)₄—cHx | F | H |
| 1-1966 | H | H | H | Et | 2 | —C≡C—(CH₂)₄—cHx | H | F |
| 1-1967 | H | H | Me | Et | 2 | —C≡C—(CH₂)₄—cHx | H | H |
| 1-1968 | Me | H | H | Et | 2 | —C≡C—(CH₂)₄—cHx | H | H |
| 1-1969 | CO₂Me | H | H | Et | 2 | —C≡C—(CH₂)₄—cHx | H | H |
| 1-1970 | H | H | H | Et | 2 | —C≡C—(CH₂)₄—(4-F—cHx) | H | H |
| 1-1971 | H | H | H | Et | 2 | —C≡C—(CH₂)₄—(4-Cl—cHx) | H | H |
| 1-1972 | H | H | H | Et | 2 | —C≡C—(CH₂)₄—(4-Br—cHx) | H | H |
| 1-1973 | H | H | H | Et | 2 | —C≡C—(CH₂)₄—(4-Me—cHx) | H | H |
| 1-1974 | H | H | H | Et | 2 | —C≡C—(CH₂)₄—(4-Et—cHx) | H | H |
| 1-1975 | H | H | H | Et | 2 | —C≡C—(CH₂)₄—(4-Pr—cHx) | H | H |
| 1-1976 | H | H | H | Et | 2 | —C≡C—(CH₂)₄—(4-iPr—cHx) | H | H |
| 1-1977 | H | H | H | Et | 2 | —C≡C—(CH₂)₄—(4-Bu—cHx) | H | H |
| 1-1978 | H | H | H | Et | 2 | —C≡C—(CH₂)₄—(4-CF₃—cHx) | H | H |
| 1-1979 | H | H | H | Et | 2 | —C≡C—(CH₂)₄—(4-MeO—cHx) | H | H |
| 1-1980 | H | H | H | Et | 2 | —C≡C—(CH₂)₄—(4-EtO—cHx) | H | H |
| 1-1981 | H | H | H | Et | 2 | —C≡C—(CH₂)₄—(4-PrO—cHx) | H | H |
| 1-1982 | H | H | H | Et | 2 | —C≡C—(CH₂)₄—(4-iPrO—cHx) | H | H |
| 1-1983 | H | H | H | Et | 2 | —C≡C—(CH₂)₄—(4-MeS—cHx) | H | H |
| 1-1984 | H | H | H | Et | 2 | —C≡C—(CH₂)₄—(2,4-diMe—cHx) | H | H |
| 1-1985 | H | H | H | Et | 2 | —C≡C—(CH₂)₄—(3,4-diMe—cHx) | H | H |
| 1-1986 | H | H | H | Et | 2 | —C≡C—(CH₂)₄—(3,5-diMe—cHx) | H | H |
| 1-1987 | H | H | H | Et | 2 | —C≡C—(CH₂)₄—Ph | H | H |
| 1-1988 | H | H | H | Et | 2 | —C≡C—(CH₂)₄—Ph | Me | H |
| 1-1989 | H | H | H | Et | 2 | —C≡C—(CH₂)₄—Ph | H | Me |
| 1-1990 | H | H | H | Et | 2 | —C≡C—(CH₂)₄—Ph | F | H |
| 1-1991 | H | H | H | Et | 2 | —C≡C—(CH₂)₄—Ph | H | F |
| 1-1992 | H | H | Me | Et | 2 | —C≡C—(CH₂)₄—Ph | H | H |
| 1-1993 | Me | H | H | Et | 2 | —C≡C—(CH₂)₄—Ph | H | H |
| 1-1994 | CO₂Me | H | H | Et | 2 | —C≡C—(CH₂)₄—Ph | H | H |
| 1-1995 | H | H | H | Et | 2 | —C≡C—(CH₂)₄—(4-F—Ph) | H | H |
| 1-1996 | H | H | H | Et | 2 | —C≡C—(CH₂)₄—(4-Cl—Ph) | H | H |
| 1-1997 | H | H | H | Et | 2 | —C≡C—(CH₂)₄—(4-Br—Ph) | H | H |
| 1-1998 | H | H | H | Et | 2 | —C≡C—(CH₂)₄—(4-Me—Ph) | H | H |
| 1-1999 | H | H | H | Et | 2 | —C≡C—(CH₂)₄—(4-Et—Ph) | H | H |
| 1-2000 | H | H | H | Et | 2 | —C≡C—(CH₂)₄—(4-Pr—Ph) | H | H |
| 1-2001 | H | H | H | Et | 2 | —C≡C—(CH₂)₄—(4-iPr—Ph) | H | H |
| 1-2002 | H | H | H | Et | 2 | —C≡C—(CH₂)₄—(4-Bu—Ph) | H | H |
| 1-2003 | H | H | H | Et | 2 | —C≡C—(CH₂)₄—(4-CF₃—Ph) | H | H |
| 1-2004 | H | H | H | Et | 2 | —C≡C—(CH₂)₄—(4-MeO—Ph) | H | H |
| 1-2005 | H | H | H | Et | 2 | —C≡C—(CH₂)₄—(4-EtO—Ph) | H | H |
| 1-2006 | H | H | H | Et | 2 | —C≡C—(CH₂)₄—(4-PrO—Ph) | H | H |
| 1-2007 | H | H | H | Et | 2 | —C≡C—(CH₂)₄—(4-iPrO—Ph) | H | H |
| 1-2008 | H | H | H | Et | 2 | —C≡C—(CH₂)₄—(3-MeS—Ph) | H | H |
| 1-2009 | H | H | H | Et | 2 | —C≡C—(CH₂)₄—(4-MeS—Ph) | H | H |
| 1-2010 | H | H | H | Et | 2 | —C≡C—(CH₂)₄—(2,4-diMe—Ph) | H | H |
| 1-2011 | H | H | H | Et | 2 | —C≡C—(CH₂)₄—(3,4-diMe—Ph) | H | H |
| 1-2012 | H | H | H | Et | 2 | —C≡C—(CH₂)₄—(3,5-diMe—Ph) | H | H |
| 1-2013 | H | H | H | Et | 2 | —C≡C—(CH₂)₅—cHx | H | H |
| 1-2014 | H | H | Me | Et | 2 | —C≡C—(CH₂)₅—cHx | H | H |
| 1-2015 | Me | H | H | Et | 2 | —C≡C—(CH₂)₅—cHx | H | H |

TABLE 1-continued (Ia)

$$\text{R}^4-\underset{\underset{\text{R}^3\text{O}}{|}}{\overset{\overset{\text{NR}^1\text{R}^2}{|}}{\text{C}}}-(\text{CH}_2)_n-\underset{\text{S}}{\text{thiophene}(\text{R}^6,\text{R}^7)}-X-Y-\text{R}^5$$

| Exemp. Compd. No. | $R^1$ | $R^2$ | $R^3$ | $R^4$ | n | —X—Y—$R^5$ | $R^6$ | $R^7$ |
|---|---|---|---|---|---|---|---|---|
| 1-2016 | CO$_2$Me | H | H | Et | 2 | —C≡C—(CH$_2$)$_5$—cHx | H | H |
| 1-2017 | H | H | H | Et | 2 | —C≡C—(CH$_2$)$_5$—Ph | H | H |
| 1-2018 | H | H | Me | Et | 2 | —C≡C—(CH$_2$)$_5$—Ph | H | H |
| 1-2019 | Me | H | H | Et | 2 | —C≡C—(CH$_2$)$_5$—Ph | H | H |
| 1-2020 | CO$_2$Me | H | H | Et | 2 | —C≡C—(CH$_2$)$_5$—Ph | H | H |
| 1-2021 | H | H | H | Et | 2 | —C≡C—(CH$_2$)$_6$—cHx | H | H |
| 1-2022 | H | H | Me | Et | 2 | —C≡C—(CH$_2$)$_6$—cHx | H | H |
| 1-2023 | Me | H | H | Et | 2 | —C≡C—(CH$_2$)$_6$—cHx | H | H |
| 1-2024 | CO$_2$Me | H | H | Et | 2 | —C≡C—(CH$_2$)$_6$—cHx | H | H |
| 1-2025 | H | H | H | Et | 2 | —C≡C—(CH$_2$)$_6$—Ph | H | H |
| 1-2026 | H | H | Me | Et | 2 | —C≡C—(CH$_2$)$_6$—Ph | H | H |
| 1-2027 | Me | H | H | Et | 2 | —C≡C—(CH$_2$)$_6$—Ph | H | H |
| 1-2028 | CO$_2$Me | H | H | Et | 2 | —C≡C—(CH$_2$)$_6$—Ph | H | H |
| 1-2029 | H | H | H | Et | 2 | —C≡C—CH$_2$O—cHx | H | H |
| 1-2030 | H | H | Me | Et | 2 | —C≡C—CH$_2$O—cHx | H | H |
| 1-2031 | Me | H | H | Et | 2 | —C≡C—CH$_2$O—cHx | H | H |
| 1-2032 | CO$_2$Me | H | H | Et | 2 | —C≡C—CH$_2$O—cHx | H | H |
| 1-2033 | H | H | H | Et | 2 | —C≡C—CH$_2$O—Ph | H | H |
| 1-2034 | H | H | Me | Et | 2 | —C≡C—CH$_2$O—Ph | H | H |
| 1-2035 | Me | H | H | Et | 2 | —C≡C—CH$_2$O—Ph | H | H |
| 1-2036 | CO$_2$Me | H | H | Et | 2 | —C≡C—CH$_2$O—Ph | H | H |
| 1-2037 | H | H | H | Et | 2 | —C≡C—(CH$_2$)$_2$O—cPn | H | H |
| 1-2038 | H | H | H | Et | 2 | —C≡C—(CH$_2$)$_2$O—cHx | H | H |
| 1-2039 | H | H | H | Et | 2 | —C≡C—(CH$_2$)$_2$O—cHx | Me | H |
| 1-2040 | H | H | H | Et | 2 | —C≡C—(CH$_2$)$_2$O—cHx | H | Me |
| 1-2041 | H | H | H | Et | 2 | —C≡C—(CH$_2$)$_2$O—cHx | F | H |
| 1-2042 | H | H | H | Et | 2 | —C≡C—(CH$_2$)$_2$O—cHx | H | F |
| 1-2043 | H | H | Me | Et | 2 | —C≡C—(CH$_2$)$_2$O—cHx | H | H |
| 1-2044 | Me | H | H | Et | 2 | —C≡C—(CH$_2$)$_2$O—cHx | H | H |
| 1-2045 | CO$_2$Me | H | H | Et | 2 | —C≡C—(CH$_2$)$_2$O—cHx | H | H |
| 1-2046 | H | H | H | Et | 2 | —C≡C—(CH$_2$)$_2$O—(4-F—cHx) | H | H |
| 1-2047 | H | H | H | Et | 2 | —C≡C—(CH$_2$)$_2$O—(4-Cl—cHx) | H | H |
| 1-2048 | H | H | H | Et | 2 | —C≡C—(CH$_2$)$_2$O—(4-Br—cHx) | H | H |
| 1-2049 | H | H | H | Et | 2 | —C≡C—(CH$_2$)$_2$O—(4-Me—cHx) | H | H |
| 1-2050 | H | H | H | Et | 2 | —C≡C—(CH$_2$)$_2$O—(4-Et—cHx) | H | H |
| 1-2051 | H | H | H | Et | 2 | —C≡C—(CH$_2$)$_2$O—(4-Pr—cHx) | H | H |
| 1-2052 | H | H | H | Et | 2 | —C≡C—(CH$_2$)$_2$O—(4-iPr—cHx) | H | H |
| 1-2053 | H | H | H | Et | 2 | —C≡C—(CH$_2$)$_2$O—(4-Bu—cHx) | H | H |
| 1-2054 | H | H | H | Et | 2 | —C≡C—(CH$_2$)$_2$O—(4-CF$_3$—cHx) | H | H |
| 1-2055 | H | H | H | Et | 2 | —C≡C—(CH$_2$)$_2$O—(4-MeO—cHx) | H | H |
| 1-2056 | H | H | H | Et | 2 | —C≡C—(CH$_2$)$_2$O—(4-EtO—cHx) | H | H |
| 1-2057 | H | H | H | Et | 2 | —C≡C—(CH$_2$)$_2$O—(4-PrO—cHx) | H | H |
| 1-2058 | H | H | H | Et | 2 | —C≡C—(CH$_2$)$_2$O—(4-iPrO—cHx) | H | H |
| 1-2059 | H | H | H | Et | 2 | —C≡C—(CH$_2$)$_2$O—(3-MeS—cHx) | H | H |
| 1-2060 | H | H | H | Et | 2 | —C≡C—(CH$_2$)$_2$O—(4-MeS—cHx) | H | H |
| 1-2061 | H | H | H | Et | 2 | —C≡C—(CH$_2$)$_2$O—(2,4-diMe—cHx) | H | H |
| 1-2062 | H | H | H | Et | 2 | —C≡C—(CH$_2$)$_2$O—(3,4-diMe—cHx) | H | H |
| 1-2063 | H | H | H | Et | 2 | —C≡C—(CH$_2$)$_2$O—(3,5-diMe—cHx) | H | H |
| 1-2064 | H | H | H | Et | 2 | —C≡C—(CH$_2$)$_2$O—Ph | H | H |
| 1-2065 | H | H | H | Et | 2 | —C≡C—(CH$_2$)$_2$O—Ph | Me | H |
| 1-2066 | H | H | H | Et | 2 | —C≡C—(CH$_2$)$_2$O—Ph | H | Me |
| 1-2067 | H | H | H | Et | 2 | —C≡C—(CH$_2$)$_2$O—Ph | F | H |
| 1-2068 | H | H | H | Et | 2 | —C≡C—(CH$_2$)$_2$O—Ph | H | F |
| 1-2069 | H | H | Me | Et | 2 | —C≡C—(CH$_2$)$_2$—OCH$_2$—Ph | H | H |
| 1-2070 | Me | H | H | Et | 2 | —C≡C—(CH$_2$)$_2$O—Ph | H | H |
| 1-2071 | CO$_2$Me | H | H | Et | 2 | —C≡C—(CH$_2$)$_2$O—Ph | H | H |
| 1-2072 | H | H | H | Et | 2 | —C≡C—(CH$_2$)$_2$O—(4-F—Ph) | H | H |
| 1-2073 | H | H | H | Et | 2 | —C≡C—(CH$_2$)$_2$O—(4-Cl—Ph) | H | H |
| 1-2074 | H | H | H | Et | 2 | —C≡C—(CH$_2$)$_2$O—(4-Br—Ph) | H | H |
| 1-2075 | H | H | H | Et | 2 | —C≡C—(CH$_2$)$_2$O—(4-Me—Ph) | H | H |
| 1-2076 | H | H | H | Et | 2 | —C≡C—(CH$_2$)$_2$O—(4-Et—Ph) | H | H |
| 1-2077 | H | H | H | Et | 2 | —C≡C—(CH$_2$)$_2$O—(4-Pr—Ph) | H | H |
| 1-2078 | H | H | H | Et | 2 | —C≡C—(CH$_2$)$_2$O—(4-iPr—Ph) | H | H |
| 1-2079 | H | H | H | Et | 2 | —C≡C—(CH$_2$)$_2$O—(4-Bu—Ph) | H | H |
| 1-2080 | H | H | H | Et | 2 | —C≡C—(CH$_2$)$_2$O—(4-CF$_3$—Ph) | H | H |

TABLE 1-continued (Ia)

Structure: thiophene with $NR^1R^2$, $R^4$, $R^3O$, $(CH_2)_n$ substituents at one position, and $X-Y-R^5$ at the other, with $R^6$ and $R^7$ on the ring.

| Exemp. Compd. No. | $R^1$ | $R^2$ | $R^3$ | $R^4$ | n | —X—Y—$R^5$ | $R^6$ | $R^7$ |
|---|---|---|---|---|---|---|---|---|
| 1-2081 | H | H | H | Et | 2 | —C≡C—$(CH_2)_2$O—(4-MeO—Ph) | H | H |
| 1-2082 | H | H | H | Et | 2 | —C≡C—$(CH_2)_2$O—(4-EtO—Ph) | H | H |
| 1-2083 | H | H | H | Et | 2 | —C≡C—$(CH_2)_2$O—(4-PrO—Ph) | H | H |
| 1-2084 | H | H | H | Et | 2 | —C≡C—$(CH_2)_2$O—(4-iPrO—Ph) | H | H |
| 1-2085 | H | H | H | Et | 2 | —C≡C—$(CH_2)_2$O—(4-MeS—Ph) | H | H |
| 1-2086 | H | H | H | Et | 2 | —C≡C—$(CH_2)_2$O—(2,4-diMe—Ph) | H | H |
| 1-2087 | H | H | H | Et | 2 | —C≡C—$(CH_2)_2$O—(3,4-diMe—Ph) | H | H |
| 1-2088 | H | H | H | Et | 2 | —C≡C—$(CH_2)_2$O—(3,5-diMe—Ph) | H | H |
| 1-2089 | H | H | H | Et | 2 | —CO—$(CH_2)_3$—cHx | H | H |
| 1-2090 | H | H | Me | Et | 2 | —CO—$(CH_2)_3$—cHx | H | H |
| 1-2091 | Me | H | H | Et | 2 | —CO—$(CH_2)_3$—cHx | H | H |
| 1-2092 | $CO_2Me$ | H | H | Et | 2 | —CO—$(CH_2)_3$—cHx | H | H |
| 1-2093 | H | H | H | Et | 2 | —CO—$(CH_2)_3$—Ph | H | H |
| 1-2094 | H | H | Me | Et | 2 | —CO—$(CH_2)_3$—Ph | H | H |
| 1-2095 | Me | H | H | Et | 2 | —CO—$(CH_2)_3$—Ph | H | H |
| 1-2096 | $CO_2Me$ | H | H | Et | 2 | —CO—$(CH_2)_3$—Ph | H | H |
| 1-2097 | H | H | H | Et | 2 | —CO—$(CH_2)_4$—cHx | H | H |
| 1-2098 | H | H | Me | Et | 2 | —CO—$(CH_2)_4$—cHx | H | H |
| 1-2099 | Me | H | H | Et | 2 | —CO—$(CH_2)_4$—cHx | H | H |
| 1-2100 | $CO_2Me$ | H | H | Et | 2 | —CO—$(CH_2)_4$—cHx | H | H |
| 1-2101 | H | H | H | Et | 2 | —CO—$(CH_2)_4$—Ph | H | H |
| 1-2102 | H | H | Me | Et | 2 | —CO—$(CH_2)_4$—Ph | H | H |
| 1-2103 | Me | H | H | Et | 2 | —CO—$(CH_2)_4$—Ph | H | H |
| 1-2104 | $CO_2Me$ | H | H | Et | 2 | —CO—$(CH_2)_4$—Ph | H | H |
| 1-2105 | H | H | H | Et | 2 | —CO—$(CH_2)_5$—cHx | H | H |
| 1-2106 | H | H | Me | Et | 2 | —CO—$(CH_2)_5$—cHx | H | H |
| 1-2107 | Me | H | H | Et | 2 | —CO—$(CH_2)_5$—cHx | H | H |
| 1-2108 | $CO_2Me$ | H | H | Et | 2 | —CO—$(CH_2)_5$—cHx | H | H |
| 1-2109 | H | H | H | Et | 2 | —CO—$(CH_2)_5$—Ph | H | H |
| 1-2110 | H | H | Me | Et | 2 | —CO—$(CH_2)_5$—Ph | H | H |
| 1-2111 | Me | H | H | Et | 2 | —CO—$(CH_2)_5$—Ph | H | H |
| 1-2112 | $CO_2Me$ | H | H | Et | 2 | —CO—$(CH_2)_5$—Ph | H | H |
| 1-2113 | H | H | H | Et | 2 | —CH(OH)—$(CH_2)_4$—cHx | H | H |
| 1-2114 | H | H | Me | Et | 2 | —CH(OH)—$(CH_2)_4$—cHx | H | H |
| 1-2115 | Me | H | H | Et | 2 | —CH(OH)—$(CH_2)_4$—cHx | H | H |
| 1-2116 | $CO_2Me$ | H | H | Et | 2 | —CH(OH)—$(CH_2)_4$—cHx | H | H |
| 1-2117 | H | H | H | Et | 2 | —CH(OH)—$(CH_2)_4$—Ph | H | H |
| 1-2118 | H | H | Me | Et | 2 | —CH(OH)—$(CH_2)_4$—Ph | H | H |
| 1-2119 | Me | H | H | Et | 2 | —CH(OH)—$(CH_2)_4$—Ph | H | H |
| 1-2120 | $CO_2Me$ | H | H | Et | 2 | —CH(OH)—$(CH_2)_4$—Ph | H | H |
| 1-2121 | H | H | H | Et | 2 | —CH(OH)—$(CH_2)_5$—cHx | H | H |
| 1-2122 | H | H | Me | Et | 2 | —CH(OH)—$(CH_2)_5$—cHx | H | H |
| 1-2123 | Me | H | H | Et | 2 | —CH(OH)—$(CH_2)_5$—cHx | H | H |
| 1-2124 | $CO_2Me$ | H | H | Et | 2 | —CH(OH)—$(CH_2)_5$—cHx | H | H |
| 1-2125 | H | H | H | Et | 2 | —CH(OH)—$(CH_2)_5$—Ph | H | H |
| 1-2126 | H | H | Me | Et | 2 | —CH(OH)—$(CH_2)_5$—Ph | H | H |
| 1-2127 | Me | H | H | Et | 2 | —CH(OH)—$(CH_2)_5$—Ph | H | H |
| 1-2128 | $CO_2Me$ | H | H | Et | 2 | —CH(OH)—$(CH_2)_5$—Ph | H | H |
| 1-2129 | H | H | H | Et | 2 | -4-(cHx—$CH_2$O)Ph | H | H |
| 1-2130 | H | H | Me | Et | 2 | -4-(cHx—$CH_2$O)Ph | H | H |
| 1-2131 | Me | H | H | Et | 2 | -4-(cHx—$CH_2$O)Ph | H | H |
| 1-2132 | $CO_2Me$ | H | H | Et | 2 | -4-(cHx—$CH_2$O)Ph | H | H |
| 1-2133 | H | H | H | Et | 2 | -4-[cHx—$(CH_2)_2$O]Ph | H | H |
| 1-2134 | H | H | H | Et | 2 | -4-[cHx—$(CH_2)_3$O]Ph | H | H |
| 1-2135 | H | H | H | Et | 2 | -(4-BzO—Ph) | H | H |
| 1-2136 | H | H | Me | Et | 2 | -(4-BzO—Ph) | H | H |
| 1-2137 | Me | H | H | Et | 2 | -(4-BzO—Ph) | H | H |
| 1-2138 | $CO_2Me$ | H | H | Et | 2 | -(4-BzO—Ph) | H | H |
| 1-2139 | H | H | H | Et | 2 | -(4-BzO-2-F—Ph) | H | H |
| 1-2140 | H | H | H | Et | 2 | -(4-BzO-3-F—Ph) | H | H |
| 1-2141 | H | H | H | Et | 2 | -(4-BzO-2,3-diF—Ph) | H | H |
| 1-2142 | H | H | H | Et | 2 | -(4-BzO-2-Cl—Ph) | H | H |
| 1-2143 | H | H | H | Et | 2 | -(4-BzO-3-Cl—Ph) | H | H |
| 1-2144 | H | H | H | Et | 2 | -(4-BzO-2,3-diCl—Ph) | H | H |
| 1-2145 | H | H | H | Et | 2 | -(4-BzO-2-Me—Ph) | H | H |

TABLE 1-continued (Ia)

| Exemp. Compd. No. | $R^1$ | $R^2$ | $R^3$ | $R^4$ | n | —X—Y—$R^5$ | $R^6$ | $R^7$ |
|---|---|---|---|---|---|---|---|---|
| 1-2146 | H | H | H | Et | 2 | -(4-BzO-3-Me—Ph) | H | H |
| 1-2147 | H | H | H | Et | 2 | -(4-BzO-2,3-diMe—Ph) | H | H |
| 1-2148 | H | H | H | Et | 2 | -4-[Ph—(CH$_2$)$_2$O]—Ph | H | H |
| 1-2149 | H | H | H | Et | 2 | -4-[Ph—(CH$_2$)$_3$O]—Ph | H | H |
| 1-2150 | H | H | H | Pr | 2 | —(CH$_2$)$_5$—cHx | H | H |
| 1-2151 | H | H | H | Pr | 2 | —(CH$_2$)$_5$—Ph | H | H |
| 1-2152 | H | H | H | Pr | 2 | —(CH$_2$)$_6$—cHx | H | H |
| 1-2153 | H | H | H | Pr | 2 | —(CH$_2$)$_6$—Ph | H | H |
| 1-2154 | H | H | H | Pr | 2 | —C≡C—CH$_2$—cHx | H | H |
| 1-2155 | H | H | H | Pr | 2 | —C≡C—(CH$_2$)$_3$—cHx | H | H |
| 1-2156 | H | H | H | Pr | 2 | —C≡C—(CH$_2$)$_3$—Ph | H | H |
| 1-2157 | H | H | H | Pr | 2 | —C≡C—(CH$_2$)$_4$—cHx | H | H |
| 1-2158 | H | H | H | Pr | 2 | —C≡C—(CH$_2$)$_4$—Ph | H | H |
| 1-2159 | Me | H | H | Pr | 2 | —C≡C—CH$_2$O—Ph | H | H |
| 1-2160 | CO$_2$Me | H | H | Pr | 2 | —C≡C—CH$_2$O—Ph | H | H |
| 1-2161 | H | H | H | Pr | 2 | —C≡C—(CH$_2$)$_2$O—cHx | H | H |
| 1-2162 | H | H | H | Pr | 2 | —C≡C—(CH$_2$)$_2$O—Ph | H | H |
| 1-2163 | H | H | H | Pr | 2 | -4-(cHx—CH$_2$O)Ph | H | H |
| 1-2164 | H | H | H | Pr | 2 | -(4-BzO—Ph) | H | H |
| 1-2165 | H | H | H | Me | 3 | —(CH$_2$)$_5$—cHx | H | H |
| 1-2166 | H | H | H | Me | 3 | —(CH$_2$)$_6$—cHx | H | H |
| 1-2167 | H | H | H | Me | 3 | —CH=CH—(CH$_2$)$_3$—cHx | H | H |
| 1-2168 | H | H | H | Me | 3 | —CH=CH—(CH$_2$)$_4$—cHx | H | H |
| 1-2169 | H | H | H | Me | 3 | —C≡C—(CH$_2$)$_3$—cHx | H | H |
| 1-2170 | H | H | H | Me | 3 | —C≡C—(CH$_2$)$_4$—cHx | H | H |
| 1-2171 | H | H | H | Me | 3 | —CO—(CH$_2$)$_4$—cHx | H | H |
| 1-2172 | H | H | H | Me | 3 | —CO—(CH$_2$)$_5$—cHx | H | H |
| 1-2173 | H | H | H | Me | 3 | —CO—(CH$_2$)$_4$—Ph | H | H |
| 1-2174 | H | H | H | Me | 3 | —CO—(CH$_2$)$_5$—Ph | H | H |
| 1-2175 | H | H | H | Me | 3 | —CH(OH)—(CH$_2$)$_4$—cHx | H | H |
| 1-2176 | H | H | H | Me | 3 | —CH(OH)—(CH$_2$)$_5$—cHx | H | H |
| 1-2177 | H | H | H | Me | 3 | -4-(cHx—CH$_2$O)Ph | H | H |
| 1-2178 | H | H | H | Me | 3 | -(4-BzO—Ph) | H | H |
| 1-2179 | H | H | H | Me | 3 | —C≡C—CH$_2$O—cPn | H | H |
| 1-2180 | H | H | H | Me | 3 | —C≡C—(CH$_2$)$_2$O—cPn | H | H |
| 1-2181 | H | H | H | Me | 3 | —C≡C—CH$_2$O—cHx | H | H |
| 1-2182 | H | H | H | Me | 3 | —C≡C—(CH$_2$)$_2$O—cHx | H | H |
| 1-2183 | H | H | H | Me | 3 | —C≡C—CH$_2$O—Ph | H | H |
| 1-2184 | H | H | H | Me | 3 | —C≡C—(CH$_2$)$_2$O—Ph | H | H |
| 1-2185 | H | H | H | Me | 2 | —(CH$_2$)$_4$—(3-F—Ph) | H | H |
| 1-2186 | H | H | H | Me | 2 | —(CH$_2$)$_4$—(3,4-diF—Ph) | H | H |
| 1-2187 | H | H | H | Me | 2 | —(CH$_2$)$_4$—(3,5-diF—Ph) | H | H |
| 1-2188 | H | H | H | Me | 2 | —(CH$_2$)$_4$—(3-Cl—Ph) | H | H |
| 1-2189 | H | H | H | Me | 2 | —(CH$_2$)$_4$—(4-Cl—Ph) | H | H |
| 1-2190 | H | H | H | Me | 2 | —(CH$_2$)$_4$—(3,4-diCl—Ph) | H | H |
| 1-2191 | H | H | H | Me | 2 | —(CH$_2$)$_4$—(3,5-diCl—Ph) | H | H |
| 1-2192 | H | H | H | Me | 2 | —(CH$_2$)$_4$—(3-Me—Ph) | H | H |
| 1-2193 | H | H | H | Me | 2 | —(CH$_2$)$_4$—(3,4-diMe—Ph) | H | H |
| 1-2194 | H | H | H | Me | 2 | —(CH$_2$)$_4$—(3,5-diMe—Ph) | H | H |
| 1-2195 | H | H | H | Me | 2 | —(CH$_2$)$_4$—(3-CF$_3$—Ph) | H | H |
| 1-2196 | H | H | H | Me | 2 | —(CH$_2$)$_4$—(3,4-diCF$_3$—Ph) | H | H |
| 1-2197 | H | H | H | Me | 2 | —(CH$_2$)$_4$—(3,5-diCF$_3$—Ph) | H | H |
| 1-2198 | H | H | H | Me | 2 | —(CH$_2$)$_4$—(3-MeO—Ph) | H | H |
| 1-2199 | H | H | H | Me | 2 | —(CH$_2$)$_4$—(3,4-diMeO—Ph) | H | H |
| 1-2200 | H | H | H | Me | 2 | —(CH$_2$)$_4$—(3,5-diMeO—Ph) | H | H |
| 1-2201 | H | H | H | Me | 2 | —(CH$_2$)$_4$—(3,4,5-triMeO—Ph) | H | H |
| 1-2202 | H | H | H | Me | 2 | —(CH$_2$)$_4$—(3-Ac—Ph) | H | H |
| 1-2203 | H | H | H | Me | 2 | —(CH$_2$)$_4$—(4-Ac—Ph) | H | H |
| 1-2204 | H | H | H | Me | 2 | —(CH$_2$)$_5$—(3,4-diF—Ph) | H | H |
| 1-2205 | H | H | H | Me | 2 | —(CH$_2$)$_5$—(3,5-diF—Ph) | H | H |
| 1-2206 | H | H | H | Me | 2 | —(CH$_2$)$_5$—(3-Cl—Ph) | H | H |
| 1-2207 | H | H | H | Me | 2 | —(CH$_2$)$_5$—(3,4-diCl—Ph) | H | H |
| 1-2208 | H | H | H | Me | 2 | —(CH$_2$)$_5$—(3,5-diCl—Ph) | H | H |
| 1-2209 | H | H | H | Me | 2 | —(CH$_2$)$_5$—(3,4-diCF$_3$—Ph) | H | H |
| 1-2210 | H | H | H | Me | 2 | —(CH$_2$)$_5$—(3,5-diCF$_3$—Ph) | H | H |

TABLE 1-continued (Ia)

| Exemp. Compd. No. | R¹ | R² | R³ | R⁴ | n | —X—Y—R⁵ | R⁶ | R⁷ |
|---|---|---|---|---|---|---|---|---|
| 1-2211 | H | H | H | Me | 2 | —(CH$_2$)$_5$—(3,4-diMeO—Ph) | H | H |
| 1-2212 | H | H | H | Me | 2 | —(CH$_2$)$_5$—(3,5-diMeO—Ph) | H | H |
| 1-2213 | H | H | H | Me | 2 | —(CH$_2$)$_5$—(3,4,5-triMeO—Ph) | H | H |
| 1-2214 | H | H | H | Me | 2 | —(CH$_2$)$_5$—(3-Ac—Ph) | H | H |
| 1-2215 | H | H | H | Me | 2 | —(CH$_2$)$_5$—(4-Ac—Ph) | H | H |
| 1-2216 | H | H | H | Me | 2 | —(CH$_2$)$_3$—O—(3-F—Ph) | H | H |
| 1-2217 | H | H | H | Me | 2 | —(CH$_2$)$_3$—O—(3,4-diF—Ph) | H | H |
| 1-2218 | H | H | H | Me | 2 | —(CH$_2$)$_3$—O—(3,5-diF—Ph) | H | H |
| 1-2219 | H | H | H | Me | 2 | —(CH$_2$)$_3$—O—(3-Me—Ph) | H | H |
| 1-2220 | H | H | H | Me | 2 | —(CH$_2$)$_3$—O—(3,4-diMe—Ph) | H | H |
| 1-2221 | H | H | H | Me | 2 | —(CH$_2$)$_3$—O—(3,5-diMe—Ph) | H | H |
| 1-2222 | H | H | H | Me | 2 | —(CH$_2$)$_3$—O—(3-CF$_3$—Ph) | H | H |
| 1-2223 | H | H | H | Me | 2 | —(CH$_2$)$_3$—O—(3,4-diCF$_3$—Ph) | H | H |
| 1-2224 | H | H | H | Me | 2 | —(CH$_2$)$_3$—O—(3,5-diCF$_3$—Ph) | H | H |
| 1-2225 | H | H | H | Me | 2 | —(CH$_2$)$_3$—O—(3-MeO—Ph) | H | H |
| 1-2226 | H | H | H | Me | 2 | —(CH$_2$)$_3$—O—(3,4-diMeO—Ph) | H | H |
| 1-2227 | H | H | H | Me | 2 | —(CH$_2$)$_3$—O—(3,5-diMeO—Ph) | H | H |
| 1-2228 | H | H | H | Me | 2 | —(CH$_2$)$_3$—O—(3,4,5-triMeO—Ph) | H | H |
| 1-2229 | H | H | H | Me | 2 | —(CH$_2$)$_3$—O—(3-Ac—Ph) | H | H |
| 1-2230 | H | H | H | Me | 2 | —(CH$_2$)$_3$—O—(4-Ac—Ph) | H | H |
| 1-2231 | H | H | H | Me | 2 | —(CH$_2$)$_4$—O—(3,4-diF—Ph) | H | H |
| 1-2232 | H | H | H | Me | 2 | —(CH$_2$)$_4$—O—(3,5-diF—Ph) | H | H |
| 1-2233 | H | H | H | Me | 2 | —(CH$_2$)$_4$—O—(3,4-diMeO—Ph) | H | H |
| 1-2234 | H | H | H | Me | 2 | —(CH$_2$)$_4$—O—(3,5-diMeO—Ph) | H | H |
| 1-2235 | H | H | H | Me | 2 | —(CH$_2$)$_4$—O—(3,4,5-triMeO—Ph) | H | H |
| 1-2236 | H | H | H | Me | 2 | —(CH$_2$)$_4$—O—(3-Ac—Ph) | H | H |
| 1-2237 | H | H | H | Me | 2 | —(CH$_2$)$_4$—O—(4-Ac—Ph) | H | H |
| 1-2238 | H | H | H | Me | 2 | —C≡C—(CH$_2$)$_2$—(3-F—Ph) | H | H |
| 1-2239 | H | H | H | Me | 2 | —C≡C—(CH$_2$)$_2$—(3,4-diF—Ph) | H | H |
| 1-2240 | H | H | H | Me | 2 | —C≡C—(CH$_2$)$_2$—(3,5-diF—Ph) | H | H |
| 1-2241 | H | H | H | Me | 2 | —C≡C—(CH$_2$)$_2$—(3-Cl—Ph) | H | H |
| 1-2242 | H | H | H | Me | 2 | —C≡C—(CH$_2$)$_2$—(4-Cl—Ph) | H | H |
| 1-2243 | H | H | H | Me | 2 | —C≡C—(CH$_2$)$_2$—(3,4-diCl—Ph) | H | H |
| 1-2244 | H | H | H | Me | 2 | —C≡C—(CH$_2$)$_2$—(3,5-diCl—Ph) | H | H |
| 1-2245 | H | H | H | Me | 2 | —C≡C—(CH$_2$)$_2$—(3-Me—Ph) | H | H |
| 1-2246 | H | H | H | Me | 2 | —C≡C—(CH$_2$)$_2$—(3,4-diMe—Ph) | H | H |
| 1-2247 | H | H | H | Me | 2 | —C≡C—(CH$_2$)$_2$—(3,5-diMe—Ph) | H | H |
| 1-2248 | H | H | H | Me | 2 | —C≡C—(CH$_2$)$_2$—(3-CF$_3$—Ph) | H | H |
| 1-2249 | H | H | H | Me | 2 | —C≡C—(CH$_2$)$_2$—(3,4-diCF$_3$—Ph) | H | H |
| 1-2250 | H | H | H | Me | 2 | —C≡C—(CH$_2$)$_2$—(3,5-diCF$_3$—Ph) | H | H |
| 1-2251 | H | H | H | Me | 2 | —C≡C—(CH$_2$)$_2$—(3-MeO—Ph) | H | H |
| 1-2252 | H | H | H | Me | 2 | —C≡C—(CH$_2$)$_2$—(3,4-diMeO—Ph) | H | H |
| 1-2253 | H | H | H | Me | 2 | —C≡C—(CH$_2$)$_2$—(3,5-diMeO—Ph) | H | H |
| 1-2254 | H | H | H | Me | 2 | —C≡C—(CH$_2$)$_2$—(3,4,5-triMeO—Ph) | H | H |
| 1-2255 | H | H | H | Me | 2 | —C≡C—(CH$_2$)$_2$—(3-Ac—Ph) | H | H |
| 1-2256 | H | H | H | Me | 2 | —C≡C—(CH$_2$)$_2$—(4-Ac—Ph) | H | H |
| 1-2257 | H | H | H | Me | 2 | —C≡C—(CH$_2$)$_3$—(3,4-diF—Ph) | H | H |
| 1-2258 | H | H | H | Me | 2 | —C≡C—(CH$_2$)$_3$—(3,5-diF—Ph) | H | H |
| 1-2259 | H | H | H | Me | 2 | —C≡C—(CH$_2$)$_3$—(3-Cl—Ph) | H | H |
| 1-2260 | H | H | H | Me | 2 | —C≡C—(CH$_2$)$_3$—(3,4-diCl—Ph) | H | H |
| 1-2261 | H | H | H | Me | 2 | —C≡C—(CH$_2$)$_3$—(3,5-diCl—Ph) | H | H |
| 1-2262 | H | H | H | Me | 2 | —C≡C—(CH$_2$)$_3$—(3,4-diCF$_3$—Ph) | H | H |
| 1-2263 | H | H | H | Me | 2 | —C≡C—(CH$_2$)$_3$—(3,5-diCF$_3$—Ph) | H | H |
| 1-2264 | H | H | H | Me | 2 | —C≡C—(CH$_2$)$_3$—(3,4-diMeO—Ph) | H | H |
| 1-2265 | H | H | H | Me | 2 | —C≡C—(CH$_2$)$_3$—(3,5-diMeO—Ph) | H | H |
| 1-2266 | H | H | H | Me | 2 | —C≡C—(CH$_2$)$_3$—(3,4,5-triMeO—Ph) | H | H |
| 1-2267 | H | H | H | Me | 2 | —C≡C—(CH$_2$)$_3$—(3-Ac—Ph) | H | H |
| 1-2268 | H | H | H | Me | 2 | —C≡C—(CH$_2$)$_3$—(4-Ac—Ph) | H | H |
| 1-2269 | H | H | H | Me | 2 | —C≡C—CH$_2$—O—(3-F—Ph) | H | H |
| 1-2270 | H | H | H | Me | 2 | —C≡C—CH$_2$—O—(3,4-diF—Ph) | H | H |
| 1-2271 | H | H | H | Me | 2 | —C≡C—CH$_2$—O—(3,5-diF—Ph) | H | H |
| 1-2272 | H | H | H | Me | 2 | —C≡C—CH$_2$—O—(3-Cl—Ph) | H | H |
| 1-2273 | H | H | H | Me | 2 | —C≡C—CH$_2$—O—(4-Cl—Ph) | H | H |
| 1-2274 | H | H | H | Me | 2 | —C≡C—CH$_2$—O—(3,4-diCl—Ph) | H | H |
| 1-2275 | H | H | H | Me | 2 | —C≡C—CH$_2$—O—(3,5-diCl—Ph) | H | H |

TABLE 1-continued (Ia)

Structure: Thiophene with substituents — R⁴ and (CH₂)ₙ on carbon bearing NR¹R² and CH₂OR³; X—Y—R⁵ on other side; R⁶ and R⁷ on thiophene.

| Exemp. Compd. No. | R¹ | R² | R³ | R⁴ | n | —X—Y—R⁵ | R⁶ | R⁷ |
|---|---|---|---|---|---|---|---|---|
| 1-2276 | H | H | H | Me | 2 | —C≡C—CH₂—O—(3-Me—Ph) | H | H |
| 1-2277 | H | H | H | Me | 2 | —C≡C—CH₂—O—(2,4-diMe—Ph) | H | H |
| 1-2278 | H | H | H | Me | 2 | —C≡C—CH₂—O—(3,4-diMe—Ph) | H | H |
| 1-2279 | H | H | H | Me | 2 | —C≡C—CH₂—O—(3,5-diMe—Ph) | H | H |
| 1-2280 | H | H | H | Me | 2 | —C≡C—CH₂—O—(3-CF₃—Ph) | H | H |
| 1-2281 | H | H | H | Me | 2 | —C≡C—CH₂—O—(3,4-diCF₃—Ph) | H | H |
| 1-2282 | H | H | H | Me | 2 | —C≡C—CH₂—O—(3,5-diCF₃—Ph) | H | H |
| 1-2283 | H | H | H | Me | 2 | —C≡C—CH₂—O—(3-MeO—Ph) | H | H |
| 1-2284 | H | H | H | Me | 2 | —C≡C—CH₂—O—(3,4-diMeO—Ph) | H | H |
| 1-2285 | H | H | H | Me | 2 | —C≡C—CH₂—O—(3,5-diMeO—Ph) | H | H |
| 1-2286 | H | H | H | Me | 2 | —C≡C—CH₂—O—(3,4,5-triMeO—Ph) | H | H |
| 1-2287 | H | H | H | Me | 2 | —C≡C—CH₂—O—(3-Ac—Ph) | H | H |
| 1-2288 | H | H | H | Me | 2 | —C≡C—CH₂—O—(4-Ac—Ph) | H | H |
| 1-2289 | H | H | H | Me | 2 | —C≡C—CH₂—O—(4-CO₂H—Ph) | H | H |
| 1-2290 | H | H | H | Me | 2 | —C≡C—(CH₂)₂—O—(3,4-diF—Ph) | H | H |
| 1-2291 | H | H | H | Me | 2 | —C≡C—(CH₂)₂—O—(3,5-diF—Ph) | H | H |
| 1-2292 | H | H | H | Me | 2 | —C≡C—(CH₂)₂—O—(3-Cl—Ph) | H | H |
| 1-2293 | H | H | H | Me | 2 | —C≡C—(CH₂)₂—O—(3,4-diCl—Ph) | H | H |
| 1-2294 | H | H | H | Me | 2 | —C≡C—(CH₂)₂—O—(3,5-diCl—Ph) | H | H |
| 1-2295 | H | H | H | Me | 2 | —C≡C—(CH₂)₂—O—(3,4-diCF₃—Ph) | H | H |
| 1-2296 | H | H | H | Me | 2 | —C≡C—(CH₂)₂—O—(3,5-diCF₃—Ph) | H | H |
| 1-2297 | H | H | H | Me | 2 | —C≡C—(CH₂)₂—O—(3,4-diMeO—Ph) | H | H |
| 1-2298 | H | H | H | Me | 2 | —C≡C—(CH₂)₂—O—(3,5-diMeO—Ph) | H | H |
| 1-2299 | H | H | H | Me | 2 | —C≡C—(CH₂)₂—O—(3,4,5-triMeO—Ph) | H | H |
| 1-2300 | H | H | H | Me | 2 | —C≡C—(CH₂)₂—O—(3-Ac—Ph) | H | H |
| 1-2301 | H | H | H | Me | 2 | —C≡C—(CH₂)₂—O—(4-Ac—Ph) | H | H |
| 1-2302 | H | H | H | Me | 2 | —CO—(CH₂)₃—(3-F—Ph) | H | H |
| 1-2303 | H | H | H | Me | 2 | —CO—(CH₂)₃—(4-F—Ph) | H | H |
| 1-2304 | H | H | H | Me | 2 | —CO—(CH₂)₃—(3,4-diF—Ph) | H | H |
| 1-2305 | H | H | H | Me | 2 | —CO—(CH₂)₃—(3,5-diF—Ph) | H | H |
| 1-2306 | H | H | H | Me | 2 | —CO—(CH₂)₃—(3-Cl—Ph) | H | H |
| 1-2307 | H | H | H | Me | 2 | —CO—(CH₂)₃—(4-Cl—Ph) | H | H |
| 1-2308 | H | H | H | Me | 2 | —CO—(CH₂)₃—(3,4-diCl—Ph) | H | H |
| 1-2309 | H | H | H | Me | 2 | —CO—(CH₂)₃—(3,5-diCl—Ph) | H | H |
| 1-2310 | H | H | H | Me | 2 | —CO—(CH₂)₃—(3-Me—Ph) | H | H |
| 1-2311 | H | H | H | Me | 2 | —CO—(CH₂)₃—(4-Me—Ph) | H | H |
| 1-2312 | H | H | H | Me | 2 | —CO—(CH₂)₃—(3,4-diMe—Ph) | H | H |
| 1-2313 | H | H | H | Me | 2 | —CO—(CH₂)₃—(3,5-diMe—Ph) | H | H |
| 1-2314 | H | H | H | Me | 2 | —CO—(CH₂)₃—(3-Et—Ph) | H | H |
| 1-2315 | H | H | H | Me | 2 | —CO—(CH₂)₃—(4-Et—Ph) | H | H |
| 1-2316 | H | H | H | Me | 2 | —CO—(CH₂)₃—(3-CF₃—Ph) | H | H |
| 1-2317 | H | H | H | Me | 2 | —CO—(CH₂)₃—(4-CF₃—Ph) | H | H |
| 1-2318 | H | H | H | Me | 2 | —CO—(CH₂)₃—(3,4-diCF₃—Ph) | H | H |
| 1-2319 | H | H | H | Me | 2 | —CO—(CH₂)₃—(3,5-diCF₃—Ph) | H | H |
| 1-2320 | H | H | H | Me | 2 | —CO—(CH₂)₃—(3-MeO—Ph) | H | H |
| 1-2321 | H | H | H | Me | 2 | —CO—(CH₂)₃—(4-MeO—Ph) | H | H |
| 1-2322 | H | H | H | Me | 2 | —CO—(CH₂)₃—(3,4-diMeO—Ph) | H | H |
| 1-2323 | H | H | H | Me | 2 | —CO—(CH₂)₃—(3,5-diMeO—Ph) | H | H |
| 1-2324 | H | H | H | Me | 2 | —CO—(CH₂)₃—(3,4,5-triMeO—Ph) | H | H |
| 1-2325 | H | H | H | Me | 2 | —CO—(CH₂)₃—(4-MeS—Ph) | H | H |
| 1-2326 | H | H | H | Me | 2 | —CO—(CH₂)₃—(3-Ac—Ph) | H | H |
| 1-2327 | H | H | H | Me | 2 | —CO—(CH₂)₃—(4-Ac—Ph) | H | H |
| 1-2328 | H | H | H | Me | 2 | —CO—(CH₂)₄—(3-F—Ph) | H | H |
| 1-2329 | H | H | H | Me | 2 | —CO—(CH₂)₄—(3,4-diF—Ph) | H | H |
| 1-2330 | H | H | H | Me | 2 | —CO—(CH₂)₄—(3,5-diF—Ph) | H | H |
| 1-2331 | H | H | H | Me | 2 | —CO—(CH₂)₄—(3-Cl—Ph) | H | H |
| 1-2332 | H | H | H | Me | 2 | —CO—(CH₂)₄—(4-Cl—Ph) | H | H |
| 1-2333 | H | H | H | Me | 2 | —CO—(CH₂)₄—(3,4-diCl—Ph) | H | H |
| 1-2334 | H | H | H | Me | 2 | —CO—(CH₂)₄—(3,5-diCl—Ph) | H | H |
| 1-2335 | H | H | H | Me | 2 | —CO—(CH₂)₄—(3-Me—Ph) | H | H |
| 1-2336 | H | H | H | Me | 2 | —CO—(CH₂)₄—(3,4-diMe—Ph) | H | H |
| 1-2337 | H | H | H | Me | 2 | —CO—(CH₂)₄—(3,5-diMe—Ph) | H | H |
| 1-2338 | H | H | H | Me | 2 | —CO—(CH₂)₄—(3-CF₃—Ph) | H | H |
| 1-2339 | H | H | H | Me | 2 | —CO—(CH₂)₄—(3,4-diCF₃—Ph) | H | H |
| 1-2340 | H | H | H | Me | 2 | —CO—(CH₂)₄—(3,5-diCF₃—Ph) | H | H |

TABLE 1-continued (Ia)

Structure: R⁴, NR¹R², R³O groups on carbon with (CH₂)ₙ linker to thiophene ring (with R⁶, R⁷ substituents) connected to X—Y—R⁵

| Exemp. Compd. No. | R¹ | R² | R³ | R⁴ | n | —X—Y—R⁵ | R⁶ | R⁷ |
|---|---|---|---|---|---|---|---|---|
| 1-2341 | H | H | H | Me | 2 | —CO—(CH₂)₄—(3-MeO—Ph) | H | H |
| 1-2342 | H | H | H | Me | 2 | —CO—(CH₂)₄—(3,4-diMeO—Ph) | H | H |
| 1-2343 | H | H | H | Me | 2 | —CO—(CH₂)₄—(3,5-diMeO—Ph) | H | H |
| 1-2344 | H | H | H | Me | 2 | —CO—(CH₂)₄—(3,4,5-triMeO—Ph) | H | H |
| 1-2345 | H | H | H | Me | 2 | —CO—(CH₂)₄—(3-Ac—Ph) | H | H |
| 1-2346 | H | H | H | Me | 2 | —CO—(CH₂)₄—(4-Ac—Ph) | H | H |
| 1-2347 | H | H | H | Me | 2 | —CH(OH)—(CH₂)₃—(3-F—Ph) | H | H |
| 1-2348 | H | H | H | Me | 2 | —CH(OH)—(CH₂)₃—(4-F—Ph) | H | H |
| 1-2349 | H | H | H | Me | 2 | —CH(OH)—(CH₂)₃—(3,4-diF—Ph) | H | H |
| 1-2350 | H | H | H | Me | 2 | —CH(OH)—(CH₂)₃—(3,5-diF—Ph) | H | H |
| 1-2351 | H | H | H | Me | 2 | —CH(OH)—(CH₂)₃—(3-Cl—Ph) | H | H |
| 1-2352 | H | H | H | Me | 2 | —CH(OH)—(CH₂)₃—(4-Cl—Ph) | H | H |
| 1-2353 | H | H | H | Me | 2 | —CH(OH)—(CH₂)₃—(3,4-diCl—Ph) | H | H |
| 1-2354 | H | H | H | Me | 2 | —CH(OH)—(CH₂)₃—(3,5-diCl—Ph) | H | H |
| 1-2355 | H | H | H | Me | 2 | —CH(OH)—(CH₂)₃—(3-Me—Ph) | H | H |
| 1-2356 | H | H | H | Me | 2 | —CH(OH)—(CH₂)₃—(4-Me—Ph) | H | H |
| 1-2357 | H | H | H | Me | 2 | —CH(OH)—(CH₂)₃—(3,4-diMe—Ph) | H | H |
| 1-2358 | H | H | H | Me | 2 | —CH(OH)—(CH₂)₃—(3,5-diMe—Ph) | H | H |
| 1-2359 | H | H | H | Me | 2 | —CH(OH)—(CH₂)₃—(3-Et—Ph) | H | H |
| 1-2360 | H | H | H | Me | 2 | —CH(OH)—(CH₂)₃—(4-Et—Ph) | H | H |
| 1-2361 | H | H | H | Me | 2 | —CH(OH)—(CH₂)₃—(3-CF₃—Ph) | H | H |
| 1-2362 | H | H | H | Me | 2 | —CH(OH)—(CH₂)₃—(4-CF₃—Ph) | H | H |
| 1-2363 | H | H | H | Me | 2 | —CH(OH)—(CH₂)₃—(3,4-diCF₃—Ph) | H | H |
| 1-2364 | H | H | H | Me | 2 | —CH(OH)—(CH₂)₃—(3,5-diCF₃—Ph) | H | H |
| 1-2365 | H | H | H | Me | 2 | —CH(OH)—(CH₂)₃—(3-MeO—Ph) | H | H |
| 1-2366 | H | H | H | Me | 2 | —CH(OH)—(CH₂)₃—(4-MeO—Ph) | H | H |
| 1-2367 | H | H | H | Me | 2 | —CH(OH)—(CH₂)₃—(3,4-diMeO—Ph) | H | H |
| 1-2368 | H | H | H | Me | 2 | —CH(OH)—(CH₂)₃—(3,5-diMeO—Ph) | H | H |
| 1-2369 | H | H | H | Me | 2 | —CH(OH)—(CH₂)₃—(3,4,5-triMeO—Ph) | H | H |
| 1-2370 | H | H | H | Me | 2 | —CH(OH)—(CH₂)₃—(4-MeS—Ph) | H | H |
| 1-2371 | H | H | H | Me | 2 | —CH(OH)—(CH₂)₃—(3-Ac—Ph) | H | H |
| 1-2372 | H | H | H | Me | 2 | —CH(OH)—(CH₂)₃—(4-Ac—Ph) | H | H |
| 1-2373 | H | H | H | Me | 2 | —CH(OH)—(CH₂)₄—(3-F—Ph) | H | H |
| 1-2374 | H | H | H | Me | 2 | —CH(OH)—(CH₂)₄—(3,4-diF—Ph) | H | H |
| 1-2375 | H | H | H | Me | 2 | —CH(OH)—(CH₂)₄—(3,5-diF—Ph) | H | H |
| 1-2376 | H | H | H | Me | 2 | —CH(OH)—(CH₂)₄—(3-Cl—Ph) | H | H |
| 1-2377 | H | H | H | Me | 2 | —CH(OH)—(CH₂)₄—(4-Cl—Ph) | H | H |
| 1-2378 | H | H | H | Me | 2 | —CH(OH)—(CH₂)₄—(3,4-diCl—Ph) | H | H |
| 1-2379 | H | H | H | Me | 2 | —CH(OH)—(CH₂)₄—(3,5-diCl—Ph) | H | H |
| 1-2380 | H | H | H | Me | 2 | —CH(OH)—(CH₂)₄—(3-Me—Ph) | H | H |
| 1-2381 | H | H | H | Me | 2 | —CH(OH)—(CH₂)₄—(3,4-diMe—Ph) | H | H |
| 1-2382 | H | H | H | Me | 2 | —CH(OH)—(CH₂)₄—(3,5-diMe—Ph) | H | H |
| 1-2383 | H | H | H | Me | 2 | —CH(OH)—(CH₂)₄—(3-CF₃—Ph) | H | H |
| 1-2384 | H | H | H | Me | 2 | —CH(OH)—(CH₂)₄—(3,4-diCF₃—Ph) | H | H |
| 1-2385 | H | H | H | Me | 2 | —CH(OH)—(CH₂)₄—(3,5-diCF₃—Ph) | H | H |
| 1-2386 | H | H | H | Me | 2 | —CH(OH)—(CH₂)₄—(3-MeO—Ph) | H | H |
| 1-2387 | H | H | H | Me | 2 | —CH(OH)—(CH₂)₄—(3,4-diMeO—Ph) | H | H |
| 1-2388 | H | H | H | Me | 2 | —CH(OH)—(CH₂)₄—(3,5-diMeO—Ph) | H | H |
| 1-2389 | H | H | H | Me | 2 | —CH(OH)—(CH₂)₄—(3,4,5-triMeO—Ph) | H | H |
| 1-2390 | H | H | H | Me | 2 | —CH(OH)—(CH₂)₄—(3-Ac—Ph) | H | H |
| 1-2391 | H | H | H | Me | 2 | —CH(OH)—(CH₂)₄—(4-Ac—Ph) | H | H |
| 1-2392 | H | H | H | Me | 2 | —O—(CH₂)₃—cHx | H | H |
| 1-2393 | H | H | H | Me | 2 | —O—(CH₂)₄—cHx | H | H |
| 1-2394 | H | H | H | Me | 2 | —O—(CH₂)₅—cHx | H | H |
| 1-2395 | H | H | H | Me | 2 | —O—(CH₂)₃—Ph | H | H |
| 1-2396 | H | H | H | Me | 2 | —O—(CH₂)₄—Ph | H | H |
| 1-2397 | H | H | H | Me | 2 | —O—(CH₂)₅—Ph | H | H |

TABLE 2

(Ib) structure: R⁴—C(NR¹R²)(CH₂OR³)—(CH₂)ₙ— attached to thiophene ring with R⁶, X—Y—R⁵, R⁷ substituents.

| Exemp. Compd. No. | R¹ | R² | R³ | R⁴ | n | —X—Y—R⁵ | R⁶ | R⁷ |
|---|---|---|---|---|---|---|---|---|
| 2-1 | H | H | H | Me | 1 | —(CH₂)₅—cHx | H | H |
| 2-2 | H | H | H | Me | 1 | —(CH₂)₆—cHx | H | H |
| 2-3 | H | H | H | Me | 1 | —C≡C—(CH₂)₃—cHx | H | H |
| 2-4 | H | H | H | Me | 1 | —C≡C—(CH₂)₄—cHx | H | H |
| 2-5 | H | H | H | Me | 1 | -4-(cHx—CH₂O)Ph | H | H |
| 2-6 | H | H | H | Me | 1 | -(4-BzO—Ph) | H | H |
| 2-7 | H | H | H | Me | 1 | —C≡C—(CH₂)₂O—cHx | H | H |
| 2-8 | H | H | H | Me | 1 | —C≡C—(CH₂)₂O—Ph | H | H |
| 2-9 | H | H | H | Me | 2 | —(CH₂)₃—cHx | H | H |
| 2-10 | H | H | H | Me | 2 | —(CH₂)₃—Ph | H | H |
| 2-11 | H | H | H | Me | 2 | —(CH₂)₄—cHx | H | H |
| 2-12 | H | H | H | Me | 2 | —(CH₂)₄—Ph | H | H |
| 2-13 | H | H | H | Me | 2 | —(CH₂)₅—cPn | H | H |
| 2-14 | H | H | H | Me | 2 | —(CH₂)₅—cHx | H | H |
| 2-15 | H | H | H | Me | 2 | —(CH₂)₅—cHx | Me | H |
| 2-16 | H | H | H | Me | 2 | —(CH₂)₅—cHx | H | Me |
| 2-17 | H | H | H | Me | 2 | —(CH₂)₅—cHx | F | H |
| 2-18 | H | H | H | Me | 2 | —(CH₂)₅—cHx | H | F |
| 2-19 | H | H | Me | Me | 2 | —(CH₂)₅—cHx | H | H |
| 2-20 | Me | H | H | Me | 2 | —(CH₂)₅—cHx | H | H |
| 2-21 | CO₂Me | H | H | Me | 2 | —(CH₂)₅—cHx | H | H |
| 2-22 | H | H | H | Me | 2 | —(CH₂)₅—(4-F—cHx) | H | H |
| 2-23 | H | H | H | Me | 2 | —(CH₂)₅—(4-Cl—cHx) | H | H |
| 2-24 | H | H | H | Me | 2 | —(CH₂)₅—(4-Br—cHx) | H | H |
| 2-25 | H | H | H | Me | 2 | —(CH₂)₅—(4-Me—cHx) | H | H |
| 2-26 | H | H | H | Me | 2 | —(CH₂)₅—(4-Et—cHx) | H | H |
| 2-27 | H | H | H | Me | 2 | —(CH₂)₅—(4-Pr—cHx) | H | H |
| 2-28 | H | H | H | Me | 2 | —(CH₂)₅—(4-iPr—cHx) | H | H |
| 2-29 | H | H | H | Me | 2 | —(CH₂)₅—(4-CF₃—cHx) | H | H |
| 2-30 | H | H | H | Me | 2 | —(CH₂)₅—(4-MeO—cHx) | H | H |
| 2-31 | H | H | H | Me | 2 | —(CH₂)₅—(4-EtO—cHx) | H | H |
| 2-32 | H | H | H | Me | 2 | —(CH₂)₅—(4-PrO—cHx) | H | H |
| 2-33 | H | H | H | Me | 2 | —(CH₂)₅—(4-iPrO—cHx) | H | H |
| 2-34 | H | H | H | Me | 2 | —(CH₂)₅—(3-MeS—cHx) | H | H |
| 2-35 | H | H | H | Me | 2 | —(CH₂)₅—(4-MeS—cHx) | H | H |
| 2-36 | H | H | H | Me | 2 | —(CH₂)₅—(2,4-diMe—cHx) | H | H |
| 2-37 | H | H | H | Me | 2 | —(CH₂)₅—(3,4-diMe—cHx) | H | H |
| 2-38 | H | H | H | Me | 2 | —(CH₂)₅—(3,5-diMe—cHx) | H | H |
| 2-39 | H | H | H | Me | 2 | —(CH₂)₅—Ph | H | H |
| 2-40 | H | H | H | Me | 2 | —(CH₂)₅—Ph | Me | H |
| 2-41 | H | H | H | Me | 2 | —(CH₂)₅—Ph | H | Me |
| 2-42 | H | H | H | Me | 2 | —(CH₂)₅—Ph | F | H |
| 2-43 | H | H | H | Me | 2 | —(CH₂)₅—Ph | H | F |
| 2-44 | H | H | Me | Me | 2 | —(CH₂)₅—Ph | H | H |
| 2-45 | Me | H | H | Me | 2 | —(CH₂)₅—Ph | H | H |
| 2-46 | CO₂Me | H | H | Me | 2 | —(CH₂)₅—Ph | H | H |
| 2-47 | H | H | H | Me | 2 | —(CH₂)₅—(4-F—Ph) | H | H |
| 2-48 | H | H | H | Me | 2 | —(CH₂)₅—(4-Cl—Ph) | H | H |
| 2-49 | H | H | H | Me | 2 | —(CH₂)₅—(4-Br—Ph) | H | H |
| 2-50 | H | H | H | Me | 2 | —(CH₂)₅—(4-Me—Ph) | H | H |
| 2-51 | H | H | H | Me | 2 | —(CH₂)₅—(4-Et—Ph) | H | H |
| 2-52 | H | H | H | Me | 2 | —(CH₂)₅—(4-Pr—Ph) | H | H |
| 2-53 | H | H | H | Me | 2 | —(CH₂)₅—(4-iPr—Ph) | H | H |
| 2-54 | H | H | H | Me | 2 | —(CH₂)₅—(4-Bu—Ph) | H | H |
| 2-55 | H | H | H | Me | 2 | —(CH₂)₅—(4-CF₃—Ph) | H | H |
| 2-56 | H | H | H | Me | 2 | —(CH₂)₅—(4-MeO—Ph) | H | H |
| 2-57 | H | H | H | Me | 2 | —(CH₂)₅—(4-EtO—Ph) | H | H |
| 2-58 | H | H | H | Me | 2 | —(CH₂)₅—(4-PrO—Ph) | H | H |
| 2-59 | H | H | H | Me | 2 | —(CH₂)₅—(4-iPrO—Ph) | H | H |
| 2-60 | H | H | H | Me | 2 | —(CH₂)₅—(3-MeS—Ph) | H | H |
| 2-61 | H | H | H | Me | 2 | —(CH₂)₅—(4-MeS—Ph) | H | H |
| 2-62 | H | H | H | Me | 2 | —(CH₂)₅—(2,4-diMe—Ph) | H | H |
| 2-63 | H | H | H | Me | 2 | —(CH₂)₅—(3,4-diMe—Ph) | H | H |
| 2-64 | H | H | H | Me | 2 | —(CH₂)₅—(3,5-diMe—Ph) | H | H |
| 2-65 | H | H | H | Me | 2 | —(CH₂)₆—cPn | H | H |

TABLE 2-continued (Ib)

| Exemp. Compd. No. | R¹ | R² | R³ | R⁴ | n | —X—Y—R⁵ | R⁶ | R⁷ |
|---|---|---|---|---|---|---|---|---|
| 2-66 | H | H | H | Me | 2 | —(CH$_2$)$_6$—cHx | H | H |
| 2-67 | H | H | H | Me | 2 | —(CH$_2$)$_6$—cHx | Me | H |
| 2-68 | H | H | H | Me | 2 | —(CH$_2$)$_6$—cHx | H | Me |
| 2-69 | H | H | H | Me | 2 | —(CH$_2$)$_6$—cHx | F | H |
| 2-70 | H | H | H | Me | 2 | —(CH$_2$)$_6$—cHx | H | F |
| 2-71 | H | H | Me | Me | 2 | —(CH$_2$)$_6$—cHx | H | H |
| 2-72 | Me | H | H | Me | 2 | —(CH$_2$)$_6$—cHx | H | H |
| 2-73 | CO$_2$Me | H | H | Me | 2 | —(CH$_2$)$_6$—cHx | H | H |
| 2-74 | H | H | H | Me | 2 | —(CH$_2$)$_6$—(4-F—cHx) | H | H |
| 2-75 | H | H | H | Me | 2 | —(CH$_2$)$_6$—(4-Cl—cHx) | H | H |
| 2-76 | H | H | H | Me | 2 | —(CH$_2$)$_6$—(4-Br—cHx) | H | H |
| 2-77 | H | H | H | Me | 2 | —(CH$_2$)$_6$—(4-Me—cHx) | H | H |
| 2-78 | H | H | H | Me | 2 | —(CH$_2$)$_6$—(4-Et—cHx) | H | H |
| 2-79 | H | H | H | Me | 2 | —(CH$_2$)$_6$—(4-Pr—cHx) | H | H |
| 2-80 | H | H | H | Me | 2 | —(CH$_2$)$_6$—(4-iPr—cHx) | H | H |
| 2-81 | H | H | H | Me | 2 | —(CH$_2$)$_6$—(4-Bu—cHx) | H | H |
| 2-82 | H | H | H | Me | 2 | —(CH$_2$)$_6$—(4-CF$_3$—cHx) | H | H |
| 2-83 | H | H | H | Me | 2 | —(CH$_2$)$_6$—(4-MeO—cHx) | H | H |
| 2-84 | H | H | H | Me | 2 | —(CH$_2$)$_6$—(4-EtO—cHx) | H | H |
| 2-85 | H | H | H | Me | 2 | —(CH$_2$)$_6$—(4-PrO—cHx) | H | H |
| 2-86 | H | H | H | Me | 2 | —(CH$_2$)$_6$—(4-iPrO—cHx) | H | H |
| 2-87 | H | H | H | Me | 2 | —(CH$_2$)$_6$—(3-MeS—cHx) | H | H |
| 2-88 | H | H | H | Me | 2 | —(CH$_2$)$_6$—(4-MeS—cHx) | H | H |
| 2-89 | H | H | H | Me | 2 | —(CH$_2$)$_6$—(2,4-diMe—cHx) | H | H |
| 2-90 | H | H | H | Me | 2 | —(CH$_2$)$_6$—(3,4-diMe—cHx) | H | H |
| 2-91 | H | H | H | Me | 2 | —(CH$_2$)$_6$—(3,5-diMe—cHx) | H | H |
| 2-92 | H | H | H | Me | 2 | —(CH$_2$)$_6$—Ph | H | H |
| 2-93 | H | H | H | Me | 2 | —(CH$_2$)$_6$—Ph | Me | H |
| 2-94 | H | H | H | Me | 2 | —(CH$_2$)$_6$—Ph | H | Me |
| 2-95 | H | H | H | Me | 2 | —(CH$_2$)$_6$—Ph | F | H |
| 2-96 | H | H | H | Me | 2 | —(CH$_2$)$_6$—Ph | H | F |
| 2-97 | H | H | Me | Me | 2 | —(CH$_2$)$_6$—Ph | H | H |
| 2-98 | Me | H | H | Me | 2 | —(CH$_2$)$_6$—Ph | H | H |
| 2-99 | CO$_2$Me | H | H | Me | 2 | —(CH$_2$)$_6$—Ph | H | H |
| 2-100 | H | H | H | Me | 2 | —(CH$_2$)$_6$—(4-F—Ph) | H | H |
| 2-101 | H | H | H | Me | 2 | —(CH$_2$)$_6$—(4-Cl—Ph) | H | H |
| 2-102 | H | H | H | Me | 2 | —(CH$_2$)$_6$—(4-Br—Ph) | H | H |
| 2-103 | H | H | H | Me | 2 | —(CH$_2$)$_6$—(4-Me—Ph) | H | H |
| 2-104 | H | H | H | Me | 2 | —(CH$_2$)$_6$—(4-Et—Ph) | H | H |
| 2-105 | H | H | H | Me | 2 | —(CH$_2$)$_6$—(4-Pr—Ph) | H | H |
| 2-106 | H | H | H | Me | 2 | —(CH$_2$)$_6$—(4-iPr—Ph) | H | H |
| 2-107 | H | H | H | Me | 2 | —(CH$_2$)$_6$—(4-Bu—Ph) | H | H |
| 2-108 | H | H | H | Me | 2 | —(CH$_2$)$_6$—(4-CF$_3$—Ph) | H | H |
| 2-109 | H | H | H | Me | 2 | —(CH$_2$)$_6$—(4-MeO—Ph) | H | H |
| 2-110 | H | H | H | Me | 2 | —(CH$_2$)$_6$—(4-EtO—Ph) | H | H |
| 2-111 | H | H | H | Me | 2 | —(CH$_2$)$_6$—(4-PrO—Ph) | H | H |
| 2-112 | H | H | H | Me | 2 | —(CH$_2$)$_6$—(4-iPrO—Ph) | H | H |
| 2-113 | H | H | H | Me | 2 | —(CH$_2$)$_6$—(3-MeS—Ph) | H | H |
| 2-114 | H | H | H | Me | 2 | —(CH$_2$)$_6$—(4-MeS—Ph) | H | H |
| 2-115 | H | H | H | Me | 2 | —(CH$_2$)$_6$—(2,4-diMe—Ph) | H | H |
| 2-116 | H | H | H | Me | 2 | —(CH$_2$)$_6$—(3,4-diMe—Ph) | H | H |
| 2-117 | H | H | H | Me | 2 | —(CH$_2$)$_6$—(3,5-diMe—Ph) | H | H |
| 2-118 | H | H | H | Me | 2 | —(CH$_2$)$_7$—cHx | H | H |
| 2-119 | H | H | H | Me | 2 | —(CH$_2$)$_7$—Ph | H | H |
| 2-120 | H | H | H | Me | 2 | —(CH$_2$)$_8$—cHx | H | H |
| 2-121 | H | H | H | Me | 2 | —(CH$_2$)$_8$—Ph | H | H |
| 2-122 | H | H | H | Me | 2 | —CH=CH—(CH$_2$)$_3$—cHx | H | H |
| 2-123 | H | H | Me | Me | 2 | —CH=CH—(CH$_2$)$_3$—cHx | H | H |
| 2-124 | Me | H | H | Me | 2 | —CH=CH—(CH$_2$)$_3$—cHx | H | H |
| 2-125 | CO$_2$Me | H | H | Me | 2 | —CH=CH—(CH$_2$)$_3$—cHx | H | H |
| 2-126 | H | H | H | Me | 2 | —CH=CH—(CH$_2$)$_3$—Ph | H | H |
| 2-127 | H | H | Me | Me | 2 | —CH=CH—(CH$_2$)$_3$—Ph | H | H |
| 2-128 | Me | H | H | Me | 2 | —CH=CH—(CH$_2$)$_3$—Ph | H | H |
| 2-129 | CO$_2$Me | H | H | Me | 2 | —CH=CH—(CH$_2$)$_3$—Ph | H | H |
| 2-130 | H | H | H | Me | 2 | —CH=CH—(CH$_2$)$_4$—cHx | H | H |

TABLE 2-continued (Ib)

| Exemp. Compd. No. | R¹ | R² | R³ | R⁴ | n | —X—Y—R⁵ | R⁶ | R⁷ |
|---|---|---|---|---|---|---|---|---|
| 2-131 | H | H | Me | Me | 2 | —CH=CH—(CH$_2$)$_4$—cHx | H | H |
| 2-132 | Me | H | H | Me | 2 | —CH=CH—(CH$_2$)$_4$—cHx | H | H |
| 2-133 | CO$_2$Me | H | H | Me | 2 | —CH=CH—(CH$_2$)$_4$—cHx | H | H |
| 2-134 | H | H | H | Me | 2 | —CH=CH—(CH$_2$)$_4$—Ph | H | H |
| 2-135 | H | H | Me | Me | 2 | —CH=CH—(CH$_2$)$_4$—Ph | H | H |
| 2-136 | Me | H | H | Me | 2 | —CH=CH—(CH$_2$)$_4$—Ph | H | H |
| 2-137 | CO$_2$Me | H | H | Me | 2 | —CH=CH—(CH$_2$)$_4$—Ph | H | H |
| 2-138 | H | H | H | Me | 2 | —C≡C—CH$_2$O—cHx | H | H |
| 2-139 | H | H | H | Me | 2 | —C≡C—CH$_2$O—Ph | H | H |
| 2-140 | H | H | H | Me | 2 | —C≡C—(CH$_2$)$_2$O—cHx | H | H |
| 2-141 | H | H | H | Me | 2 | —C≡C—(CH$_2$)$_2$O—Ph | H | H |
| 2-142 | H | H | H | Me | 2 | —C≡C—CH$_2$—cHx | H | H |
| 2-143 | H | H | Me | Me | 2 | —C≡C—CH$_2$—cHx | H | H |
| 2-144 | Me | H | H | Me | 2 | —C≡C—CH$_2$—cHx | H | H |
| 2-145 | CO$_2$Me | H | H | Me | 2 | —C≡C—CH$_2$—cHx | H | H |
| 2-146 | H | H | H | Me | 2 | —C≡C—CH$_2$—Ph | H | H |
| 2-147 | H | H | Me | Me | 2 | —C≡C—CH$_2$—Ph | H | H |
| 2-148 | Me | H | H | Me | 2 | —C≡C—CH$_2$—Ph | H | H |
| 2-149 | CO$_2$Me | H | H | Me | 2 | —C≡C—CH$_2$—Ph | H | H |
| 2-150 | H | H | H | Me | 2 | —C≡C—(CH$_2$)$_2$—cHx | H | H |
| 2-151 | H | H | Me | Me | 2 | —C≡C—(CH$_2$)$_2$—cHx | H | H |
| 2-152 | Me | H | H | Me | 2 | —C≡C—(CH$_2$)$_2$—cHx | H | H |
| 2-153 | CO$_2$Me | H | H | Me | 2 | —C≡C—(CH$_2$)$_2$—cHx | H | H |
| 2-154 | H | H | H | Me | 2 | —C≡C—(CH$_2$)$_2$—Ph | H | H |
| 2-155 | H | H | Me | Me | 2 | —C≡C—(CH$_2$)$_2$—Ph | H | H |
| 2-156 | Me | H | H | Me | 2 | —C≡C—(CH$_2$)$_2$—Ph | H | H |
| 2-157 | CO$_2$Me | H | H | Me | 2 | —C≡C—(CH$_2$)$_2$—Ph | H | H |
| 2-158 | H | H | H | Me | 2 | —C≡C—(CH$_2$)$_3$—cPn | H | H |
| 2-159 | H | H | H | Me | 2 | —C≡C—(CH$_2$)$_3$—cHx | H | H |
| 2-160 | H | H | H | Me | 2 | —C≡C—(CH$_2$)$_3$—cHx | Me | H |
| 2-161 | H | H | H | Me | 2 | —C≡C—(CH$_2$)$_3$—cHx | H | Me |
| 2-162 | H | H | H | Me | 2 | —C≡C—(CH$_2$)$_3$—cHx | F | H |
| 2-163 | H | H | H | Me | 2 | —C≡C—(CH$_2$)$_3$—cHx | H | F |
| 2-164 | H | H | Me | Me | 2 | —C≡C—(CH$_2$)$_3$—cHx | H | H |
| 2-165 | Me | H | H | Me | 2 | —C≡C—(CH$_2$)$_3$—cHx | H | H |
| 2-166 | CO$_2$Me | H | H | Me | 2 | —C≡C—(CH$_2$)$_3$—cHx | H | H |
| 2-167 | H | H | H | Me | 2 | —C≡C—(CH$_2$)$_3$—(4-F—cHx) | H | H |
| 2-168 | H | H | H | Me | 2 | —C≡C—(CH$_2$)$_3$—(4-Cl—cHx) | H | H |
| 2-169 | H | H | H | Me | 2 | —C≡C—(CH$_2$)$_3$—(4-Br—cHx) | H | H |
| 2-170 | H | H | H | Me | 2 | —C≡C—(CH$_2$)$_3$—(4-Me—cHx) | H | H |
| 2-171 | H | H | H | Me | 2 | —C≡C—(CH$_2$)$_3$—(4-Et—cHx) | H | H |
| 2-172 | H | H | H | Me | 2 | —C≡C—(CH$_2$)$_3$—(4-Pr—cHx) | H | H |
| 2-173 | H | H | H | Me | 2 | —C≡C—(CH$_2$)$_3$—(4-iPr—cHx) | H | H |
| 2-174 | H | H | H | Me | 2 | —C≡C—(CH$_2$)$_3$—(4-Bu—cHx) | H | H |
| 2-175 | H | H | H | Me | 2 | —C≡C—(CH$_2$)$_3$—(4-CF$_3$—cHx) | H | H |
| 2-176 | H | H | H | Me | 2 | —C≡C—(CH$_2$)$_3$—(4-MeO—cHx) | H | H |
| 2-177 | H | H | H | Me | 2 | —C≡C—(CH$_2$)$_3$—(4-EtO—cHx) | H | H |
| 2-178 | H | H | H | Me | 2 | —C≡C—(CH$_2$)$_3$—(4-PrO—cHx) | H | H |
| 2-179 | H | H | H | Me | 2 | —C≡C—(CH$_2$)$_3$—(4-iPrO—cHx) | H | H |
| 2-180 | H | H | H | Me | 2 | —C≡C—(CH$_2$)$_3$—(3-MeS—cHx) | H | H |
| 2-181 | H | H | H | Me | 2 | —C≡C—(CH$_2$)$_3$—(4-MeS—cHx) | H | H |
| 2-182 | H | H | H | Me | 2 | —C≡C—(CH$_2$)$_3$—(2,4-diMe—cHx) | H | H |
| 2-183 | H | H | H | Me | 2 | —C≡C—(CH$_2$)$_3$—(3,4-diMe—cHx) | H | H |
| 2-184 | H | H | H | Me | 2 | —C≡C—(CH$_2$)$_3$—(3,5-diMe—cHx) | H | H |
| 2-185 | H | H | H | Me | 2 | —C≡C—(CH$_2$)$_3$—Ph | H | H |
| 2-186 | H | H | H | Me | 2 | —C≡C—(CH$_2$)$_3$—Ph | Me | H |
| 2-187 | H | H | H | Me | 2 | —C≡C—(CH$_2$)$_3$—Ph | H | Me |
| 2-188 | H | H | H | Me | 2 | —C≡C—(CH$_2$)$_3$—Ph | F | H |
| 2-189 | H | H | H | Me | 2 | —C≡C—(CH$_2$)$_3$—Ph | H | F |
| 2-190 | H | H | Me | Me | 2 | —C≡C—(CH$_2$)$_3$—Ph | H | H |
| 2-191 | Me | H | H | Me | 2 | —C≡C—(CH$_2$)$_3$—Ph | H | H |
| 2-192 | CO$_2$Me | H | H | Me | 2 | —C≡C—(CH$_2$)$_3$—Ph | H | H |
| 2-193 | H | H | H | Me | 2 | —C≡C—(CH$_2$)$_3$—(4-F—Ph) | H | H |
| 2-194 | H | H | H | Me | 2 | —C≡C—(CH$_2$)$_3$—(4-Cl—Ph) | H | H |
| 2-195 | H | H | H | Me | 2 | —C≡C—(CH$_2$)$_3$—(4-Br—Ph) | H | H |

TABLE 2-continued (Ib)

[Structure: thiophene core with substituents NR¹R², R⁴, R³O, (CH₂)n, R⁶, X—Y—R⁵, R⁷]

| Exemp. Compd. No. | R¹ | R² | R³ | R⁴ | n | —X—Y—R⁵ | R⁶ | R⁷ |
|---|---|---|---|---|---|---|---|---|
| 2-196 | H | H | H | Me | 2 | —C≡C—(CH₂)₃—(4-Me—Ph) | H | H |
| 2-197 | H | H | H | Me | 2 | —C≡C—(CH₂)₃—(4-Et—Ph) | H | H |
| 2-198 | H | H | H | Me | 2 | —C≡C—(CH₂)₃—(4-Pr—Ph) | H | H |
| 2-199 | H | H | H | Me | 2 | —C≡C—(CH₂)₃—(4-iPr—Ph) | H | H |
| 2-200 | H | H | H | Me | 2 | —C≡C—(CH₂)₃—(4-Bu—Ph) | H | H |
| 2-201 | H | H | H | Me | 2 | —C≡C—(CH₂)₃—(4-CF₃—Ph) | H | H |
| 2-202 | H | H | H | Me | 2 | —C≡C—(CH₂)₃—(4-MeO—Ph) | H | H |
| 2-203 | H | H | H | Me | 2 | —C≡C—(CH₂)₃—(4-EtO—Ph) | H | H |
| 2-204 | H | H | H | Me | 2 | —C≡C—(CH₂)₃—(4-PrO—Ph) | H | H |
| 2-205 | H | H | H | Me | 2 | —C≡C—(CH₂)₃—(4-iPrO—Ph) | H | H |
| 2-206 | H | H | H | Me | 2 | —C≡C—(CH₂)₃—(3-MeS—Ph) | H | H |
| 2-207 | H | H | H | Me | 2 | —C≡C—(CH₂)₃—(4-MeS—Ph) | H | H |
| 2-208 | H | H | H | Me | 2 | —C≡C—(CH₂)₃—(2,4-diMe—Ph) | H | H |
| 2-209 | H | H | H | Me | 2 | —C≡C—(CH₂)₃—(3,4-diMe—Ph) | H | H |
| 2-210 | H | H | H | Me | 2 | —C≡C—(CH₂)₃—(3,5-diMe—Ph) | H | H |
| 2-211 | H | H | H | Me | 2 | —C≡C—(CH₂)₄—cPn | H | H |
| 2-212 | H | H | H | Me | 2 | —C≡C—(CH₂)₄—cHx | H | H |
| 2-213 | H | H | H | Me | 2 | —C≡C—(CH₂)₄—cHx | Me | H |
| 2-214 | H | H | H | Me | 2 | —C≡C—(CH₂)₄—cHx | H | Me |
| 2-215 | H | H | H | Me | 2 | —C≡C—(CH₂)₄—cHx | F | H |
| 2-216 | H | H | H | Me | 2 | —C≡C—(CH₂)₄—cHx | H | F |
| 2-217 | H | H | Me | Me | 2 | —C≡C—(CH₂)₄—cHx | H | H |
| 2-218 | Me | H | H | Me | 2 | —C≡C—(CH₂)₄—cHx | H | H |
| 2-219 | CO₂Me | H | H | Me | 2 | —C≡C—(CH₂)₄—cHx | H | H |
| 2-220 | H | H | H | Me | 2 | —C≡C—(CH₂)₄—(4-F—cHx) | H | H |
| 2-221 | H | H | H | Me | 2 | —C≡C—(CH₂)₄—(4-Cl—cHx) | H | H |
| 2-222 | H | H | H | Me | 2 | —C≡C—(CH₂)₄—(4-Br—cHx) | H | H |
| 2-223 | H | H | H | Me | 2 | —C≡C—(CH₂)₄—(4-Me—cHx) | H | H |
| 2-224 | H | H | H | Me | 2 | —C≡C—(CH₂)₄—(4-Et—cHx) | H | H |
| 2-225 | H | H | H | Me | 2 | —C≡C—(CH₂)₄—(4-Pr—cHx) | H | H |
| 2-226 | H | H | H | Me | 2 | —C≡C—(CH₂)₄—(4-iPr—cHx) | H | H |
| 2-227 | H | H | H | Me | 2 | —C≡C—(CH₂)₄—(4-Bu—cHx) | H | H |
| 2-228 | H | H | H | Me | 2 | —C≡C—(CH₂)₄—(4-CF₃—cHx) | H | H |
| 2-229 | H | H | H | Me | 2 | —C≡C—(CH₂)₄—(4-MeO—cHx) | H | H |
| 2-230 | H | H | H | Me | 2 | —C≡C—(CH₂)₄—(4-EtO—cHx) | H | H |
| 2-231 | H | H | H | Me | 2 | —C≡C—(CH₂)₄—(4-PrO—cHx) | H | H |
| 2-232 | H | H | H | Me | 2 | —C≡C—(CH₂)₄—(4-iPrO—cHx) | H | H |
| 2-233 | H | H | H | Me | 2 | —C≡C—(CH₂)₄—(4-MeS—cHx) | H | H |
| 2-234 | H | H | H | Me | 2 | —C≡C—(CH₂)₄—(2,4-diMe—cHx) | H | H |
| 2-235 | H | H | H | Me | 2 | —C≡C—(CH₂)₄—(3,4-diMe—cHx) | H | H |
| 2-236 | H | H | H | Me | 2 | —C≡C—(CH₂)₄—(3,5-diMe—cHx) | H | H |
| 2-237 | H | H | H | Me | 2 | —C≡C—(CH₂)₄—Ph | H | H |
| 2-238 | H | H | H | Me | 2 | —C≡C—(CH₂)₄—Ph | Me | H |
| 2-239 | H | H | H | Me | 2 | —C≡C—(CH₂)₄—Ph | H | Me |
| 2-240 | H | H | H | Me | 2 | —C≡C—(CH₂)₄—Ph | F | H |
| 2-241 | H | H | H | Me | 2 | —C≡C—(CH₂)₄—Ph | H | F |
| 2-242 | H | H | Me | Me | 2 | —C≡C—(CH₂)₄—Ph | H | H |
| 2-243 | Me | H | H | Me | 2 | —C≡C—(CH₂)₄—Ph | H | H |
| 2-244 | CO₂Me | H | H | Me | 2 | —C≡C—(CH₂)₄—Ph | H | H |
| 2-245 | H | H | H | Me | 2 | —C≡C—(CH₂)₄—(4-F—Ph) | H | H |
| 2-246 | H | H | H | Me | 2 | —C≡C—(CH₂)₄—(4-Cl—Ph) | H | H |
| 2-247 | H | H | H | Me | 2 | —C≡C—(CH₂)₄—(4-Br—Ph) | H | H |
| 2-248 | H | H | H | Me | 2 | —C≡C—(CH₂)₄—(4-Me—Ph) | H | H |
| 2-249 | H | H | H | Me | 2 | —C≡C—(CH₂)₄—(4-Et—Ph) | H | H |
| 2-250 | H | H | H | Me | 2 | —C≡C—(CH₂)₄—(4-Pr—Ph) | H | H |
| 2-251 | H | H | H | Me | 2 | —C≡C—(CH₂)₄—(4-iPr—Ph) | H | H |
| 2-252 | H | H | H | Me | 2 | —C≡C—(CH₂)₄—(4-Bu—Ph) | H | H |
| 2-253 | H | H | H | Me | 2 | —C≡C—(CH₂)₄—(4-CF₃—Ph) | H | H |
| 2-254 | H | H | H | Me | 2 | —C≡C—(CH₂)₄—(4-MeO—Ph) | H | H |
| 2-255 | H | H | H | Me | 2 | —C≡C—(CH₂)₄—(4-EtO—Ph) | H | H |
| 2-256 | H | H | H | Me | 2 | —C≡C—(CH₂)₄—(4-PrO—Ph) | H | H |
| 2-257 | H | H | H | Me | 2 | —C≡C—(CH₂)₄—(4-iPrO—Ph) | H | H |
| 2-258 | H | H | H | Me | 2 | —C≡C—(CH₂)₄—(3-MeS—Ph) | H | H |
| 2-259 | H | H | H | Me | 2 | —C≡C—(CH₂)₄—(4-MeS—Ph) | H | H |
| 2-260 | H | H | H | Me | 2 | —C≡C—(CH₂)₄—(2,4-diMe—Ph) | H | H |

TABLE 2-continued (Ib) structure: thiophene with NR¹R² group, R⁴, R³O, (CH₂)ₙ, R⁶, X—Y—R⁵, R⁷ substituents.

| Exemp. Compd. No. | R¹ | R² | R³ | R⁴ | n | —X—Y—R⁵ | R⁶ | R⁷ |
|---|---|---|---|---|---|---|---|---|
| 2-261 | H | H | H | Me | 2 | —C≡C—(CH₂)₄—(3,4-diMe—Ph) | H | H |
| 2-262 | H | H | H | Me | 2 | —C≡C—(CH₂)₄—(3,5-diMe—Ph) | H | H |
| 2-263 | H | H | H | Me | 2 | —C≡C—(CH₂)₅—cHx | H | H |
| 2-264 | H | H | Me | Me | 2 | —C≡C—(CH₂)₅—cHx | H | H |
| 2-265 | Me | H | H | Me | 2 | —C≡C—(CH₂)₅—cHx | H | H |
| 2-266 | CO₂Me | H | H | Me | 2 | —C≡C—(CH₂)₅—cHx | H | H |
| 2-267 | H | H | H | Me | 2 | —C≡C—(CH₂)₅—Ph | H | H |
| 2-268 | H | H | Me | Me | 2 | —C≡C—(CH₂)₅—Ph | H | H |
| 2-269 | Me | H | H | Me | 2 | —C≡C—(CH₂)₅—Ph | H | H |
| 2-270 | CO₂Me | H | H | Me | 2 | —C≡C—(CH₂)₅—Ph | H | H |
| 2-271 | H | H | H | Me | 2 | —C≡C—(CH₂)₆—cHx | H | H |
| 2-272 | H | H | Me | Me | 2 | —C≡C—(CH₂)₆—cHx | H | H |
| 2-273 | Me | H | H | Me | 2 | —C≡C—(CH₂)₆—cHx | H | H |
| 2-274 | CO₂Me | H | H | Me | 2 | —C≡C—(CH₂)₆—cHx | H | H |
| 2-275 | H | H | H | Me | 2 | —C≡C—(CH₂)₆—Ph | H | H |
| 2-276 | H | H | Me | Me | 2 | —C≡C—(CH₂)₆—Ph | H | H |
| 2-277 | Me | H | H | Me | 2 | —C≡C—(CH₂)₆—Ph | H | H |
| 2-278 | CO₂Me | H | H | Me | 2 | —C≡C—(CH₂)₆—Ph | H | H |
| 2-279 | H | H | H | Me | 2 | —C≡C—CH₂O—cHx | H | H |
| 2-280 | H | H | Me | Me | 2 | —C≡C—CH₂O—cHx | H | H |
| 2-281 | Me | H | H | Me | 2 | —C≡C—CH₂O—cHx | H | H |
| 2-282 | CO₂Me | H | H | Me | 2 | —C≡C—CH₂O—cHx | H | H |
| 2-283 | H | H | H | Me | 2 | —C≡C—CH₂O—Ph | H | H |
| 2-284 | H | H | Me | Me | 2 | —C≡C—CH₂O—Ph | H | H |
| 2-285 | Me | H | H | Me | 2 | —C≡C—CH₂O—Ph | H | H |
| 2-286 | CO₂Me | H | H | Me | 2 | —C≡C—CH₂O—Ph | H | H |
| 2-287 | H | H | H | Me | 2 | —C≡C—(CH₂)₂O—cPn | H | H |
| 2-288 | H | H | H | Me | 2 | —C≡C—(CH₂)₂O—cHx | H | H |
| 2-289 | H | H | H | Me | 2 | —C≡C—(CH₂)₂O—cHx | Me | H |
| 2-290 | H | H | H | Me | 2 | —C≡C—(CH₂)₂O—cHx | H | Me |
| 2-291 | H | H | H | Me | 2 | —C≡C—(CH₂)₂O—cHx | F | H |
| 2-292 | H | H | H | Me | 2 | —C≡C—(CH₂)₂O—cHx | H | F |
| 2-293 | H | H | Me | Me | 2 | —C≡C—(CH₂)₂—OCH₂—cHx | H | H |
| 2-294 | Me | H | H | Me | 2 | —C≡C—(CH₂)₂O—cHx | H | H |
| 2-295 | CO₂Me | H | H | Me | 2 | —C≡C—(CH₂)₂O—cHx | H | H |
| 2-296 | H | H | H | Me | 2 | —C≡C—(CH₂)₂O—(4-F—cHx) | H | H |
| 2-297 | H | H | H | Me | 2 | —C≡C—(CH₂)₂O—(4-Cl—cHx) | H | H |
| 2-298 | H | H | H | Me | 2 | —C≡C—(CH₂)₂O—(4-Br—cHx) | H | H |
| 2-299 | H | H | H | Me | 2 | —C≡C—(CH₂)₂O—(4-Me—cHx) | H | H |
| 2-300 | H | H | H | Me | 2 | —C≡C—(CH₂)₂O—(4-Et—cHx) | H | H |
| 2-301 | H | H | H | Me | 2 | —C≡C—(CH₂)₂O—(4-Pr—cHx) | H | H |
| 2-302 | H | H | H | Me | 2 | —C≡C—(CH₂)₂O—(4-iPr—cHx) | H | H |
| 2-303 | H | H | H | Me | 2 | —C≡C—(CH₂)₂O—(4-Bu—cHx) | H | H |
| 2-304 | H | H | H | Me | 2 | —C≡C—(CH₂)₂O—(4-CF₃—cHx) | H | H |
| 2-305 | H | H | H | Me | 2 | —C≡C—(CH₂)₂O—(4-MeO—cHx) | H | H |
| 2-306 | H | H | H | Me | 2 | —C≡C—(CH₂)₂O—(4-EtO—cHx) | H | H |
| 2-307 | H | H | H | Me | 2 | —C≡C—(CH₂)₂O—(4-PrO—cHx) | H | H |
| 2-308 | H | H | H | Me | 2 | —C≡C—(CH₂)₂O—(4-iPrO—cHx) | H | H |
| 2-309 | H | H | H | Me | 2 | —C≡C—(CH₂)₂O—(3-MeS—cHx) | H | H |
| 2-310 | H | H | H | Me | 2 | —C≡C—(CH₂)₂O—(4-MeS—cHx) | H | H |
| 2-311 | H | H | H | Me | 2 | —C≡C—(CH₂)₂O—(2,4-diMe—cHx) | H | H |
| 2-312 | H | H | H | Me | 2 | —C≡C—(CH₂)₂O—(3,4-diMe—cHx) | H | H |
| 2-313 | H | H | H | Me | 2 | —C≡C—(CH₂)₂O—(3,5-diMe—cHx) | H | H |
| 2-314 | H | H | H | Me | 2 | —C≡C—(CH₂)₂O—Ph | H | H |
| 2-315 | H | H | H | Me | 2 | —C≡C—(CH₂)₂O—Ph | Me | H |
| 2-316 | H | H | H | Me | 2 | —C≡C—(CH₂)₂O—Ph | H | Me |
| 2-317 | H | H | H | Me | 2 | —C≡C—(CH₂)₂O—Ph | F | H |
| 2-318 | H | H | H | Me | 2 | —C≡C—(CH₂)₂O—Ph | H | F |
| 2-319 | H | H | Me | Me | 2 | —C≡C—(CH₂)₂—OCH₂—Ph | H | H |
| 2-320 | Me | H | H | Me | 2 | —C≡C—(CH₂)₂O—Ph | H | H |
| 2-321 | CO₂Me | H | H | Me | 2 | —C≡C—(CH₂)₂O—Ph | H | H |
| 2-322 | H | H | H | Me | 2 | —C≡C—(CH₂)₂O—(4-F—Ph) | H | H |
| 2-323 | H | H | H | Me | 2 | —C≡C—(CH₂)₂O—(4-Cl—Ph) | H | H |
| 2-324 | H | H | H | Me | 2 | —C≡C—(CH₂)₂O—(4-Br—Ph) | H | H |
| 2-325 | H | H | H | Me | 2 | —C≡C—(CH₂)₂O—(4-Me—Ph) | H | H |

TABLE 2-continued (Ib)

Structure: Thiophene with NR¹R² substituent, R⁴, R³O, (CH₂)ₙ, R⁶, X—Y—R⁵, R⁷ groups

| Exemp. Compd. No. | R¹ | R² | R³ | R⁴ | n | —X—Y—R⁵ | R⁶ | R⁷ |
|---|---|---|---|---|---|---|---|---|
| 2-326 | H | H | H | Me | 2 | —C≡C—(CH₂)₂O—(4-Et—Ph) | H | H |
| 2-327 | H | H | H | Me | 2 | —C≡C—(CH₂)₂O—(4-Pr—Ph) | H | H |
| 2-328 | H | H | H | Me | 2 | —C≡C—(CH₂)₂O—(4-iPr—Ph) | H | H |
| 2-329 | H | H | H | Me | 2 | —C≡C—(CH₂)₂O—(4-Bu—Ph) | H | H |
| 2-330 | H | H | H | Me | 2 | —C≡C—(CH₂)₂O—(4-CF₃—Ph) | H | H |
| 2-331 | H | H | H | Me | 2 | —C≡C—(CH₂)₂O—(4-MeO—Ph) | H | H |
| 2-332 | H | H | H | Me | 2 | —C≡C—(CH₂)₂O—(4-EtO—Ph) | H | H |
| 2-333 | H | H | H | Me | 2 | —C≡C—(CH₂)₂O—(4-PrO—Ph) | H | H |
| 2-334 | H | H | H | Me | 2 | —C≡C—(CH₂)₂O—(4-iPrO—Ph) | H | H |
| 2-335 | H | H | H | Me | 2 | —C≡C—(CH₂)₂O—(4-MeS—Ph) | H | H |
| 2-336 | H | H | H | Me | 2 | —C≡C—(CH₂)₂O—(2,4-diMe—Ph) | H | H |
| 2-337 | H | H | H | Me | 2 | —C≡C—(CH₂)₂O—(3,4-diMe—Ph) | H | H |
| 2-338 | H | H | H | Me | 2 | —C≡C—(CH₂)₂O—(3,5-diMe—Ph) | H | H |
| 2-339 | H | H | H | Me | 2 | —CO—(CH₂)₄—cHx | H | H |
| 2-340 | H | H | Me | Me | 2 | —CO—(CH₂)₄—cHx | H | H |
| 2-341 | Me | H | H | Me | 2 | —CO—(CH₂)₄—cHx | H | H |
| 2-342 | CO₂Me | H | H | Me | 2 | —CO—(CH₂)₄—cHx | H | H |
| 2-343 | H | H | H | Me | 2 | —CO—(CH₂)₄—Ph | H | H |
| 2-344 | H | H | Me | Me | 2 | —CO—(CH₂)₄—Ph | H | H |
| 2-345 | Me | H | H | Me | 2 | —CO—(CH₂)₄—Ph | H | H |
| 2-346 | CO₂Me | H | H | Me | 2 | —CO—(CH₂)₄—Ph | H | H |
| 2-347 | H | H | H | Me | 2 | —CO—(CH₂)₅—cHx | H | H |
| 2-348 | H | H | Me | Me | 2 | —CO—(CH₂)₅—cHx | H | H |
| 2-349 | Me | H | H | Me | 2 | —CO—(CH₂)₅—cHx | H | H |
| 2-350 | CO₂Me | H | H | Me | 2 | —CO—(CH₂)₅—cHx | H | H |
| 2-351 | H | H | H | Me | 2 | —CO—(CH₂)₅—Ph | H | H |
| 2-352 | H | H | Me | Me | 2 | —CO—(CH₂)₅—Ph | H | H |
| 2-353 | Me | H | H | Me | 2 | —CO—(CH₂)₅—Ph | H | H |
| 2-354 | CO₂Me | H | H | Me | 2 | —CO—(CH₂)₅—Ph | H | H |
| 2-355 | H | H | H | Me | 2 | —CH(OH)—(CH₂)₄—cHx | H | H |
| 2-356 | H | H | Me | Me | 2 | —CH(OH)—(CH₂)₄—cHx | H | H |
| 2-357 | Me | H | H | Me | 2 | —CH(OH)—(CH₂)₄—cHx | H | H |
| 2-358 | CO₂Me | H | H | Me | 2 | —CH(OH)—(CH₂)₄—cHx | H | H |
| 2-359 | H | H | H | Me | 2 | —CH(OH)—(CH₂)₄—Ph | H | H |
| 2-360 | H | H | Me | Me | 2 | —CH(OH)—(CH₂)₄—Ph | H | H |
| 2-361 | Me | H | H | Me | 2 | —CH(OH)—(CH₂)₄—Ph | H | H |
| 2-362 | CO₂Me | H | H | Me | 2 | —CH(OH)—(CH₂)₄—Ph | H | H |
| 2-363 | H | H | H | Me | 2 | —CH(OH)—(CH₂)₅—cHx | H | H |
| 2-364 | H | H | Me | Me | 2 | —CH(OH)—(CH₂)₅—cHx | H | H |
| 2-365 | Me | H | H | Me | 2 | —CH(OH)—(CH₂)₅—cHx | H | H |
| 2-366 | CO₂Me | H | H | Me | 2 | —CH(OH)—(CH₂)₅—cHx | H | H |
| 2-367 | H | H | H | Me | 2 | —CH(OH)—(CH₂)₅—Ph | H | H |
| 2-368 | H | H | Me | Me | 2 | —CH(OH)—(CH₂)₅—Ph | H | H |
| 2-369 | Me | H | H | Me | 2 | —CH(OH)—(CH₂)₅—Ph | H | H |
| 2-370 | CO₂Me | H | H | Me | 2 | —CH(OH)—(CH₂)₅—Ph | H | H |
| 2-371 | H | H | H | Me | 2 | -4-(cHx—CH₂O)Ph | H | H |
| 2-372 | H | H | Me | Me | 2 | -4-(cHx—CH₂O)Ph | H | H |
| 2-373 | Me | H | H | Me | 2 | -4-(cHx—CH₂O)Ph | H | H |
| 2-374 | CO₂Me | H | H | Me | 2 | -4-(cHx—CH₂O)Ph | H | H |
| 2-375 | H | H | H | Me | 2 | -4-[cHx—(CH₂)₂O]Ph | H | H |
| 2-376 | H | H | H | Me | 2 | -4-[cHx—(CH₂)₃O]Ph | H | H |
| 2-377 | H | H | H | Me | 2 | -(4-BzO—Ph) | H | H |
| 2-378 | H | H | Me | Me | 2 | -(4-BzO—Ph) | H | H |
| 2-379 | Me | H | H | Me | 2 | -(4-BzO—Ph) | H | H |
| 2-380 | CO₂Me | H | H | Me | 2 | -(4-BzO—Ph) | H | H |
| 2-381 | H | H | H | Me | 2 | -(4-BzO-2-F—Ph) | H | H |
| 2-382 | H | H | H | Me | 2 | -(4-BzO-3-F—Ph) | H | H |
| 2-383 | H | H | H | Me | 2 | -(4-BzO-2,3-diF—Ph) | H | H |
| 2-384 | H | H | H | Me | 2 | -(4-BzO-2-Cl—Ph) | H | H |
| 2-385 | H | H | H | Me | 2 | -(4-BzO-3-Cl—Ph) | H | H |
| 2-386 | H | H | H | Me | 2 | -(4-BzO-2,3-diCl—Ph) | H | H |
| 2-387 | H | H | H | Me | 2 | -(4-BzO-2-Me—Ph) | H | H |
| 2-388 | H | H | H | Me | 2 | -(4-BzO-3-Me—Ph) | H | H |
| 2-389 | H | H | H | Me | 2 | -(4-BzO-2,3-diMe—Ph) | H | H |
| 2-390 | H | H | H | Me | 2 | -4-[Ph—(CH₂)₂O]—Ph | H | H |

TABLE 2-continued

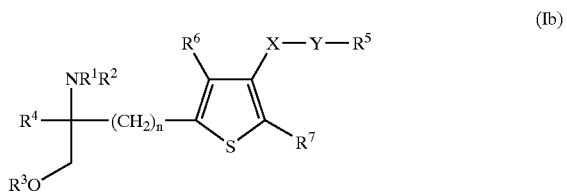
(Ib)

| Exemp. Compd. No. | $R^1$ | $R^2$ | $R^3$ | $R^4$ | n | —X—Y—$R^5$ | $R^6$ | $R^7$ |
|---|---|---|---|---|---|---|---|---|
| 2-391 | H | H | H | Me | 2 | -4-[Ph—(CH$_2$)$_3$O]—Ph | H | H |
| 2-392 | H | H | H | Et | 2 | —(CH$_2$)$_5$—cHx | H | H |
| 2-393 | H | H | H | Et | 2 | —(CH$_2$)$_6$—cHx | H | H |
| 2-394 | H | H | H | Et | 2 | —C≡C—(CH$_2$)$_3$—cHx | H | H |
| 2-395 | H | H | H | Et | 2 | —C≡C—(CH$_2$)$_4$—cHx | H | H |
| 2-396 | H | H | H | Et | 2 | -4-(cHx—CH$_2$O)Ph | H | H |
| 2-397 | H | H | H | Et | 2 | -(4-BzO—Ph) | H | H |
| 2-398 | H | H | H | Et | 2 | —C≡C—(CH$_2$)$_2$O—cHx | H | H |
| 2-399 | H | H | H | Et | 2 | —C≡C—(CH$_2$)$_2$O—Ph | H | H |
| 2-400 | H | H | H | Pr | 2 | —(CH$_2$)$_5$—cHx | H | H |
| 2-401 | H | H | H | Pr | 2 | —(CH$_2$)$_6$—cHx | H | H |
| 2-402 | H | H | H | Pr | 2 | —C≡C—(CH$_2$)$_3$—cHx | H | H |
| 2-403 | H | H | H | Pr | 2 | —C≡C—(CH$_2$)$_4$—cHx | H | H |
| 2-404 | H | H | H | Pr | 2 | -4-(cHx—CH$_2$O)Ph | H | H |
| 2-405 | H | H | H | Pr | 2 | -(4-BzO—Ph) | H | H |
| 2-406 | H | H | H | Pr | 2 | —C≡C—(CH$_2$)$_2$O—cHx | H | H |
| 2-407 | H | H | H | Pr | 2 | —C≡C—(CH$_2$)$_2$O—Ph | H | H |
| 2-408 | H | H | H | Me | 3 | —(CH$_2$)$_5$—cHx | H | H |
| 2-409 | H | H | H | Me | 3 | —(CH$_2$)$_6$—cHx | H | H |
| 2-410 | H | H | H | Me | 3 | —C≡C—(CH$_2$)$_3$—cHx | H | H |
| 2-411 | H | H | H | Me | 3 | —C≡C—(CH$_2$)$_4$—cHx | H | H |
| 2-412 | H | H | H | Me | 3 | -4-(cHx—CH$_2$O)Ph | H | H |
| 2-413 | H | H | H | Me | 3 | -(4-BzO—Ph) | H | H |
| 2-414 | H | H | H | Me | 3 | —C≡C—(CH$_2$)$_2$O—cHx | H | H |
| 2-415 | H | H | H | Me | 3 | —C≡C—(CH$_2$)$_2$O—Ph | H | H |

Preferred compounds in Tables 1 to 2 are those of Exemplification compounds numbers 1-19, 1-23 to 1-32, 1-36 to 1-45, 1-49 to 1-58, 1-62 to 1-71, 1-75 to 1-84, 1-88 to 1-102, 1-106 to 1-156, 1-160 to 1-214, 1-218 to 1-268, 1-272 to 1-322, 1-325 to 1-334, 1-338 to 1-347, 1-360, 1-364 to 1-372, 1-377 to 1-386, 1-390 to 1-404, 1-408 to 1-458, 1-462 to 1-513, 1-517 to 1-526, 1-530 to 1-544, 1-548 to 1-598, 1-602 to 1-657, 1-670, 1-674 to 1-683, 1-696, 1-700 to 1-717, 1-721 to 1-730, 1-734 to 1-743, 1-747 to 1-756, 1-760 to 1-774, 1-778 to 1-828, 1-832 to 1-886, 1-890 to 1-940, 1-944 to 1-993, 1-997 to 1-1006, 1-1010 to 1-1019, 1-1045, 1-1049 to 1-1058, 1-1062 to 1-1076, 1-1080 to 1-1130, 1-1-1134 to 1-1185, 1-1189 to 1-1198, 1-1202 to 1-1208, 1-1212 to 1-1216, 1-1220 to 1-1270, 1-1274 to 1-1331, 1-1335 to 1-1344, 1-1348 to 1-1357, 1-1361 to 1-1370, 1-1374 to 1-1387, 1-1391 to 1-1400, 1-1404 to 1-1418, 1-1422 to 1-1472, 1-1476 to 1-1527, 1-1531 to 1-1540, 1-1544 to 1-1558, 1-1562 to 1-1612, 1-1616 to 1-1673, 1-1677 to 1-1686, 1-1690 to 1-1699, 1-1703 to 1-1712, 1-1716 to 1-1729, 1-1733 to 1-1744, 1-1748 to 1-1767, 1-1772 to 1-1793, 1-1797 to 1-1818, 1-1824 to 1-1846, 1-1850 to 1-1869, 1-1872, 1-1876, 1-1880, 1-1884, 1-1888 to 1-1892, 1-1896, 1-1900, 1-1908 to 1-1913, 1-1917 to 1-1939, 1-1943 to 1-1966, 1-1970 to 1-1991, 1-1995 to 1-2013, 1-2017, 1-2021, 1-2025, 1-2029, 1-2033, 1-2037 to 1-2042, 1-2045 to 1-2068, 1-2072 to 1-2089, 1-2093, 1-2097, 1-2101, 1-2105, 1-2109, 1-2113, 1-2117, 1-2121, 1-2125, 1-2129, 1-2133, 1-2135, 1-2139 to 1-2158, 1-2161 to 1-2164, 1-2184 to 1-2346, 2-9 to 2-18, 2-22 to 2-43, 2-47 to 2-70, 2-74 to 2-96, 2-100 to 2-119, 2-142, 2-146, 2-150, 2-154, 2-158 to 2-163, 2-167 to 2-183, 2-185 to 2-189, 2-193 to 2-216, 2-220 to 2-241, 2-245 to 2-263, 2-267, 2-271, 2-275, 2-279, 2-283, 2-287 to 2-292, 2-296 to 2-318, 2-322 to 2-338, 2-343, 2-347, 2-351, 2-371, 2-375 to 2-377, 2-381 to 2-407.

More preferred compounds are those of Exemplification compounds numbers 1-19, 1-32, 1-36 to 1-45, 1-57, 1-62 to 1-71, 1-84, 1-88, 1-97 to 1-100, 1-152 to 1-154, 1-160 to 1-214, 1-218 to 1-227, 1-264 to 1-268, 1-272 to 1-322, 1-344, 1-347, 1-360, 1-373, 1-386, 1-390 to 1-402, 1-454 to 1-458, 1-462 to 1-513, 1-526, 1-530 to 1-542, 1-594 to 1-598, 1-602 to 1-653, 1-743, 1-756, 1-760 to 1-768, 1-770 to 1-774, 1,-778 to 1-828, 1-832 to 1-886, 1-890 to 1-940, 1-944 to 1-993, 1-1045, 1-1058, 1-1062 to 1-1074, 1-1126 to 1-1130, 1-1134 to 1-1185, 1-1198, 1-1202 to -1208, 1-1212, 1-1213, 1-1214, 1-1266 to 1270, 1-1274 to 1331, 1-1344, 1-1348 to 1-1357, 1-1370, 1-1374 to 1-1387, 1-1400, 1-1404 to 1-1416, 1-1468 to 1-1472, 1-1476 to 1-1527, 1-1540, 1-1544 to 1-1556, 1-1608 to 1-1612, 1-1616 to 1-1666, 1-1729, 1-1742, 1-1744, 1-1759 to 1-1767, 1-1789 to 1-1793, 1-1797 to 1-1818, 1-1842 to 1-1846, 1-1900, 1-1908 to 1-1913, 1-1935 to 1-1939, 1-1943 to 1-1966, 1-1987 to 1-1991, 2-013, 1-2017, 1-2029, 1-2033, 1-2037 to 1-2042, 1-2064 to 1-2068, 1-2072 to 1-2089, 1-2093, 1-2097, 1-2101, 1-2105, 1-2109, 1-2129, 1-2133, 1-2135, 1-2184 to 1-2346, 2-11 to 2-18, 2-39 to 2-43, 2-47 to 2-70, 2-185 to 2-189, 2-193 to 2-216, 2-287 to 2-292, 2-338, 2-343, 2-347, 2-351.

More preferred compounds are those of Exemplification compounds numbers 1-45, 1-71, 1-84, 1-88, 1-97 to 1-100, 1-152 to 1-154, 1-160 to 1-206, 1-209 to 1-212, 1-264 to 1-266, 1-334, 1-373, 1-386, 1-390 to 1-402, 1-454 to 1-458, 1-462 to 1-485, 1-509, 1-513, 1-526, 1-530 to 1-542, 1-594-to 1-598, 1-602 to 1-613, 1-649, 1-650, 1-743, 1-756, 1-760 to 1-768, 1-770 to 1-772, 1-824 to 1-828, 1-832 to 1-884, 1-936, 1-1045, 1-1058, 1-1062 to 1-1074, 1-1126 to 1-1130, 1-1134 to 1-1145, 1-1148 to 1-1151, 1-1162, 1-1163, 1-1179 to 1-1182, 1-1185, 1-1198, 1-1202 to 1-1208, 1-1212, 1-1213, 1-1214, 1-1266 to 1-1270, 1-1274 to 1-1285, 1-1288 to 1-1291, 1-1319 to 1-1322, 1-1329 to 1-1331, 1-1344, 1-1348 to 1-1357, 1-1370, 1-1387, 1-1400, 1-1404 to 1-1416, 1-1468 to 1-1472, 1-1476 to 1-1487, 1-1490 to 1-1493, 1-1504, 1-1505, 1-1521 to 1-1524, 1-1527, 1-1540, 1-1544 to 1-1556, 1-1608 to 1-1612, 1-1616 to 1-1627, 1-1663, 1-1664, 1-1729, 1-1742, 1-1744, 1-1761 to 1-1766, 1-1789 to 1-1791, 1-1815 to 1-1818, 1-1900, 1-1909, 1-1962, 1-2064 to 1-2066, 1-2089, 1-2093, 1-2097, 1-2105, 1-2133, 1-2216 to 1-2288, 1-2290 to 1-2346.

Still more preferred compounds in Tables 1 and 2 are those exemplification compounds numbers:

1-71: 2-amino-2-methyl-4-[5-(4-cyclohexylbutyl)thiophen-2-yl]butan-1-ol,
1-84: 2-amino-2-methyl-4-[5-(4-phenylbutyl)thiophen-2-yl]butan-1-ol,
1-98: 2-amino-2-methyl-4-[5-(5-cyclohexylpentyl)thiophen-2-yl]butan-1-ol,
1-152: 2-amino-2-methyl-4-[5-(5-phenylpentyl)thiophen-2-yl]butan-1-ol,
1-210: 2-amino-2-methyl-4-[5-(6-cyclohexylhexyl)thiophen-2-yl]butan-1-ol,
1-264: 2-amino-2-methyl-4-[5-(6-phenylhexyl)thiophen-2-yl]butan-1-ol,
1-373: 2-amino-2-methyl-4-[5-(3-cyclohexyloxypropyl)thiophen-2-yl]butan-1-ol,
1-386: 2-amino-2-methyl-4-[5-(3-phenoxypropyl)thiophen-2-yl]butan-1-ol,
1-400: 2-amino-2-methyl-4-[5-(4-cyclohexyloxybutyl)thiophen-2-yl]butan-1-ol,
1-454: 2-amino-2-methyl-4-[5-(4-phenoxybutyl)thiophen-2-yl]butan-1-ol,
1-509: 2-amino-2-methyl-4-[5-(5-cyclohexyloxypentyl)thiophen-2-yl]butan-1-ol,
1-510: 2-amino-2-methyl-4-[5-(5-phenoxypentyl)thiophen-2-yl]butan-1-ol,
1-513: 2-amino-2-methyl-4-[5-(3-cyclohexylmethoxypropyl)thiophen-2-yl]butan-1-ol,
1-743: 2-amino-2-methyl-4-[5-(4-cyclohexylbut-1-ynyl)thiophen-2-yl]butan-1-ol,
1-756: 2-amino-2-methyl-4-[5-(4-phenylbut-1-ynyl)thiophen-2-yl]butan-1-ol,
1-770: 2-amino-2-methyl-4-[5-(5-cyclohexylpent-1-ynyl)thiophen-2-yl]butan-1-ol,
1-824: 2-amino-2-methyl-4-[5-(5-phenylpent-1-ynyl)thiophen-2-yl]butan-1-ol,
1-882: 2-amino-2-methyl-4-[5-(6-cyclohexylhex-1-ynyl)thiophen-2-yl]butan-1-ol,
1-936: 2-amino-2-methyl-4-[5-(6-phenylhex-1-ynyl)thiophen-2-yl]butan-1-ol,
1-1045: 2-amino-2-methyl-4-[5-(3-cyclohexyloxypropynyl)thiophen-2-yl]butan-1-ol,
1-1058: 2-amino-2-methyl-4-[5-(3-phenoxypropynyl)thiophen-2-yl]butan-1-ol,
1-1072: 2-amino-2-methyl-4-[5-(4-cyclohexyloxybut-1-ynyl)thiophen-2-yl]butan-1-ol,
1-1126: 2-amino-2-methyl-4-[5-(4-phenoxybut-1-ynyl)thiophen-2-yl]butan-1-ol,
1-1181: 2-amino-2-methyl-4-[5-(5-cyclohexyloxypent-1-ynyl)thiophen-2-yl]butan-1-ol,
1-1182: 2-amino-2-methyl-4-[5-(5-phenoxypent-1-ynyl)thiophen-2-yl]butan-1-ol,
1-1185: 2-amino-2-methyl-4-[5-(3-cyclohexylmethoxypropynyl)thiophen-2-yl]butan-1-ol,
1-1329: 2-amino-2-methyl-4-[5-(4-cyclohexylbutanoyl)thiophen-2-yl]butan-1-ol,
1-1330: 2-amino-2-methyl-4-[5-(4-phenylbutanoyl)thiophen-2-yl]butan-1-ol,
1-1331: 2-amino-2-methyl-4-[5-(5-cyclohexylpentanoyl)thiophen-2-yl]butan-1-ol,
1-1344: 2-amino-2-methyl-4-[5-(5-phenylpentanoyl)thiophen-2-yl]butan-1-ol,
1-1357: 2-amino-2-methyl-4-[5-(6-cyclohexylhexanoyl)thiophen-2-yl]butan-1-ol,
1-1370: 2-amino-2-methyl-4-[5-(6-phenylhexanoyl)thiophen-2-yl]butan-1-ol,
1-1387: 2-amino-2-methyl-4-[5-(3-cyclohexyloxypropanoyl)thiophen-2-yl]butan-1-ol,
1-1400: 2-amino-2-methyl-4-[5-(3-phenoxypropanoyl)thiophen-2-yl]butan-1-ol,
1-1414: 2-amino-2-methyl-4-[5-(4-cyclohexyloxybutanoyl)thiophen-2-yl]butan-1-ol,
1-1468: 2-amino-2-methyl-4-[5-(4-phenoxybutanoyl)thiophen-2-yl]butan-1-ol, 1-1523: 2-amino-2-methyl-4-[5-(5-cyclohexyloxypentanoyl)thiophen-2-yl]butan-1-ol,
1-1523: 2-amino-2-methyl-4-[5-(5-cyclohexyloxypentanoyl)thiophen-2-yl]butan-1-ol,
1-1524: 2-amino-2-methyl-4-[5-(5-phenoxypentanoyl)thiophen-2-yl]butan-1-ol,
1-1527: 2-amino-2-methyl-4-[5-(3-cyclohexylmethoxypropanoyl)thiophen-2-yl]butan-1-ol,
1-1729: 2-amino-2-methyl-4-[5-(4-cyclohexylmethoxyphenyl)thiophen-2-yl]butan-1-ol,
1-1742: 2-amino-2-methyl-4-[5-(4-cyclohexylethoxyphenyl)thiophen-2-yl]butan-1-ol,
1-1744: 2-amino-2-methyl-4-[5-(4-benzyloxyphenyl)thiophen-2-yl]butan-1-ol,
1-1761: 2-amino-2-ethyl-4-[5-(4-cyclohexylbutyl)thiophen-2-yl]butan-1-ol,
1-1764: 2-amino-2-ethyl-4-[5-(5-cyclohexylpentyl)thiophen-2-yl]butan-1-ol,
1-1816: 2-amino-2-ethyl-4-[5-(6-cyclohexylhexyl)thiophen-2-yl]butan-1-ol,
1-1900: 2-amino-2-ethyl-4-[5-(4-cyclohexylbut-1-ynyl)thiophen-2-yl]butan-1-ol,
1-1909: 2-amino-2-ethyl-4-[5-(5-cyclohexylpent-1-ynyl)thiophen-2-yl]butan-1-ol,
1-1962: 2-amino-2-ethyl-4-[5-(6-cyclohexylhex-1-ynyl)thiophen-2-yl]butan-1-ol,
1-2089: 2-amino-2-ethyl-4-[5-(4-cyclohexylbutanoyl)thiophen-2-yl]butan-1-ol,
1-2097: 2-amino-2-ethyl-4-[5-(5-cyclohexylpentanoyl)thiophen-2-yl]butan-1-ol,
1-463: 2-amino-2-methyl-4-{5-[4-(4-fluorophenoxy)butyl]thiophen-2-yl}butan-1-ol,
1-479: 2-amino-2-methyl-4-{5-[4-(4-methoxyphenoxy)butyl]thiophen-2-yl}butan-1-ol,
1-594: 2-amino-2-methyl-4-[5-(4-benzyloxybutyl)thiophen-2-yl]butan-1-ol,
1-760: 2-amino-2-methyl-4-{5-[4-(4-fluorophenyl)but-1-ynyl]thiophen-2-yl}butan-1-ol,
1-761: 2-amino-2-methyl-4-{5-[4-(4-methylphenyl)but-1-ynyl]thiophen-2-yl}butan-1-ol,
1-762: 2-amino-2-methyl-4-{5-[4-(4-ethylphenyl)but-1-ynyl]thiophen-2-yl}butan-1-ol,
1-763: 2-amino-2-methyl-4-{5-[4-(4-trifluoromethylphenyl)but-1-ynyl]thiophen-2-yl}butan-1-ol,
1-764: 2-amino-2-methyl-4-{5-[4-(4-methoxyphenyl)but-1-ynyl]thiophen-2-yl}butan-1-ol, 1-765: 2-amino-2-methyl-4-{5-[4-(4-ethoxyphenyl)but-1-ynyl]thiophen-2-yl}butan-1-ol,
1-766: 2-amino-2-methyl-4-{5-[4-(4-methylthiophenyl)but-1-ynyl]thiophen-2-yl}butan-1-ol,
1-832: 2-amino-2-methyl-4-{5-[5-(3-fluorophenyl)pent-1-ynyl]thiophen-2-yl}butan-1-ol,
1-833: 2-amino-2-methyl-4-{5-[5-(4-fluorophenyl)pent-1-ynyl]thiophen-2-yl}butan-1-ol,
1-834: 2-amino-2-methyl-4-{5-[5-(4-chlorophenyl)pent-1-ynyl]thiophen-2-yl}butan-1-ol,
1-836: 2-amino-2-methyl-4-{5-[5-(3-methylphenyl)pent-1-ynyl]thiophen-2-yl}butan-1-ol,
1-837: 2-amino-2-methyl-4-{5-[5-(4-methylphenyl)pent-1-ynyl]thiophen-2-yl}butan-1-ol,
1-846: 2-amino-2-methyl-4-{5-[5-(3-trifluoromethylphenyl)pent-1-ynyl]thiophen-2-yl}butan-1-ol,
1-847: 2-amino-2-methyl-4-{5-[5-(4-trifluorophenyl)pent-1-ynyl]thiophen-2-yl}butan-1-ol,
1-848: 2-amino-2-methyl-4-{5-[5-(3-methoxyphenyl)pent-1-ynyl]thiophen-2-yl}butan-1-ol,
1-849: 2-amino-2-methyl-4-{5-[5-(4-methoxyphenyl)pent-1-ynyl]thiophen-2-yl}butan-1-ol,
1-860: 2-amino-2-methyl-4-{5-[5-(3-methylthiophenyl)pent-1-ynyl]thiophen-2-yl}butan-1-ol,
1-861: 2-amino-2-methyl-4-{5-[5-(4-methylphenyl)pent-1-ynyl]thiophen-2-yl}butan-1-ol,
1-877: 2-amino-2-methyl-4-{5-[5-(3,4-dimethylphenyl)pent-1-ynyl]thiophen-2-yl}butan-1-ol,
1-878: 2-amino-2-methyl-4-{5-[5-(3,5-dimethylphenyl)pent-1-ynyl]thiophen-2-yl}butan-1-ol,
1-1050: 2-amino-2-methyl-4-{5-[3-(4-methylcyclohexyloxy)propynyl]thiophen-2-yl}butan-1-ol,
1-1062: 2-amino-2-methyl-4-{5-[3-(4-fluorophenoxy)propynyl]thiophen-2-yl}butan-1-ol,
1-1063: 2-amino-2-methyl-4-{5-[3-(4-methylphenoxy)propynyl]thiophen-2-yl}butan-1-ol,
1-1064: 2-amino-2-methyl-4-{5-[3-(4-ethylphenoxy)propynyl]thiophen-2-yl}butan-1-ol,
1-1065: 2-amino-2-methyl-4-{5-[3-(4-trifluoromethylphenyl)propynyl]thiophen-2-yl}butan-1-ol,
1-1066: 2-amino-2-methyl-4-{5-[3-(4-methoxyphenoxy)propynyl]thiophen-2-yl}butan-1-ol,
1-1067: 2-amino-2-methyl-4-{5-[3-(4-methoxyphenoxy)propynyl]thiophen-2-yl}butan-1-ol,
1-1068: 2-amino-2-methyl-4-{5-[3-(4-methylthiophenoxy)propynyl]thiophen-2-yl}butan-1-ol,
1-1134: 2-amino-2-methyl-4-{5-[4-(3-fluorophenoxy)but-1-ynyl]thiophen-2-yl}butan-1-ol,
1-1135: 2-amino-2-methyl-4-{5-[4-(4-fluorophenoxy)but-1-ynyl]thiophen-2-yl}butan-1-ol,
1-1136: 2-amino-2-methyl-4-{5-[4-(4-chlorophenoxy)but-1-ynyl]thiophen-2-yl}butan-1-ol,
1-1138: 2-amino-2-methyl-4-{5-[4-(3-methylphenoxy)but-1-ynyl]thiophen-2-yl}butan-1-ol,
1-1139: 2-amino-2-methyl-4-{5-[4-(4-methylphenoxy)but-1-ynyl]thiophen-2-yl}butan-1-ol,
1-1148: 2-amino-2-methyl-4-{5-[4-(3-trifluoromethylphenoxy)but-1-ynyl]thiophen-2-yl}butan-1-ol,
1-1149: 2-amino-2-methyl-4-{5-[4-(4-trifluoromethylphenoxy)but-1-ynyl]thiophen-2-yl}butan-1-ol,
1-1150: 2-amino-2-methyl-4-{5-[4-(3-methoxyphenoxy)but-1-ynyl]thiophen-2-yl}butan-1-ol,
1-1151: 2-amino-2-methyl-4-{5-[4-(4-methoxyphenoxy)but-1-ynyl]thiophen-2-yl}butan-1-ol,
1-1162: 2-amino-2-methyl-4-{5-[4-(3-methylthiophenoxy)but-1-ynyl]thiophen-2-yl}butan-1-ol,
1-1163: 2-amino-2-methyl-4-{5-[4-(4-methylthiophenoxy)but-1-ynyl)thiophen-2-yl}butan-1-ol,
1-1179: 2-amino-2-methyl-4-{5-[4-(3,4-dimethylphenoxy)but-1-ynyl]thiophen-2-yl}butan-1-ol,
1-1180: 2-amino-2-methyl-4-{5-[4-(3,4-dimethylphenoxy)but-I-ynyl]thiophen-2-yl}butan-1-ol,
1-1198: 2-amino-2-methyl-4-[5-(3-phenylmethoxypropynyl)thiophen-2-yl]butan-1-ol,
1-1202: 2-amino-2-methyl-4-{5-[3-(4-fluorophenyl)methoxypropynyl]thiophen-2-yl}butan-1-ol,
1-1203: 2-amino-2-methyl-4-{5-[3-(4-methylphenyl)methoxypropynyl]thiophen-2-yl}butan-1-ol,
1-1204: 2-amino-2-methyl-4-{5-[3-(4-ethylphenyl)methoxypropynyl]thiophen-2-yl}butan-1-ol,
1-1205: 2-amino-2-methyl-4-{5-[3-(4-trifluoromethylphenyl)methoxypropynyl]-thiophen-2-yl}butan-1-ol,
1-1206: 2-amino-2-methyl-4-{5-[3-(4-methoxyphenyl)methoxyproynyl]thiophen-2-yl}butan-1-ol,
1-1207: 2-amino-2-methyl-4-{5-[3-(4-ethoxyphenyl)methoxypropynyl]thiophen-2-yl}butan-1-ol,
1-1208: 2-amino-2-methyl-4-{5-[3-(4-methylthiophenyl)methoxypropynyl]-thiophen-2-yl}butan-1-ol,
1-1212: 2-amino-2-methyl-4-[5-(4-cyclohexylmethoxybut-1-ynyl)thiophen-2-yl]butan-1-ol,
1-1266: 2-amino-2-methyl-4-[5-(4-phenylmethoxybut-1-ynyl)thiophen-2-yl]butan-1-ol,
1-1274: 2-amino-2-methyl-4-{5-[4-(3-fluorophenyl)methoxybut-1-ynyl]thiophen-2-yl}butan-1-ol,
1-1275: 2-amino-2-methyl-4-{5-[4-(4-fluorophenyl)methoxybut-1-ynyl]thiophen-2-yl}butan-1-ol,
1-1276: 2-amino-2-methyl-4-{5-[4-(4-chlorophenyl)methoxybut-1-ynyl]thiophen-2-yl}butan-1-ol,
1-1278: 2-amino-2-methyl-4-{5-[4-(3-methylphenyl)methoxybut-1-ynyl]thiophen-2-yl}butan-1-ol,
1-1279: 2-amino-2-methyl-4-{5-[4-(4-methylphenyl)methoxybut-1-ynyl]thiophen-2-yl}butan-1-ol,
1-1288: 2-amino-2-methyl-4-{5-[4-(3-trifluoromethylphenyl)methoxybut-1-ynyl]thiophen-2-yl}butan-1-ol,
1-1289: 2-amino-2-methyl-4-{5-[4-(4-trifluoromethylphenyl)methoxybut-1-ynyl]thiophen-2-yl}butan-1-ol,
1-1290: 2-amino-2-methyl-4-{5-[4-(3-methoxyphenyl)methoxybut-1-ynyl]thiophen-2-yl}butan-1-ol,
1-1291: 2-amino-2-methyl-4-{5-[4-(4-methoxyphenyl)methoxybut-1-ynyl]thiophen-2-yl}butan-1-ol,
1-1319: 2-amino-2-methyl-4-{5-[4-(3,4-dimethylphenyl)methoxybut-1-ynyl]thiophen-2-yl}butan-1-ol,
1-1320: 2-amino-2-methyl-4-{5-[4-(3,5-dimethylphenyl)methoxybut-1-ynyl]thiophen-2-yl}butan-1-ol,
1-1348: 2-amino-2-methyl-4-{5-[5-(4-fluorophenyl)pentanoyl]thiophen-2-yl}butan-1-ol,
1-1349: 2-amino-2-methyl-4-{5-[5-(4-methylphenyl)pentanoyl]thiophen-2-yl}butan-1-ol,
1-1350: 2-amino-2-methyl-4-{5-[5-(4-ethylphenyl)pentanoyl]thiophen-2-yl}butan-1-ol,
1-1351: 2-amino-2-methyl-4-{5-[5-(4-trifluoromethylphenyl)pentanoyl]thiophen-2-yl}butan-1-ol,
1-1352: 2-amino-2-methyl-4-{5-[5-(4-methoxyphenyl)pentanoyl]thiophen-2-yl}butan-1-ol,
1-1353: 2-amino-2-methyl-4-{5-[5-(4-ethoxyphenyl)pentanoyl]thiophen-2-yl}butan-1-ol, 1-1354: 2-amino-2-methyl-4-{5-[5-(4-methylthiophenyl)pentanoyl]thiophen-2-yl}butan-1-ol,
1-1476: 2-amino-2-methyl-4-{5-[4-(3-fluorophenoxy)butanoyl]thiophen-2-yl}butan-1-ol,
1-1477: 2-amino-2-methyl-4-{5-[4-(4-fluorophenoxy)butanoyl]thiophen-2-yl}butan-1-ol,
1-1478: 2-amino-2-methyl-4-{5-[4-(4-chlorophenoxy)butanoyl]thiophen-2-yl}butan-1-ol,
1-1480: 2-amino-2-methyl-4-{5-[4-(3-methylphenoxy)butanoyl]thiophen-2-yl}butan-1-ol,
1-1481: 2-amino-2-methyl-4-{5-[4-(4-methylphenoxy)butanoyl]thiophen-2-yl}butan-1-ol,
1-1490: 2-amino-2-methyl-4-{5-[4-(3-trifluoromethylphenoxy)butanoyl]thiophen-2-yl}butan-1-ol,
1-1491: 2-amino-2-methyl-4-{5-[4-(4-trifluoromethylphenoxy)butanoyl]thiophen-2-yl}butan-1-ol,
1-1492: 2-amino-2-methyl-4-{5-[4-(3-methoxyphenoxy)butanoyl]thiophen-2-yl}butan-1-ol,
1-1493: 2-amino-2-methyl-4-{5-[4-(4-methoxyphenoxy)butanoyl]thiophen-2-yl}butan-1-ol,
1-1504: 2-amino-2-methyl-4-{5-[4-(3-methylthiophenyl)butanoyl]thiophen-2-yl}butan-1-ol,
1-1505: 2-amino-2-methyl-4-{5-[4-(4-methylthiophenyl)butanoyl]thiophen-2-yl}butan-1-ol,
1-1521: 2-amino-2-methyl-4-{5-[4-(3,4-dimethylphenoxy)butanoyl]thiophen-2-yl}butan-1-ol,
1-1522: 2-amino-2-methyl-4-{5-[4-(3,5-dimethylphenoxy)butanoyl]thiophen-2-yl}butan-1-ol,
1-2093: 2-amino-2-ethyl-4-[5-(4-phenylbutanoyl)thiophen-2-yl]butan-1-ol,
1-2101: 2-amino-2-ethyl-4-[5-(5-phenylpentanoyl)thiophen-2-yl]butan-1-ol,
1-2109: 2-amino-2-ethyl-4-[5-(4-phenylhexanoyl)thiophen-2-yl]butan-1-ol,
1-2257: 2-amino-2-methyl-4-{5-[5-(3,4-difluorophenyl)pent-1-ynyl]thiophen-2-yl}butan-1-ol,
1-2258: 2-amino-2-methyl-4-{5-[5-(3,4-difluorophenyl)pent-1-ynyl]thiophen-2-yl}butan-1-ol,
1-2259: 2-amino-2-methyl-4-{5-[5-(3-chlorophenyl)pent-1-ynyl]thiophen-2-yl}butan-1-ol,
1-2260: 2-amino-2-methyl-4-{5-[5-(3,4-dichlorophenyl)pent-1-ynyl]thiophen-2-yl}butan-1-ol,
1-2261: 2-amino-2-methyl-4-{5-[5-(3,4-dichlorophenyl)pent-1-ynyl]thiophen-2-yl}butan-1-ol,
1-2262: 2-amino-2-methyl-4-{5-[5-(3,4-ditrifluoromethylphenyl)pent-1-ynyl]thiophen-2-yl}butan-1-ol,
1-2263: 2-amino-2-methyl-4-{5-[5-(3,5-ditrifluoromethylphenyl)pent-1-ynyl]thiophen-2-yl}butan-1-ol,
1-2264: 2-amino-2-methyl-4-{5-[5-(3,4-dimethoxyphenyl)pent-1-ynyl]thiophen-2-yl}butan-1-ol,
1-2265: 2-amino-2-methyl-4-{5-[5-(3,5-dimethoxyphenyl)pent-1-ynyl]thiophen-2-yl}butan-1-ol,
1-2266: 2-amino-2-methyl-4-{5-[5-(3,4,5-trimethoxyphenyl)pent-1-ynyl]thiophen-2-yl}butan-1-ol,
1-2267: 2-amino-2-methyl-4-{5-[5-(3-acetylphenyl)pent-1-ynyl]thiophen-2-yl}butan-1-ol,
1-2268: 2-amino-2-methyl-4-{5-[5-(4-acetylphenyl)pent-1-ynyl]thiophen-2-yl}butan-1-ol,
1-2269: 2-amino-2-methyl-4-{5-[3-(3-fluorophenoxy)propynyl]thiophen-2-yl}butan-1-ol,
1-2270: 2-amino-2-methyl-4-{5-[3-(3,4-difluorophenoxy)propynyl]thiophen-2-yl}butan-1-ol,
1-2271: 2-amino-2-methyl-4-{5-[3-(3,5-difluorophenoxy)propynyl]thiophen-2-yl}butan-1-ol,
1-2272: 2-amino-2-methyl-4-{5-[3-(3-chlorophenoxy)propynyl]thiophen-2-yl}butan-1-ol,
1-2273: 2-amino-2-methyl-4-{5-[3-(4-chlorophenoxy)propynyl]thiophen-2-yl}butan-1-ol,
1-2274: 2-amino-2-methyl-4-{5-[3-(3,4-dichlorophenoxy)propynyl]thiophen-2-yl}butan-1-ol,
1-2275: 2-amino-2-methyl-4-{5-[3-(3,5-dichlorophenoxy)propynyl]thiophen-2-yl}butan-1-ol,
1-2276: 2-amino-2-methyl-4-{5-[3-(3-methylphenoxy)propynyl]thiophen-2-yl}butan-1-ol,
1-2278: 2-amino-2-methyl-4-{5-[3-(3,4-dimethylphenoxy)propynyl]thiophen-2-yl}butan-1-ol,
1-2279: 2-amino-2-methyl-4-{5-[3-(3,5-dimethylphenoxy)propynyl]thiophen-2-yl}butan-1-ol,
1-2280: 2-amino-2-methyl-4-{5-[3-(3-trifluoromethylphenoxy)propynyl]thiophen-2-yl}butan-1-ol,
1-2281: 2-amino-2-methyl-4-{5-[3-(3,4-difluoromethylphenoxy)propynyl]thiophen-2-yl}butan-1-ol,
1-2282: 2-amino-2-methyl-4-{5-[3-(3,5-ditrifluoromethylphenoxy)propynyl]thiophen-2-yl}butan-1-ol,
1-2283: 2-amino-2-methyl-4-{5-[3-(3-methoxyphenoxy)propynyl]thiophen-2-yl}butan-1-ol,
1-2284: 2-amino-2-methyl-4-{5-[3-(3,4-dimethoxyphenyl)propynyl]thiophen-2-yl}butan-1-ol,
1-2285: 2-amino-2-methyl-4-{5-[3-(3,5-dimethoxyphenoxy)propynyl]thiophen-2-yl}butan-1-ol,
1-2286: 2-amino-2-methyl-4-{5-[3-(3,4,5-trimethoxyphenoxy)propynylthiophen-2-yl}butan-1-ol,
1-2287: 2-amino-2-methyl-4-{5-[3-(3-acetylphenoxy)propynyl]thiophen-2-yl}butan-1-ol,
1-2288: 2-amino-2-methyl-4-{5-[3-(4-acetylphenoxy)propynyl]thiophen-2-yl}butan-1-ol,
1-2290: 2-amino-2-methyl-4-{5-[4-(3,4-difluorophenoxy)but-1-ynyl]thiophen-2-yl}butan-1-ol,
1-2291: 2-amino-2-methyl-4-{5-[4-(3,5-difluorophenoxy)but-1-ynyl]thiophen-2-yl}butan-1-ol,
1-2292: 2-amino-2-methyl-4-{5-[4-(3-chlorophenoxy)but-1-ynyl]thiophen-2-yl}butan-1-ol,
1-2293: 2-amino-2-methyl-4-{5-[4-(3,4-dichlorophenoxy)but-1-ynyl]thiophen-2-yl}butan-1-ol,
1-2294: 2-amino-2-methyl-4-{5-[4-(3,5-dichlorophenoxy)but-1-ynyl]thiophen-2-yl}butan-1-ol,
1-2295: 2-amino-2-methyl-4-{5-[4-(3,4-ditrifluoromethylphenoxy)but-1-ynyl]thiophen-2-yl}butan-1-ol,
1-2296: 2-amino-2-methyl-4-{5-[4-(3,5-ditrifluoromethylphenoxy)but-1-ynyl]thiophen-2-yl}butan-1-ol,
1-2297: 2-amino-2-methyl-4-{5-[4-(3,4-dimethoxyphenoxyl)but-1-ynyl]thiophen-2-yl}butan-1-ol,
1-2298: 2-amino-2-methyl-4-{5-[4-(3,5-dimethoxyphenoxy)but-1-ynyl]thiophen-2-yl}butan-1-ol,
1-2299: 2-amino-2-methyl-4-{5-[4-(3,4,5-trimethoxyphenoxy)but-1-ynyl]thiophen-2-yl}butan-1-ol,
1-2300: 2-amino-2-methyl-4-{5-[4-(3-acetylphenoxy)but-1-ynyl]thiophen-2-yl}butan-1-ol,
1-2301: 2-amino-2-methyl-4-{5-[4-(4-acetylphenoxy)but-1-ynyl]thiophen-2-yl}butan-1-ol,
1-2328: 2-amino-2-methyl-4-{5-[5-(3-fluorophenyl)pentanoyl]thiophen-2-yl}butan-1-ol,
1-2329: 2-amino-2-methyl-4-{5-[5-(3,4-difluorophenyl)pentanoyl]thiophen-2-yl}butan-1-ol, 1-2330: 2-amino-2-methyl-4-{5-[5-(3,5-difluorophenyl)pentanoyl]thiophen-2-yl}butan-1-ol,
1-2331: 2-amino-2-methyl-4-{5-[5-(3-chlorophenyl)pentanoyl]thiophen-2-yl}butan-1-ol,
1-2332: 2-amino-2-methyl-4-{5-[5-(4-chlorophenyl)pentanoyl]thiophen-2-yl}butan-1-ol,
1-2333: 2-amino-2-methyl-4-{5-[5-(3,4-dichlorophenyl)pentanoyl]thiophen-2-yl}butan-1-ol,
1-2334: 2-amino-2-methyl-4-{5-[5-(3,5-dichlorophenyl)pentanoyl]thiophen-2-yl}butan-1-ol,
1-2335: 2-amino-2-methyl-4-{5-[5-(3-methylphenyl)pentanoyl]thiophen-2-yl}butan-1-ol,
1-2336: 2-amino-2-methyl-4-{5-[5-(3,4-dimethylphenyl)pentanoyl]thiophen-2-yl}butan-1-ol,
1-2337: 2-amino-2-methyl-4-{5-[5-(3,4-dimethylphenyl)pentanoyl]thiophen-2-yl}butan-1-ol,
1-2338: 2-amino-2-methyl-4-{5-[5-(3-trifluoromethylphenyl)pentanoyl]thiophen-2-yl}butan-1-ol,
1-2339: 2-amino-2-methyl-4-{5-[5-(3,4-ditrifluoromethylphenyl)pentanoyl]-thiophen-2-yl}butan-1-ol,
1-2340: 2-amino-2-methyl-4-{5-[5-(3,5-ditrifluoromethylphenyl)pentanoyl]-thiophen-2-yl}butan-1-ol,
1-2341: 2-amino-2-methyl-4-{5-[5-(3-methoxyphenyl)pentanoyl]thiophen-2-yl}butan-1-ol,
1-2342: 2-amino-2-methyl-4-{5-[5-(3,4-dimethoxyphenyl)pentanoyl]thiophen-2-yl}butan-1-ol,
1-2343: 2-amino-2-methyl-4-{5-[5-(3,5-dimethoxyphenyl)pentanoyl]thiophen-2-yl}butan-1-ol,
1-2344: 2-amino-2-methyl-4-{5-[5-(3,4,5-trimethoxyphenyl)pentanoyl]thiophen-2-yl}butan-1-ol,
1-2345: 2-amino-2-methyl-4-{5-[5-(3-acetylphenyl)pentanoyl]thiophen-2-yl}butan-1-ol, and
1-2346: 2-amino-2-methyl-4-{5-[5-(4-acetylphenyl)pentanoyl]thiophen-2-yl}butan-1-ol.

Most preferred compounds are those of Exemplificaion compounds numbers:

1-71: 2-amino-2-methyl-4-[5-(4-cyclohexylbutyl)thiophen-2-yl]butan-1-ol,
1-98: 2-amino-2-methyl-4-[5-(5-cyclohexylpentyl)thiophen-2-yl]butan-1-ol,
1-152: 2-amino-2-methyl-4-[5-(5-phenylpentyl)thiophen-2-yl]butan-1-ol,
1-400: 2-amino-2-methyl-4-[5-(4-cyclohexyloxybutyl)thiophen-2-yl]butan-1-ol,
1-463: 2-amino-2-methyl-4-{5-[4-(4-fluorophenoxy)butyl]thiophen-2-yl}butan-1-ol,
1-479: 2-amino-2-methyl-4-{5-[4-(4-methoxyphenoxy)butyl]thiophen-2-yl}butan-1-ol,
1-594: 2-amino-2-methyl-4-[5-(4-benzyloxybutyl)thiophen-2-yl]butan-1-ol,
1-743: 2-amino-2-methyl-4-[5-(4-cyclohexylbut-1-ynyl)thiophen-2-yl]butan-1-ol,
1-756: 2-amino-2-methyl-4-[5-(4-phenylbut-1-ynyl)thiophen-2-yl]butan-1-ol,
1-770: 2-amino-2-methyl-4-[5-(5-cyclohexylpent-1-ynyl)thiophen-2-yl]butan-1-ol,
1-824: 2-amino-2-methyl-4-[5-(5-phenylpent-1-ynyl)thiophen-2-yl]butan-1-ol,
1-833: 2-amino-2-methyl-4-{5-[5-(4-fluorophenyl)pent-1-ynyl]thiophen-2-yl}butan-1-ol,
1-849: 2-amino-2-methyl-4-{5-[5-(4-methoxyphenyl)pent-1-ynyl]thiophen-2-yl}butan-1-ol,
1-1050: 2-amino-2-methyl-4-{5-[3-(4-methylcyclohexyloxy)propynyl]thiophen-2-yl}butan-1-ol,
1-1063: 2-amino-2-methyl-4-{5-[3-(4-methylphenoxy)propynyl]thiophen-2-yl}butan-1-ol,
1-1064: 2-amino-2-methyl-4-{5-[3-(4-ethylphenoxy)propynyl]thiophen-2-yl}butan-1-ol,
1-1068: 2-amino-2-methyl-4-{5-[3-(4-methylthiophenoxy)propynyl]thiophen-2-yl}butan-1-ol,
1-1072: 2-amino-2-methyl-4-[5-(4-cyclohexyloxybut-1-ynyl)thiophen-2-yl]butan-1-ol,
1-1135: 2-amino-2-methyl-4-{5-[4-(4-fluorophenoxy)but-1-ynyl]thiophen-2-yl}butan-1-ol,
1-1139: 2-amino-2-methyl-4-{5-[4-(4-methylphenoxy)but-1-ynyl]thiophen-2-yl}butan-1-ol,
1-1185: 2-amino-2-methyl-4-[5-(3-cyclohexylmethoxypropynyl)thiophen-2-yl]butan-1-ol,
1-1266: 2-amino-2-methyl-4-[5-(4-phenylmethoxybut-1-ynyl)thiophen-2-yl]butan-1-ol,
1-1329: 2-amino-2-methyl-4-[5-(4-cyclohexylbutanoyl)thiophen-2-yl]butan-1-ol,
1-1330: 2-amino-2-methyl-4-[5-(4-phenylbutanoyl)thiophen-2-yl]butan-1-ol,
1-1331: 2-amino-2-methyl-4-[5-(5-cyclohexylpentanoyl)thiophen-2-yl]butan-1-ol,
1-1344: 2-amino-2-methyl-4-[5-(5-phenylpentanoyl)thiophen-2-yl]butan-1-ol,
1-1348: 2-amino-2-methyl-4-{5-[5-(4-fluorophenyl)pentanoyl]thiophen-2-yl}butan-1-ol,
1-1764: 2-amino-2-ethyl-4-[5-(5-cyclohexylpentyl)thiophen-2-yl]butan-1-ol,
1-1909: 2-amino-2-ethyl-4-[5-(5-cyclohexylpent-1-ynyl)thiophen-2-yl]butan-1-ol,
1-2097: 2-amino-2-ethyl-4-[5-(5-cyclohexylpentanoyl)thiophen-2-yl]butan-1-ol,
1-2273: 2-amino-2-methyl-4-{5-[3-(4-chlorophenoxy)propynyl]thiophen-2-yl}butan-1-ol,
1-2276: 2-amino-2-methyl-4-{5-[3-(3-methylphenoxy)propynyl]thiophen-2-yl}butan-1-ol,
1-2278: 2-amino-2-methyl-4-{5-[3-(3,4-dimethylphenoxy)propynyl]thiophen-2-yl}butan-1-ol,
1-2283: 2-amino-2-methyl-4-{5-[3-(3-methoxyphenoxy)propynyl]thiophen-2-yl}butan-1-ol,
1-2284: 2-amino-2-methyl-4-{5-[3-(3,4-dimethoxyphenyl)propynyl]thiophen-2-yl}butan-1-ol,
1-2285: 2-amino-2-methyl-4-{5-[3-(3,5-dimethoxyphenoxy)propynyl]thiophen-2-yl}butan-1-ol,
1-2287: 2-amino-2-methyl-4-{5-[3-(3-acetylphenoxy)propynyl)thiophen-2-yl}butan-1-ol, and
1-2288: 2-amino-2-methyl-4-{5-[3-(4-acetylphenoxy)propynyl]thiophen-2-yl}butan-1-ol.

TABLE 3

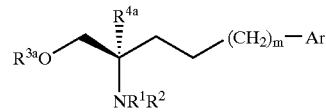

(La)

| Exemp. Compd. No. | $R^{4a}$ | $R^1$ | $R^2$ | $R^{3a}$ | Ar | m |
|---|---|---|---|---|---|---|
| 3-1 | Me | H | Boc | TBDMS | Ph | 0 |
| 3-2 | Me | H | Bz | TBDMS | Ph | 0 |
| 3-3 | Me | H | Ac | TBDMS | Ph | 0 |
| 3-4 | Me | H | Boc | H | 2-Fur | 0 |
| 3-5 | Me | H | Boc | H | 2-The | 0 |
| 3-6 | Me | H | Ac | H | 2-The | 0 |
| 3-7 | Me | H | Bz | H | 2-The | 0 |

TABLE 3-continued (La)

R³ᵃO—CH₂—C(R⁴ᵃ)(NR¹R²)—(CH₂)ₘ—Ar

| Exemp. Compd. No. | R⁴ᵃ | R¹ | R² | R³ᵃ | Ar | m |
|---|---|---|---|---|---|---|
| 3-8 | Me | H | Boc | H | 6-Bzt | 0 |
| 3-9 | Et | H | Boc | TBDMS | Ph | 0 |
| 3-10 | Et | H | Ac | H | 2-Fur | 0 |
| 3-11 | Et | H | Boc | H | 2-The | 0 |
| 3-12 | Et | H | Boc | H | 6-Bzt | 0 |
| 3-13 | Me | H | Ac | Ac | 2-The | 0 |
| 3-14 | Me | H | Ac | Ac | 2-Fur | 0 |
| 3-15 | Me | H | Ac | Ac | 2-Bzt | 0 |

TABLE 4

(La-1)

| Exemp. Compd. No. | R⁴ᵃ | Ar | m |
|---|---|---|---|
| 4-1 | Me | Ph | 0 |
| 4-2 | Me | 2-Fur | 0 |
| 4-3 | Me | 3-Fur | 0 |
| 4-4 | Me | 2-The | 0 |
| 4-5 | Me | 3-The | 0 |
| 4-6 | Me | 4-Br-2-The | 0 |
| 4-7 | Me | 4-Br-3-The | 0 |
| 4-8 | Me | 5-Br-2-The | 0 |
| 4-9 | Me | 5-Br-3-The | 0 |
| 4-10 | Me | 4-Cl-2-The | 0 |
| 4-11 | Me | 4-Cl-3-The | 0 |
| 4-12 | Me | 5-Cl-2-The | 0 |
| 4-13 | Me | 5-Cl-3-The | 0 |
| 4-14 | Me | 2-Pyr | 0 |
| 4-15 | Me | 3-Pyr | 0 |
| 4-16 | Me | 4-Pyr | 0 |
| 4-17 | Me | 6-Bzt | 0 |
| 4-18 | Me | Np(1) | 0 |
| 4-19 | Me | Np(2) | 0 |
| 4-20 | Me | 6-Bpyrr | 0 |
| 4-21 | Et | Ph | 0 |
| 4-22 | Et | 2-Fur | 0 |
| 4-23 | Et | 2-The | 0 |
| 4-24 | Et | 6-Bzt | 0 |
| 4-25 | Pr | Ph | 0 |
| 4-26 | Pr | 2-Fur | 0 |
| 4-27 | Et | 2-The | 0 |
| 4-28 | Et | 6-Bzt | 0 |
| 4-29 | Bu | Ph | 0 |
| 4-30 | Bu | 2-Fur | 0 |
| 4-31 | Et | 2-The | 0 |
| 4-32 | Et | 6-Bzt | 0 |

Preferred compounds in Table 3 and 4 are those of Exemplification compounds numbers 3-5, 3-6, 3-7, 3-8, 3-11, 3-12, 4-4, 4-5, 4-6, 4-7, 4-8, 4-9, 4-10, 4-11, 4-12, 4-13, 4-17, 4-23, 4-24, 4-27, 4-28, 4-31, and 4-32.

Most preferred compounds are those Exemplification compounds numbers:

4-4: 4-methyl-4-[(thiophen-3-yl)ethyl]oxazolidinone,
4-5: 4-methyl-4-[(thiophen-3-yl)ethyl]oxazolidinone,
4-8: 4-methyl-4-[(5-bromothiophen-3-yl)ethyl]oxazolidinone, and
4-9: 4-methyl-4-[(5-bromothiophen-3-yl)ethyl]oxazolidinone.

Compounds of formulae (I), (XLIVa), (XLIVb), (La) and (Lb) can be prepared according to the methods described below.

In method A, a compound (I) and a compound (Ic) (which is a compound (I) where $R^1$ is a hydrogen atom and $R^2$ is a lower alkoxycarbonyl group, an aralkyloxycarbonyl group or an aralkyloxycarbonyl group substituted by 1–3 substituents selected from the substituent group a) are synthesized.

Method A

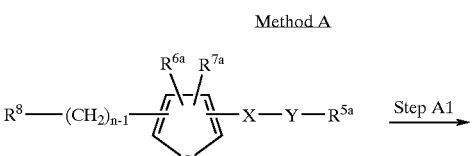

(II)

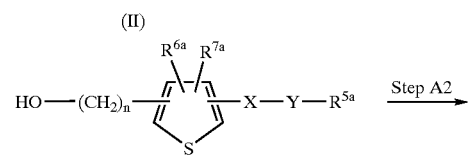

(III)

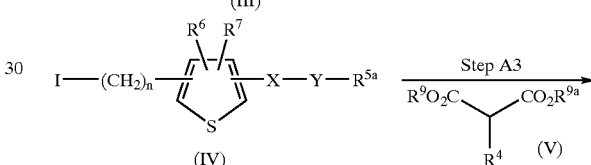

(IV)

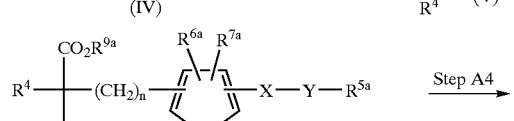

(VI)

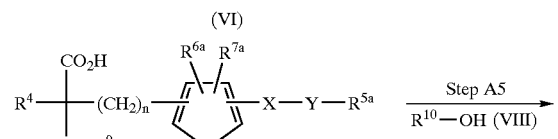

(VII)

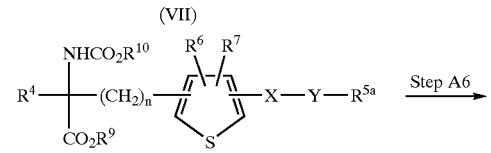

(IX)

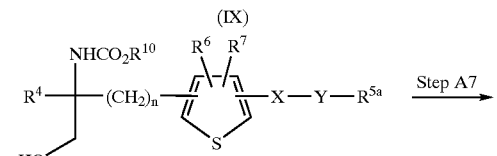

(X)

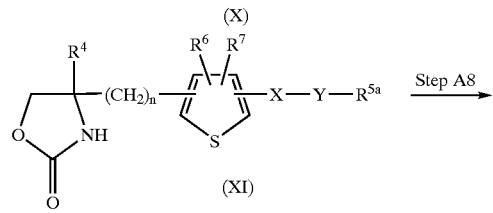

(XI)

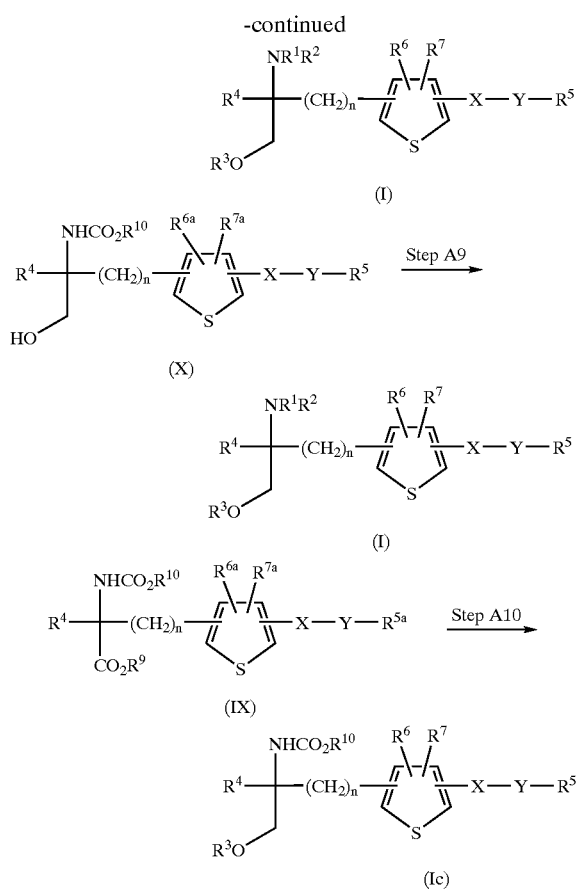

In the above scheme, $R^1$, $R^2$, $R^3$, $R^4$, $R^5$, $R^6$, $R^7$, X, Y and n are as defined earlier; $R^8$ is a formyl group, a carboxyl group or a lower alkoxycarbonyl group; $R^9$ and $R^{9a}$ are the same or different and each is independently a hydrogen atom or a lower alkyl group; $R^{10}$ is a lower alkyl group, an aralkyl group or an aralkyl group substituted by 1–3 substituents selected from the substituent group a; and $R^{5a}$, $R^{6a}$ and $R^{7a}$ are an amino group, a hydroxyl group and/or a carboxyl group, each of which is contained as the substituent in each definition of $R^5$, $R^6$ and $R^7$ and optionally protected by a suitable protecting group, in addition to the same groups as those defined earlier for $R^5$, $R^6$ and $R^7$.

In the above description, the "protecting group" of the "amino group optionally protected" in the definition of $R^{5a}$, $R^{6a}$ and $R^{7a}$ is not particularly limited provided that it is a protecting group of an amino group used in the field of the organic synthetic chemistry and is the same as that defined earlier. A lower alkoxycarbonyl group is preferred and a t-butoxycarbonyl group is most preferred.

In the above description, the "protecting group" of the "hydroxyl group optionally protected" in the definition of $R^{5a}$, $R^{6a}$ and $R^{7a}$ is not particularly limited provided that it is a protecting group of a hydroxyl group used in the field of the organic synthetic chemistry. This protecting group is, for example, the same as that defined earlier as the "common protecting group used for the protection of a hydroxyl group by esterification", and the preferable examples include a lower aliphatic acyl group, an aromatic acyl group, a lower alkoxycarbonyl group or a (lower alkoxy)methyl group, and more preferable examples are a lower aliphatic acyl group or a (lower alkoxycarbonyl)methyl group. The most preferable example is an acetyl group or a methoxymethyl group.

In the above description, the "protecting group" of the "carboxyl group optionally protected" in the definition of $R^{5a}$, $R^{6a}$ and $R^{7a}$ is not particularly limited provided that it is a protecting group of a carboxyl group used in the field of the organic synthetic chemistry. This protecting group is, for example, the same as that defined earlier as the "common protecting groups used for the protection of a carboxyl group by esterification", and the preferable examples include a lower alkyl group, and a methyl group is most preferable.

In Step A1, a compound of general formula (III) is prepared by the reaction of a compound of general formula (II) with a reducing agent in an inert solvent in the presence or absence of a base (preferably in the presence of a base).

The inert solvent used in the above-mentioned reaction is not particularly limited provided that it has no adverse effect on the reaction and dissolves the starting materials to some extent. Examples of suitable solvents include aliphatic hydrocarbons such as hexane, heptane, ligroin or petroleum ether; aromatic hydrocarbons such as benzene, toluene or xylene; halogenated hydrocarbons such as chloroform, methylene chloride, 1,2-dichloroethane or carbon tetrachloride; esters such as acetic acid, methyl acetate, ethyl acetate, propyl acetate, butyl acetate or diethyl carbonate; ethers such as diethyl ether, diisopropyl ether, tetrahydrofuran, dioxane, dimethoxyethane or di(ethylene glycol) dimethyl ether; alcohols such as methanol, ethanol, n-propanol, isopropanol, n-butanol, isobutanol, t-butanol, isoamyl alcohol, diethylene glycol, glycerol, octanol, cyclohexanol or methyl cellosolve; amides such as formamide, dimethylformamide, dimethylacetamide or hexamethylphosphoric triamide; water; or mixtures of water and solvents thereof or of solvents thereof. Of these solvents, ethers are preferred and tetrahydrofuran is most preferred.

The reducing agent used in the above-mentioned reaction is, for example, an alkali metal borohydride such as sodium borohydride, lithium borohydride or sodium cyanoborohydride; or an aluminium hydride derivative such as diisobutylaluminium hydride, lithium aluminium hydride or triethoxyaluminium lithium hydride. The preferred examples are alkali metal borohydrides, and sodium borohydride is most preferred.

The reaction temperature mainly depends on the starting material compounds, the reducing agent and the solvent employed in the reaction. The reaction is usually carried out at a temperature of from –50° C. to 100° C. (preferably from 0° C. to 50° C.).

The reaction time mainly depends on the starting material compounds, the reducing agent, the solvent and the reaction temperature employed in the reaction. The reaction is usually carried out in a period of from 15 minutes to 150 hours (preferably from 1 hour to 100 hours). After the completion of the reaction, the target compounds (III) of this reaction may be collected from the reaction mixture according to conventional methods. For example, the target compound can be obtained by conducting the following steps successively: appropriately neutralizing the reaction mixture; removing, if any, insoluble material(s) by filtration; adding an organic solvent which is not miscible with water (e.g. ethyl acetate); separating the organic layer containing the target compound; washing the extract with, for example, water and then drying over anhydrous magnesium sulfate, anhydrous sodium sulfate, anhydrous sodium bicarbonate or the like; and removing solvent by evaporation. The target compound can be isolated and purified, if necessary, by a suitable combination of the conventional methods commonly used for the separation/purification of organic compounds such as recrystallization, reprecipitation and chromatography using appropriate eluent(s).

In Step A2, a compound of general formula (IV) is prepared by converting a hydroxyl group in the compound of formula (III) into a leaving group in an inert solvent in the presence of a base and then by iodination reaction of the resulting leaving group with an iodination agent. The reagent used for the formation of the leaving group is, for example, a halogenation agent including sulfonyl halides such as methanesulfonyl chloride or p-toluenesulfonyl chloride; thionyl halides such as thionyl chloride, thionyl bromide or thionyl iodide; sulfuryl halides such as sulfuryl chloride, sulfuryl bromide or sulfuryl iodide; phosphorus trihalogenides such as phosphorus trichloride, phosphorus tribromide or phosphorus triiodide; phosphorus pentahalogenides such as phosphorus pentachloride, phosphorus pentabromide or phosphorus pentaiodide; phosphorus oxyhalogenides such as phosphorus oxychloride, phosphorus oxybromide or phosphorus oxyiodide; or rhenium reagents such as methyltrioxorhenium (VII). Of these reagents, sulfonyl halides are preferred.

Examples of bases which can be used in the conversion of the hydroxyl group into the leaving group include alkali metal carbonates such as lithium carbonate, sodium carbonate or potassium carbonate; alkali metal bicarbonates such as lithium bicarbonate, sodium bicarbonate or potassium bicarbonate; alkali metal hydrides such as lithium hydride, sodium hydride or potassium hydride; alkali metal hydroxides such as lithium hydroxide, sodium hydroxide or potassium hydroxide; alkali metal alkoxides such as lithium methoxide, sodium methoxide, sodium ethoxide or potassium t-butoxide; and organic amines such as triethylamine, tributylamine, diisopropylethylamine, N-methylmorpholine, pyridirie, 4-(N,N-dimethylamino)pyridine, N,N-dimethylaniline, N,N-diethylaniline, 1,5-diazabicyclo[4.3.0]nona-5-ene, 1,4-diazabicyclo[2.2.2]-octane (DABCO) or 1,8-diazabicyclo[5.4.0]undec-7-ene (DBU). The organic amines (particularly triethylamine) are preferable.

The inert solvent which can be used in the conversion of the hydroxyl group into the leaving group is not particularly limited provided that it has no adverse effect on the reaction. Examples of suitable solvents include aliphatic hydrocarbons such as hexane, heptane, ligroin or petroleum ether; aromatic hydrocarbons such as benzene, toluene or xylene; halogenated hydrocarbons such as chloroform, methylene chloride, 1,2-dichloroethane or carbon tetrachloride; ethers such as diethyl ether, diisopropyl ether, tetrahydrofuran, dioxane, dimethoxyethane or di(ethylene glycol) dimethyl ether; ketones such as acetone or 2-butanone; amides such as formamide, dimethylformamide, dimethylacetamide or hexamethylphosphoric triamide; sulfoxides such as dimethyl sulfoxide; or sulfolane. Of these solvents, halogenated hydrocarbons are preferred and methylene chloride is most preferred.

The reaction temperature-in the case of the conversion of the hydroxyl group into the leaving group mainly depends on the starting material compounds, the reagent and the solvent employed in the reaction. The reaction is usually carried out at a temperature of from −50° C. to 200° C. (preferably from −10° C. to 150° C.).

The reaction time in the case of the conversion of the hydroxyl group into the leaving group mainly depends on the starting material compounds, the reagent, the solvent and the reaction temperature employed in the reaction. The reaction is usually carried out in a period of from 15 minutes to 24 hours (preferably from 30 minutes to 12 hours).

The iodination agent that can be used in the above-mentioned reaction is, for example, phosphorus pentaiodide, phosphorus oxyiodide, sodium iodide or potassium iodide, and sodium iodide is preferred.

The reaction temperature in the case of the iodination of the leaving group mainly depends on the starting material compounds, the reagent and the solvent employed in the reaction. The reaction is usually carried out at a temperature of from 0° C. to 200° C. (preferably from 10° C. to 150° C.).

The reaction time in the case of the iodination of the leaving group mainly depends on the starting material compounds, the reagent, the solvent and the reaction temperature employed in the reaction. The reaction is usually carried out in a period of from 15 minutes to 24 hrs (preferably from 30 minutes to 12 hours).

After the completion of the reaction, the target compounds (IV) of this reaction may be collected from the reaction mixture according to conventional methods. For example, the target compound can be obtained by conducting the following steps successively: appropriately neutralizing the reaction mixture; removing, if any, insoluble material(s) by filtration; adding an organic solvent which is not miscible with water (e.g. ethyl acetate); separating the organic layer containing the target compound; washing the extract with, for example, water and then drying over anhydrous magnesium sulfate, anhydrous sodium sulfate, anhydrous sodium bicarbonate or the like; and removing solvent by evaporation. The target compound can be isolated and purified, if necessary, by a suitable combination of the conventional methods commonly used for the separation/purification of organic compounds such as recrystallization, reprecipitation and chromatography using appropriate eluent(s).

In Step A3, a compound of general formula (VI) is prepared by the reaction of a compound (IV) with a compound of general formula (V) in an inert solvent in the presence of a base.

The inert solvent used in the above-mentioned reaction is not particularly limited provided that it has no adverse effect on the reaction. Examples of suitable solvents include ethers such as diethyl ether, diisopropyl ether, tetrahydrofuran, dioxane, dimethoxyethane or di(ethylene glycol) dimethyl ether; alcohols such as methanol, ethanol, n-propanol, isopropanol, n-butanol, isobutanol, t-butanol, isoamyl alcohol, diethylene glycol, glycerol, octanol, glycol) dimethyl ether; alcohols such as methanol, ethanol, n-propanol, isopropanol, n-butanol, isobutanol, t-butanol, isoamyl alcohol, diethylene glycol, glycerol, octanol, solvents thereof or of solvents thereof. Of these solvents, alcohols or amides are preferred and dimethylformamide is most preferred.

The base used in the above-mentioned reaction is, for example, the same as that used for the conversion of the hydroxyl group into the leaving group described in Step A2 of the method A, and alkali metal hydrides or alkali metal alkoxides (most preferably sodium hydride) are preferred.

The reaction temperature mainly depends on the starting material compounds, the base and the solvent employed in the reaction. The reaction is usually carried out at a temperature of from −78° C. to 100° C. (preferably from 0° C. to 50° C.).

The reaction time mainly depends on the starting material compounds, the base, the solvent and the reaction temperature employed in the reaction. The reaction is usually carried out in a period of from 15 minutes to 48 hours (preferably from 30 minutes to 12 hours). After the completion of the reaction, the target compounds (VI) of this reaction may be collected from the reaction mixture according to conventional methods. For example, the target compound can be obtained by conducting the following steps successively: appropriately neutralizing the reaction mixture; removing, if any, insoluble material(s) by filtration; adding an organic solvent which is not miscible with water (e.g. ethyl acetate);

separating the organic layer containing the target compound; washing the extract with, for example, water and then drying over anhydrous magnesium sulfate, anhydrous sodium sulfate, anhydrous sodium bicarbonate or the like; and removing solvent by evaporation. The target compound can be isolated and purified, if necessary, by a suitable combination of the conventional methods commonly used for the separation/purification of organic compounds such as recrystallization, reprecipitation and chromatography using appropriate eluent(s).

In Step A4, a compound of general formula (VII) is prepared by converting an ester group of a compound (VI) into a carboxyl group by a hydrolysis reaction with a base.

The inert solvent used in the above-mentioned reaction is not particularly limited provided that it has no adverse effect on the reaction. Examples of suitable solvents include aliphatic hydrocarbons such as hexane, heptane, ligroin or petroleum ether; aromatic hydrocarbons such as benzene, toluene or xylene; ethers such as diethyl ether, diisopropyl ether, tetrahydrofuran, dioxane, dimethoxyethane or di(ethylene glycol) dimethyl ether; alcohols such as methanol, ethanol, n-propanol, isopropanol, n-butanol, isobutanol, t-butanol, isoamyl alcohol, diethylene glycol, glycerol, octanol, cyclohexanol or methyl cellosolve; water; or mixtures of water and solvents thereof or of solvents thereof. Of these solvents, alcohols (particularly ethanol) are preferred.

The base used in the above-mentioned reaction is, for example, the same as that used for the conversion of a hydroxyl group into a leaving group described in Step A2 of the method A, and alkali metal hydroxides (most preferably potassium hydroxide) are preferred.

The reaction temperature mainly depends on the starting material compounds, the base and the solvent employed in the reaction. The reaction is usually carried out at a temperature of from −20° C. to 200° C. (preferably from 0° C. to 50° C.).

The reaction time mainly depends on the starting material compounds, the base, the solvent and the reaction temperature employed in the reaction. The reaction is usually carried out in a period of from 30 minutes to 120 hours (preferably from 1 hour to 80 hours). After the completion of the reaction, the compound (VII) prepared as the target compound in this reaction may be collected from the reaction mixture according to a conventional method. For example, the target compound can be obtained by conducting the following steps successively: appropriately neutralizing the reaction mixture; removing, if any, insoluble material(s) by filtration; adding an organic solvent which is not miscible with water (e.g. ethyl acetate); separating the organic layer containing the target compound; washing the extract with, for example, water and then drying over anhydrous magnesium sulfate, anhydrous sodium sulfate, anhydrous sodium bicarbonate or the like; and removing solvent by evaporation. The target compound can be isolated and purified, if necessary, by a suitable combination of the conventional methods commonly used for the separation/purification of organic compounds such as recrystallization, reprecipitation and chromatography using appropriate eluent(s).

Step A5 is a step for converting a carboxyl group into a carbamoyl group by the Curtius Rearrangement Reaction, and in this step, a compound of general formula (IX) is synthesized by the reaction of a compound (VII) with a diarylphosphoryl azide derivative such as diphenylphosphoryl azide in an inert solvent in the presence of a base and then by heating the resulting product with a compound of general formula (VIII).

The inert solvent used in the above-mentioned reaction is not particularly limited provided that it has no adverse effect on the reaction. Examples of suitable solvents include aliphatic hydrocarbons such as hexane, heptane, ligroin or petroleum ether; aromatic hydrocarbons such as benzene, toluene or xylene; halogenated hydrocarbons such as chloroform, methylene chloride, 1,2-dichloroethane or carbon tetrachloride; ethers such as diethyl ether, diisopropyl ether, tetrahydrofuran, dioxane, dimethoxyethane or di(ethylene glycol) dimethyl ether; water; or mixtures of water and solvents thereof or of solvents thereof. Of these solvents, aromatic hydrocarbons (particularly benzene) are preferred.

The base used in the above-mentioned reaction is, for example, the same as that used for the conversion of a hydroxyl group into a leaving group described in Step A2 of the method A, and organic amines (most preferably triethylamine) are preferred.

The reaction temperature for the reactions of the compound (VII) with diarylphophoryl azide derivative and of the resulting product with the compound (VIII) mainly depends on the starting material compounds, the base and the solvent employed in the reaction. The reaction is usually carried out at a temperature of from 0° C. to 200° C. (preferably from 20° C. to 150° C.). The reaction time for the reactions of the compound (VII) with diarylphophoryl azide derivative and of the resulting product with the compound (VIII) mainly depends on the starting material compounds, the base, the solvent and the reaction temperature employed in the reaction. The reaction is usually carried out in the period of from 15 minutes to 24 hours (preferably from 30 minutes to 12 hours).

In addition, even in the case where a compound (VIII) which is difficult to react directly with a diarylphophoryl azide derivative is used, the carboxyl group of the compound (VII) can be converted into the carbamoyl group without any problem by the reaction mentioned above. After the completion of the reaction, the compound (IX) prepared as the target compound in this reaction may be collected from the reaction mixture according to a conventional method. For example, the target compound can be obtained by conducting the following steps successively: appropriately neutralizing the reaction mixture; removing, if any, insoluble material(s) by filtration; adding an organic solvent which is not miscible with water (e.g. ethyl acetate); separating the organic layer containing the target compound; washing the extract with, for example, water and then drying over anhydrous magnesium sulfate, anhydrous sodium sulfate, anhydrous sodium bicarbonate or the like; and removing solvent by evaporation. The target compound can be isolated and purified, if necessary, by a suitable combination of the conventional methods commonly used for the separation/ purification of organic compounds such as recrystallization, reprecipitation and chromatography using appropriate eluent(s).

In Step A6, a compound of general formula (X) is prepared by reducing an ester group of a compound (IX) with a reducing agent in an inert solvent.

The inert solvent used in the above-mentioned reaction is not particularly limited provided that it has no adverse effect on the reaction. Examples of suitable solvents include aliphatic hydrocarbons such as hexane, heptane, ligroin or petroleum ether; aromatic hydrocarbons such as benzene, toluene or xylene; halogenated hydrocarbons such as chloroform, methylene chloride, 1,2-dichloroethane or carbon tetrachloride; ethers such as diethyl ether, diisopropyl ether, tetrahydrofuran, dioxane, dimethoxyethane or di(ethylene glycol) dimethyl ether; alcohols such as methanol, ethanol, n-propanol, isopropanol, n-butanol, isobutanol, t-butanol, isoamyl alcohol, diethylene glycol, glycerol, octanol, cyclohexanol or methyl cellosolve; or mixtures of solvents thereof. Of these solvents, mixtures of alcohols and ethers (particularly a mixture of ethanol and tetrahydrofuran) are preferred.

The reducing agent used in the above-mentioned reaction is, for example, the same as that used in Step A1 of the method A, and alkali metal borohydrides (most preferably sodium borohydride or lithium borohydride) are preferred.

The reaction temperature mainly depends on the starting material compounds and the solvent employed in the reaction. The reaction is usually carried out at a temperature of from −78° C. to 150° C. (preferably from −20° C. to 50° C.).

The reaction time mainly depends on the starting material compounds, the solvent and the reaction temperature employed in the reaction. The reaction is usually carried out in a period of from 5 minutes to 48 hours (preferably from 30 minutes to 24 hours).

After the completion of the reaction, the compound (X) prepared as the target compound in this reaction may be collected from the reaction mixture according to a conventional method. For example, the target compound can be obtained by conducting following the steps successively: appropriately neutralizing the reaction mixture; removing, if any, insoluble material(s) by filtration; adding an organic solvent which is not miscible with water (e.g. ethyl acetate); separating the organic layer containing the target compound; washing the extract with, for example, water and then drying over anhydrous magnesium sulfate, anhydrous sodium sulfate, anhydrous sodium bicarbonate or the like; and removing solvent by evaporation. The target compound can be isolated and purified, if necessary, by a suitable combination of the conventional methods commonly used for the separation/purification of organic compounds such as recrystallization, reprecipitation and chromatography using appropriate eluent(s).

In Step A7, a compound of general formula (XI) having an oxazolidine ring is prepared by the reaction of a compound (X) with a base.

The inert solvent used in the above-mentioned reaction is not particularly limited provided that it has no adverse effect on the reaction. Examples of suitable solvents include ethers such as diethyl ether, diisopropyl ether, tetrahydrofuran, dioxane, dimethoxyethane or di(ethylene glycol) dimethyl ether; alcohols such as methanol, ethanol, n-propanol, isopropanol, n-butanol, isobutanol, t-butanol, isoamyl alcohol, diethylene glycol, glycerol, octanol, glycol) dimethyl ether; alcohols such as methanol, ethanol, n-propanol, isopropanol, n-butanol, isobutanol, t-butanol, isoamyl alcohol, diethylene glycol, glycerol, octanol, solvents thereof or of solvents thereof. Of these solvents, alcohols or amides (particularly dimethylformamide) are preferred.

The base used in the above-mentioned reaction is, for example, the same as that used for the conversion of the hydroxyl group into the leaving group described in Step A2 of the method A, and alkali metal alkoxides (most preferably potassium t-butoxide) are preferred.

The reaction temperature mainly depends on the starting material compounds, the base and the solvent employed in the reaction. The reaction is usually carried out at a temperature of from −78° C. to 100° C. (preferably from −50° C. to 50° C.).

The reaction time mainly depends on the starting material compounds, the base, the solvent and the reaction temperature employed in the reaction. The reaction is usually carried out in a period of from 15 minutes to 48 hours (preferably from 30 minutes to 12 hours). After the completion of the reaction, the compound (XI) prepared as the target compound in this reaction may be collected from the reaction mixture according to a conventional method. For example, the target compound can be obtained by conducting the following steps successively: appropriately neutralizing the reaction mixture; removing, if any, insoluble material(s) by filtration; adding an organic solvent which is not miscible with water (e.g. ethyl acetate); separating the organic layer containing the target compound; washing the extract with, for example, water and then drying over anhydrous magnesium sulfate, anhydrous sodium sulfate, anhydrous sodium bicarbonate or the like; and removing solvent by evaporation. The target compound can be isolated and purified, if necessary, by a suitable combination of conventional methods commonly used for the separation/purification of organic compounds such as recrystallization, reprecipitation and chromatography using appropriate eluent(s).

In Step A8, a compound of general formula (I) is prepared by hydrolyzing a compound (XI) with a base in an inert solvent and then, if necessary, by conducting successively the removal of an amino-, a hydroxyl- and/or a carboxyl-protecting group in $R^1$, $R^2$, $R^3$, $R^{5a}$, $R^{6a}$ and $R^{7a}$, and the protection of an amino group in $R^1$ and/or $R^2$, and/or a protection of a hydroxyl group in $R^3$.

The inert solvent used in the reaction of the compound (XI) with the base is not particularly limited provided that it has no adverse effect on the reaction. Examples of suitable solvents include aliphatic hydrocarbons such as hexane, heptane, ligroin or petroleum ether; aromatic hydrocarbons such as benzene, toluene or xylene; halogenated hydrocarbons such as chloroform, methylene chloride, 1,2-dichloroethane or carbon tetrachloride; ethers such as diethyl ether, diisopropyl ether, tetrahydrofuran, dioxane, dimethoxyethane or di(ethylene glycol) dimethyl ether; alcohols such as methanol, ethanol, n-propanol, isopropanol, n-butanol, isobutanol, t-butanol, isoamyl alcohol, di ethylene glycol, glycerol, octanol, glycol) dimethyl ether; alcohols such as methanol, ethanol, n-propanol, isopropanol, n-butanol, isobutanol, t-butanol, isoamyl alcohol, di ethylene glycol, glycerol, octanol, preferred.

The base used in the reaction of the compound (XI) with the base is, for example, the same as that used for the conversion of a hydroxyl group into a leaving group described in Step A2 of the method A, and alkali metal hydroxides (most preferably potassium hydroxide) are preferred.

The reaction temperature mainly depends on the starting material compounds, the base and the solvent employed in the reaction. The reaction is usually carried out at a temperature of from −20° C. to 200° C. (preferably from 0° C. to 100° C.).

The reaction time mainly depends on the starting material compounds, the base, the solvent and the reaction temperature employed in the reaction. The reaction is usually carried out in a period of from 30 minutes to 48 hours (preferably from 1 hour to 24 hours).

The procedures for removing the amino- and the hydroxyl-protecting groups depend on the nature of the protecting group used, but the removal of the protecting group is generally carried out according to the known procedures commonly used in organic synthetic chemistry. This deprotection reaction is, for example, performed by the procedures described in the literature (T. W. Green: Protective Groups in Organic Synthesis, John Wiley & Sons, and J. F. W. McOmis: Protective Groups in Organic Chemistry, Plenum Press) as described below.

Where the amino-protecting group is a silyl group, the deprotection reaction is usually carried out by treating with a compound from which a fluorine anion is generated, such as tetrabutylammonium fluoride, hydrofluoric acid, hydrofluoric acid-pyridine or potassium fluoride.

The solvent used in the above-mentioned reaction is not particularly limited provided that it has no adverse effect on the reaction. Examples of preferable solvents include ethers such as diethyl ether, diisopropyl ether, tetrahydrofuran, dioxane, dimethoxyethane or di(ethylene glycol) dimethyl ether.

The reaction temperature and reaction time are not particularly limited. The deprotection reaction is usually carried out at a temperature of from 0° C. to 50° C. in a period of from 10 minutes to 18 hours.

Where the amino-protecting group is either an aliphatic acyl group, an aromatic acyl group, reaction is usually carried out at a temperature of from 0 ° C. to 50° C. in a period of from 10 reaction is usually carried out at a temperature of from 0 ° C. to 50° C. in a period of from 10 aqueous solvent.

The acid used in the above-mentioned reaction is not particularly limited provided that it is usually used as an acid and has no adverse effect on the reaction. Examples of suitable acids include inorganic acids such as hydrobromic acid, hydrochloric acid, sulfuric acid, perchloric acid or phosphoric acid, and hydrochloric acid is preferable.

The base that can be used in the above-described reaction is not particularly limited provided that it has no adverse effect on the structural moieties other than the protecting group. Examples of preferred bases include alkali metal carbonates such as lithium carbonate, sodium carbonate or potassium carbonate; alkali metal hydroxides such as lithium hydroxide, sodium hydroxide or potassium hydroxide; alkali metal alkoxides such as lithium methoxide, sodium methoxide, sodium ethoxide or potassium t-butoxide; or ammonia solutions such as ammonia solution or concentrated methanolic ammonia solution.

The solvent used in the above-mentioned reaction is not particularly limited provided that it is usually used in hydrolysis reactions. Examples of suitable solvents include alcohols such as methanol, ethanol, n-propanol, isopropanol, n-butanol, isobutanol, t-butanol, isoamyl alcohol, diethylene glycol, glycerol, octanol, cyclohexanol or methyl cellosolve; ethers such as diethyl ether, diisopropyl ether, tetrahydrofuran, dioxane, dimethoxyethane or di(ethylene glycol) dimethyl ether; water; or mixtures of water and one or more organic solvents thereof. Ethers (particularly dioxane) are preferable.

The reaction temperature and reaction time mainly depend on the starting material compounds, the solvent and the acid or base employed in the reaction but are not particularly limited. The deprotection reaction is usually carried out at a temperature of from 0° C. to 150° C. in a period of from 1 to 10 hours in order to lower the occurrence of the side reactions.

Where the amino-protecting group is an aralkyl group or an aralkyloxycarbonyl group, the protecting group is usually and preferably removed by treating with a reducing agent in an inert solvent (preferably by catalytic hydrogenation with a catalyst at room temperature) or treating with an oxidizing agent.

The solvent used in the deprotection reaction by the catalytic hydrogenation is not particularly limited provided that it has no adverse effect on the reaction. Examples of suitable solvents include aliphatic hydrocarbons such as hexane, heptane, ligroin or petroleum ether; aromatic hydrocarbons such as toluene, benzene or xylene; esters such as methyl acetate, ethyl acetate, propyl acetate, butyl acetate or diethyl carbonate; ethers such as diethyl ether, diisopropyl ether, tetrahydrofuran, dioxane, dimethoxyethane or di(ethylene glycol) dimethyl ether; alcohols such as methanol, ethanol, n-propanol, isopropanol, n-butanol, isobutanol, t-butanol, isoamyl alcohol, diethylene glycol, glycerol, octanol, cyclohexanol or methyl cellosolve; organic acids such as acetic acid; water; or mixtures of water and one or more organic solvents thereof. Of these solvents, alcohols, ethers, organic acids or water are preferred, and alcohols or organic acids are particularly preferred.

The catalyst used in the deprotection reaction by catalytic hydrogenation is not particularly limited provided that it is usually used in catalytic hydrogenation. Examples of preferable catalysts used in catalytic hydrogenation include palladium-on-charcoal, Raney nickel, platinum oxide, platinum black, rhodium-aluminium oxide, triphenylphosphine-rhodium chloride and palladium-barium sulfate.

The pressure in catalytic hydrogenation is not particularly limited, but the deprotection by catalytic hydrogenation is usually carried out at a pressure of from 1 to 10 atmospheric pressure.

The reaction temperature and reaction time mainly depend on the starting material compounds, the catalyst and the solvent employed in the reaction. The deprotection reaction is usually carried out at a temperature of from 0° C. to 100° C. in a period of from 5 minutes to 24 hours.

The solvent used in the deprotection by oxidation reaction is not particularly limited provided that it has no adverse effect on the reaction. This reaction is preferably carried out in an organic solvent containing water.

Examples of the preferable organic solvent used in this reaction include halogenated hydrocarbons such as chloroform, methylene chloride, 1,2-dichloroethane or carbon tetrachloride; nitriles such as acetonitrile; ethers such as diethyl ether, diisopropyl ether, tetrahydrofuran, dioxane, dimethoxyethane or di(ethylene glycol) dimethyl ether; ketones such as acetone; amides such as formamide, dimethylformamide, dimethylacetamide or hexamethylphosphoric triamide; sulfoxides such as dimethyl sulfoxide; or sulfolane. Halogenated hydrocarbons, ethers or sulfoxides (particularly halogenated hydrocarbons or sulfoxides) are preferable.

The oxidizing agent used in this reaction is not particularly limited provided that it is usually used for oxidation reactions. Examples of the preferable oxidizing agents used in this reaction include potassium persulfate, sodium persulfate, ammonium cerium nitrate (CAN) and 2,3-dichloro-5,6-dicyano-p-benzoquinone (DDQ).

The reaction temperature and reaction time mainly depend on the starting material compounds, the catalyst and the soluvent employed in the reaction. The deprotection reaction is usually carried out at a temperature of from 0° C. to 150° C. in a period of from 10 minutes to 24 hours.

Alternatively, where the amino-protecting group is an aralkyl group, the protecting group may be removed using an acid.

The acid used in the above-mentioned reaction is not particularly limited provided that it is usually used as the acid catalyst in common reactions. Examples of a suitable acid include Brönsted acids including inorganic acids such as hydrochloric acid, hydrobromic acid, sulfuric acid, perchloric acid or phosphoric acid; or organic acids such as acetic acid, formic acid, oxalic acid, methanesulfonic acid, p-toluenesulfonic acid, camphorsulfonic acid, trifluoroacetic acid or trifluoromethanesulfonic acid; Lewis acids such as zinc chloride, tin tetrachloride, boron trichloride, boron trifluoride or boron tribromide; and acidic ion-exchange resins. Inorganic and organic acids (most preferably hydrochloric acid, acetic acid or trifluoroacetic acid) are preferable.

The inert solvent used in the first stage of the above-mentioned reaction is not particularly limited provided that it has no adverse effect on the reaction. Examples of suitable solvents include aliphatic hydrocarbons such as hexane, heptane, ligroin or petroleum ether; aromatic hydrocarbons such as benzene, toluene or xylene; halogenated hydrocarbons such as chloroform, methylene chloride, 1,2-dichloroethane or carbon tetrachloride; esters such as methyl acetate, ethyl acetate, propyl acetate, butyl acetate or diethyl carbonate; ethers such as diethyl ether, diisopropyl ether, tetrahydrofuran, dioxane, dimethoxyethane or di(ethylene glycol) dimethyl ether; alcohols such as methanol, ethanol, n-propanol, isopropanol, n-butanol, isobutanol, t-butanol, isoamyl alcohol, diethylene glycol, glycerol, octanol, glycol) dimethyl ether; alcohols such as methanol, ethanol, n-propanol, isopropanol, n-butanol, isobutanol, t-butanol, isoamyl alcohol, diethylene glycol, glycerol, octanol, solvents thereof or of solvents thereof. Of these solvents, ethers, alcohols or water (most preferably dioxane, tetrahydrofuran, ethanol or water) are preferred.

The reaction temperature mainly depends on the starting material compounds, the acid and the solvent employed in the reaction. The reaction is usually carried out at a temperature of from −20° C. to the boiling point of the solvent used (preferably from 0° C. to 100° C.).

The reaction time mainly depends on the starting material compounds, the acid, the solvent and the reaction temperature employed in the reaction. The reaction is usually carried out in a period of from 15 minutes to 48 hours (preferably from 30 minutes to 20 hours).

Where the amino-protecting group is an alkenyloxycarbonyl group, the deprotection reaction is usually carried out by treating with a base under the same reaction conditions as that described for the deprotection of the amino group protected with an aliphatic acyl group, an aromatic acyl group, an alkoxycarbonyl group or a substituted methylene group which forms a Schiff base.

Where the amino-protecting group is an allyoxycarbonyl group, however, the deprotection is commonly carried out by catalytic hydrogenation using a palladium, triphenylphosphine or nickel tetracarbonyl derivative, since this deprotection procedure is simple and the occurrence of side reactions is low.

Where the hydroxyl-protecting group is a silyl group, the protecting group is usually removed by treating with a compound from which a fluorine anion is generated, such as tetrabutylammonium fluoride, hydrofluoric acid, hydrofluoric acid-pyridine and potassium fluoride or by treating with an inorganic acid such as hydrochloric acid, hydrobromic acid, sulfuric acid, perchloric acid or phosphoric acid; or an organic acid such as acetic acid, formic acid, oxalic acid, methanesulfonic acid, p-toluenesulfonic acid, camphorsulfonic acid, trifluoroacetic acid or trifluoromethanesulfonic acid.

In some cases of the removal of the protecting group by a fluorine anion, the reaction is accelerated by the addition of an organic acid such as formic acid, acetic acid or propionic acid.

The inert solvent used in the above-mentioned reaction is not particularly limited provided that it has no adverse effect on the reaction. Examples of preferable solvents include ethers such as diethyl ether, diisopropyl ether, tetrahydrofuran, dioxane, dimethoxyethane or di(ethylene glycol) dimethyl ether; nitriles such as acetonitrile or isobutyronitrile; organic acids such as acetic acid; water; or mixtures of solvents thereof.

The reaction temperature and reaction time mainly depend on the starting material compound, the catalyst and the solvent employed in the reaction. The reaction is usually carried out at a temperature of from 0° C. to 100° C. (preferably from 10° C. to 50° C.) in a period of from 1 to 24 hours.

Where the hydroxyl-protecting group is an aralkyl group or an aralkyloxycarbonyl group, the protecting group is usually and preferably removed by treating with a reducing agent (preferably by catalytic hydrogenatin with a catalyst at room temperature) in an inert solvent or by treating with an oxidizing agent.

The solvent used in the deprotection reaction by catalytic hydrogenation is not particularly limited provided that it has no adverse effect on the reaction. Examples of suitable solvents include aliphatic hydrocarbons such as hexane, heptane, ligroin or petroleum ether; aromatic hydrocarbons such as toluene, benzene or xylene; esters such as ethyl acetate or propyl acetate; ethers such as diethyl ether, diisopropyl ether, tetrahydrofuran, dioxane, dimethoxyethane or di(ethylene glycol) dimethyl ether; alcohols such as methanol, ethanol, n-propanol, isopropanol, n-butanol, isobutanol, t-butanol, isoamyl alcohol, diethylene glycol, dimethoxyethane or di(ethylene glycol) dimethyl ether; alcohols such as methanol, ethanol, n-propanol, isopropanol, n-butanol, isobutanol, t-butanol, isoamyl alcohol, diethylene glycol, triamide; aliphatic acids such as formic acid or acetic acid; water; or mixtures of solvents thereof. Of these solvents, alcohols (particularly methanol) are preferred.

The catalyst used in the deprotection reaction by catalytic hydrogenation is not particularly limited provided that it is usually used in catalytic hydrogenation. Examples of suitable catalysts used in the catalytic hydrogenation include palladium-on-charcoal, palladium black, Raney nickel, platinum oxide, platinum black, rhodium-aluminium oxide, triphenylphosphine-rhodium chloride and palladium-barium sulfate, and palladium-on-charcoal is preferred.

The pressure in the catalytic hydrogenation is not particularly limited, but the deprotection by catalytic hydrogenation is usually carried out at a pressure of from 1 to 10 atmospheric pressure.

The reaction temperature and reaction time mainly depend on the starting material compound, the catalyst and the solvent employed in the reaction. The deprotection reaction is usually carried out at a temperature of from 0° C. to 100° C. in a period of from 5 minutes to 48 hours, and preferably carried out at a temperature of from 20° C. to 70° C. in a period of from 1 to 24 hours.

The solvent used in the deprotection by oxidation reaction is not particularly limited provided that it has no adverse effect on the reaction. This reaction is preferably carried out in an organic solvent containing water.

Examples of the preferable organic solvent used in this reaction include ketones such as acetone; halogenated hydrocarbons such as methylene chloride, chloroform or carbon tetrachloride; nitriles such as acetonitrile; ethers such as diethyl ether, tetrahydrofuran or dioxane; amides such as dimethylformamide, dimethylacetamide or hexamethylphosphoric triamide; or sulfoxides such as dimethyl sulfoxide.

The oxidizing agent used in this reaction is not particularly limited provided that it is usually used for oxidation reactions. Examples of the preferable oxidizing agents used in this reaction include potassium persulfate, sodium persulfate, ammonium cerium nitrate (CAN) and 2,3-dichloro-5,6-dicyano-p-benzoquinone (DDQ).

The reaction temperature and reaction time mainly depend on the starting material compound, the catalyst and the solvent employed in the reaction. The deprotection reaction is usually carried out at a temperature of from 0° C. to 150° C. in a period of from 10 minutes to 24 hours. Alternatively, the protecting group can also be removed by treating with alkali metals such as metallic lithium or metallic sodium at a temperature of from −78° C. to 0° C. in liquid ammonia. or alcohol such as methanol, ethanol, n-propanol, isopropanol, n-butanol, isobutanol, t-butanol, isoamyl alcohol, diethylene glycol, glycerol, octanol, cyclohexanol or methyl cellosolve.

Additionally, the protecting group can also be removed by treating with aluminium chloride-sodium iodide or an alkylsilyl halide such as trimethylsilyl iodide in a solvent.

The solvent used in the deprotection reaction is not particularly limited provided that it has no adverse effect on the reaction. Examples of the preferable solvents used in this reaction include halogenated hydrocarbons such as methylene chloride, chloroform or carbon tetrachloride; nitriles such as acetonitrile; or mixtures of solvents thereof.

The reaction temperature and reaction time mainly depend on the starting material compound and the solvent employed in the reaction. The deprotection reaction is usually carried out at a temperature of from 0° C. to 50° C. in a period of from 5 minutes to 72 hours.

Where a sulfur atom is contained in a compound subjected to the deprotection reaction, aluminium chloride-sodium iodide is preferably used.

Where the hydroxyl-protecting group is an aliphatic acyl group, an aromatic acyl group or an alkoxycarbonyl group, the protecting group is removed by treating with a base in a solvent. The base that can be used in the above-described reaction is not particularly limited provided that it has no adverse effect on the structural moieties other than the protection group. Examples of preferable bases include alkali metal carbonates such as lithium carbonate, sodium carbonate or potassium carbonate; alkali metal bicarbonates such as lithium bicarbonate, sodium bicarbonate or potassium bicarbonate; alkali metal hydroxides such as lithium hydroxide, sodium hydroxide or potassium hydroxide; alkali metal alkoxides such as lithium methoxide, sodium methoxide, sodium ethoxide or potassium t-butoxide; or ammonia solutions such as ammonia solution or concentrated methanolic ammonia solution. Alkali metal hydroxides, alkali metal alkoxides or ammonia solutions are preferred, and alkali metal hydroxides and alkali metal alkoxides are particularly preferred.

The solvent used in the above-mentioned reaction is not particularly limited provided that it is usually used in hydrolysis reactions. Examples of preferable solvents include ethers such as diethyl ether, diisopropyl ether, tetrahydrofuran, dioxane, dimethoxyethane or di(ethylene glycol) dimethyl ether; alcohols such as methanol, ethanol, n-propanol, isopropanol, n-butanol, isobutanol, t-butanol, isoamyl alcohol, diethylene glycol, glycerol, octanol, cyclohexanol or methyl cellosolve; water; or mixtures of solvents thereof. The reaction temperature and reaction time mainly depend on the starting material compounds, the base and the solvent employed in the reaction but are not particularly limited. The deprotection reaction is usually carried out at a temperature of from −20° C. to 150° C. in a period of from 1 to 10 hours in order to lower the occurrence of the side reactions.

Where the hydroxyl-protecting group is any of an alkoxymethyl group, tetrahydropyranyl group, tetrahydrothiopyranyl group, tetrahydrofuranyl group, tetrahydrothiofuranyl group or substituted ethyl group, the protecting group is usually removed by treating with an acid in a solvent.

The acid used in this reaction is not particularly limited provided that it is usually used as a Brønsted acid or Lewis acid. Examples of preferable Brønsted acids include inorganic acids such as hydrogen chloride, hydrochloric acid, sulfuric acid or nitric acid or organic acids such as acetic acid, trifluoroacetic acid, methanesulfonic acid or p-toluenesulfonic acid, and examples of preferable Lewis acids include boron trifluoride. Additionally, strongly acidic cation exchange resins such as Dowex 50W can be also used.

The solvent used in the above-mentioned reaction is not particularly limited provided that it has no adverse effect on the reaction. Examples of suitable solvents include aliphatic hydrocarbons such as hexane, heptane, ligroin or petroleum ether; aromatic hydrocarbons such as benzene, toluene or xylene; halogenated hydrocarbons such as methylene chloride, chloroform, carbon tetrachloride, dichloroethane, chlorobenzene or dichlorobenzene; esters such as ethyl formate, ethyl acetate, propyl acetate, butyl acetate or diethyl carbonate; ethers such as diethyl ether, diisopropyl ether, tetrahydrofuran, dioxane, dimethoxyethane or di(ethylene glycol) dimethyl ether; alcohols such as methanol, ethanol, n-propanol, isopropanol, n-butanol, isobutanol, t-butanol, isoamyl alcohol, diethylene glycol, glycerol, octanol, cyclohexanol or methyl cellosolve; ketones such as acetone, methyl ethyl ketone, methyl isobutyl ketone, isophorone or cyclohexanone; water; or mixtures of solvents thereof. Of these solvents, ethers (particularly tetrahydrofuran) and alcohols (particularly methanol) are preferred.

The reaction temperature and reaction time mainly depend on the starting material compounds, the acid and the solvent employed in the reaction. The reaction is usually carried out at a temperature of from −10° C. to 200° C. (preferably from 0° C. to 150° C.) in a period of from 5 minutes to 48 hours (preferably from 30 minutes to 10 hours).

Where the hydroxyl-protecting group is an alkenyloxycarbonyl group, the deprotection reaction is usually carried out by treating with a base under the same reaction conditions as that described for the deprotection of the hydroxyl group protected with an aliphatic acyl group, an aromatic acyl group or an alkoxycarbonyl group. Where the hydroxyl-protecting group is an allyloxycarbonyl group, however, the deprotection reaction is usually and preferably carried out by a catalytic hydrogenation using palladium, triphenylphosphine or bis(methyldiphenylphosphine)(1,5-cyclooctadiene) iridium (I) hexafluorophosphate, since this procedure is simple and the occurrence of side reactions is low.

Where the carboxyl-protecting group is a $C_1$–$C_6$ alkyl group or a $C_1$–$C_6$ alkyl group substituted with one to three $C_6$–$C_{10}$ aryl substituents which is optionally substituted with $C_1$–$C_6$ alkyl, $C_1$–$C_{10}$ alkoxy, nitro, halogen or cyano, the deprotection reaction is usually carried out by treatment with a base under the same reaction conditions as that described for the deprotection of the hydroxyl group protected with an aliphatic acyl group, an aromatic acyl group or an alkoxycarbonyl group.

In addition, the removal of the amino-, the hydroxyl- and/or the carboxyl-protecting groups can be carried out by conducting the suitable deprotection reactions successively without any special order, if necessary.

The procedures for protecting the amino group and the hydroxyl group depend on the nature of the protecting group used, but the protection is generally carried out according to the known procedures commonly used in organic synthetic chemistry as shown below.

In the case of a compound (I) where $R^1$ and $R^2$ are each a hydrogen atom, the protection of the amino group can be carried out by the reaction of the relevant compound with a compound of general formula (XII) shown below in an inert solvent (examples of a preferable solvent include ethers such as diethyl ether, diisopropyl ether, tetrahydrofuran, dioxane, dimethoxyethane or di(ethylene glycol) dimethyl ether; or alcohols such as methanol, ethanol, n-propanol, isopropanol, n-butanol, isobutanol, t-butanol, isoamyl alcohol, diethylene glycol, glycerol, octanol, cyclohexanol or methyl cellosolve) in the presence or absence of a base (organic amines such as triethylamine, tributylamine, diisopropylethylamine, N-methylmorpholine or pyridine) at a temperature of from 0° C. to 50° C. (preferably at room temperature) in a period of from 30 minutes to 10 hours (preferably from 1 to 5 hours).

$$R^{1a}\text{—}Z \quad (XII)$$

[in the formula, $R^{1a}$ is an amino-protecting group (as defined earlier) and Z is a halogen atom]

In the case of a compound (I) where $R^3$ is a hydrogen atom, the protection of the hydroxyl group can be carried out by the reaction of the relevant compound with a compound of general formula (XIII) shown below in an inert solvent (examples of a preferable solvent include halogenated hydrocarbons such as chloroform, methylene chloride, 1,2-dichloroethane or carbon tetrachloride; amides such as formamide, dimethylformamide, dimethylacetamide or hexamethylphosphoric triamide; or sulfoxides such as dimethylsulfoxide) in the presence of a base (examples of a preferable base include alkali metal hydrides such as lithium hydride, sodium hydride or potassium hydride; and organic amines such as triethylamine, tributylamine, diisopropylethylamine, N-methylmorpholine or pyridines) at a temperature of from 0° C. to 50° C. (preferably at around room temperature) in a period of from 30 minutes to 24 hours (preferably from 1 to 24 hours).

$$R^{3a}\text{—}Z \quad (XIII)$$

[in the formula, $R^{3a}$ is a hydroxyl-protecting group (as defined earlier) and Z is as defined earlier]

Furthermore, the removal of the amino-, the hydroxyl- and/or the carboxyl-protecting groups and the protection of the amino group, the hydroxyl group and/or the carboxyl group can be carried out by conducting the suitable deprotection or protection reactions successively without any special order, if necessary.

After the completion of the reaction, the target compounds (I) of this reaction may be collected from the reaction mixture according to the conventional method. For example, the target compound can be obtained by conducting the following steps successively: appropriately neutralizing the reaction mixture; removing, if any, insoluble material(s) by filtration; adding an organic solvent which is not miscible with water (e.g. ethyl acetate); separating the organic layer containing the target compound; washing the extract with, for example, water and then drying over anhydrous magnesium sulfate, anhydrous sodium sulfate, anhydrous sodium bicarbonate or the like; and removing solvent by evaporation. The target compound can be isolated and purified, if necessary, by a suitable combination of conventional methods commonly used for the separation/purification of organic compounds such as recrystallization, reprecipitation and chromatography using appropriate eluent(s).

In Step A9, a compound of general formula (I) is synthesized by hydrolyzing a compound (X) with a base and then, if necessary, by conducting successively the removal of an amino, a hydroxyl- and/or a carboxyl-protecting group in $R^1$, $R^2$, $R^3$, $R^{5a}$, $R^{6a}$ and $R^{7a}$, the protection of an amino group in $R^1$ and/or $R^2$, and/or the protection of a hydroxyl group in $R^3$. This step is carried out in a similar manner to that described earlier in Step A8 of the method A.

In Step A10, a compound of general formula (Ic) is synthesized by reducing the ester group of a compound (IX) and then, if necessary, by conducting successively the removal of an amino, a hydroxyl- and/or a carboxyl-protecting group in $R^1$, $R^2$, $R^3$, $R^{5a}$, $R^{6a}$ and $R^{7a}$, the protection of an amino group in $R^1$ and/or $R^2$, and/or the protection of a hydroxyl group in $R^3$. The reduction of the ester group of the compound (IX) is carried out in a similar manner to that described earlier in Step A6 of the method A.

In Method B, a compound (Id) which is a compound (I) where X is an ethynylene group, a compound (Ie) which is a compound (I) where X is a vinylene group, a compound (If) which is a compound (I) where X is an ethylene group, a compound (Ig) which is a compound (I) where X is a "—CO—CH$_2$—" group, a compound (Ig-1) which is a compound (I) where X is a "—CO—CH$_2$—" group and $R^1$ is a "—CO$_2$R$^{10}$" group, a compound (Ih) which is a compound (I) where X is a "—CH(OH)—CH$_2$—" group, a compound (Ii) which is a compound (I) where X is an aryl group or an aryl group substituted with 1–3 substituents selected from the substituent group a, and a compound (Ij) which is a compound (I) where X is an oxygen atom or a sulfur atom are prepared.

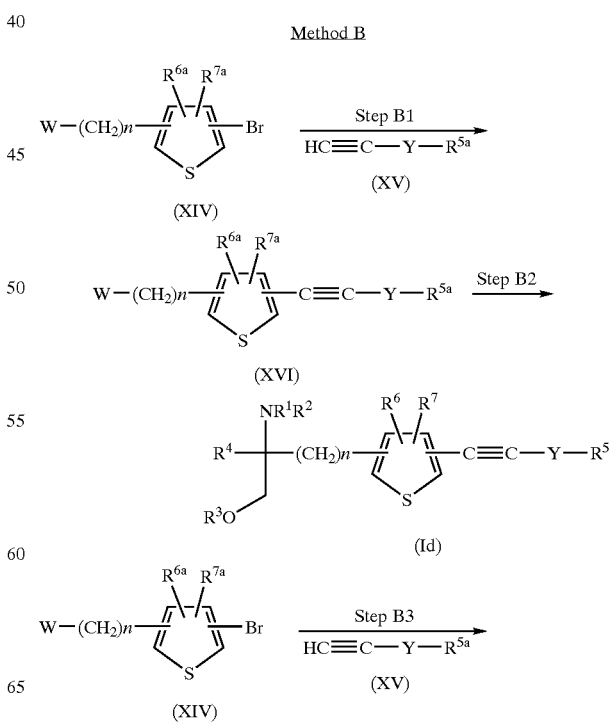

Method B

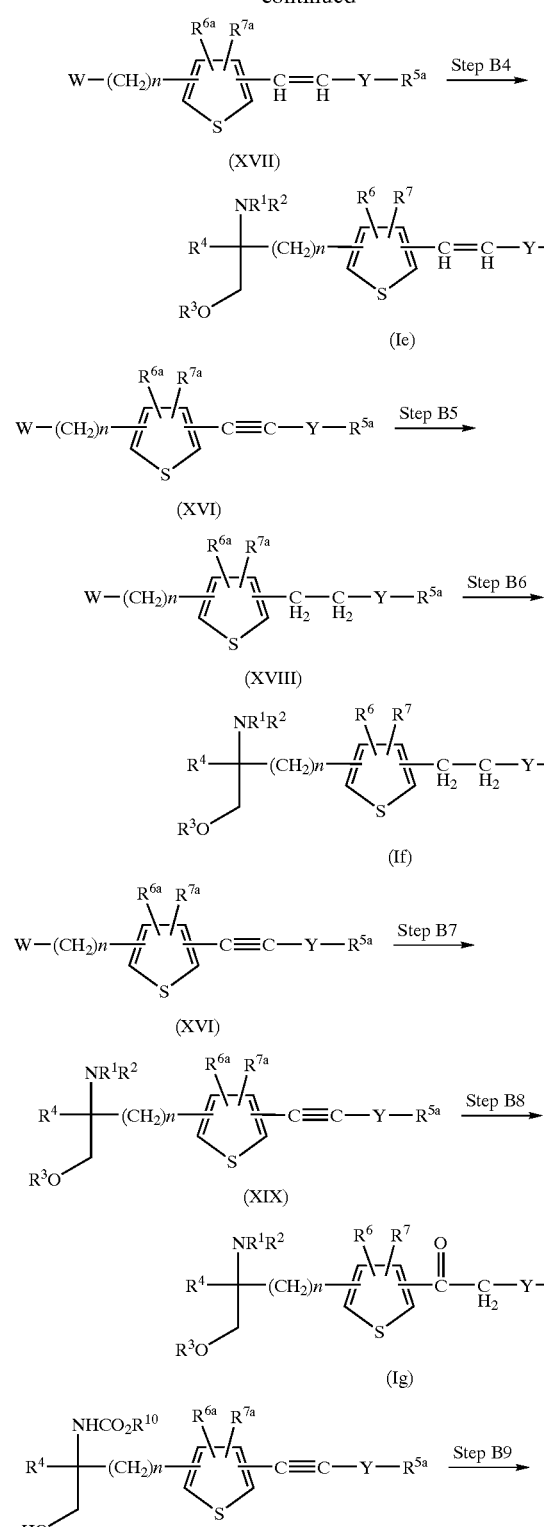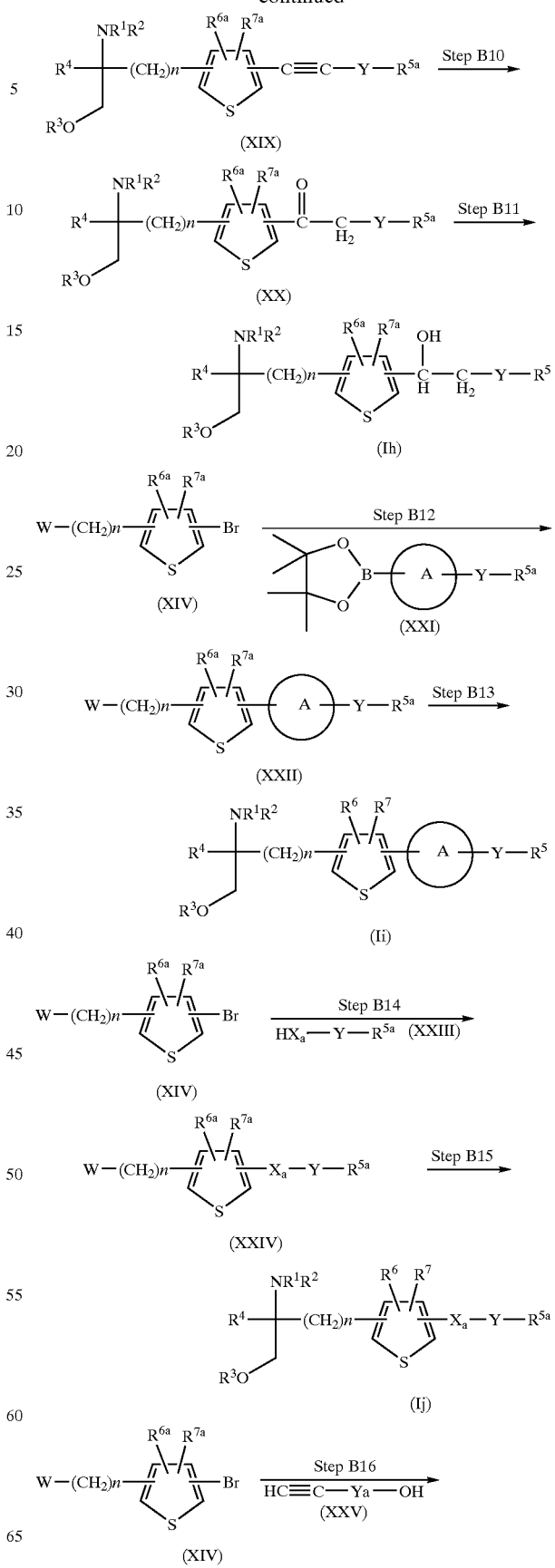

-continued

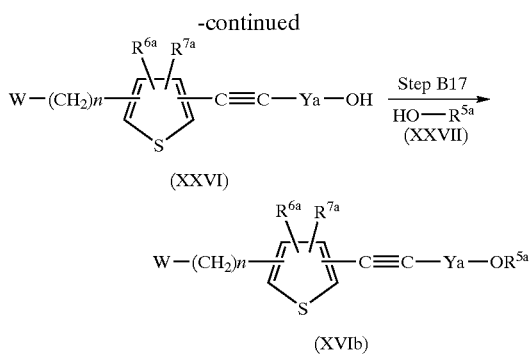

In the above scheme, $R^1, R^2, R^3, R^4, R^5, R^{5a}, R^6, R^{6a}, R^7, R^{7a}, R^{10}$, Y and n are as defined earlier, $X_a$ is an oxygen atom or a sulfur atom, $Y_a$ is a $C_1$–$C_{10}$ alkylene group or a $C_1$–$C_{10}$ alkylene group substituted with 1–3 substituents selected from the substituent groups a and b, ring A is an aryl group or an aryl group substituted with 1–3 substituents selected from the substituent group a, and W is a group having the following general formulae.

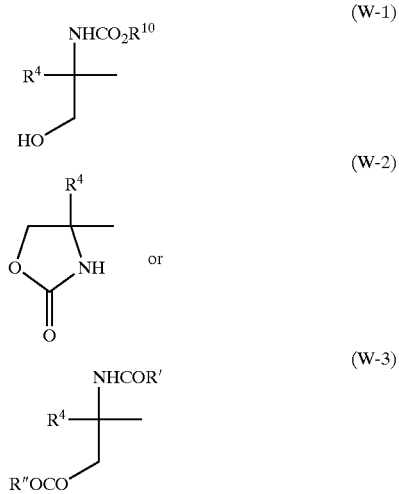

[in the above formulae, $R^4$ and $R^{10}$ are as defined earlier, R' and R" are the same or different and each is independently a lower alkyl group, an aryl group or an aryl group substituted with 1–3 substituents selected from the substituent group a].

In Step B1, a compound of general formula (XVI) is synthesized by the Sonogashira coupling reaction of a compound of general formula (XIV) and a compound of general formula (XV) in an inert solvent in the presence of a base and palladium catalyst.

The solvent used in the above-mentioned reaction is not particularly limited provided that it has no adverse effect on the reaction. Examples of suitable solvents include aliphatic hydrocarbons such as hexane, heptane, ligroin or petroleum ether; aromatic hydrocarbons such as benzene, toluene or xylene; halogenated hydrocarbons such as methylene chloride, chloroform, carbon tetrachloride, dichloroethane, chlorobenzene or dichlorobenzene; esters such as ethyl formate, ethyl acetate, propyl acetate, butyl acetate or diethyl carbonate; ethers such as diethyl ether, diisopropyl ether, tetrahydrofuran, dioxane, dimethoxyethane or di(ethylene glycol) dimethyl ether; ketones such as acetone, methyl ethyl ketone, methyl isobutyl ketone, isophorone or cyclohexanone; nitriles such as acetonitrile or isobutyronitrile; amides such as formamide, dimethylformamide, dimethylacetamide or hexamethylphosphoric triamide; and sulfoxides such as dimethyl sulfoxide or sulfolane. Ethers, amides or sufoxides (particularly amides or ethers) are preferable. In some cases, the reaction is accelerated by the addition of a small amount of water to the reaction solvent.

The base used in the above-mentioned reaction is, for example, the same as that used for the conversion of the hydroxyl group into the leaving group described in Step A2 of the method A, and organic amines (most preferably triethylamine) are preferred.

The palladium catalyst used in the above-mentioned reaction is not particularly limited provided that it is usually used for the Sonogashira coupling reaction. Examples of the preferred catalysts include palladium salts such as palladium acetate, palladium chloride or palladium carbonate; and palladium complexes such as bis(triphenylphosphine) palladium chloride complex formed from complexes with ligands.

Furthermore, the yield can be improved by the addition of cuprous chloride or benzyltriethylammonium chloride as an additive.

The reaction temperature mainly depends on the starting material compounds, the base and the solvent employed in the reaction. The reaction is usually carried out at a temperature of from −20° C. to 200° C. (preferably from 0° C. to 120° C.).

The reaction time mainly depends on the starting material compounds, the base, the solvent and the reaction temperature employed in the reaction. The reaction is usually carried out in a period of from 5 minutes to 48 hours (preferably from 15 minutes to 24 hours).

After the completion of the reaction, the target compounds (XVI) of this reaction may be collected from the reaction mixture according to conventional methods. For example, the target compound can be obtained by conducting the following steps successively: appropriately neutralizing the reaction mixture; removing, if any, insoluble material(s) by filtration; adding an organic solvent which is not miscible with water (e.g. ethyl acetate); separating the organic layer containing the target compound; washing the extract with, for example, water and then drying over anhydrous magnesium sulfate, anhydrous sodium sulfate, anhydrous sodium bicarbonate or the like; and removing solvent by evaporation. The target compound can be isolated and purified, if necessary, by a suitable combination of the conventional methods commonly used for the separation/purification of organic compounds such as recrystallization, reprecipitation and chromatography using appropriate eluent(s).

In Step B2, a compound of general formula (Id) is prepared as follows. Where W of a compound (XVI) is a (W-1) group, the compound of general formula (Id) is synthesized in a similar manner to that described either in steps A7 and A8 of the method A or step A9 of the method A. On the other hand, where W of a compound (XVI) is a (W-2) group or a (W-3) group, the compound (Id) is prepared in a similar manner to that described earlier in step A8 of the method A.

In Step B3, a compound of general formula (XVII) is prepared by conducting the reaction of a compound (XV) with catecholborane and subsequently by conducting the Suzuki coupling reaction of the resulting product and a compound (XIV).

The reaction temperature for the reaction of the compound (XV) with catecholborane mainly depends on the starting material compounds, the base and the solvent employed in the reaction. The reaction is usually carried out at a temperature of from 0° C. to 150° C. (preferably from 10° C. to 100° C.).

The reaction time for the reactions of the compound (XV) with catecholborane mainly depends on the starting material compounds, the base, the solvent and the reaction temperature employed in the reaction. The reaction is usually carried out in a period of from 15 minutes to 24 hours (preferably from 30 minutes to 12 hours).

The Suzuki coupling reaction is carried out in a similar manner to that described for the Sonogashira coupling reaction in step B1 of the method B.

The solvent used in the above-mentioned reaction is the same as that used in Step B1 of the method B, and aromatic hydrocarbons (most preferably toluene) are preferred.

The base used in the above-mentioned reaction is, for example, the same as that used for the conversion of the hydroxyl group into the leaving group described in Step A2 of the method A, and alkali metal alkoxides (most preferably sodium ethoxide) are preferred.

The palladium catalyst used in the above-mentioned reaction is the same as that used in Step B1 of the method B, and palladium complexes (most preferably bis(triphenylphosphine)palladium chloride complex) are preferred.

In Step B4, a compound of general formula (Ie) is prepared as follows. Where W of a compound (XVII) is a (W-1) group, the compound of general formula (Ie) is synthesized in a similar manner to that described either in steps A7 and A8 of the method A or step A9 of the method A. On the other hand, where W of a compound (XVII) is a (W-2) group or a (W-3) group, the compound (Ie) is prepared in a similar manner to that described earlier in step A8 of the method A.

In Step B5, a compound of general formula (XVIII) is prepared by reducing a compound (XVI) in an inert solvent (preferably a catalytic hydrogenation at room temperature in the presence of a catalyst).

The solvent used in the deprotection by the catalytic hydrogenation is not particularly limited provided that it has no adverse effect on the reaction. Examples of suitable solvents include aliphatic hydrocarbons such as hexane, heptane, ligroin or petroleum ether; aromatic hydrocarbons such as toluene, benzene or xylene; halogenated hydrocarbons such as methylene chloride, chloroform, carbon tetrachloride, dichloroethane, chlorobenzene or dichlorobenzene; esters such as methyl acetate, ethyl acetate, propyl acetate, butyl acetate or diethyl carbonate; ethers such as diethyl ether, diisopropyl ether, tetrahydrofuran, dioxane, dimethoxyethane or di(ethylene glycol) dimethyl ether; alcohols such as methanol, ethanol, n-propanol, isopropanol, n-butanol, isobutanol, t-butanol, isoamyl alcohol, diethylene glycol, glycerol, octanol, cyclohexanol or methyl cellosolve; organic acids such as acetic acid or hydrochloric acid; water; or mixtures of water and solvents thereof. Of these solvents, alcohols and ethers (particularly methanol) are preferred.

The catalyst used in the deprotection by the catalytic hydrogenation is not particularly limited provided that it is usually used in catalytic hydrogenation. Examples of preferred catalysts used in catalytic hydrogenation include palladium-on-charcoal, Raney nickel, platinum oxide, platinum black, rhodium-aluminium oxide, triphenylphosphine-rhodium chloride and palladium-barium sulfate.

The reaction temperature mainly depends on the starting material compounds, the base and the solvent employed in the reaction. The reaction is usually carried out at a temperature of from –20° C. to 200° C. (preferably from 0° C. to 100° C.).

The reaction time mainly depends on the starting material compounds, the base, the solvent and the reaction temperature employed in the reaction. The reaction is usually carried out in a period of from 5 minutes to 96 hours (preferably from 15 minutes to 72 hours).

After the completion of the reaction, the target compounds (XVIII) of this reaction may be collected from the reaction mixture according to conventional methods. For example, the target compound can be obtained by conducting the following steps successively: appropriately neutralizing the reaction mixture; removing, if any, insoluble material(s) by filtration; adding an organic solvent which is not miscible with water (e.g. ethyl acetate); separating the organic layer containing the target compound; washing the extract with, for example, water and then drying over anhydrous magnesium sulfate, anhydrous sodium sulfate, anhydrous sodium bicarbonate or the like; and removing solvent by evaporation. The target compound can be isolated and purified, if necessary, by a suitable combination of the conventional methods commonly used for the separation/purification of organic compounds such as recrystallization, reprecipitation and chromatography using appropriate eluent(s).

In Step B6, a compound of general formula (If) is prepared as follows. Where W of a compound (XVIII) is a (W-1) group, the compound of general formula (If) is synthesized in a similar manner to that described either in steps A7 and A8 of the method A or step A9 of the method A. On the other hand, where W of a compound (XVIII) is a (W-2) group or a (W-3) group, the compound (If) is prepared in a similar manner to that described earlier in step A8 of the method A.

In Step B7, a compound of general formula (XIX) is prepared as follows. Where W of a compound (XVI) is a (W-1) group, the compound of general formula (XIX) is synthesized in a similar manner to that described either in steps A7 and A8 of the method A or step A9 of the method A. On the other hand, where W of a compound (XVI) is a (W-2) group or a (W-3) group, the compound (XIX) is prepared in a similar manner to that described earlier in step A8 of the method A.

In Step B8, a compound of general formula (Ig) is prepared by treating a compound (XIX) in an inert solvent by procedures comprising the addition reaction of water in the presence of an acid catalyst or the oxymercuration reaction with mercury oxide and then, if necessary, by conducting successively the removal of an amino-, a hydroxyl- and/or a carboxyl-protecting group in $R^1$, $R^2$, $R^3$, $R^{5a}$, $R^{6a}$ and $R^{7a}$, the protection of an amino group in $R^1$ and/or $R^2$, and/or the protection of a hydroxyl group in $R^3$.

The solvent used in the above-mentioned reaction is not particularly limited provided that it has no adverse effect on the reaction. Examples of suitable solvents include aliphatic hydrocarbons such as hexane, heptane, ligroin or petroleum ether; aromatic hydrocarbons such as benzene, toluene or xylene; halogenated hydrocarbons such as methylene chloride, chloroform, carbon tetrachloride, dichloroethane, chlorobenzene or dichlorobenzene; esters such as ethyl formate, ethyl acetate, propyl acetate, butyl acetate or diethyl carbonate; ethers such as diethyl ether, diisopropyl ether, tetrahydrofuran, dioxane, dimethoxyethane or di(ethylene glycol) dimethyl ether; alcohols such as methanol, ethanol, n-propanol, isopropanol, n-butanol, isobutanol, t-butanol, isoamyl alcohol, diethylene glycol, glycerol, octanol, cyclohexanol or methyl cellosolve; ketones such as acetone, methyl ethyl ketone, methyl isobutyl ketone, isophorone, cyclohexanone; water; or mixtures of solvents thereof. Of these solvents, alcohols (particularly methanol) are preferred.

The acid catalyst used in the above-mentioned reaction is not particularly limited provided that it is usually used as an acid catalyst in common reactions. Examples of suitable acids include Brönsted acids including inorganic acids such as hydrochloric acid, hydrobromic acid, sulfuric acid, perchloric acid or phosphoric acid; and organic acids such as acetic acid, formic acid, oxalic acid, methanesulfonic acid, p-toluenesulfonic acid, camphorsulfonic acid, trifluoroacetic acid or trifluoromethanesulfonic acid; Lewis acids such as zinc chloride, tin tetrachloride, boron trichloride, boron trifluoride or boron tribromide; and acidic ion-exchange resins. Inorganic acids (most preferably sulfuric acid) are preferable.

The reaction temperature mainly depends on the starting material compounds, the base and the solvent employed in the reaction. The reaction is usually carried out at a temperature of from −20° C. to 200° C. (preferably from 0° C. to 100° C.).

The reaction time mainly depends on the starting material compounds, the base, the solvent and the reaction temperature employed in the reaction. The reaction is usually carried out in a period of from 5 minutes to 96 hours (preferably from 15 minutes to 72 hours).

The removal of an amino-, a hydroxyl- and/or a carboxyl-protecting group in $R^1$, $R^2$, $R^3$, $R^{5a}$, $R^{6a}$ and $R^{7a}$, the protection of an amino group in $R^1$ and/or $R^2$, and/or the protection of a hydroxyl group in $R^3$, all of which are, if necessary, carried out, are performed in a similar manner to that described in step A8 of the method A.

In Step B9, a compound of general formula (Ig-1) is prepared by treating a compound (XVIa) in an inert solvent by procedures comprising the addition reaction of water in the presence of an acid catalyst or the oxymercuration reaction with mercury oxide and then, if necessary, by conducting successively the removal of an amino-, a hydroxyl- and/or a carboxyl-protecting group in $R^1$, $R^2$, $R^3$, $R^{5a}$, $R^{6a}$ and $R^{7a}$, and/or the protection of a hydroxyl group in $R^3$. This step is carried out in a similar manner to that described earlier in Step B8 of the method B.

In Step B10, a compound of general formula (XX) is prepared by treating a compound (XIX) in an inert solvent by procedures comprising the addition reaction of water in the presence of an acid catalyst or the oxymercuration reaction with mercury oxide and then, if necessary, by conducting successively the removal of an amino-, a hydroxyl- and/or a carboxyl-protecting group in $R^1$, $R^2$, $R^3$, $R^{5a}$, $R^{6a}$ and $R^{7a}$, the protection of an amino group in $R^1$ and/or $R^2$, and/or the protection of a hydroxyl group in $R^3$. This step is carried out in a similar manner to that described earlier in Step B8 of the method B.

In Step B11, a compound of general formula (Ih) is synthesized by reducing a compound (XX) in an inert solvent and then, if necessary, by conducting successively the removal of an amino-, a hydroxyl- and/or a carboxyl-protecting group in $R^1$, $R^2$, $R^3$, $R^{5a}$, $R^{6a}$ and $R^{7a}$, the protection of an amino group in $R^1$ and/or $R^2$, and/or the protection of a hydroxyl group in $R^3$.

The inert solvent used in the above-mentioned reaction is not particularly limited provided that it has no adverse effect on the reaction. Examples of suitable solvents include aliphatic hydrocarbons such as hexane, heptane, ligroin or petroleum ether; aromatic hydrocarbons such as benzene, toluene or xylene; halogenated hydrocarbons such as chloroform, methylene chloride, 1,2-dichloroethane or carbon tetrachloride; ethers such as diethyl ether, diisopropyl ether, tetrahydrofuran, dioxane, dimethoxyethane or di(ethylene glycol) dimethyl ether; alcohols such as methanol, ethanol, n-propanol, isopropanol, n-butanol, isobutanol, t-butanol, isoamyl alcohol, diethylene glycol, glycerol, octanol, cyclohexanol or methyl cellosolve; or mixtures of solvents thereof. Of these solvents, ethers or alcohols (particularly methanol or ethanol) are preferred.

The reducing agent used in the above-mentioned reaction is, for example, an alkali metal borohydride such as sodium borohydride, lithium borohydride or sodium cyanoborohydride; or an aluminium hydride such as diisobutylaluminium hydride, lithium aluminium hydride or triethoxyaluminium lithium hydride. The preferred example is an alkali metal borohydride (sodium cyanoborohydride).

The reaction temperature mainly depends on the starting material compounds, the base and the solvent employed in the reaction. The reaction is usually carried out at a temperature of from −10° C. to 100° C. (preferably from −20° C. to 20° C.).

The reaction time mainly depends on the starting material compounds, the base, the solvent and the reaction temperature employed in the reaction. The reaction is usually carried out in a period of from 10 minutes to 48 hours (preferably from 30 minutes to 12 hours).

The removal of an amino-, a hydroxyl- and/or a carboxyl-protecting group in $R^1$, $R^2$, $R^3$, $R^{5a}$, $R^{6a}$ and $R^{7a}$, the protection of an amino group in $R^1$ and/or $R^2$, and/or the protection of a hydroxyl group in $R^3$, all of which are, if necessary, carried out, are performed in a similar manner to that described in step A8 of the method A.

After the completion of the reaction, the target compounds (Ih) of this reaction may be collected from the reaction mixture according to conventional methods. For example, the target compound can be obtained by conducting the following steps successively: appropriately neutralizing the reaction mixture; removing, if any, insoluble material(s) by filtration; adding an organic solvent which is not miscible with water (e.g. ethyl acetate); separating the organic layer containing the target compound; washing the extract with, for example, water and then drying over anhydrous magnesium sulfate, anhydrous sodium sulfate, anhydrous sodium bicarbonate or the like; and removing solvent by evaporation. The target compound can be isolated and purified, if necessary, by a suitable combination of the conventional methods commonly used for the separation/purification of organic compounds such as recrystallization, reprecipitation and chromatography using appropriate eluent(s).

In Step B12, a compound of general formula (XXII) is prepared by conducting the Suzuki coupling reaction of a compound (XXI) and a compound (XIV). This step is carried out in a similar manner to that described for the Sonogashira coupling reaction in Step B3 of the method B.

In Step B13, a compound of general formula (Ii) is prepared as follows. Where W of a compound (XXII) is a (W-1) group, the compound of general formula (Ii) is synthesized in a similar manner to that described either in steps A7 and A8 of the method A or step A9 of the method A. On the other hand, where W of a compound (XXII) is a (W-2) group or a (W-3) group, the compound (Ii) is prepared in a similar manner to that described earlier in step A8 of the method A.

In Step B 14, a compound of general formula (XXIV) is prepared by the reaction of a compound (XIV) with an alkali metal salt of a compound (XXIII) under conditions without solvent or in an inert solvent in the presence of a copper catalyst. This step is carried out by the procedures, for example, described in J. Heterocyclic. Chem., 20, 1557 (1983). The solvent used in the above-mentioned reaction is not particularly limited provided that it has no adverse effect on the reaction. Examples of suitable solvents include ethers such as diethyl ether, dioxane, tetrahydrofuran, dimethoxyethane, or di(ethylene glycol) dimethyl ether; or pyridines such as pyridine, picoline, lutidine or collidine. The reaction is carried out preferably under conditions without solvent.

The copper catalyst used in the above-mentioned reaction is, for example, cuprous iodide, cuprous bromide, cuprous oxide or cupric oxide, and cuprous oxide is preferred. The alkali metal salt of the compound (XXIII) used in the above-mentioned reaction is prepared by treating the compound of general formula (XXIII) and an alkali metal or alkali metallic compound. Examples of suitable alkali metals include metallic lithium, metallic sodium or metallic potassium, and examples of suitable alkali metallic compounds include alkali metal hydrides such as lithium hydride, sodium hydride or potassium hydride. The alkali metal salt of the compound (XXIII) is preferably prepared using metallic sodium. Furthermore, the yield can be improved by the addition of potassium iodide as an additive.

The reaction temperature mainly depends on the starting material compounds, the catalyst and the solvent employed in the reaction. The reaction is usually carried out at a temperature of from room temperature to 150° C. (preferably from 60° C. to 120° C.).

The reaction time mainly depends on the starting material compounds, the catalyst and the solvent employed in the reaction. The reaction is usually carried out in a period of from 1 hour to 7 days (preferably from 3 hours to 72 hours).

After the completion of the reaction, the target compounds (XXIV) of this reaction may be collected from the reaction mixture according to conventional methods. For example, the target compound can be obtained by conducting the following steps successively: appropriately neutralizing the reaction mixture; removing, if any, insoluble material(s) by filtration; adding an organic solvent which is not miscible with water (e.g. ethyl acetate); separating the organic layer containing the target compound; washing the extract with, for example, water and then drying over anhydrous magnesium sulfate, anhydrous sodium sulfate, anhydrous sodium bicarbonate or the like; and removing solvent by evaporation. The target compound can be isolated and purified, if necessary, by a suitable combination of the conventional methods commonly used for the separation/purification of organic compounds such as recrystallization, reprecipitation and chromatography using appropriate eluent(s).

In Step B15, a compound of general formula (Ij) is prepared as follows. Where W of a compound (XXIV) is a (W-1) group, the compound of general formula (Ij) is synthesized in a similar manner to that described either in steps A7 and A8 of the method A or step A9 of the method A. On the other hand, where W of a compound (XXIV) is a (W-2) group-or a (W-3) group, the compound (Ij) is prepared in a similar manner to that described earlier in step A8 of the method A.

In Step B16, a compound of general formula (XXVI) is prepared by the reaction of a compound of general formula (XIV) with a compound of general formula (XXV). This step is carried out in a similar manner to that described in Step B1 of the method B.

In Step B17, a compound (XVIb) which is a compound (XVI) where Y is a "$Y_a$—O—" group is synthesized by condensing a compound (XXVI) and a compound of general formula (XXVII) in an inert solvent by the Mitsunobu reaction.

The reagent used in the Mitsunobu reaction is not particularly limited provided that it is commonly used in the Mitsunobu reaction. Examples of preferred reagents include combinations of azo compounds including di(lower alkyl) azodicarboxylates such as diethyl azodicarboxylate or diisopropyl azodicarboxylate; or azodicarbonyl derivatives such as 1,1'-(azadicarbonyl)dipiperidine; and phosphines including triarylphosphines such as triphenylphosphine or tri (lower alkyl)phosphines such as tri-n-butylphosphine. The combinations of di(lower alkyl) azodicarboxylates and triarylphosphines are more preferred. The solvent used in the above-mentioned reaction is not particularly limited provided that it has no adverse effect on the reaction and dissolves the starting materials to some extent. Examples of preferred solvents include aromatic hydrocarbons such as benzene, toluene or xylene; halogenated hydrocarbons such as methylene chloride, chloroform, carbon tetrachloride, dichloroethane, chlorobenzene or dichlorobenzene; esters such as ethyl formate, ethyl acetate, propyl acetate, butyl acetate or diethyl carbonate; ethers such as diethyl ether, diisopropyl ether, tetrahydro furan, dioxane, dimethoxyethane or di(ethylene glycol) dimethyl ether; nitriles such as acetonitrile or isobutyronitrile; amides such as formamide, N,N-dimethylformamide, N,N-dimethylacetamide, N-methyl-2-pyrrolidone, N-methylpyrrolidindne or hexamethylphosphoric triamide; or sulfoxides such as dimethyl sulfoxide or sulfolane. Aromatic hydrocarbons and ethers are preferable. The reaction is usually carried out at a temperature of from −20° C. to 100° C. and preferably from 0° C. to 50° C.

The reaction time mainly depends on the reaction temperature, the starting material compounds, the reagent or the solvent employed in the reaction. The reaction is usually carried out in a period of from 10 minutes to 3 days and preferably from 30 minutes to 12 hours.

After the completion of the reaction, the target compounds (XVIb) of this reaction may be collected from the reaction mixture according to conventional methods. For example, the target compound can be obtained by conducting the following steps successively: appropriately neutralizing the reaction mixture; removing, if any, insoluble material(s) by filtration; adding an organic solvent which is not miscible with water (e.g. ethyl acetate); separating the organic layer containing the target compound; washing the extract with, for example, water and then drying over anhydrous magnesium sulfate, anhydrous sodium sulfate, anhydrous sodium bicarbonate or the like; and removing solvent by evaporation. The target compound can be isolated and purified, if necessary, by a suitable combination of the conventional methods commonly used for the separation/purification of organic compounds such as recrystallization, reprecipitation and chromatography using appropriate eluent(s).

Alternatively, the compounds (Id)-(Ij) may be synthesized by hydrolyzing the W group of a compound (XIV) and then by conducting the reaction of the resulting product with a compound (XV), a compound (XXI), a compound (XXIII) or a compound (XXV), respectively.

The compounds (II), (V), (VIII), (XII), (XIII), (XIV), (XV), (XXI), (XXIII), (XXV) and (XXVII) used as the starting materials are either known compounds or can be prepared easily by known or similar methods.

Alternatively, the compounds (II) and (XIV) used as the starting materials can be synthesized by the following methods.

In Method C, a compound (XIV) and a compound (XIVa) which is the compound (XIV) having a bromine atom at the 2-position of the thiophene moiety and a "—(CH$_2$)n-W" group at the 5-position of the thiophene moiety as the substituents, respectively, are prepared.

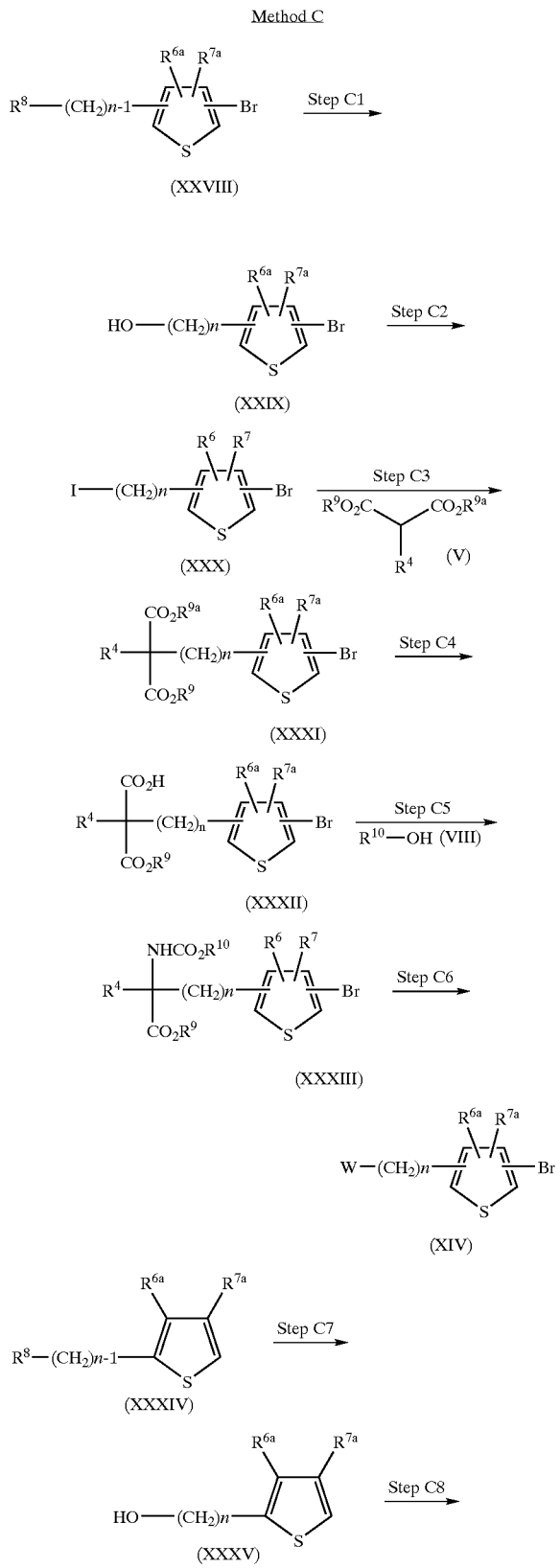

In the above scheme, $R^4$, $R^{6a}$, $R^{7a}$, $R^8$, $R^9$, $R^{9a}$, $R^{10}$, n and W are as defined earlier.

In Step C1, a compound of general formula (XXIX) is prepared by the reaction of a compound of general formula (XXVIII) with a reducing agent in an inert solvent in the presence or absence of a base (preferably in the presence of a base). This step is carried out in a similar manner to that described in Step A1 of the method A.

In Step C2, a compound of general formula (XXX) is prepared by converting a hydroxyl group of compound (XXIX) into a leaving group in an inert solvent in the presence of a base and then by conducting an iodination reaction on the resulting leaving group with an iodination agent. This step is carried out in a similar manner to that described in Step A2 of the method A.

In Step C3, a compound of general formula (XXXI) is prepared by the reaction of a compound (XXX) with a compound (V) in an inert solvent in the presence of a base. This step is carried out in a similar manner to that described in Step A3 of the method A.

In Step C4, a compound of general formula (XXXII) is prepared by hydrolyzing a compound (XXXI) with a base in an inert solvent. This step is carried out in a similar manner to that described in Step A4 of the method A.

Step C5 is a step for converting the carboxyl group into a carbamoyl group by the Curtius Rearrangement Reaction, and in this step, a compound of general formula (XXXIII) is synthesized by the reaction of a compound (XXXII) with a diarylphosphoryl azide derivative such as diphenylphosphoryl azide in an inert solvent in the presence of a base and then by the reaction of the resulting product with a compound (VIII). This step is carried out in a similar manner to that described in Step A5 of the method A.

In Step C6, a compound (XIV) is prepared by reducing an ester group of a compound (XXXIII). This step is carried out in a similar manner to that described in Step A6 of the method A.

After the completion of the reaction, the target compounds (XIV) of this reaction may be collected from the reaction mixture according to conventional methods. For example, the target compound can be obtained by conducting the following steps successively: appropriately neutralizing the reaction mixture; removing, if any, insoluble material(s) by filtration; adding an organic solvent which is not miscible with water (e.g. ethyl acetate); separating the organic layer containing the target compound; washing the extract with, for example, water and then drying over anhydrous magnesium sulfate, anhydrous sodium sulfate, anhydrous sodium bicarbonate or the like; and removing solvent by evaporation. The target compound can be isolated and purified, if necessary, by a suitable combination of the conventional methods commonly used for the separation/purification of organic compounds such as recrystallization, reprecipitation and chromatography using appropriate eluent(s).

In Step C7, a compound of general formula (XXXV) is prepared by the reaction of a compound of general formula (XXXIV) with a reducing agent in an inert solvent in the presence or absence of a base (preferably in the presence of a base). This step is carried out in a similar manner to that described in Step A1 of the method A.

In Step C8, a compound of general formula (XXXVI) is prepared by converting a hydroxyl group of compound (XXXV) into a leaving group in an inert solvent in the presence of a base and then by conducting an iodination reaction. This step is carried out in a similar manner to that described in Step A2 of the method A.

In Step C9, a compound of general formula (XXXVII) is prepared by the reaction of a compound (XXXVI) with a compound (V) in an inert solvent in the presence of a base. This step is carried out in a similar manner to that described in Step A3 of the method A.

In Step C10, a compound of general formula (XXXVIII) is prepared by hydrolyzing a compound (XXXVII) with a base in an inert solvent. This step is carried out in a similar manner to that described in Step A4 of the method A.

Step C11 is a step for converting the carboxyl group into a carbamoyl group by the Curtius Rearrangement Reaction, and in this step, a compound of general formula (XXXIX) is synthesized by the reaction of the compound (XXXVIII) with a diarylphosphoryl azide derivative such as diphenylphosphoryl azide in an inert solvent in the presence of a base and then by the reaction of the resulting product with a compound (VIII). This step is carried out in a similar manner to that described in Step A5 of the method A.

In Step C12, a compound (XL) is prepared by reducing an ester group of a compound (XXXIX). This step is carried out in a similar manner to that described in Step A6 of the method A.

In Step C13, a compound (XIVa) is prepared by the reaction of a compound (XL) with a brominating agent.

The solvent used in the above-mentioned reaction is not particularly limited provided that it has no adverse effect on the reaction. Examples of suitable solvents include halogenated hydrocarbons such as methylene chloride, chloroform, carbon tetrachloride, dichloroethane, chlorobenzene or dichlorobenzene; ethers such as diethyl ether, diisopropyl ether, tetrahydrofuran, dioxane, dimethoxyethane or di(ethylene glycol) dimethyl ether;.or amides such as formamide, dimethylformamide, dimethyl acetamide or hexamethylphosphoric triamide. Amides are preferable and dimethylformamide is most preferable.

The brominating agent used in the above-mentioned reaction is not particularly limited. Examples of suitable brominating agents include those described in "Comprehensive Organic Transformation" (Larock, VCH, p 316–317), and N-bromosuccinimide or bromine is preferred.

The reaction temperature mainly depends on the starting material compounds, the brominating agent and the solvent employed in the reaction. The reaction is usually carried out at a temperature of from −78° C. to 150° C. and preferably from −20° C. to 100° C.

The reaction time mainly depends on the starting material compounds, the brominating agent, the solvent and the reaction temperature employed in the reaction. The reaction is usually carried out in a period of from 5 minutes to 48 hours and preferably from 30 minutes to 24 hours.

After the completion of the reaction, the target compounds (XIVa) of this reaction may be collected from the reaction mixture according to conventional methods. For example, the target compound can be obtained by conducting the following steps successively: appropriately neutralizing the reaction mixture; removing, if any, insoluble material(s) by filtration; adding an organic solvent which is not miscible with water (e.g. ethyl acetate); separating the organic layer containing the target compound; washing the extract with, for example, water and then drying over anhydrous magnesium sulfate, anhydrous sodium sulfate, anhydrous sodium bicarbonate or the like; and removing solvent by evaporation. The target compound can be isolated and purified, if necessary, by a suitable combination of the conventional methods commonly used for the separation/purification of organic compounds such as recrystallization, reprecipitation and chromatography using appropriate eluent(s).

In Method D, a compound (IIa) which is a compound (II) where X is an ethyhylene group, a compound (IIb) which is a compound (II) where X is an ethylene group, a compound (IIc) which is a compound (II) where X is a vinylene group, a compound (IId) which is a compound (II) where X is a "—CO—CH$_2$—" group, a compound (IIe) which is a compound (II) where X is a "—CH(OH)—CH$_2$—" group, a compound (IIf) which is a compound (II) where X is an aryl group or an aryl group substituted with 1-3 substituents selected from the substituting moieties a, and a compound (IIg) which is a compound (II) where X is an oxygen atom or a sulfur atom are prepared.

Method D

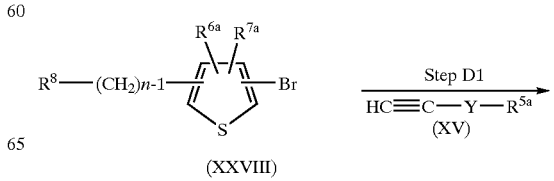

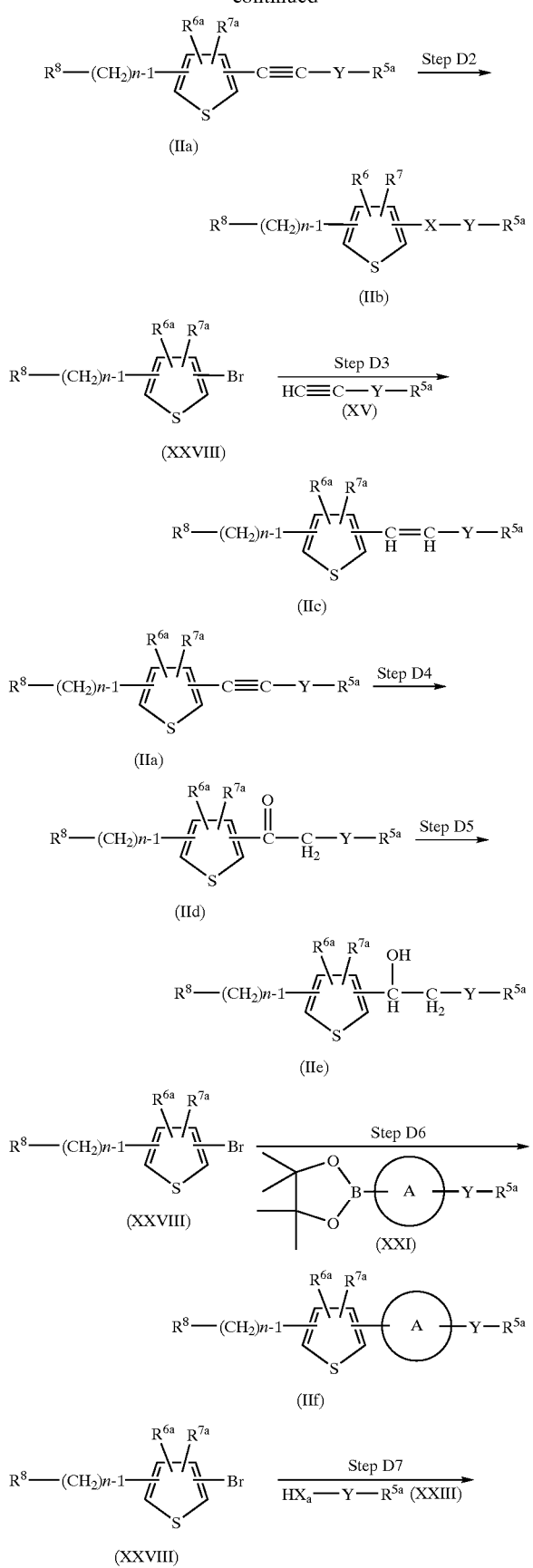

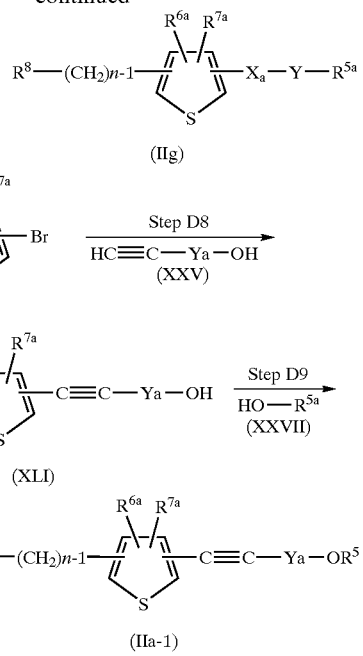

In the above scheme, $R^{5a}$, $R^{6a}$, $R^{7a}$, $R^8$, n, $X_a$, Y, $Y_a$ and ring A are as defined earlier.

In Step D1, a compound (IIa) is synthesized by the Sonogashira coupling reaction of a compound (XXVIII) and a compound (XV) in an inert solvent in the presence of a base and palladium catalyst. This step is carried out in a similar manner to that described earlier in Step B1 of the method B.

In Step D2, a compound (IIb) is prepared by reducing a compound (IIa) in an inert solvent (preferably by a catalytic hydrogenation at room temperature in the presence of a catalyst). This step is carried out in a similar manner to that described earlier in Step B5 of the method B.

In Step D3, a compound (IIc) is prepared by conducting the reaction of a compound (XV) with catecholborane and subsequently by conducting the Suzuki coupling reaction of the resulting product and a compound (XXVIII). This step is carried out in a similar manner to that described earlier in Step B3 of the method B.

In Step D4, a compound (IId) is prepared by treating a compound (IIa) in an inert solvent by procedures comprising the addition reaction of water in the presence of an acid catalyst or the oxymercuration reaction with mercury oxide. This step is carried out in a similar manner to that described earlier in Step B8 of the method B.

In Step D5, a compound (IIe) is prepared by reducing a compound (IId) in an inert solvent. This step is carried out in a similar manner to that described earlier in Step B11 of the method B.

In Step D6, a compound (IIf) is synthesized by conducting the Suzuki coupling reaction of a compound (XXI) and a compound (XXVIII). This step is carried out in a similar manner to that described earlier in Step B3 of the method B.

In Step D7, a compound (IIg) is prepared by conducting the reaction of a compound (XXVIII) with an alkali metal salt of a compound (XXIII) under conditions without solvent or in an inert solvent in the presence of a copper catalyst. This step is carried out in a similar manner to that described earlier in Step B14 of the method B.

In Step D8, a compound of general formula (XLI) is prepared by the reaction of a compound (XXVIII) with a compound (XXV). This step is carried out in a similar manner to that described earlier in Step B1 of the method B.

In Step D9, a compound (IIa-1) which is a compound (IIa) where Y is a "$Y_a$—O—" group is prepared by the reaction of a compound (XLI) with a compound (XXVII). This step is carried out in a similar manner to that described earlier in Step B17 of the method B.

In Method E, compounds (XLIVa), (XLIVb), (La) and (Lb), all of which are an intermediate of the compound (I) of the present invention, are prepared.

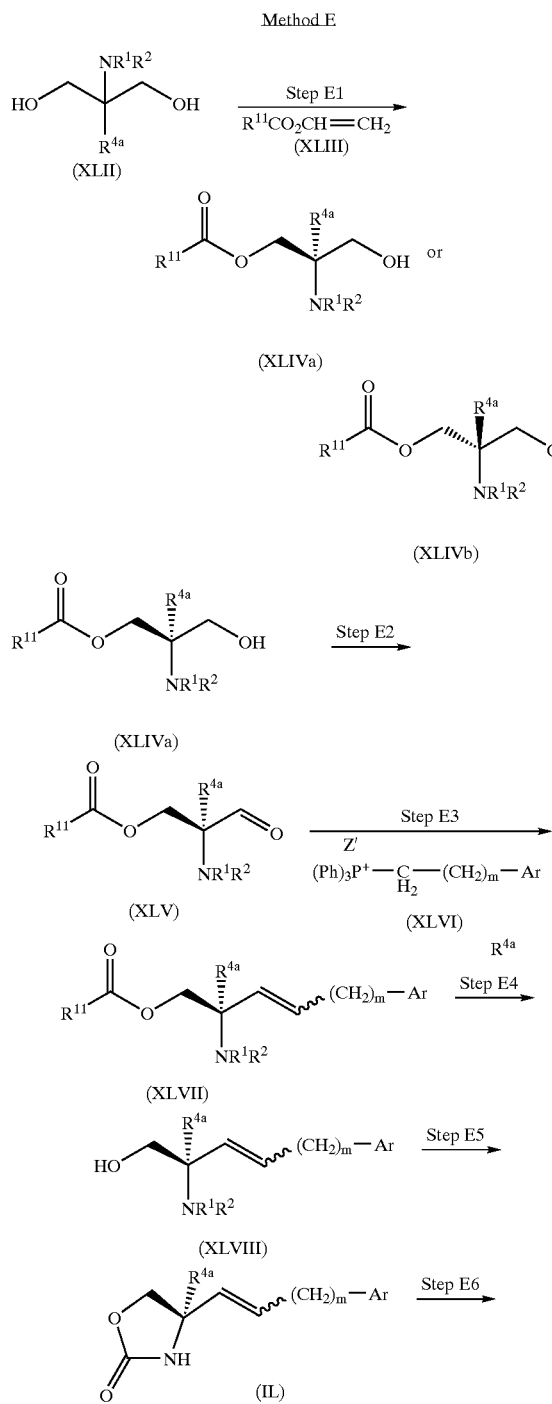

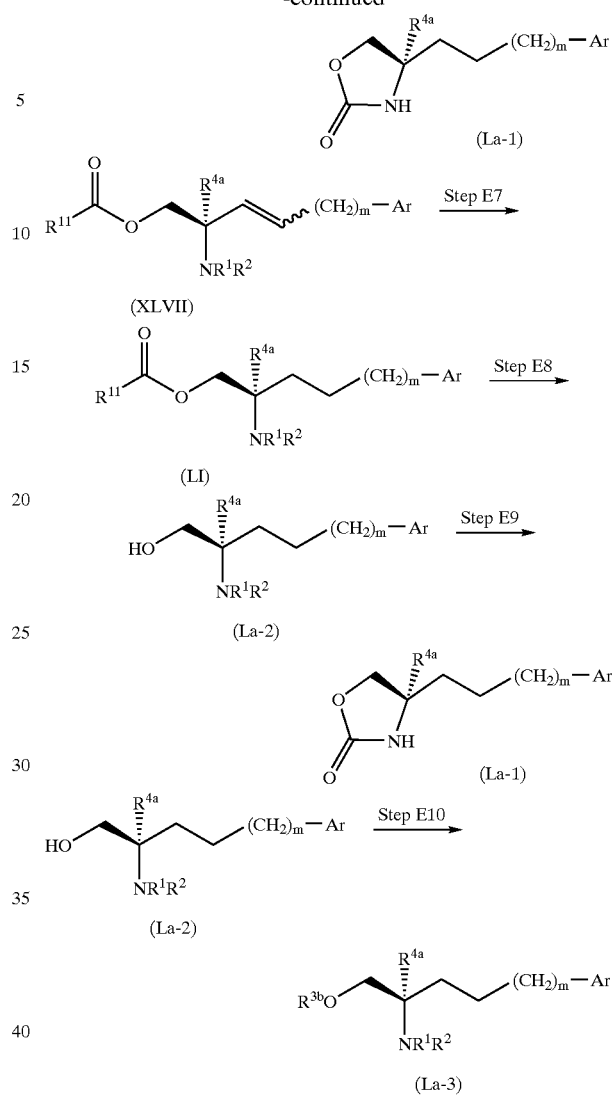

In the above scheme, $R^1$, $R^2$, $R^3$, $R^{4a}$, $R^{11}$, Ar, m and Z are as defined earlier.

In Step E1, a compound of general formula (XLIVa) or a compound of general formula (XLIVb) is prepared by acylating selectively only one of the hydroxyl groups of a compound of general formula (XLII) with a compound of general formula (XLIII) in the presence or absence of a solvent and in the presence of lipase.

The solvent used in the present invention is not particularly limited. The reaction proceeds without any problem even when only the compound (XLIII) is used without any solvent. In addition, a variety of organic solvents and of mixtures of water and organic solvents can be used although the most preferred solvent in this reaction differs due to the nature of the compound used as the starting material. Examples of preferred solvent include ethers such as diisopropyl ether, t-butylmethyl ether, diethyl ether or tetrahydrofuran; aliphatic hydrocarbons such as n-hexane or n-pentane; aromatic hydrocarbons such as benzene or toluene; or halogenated hydrocarbons such as methylene chloride or 1,2-dichloroethane. Ethers are preferred, and diisopropyl ether is most preferred.

The reaction temperature mainly depends on the starting material compounds, the solvent, the lipase and the nature of the compound (XLIII) employed in the reaction. The reaction is usually carried out at a temperature of from −50° C. to 50° C. and preferably from 0° C. to 40° C. The reaction time mainly depends on the starting material compounds, the solvent, lipase and the nature of a compound (XLIII) employed in the reaction. The reaction is usually carried out in a period of from 15 minutes to 150 hours and preferably from 30 minutes to 24 hours. After the completion of the reaction, the target compounds (XLIVa) and (XLIVb) of this reaction may be collected from the reaction mixture according to conventional methods. For example, after removing, if any, insoluble material(s) by filtration, the target compound can be obtained by concentrating the reaction mixture or conducting the following steps successively: adding an organic solvent which is not miscible with water (e.g. ethyl acetate); separating the organic layer containing the target compound; and then drying over anhydrous sodium sulfate, anhydrous magnesium sulfate or the like; and removing solvent by evaporation.

The target compound obtained can be isolated and purified, if necessary, by conventional methods such as recrystallization, reprecipitation or chromatography using appropriate eluent(s).

In step E2, a compound of general formula (XLV) is prepared by oxidizing the alcohol moiety of a compound (XLIVa) into an aldehyde moiety in an inert solvent in the presence of an oxidizing agent.

The oxidation reaction employed in this step is not particularly limited provided that it can be used for the preparation of the aldehyde moiety from the primary alcohol moiety. Examples of suitable reactions include the Collins oxidation performed using pyridine and chromic acid in methylene chloride; PCC oxidation performed using pyridinium chlorochromate (PCC) in methylene chloride; PDC oxidation performed using pyridinium dichromate (PDC) in methylene chloride; Dimethylsulfoxide (DMSO) oxidation such as Swern oxidation performed using an electrophilic agent (for example, acetic anhydride, trifluoroacetic anhydride, thionyl chloride, sulfuryl chloride, oxalyl chloride, dicyclohexylcarbodiimide, diphenylketene-p-tolylimine; N,N-diethylaminoacetylene; or sulfur trioxide-pyridine complex) and dimethylsulfoxide (DMSO) in methylene chloride; and Manganese oxide oxidation performed using manganese oxide in methylene chloride or benzene.

Of these oxidation reactions, PCC oxidation or Swern oxidation performed in methylene chloride is preferred.

The reaction temperature mainly depends on the starting material compounds, the solvent and the oxidizing agent employed in the reaction. The reaction is usually carried out at a temperature of from −50° C. to 50° C. and preferably from −10° C. to 30° C.

The reaction time mainly depends on the starting material compounds, the solvent, the oxidizing agent and the reaction temperature employed in the reaction. The reaction is usually carried out in a period of from 10 minutes to 2 days and preferably from 30 minutes to 24 hours.

For example, after neutralizing the oxidizing agent with sodium hydrogen sulfite and removing, if any, insoluble material(s) by filtration, the target compound can be obtained by concentrating the reaction mixture or conducting the following steps successively: adding an organic solvent which is not miscible with water (e.g. ethyl acetate); separating the organic layer containing the target compound; and then drying over anhydrous sodium sulfate, anhydrous magnesium sulfate or the like; and removing solvent by evaporation. The target compound obtained can be isolated and purified, if necessary, by conventional methods such as recrystallization, reprecipitation or chromatography using appropriate eluent(s).

In step E3, a compound of general formula (XLVII) is prepared by the reaction of the aldehyde group of the compound (XLV) with a compound of general formula (XLVI) in an inert solvent in the presence of a base.

The solvent used in the above-mentioned reaction is not particularly limited provided that it has no adverse effect on the reaction. Examples of preferred solvents include aromatic hydrocarbons such as benzene, toluene or xylene; halogenated hydrocarbons such as methylene chloride, chloroform, carbon tetrachloride, 1,2-dichloroethane, chlorobenzene or dichlorobenzene; ethers such as diethyl ether, diisopropyl ether, t-butylmethyl ether or tetrahydrofuran; nitriles such as acetonitrile or isobutyronitrile; amides such as formamide, N,N-dimethylformamide, N,N-dimethylacetamide, or hexamethylphosphoric triamide; or sulfoxides such as dimethyl sulfoxide or sulfolane, and ethers are more preferred.

The base used in the above reaction is not particularly limited provided that it can be used as the base in conventional reactions. Examples of preferred bases include inorganic bases including alkali metal carbonates such as sodium carbonate, potassium carbonate or lithium carbonate; alkali metal bicarbonates such as sodium bicarbonate, potassium bicarbonate or lithium bicarbonate; alkali metal hydrides such as lithium hydride, sodium hydride or potassium hydride; alkali metal hydroxides such as sodium hydroxide, potassium hydroxide, barium hydroxide or lithium hydroxide; and alkali metal fluorides such as sodium fluoride or potassium fluoride; alkali metal alkoxides such as sodium methoxide, sodium ethoxide, potassium methoxide, potassium ethoxide, potassium t-butoxide or lithium methoxide; organic amines such as N-methylmorpholine, triethylamine, tripropylamine, tributylamine, diisopropylethylamine, dicyclohexylamine, N-methylpiperidine, 4-pyrrolidinopyridine, picoline, 4-(N, N-dimethylamino)pyridine, 2,6-di(t-butyl)-4-methylpyridine, N,N-dimethylaniline, N,N-diethylaniline, 1,4-diazabicyclo[4.3.0]octane (DABCO), 1,8-diazabicyclo [5.4.0]undec-7-ene (DBU) or 1,5-diazabicyclo[4.3.0]nona-5-ene (DBN); or organic metallic bases such as butyl lithium, lithium diisopropylamide, lithium bis (trimethylsilyl)amide, and mote preferred examples are alkali metal alkoxides, alkali metal hydrides and organic metallic bases.

The reaction temperature mainly depends on the starting material compounds, the solvent, the phosphonium salt and the base employed in the reaction. The reaction is usually carried out at a temperature of from −80° C. to 100° C. and preferably from −20° C. to 50° C.

The reaction time mainly depends on the starting material compounds, the solvent, the phosphonium salt and the base employed in the reaction. The reaction is usually carried out in a period of from 10 minutes to 2 days and preferably from 30 minutes to 12 hours.

For example, after neutralizing the reaction mixture with diluted hydrochloric acid and removing, if any, insoluble material(s) by filtration, the target compound can be obtained by concentrating the reaction mixture or conducting the following steps successively: adding an organic solvent which is not miscible with water (e.g. ethyl acetate); separating the organic layer containing the target compound; and then drying over anhydrous sodium sulfate, anhydrous magnesium sulfate or the like; and removing solvent by evaporation.

The target compound obtained can be isolated and purified, if necessary, by conventional methods such as recrystallization, reprecipitation or chromatography using appropriate eluent(s).

In step E4, a compound of general formula (XLVIII) is prepared by hydrolyzing a compound (XLVII) in an inert solvent in the presence of a base.

The solvent used in the above-mentioned reaction is not particularly limited provided that it has no adverse effect on the reaction and dissolves the starting materials to some extent. Examples of preferred solvents include alcohols such as methanol or ethanol; aromatic hydrocarbons such as benzene, toluene or xylene; halogenated hydrocarbons such as methylene chloride, chloroform, carbon tetrachloride or dichloroethane; ethers such as diethyl ether, tetrahydrofuran, dioxane, dimethoxyethane or di(ethylene glycol) dimethyl ether; and mixtures of solvents thereof or mixtures of solvents thereof and water. Of these solvents, alcohols and ethers are more preferred.

The base used in the above reaction is not particularly limited provided that it can be used as the base in conventional reactions. Examples of preferred bases include alkali metal hydroxides such as sodium hydroxide, potassium hydroxide, lithium hydroxide or barium hydroxide.

The reaction temperature mainly depends on the starting material compounds, the solvent and the base employed in the reaction. The reaction is usually carried out at a temperature of from −20° C. to 200° C. and preferably from 0° C. to 20° C.

The reaction time mainly depends on the starting material compounds, the reaction temperature, the solvent and the base employed in the reaction. The reaction is usually carried out in a period of from 30 minutes to 48 hours and preferably from 1 hour to 24 hours. For example, after neutralizing the reaction mixture with diluted hydrochloric acid and removing, if any, insoluble material(s) by filtration, the target compound can be obtained by concentrating the reaction mixture or conducting the following steps successively: adding organic solvent which is not miscible with water (e.g. ethyl acetate); separating the organic layer containing the target compound; and then drying over anhydrous sodium sulfate, anhydrous magnesium sulfate or the like; and removing solvent by evaporation.

The target compound obtained can be isolated and purified, if necessary, by conventional methods such as recrystallization, reprecipitation or chromatography using appropriate eluent(s).

Step E5 is a step for preparing a compound of general formula (IL), and in this step, a compound (XLVIII) is converted into the compound (IL) in an inert solvent in the presence of a base.

The solvent used in the above-mentioned reaction is not particularly limited provided that it has no adverse effect on the reaction and dissolves the starting materials to some extent. Examples of preferred solvents include ethers such as diethyl ether, dioxane, tetrahydrofuran, dimethoxyethane or di(ethylene glycol) dimethyl ether; amides such as N,N-dimethylformamide, N,N-dimethylacetamide, N-methyl-2-pyrrolidone, N-methylpyrrolidinone or hexamethylphosphoric triamide; or aromatic hydrocarbons such as benzene, toluene or xylene, and more preferred examples are ethers and amides.

The base used in the above reaction is not particularly limited provided that it can be used as the base in conventional reactions. Examples of preferred bases include inorganic bases including alkali metal hydrides such as lithium hydride, sodium hydride or potassium hydride; and alkali metal fluorides such as sodium fluoride or potassium fluoride; alkali metal alkoxides such as sodium methoxide, sodium ethoxide, potassium methoxide, potassium ethoxide, potassium t-butoxide or lithium methoxide; or organic metallic bases such as butyl lithium, lithium diisopropylamide or lithium bis(trimethylsilyl)amide, and more preferred examples are alkali metal alkoxides and alkali metal hydrides.

The reaction temperature mainly depends on the starting material compounds, the solvent and the base employed in the reaction. The reaction is usually carried out at a temperature of from −80° C. to 100° C. and preferably from 0° C. to 50° C.

The reaction time mainly depends on the starting material compounds, the reaction temperature, the solvent and the base employed in the reaction. The reaction is usually carried out in a period of from 5 minute to 48 hours.

For example, after neutralizing the reaction mixture with diluted hydrochloric acid and the like and removing, if any, insoluble material(s) by filtration, the target compound can be obtained by concentrating the reaction mixture or conducting the following steps successively: adding an organic solvent which is not miscible with water (e.g. ethyl acetate); separating the organic layer containing the target compound; and then drying over anhydrous sodium sulfate, anhydrous magnesium sulfate or the like; and removing solvent by evaporation.

The target compound obtained can be isolated and purified, if necessary, by conventional methods such as recrystallization, reprecipitation or chromatography using appropriate eluent(s).

Step E6 is a step for preparing a compound (La-1) which is a compound (La) where $R^1$ is a hydrogen atom and $R^2$ and $R^{3a}$ together form a group (—(C=O)—). In this step, a compound (IL) is converted into the target compound (La-1) in an inert solvent in the presence of a reducing agent.

The solvent used in the above-mentioned reaction is not particularly limited provided that it has no adverse effect on the reaction and dissolves the starting materials to some extent. Examples of preferred solvents include alcohols such as methanol, ethanol or isopropanol; ethers such as diethyl ether, diisopropyl ether, t-butyl methyl ether, tetralydrofuran or dioxane, aromatic hydrocarbons such as benzene, toluene or xylene; aliphatic hydrocarbons such as hexane or cyclohexane; or esters such as ethyl acetate or propyl acetate. Of these solvents, alcohols are preferred.

The reducing agent used in the above reaction is not particularly limited provided that it is usually used in catalytic hydrogenations. Examples of preferred reducing agents include palladium-on-charcoal, platinum oxide, platinum black, rhodium-aluminium oxide, triphenylphosphine-rhodium chloride (Wilkinson complex), palladium-barium sulfate or Raney nickel, and palladium-on-charcoal is most preferred.

The pressure in the reduction reaction is not particularly limited, but the reaction is usually carried out at a pressure of from 1 to 10 atmospheric pressures.

The reaction temperature mainly depends on the starting material compounds, the solvent and the base employed in the reaction. The reaction is usually carried out at a temperature of from 0° C. to 100° C.

The reaction time mainly depends on the starting material compounds, the reaction temperature, the solvent and the base employed in the reaction. The reaction is usually carried out in a period of from 5 minutes to 48 hours.

For example, after removing the catalyst by filtration, the target compound can be obtained by concentrating the reaction mixture or conducting the following steps successively: adding an organic solvent which is not miscible with water (e.g. ethyl acetate); separating the organic layer containing the target compound; and then drying over anhydrous sodium sulfate, anhydrous magnesium sulfate or the like; and removing solvent by evaporation.

The target compound obtained can be isolated and purified, if necessary, by conventional methods such as recrystallization, reprecipitation or chromatography using appropriate eluent(s).

In Step E7, a compound (XLVII) is converted into a compound of general formula (LI) in an inert solvent in the presence of a reducing agent. This step is carried out in a similar manner to that described earlier in Step E6 of the method E.

In Step E8, a compound (La-2) which is a compound (La) where $R^{3a}$ is a hydrogen atom is prepared by hydrolyzing a compound (LI) in an inert solvent in the presence of a base. This step is carried out in a similar manner to that described earlier in Step E4 of the method E.

Step E9 is a step for preparing a compound (La-1), and in this step, a compound (La-2) is converted into the compound (La-1) in an inert solvent in the presence of a base. This step is carried out in a similar manner to that described earlier in Step E5 of the method E.

In Step E10, if necessary, a compound (La-3) which is a compound (La) where $R^2$ and $R^{3a}$ together do not form a group (—(C=O)—) is prepared by protecting a hydroxyl group of the compound (La-2). The reaction of this step depends on the nature of the hydroxyl group to be protected, but it can be carried out by the procedures, for example, described in Protective Groups in Organic Synthesis (third Edition, 1999, John Wiley & Sons, Inc.).

Alternatively, a compound (Lb-3) can be prepared by conducting the steps E2–E10 of the method E successively using a compound (XLIVb) as the starting material instead of a compound (XLTVa).

In Method F, a compound (XLVI) is synthesized.

Method F

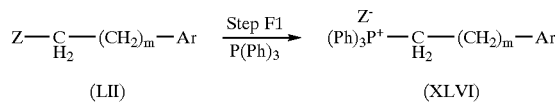

In the above scheme, Ar and Z are as defined earlier.

In Step F1, a compound (XLVI) is prepared by the reaction of a compound of general formula (LII) with triphenylphosphine in an inert solvent.

The inert solvent used in the above-mentioned reaction is not particularly limited provided that it has no adverse effect on the reaction. Examples of suitable solvents include aliphatic hydrocarbons such as hexane, heptane, ligroin or petroleum ether; aromatic hydrocarbons such as toluene, benzene or xylene; halogenated hydrocarbons such as methylene chloride, chloroform, carbon tetrachloride, dichloroethane, chlorobenzene or dichlorobenzene; or ethers such as diethyl ether, diisopropyl ether, tetrahydrofuran, dioxane, dimethoxyethane or di(ethylene glycol) dimethyl ether. Of these solvents, aromatic hydrocarbons (particularly benzene) are preferred.

The reaction temperature mainly depends on the starting material compounds and the solvent employed in the reaction. The reaction is usually carried out at a temperature of from room temperature to 200° C., preferably from 0° C. to 150° C. and most preferably at 10° C.

The reaction time mainly depends on the reaction temperature, the starting material compounds and the solvent employed in the reaction. The reaction is usually carried out in a period of from 5 minutes to 96 hours, preferably from 15 minutes to 48 hours and most preferably in 24 hours.

The product thus prepared in each step of the Method F can be, if necessary, isolated and purified by conventional techniques such as recrystallization, reprecipitation or procedures that are usually used for the isolation and purification of organic compounds. Examples of the suitable techniques include adsorption column chromatography using a stationary phase such as silica gel, alumina or florisil composed of magnesium-silica gel; partition chromatography using a synthetic adsorbent such as Sephadex LH-20 (Pharmacia), Amberlite XAD-11 (Rohm & Haas) or Diaion HP-20(Mitsubishi Chemical Company); ion-exchange chromatography; or normal and reversed phase liquid chromatography using silica gel or alkylated silica gel (preferably high performance liquid chromatography). The target compound prepared at each step is isolated and purified by any of these techniques or a suitable combination of these techniques using an appropriate solvent(s) as an eluent.

The separation of the isomers can be, if necessary, carried out by means of any of the separation/purification procedures mentioned above after the completion of the reaction of each step or at the suitable stage after the completion of the desired step.

The compounds such as (XXVIII), (XXXIV), (XLII), (XLIII) and (LII) used as the starting materials are either known compounds or can be prepared easily by known or similar methods.

The aminoalcohol derivatives of the general formula (I) of the present invention, pharmacologically acceptable salts, esters or other derivatives thereof exhibit an excellent immunosuppressive effect with low toxicity. Further, pharmaceutical compositions containing the compound having the general formula (I) of the present invention or a pharmacologically acceptable salt, ester or other derivative thereof as the active ingredient are useful as preventives and/or therapeutic agents for, particularly, autoimmune diseases such as systemic lupus erythematosus, rheumatoid arthritis, polymyositis, dermatomyositis, scleoderma, Behcet's disease, Chron disease, ulcerative colitis, autoimmune hepatitis, aplastic anemia, idiopathic thrombocytopenic purpura, autoimmune hemolytic anemia, multiple sclerosis, autoimmune bullosis, vulgarity psoriasis, vasculitis syndrome, Wegener's granuloma, uveitis, cryptogenic fibrosing alveolitis, Goodpasture's syndrome, sarcoidosis, allergic granulomatous angitis, bronchial asthma, myocarditis, cardiomyopathy, aortic arch syndrome, myocardial postinfarction syndrome, primary pulmonary hypertension, minimal change nephrotic syndrome, membranous nephropathy, membranoproliferative glomerulonephritis, focal glomerular sclerosis, crescent glomerulonephritis, myasthenia gravis, inflammatory neuropathy, atopic dermatitis, chronic actinic dermatitis, acute polyarthritis, Sydenhan chorea disease, progressive systemic sclerosis, adult onset type diabetes mellitus, insulin dependent diabetes mellitus, juvenile diabetes, atherosclerosis, glomerular nephritis, tuburointerstitial nephritis, primary biliary cirrhosis, primary sclerosing cholangitis, fulminant hepatic failure, viral hepatitis, GVHD, immunological rejection following organ transplantation, contact dermatitis, sepsis, or other immunology related diseases.

In addition, the novel optically active aminoalcohol compounds such as (La) and (Lb) of the present invention are useful as intermediates for the manufacturing of the medicaments.

On the other hand, optically active 2-substituted-2-amino-1,3-propanediol monoester derivatives (XLIVa) and (XLIVb) are preferred synthetic intermediates in the production of the optically active aminoalcohol compounds (La) and (Lb) mentioned above and can be prepared easily and conveniently in a good yield by acylating selectively only one of the hydroxyl groups of the 2-substituted-2-amino-1,3-propanediol derivative (XLII) used as the starting material with a vinyl carboxylate derivative (XLIII) in the presence of lipase.

The compounds of general formula (I) of the present invention and pharrnacologically acceptable salts or esters thereof can be administered for treatment or prevention of the above-mentioned diseases as a suitable dosage form, which is prepared from the compound alone or by mixing with a suitable pharmacologically acceptable excipient and/or diluent, such as tablets, capsules, granules, powders or syrups for oral administration, or injections or suppositories for parenteral administration.

Such formulations may be prepared, according to well known techniques, using additives such as excipients, lubricants, binders, disintegrators, stabilizers, corrigents and/or diluents. Examples of suitable excipients include organic excipients including glucose derivatives such as lactose, sucrose, glucose, mannitol and sorbitol; starch derivatives such as corn starch, potato starch, α-starch and dextrin; cellulose derivatives such as crystalline cellulose; gum Arabic; dextran; and Pullulan, and inorganic excipients including silicate derivatives such as anhydrous light silicic acid, synthetic aluminium silicate, calcium silicate and magnesium metaaluminosilicate; phosphates such as calcium hydrogen phosphate; carbonates such as calcium carbonate; and sulfates such as calcium sulfate. Examples of suitable lubricants include stearic acid; metal stearates such as calcium stearate and magnesium stearate; talc; colloidal silica; waxes such as bee gum or spermaceti; boric acid; adipic acid; sulfates such as sodium sulfate; glycol; fumaric acid; sodium benzoate; DL leucine; sodium salt of fatty acid; lauryl sulfates such as lauryl sodium sulfate or lauryl magnesium sulfate; silicates such as anhydrous silicic acid or silicic hydrate; and the above-mentioned starch derivatives. Examples of suitable binders include hydroxypropyl cellulose, hydroxypropyl methylcellulose, polyvinylpyrrolidone, Macrogol and the compounds described above as an excipient. Examples of suitable disintegrators include cellulose derivatives such as low substituted hydroxypropylcellulose, carboxymethyl cellulose, calcium carboxymethyl cellulose, internal-crosslinked sodium carboxymethyl cellulose; chemically modified starch-cellulose derivatives such as carboxymethyl starch, sodium carboxymethyl starch or cross-linked polyvinylpyrrolidone. Examples of suitable stabilizers include p-hydroxybenzoic esters such as methylparaben or propylparaben; alcohols such as chlorobutanol, benzyl alcohol or phenylethyl alcohol; benzalkonium chloride; phenols such as phenol or cresol; thimerosal; dehydroacetic acid; and sorbic acid. Corrigents include sweeteners, souring agents and flavors that are commonly used in the art.

The dosage may vary depending on a variety of factors such as the symptoms and age of the patient and route of administration. A suitable dosage level for oral administration is from 0.05 mg (preferably 5 mg) per day as a lower limit to 200 mg (preferably 40 mg) per day as an upper limit for adults (e.g. human adults). On the other hand, a suitable dosage level for intravenous administration is from 0.01 mg (preferably 1 mg) per day as a lower limit to 100 mg (preferably 10 mg) per day as an upper limit for adults. The dosage can be administered either as a single unit dosage or, if necessary, the dosage may be divided into convenient sub-units and administered from one to six times throughout the day depending on the symptoms of the patient (e.g. human patient).

The present invention is further dscribed by Examples and Test examples, however this invention is not limited to these Examples and Test examples.

EXAMPLE 1
(2R)-Amino-2-methyl-4-[5-(5-cyclohexylpent-1-ynyl)thiophen-2-yl]butan-1-ol (Exemplification Compound No.1-770)

EXAMPLE 1 (a)
2-Methyl-2-(2-thienyl)ethylmalonic acid diethylester

Sodium hydride (55%, 18.8 g, 0.43 mol) was suspended in dimethylformamide (200 ml), and methylmalonic acid diethylester (50.0 g, 0.29 mol) was slowly added thereto for 30 minutes in an ice bath, and then the reaction solution was stirred for 30 minutes. To the reaction solution was added 2-(2-iodoethyl)thiophene (75.2 g, 0.32 mol) dissolved in dimethylformamide (200 ml) under-a nitrogen atmosphere for 15 minutes, and then the reaction mixture was stirred for 4 hours at room temperature. The reaction mixture was poured into ice-cold 10% hydrochloric acid (500 ml), and extracted with ethyl acetate. The organic layer was washed with a saturated aqueous sodium chloride solution, and dried over anhydrous magnesium sulfate. The solvent was concentrated under reduced pressure, and the residue was purified by flash chromatography on a silica gel column (elution solvent; hexane:ethyl acetate=10:1–5:1) to afford the title compound (53.1 g, 65% yield) as a colorless oil.

Infrared absorption spectrum $v_{max}$ cm$^{-1}$ (CHCl$_3$): 2986, 1726, 1271, 1252

Mass spectrum (FAB) m/z: 285 (((M+H)$^+$)

EXAMPLE 1 (b)
2-Methyl-2-(2-thienyl)ethylmalonic acid monoethylester

2-Methyl-2-(2-thienyl)ethylmalonic acid diethylester (52.7 g, 0.19 mol) obtained in Example 1) (a) was dissolved in a mixture of ethanol (240 ml) and water (80 ml), potassium hydroxide (11.4 g, 0.20 mol) was added thereto in an ice bath, and the solution was stirred for 2 hours. And then potassium hydroxide (5.7 g, 0.1 mol) was added thereto three times, one portion every 1 hour, and the reaction solution was stirred for 6 hours in total. Water (300 ml) and ice-cold 10% hydrochloric acid (500 ml) were added to the reaction solution, and the solution was extracted with ethyl acetate. The organic layer was washed with a saturated aqueous sodium chloride solution, and dried over anhydrous magnesium sulfate. The solvent was concentrated in vacuo, and the residue was purified by flash chromatography on a silica gel column (elution solvent; hexane:ethyl acetate=2:1–0:1) to afford the title compound (28.6 g, 60% yield) as a pale yellow oil.

Infrared absorption spectrum $v_{max}$ cm$^{-1}$ (CHCl$_3$): 2987, 1732, 1712, 1251, 1109

Mass spectrum (FAB) m/z: 257 ((M+H)$^+$)

EXAMPLE 1 (c)
2-Methoxycarbonylamino-2-methyl-4-(2-thienyl)butanoic acid ethylester 2-Methyl-2-(2-thienyl)ethylmalonic acid monoethylester (19.0 g, 74.3 mmol) obtained in Example 1 (b) was dissolved in benzene (450 ml), and triethylamine (11.4 ml, 81.7 mmol) and diphenylphosphoric acid azide (17.6 ml, 81.7 mmol) were added thereto, and after stirring for 10 minutes at room temperature, the reaction solution was stirred for another 1.5 hours at 80° C. Subsequently, methanol (60.3 ml, 1.49 mol) was slowly added dropwise thereto for 30 minutes at 80° C. followed by stirring for 8 hours. The reaction mixture was poured into water (500 ml) and extracted with ethyl acetate. The organic layer was washed with a saturated aqueous sodium chloride solution, and dried over anhydrous magnesium sulfate. The solvent was concentrated in vacuo, and the residue was purified by flash chromatography on a silica gel column (elution solvent; hexane:ethyl acetate= 8:1–4:1) to afford the title compound (14.7 g, 69% yield) as a colorless oil.

Nuclear magnetic resonance spectrum (400 MHz, CDCl$_3$) δ ppm: 7.11 (1H, d, J=5.1 Hz), 6.90 (1H, dd, J=5.1, 3.5 Hz), 6.77 (1H, d, J=3.5 Hz), 5.69 (1H, brs), 4.19 (2H, q. J=7.3 Hz), 3.66 (3H, s), 2.84 (2H, dd, J=10.5, 10.5 Hz), 2.64 (2H, m), 2.20 (2H, dd, J=10.5, 8.4 Hz), 1.61 (3H, s), 1.28 (3H, t, J=7.3 Hz)

Infrared absorption spectrum $v_{max}$ cm$^{-1}$ (CHCl$_3$): 3417, 2987, 1719, 1503, 1453, 1081

Mass spectrum (FAB) m/z: 286 ((M+H)$^+$)

EXAMPLE 1 (d)
2-Methoxycarbonylamino-2-methyl-4-(2-thienyl)butan-1-ol

2-Methoxycarbonylamino-2-methyl-4-(2-thienyl) butanoic acid ethylester (14.7 g, 51.6 mmol) obtained in Example 1 (c) was dissolved in a mixture of ethanol (150 ml) and tetrahydrofuran (100 ml), and then sodium borohydride (5.07 g, 0.13 mol) and lithium chloride (5.68 g, 0.13 mol) were added thereto followed by stirring overnight at room temperature under a nitrogen atmosphere. And next morning, sodium borohydride (5.07 g, 0.13 mol) and lithium chloride (5.68 g, 0.13 mol) were added thereto in a similar way, and the reaction mixture was stirred once more overnight at room temperature under a nitrogen atmosphere. Similar procedures described above were carried out for more two days. The reaction mixture was poured into ice-cold 10% hydrochloric acid (500 ml), and the resulting solution was extracted with ethyl acetate. The organic layer was washed with a saturated aqueous sodium chloride solution, and dried over anhydrous magnesium sulfate. The solvent was concentrated in vacuo, and the residue was purified by flash chromatography on a silica gel column (elution solvent; hexane:ethyl acetate=2:1–1:5) to afford the title compound (11.7 g, 93% yield) as a white crystalline solid.

Infrared absorption spectrum $v_{max}$ cm$^{-1}$ (KBr): 3406, 3244, 1687, 1562, 1264, 1089

Mass spectrum (FAB) m/z: 244 ((M+H)$^+$) Anal. Calcd. (%) for C$_{11}$H$_{17}$NO$_3$S: C, 54.30; H, 7.04; N, 5.76; S, 13.18. Found: C, 54.18; H, 6.98; N, 5.78; S, 13.34.

EXAMPLE 1 (e)
2-Methoxycarbonylamino-2-methyl-4-(5-bromothiophen-2-yl)butan-1-ol 2-Methoxycarbonylamino-2-methyl-4-(2-thienyl)butan-1-ol (11.7 g, 48.0 mmol) obtained in Example 1 (d) was dissolved in dimethylformamide (120 ml), and N-bromosuccinimide (10.8 g, 60.8 mmol) was added thereto in an ice bath followed by stirring for 4 hours at room temperature under a nitrogen atmosphere. The reaction mixture was poured into ice-cold 10% hydrochloric acid (300 ml), and extracted with ethyl acetate. The organic layer was washed with a saturated aqueous sodium chloride solution, and dried over anhydrous magnesium sulfate. The solvent was concentrated in vacuo, and the residue was purified by flash chromatography on a silica gel column (elution solvent; hexane:ethyl acetate=4:1–1:3) to afford the title compound (12.4 g, 80% yield) as a pale yellow oil.

Nuclear magnetic resonance spectrum (400 MHz, CDCl$_3$) δ ppm: 6.84 (1H, d, J=3.7 Hz), 6.57 (1H, d, J=3.7 Hz), 4.80 (1H, brs), 3.68 (2H, m), 3.64 (3H, s), 2.80 (2H, m), 1.9–2.2 (2H, m), 1.24 (3H, s)

Infrared absorption spectrum $v_{max}$ cm$^{-1}$ (CHCl$_3$): 3627, 3436, 2956, 1722, 1711, 1513, 1259, 1087, 1048

Mass spectrum (FAB) m/z: 322 ((M+H)$^+$)

EXAMPLE 1 (f)
4-[2-(5-Bromothiophen-2-yl)]ethyl-4-methyloxazolidin-2-one

2-Methoxycarbonylamino-2-methyl-4-(5-bromothiophen-2-yl)butan-1-ol (12.4 g, 38.6 mmol) obtained in Example 1 (e) was dissolved in dimethylformamide (125 ml), and potassium t-butoxide (6.50 g, 57.9 mmol) was added thereto in an ice bath under a nitrogen atmosphere followed by stirring for 3 hours at the same temperature. The reaction mixture was poured into ice-cold 10% hydrochloric acid (300 ml), and extracted with ethyl acetate. The organic layer was washed with a saturated aqueous sodium chloride solution, and dried over anhydrous magnesium sulfate. The solvent was concentrated in vacuo, and the residue was purified by flash chromatography on a silica gel column (elution solvent; hexane:ethyl acetate= 4:1–1:2) to afford the title compound (10.7 g, 95% yield) as a white crystalline solid.

Nuclear magnetic resonance spectrum (400 MHz, CDCl$_3$) δ ppm: 6.86 (1H, d, J=3.7 Hz), 6.58 (1H, d, J=3.7 Hz), 5.73 (1H, brs), 4.18 (1H, d, J=8.6 Hz), 4.08 (1H, d, J=8.6 Hz), 2.84 (2H, m), 1.94 (2H, m), 1.41 (3H, s)

Infrared absorption spectrum $v_{max}$ cm$^{-1}$ (KBr): 3211, 1749, 1399, 1037, 798

Mass spectrum (FAB) m/z: 290 ((M+H)$^+$) Anal. Calcd. (%) for C$_{10}$H$_{12}$NO$_2$SBr: C, 41.39; H, 4.17; N, 4.83; S, 11.05; Br, 27.54. Found: C, 41.36; H, 4.04; N, 4.82; S, 11.08; Br, 27.29.

EXAMPLE 1 (g)
(4R)-[2-(5-Bromothiophen-2-yl)]ethyl-4-methyloxazolidin-2-one and (4S)-[2-(5-Bromothiophen-2-yl)]ethyl-4-methyloxazolidin-2-one 4-[2-(5-Bromothiophen-2-yl)]ethyl-4-methyloxazolidin-2-one obtained in Example 1 (f) was subjected to chromatographic optical resolution using preparative HPLC with a chiral stationary phase column (ChiralCel OD, Daicel Chemical Industries, LTD.), (column, ChiralCel OD (2 cmφ×25 cm); elution solvent, hexane:2-propanol=70:30; flow rate, 5 ml/min). The former compound, which was eluted at 55 minutes, was the 4S-form, and the latter compound eluted at 77 minutes was the 4R-form. Their absolute configurations were determined by X-ray crystal structure analysis.

(4S) Form; [α]$_D^{24}$ −4.2 (c 1.03, methanol)
(4R) Form; [α]$_D^{24}$ +4.2 (c 1.00, methanol)

EXAMPLE 1 (h)
(4R)-{2-[5-(5-Cyclohexylpent-1-ynyl)thiophen-2-yl]}ethyl-4-methyloxazolidin-2-one (4R)-[2-(5-Bromothiophen-2-yl)]ethyl-4-methyloxazolidin-2-one (450 mg, 1.55 mmol) obtained in Example 1 (g) was dissolved in dimethylformamide (4.5 ml), and 5-cyclohexylpent-1-yne (50% xylene solution) (1.4 g, 4.65 mmol), triethylamine (2.16 ml, 15.5 mmol), copper (I) iodide (30 mg, 0.16 mmol) and dichlorobis (triphenylphosphine)palladium (109 mg, 0.16 mmol) were added thereto, and then the reaction mixture was stirred for 2 hours at 80° C. under a nitrogen atmosphere. The reaction solution was poured into water, extracted with ethyl acetate, and the ethyl acetate layer was washed with a saturated aqueous sodium chloride solution. After the ethyl acetate layer was dried over anhydrous sodium sulfate, the solvent was concentrated in vacuo, and the residue was purified by chromatography on a silica gel column (elution solvent; hexane:ethyl acetate=4:1–3:2) to afford the title compound (56 mg, 82% yield).

Nuclear magnetic resonance spectrum (400 MHz, CDCl$_3$) δ ppm: 6.92 (1H, d, J=3.6 Hz), 6.63 (1H, d, J=3.6 Hz), 5.45 (1H, brs), 4.18 (1H, d, J=8.6 Hz), 4.07 (1H, d, J=8.6 Hz), 2.78–2.90 (2H, m), 2.38 (2H, t, J=7.2 Hz), 1.92–2.00 (2H, m), 1.55–1.75 (7H, m), 1.40 (3H, s), 1.10–1.35 (6H, m), 0.83–0.95 (2H, m)

Infrared absorption spectrum $v_{max}$ cm$^{-1}$ (KBr): 3450, 2926, 2852, 1758, 1382, 1046

EXAMPLE 1 (i)
(2R)-Amino-2-methyl-4-[5-(5-cyclohexylpent-1-ynyl) thiophen-2-yl]butan-1-ol (4R)-{2-[5-(5-Cyclohexylpent-1-ynyl)thiophen-2-yl]}ethyl-4-methyloxazolidin-2-one (456 mg, 1.27 mmol) obtained in Example 1 (h) was dissolved in a mixture of tetrahydrofuran (1 ml) and methanol (2 ml), and a 5 N aqueous potassium hydroxide solution (2 ml) was added thereto in an ice bath followed by heating under reflux for 18 hours. Water was added to the reaction solution, and the resulting mixture was extracted with dichloromethane. After the layer of dichloromethane was dried over anhydrous sodium sulfate, the solvent was concentrated in vacuo, and the residue was purified by chromatography on a silica gel column (elution solvent; dichloromethane:methanol=20:1-dichloromethane:methanol:aqueous ammonia=10:1:0.1) to afford the title compound (353 mg, 83% yield).

Nuclear magnetic resonance spectrum (400 MHz, CDCl$_3$) δ ppm: 6.92 (1H, d, J=3.5 Hz), 6.62 (1H, d, J=3.5 Hz), 3.37 (1H, d, J=10.5 Hz), 3.32 (1H, d, J=10.5 Hz), 2.75–2.90 (2H, m), 2.38 (2H, t, J=7.1 Hz), 1.52–1.79 (9H, m), 1.12–1.33 (6H, m), 1.11 (3H, s), 0.81–0.96 (2H, m)

Infrared absorption spectrum $v_{max}$ cm$^{-1}$ (CHCl$_3$): 2925, 2852, 1449, 1041

Mass spectrum (FAB) m/z: 334 ((M+H)$^+$) Anal. Calcd. (%) for C$_{20}$H$_{31}$NOS.0.3H$_2$O: C, 70.87; H, 9.40; N, 4.13; S, 9.46. Found: C, 70.83; H, 9.21; N, 4.22; S, 9.64. [α]$_D^{24}$ –2.0(c 0.60, methanol)

EXAMPLE 2
(2R)-Amino-2-methyl-4-[5-(6-cyclohexylhex-1-ynyl) thiophen-2-yl]butan-1-ol (Exemplification Compound No.1-882)

The title compound was obtained according to a similar reaction to that described in Example 1.

Nuclear magnetic resonance spectrum (400 MHz, CDCl$_3$) δ ppm: 6.91 (1H, d, J=3.6 Hz), 6.62 (1H, d, J=3.6 Hz), 3.39 (1H, d, J=10.7 Hz), 3.34 (1H, d, J=10.7 Hz), 2.82 (2t, J=8.5 Hz), 2.40 (2H, t, J=6.9 Hz), 2.18–1.92 (4H, m), 1.88–1.51 (8H, m), 1.47–1.38 (2H, m), 1.28–1.07 (9H, m), 0.93–0.78 (2H, m)

Infrared absorption spectrum $v_{max}$ cm$^{-1}$ (KBr): 3327, 3275, 2922, 2850, 1611, 1563, 1539, 1447, 1065, 1040, 803, 521

EXAMPLE 3
2-Amino-2-methyl-4-[5-(5-phenylpent-1-ynyl)thiophen-2-yl]butan-1-ol (Exemplification Compound No.1-824)

The title compound was obtained according to a similar reaction to that described in Example 1 using a racemic mixture of 4-[2-(5-bromothiophen-2-yl)]ethyl-4-methyloxazolidin-2-one as a starting material.

Nuclear magnetic resonance spectrum (400 MHz, CDCl$_3$) δ ppm: 7.32–7.26 (2H, m), 7.25–7.16 (3H, m), 6.94 (1H, d, J=3.6 Hz), 6.93 (1H, d, J=3.6 Hz), 3.37 (1H, d, J=10.8 Hz), 3.31 (1H, d, J=10.4 Hz), 2.83 (2H, t, J=8.4 Hz), 2.77 (2H, t J=7.6 Hz), 2.42 (2H, t, J=7.2 Hz), 1.96–1.85 (2H, m), 1.84–1.64(2H, m), 1.50 (3H, brs), 1.11 (3H, s)

Infrared absorption spectrum $v_{max}$ cm$^{-1}$ (liquid film): 2931, 2859, 1748, 1602, 1584, 1538, 1496, 1455, 1191, 1053, 908, 804, 747, 700, 573

EXAMPLE 4
2-Amino-2-methyl-4-{5-[5-(4-methoxyphenyl)pent-1-ynyl]thiophen-2-yl}butan-1-ol hydrochloride (Exemplification Compound No.1-849)

The title compound was obtained according to a similar reaction to that described in Example 1 using a racemic mixture of 4-[2-(5-bromothiophen-2-yl)]ethyl-4-methyloxazolidin-2-one as a starting material.

Nuclear magnetic resonance spectrum (400 MHz, CDCl$_3$) δ ppm: 8.07 (3H, brs), 7.10 (2H, d, J=8.6 Hz), 6.89 (1H, d, J=3.5 Hz), 6.81 (2H, d, J=8.6 Hz), 6.65 (1H, d, J=3.5 Hz), 4.72 (1H, brs), 3.77 (3H, s), 3.65 (2H, s), 2.78–2.97 (2H, m), 2.66 (2H, t, J=7.5 Hz), 2.36 (2H, t, J=7.1 Hz), 1.77–2.20 (4H, m), 1.36 (3H, s)

Infrared absorption spectrum $v_{max}$ cm$^{-1}$ (KBr): 3370, 3009, 2932, 1589, 1511, 1245, 1070, 1036

EXAMPLE 5
2-Amino-2-methyl-4-{5-[5-(4-fluorophenyl)pent-1-ynyl]thiophen-2-yl}butan-1-ol maleate (Exemplification Compound No. 1-833)

The title compound was obtained according to a similar reaction to that described in Example 1 using a racemic mixture of 4-[2-(5-bromothiophen-2-yl)]ethyl-4-methyloxazolidin-2-one as a starting material.

Nuclear magnetic resonance spectrum (400 MHz, CD$_3$OD) δ ppm: 7.18–7.25 (2H, m), 6.95–7.03 (2H, m), 6.94 (1H, d, J=3.6 Hz), 6.73 (1H, d, J=3.6 Hz), 6.25 (2H, s), 3.61 (1H, d, J=11.6 Hz), 3.52 (1H, d, J=11.6 Hz), 2.80–2.95 (2H, m), 2.74 (2H, t, J=7.6 Hz), 2.40 (2H, t, J=7.0 Hz), 1.80–2.10 (4H, m), 1.31 (3H, s)

Infrared absorption spectrum $v_{max}$ cm$^{-1}$ (KBr): 3352, 2940, 1578, 1509, 1385, 1367, 1221, 1194

EXAMPLE 6
2-Amino-2-methyl-4-[5-(biphenyl-4-yl)ethynylthiophen-2-yl]butan-1-ol (Exemplification Compound No.1-742)

The title compound was obtained according to a similar reaction to that described in Example 1 using a racemic mixture of 4-[2-(5-bromothiophen-2-yl)]ethyl-4-methyloxazolidin-2-one as a starting material.

Nuclear magnetic resonance spectrum (400 MHz, CDCl$_3$) δ ppm: 7.55–7.65 (6H, m), 7.43–7.50 (2H, m), 7.33–7.40 (1H, m), 7.11 (1H, d, J=3.6 Hz), 6.72 (1H, d, J=3.6 Hz), 3.39 (1H, d, J=10.4 Hz), 3.34 (1H, d, J=10.4 Hz), 2.80–2.95 (2H, m), 1.70–1.90 (2H, m), 1.13 (3H, s)

Infrared absorption spectrum $v_{max}$ cm$^{-1}$ (KBr): 3335, 3075, 2924, 1485, 1463, 1051, 837, 809, 764, 698

EXAMPLE 7
2-Amino-2-methyl-4-[5-(4-butylphenyl)ethynylthiophen-2-yl]butan-1-ol (Exemplification Compound No.1-737)

The title compound was obtained according to a similar reaction to that described in Example 1 using a racemic mixture of 4-[2-(5-bromothiophen-2-yl)]ethyl-4-methyloxazolidin-2-one as a starting material.

Nuclear magnetic resonance spectrum (400 MHz, CDCl$_3$) δ ppm: 7.42 (2H, d, J=8.1 Hz), 7.36–7.15 (5H, m), 7.16 (2H, d, J=8.1 Hz), 7.07 (1H, d, J=3.3 Hz), 6.70 (1H, d, J=3.3 Hz), 3.99 (2H, s), 3.36–3.24 (2H, m), 2.92–2.81 (2H, m), 2.01–1.95 (2H, m), 2.65–2.26 (3H, m), 1.11 (3H, s) Infrared absorption spectrum $\nu_{max}$ cm$^{-1}$ (KBr): 3326, 3264, 2926, 2904, 1603, 1541, 1485, 1468, 1454, 1211, 1063, 1033, 803, 701

EXAMPLE 8

2-Amino-2-methyl-4-[5-(4-cyclohexylphenyl)ethynylthiophen-2-yl]butan-1-ol (Exemplification Compound No.1-741)

The title compound was obtained according to a similar reaction to that described in Example 1 using a racemic mixture of 4-[2-(5-bromothiophen-2-yl)]ethyl-4-methyloxazolidin-2-one as a starting material.

Nuclear magnetic resonance spectrum (400 MHz, DMSO-d$_6$) δ ppm: 7.42 (2H, d, J=8.2 Hz), 7.26 (2H, d, J=8.2 Hz), 7.20 (1H, d, J=3.6 Hz), 6.83 (1H, d, J=3.6 Hz), 3.56–3.24 (5H, m), 2.88–2.70 (2H, m), 1.89–1.52 (7H, m), 1.43–1.21 (6H, m), 0.97 (3H, s)

Infrared absorption spectrum $\nu_{max}$ cm$^{-1}$ (KBr): 3326, 3279, 2924, 2850, 1645, 1567, 1539, 1448, 1385, 1055, 826, 547

EXAMPLE 9

2-Amino-2-methyl-4-[5-(4-propylphenyl)ethynylthiophen-2-yl]butan-1-ol (Exemplification Compound No.1-736)

The title compound was obtained according to a similar reaction to that described in Example 1 using a racemic mixture of 4-[2-(5-bromothiophen-2-yl)]ethyl-4-methyloxazolidin-2-one as a starting material.

Nuclear magnetic resonance spectrum (400 MHz, CD$_3$OD) δ ppm: 7.36 (2H, d, J=8.2 Hz), 7.18(2H, d, J=8.2 Hz), 7.06 (1H, d, J=3.5 Hz), 6.76 (1H, d, J=3.5 Hz), 3.39 (1H, d, J=10.7 Hz), 3.38 (1H, d, J=10.7 Hz), 2.93–2.80 (2H, m), 2.69–2.58 (2H, m), 1.83–1.59 (4H, m), 1.10 (3H, s), 0.94 (3H, t, J=7.3 Hz)

Infrared absorption spectrum $\nu_{max}$ cm$^{-1}$ (KBr): 3323, 3267, 2959, 2929, 2869, 1611, 1540, 1510, 1468, 1213, 1066, 1035, 816, 804, 510

EXAMPLE 10

2-Amino-2-methyl-4-[5-(4-propyloxyphenyl)ethynylthiophen-2-yl]butan-1-ol (Exemplification Compound No.1-740)

The title compound was obtained according to a similar reaction to that described in Example 1 using a racemic mixture of 4-[2-(5-bromothiophen-2-yl)]ethyl-4-methyloxazolidin-2-one as a starting material.

Nuclear magnetic resonance spectrum (400 MHz, CD$_3$OD) δ ppm: 7.37 (2H, d, J=8.9 Hz), 7.03 (1H, d, J=3.6 Hz), 6.89 (2H, d, J=8.9 Hz), 6.75 (1H, d, J=3.6 Hz), 3.95 (2H, t, J=6.3 Hz), 3.39 (1H, d, J=10.7 Hz), 3.35 (1H, d, J=10.7 Hz), 2.92–2.78 (2H, m), 1.86–1.72 (4H, m), 1.09 (3H, s), 1.04 (3H, t, J=7.6 Hz)

Infrared absorption spectrum $\nu_{max}$ cm$^{-1}$ (KBr): 3329, 3275, 2964, 2936, 1604, 1509, 1466, 1249, 1065, 975, 832, 807

EXAMPLE 11

(2R)-Amino-2-methyl-4-[5-(5-cyclohexylpentyl)thiophen-2-yl]butan-1-ol (Exemplification Compound No.1-98)

(2R)-Amino-2-methyl-4-[5-(5-cyclohexylpent-1-ynyl)thiophen-2-yl]butan-1-ol (175 mg, 0.53 mmol) obtained in Example 1 was dissolved in ethanol (9 ml), and 10% palladium-charcoal (90 mg) was added thereto, and then the mixture was stirred under a hydrogen atmosphere for 2 hours. After the palladium-charcoal was filtered out through Celite, the filtrate was evaporated to dryness under reduced pressure to give the title compound (150 mg, 85% yield).

Nuclear magnetic resonance spectrum (400 MHz, CDCl$_3$) δ ppm: 6.58 (1H, d, J=3.2 Hz), 6.55 (1H, d, J=3.2 Hz), 3.36 (1H, d, J=10.5 Hz), 3.31 (1H, d, J=10.5 Hz), 2.75–2.90 (2H, m), 2.73 (2H, t, J=7.6 Hz), 1.59–1.83 (9H, m), 1.12–1.32 (10H, m), 1.11(3H, s), 0.81–0.89 (2H, m)

Infrared absorption spectrum $\nu_{max}$ cm$^{-1}$ (CHCl$_3$): 2926, 2853, 1440, 1042

Mass spectrum (FAB) m/z: 338 ((M+H)$^+$) Anal. Calcd. (%) for C$_{20}$H$_{35}$NOS.H$_2$O: C, 67.56; H, 10.49; N, 3.94; S, 9.01. Found: C, 67.11; H, 10.03; N, 3.93; S, 8.88. [α]$_D^{24}$–0.7 (c 3.03, methanol)

EXAMPLE 12

(2R)-Amino-2-methyl-4-[5-(6-cyclohexylhexyl)thiophen-2-yl]butan-1-ol (Exemplification Compound No.1–210)

The title compound was obtained according to a similar reaction to that described in Example 11 using (2R)-Amino-2-methyl-4-[5-(6-cyclohexylhex-1-ynyl)thiophen-2-yl]butan-1-ol obtained in Example 2.

Nuclear magnetic resonance spectrum (400 MHz, CDCl$_3$) δ ppm: 6.58 (1H, d, J=3.3 Hz), 6.55 (1H, d, J=3.3 Hz), 3.37 (1H, d, J=10.4 Hz), 3.32 (1H, d, J=10.4 Hz), 2.68–2.93 (4H, m), 1.05–1.85 (24H, m), 0.77–0.93 (2H, m)

Infrared absorption spectrum $\nu_{max}$ cm$^{-1}$ (KBr): 3334, 3269, 3159, 2922, 2850, 1465, 1448, 1060

Mass spectrum (EI) m/z: 351 (M$^+$) Anal. Calcd.(%) for C$_{21}$H$_{37}$NOS: C, 71.74; H, 10.61; N, 3.98; S, 9.12. Found: C, 71.47; H, 10.48; N, 3.98; S, 9.37. [α]$_D^{24}$–1.3 (c 1.15, methanol)

EXAMPLE 13

2-Amino-2-methyl-4-[5-(5-phenylpentyl)thiophen-2-yl]butan-1-ol (exemplification compound No.1–152)

The title compound was obtained according to a similar reaction to that described in Example 11 using 2-amino-2-methyl-4-[5-(5-phenylpent-1-ynyl)thiophen-2-yl]butan-1-ol obtained in Example 3.

Nuclear magnetic resonance spectrum (400 MHz, CDCl$_3$) δ ppm: 7.31–7.24 (2H, m), 7.20–7.14 (3H, m), 6.58 (1H, d, J=2.8 Hz), 6.54 (1H, d, J=3.6 Hz), 3.36 (1H, d, J=10.8 Hz), 3.31 (1H, d, J=10.4 Hz), 2.81 (2H, t, J=8.4 Hz), 2.74 (2H, t, J=7.6 Hz), 2.61 (2H, t, J=7.6 Hz), 1.84–1.56 (6H, m), 1.52(3H, brs), 1.46–1.37 (2H, m), 1.11(3H, s)

Infrared absorption spectrum $\nu_{max}$ cm$^{-1}$ (KBr): 3333, 3263, 2927, 2852, 1496, 1453, 1059, 969, 928, 798, 747, 699, 569

EXAMPLE 14

2-Amino-2-methyl-4-{5-[5-(4-methoxyphenyl)pentyl]thiophen-2-yl}butan-1-ol (Exemplification Compound No.1-177)

The title compound was obtained according to a similar reaction to that described in Example 11 using 2-amino-2-methyl-4-{5-[5-(4-methoxyphenyl)pent-1-ynyl]thiophen-2-yl}butan-1-ol obtained in Example 4.

Nuclear magnetic resonance spectrum (400 MHz, CDCl$_3$) δ ppm: 7.08 (2H, d, J=8.5 Hz), 6.82 (2H, d, J=8.5 Hz), 6.58 (1H, d, J=3.3 Hz), 6.54 (1H, d, J=3.3 Hz), 3.79 (3H, s) 3.36 (1H, d, J=10.5 Hz), 3.31 (1H, d, J=10.5 Hz), 2.70–2.85 (4H, m), 2.55 (2H, t, J=7.7 Hz), 1.55–1.85 (6H, m), 1.35–1.45 (2H, m), 1.11 (3H, s)

Infrared absorption spectrum $\nu_{max}$ cm$^{-1}$ (KBr): 3333, 3263, 2926, 2852, 1514, 1247, 1061, 1029

EXAMPLE 15
2-Amino-2-methyl-4-{5-[5-(4-fluorophenyl)pentyl]thiophen-2-yl}butan-1-ol (Exemplification Compound No.1–161)

The title compound was obtained according to a similar reaction to that described in Example 11 using 2-amino-2-methyl-4-{5-[5-(4-fluorophenyl)pent-1-ynyl]thiophen-2-yl}butan-1-ol obtained in Example 5.3985

Nuclear magnetic resonance spectrum (400 MHz, CD$_3$OD) δ ppm: 7.12–7.18 (2H, m), 6.92–6.98 (2H, m), 6.63 (1H, d, J=3.5 Hz), 6.56 (1H, d, J=3.5 Hz), 6.25 (2H, s), 3.61 (1H, d, J=11.6 Hz), 3.51 (1H, d, J=11.6 Hz), 2.70–2.90 (4H, m), 2.58 (2H, t, J=7.6 Hz), 1.88–2.03 (2H, m), 1.57–1.70 (4H, m), 1.28–1.42 (5H, m)

Infrared absorption spectrum $v_{max}$ cm$^{-1}$ (KBr): 2929, 2854, 1578, 1509, 1464, 1387, 1356, 1223

EXAMPLE 16
2-Amino-2-methyl-4-{5-[2-(biphenyl-4-yl)ethyl]thiophen-2-yl}butan-1-ol (Exemplification Compound No.1–44)

The title compound was obtained according to a similar reaction to that described-in Example 11 using 2-amino-2-methyl-4-[5-(biphenyl-4-yl)ethynylthiophen-2-yl]butan-1-ol obtained in Example 6.

Nuclear magnetic resonance spectrum (400 MHz, CDCl$_3$) δ ppm: 7.25–7.65 (9H, m), 6.60 (1H, d, J=3.5 Hz), 6.59 (1H, d, J=3.5 Hz), 3.37 (1H, d, J=10.5 Hz), 3.32 (1H, d, J=10.5 Hz), 3.06–3.15 (2H, m), 2.95–3.04 (2H, m), 2.75–2.90 (2H, m), 1.65–1.85 (2H, m), 1.12 (3H, s)

Infrared absorption spectrum $v_{max}$ cm$^{-1}$ (KBr): 3333, 3265, 2924, 2852, 1598, 1486, 1448, 1059, 798, 695

EXAMPLE 17
(2R)-Amino-2-methyl-4-[5-(5-cyclohexylpentanoyl)thiophen-2-yl]butan-1-ol (Exemplification Compound No.1-1331)

(2R)-Amino-2-methyl-4-[5-(5-cyclohexylpent-1-ynyl)thiophen-2-yl]butan-1-ol (126 mg, 0.41 mmol) obtained in Example 1 was dissolved in methanol (2 ml), and 6N sulfuric acid (2 ml) was added thereto followed by heating under reflux for 4 hours. After the reaction solution was made alkaline with a 1N aqueous sodium hydroxide solution, the resulting solution was extracted with dichloromethane. The dichloromethane layer was dried over anhydrous sodium sulfate, and the solvent was evaporated under reduced pressure to give the title compound (130 mg, 91% yield).

Nuclear magnetic resonance spectrum (400 MHz, CDCl$_3$) δ ppm: 7.54 (1H, d, J=3.7 Hz), 6.84 (1H, d, J=3.7 Hz), 3.39 (1H, d, J=10.4 Hz), 3.34 (1H, d, J=10.4 Hz), 2.78–2.98 (4H, m), 1.13 (3H, brs), 0.8–1.9 (19H, m)

Infrared absorption spectrum $v_{max}$ cm$^{-1}$ (KBr): 3332, 3267, 3134, 2922, 2851, 1647, 1457, 1057

Mass spectrum (EI) mz: 351 (M$^+$) Anal. Calcd.(%) for C$_{20}$H$_{33}$NO$_2$S: C, 68.33; H, 9:46; N, 3.98; S, 9.12. Found: C, 67.99; H, 9.48; N, 3.92; S, 9.11. [α]$_D^{24}$–2.1 (c 1.03, methanol)

EXAMPLE 18
(2R)-Amino-2-methyl-4-[5-(6-cyclohexylhexanoyl)thiophen-2-yl]butan-1-ol (Exemplification Compound No.1-1357)

The title compound was obtained according to a similar reaction to that described in Example 17 using (2R)-amino-2-methyl-4-[5-(6-cyclohexylhex-1-ynyl)thiophen-2-yl]butan-1-ol obtained in Example 2.

Nuclear magnetic resonance spectrum (400 MHz, CDCl$_3$) δ ppm: 7.53 (1H, d, J=3.9 Hz), 6.63 (1H, d, J=3.9 Hz), 3.39 (1H, d, J=10.5 Hz), 3.34 (1H, d, J=10.5 Hz), 2.80–2.95 (4H, m), 1.33 (3H, brs), 0.8–1.9 (21H, m)

Infrared absorption spectrum $v_{max}$ cm$^{-1}$ (KBr): 3149, 2922, 2851, 1654, 1460, 1059, 922

Mass spectrum (EI) m/z: 365 (M$^+$) Anal. Calcd.(%) for C$_{21}$H$_{35}$NO$_2$S: C, 69.00; H, 9.65; N, 3.83; S, 8.77. Found: C, 68.74; H, 9.50; N, 3.83; S, 8.85. [α]$_D^{24}$–1.3 (c 1.15, methanol)

EXAMPLE 19
2-Amino-2-methyl-4-[5-(5-phenylpentanoyl)thiophen-2-yl]butan-1-ol hydrochloride (Exemplification Compound No.1-1344)

The title compound was obtained according to a similar reaction to that described in Example 17 using 2-amino-2-methyl-4-[5-(5-phenylpent-1-ynyl)thiophen-2-yl]butan-1-ol obtained in Example 3.

Nuclear magnetic resonance spectrum (400 MHz, CD$_3$OD) δ ppm: 7.71 (1H, d, J=4.0 Hz), 7.28–7.20 (2H, m), 7.20–7.10 (3H, m), 6.98 (1H, d, J=3.6 Hz), 3.62 (1H, d, J=7.6 Hz), 3.53 (1H, d, J=12.0 Hz), 3.04–2.88 (4H, m), 2.64 (2H, t, J=7.2 Hz), 2.15–2.04 (1H, m), 2.04–1.92 (1H, m), 1.78–1.62 (4H, m), 1.32 (3H, s)

Infrared absorption spectrum $v_{max}$ cm$^{-1}$ (KBr): 3378, 2927, 1648, 1588, 1562, 1504, 1456, 1230, 1067, 827, 748, 698, 578

EXAMPLE 20
2-Amino-2-methyl-4-{5-[5-(4-fluorophenyl)pentanoyl]thiophen-2-yl}butan-1-ol (Exemplification Compound No.1-1348)

The title compound was obtained according to a similar reaction to that described in Example 17 using 2-amino-2-methyl-4-{5-[5-(4-fluorophenyl)pent-1-ynyl]thiophen-2-yl}butan-1-ol obtained in Example 6.

Nuclear magnetic resonance spectrum (400 MHz, CDCl$_3$) δ ppm: 7.51 (1H, d, J=3.7 Hz), 7.08–7.17 (2H, m), 6.90–7.00 (2H, m), 6.83 (1H, d, J=3.7 Hz), 3.39 (1H, d, J=10.4 Hz), 3.33 (1H, d, J=10.4 Hz), 2.80–2.98 (4H, m), 2.62 (2H, t, J=7.5 Hz), 1.60–1.90 (6H, m), 1.12 (3H, s)

Infrared absorption spectrum $v_{max}$ cm$^{-1}$ (KBr): 3178, 2935, 2858, 1645, 1455, 1218, 1058

EXAMPLE 21
2-Amino-2-methyl-4-[5-(biphenyl-4-yl)acetylthiophen-2-yl]butan-1-ol (Exemplification Compound No.1-1326)

The title compound was obtained according to a similar reaction to that described in Example 17 using 2-amino-2-methyl-4-[5-(biphenyl-4-yl)ethynylthiophen-2-yl]butan-1-ol obtained in Example 6.

Nuclear magnetic resonance spectrum (400 MHz, CDCl$_3$) δ ppm: 7.64 (1H, d, J=3.7 Hz), 7.52–7.60 (4H, m), 7.30–7.47 (5H, m), 6.86 (1H, d, J=3.7 Hz), 4.18 (2H, s), 3.38 (1H, d, J=10.3 Hz), 3.33 (1H, d, J=10.3 Hz), 2.84–2.98 (2H, m), 1.70–1.87 (2H, m), 1.12 (3H, s)

Infrared absorption spectrum $v_{max}$ cm$^{-1}$ (KBr): 3420, 2927, 1654, 1488, 1455, 1234, 1058, 751

EXAMPLE 22
2-Amino-2-methyl-4-[5-(5-phenylpent-1-enyl)thiophen-2-yl]butan-1-ol maleate (exemplification compound No.1-670)

EXAMPLE 22 (a)
4-Methyl-4-{2-[5-(5-phenylpent-1-enyl)thiophen-2-yl]}ethyloxazolidin-2-one To 5-phenylpent-1-yne (0.38 ml, 2.58 mmol) was added catecholborane (500 mg, 1.72 mmol) at room temperature, and the mixture was stirred at 60° C. for 3 hours. After the reaction solution was cooled down to room temperature, toluene (5.0 ml), 4-[2-(5-bromothiophen-2-yl)]ethyl-4-methyloxazolidin-2-one (500 mg, 1.72 mmol) obtained in Example 1 (f), bis(triphenylphosphine)palladium chloride (119 mg, 0.17 mmol), and sodium ethoxide (0.83 ml, 20% ethanol solution) were added thereto at room temperature. The reaction mixture was stirred for 2 hours at 60° C., cooled down to room temperature, and then 1N sodium hydroxide was added thereto. The resulting mixture was extracted with ethyl acetate, and the organic layer was washed with water and then with a saturated aqueous sodium chloride solution. After the ethyl acetate layer was dried over anhydrous sodium sulfate, the solvent was evaporated in vacuo. The residue was purified by preparative thin-layer chromatography (elution solvent; hexane:ethyl acetate=1:1) to give the title compound (378 mg, 68% yield).

EXAMPLE 22 (b)
2-Amino-2-methyl-4-[5-(5-phenylpent-1-enyl)thiophen-2-yl]butan-1-ol maleate 4-Methyl-4-{2-[5-(5-phenylpent-1-enyl)thiophen-2-yl]}ethyloxazolidin-2-one (370 mg, 1.15 mmol) obtained in Example 22 (a) was hydrolyzed according to a similar procedure to that described in Example 1 (i) to give 2-amino-2-methyl-4-[5-(5-phenylpent-1-enyl)thiophen-2-yl]butan-1-ol (205 mg, 0.69 mmol). The title compound was obtained as a maleate (160 mg, 34% yield) according to the general method for preparing maleates.

Nuclear magnetic resonance spectrum (400 MHz, DMSO-$d_6$) δ ppm: 7.83–7.70 (2H, m), 7.38–7.12 (5H, m), 6.78 (1H, d, J=3.5 Hz), 6.71 (1H, d, J=3.5 Hz), 6.50 (1H, d, J=15.6 Hz), 6.02 (2H, s), 5.96–5.83 (1H, m), 5.52 (2H, brs), 5.36–5.10 (1H, m), 3.51–3.38 (2H, m), 2.83–2.58 (4H, m), 2.28–2.15 (2H, m), 1.88–1.63 (4H, m), 1.18 (3H, s)

Infrared absorption spectrum $v_{max}$ cm$^{-1}$ (KBr): 3206, 2932, 1579, 1497, 1386, 1357, 1194, 1075, 1012, 865, 699, 570

EXAMPLE 23
2-Amino-2-methyl-4-[5-(5-cyclohexylpent-1-enyl)thiophen-2-yl]butan-1-ol (Exemplification Compound No.1-657)

The title compound was obtained according to a similar procedure to that described in Example 22.

Nuclear magnetic resonance spectrum (400 MHz, CDCl$_3$) δ ppm: 6.64 (1H, d, J=3.5 Hz), 6.61 (1H, d, J=3.5 Hz), 6.41 (1H, d, J=15.7 Hz), 5.95–5.88 (1H, m), 3.36 (1H, d, J=10.5 Hz), 3.31 (1H, d, J=10.5 Hz), 2.86–2.73 (2H, m), 2.29–2.08 (2H, m), 1.83–1.55 (8H, m), 1.52–1.33 (4H, m), 1.30–1.12 (6H, m), 1.11 (3H, s), 0.92–0.79 (2H, m)

Infrared absorption spectrum $v_{max}$ cm$^{-1}$ (KBr): 3328, 3275, 2921, 2850, 1610, 1447, 1225, 1066, 1038, 957, 804, 504

EXAMPLE 24
2-Amino-2-methyl-4-[5-(6-cyclohexylhex-1-enyl)thiophen-2-yl]butan-1-ol maleate (Exemplification Compound No.1-683)

The title compound was obtained according to a similar procedure to that described in Example 22.

Nuclear magnetic resonance spectrum (400 MHz, DMSO-$d_6$) δ ppm: 7.90–7.69 (2H, m), 6.77 (1H, d, J=3.4 Hz), 6.70 (1H, d, J=3.4 Hz), 6.47 (1H, d, J=15.8 Hz), 6.04 (2H, s), 5.92–5.84 (1H, m), 5.55 (1H, brs), 3.49–3.32 (2H, m), 2.85–2.71 (2H, m), 2.18–2.06 (2H, m), 1.96–1.53 (8H, m), 1.42–1.03 (14H, m), 0.93–0.78 (2H, m)

Infrared absorption spectrum $v_{max}$ cm$^{-1}$ (KBr): 3042, 2924, 2851, 1695, 1577, 1533, 1493, 1477, 1387, 1362, 1351, 1210, 1074, 866

EXAMPLE 25
2-Amino-2-methyl-4-[4-(5-phenylpent-1-ynyl)thiophen-2-yl]butan-1-ol hydrochloride (Exemplification Compound No.2-185)

EXAMPLE 25 (a)
4-(5-Phenylpent-1-ynyl)thiophen-2-carboxaldehyde

5-Phenylpent-1-yne (18.1 g, 126 mmol) was dissolved in tetrahydrofuran (100 ml), and then 4-bromothiophen-2-carboxaldehyde (18.7 g, 98 mmol) in tetrahydrofuran (200 ml), triethylamine (150 ml, 1.07 mmol), copper(I) iodide (962 mg, 5.05 mmol), and dichlorobis(triphenylphosphine)palladium (3.54 g, 5.04 mmol) were added thereto, and the mixture was stirred at 50° C. for 4 hours under a nitrogen atmosphere. After the reaction solution was filtered, the filtrate was evaporated under reduced pressure. To the residue was added ether, and the solution was washed with water and a saturated aqueous sodium chloride solution, respectively. After the ether layer was dried over anhydrous sodium sulfate, the solvent was evaporated in vacuo. The residue was purified by chromatography on a silica gel column (elution solvent; hexane:ethyl acetate=100:1–10:1) to afford the title compound (19.4 g, 78% yield).

Nuclear magnetic resonance spectrum (400 MHz, CDCl$_3$) δ ppm: 9.88 (1H, s), 7.72 (1H, s), 7.71 (1H, s), 7.35–7.27 (2H, m), 7.24–7.16 (3H, m), 2.78 (2H, t, J=7.2 Hz), 2.41 (2H, t, J=7.2 Hz), 1.98–1.88 (2H, m)

Infrared absorption spectrum $v_{max}$ cm$^{-1}$ (KBr): 2238, 1679, 1440, 1234, 1157, 858, 748, 700, 665, 620

Mass spectrum (FAB) m/z: 255 ((M+H)$^+$)

EXAMPLE 25 (b)
[4-(5-Phenylpent-1-ynyl)thiophen-2-yl]methanol 4-(5-Phenylpent-1-ynyl)thiophen-2-carboxaldehyde (15.0 g, 59.0 mmol) obtained in Example 25 (a) was dissolved in methanol (150 ml), sodium borohydride (2.29 g, 60.5 mmol) was added thereto in an ice bath. The reaction mixture was stirred for 25 minutes in the ice bath, and then the solvent was evaporated in vacuo. To the residue was added water, and the mixture was extracted with ethyl acetate, and then the ethyl acetate layer was washed with a saturated aqueous sodium chloride solution. After the ethyl acetate layer was dried over anhydrous sodium sulfate, the solvent was evaporated under reduced pressure to afford the title compound (15.2 g, 99% yield).

Nuclear magnetic resonance spectrum (400 MHz, CDCl$_3$) δ ppm: 7.34–7.27 (3H, m), 7.24–7.17 (3H, m), 6.98 (1H, s), 4.78 (2H, d, J=5.6 Hz), 2.77 (2H, t, J=7.6 Hz), 2.39 (2H, t, J=7.2 Hz), 1.96–1.85 (2H, m), 1.77 (1H, t, J=5.6 Hz)

Infrared absorption spectrum $v_{max}$ cm$^{-1}$ (liquid film): 3346, 3026, 2940, 2861, 2235, 1602, 1496, 1455, 1355, 1182, 1141, 1013, 844, 748, 700, 626

Mass spectrum (FAB) m/z: 256 (M$^+$)

EXAMPLE 25 (c)
[4-(5-Phenylpent-1-ynyl)thiophen-2-yl]acetonitrile

[4-(5-Phenylpent-1-ynyl)thiophen-2-yl]methanol (4.68 g, 18.3 mmol) obtained in Example 25 (b) was dissolved in tetrahydrofuran (70 ml), and phosphorus bromide (0.69 ml, 7.30 mmol) in tetrahydrofuran (20 ml) was added dropwise thereto in an ice bath. After the dropping was finished, the reaction solution in the ice bath was stirred for 10 minutes under a nitrogen atmosphere. To the reaction solution was added ice-cold water, and after the solution was extracted with ethyl acetate, the ethyl acetate layer was washed with a saturated aqueous sodium hydrogencarbonate solution and then with a saturated aqueous sodium chloride solution. After the ethyl acetate layer was dried over anhydrous sodium sulfate, the solvent was evaporated under reduced pressure. The residue was dissolved in acetonitrile (120 ml), and tetraethylammonium cyanide (2.85 g, 18.3 mmol) was added thereto in the ice bath followed by stirring for 1 hour at room temperature under a nitrogen atmosphere. The reaction solution was poured into 5% aqueous sodium hydrogencarbonate solution, extracted with ethyl acetate, and the ethyl acetate layer was washed with the saturated aqueous sodium chloride solution. After the ethyl acetate layer was dried over anhydrous sodium sulfate, the solvent was evaporated in vacuo. The residue was purified by chromatography on a silica gel column (elution solvent; hexane:ethyl acetate: 20:–15:1) to give the title compound (3.21 g, 66% yield).

Nuclear magnetic resonance spectrum (270 MHz, CDCl$_3$) δ ppm: 7.15–7.35 (6H, m), 7.03 (1H, s), 3.86 (2H, s), 2.77 (2H, t, J=7.5 Hz), 2.39 (2H, t, J=7.0 Hz), 1.83–1.98 (2H, m)

Infrared absorption spectrum $v_{max}$ cm$^{-1}$ (CHCl$_3$): 3691, 2946, 2236, 1603, 1497, 1454, 1416, 1361

EXAMPLE 25 (d)

2-[4-(5-Phenylpent-1-ynyl)thiophen-2-yl]ethanol

[4-(5-Phenylpent-1-ynyl)thiophen-2-yl]acetonitrile (3.21 g, 12.1 mmol) obtained in Example 25 (c) was dissolved in ethanol (15 ml), and potassium hydroxide (1.70 g, 30.2 mmol) in water (15 ml) was added thereto in an ice bath followed by heating under reflux for 2 hours. After the reaction solution was acidified with 1N hydrochloric acid, the resulting solution was extracted with ethyl acetate. After the ethyl acetate layer was dried over anhydrous sodium sulfate, the solvent was evaporated under reduced pressure. The obtained residue was dissolved in tetrahydrofuran (15 ml), and triethylamine (1.69 ml, 12.1 mmol) was added thereto. To the reaction solution was added dropwise ethyl chloroformate (1.21 ml, 12.7 mmol) in tetrahydrofuran (15 ml) in an ice bath, and the reaction mixture was stirred for 30 minutes under cooling with ice in a nitrogen atmosphere. After this reaction solution was filtered, the obtained filtrate was added slowly to an aqueous solution (10 ml) of sodium borohydride (2.29 g, 60.5 mmol) in an ice bath, and then the mixture was stirred for 3 days at room temperature. After the reaction solution was cooled down, acidified with 1N hydrochloric acid, and the resulting solution was extracted with ethyl acetate, and then the ethyl acetate layer was washed with a 1N aqueous sodium hydroxide solution and then with a saturated aqueous sodium chloride solution. The ethyl acetate layer was dried over anhydrous sodium sulfate, and the solvent was evaporated in vacuo. The residue was purified by chromatography on a silica gel column (elution solvent; hexane:ethyl acetate=10:1–4:1) to afford the title compound (2.74 g, 84% yield).

Nuclear magnetic resonance spectrum (400 MHz, CDCl$_3$) δ ppm: 7.15–7.30 (6H, m), 6.86 (1H, s), 3.85 (2H, t, J=6.2 Hz), 3.02 (2H, t, J=6.2 Hz), 2.77 (2H, t, J=7.6 Hz), 2.39 (2H, t, J=7.1 Hz), 1.85–1.95 (2H, m)

Infrared absorption spectrum $v_{max}$ cm$^{-1}$ (CHCl$_3$): 3620, 2947, 1732, 1603, 1497, 1454, 1359, 1250, 1046

EXAMPLE 25 (e)

2-(2-Iodoethyl)-4-(5-phenylpent-1-ynyl)thiophene

The title compound (3.45 g, 91% yield) was obtained according to a similar reaction to that described in Example 1 (g) using 2-[4-(5-phenylpent-1-ynyl)thiophen-2-yl]ethanol (2.69 g, 9.95 mmol) obtained in Example 25 (d).

Nuclear magnetic resonance spectrum (400 MHz, CDCl$_3$) δ ppm: 7.15–7.30 (6H, m), 6.84 (1H, s), 3.30–3.35 (4H, m), 2.77 (2H, t, J=7.6 Hz), 2.39 (2H, t, J=7.0 Hz), 1.85–1.95 (2H, m)

Infrared absorption spectrum $v_{max}$ cm$^{-1}$ (CHCl$_3$): 2946, 2863, 1603, 1497, 1454, 1429, 1360, 1172

EXAMPLE 25 (f)

2-Methyl-2-[4-(5-phenylpent-1-ynyl)thiophen-2-yl] ethylmalonic acid monoethylester Methylmalonic acid diethylester (1.57 g, 9.02 mmol) was dissolved in dimethylformamide (30 ml), and sodium hydride (0.38 g, 9.47 mmol) was added thereto in an ice bath, and then the mixture was stirred for 1 hour at room temperature in a nitrogen atmosphere. The dimethylformamide solution (30 ml) of 2-(2-iodoethyl)-4-(5-phenylpent-1-ynyl)thiophene obtained in Example 25 (e) was added dropwise to the reaction solution in an ice bath, and the mixture was stirred for 4 hours at room temperature under a nitrogen atmosphere. After the reaction solution was cooled down, acidified with 1N hydrochloric acid, and the resulting solution was extracted with ethyl acetate, and then the ethyl acetate layer was washed with a 1N aqueous sodium hydroxide solution and then with a saturated aqueous sodium chloride solution. The ethyl acetate layer was dried over anhydrous sodium sulfate, and the solvent was evaporated in vacuo. The residue was partially purified by chromatography on a silica gel column (elution solvent; hexane:ethyl acetate=50:1–20:1). The obtained mixture was dissolved in a mixture of ethanol (9 ml) and water (1 ml), and potassium hydroxide (0.80 g, 14.3 mmol) was added thereto in an ice bath, and then the reaction mixture was stirred for 3 days at room temperature. After the reaction solution was acidified with 1N hydrochloride acid, the resulting solution was extracted with ethyl acetate. The ethyl acetate layer was dried over anhydrous sodium sulfate, and the solvent was evaporated in vacuo. The residue was purified by chromatography on a silica gel column (elution solvent; dichloromethane:methanol=50:1) to afford the title compound (1.02 g, 28% yield).

Nuclear magnetic resonance spectrum (500 MHz, CDCl$_3$) δ ppm: 7.15–7.30 (6H, m), 6.79 (1H, s), 4.23 (2H, q, J=7.1 Hz), 2.60–2.85 (4H, m), 2.38 (2H, t, J=7.0 Hz), 2.20–2.32 (2H, m), 1.86–1.94 (2H, m), 1.53 (3H, s), 1.29 (3H, t, J=7.1 Hz)

Infrared absorption spectrum $v_{max}$ cm$^{-1}$ (CHCl$_3$): 3509, 2944, 1732, 1713, 1455, 1377, 1254, 1181, 1113

EXAMPLE 25 (g)

2-Methoxycarbonylamino-2-methyl-4-[4-(5-phenylpent-1-ynyl)thiophen-2-yl]butanoic acid ethylester The title compound (0.85 g, 80% yield) was obtained according to a similar reaction to that described in Example 1 (j) using 2-methyl-2-[4-(5-phenylpent-1-ynyl)thiophen-2-yl]ethylmalonic acid monoethylester (0.99 g, 2.48 mmol) obtained in Example 25 (f).

Nuclear magnetic resonance spectrum (500 MHz, CDCl$_3$) δ ppm: 7.15–7.30 (5H, m), 7.13 (1H, s), 6.75 (1H, s), 5.69 (1H, brs), 4.15–4.33 (2H, m), 3.66 (3H, s), 2.50–2.80 (5H, m), 2.38 (2H, t, J=7.0 Hz), 2.15–2.23 (1H, m), 1.87–1.93 (2H, m), 1.60 (3H, s), 1.25–1.30 (3H, m)

Infrared absorption spectrum $v_{max}$ cm$^{-1}$ (CHCl$_3$): 3417, 2987, 2945, 1719, 1504, 1453, 1323, 1077

EXAMPLE 25 (h)

4-Methyl-4-{2-[4-(5-phenylpent-1-ynyl)thiophen-2-yl]}ethyloxazolidin-2-one

2-Methoxycarbonylamino-2-methyl-4-[4-(5-phenylpent-1-ynyl)thiophen-2-yl]butanoic acid ethylester (0.82 g, 1.92 mmol) obtained in Example 25 (g) was dissolved in a mixture of ethanol (15 ml) and tetrahydrofuran (10 ml), and lithium chloride (0.24 g, 5.75 mmol) and sodium borohydride (0.22 g, 5.75 mmol) were added thereto in an ice bath, and then the reaction mixture was stirred for 2 hours at 70° C. under a nitrogen atmosphere. After the reaction solution was acidified with 1N hydrochloride acid, the resulting solution was extracted with ethyl acetate, and the ethyl acetate layer was washed with a saturated aqueous sodium chloride solution. The ethyl acetate layer was dried over anhydrous sodium sulfate, and the solvent was evaporated in vacuo. The residue was purified by chromatography on a silica gel column (elution solvent; hexane:ethyl acetate= 4:1–1:1) to give the title compound (0.65 g, 96% yield).

Nuclear magnetic resonance spectrum (400 MHz, CDCl$_3$) δ ppm: 7.15–7.35 (6H, m), 6.79 (1H, s), 5.38 (1H, brs), 4.18 (1H, d, J=8.6 Hz), 4.08 (1H, d, J=8.6 Hz), 2.80–2.90 (2H, m), 2.77 (2H, t, J=7.6 Hz), 2.38 (2H, t, J=7.0 Hz), 1.85–2.00 (4H, m), 1.41 (3H, s)

Infrared absorption spectrum $v_{max}$ cm$^{-1}$ (CHCl$_3$): 3450, 2978, 2945, 1757, 1497, 1401, 1382, 1249, 1046

EXAMPLE 25 (i)

2-Amino-2-methyl-4-[4-(5-phenylpent-1-ynyl)thiophen-2-yl]butan-1-ol hydrochloride 4-Methyl-4-{2-[4-(5-phenylpent-1-ynyl)thiophen-2-yl]}ethyloxazolidin-2-one (200 mg, 0.57 mmol) obtained in Example 25 (h) was dissolved in a mixture of tetrahydrofuran (1 ml) and methanol (2 ml), and a 5N aqueous potassium hydroxide solution (2 ml) was added thereto in an ice bath followed by heating under reflux for 18 hours. To the reaction solution was added water, and the solution was extracted with dichloromethane. The dichloromethane layer was dried over anhydrous sodium sulfate, and the solvent was evaporated in vacuo. The residue was dissolved in 1,4-dioxane (2 ml), and a dioxane solution of 4N hydrochloric acid was added thereto in an ice bath, and then the solvent was evaporated under reduced pressure. The obtained white solid was washed with ether, and dried to give the title compound (165 mg, 80% yield).

Nuclear magnetic resonance spectrum (400 MHz, CD$_3$OD) δ ppm: 7.15–7.30 (6H, m), 6.84 (1H, s), 3.61 (1H, d, J=11.5 Hz), 3.52 (1H, d, J=11.5 Hz), 2.80–2.95 (2H, m), 2.75 (2H, t, J=7.5 Hz), 2.35 (2H, t, J=7.0 Hz), 1.82–2.10 (4H, m), 1.32 (3H, s)

Infrared absorption spectrum $v_{max}$ cm$^{-1}$ (KBr): 3351, 3027, 2928, 1594, 1509, 1455, 1389, 1062

EXAMPLE 26

2-Amino-2-methyl-4-[4-(5-phenylpentyl)thiophen-2-yl]butan-1-ol hydrochloride (Exemplification Compound No.2-39)

EXAMPLE 26 (a)

4-Methyl-4-{2-[4-(5-phenylpentyl)thiophen-2-yl]}ethyloxazolidin-2-one

4-Methyl-4-{2-[4-(5-phenylpent-1-ynyl)thiophen-2-yl]}ethyloxazolidin-2-one (174 mg, 0.49 mmol) obtained in Example 25 (h) was dissolved in ethanol (9 ml), and 5% palladium-charcoal (90 mg) was added thereto followed by stirring for 4 hours under a hydrogen atmosphere. After the catalyst was filtered out through Celite, the filtrate was evaporated to dryness under reduced pressure. The residue was purified by chromatography on a silica gel column (elution solvent; hexane:ethyl acetate=1:1) to give the title compound (164 mg, 93% yield).

Nuclear magnetic resonance spectrum (400 MHz, CDCl$_3$) δ ppm: 7.25–7.30 (2H, m), 7.15–7.20 (3H, m), 6.70 (1H, s), 6.63 (1H, s), 5.33 (1H, brs), 4.18 (1H, d, J=8.6 4.07 (1H, d, J=8.6 Hz), 2.80–2.90 (2H, m), 2.61 (2H, t, J=7.8 Hz), 2.53 (2H, t, J=7.7 Hz), 1.93–2.02 (2H, m), 1.55–1.70 (4H, m), 1.35–1.45 (5H, m)

Infrared absorption spectrum $v_{max}$ cm$^{-1}$ (CHCl$_3$): 3451, 2977, 2934, 2858, 1757, 1400, 1382, 1045

EXAMPLE 26 (b)

2-Amino-2-methyl-4-[4-(5-phenylpentyl)thiophen-2-yl]butan-1-ol hydrochloride

The title compound (107 mg, 76% yield) was obtained according to a similar reaction to that described in Example 25 (i) using 4-methyl-4-{2-[4-(5-phenylpentyl)thiophen-2-yl]}ethyloxazolidin-2-one (136 mg, 0.38 mmol) obtained in Example 26 (a).

Nuclear magnetic resonance spectrum (400 MHz, CDCl$_3$) δ ppm: 7.10–7.30 (5H, m), 6.63 (1H, s), 6.61 (1H, s), 3.66 (2H, s), 2.80–2.95 (2H, m), 2.58 (2H, t, J=7.7 Hz), 2.47 (2H, t, J=7.7 Hz), 2.00–2.18 (2H, m), 1.52–1.67 (4H, m), 1.25–1.45 (5H, m)

Infrared absorption spectrum $v_{max}$ cm$^{-1}$ (KBr): 3223, 2929, 2887, 1606, 1525, 1455, 1400, 1054

EXAMPLE 27

2-Amino-2-methyl-4-[4-(5-phenylpentanoyl)thiophen-2-yl]butan-1-ol hydrochloride (Exemplification Compound No.2-343)

2-Amino-2-methyl-4-[4-(5-phenylpent-1-ynyl)thiophen-2-yl]butan-1-ol hydrochloride (178 mg, 0.49 mmol) obtained in Example 26 (i) was dissolved in methanol (2 ml), and 6N sulfuric acid (2 ml) was added thereto followed by heating under reflux for 4 hours. After the reaction solution was made alkaline with a 1N aqueous sodium hydroxide solution, the resulting solution was extracted with dichloromethane. The dichloromethane layer was dried over anhydrous sodium sulfate, and the solvent was evaporated in vacuo. The residue was dissolved in 1,4-dioxane (2 ml), and the dioxane solution of 4N hydrochloric acid was added thereto in an ice bath, and then the solvent was evaporated under reduced pressure. The obtained white solid was washed with ether, and dried to give the title compound (100 mg, 53% yield).

Nuclear magnetic resonance spectrum (400 MHz, CD$_3$OD) δ ppm: 14 (1H, s), 7.29 (1H, s), 7.10–7.27 (5H, m), 3.63 (1H, d, J=11.6 Hz), 3.53 (1H, d, J=11.6 Hz), 2.85–3.00 (4H, m), 2.64 (2H, t, J=7.0 Hz), 1.92–2.13 (2H, m), 1.67–1.75 (4H, m), 1.33 (3H, s)

Infrared absorption spectrum $v_{max}$ cm$^{-1}$ (KBr): 3361, 3026, 2939, 1666, 1591, 1456, 1154, 1072

EXAMPLE 28

2-Amino-2-ethyl-4-[5-(5-cyclohexylpent-1-ynyl)thiophen-2-yl]butan-1-ol maleate (Exemplification Compound No.1-1909)

The title compound was obtained according to a similar reaction to that described in Example 1 using a racemic mixture of 4-[2-(5-bromothiophen-2-yl)]ethyl-4-ethyloxazolidin-2-one as a starting material.

Nuclear magnetic resonance spectrum (400 MHz, CH$_3$OD) δ ppm: 6.90 (1H, d, J=3.6 Hz), 6.72 (1H, d, J=3.6 Hz), 6.25 (2H, s), 3.61 (1H, d, J=11.7 Hz), 3.57 (1H, d, J=11.7 Hz), 2.75–2.90 (2H, m), 2.38 (2H, t, J=7.0 Hz), 1.88–2.06 (2H, m), 1.52–1.82 (9H, m), 1.12–1.37 (6H, m), 0.85–1.04 (5H, m)

Infrared absorption spectrum $v_{max}$ cm$^{-1}$ (KBr): 3191, 2922, 2851, 1576, 1521, 1386, 1362, 1193, 1068

EXAMPLE 29

2-Amino-2-ethyl-4-[5-(5-cyclohexylpentyl)thiophen-2-yl]butan-1-ol maleate (exemplification compound No.1-1764)

The title compound was obtained according to a similar reaction to that described in Example 11 using 2-amino-2-ethyl-4-[5-(5-cyclohexylpent-2-ynyl)thiophen-1-yl]butan-1-ol obtained in Example 28.

Nuclear magnetic resonance spectrum (400 MHz, $CH_3OD$) δ ppm: 6.64 (1H, d, J=3.7 Hz), 6.57 (1H, d, J=3.7 Hz), 6.25 (2H, s), 3.61 (1H, d, J=11.8 Hz), 3.57 (1H, d, J=11.8 Hz), 2.70–2.87 (4H, m), 1.88–2.05 (2H, m), 1.56–1.82 (9H, m), 1.10–1.38 (10H, m), 0.99 (3H, t, J=7.5 Hz), 0.81–0.93 (2H, m)

Infrared absorption spectrum $v_{max}$ cm$^{-1}$ (KBr): 3196, 2923, 2852, 1581, 1523, 1385, 1368, 1193, 1067, 1016

EXAMPLE 30

2-Amino-2-ethyl-4-[5-(5-cyclohexylpentanoyl)thiophen-2-yl]butan-1-ol maleate (Exemplification Compound No.1-2097)

The title compound was obtained according to a similar reaction to that described in Example 17 using 2-amino-2-ethyl-4-[5-(5-cyclohexylpent-1-ynyl)thiophen-2-yl]butan-1-ol obtained in Example 28.

Nuclear magnetic resonance spectrum (400 MHz, $CH_3OD$) δ ppm: 7.72 (1H, d, J=3.7 Hz), 6.99 (1H, d, J=3.7 Hz), 6.25 (2H, s), 3.63 (1H, d, J=11.6 Hz), 3.59 (1H, d, J=11.6 Hz), 2.85–3.02 (4H, m), 1.94–2.12 (2H, m), 1.60–1.83 (9H, m), 1.10–1.42 (8H, m), 1.01 (3H, t, J=7.5 Hz), 0.82–0.96 (2H, m)

Infrared absorption spectrum $v_{max}$ cm$^{-1}$ (KBr): 3395, 2922, 2851, 1654, 1582, 1520, 1458, 1385, 1370, 1203, 1067

EXAMPLE 31

(2R)-Amino-2-methyl-4-[5-(4-cyclohexyloxybut-1-ynyl)thiophen-2-yl]butan-1-ol maleate (Exemplification Compound No.1-1072)

The title compound was obtained according to a similar reaction to that described in Example 1 using 4-[2-(5-bromothiophen-2-yl)]ethyl-4-methyloxazolidin-2-one as a starting material.

Nuclear magnetic resonance spectrum (400 MHz, $CH_3OD$) δ ppm: 6.93 (1H, d, J=3.6 Hz), 6.73 (1H, d, J=3.6 Hz), 6.25 (2H, s), 3.57–3.67 (3H, m), 3.51 (1H, d, J=11.6 Hz), 3.32–3.42 (1H, m), 2.78–2.95 (2H, m), 2.63 (2H, t, J=6.7 Hz), 1.50–2.10 (7H, m), 1.1–1.37 (8H, m)

Infrared absorption spectrum $v_{max}$ cm$^{-1}$ (KBr): 3394, 2932, 2858, 1583, 1506, 1386, 1367, 1194, 1104

EXAMPLE 32

2-Amino-2-methyl-4-[5-(4-cyclohexylmethoxyphenyl)thiophen-2-yl]butan-1-ol (Exemplification Compound No.1-1729)

The title compound was obtained according to a similar reaction to that described in Example 1 using 4-[2-(5-bromothiophen-2-yl)ethyl-4-methyloxazolidin-2-one as a starting material.

Nuclear magnetic-resonance spectrum (400 MHz, $CH_3OD$) δ ppm: 7.45 (2H, d, J=8.7 Hz), 7.02 (1H, d, J=3.6 Hz), 6.88 (2H, d, J=8.7 Hz), 6.76 (1H, d, J=3.6 Hz), 3.77 (2H, d, J=6.3 Hz), 3.40 (1H, d, J=10.9 Hz), 3.36 (1H, d, J=10.9 Hz), 2.91–2.79 (2H, m), 1.90–1.68 (8H, m), 1.41–1.08 (5H, m), 1.11 (3H, s)

EXAMPLE 33

2-Amino-2-methyl-4-[5-(4-benzyloxyphenyl)thiophen-2-yl]butan-1-ol (Exemplification Compound No.1-1744)

The title compound was obtained according to a similar reaction to that described in Example 1 using 4-[2-(5-bromothiophen-2-yl)ethyl-4-methyloxazolidin-2-one as a starting material.

Nuclear magnetic resonance spectrum (400 MHz, $CH_3OD$) δ ppm: 7.51–7.27 (7H, m), 7.07 (1H, d, J=3.6 Hz), 6.98 (2H, d, J=8.7 Hz), 6.76 (1H, d, J=3.6 Hz), 5.06 (2H, s), 3.44–3.38 (2H, m), 2.91–2.80 (2H, m), 1.86–1.74 (2H, m), 1.11 (3H, s)

EXAMPLE 34

(2R)-Amino-2-methyl-4-{5-[3-(4-methylphenoxy)propynyl]thiophen-2-yl}butan-1-ol maleate (Exemplification Compound No.1-1063)

The title compound was obtained according to a similar reaction to that described in Example 1.

Nuclear magnetic resonance spectrum (400 MHz, $CH_3OD$) δ ppm: 1.31 (3H, s), 1.88–2.10 (2H, m), 2.27 (3H, s), 2.80–2.95 (2H, m), 3.51 (1H, d, J=11.6 Hz), 3.60 (1H, d, J=11.6 Hz), 4.89 (2H, s), 6.25 (2H, s), 6.77 (1H, d, J=3.6 Hz), 6.88 (2H, d, J=8.6 Hz), 7.05 (1H, d, J=3.6 Hz), 7.09 (2H, d, J=8.6 Hz)

Infrared absorption spectrum $v_{max}$ cm$^{-1}$ (KBr): 3338, 3211, 3006, 2923, 2229, 1583, 1511, 1372, 1228, 1018

EXAMPLE 35

(2R)-Amino-2-methyl-4-{5-[3-(4-methylphenoxy)propyl]thiophen-2-yl}butan-1-ol maleate (Exemplification Compound No.1-391)

The title compound was obtained according to a similar reaction to that described in Example 11 using (2R)-amino-2-methyl-4-{5-[3-(4-methylphenoxy)propynyl]thiophen-2-yl}butan-1-ol maleate obtained in Example 34.

Nuclear magnetic resonance spectrum (400 MHz, $CH_3OD$) δ ppm: 1.31 (3H, s), 1.88–2.10 (4H, m), 2.25 (3H, s), 2.77–2.92 (2H, m), 2.94 (2H, t, J=7.5 Hz), 3.51 (1H, d, J=11.6 Hz), 3.60 (1H, d, J=11.6 Hz), 3.93 (2H, t, J=6.2 Hz), 6.25 (2H, s), 6.62 (1H, d, J=3.3 Hz), 6.65 (1H, d, J=3.3 Hz), 6.77 (2H, d, J=8.5 Hz), 7.04.(2H, d, J=8.5 Hz)

Infrared absorption spectrum $v_{max}$ cm$^{-1}$ (KBr): 3412, 3028, 2947, 2926, 1577, 1513, 1387, 1357, 1239, 1055

EXAMPLE 36

(2R)-Amino-2-methyl-4-{5-[3-(3-methylphenoxy)propynyl]thiophen-2-yl}butan-1-ol oxalate (Exemplification Compound No.1-2276)

The title compound was obtained according to a similar reaction to that described in Example 1.

Nuclear magnetic resonance spectrum (400 MHz, $CH_3OD$) δ ppm: 1.31 (3H, s), 1.90–2.10 (2H, m), 2.31 (3H, s), 2.82–2.96 (2H, m), 3.52 (1H, d, J=11.7 Hz), 3.60 (1H, d, J=11.7 Hz), 4.90 (2H, s), 6.73–6.85 (4H, m), 7.05 (1H, d, J=3.6 Hz), 7.16 (1H, m)

Infrared absorption spectrum $v_{max}$ cm$^{-1}$ (KBr): 2923, 2575, 2226, 1621, 1583, 1559, 1489, 1290, 1255, 1154, 1045

EXAMPLE 37

(2R)-Amino-2-methyl-4-{5-[3-(4-ethylphenoxy)propynyl]thiophen-2-yl}butan-1-ol maleate (Exemplification Compound No.1-1064)

The title compound was obtained according to a similar reaction to that described in Example 1.

Nuclear magnetic resonance spectrum (400 MHz, $CH_3OD$) δ ppm: 1.20 (3H, t, J=7.6 Hz), 1.31 (3H, s), 1.88–2.10 (2H, m), 2.58 (2H, q, J=7.6 Hz), 2.80–2.95 (2H, m), 3.51 (1H, d, J=11.5 Hz), 3.60 (1H, d, J=11.5 Hz), 4.89 (2H, s), 6.25 (2H, s), 6.77 (1H, d, J=3.6 Hz), 6.90 (2H, d, J=8.6 Hz), 7.05 (1H, d, J=3.6 Hz), 7.12 (2H, d, J=8.6 Hz)

Infrared absorption spectrum $v_{max}$ cm$^{-1}$ (KBr): 3385, 2959, 2928, 2226, 1581, 1510, 1384, 1232, 1020

EXAMPLE 38

(2R)-Amino-2-methyl-4-{5-[3-(4-methylthiophenoxy) propynyl]thiophen-2-yl}butan-1-ol maleate (Exemplification Compound No.1-1068)

The title compound was obtained according to a similar reaction to that described in Example 1.

Nuclear magnetic resonance spectrum (400 MHz, CH$_3$OD) δ ppm: 1.31 (3H, s), 1.88–2.10 (2H, m), 2.42 (3H, s), 2.81–2.96 (2H, m), 3.51 (1H, d, J=11.5 Hz), 3.60 (1H, d, J=11.5 Hz), 4.92 (2H, s), 6.25 (2H, s), 6.78 (1H, d, J=3.6 Hz), 6.96 (2H, d, J=8.9 Hz), 7.06 (1H, d, J=3.6 Hz), 7.27 (2H, d, J=8.9 Hz)

Infrared absorption spectrum $v_{max}$ cm$^{-1}$ (KBr): 3401, 2984, 2918, 2227, 1575, 1492, 1376, 1237, 1011

EXAMPLE 39

(2R)-Amino-2-methyl-4-{5-[3-(3,5-dimethoxyphenoxy) propynyl]thiophen-2-yl}butan-1-ol maleate (Exemplification Compound No.1-2285)

The title compound was obtained according to a similar reaction to that described in Example 1.

Nuclear magnetic resonance spectrum (400 MHz, CH$_3$OD) δ ppm: 1.31 (3H, s), 1.90–2.10 (2H, m), 2.82–2.96 (2H, m), 3.51 (1H, d, J=11.6 Hz), 3.61 (1H, d, J=11.6 Hz), 3.75 (6H, s), 4.89 (2H, s), 6.13 (1H, dd, J=2.2, 2.2 Hz), 6.43 (2H, d, J=2.2 Hz), 6.69 (2H, s), 6.78 (1H, d, J=3.6 Hz), 7.07 (1H, d, J=3.6 Hz)

Infrared absorption spectrum $v_{max}$ cm$^{-1}$ (KBr): 3382, 2936, 2222, 1682, 1601, 1476, 1205, 1152, 1066

EXAMPLE 40

(2R)-Amino-2-methyl-4-{5-[3-(3,4-dimethoxyphenoxy) propynyl]thiophen-2-yl}butan-1-ol maleate (Exemplification Compound No.1-2284)

The title compound was obtained according to a similar reaction to that described in Example 1.

Nuclear magnetic resonance spectrum (400 MHz, CH$_3$OD) δ ppm: 1.31 (3H, s), 1.88–2.10 (2H, m), 2.81–2.95 (2H, m), 3.51 (1H, d, J=11.4 Hz), 3.61 (1H, d, J=11.4 Hz), 3.78 (3H, s), 3.81 (3H, s), 4.88 (2H, s), 6.25 (2H, s), 6.54 (1H, dd, J=8.7, 2.7 Hz), 6.66 (1H, d, J=2.7 Hz), 6.78 (1H, d, J=3.6 Hz), 6.87 (1H, d, J=8.7 Hz), 7.05 (1H, d, J=3.6 Hz)

Infrared absorption spectrum $v_{max}$ cm$^{-1}$ (KBr): 3361, 2934, 2221, 1581, 1512, 1385, 1369, 1228, 1196, 1023

EXAMPLE 41

(2R)-Amino-2-methyl-4-{5-[3-(4-acetylphenoxy)propynyl] thiophen-2-yl}butan-1-ol (Exemplification Compound No.1-2288)

The title compound was obtained according to a similar reaction to that described in Example 1.

Nuclear magnetic resonance spectrum (400 MHz, CH$_3$OD) δ ppm: 1.07 (3H, s), 1.68–1.82 (2H, m), 2.56 (3H, s), 2.77–2.91 (2H, m), 3.33 (1H, d, J=11.0 Hz), 3.36 (1H, d, J=11.0 Hz), 5.05 (2H, s), 6.73 (1H, d, J=3.6 Hz), 7.04 (1H, d, J=3.6 Hz), 7.10 (2H, d, J=9.0 Hz), 8.00 (2H, d, J=9.0 Hz)

Infrared absorption spectrum $v_{max}$ cm$^{-1}$ (KBr): 3351, 3315, 3287, 2916, 2878, 2734, 2229, 1673, 1599, 1376, 1364, 1253, 1174

EXAMPLE 42

(2R)-Amino-2-methyl-4-{5-[3-(4-carboxyphenoxy) propynyl]thiophen-2-yl}butan-1-ol hydrochloride (Exemplification Compound No.1-2289)

The title compound was obtained according to a similar reaction to that described in Example 1.

Nuclear magnetic resonance spectrum (400 MHz, CH$_3$OD) δ ppm: 1.31 (3H, s), 1.90–2.10 (2H, m), 2.82–2.96 (2H, m), 3.51 (1H, d, J=11.5 Hz), 3.61 (1H, d, J=11.5 Hz), 5.04 (2H, s), 6.79 (1H, d, J=3.7 Hz), 7.05–7.11 (3H, m), 7.99 (2H, d, J=8.8 Hz)

Infrared absorption spectrum $v_{max}$ cm$^{-1}$ (KBr): 3383, 3064, 2226, 1699, 1604, 1508, 1379, 1233, 1170, 1002

EXAMPLE 43

(2R)-Amino-2-methyl-4-{5-[3-(3-methoxylphenoxy) propynyl]thiophen-2-yl}butan-1-ol maleate (Exemplification Compound No.1-2283)

The title compound was obtained according to a similar reaction to that described in Example 1.

Nuclear magnetic resonance spectrum (400 MHz, CH$_3$OD) δ ppm: 1.31 (3H, s), 1.88–2.10 (2H, m), 2.80–2.96 (2H, m), 3.51 (1H, d, J=11.6 Hz), 3.60 (1H, d, J=11.6 Hz), 3.77 (3H, s), 4.91 (2H, s), 6.25 (2H, s), 6.52–6.61 (3H, m), 6.78 (1H, d, J=3.6 Hz), 7.06 (1H, d, J=3.6 Hz), 7.18 (1H, t, J=8.4 Hz)

Infrared absorption spectrum $v_{max}$ cm$^{-1}$ (KBr): 3005, 2940, 2223, 1583, 1493, 1387, 1362, 1284, 1191, 1153, 1080, 1045, 1020, 866, 813, 758, 687, 565

EXAMPLE 44

(2R)-Amino-2-methyl-4-{5-[4-(4-methylphenoxy)but-1-ynyl]thiophen-2-yl}butan-1-ol maleate (Exemplification Compound No.1-1139)

The title compound was obtained according to a similar reaction to that described in Example 1.

Nuclear magnetic resonance spectrum (400 MHz, CH$_3$OD) δ ppm: 1.31 (3H, s), 1.87–2.10 (2H, m), 2.26 (3H, s), 2.85 (2H, t, J=6.8 Hz), 2.78–2.95 (2H, m), 3.51 (1H, d, J=11.6 Hz), 3.61 (1H, d, J=11.6 Hz), 4.09 (2H, t, J=6.8 Hz), 6.25 (2H, s), 6.73 (1H, d, J=3.6 Hz), 6.82 (2H, d, J=8.4 Hz), 6.96 (1H, d, J=3.6 Hz), 7.07 (2H, d, J=8.4 Hz)

Infrared absorption spectrum $v_{max}$ cm$^{-1}$ (KBr): 3032, 2925, 2596, 1578, 1513, 1388, 1359, 1293, 1244, 1205, 1176, 1079, 1039, 867, 812, 509

EXAMPLE 45

(2R)-Amino-2-methyl-4-{5-[4-(4-fluorophenoxy)but-1-ynyl]thiophen-2-yl}butan-1-ol (Exemplification Compound No.1-1135)

The title compound was obtained according to a similar reaction to that described in Example 1.

Nuclear magnetic resonance spectrum (400 MHz, CH$_3$OD) δ ppm: 1.15 (3H, s), 1.72–1.89 (2H, m), 2.22 (3H, brs), 2.88 (2H, t, J=6.8 Hz), 2.76–2.93 (2H, m), 3.37 (1H, d, J=10.8 Hz), 3.42 (1H, d, J=10.8 Hz), 4.11 (2H, t, J=6.8 Hz), 6.64 (1H, d, J=3.6 Hz), 6.84–6.90 (2H, m), 6.93–7.03 (3H, m)

Infrared absorption spectrum $v_{max}$ cm$^{-1}$ (KBr): 3356, 3296, 3090, 2971, 2950, 2916, 2896, 2877, 2812, 2735, 1589, 1506, 1465, 1389, 1289, 1245, 1219, 1203, 1154, 1065, 1039, 974, 923, 831, 819, 742, 568, 523, 509

EXAMPLE 46

(2R)-Amino-2-methyl-4-{5-[3-(3, 4-dimethylphenoxy) propynyl]thiophen-2-yl}butan-1-ol maleate (Exemplification Compound No.1-2278)

The title compound was obtained according to a similar reaction to that described in Example 1.

Nuclear magnetic resonance spectrum (400 MHz, CH₃OD) δ ppm: 1.31 (3H, s), 1.90–2.09 (2H, m), 2.19 (3H, s), 2.23 (3H, s), 2.81–2.94 (2H, m), 3.31 (1H, s), 3.51 (1H, d, J=11.6 Hz), 3.61 (1H, d, J=11.6 Hz), 4.87 (2H, s), 6.25 (2H, s), 6.70–6.78 (3H, m), 7.01–7.04 (2H, m)

Infrared absorption spectrum $\nu_{max}$ cm$^{-1}$ (liquid film): 3353, 3022, 2971, 2923, 2226, 1579, 1500, 1385, 1368, 1287, 1249, 1205, 1165, 1120, 1077, 1039, 930, 865, 806, 713, 573, 446

EXAMPLE 47
(2R)-Amino-2-methyl-4-]2-(3-phenylpropyloxy)thiophen-5-yl]butan-1-ol tartrate (Exemplification Compound No.1-2395)

EXAMPLE 47 (a)
(2R)-Amino-2-methyl-4-thiophen-2-ylbutan-1-ol 1/2D-(-)-tartrate (4R)-Methyl-4-[2-(thiophen-2-yl)]ethyloxazolidin-2-one (85% ee, 7.30 g, 34.6 mmol) obtained in Example 56 was dissolved in the mixture of tetrahydrofuran (35 ml) and methanol (70 ml), and a 5N aqueous potassium hydroxide solution (70 ml) was added thereto in an ice bath followed by stirring for 2 days at 80° C. To the reaction solution was added dichloromethane, and the solution was washed with water. The dichloromethane layer was dried over anhydrous magnesium sulfate, and the solvent was evaporated under reduced pressure. The obtained residue (6.20 g) was dissolved in ethanol (60 ml), and D-(-)-tartaric acid (5.19 g, 34.6 mmol) in ethanol (50 ml) was added thereto to give a precipitate. The precipitate was filtered off to afford the crude title compound (7.56 g). The obtained crude target compound (7.54 g) was recrystallized from a mixture of ethanol (75 ml) and water (50 ml), and the title compound (5.89 g, 98% ee) was-obtained. In addition, the obtained target compound (5.88 g) was recrystallized from ethanol (60 ml) and water (54 ml) to afford the title compound (5.11 g, 99.7% ee).

Infrared absorption spectrum $\nu_{max}$ cm$^{-1}$ (KBr): 3400, 3218, 3126, 2937, 2596, 1599, 1530, 1400, 1124, 1077, 715
Anal. Calcd.(%) for C₉H₁₅NOS.0.5C₄H₄O₆: C, 50.95; H, 6.61; N, 5.40; S, 12.36. Found: C, 50.68; H, 6.91; N. 5.38; S, 12.48. $[\alpha]_D^{24}$ -14(c 1.00, H₂O)

EXAMPLE 47 (b)
(2R)-Acetylamino-2-methyl-4-(thiophen-2-yl)butyl acetate

To (2R)-Amino-2-methyl-4-thiophen-2-ylbutan-1-ol 1/2D-(-)-tartrate (5.11 g, 19.6 mmol) obtained in Example 47 (a) was added a 1N aqueous sodium hydroxide solution (30 ml) in an ice bath, and the resulting free compound was extracted with dichloromethane. The dichloromethane layer was dried over anhydrous sodium sulfate, and the solvent was evaporated in vacuo to give (2R)-amino-2-methyl-4-thiophen-2-ylbutan-1-ol (3.55 g, 98% yield). To the obtained (2R)-amino-2-methyl-4-(thiophen-2-yl)butan-1-ol (1.51 g, 8.15 mmol) was added pyridine (30 ml), and then acetic anhydride (1.95 ml, 20.7 mmol) and 4-(dimethylamino) pyridine (200 mg, 1.64 mmol) were added thereto in the ice bath followed by stirring for 2 hours at room temperature under a nitrogen atmosphere. The reaction solution was poured into 1N hydrochloric acid (150 ml) in an ice bath, and then extracted with ethyl acetate. The ethyl acetate layer was washed successively with 1N hydrochloric acid and with a saturated aqueous sodium chloride solution. The ethyl acetate layer was dried over anhydrous sodium sulfate, and the solvent was evaporated under reduced pressure. The residue was purified by chromatography on a silica gel column (elution solvent; hexane:ethyl acetate=3:1–1:2) to afford the title compound (2.15 g, 98% yield).

Nuclear magnetic resonance spectrum (400 MHz, CDCl₃) δ ppm: 1.37 (3H, s), 1.93 (3H, s), 1.94–2.10 (1H, m), 2.10 (3H,s), 2.24–2.38 (1H, m), 2.85 (2H, t, J=8.0 Hz), 4.18 (1H, d, J=11.6 Hz), 4.32 (1H, d, J=11.6 Hz), 5.39 (1H, brs), 6.81 (1H, dd, J=1.2, 3.6 Hz), 6.92 (1H, dd, J=3.6, 5.2 Hz), 7.12 (1H, dd, J=1.2, 5.2 Hz)

Infrared absorption spectrum $\nu_{max}$ cm$^{-1}$ (KBr): 3265, 3079, 2933, 2862, 1735, 1638, 1559, 1472, 1441, 1374, 1318, 1241, 1179, 1039, 701, 616

EXAMPLE 47 (c)
(2R)-Acetylamino-2-methyl-4-(5-bromothiophen-2-yl) butyl acetate (2R)-Acetylamino-2-methyl-4-(thiophen-2-yl)butyl acetate (1.81 g, 6.70 mmol) obtained in Example 47 (b) was dissolved in dimethylformamide (20 ml), and N-bromosuccinimide (1.27 g, 7.11 mmol) was added thereto in an ice bath followed by stirring under a nitrogen atmosphere for 10 minutes in an ice bath and then overnight at room temperature. The reaction solution was poured into water, extracted with ethyl acetate, and the ethyl acetate layer was washed with a saturated aqueous sodium chloride solution. The ethyl acetate layer was dried over anhydrous sodium sulfate, and the solvent was evaporated in vacuo. The residue was purified by chromatography on a silica gel column (elution solvent; hexane:ethyl acetate=3:1–1:2) to afford the title compound (2.32 g, 99% yield).

Nuclear magnetic resonance spectrum (400 MHz, CDCl₃) δ ppm: 1.35 (3H, s), 1.95 (3H, s), 1.95–2.08 (1H, m), 2.10 (3H,s), 2.24–2.37 (1H, m), 2.76 (2H, t, J=8.4 Hz), 4.15 (1H, d, J=11.2 Hz), 4.30 (1H, d, J=11.2 Hz), 5.39 (1H, brs), 6.57 (1H, d, J=3.6 Hz), 6.84 (1H, d, J=3.6 Hz)

Infrared absorption spectrum $\nu_{max}$ cm$^{-1}$ (liquid film): 3300, 3076, 2980, 2937, 1740, 1657, 1544, 1466, 1446, 1373, 1242, 1045, 794, 604

EXAMPLE 47 (d)
(2R)-2-Amino-2-methyl-4-[2-(3-phenylpropyloxy) thiophen-5-yl]butan-1-ol tartrate To 3-phenyl-1-propanol (1 ml) was added sodium (0.06 g, 2.6 mmol), and the mixture was heated slowly to 80° C.–90° C. and stirred at the temperature for 3 hours. After the reaction the solution was cooled gradually, (2R)-acetylamino-2-methyl-4-(5-bromothiophen-2-yl)butyl acetate (0.177 g, 0.51 mmol) obtained in Example 47(c), potassium iodide (0.8 mg, 0.005 mmol), and copper (II) oxide (21.0 mg, 0.26 mmol) were added thereto, and the reaction mixture was stirred for 19 hours at 90° C. After cooling the reaction solution, the solution was subjected successively to chromatography on a silica gel column (elution solvent; dichloromethane:methanol:triethylamine= 10:1:0–100:10:1, V/V/V) and on an alkaline silica gel column (elution solvent; dichloromethane:methanol=100:1, V/V) to give (2R)-2-amino-2-methyl-4-[2-(3-phenylpropyloxy)thiophen-5-yl]butan-1-ol (9.1 mg, 6% yield).

The obtained (2R)-2-amino-2-methyl-4-[2-(3-phenylpropyloxy)thiophen-5-yl]butan-1-ol (15.2. mg, 0.048 mmol) was dissolved in methanol (1 ml), and tartaric acid (4.5 mg, 0.049 mmol) was added thereto followed by stirring for 1.5 hours at room temperature. The solvent was concentrated under reduced pressure, and then ethyl acetate was added thereto to precipitate crystals, which were filtered off. The precipitate was washed with ethyl acetate and dried to afford the title compound (18.5 mg, 95% yield).

Nuclear magnetic resonance spectrum (400 MHz, CH₃OD) δ ppm: 1.30(3H, s), 1.86–2.07(4H, m), 2.68–2.79 (4H, m), 3.51(1H, d, J=11.6 Hz), 3.59(1H, d, J=11.6 Hz), 3.97(2H, t, J=6.5 Hz), 6.00(1H, d, J=3.7 Hz), 6.44(1H, d, J=3.7 Hz), 7.14–7.28(5H, m) Mass spectrum (ESI) m/z: 342 ((M +Na)$^+$), 320 ((M +H)$^+$)

EXAMPLE 48
(2R)-Amino-2-methyl-4-{5-[3-(3-acetylphenoxy)propynyl]thiophen-2-yl}butan-1-ol oxalate (Exemplification Compound No.1-2287)

The title compound was obtained according to a similar reaction to that described in Example 1.

Nuclear magnetic resonance spectrum (400 MHz, CH$_3$OD) δ ppm: 1.31 (3H, s), 1.88–2.10 (2H, m), 2.60 (3H, s), 2.82–2.95 (2H, m), 3.51 (1H, d, J=11.6 Hz), 3.60 (1H, d, J=11.6 Hz), 5.02 (2H, s), 6.78 (1H, d, J=3.6 Hz), 7.06 (1H, d, J=3.6 Hz), 7.26 (1H, m), 7.44 (1H, m), 7.61–7.67 (2H, m)

Infrared absorption spectrum ν$_{max}$ cm$^{-1}$ (KBr): 3346, 3213, 2929, 2224, 1679, 1595, 1582, 1277, 1205, 721

EXAMPLE 49
(2R)-Amino-2-methyl-4-[5-(5-phenylpent-1-ypyl)thiophen-2-yl]butan-1-ol oxalate (Exemplification Compound No.1-824)

EXAMPLE 49 (a)
(2R)-Acetylamino-2-methyl-4-[5-(5-phenylpent-1-ynyl)thiophen-2-yl]butyl acetate (2R)-Acetylamino-2-methyl-4-(5-bromothiophen-2-yl)butyl acetate (1.60 g, 4.59 mmol) obtained in Example 47 (c) was dissolved in dimethylformamide (16 ml), and 5-phenylpent-1-yne (1.99 g, 13.8 mmol), triethylamine (6.40 ml, 45.9 mmol), copper(I) iodide (175 mg, 0.92 mmol), and dichlorobis(triphenylphosphine)palladium (322 mg, 0.46 mmol) were added thereto followed by stirring for 2 hours at 80° C. under a nitrogen atmosphere. The reaction solution was poured into water, extracted with ethyl acetate, and after the ethyl acetate layer was dried over anhydrous magnesium sulfate, the solvent was evaporated in vacuo. The residue was purified by chromatography on a silica gel column (elution solvent; hexane:ethyl acetate=2:1–2:3) to give the title compound (1.41 g, 75% yield).

Nuclear magnetic resonance spectrum (400 MHz, CDCl$_3$) δ ppm: 1.36 (3H, s), 1.85–2.05 (3H, m), 1.94 (3H, s), 2.10 (3H, s), 2.25–2.35 (1H, m), 2.43 (2H, t, J=7.0 Hz), 3.70–3.80 (4H, m), 4.17 (1H, d, J=11.2 Hz), 4.31 (1H, d, J=11.2 Hz), 5.38 (1H, brs), 6.64 (1H, d, J=3.6 Hz), 6.94 (1H, d, J=3.6 Hz), 7.15–7.42 (5H, m)

Infrared absorption spectrum ν$_{max}$ cm$^{-1}$ (CHCl$_3$): 3443, 2946, 2862, 1737, 1681, 1511, 1374, 1251, 1042

EXAMPLE 49 (b)
(2R)-Amino-2-methyl-4-[5-(5-phenylpent-1-ynyl)thiophen-2-yl]butan-1-ol oxalate (2R)-Acetylamino-2-methyl-4-[5-(5-phenylpent-1-ynyl)thiophen-2-yl]butyl acetate (1.40 g 3.40 mmol) obtained in Example 49 (a) was dissolved in 14 ml of a mixture solution (tetrahydrofuran:methanol:water=1:1:1), and lithium hydroxide monohydrate (1.43 g, 34.0 mmol) was added thereto followed by stirring for 4 hours at 50° C. The reaction solution was poured into water, extracted with dichloromethane, and after the dichloromethane layer was dried over anhydrous sodium sulfate, the solvent was evaporated under reduced pressure. The residue was purified by chromatography on a silica gel column (elution solvent; dichloromethane:methanol:ammonia water=20:1:0–10:1:0.1) to afford (2R)-amino-2-methyl-4-[5-(5-phenylpent-1-ynyl)thiophen-2-yl]butan-1-ol (1.11 g, 100% yield). The obtained (2R)-amino-2-methyl-4-[5-(5-phenylpent-1-ynyl)thiophen-2-yl]butan-1-ol (360 mg, 1.10 mmol) was dissolved in methanol, and oxalic acid (99 mg, 1.10 mmol) was added thereto to precipitate crystals. The crystals were recrystallized from methanol to afford the title compound (394 mg, 86% yield) as white crystals.

Nuclear magnetic resonance spectrum (400 MHz, CH$_3$OD) δ ppm: 1.31 (3H, s), 1.82–2.10 (4H, m), 2.40 (2H, t, J=7.0 Hz), 2.75 (2H, t, J=7.5 Hz), 2.80–2.95 (2H, m), 3.52 (1H, d, J=11.5 Hz), 3.61 (1H, d, J=11.5 Hz), 6.73 (1H, d, J=3.6 Hz), 6.94 (1H, d, J=3.6 Hz), 7.13–7.30 (5H, m)

Infrared absorption spectrum ν$_{max}$ cm$^{-1}$ (KBr): 3383, 3106, 3026, 2980, 2942, 2622, 2514, 1721, 1609, 1539, 1198, 699

Mass spectrum (FAB) m/z: 328 ((M +H)$^+$) (acid free form) Anal. Calcd.(%) for C$_{20}$H$_{25}$NOS.C$_2$H$_2$O$_4$.0.2H$_2$O: C, 62.75; H, 6.55; N, 3.32; S, 7.61. Found: C, 62.50; H, 6.29; N, 3.39; S, 7.70. [α]$_D^{25}$ −0.9 (c 1.00, methanol)

EXAMPLE 50
(2R)-Amino-2-methyl-4-[5-(5-phenylpentanoyl)thiophen-2-yl]butan-1-ol oxalate (Exemplification Compound No.1-1344)

(2R)-Amino-2-methyl-4-[5-(5-phenylpent-1-ynyl)thiophen-2-yl]butan-1-ol (387 mg, 1.18 mmol) obtained in Example 49 was dissolved in methanol (4 ml), and 6N sulfuric acid (4 ml) was added thereto followed by heating under reflux for 4 hours. The reaction solution was cooled to 0° C. and made alkaline (pH 14) with a 1N aqueous sodium hydroxide solution, and the resulting solution was extracted with dichloromethane. The dichloromethane layer was dried over anhydrous sodium sulfate, and the solvent was evaporated in vacuo. The residue was purified by chromatography on a silica gel column (Chromatorex NH (100–200 mesh)) (elution solvent; dichloromethane:methanol=1:0–50:1) to afford (2R)-amino-2-methyl-4-[5-(5-phenylpentanoyl)thiophen-2-yl]butan-1-ol (336 mg, 82% yield). This compound was dissolved in methanol, and oxalic acid (88 mg, 0.97 mmol) was added thereto to precipitate crystals. The crystals were recrystallized from methanol to afford-the title compound (332 mg, 78% yield) as white crystals.

Nuclear magnetic resonance spectrum (400 MHz, DMSO-d$_6$) δ ppm: 1.19 (3H, s), 1.55–1.67 (4H, m), 1.80–1.98 (2H, m), 2.60 (2H, t, J=6.7 Hz), 2.83–2.96 (4H, m), 3.40 (1H, d, J=11.3 Hz), 3.47 (1H, d, J=11.3 Hz), 7.00 (1H, d, J=3.7 Hz), 7.13–7.22 (3H, m), 7.23–7.31 (2H, m), 7.80 (1H, d, J=3.7 Hz)

Infrared absorption spectrum ν$_{max}$ cm$^{-1}$ (KBr): 3126, 2942, 2657, 1915, 1718, 1649, 1609, 1547, 1445, 1205, 700

Mass spectrum (FAB) m/z: 346 ((M +H)$^+$) (acid free form) Anal. Calcd.(%) for C$_{20}$H$_{27}$NO$_2$S.C$_2$H$_2$O$_4$.0.5H$_2$O: C, 59.44; H, 6.80; N, 3.15; S, 7.21. Found: C, 59.62; H, 6.53; N, 3.31; S, 7.43.

EXAMPLE 51
(2R)-Amino-2-methyl-4-[5-(5-phenylpentyl)thiophen-2-yl]butan-1-ol oxalate (Exemplification Compound No.1-152)

(2R)-Acetylamino-2-methyl-4-[5-(5-phenylpent-1-ynyl)thiophen-2-yl]butyl acetate (337 mg, 0.82 mmol) obtained in Example 49(a) was dissolved in methanol (17 ml), and 10% palladium-charcoal (170 mg) was added thereto followed by stirring for 16 hours under a hydrogen atmosphere. After the catalyst was filtered out through Celite, the filtrate was evaporated to dryness under reduced pressure to give (2R)-acetylamino-2-methyl-4-[5-(5-phenylpentyl)thiophen-2-yl]butyl acetate (318 mg, 93% yield). The obtained (2R)-acetylamino-2-methyl-4-[5-(5-phenylpentyl)thiophen-2-yl]butyl acetate (298 mg, 0.72 mmol) was dissolved in 6 ml of a mixture solvent (tetrahydrofuran:methanol:water=1:1:1), and lithium hydroxide monohydrate (301 mg, 7.17 mmol)

was added thereto followed by stirring for 6 hours at 50° C. The reaction solution was poured into water, extracted with ethyl acetate, and after the ethyl acetate layer was dried over anhydrous sodium sulfate, the solvent was evaporated in vacuo. The residue (243 mg) was dissolved in methanol, and oxalic acid (65 mg, 0.72 mmol) was added thereto to precipitate crystals. The crystals were filtered off to afford the title compound (251 mg, 83% yield) as white crystals.

Nuclear magnetic resonance spectrum (400 MHz, CH$_3$OD) δ ppm: 1.31 (3H, s), 1.32–1.42 (2H, m), 1.58–1.70 (4H, m), 1.88–2.08 (2H, m), 2.59 (2H, t, J=7.6 Hz), 2.74 (2H, t, J=7.4 Hz), 2.75–2.91 (2H, m), 3.52 (1H, d, J=11.6 Hz), 3.61 (1H, d, J=11.6 Hz), 6.56 (1H, d, J=3.3 Hz), 6.63 (1H, d, J=3.3 Hz), 7.09–7.17 (3H, m), 7.19–7.27 (2H, m)

Infrared absorption spectrum $v_{max}$ cm$^{-1}$ (KBr): 3458, 3134, 2929, 2855, 2595, 1724, 1642, 1543, 1219, 710

EXAMPLE 52
(2R)-Amino-2-methyl-4-{5-[3-(4-chlorophenoxy)propynyl]thiophen-2-yl]butan-1-ol oxalate (Exemplification Compound No.1-2273)

EXAMPLE 52 (a)
(2R)-Acetylamino-2-methyl-4-[5-(3-hydroxypropynyl)thiophen-2-yl]butyl acetate (2R)-Acetylamino-2-methyl-4-(5-bromothiophen-2-yl)butyl acetate (1.38 g, 3.95 mmol) obtained in Example 47 (c) was dissolved in dimethylformamide (20 ml), and then propargylalcohol (0.69 ml, 11.9 mmol), triethylamine (5.60 ml, 40.1 mmol), copper(I) iodide (76 mg, 0.40 mmol), and dichlorobis(triphenylphosphine)palladium (276 mg, 0.39 mmol) were added thereto followed by stirring for 1 hour at 80° C. under a nitrogen atmosphere. The reaction solution was poured into water, extracted with ethyl acetate, and after the ethyl acetate layer was dried over anhydrous sodium sulfate, the solvent was evaporated in vacuo. The residue was purified by chromatography on a silica gel column (elution solvent; hexane:ethyl acetate=3:1–1:3) to afford the title compound (685 mg, 54% yield) as a white crystalline solid.

Nuclear magnetic resonance spectrum (500 MHz, CDCl$_3$) δ ppm: 1.35 (3H, s), 1.91 (1H, brs), 1.94 (3H, s), 1.97–2.05 (1H, m), 2.10 (3H, s), 2.27–2.35 (1H, m), 2.75–2.82 (2H, m), 4.16 (1H, d, J=11.2 Hz), 4.31 (1H, d, J=11.2 Hz), 4.49 (2H, s), 5.43 (1H, brs), 6.66 (1H, d, J=3.6 Hz), 7.02 (1H, d, J=3.6 Hz)

Infrared absorption spectrum $\lambda_{max}$ cm$^{-1}$ (KBr): 3295, 3077, 2981, 2217, 1740, 1644, 1556, 1373, 1251, 1028

EXAMPLE 52 (b)
(2R)-Amino-2-methyl-4-{5-[3-(4-chlorolphenoxy)propnypyl]thiophen-2-yl]butan-1-ol oxalate (2R)-Acetylamino-2-methyl-4-[5-(3-hydroxypropynyl)thiophen-2-yl]butyl acetate (285 mg, 0.88 mmol) obtained in Example 52 (a) and 4-chlorophenol (136 mg, 1.06 mmol) were dissolved in anhydrous tetrahydrofuran (5 ml), and then azodicarboxylic acid diethylester (230 mg, 1.32 mmol) and triphenylphosphine (346 mg, 1.32 mmol) were added thereto in an ice bath followed by stirring for 4 hours at room temperature. Into the reaction mixture was poured water, and the resulting solution was extracted with ethyl acetate. The ethyl acetate layer was dried over anhydrous magnesium sulfate, and the solvent was evaporated under reduced pressure. The residue was purified by chromatography on a silica gel column (elution solvent; hexane:ethyl acetate= 2:1–1:3) to give (2R)-acetylamino-2-methyl-4-{5-[3-(4-chlorophenoxy)propynyl]thiophen-2-yl}butyl acetate (195 mg, 51% yield) as a yellow oil. This product was dissolved in 6 ml of a mixture solvent (tetrahydrofuran:methanol:water=1:1:1), and lithium hydroxide monohydrate (370 mg, 8.82 mmol) was added thereto followed by stirring for 6 hours at 50° C. The reaction solution was poured into water, extracted with dichloromethane, and after the dichloromethane layer was dried over anhydrous sodium sulfate, the solvent was evaporated in vacuo. The residue (175 mg, 0.50 mmol) was dissolved in ethyl acetate (5 ml), and oxalic acid (45 mg, 0.50 mmol) was added thereto to precipitate crystals. The crystals were filtered off to afford the title compound (198 mg, 86% yield) as white crystals.

Nuclear magnetic resonance spectrum (400 MHz, DMSO-d$_6$) δ ppm: 1.18 (3H, s), 1.7–2.0 (2H, m), 2.84 (2H, t, J=8.7 Hz), 3.43 (2H, m), 5.07 (2H, s), 6.83 (1H, d, J=3.6 Hz), 7.05 (2H, d, J=9.0 Hz), 7.19 (1H, d, J=3.6 Hz), 7.37 (2H, d, J=9.0 Hz)

Infrared absorption spectrum $v_{max}$ cm$^{-1}$ (KBr): 3416, 1719, 1597, 1490, 1375, 1241, 1201, 1092, 1006, 830

Mass spectrum (FAB) m/z: 350 ((M +H)$^+$) (acid free form) Anal. Calcd.(%) for C$_{18}$H$_{20}$NO$_2$SCl.C$_2$H$_2$O$_4$: C, 54.61; H, 5.04; N, 3.18; S, 7.29; Cl, 8.06. Found: C, 54.61; H, 5.04; N, 3.01; S, 7.16; Cl, 7.77.

EXAMPLE 53
(2R)-Amino-2-methyl-4-[5-(1-hydroxy-5-phenylpentyl)thiophen-2-yl]butan-1-ol oxalate (Exemplification Compound No.1-1686)

(2R)-Amino-2-methyl-4-[5-(5-phenylpentanoyl)thiophen-2-yl]butan-1-ol (130 mg, 0.38 mmol) obtained in Example 50 was dissolved in methanol (3 ml), and sodium borohydride (17 mg, 0.45 mmol) was added thereto in an ice bath followed by stirring for 1 hour at room temperature. To the reaction solution was added water in the ice bath, and the resulting solution was extracted with ethyl acetate. The ethyl acetate layer was washed with a saturated aqueous sodium chloride solution, dried over anhydrous magnesium sulfate, and the solvent was evaporated under reduced pressure. The obtained residue was dissolved in methanol, and oxalic acid (34 mg, 0.38 mmol) was added thereto, and the solvent was evaporated in vacuo. To the residue was added ethanol (3 ml), and the resulting precipitate was filtered off to give the title compound (95 mg, 58% yield) as a white crystalline solid.

Nuclear magnetic resonance spectrum (400 MHz, CH$_3$OD) δ ppm: 1.25–1.50 (2H, m), 1.30 (3H, s), 1.58–1.68 (2H, m), 1.70–2.08 (4H, m), 2.52–2.64 (2H, m), 2.80–2.94 (2H, m), 3.53 (1H, d, J=11.7 Hz), 3.59 (1H, d, J=11.7 Hz), 4.74 (1H, t, J=6.8 Hz), 6.69 (1H; d, J=3.6 Hz), 6.74 (1H, d, J=3.6 Hz), 7.08–7.27 (5H, m)

Infrared absorption spectrum $v_{max}$ cm$^{-1}$ (KBr): 3357, 2933, 2857, 1579, 1496, 1454, 1310, 1070, 699

EXAMPLE 54
(2R)-Amino-2-methyl-4-[5-(4-phenylbut-1-ynyl)thiophen-2-yl]butan-1-ol oxalate (Exemplification Compound No.1-756)

The title compound was obtained according to a similar reaction to that described in Example 49 using (2R)-acetylamino-2-methyl-4-(5-bromothiophen-2-yl)butyl acetate and 4-phenylbut-1-yne.

Nuclear magnetic resonance spectrum (400 MHz, CH$_3$OD) δ ppm: 1.31 (3H, s), 1.88–2.09 (2H, m), 2.68 (2H, t, J=7.3 Hz), 2.78–2.93 (4H, m), 3.52 (1H, d, J=11.6 Hz), 3.61 (1H, d, J=11.6 Hz), 6.72 (1H, d, J=3.6 Hz), 6.88 (1H, d, J=3.6 Hz), 7.16–7.31 (5H, m)

Infrared absorption spectrum $v_{max}$ cm$^{-1}$ (KBr): 3204, 3110, 3026, 2981, 2929, 2887, 1719, 1608, 1541, 1202, 699

EXAMPLE 55

(2R)-Amino-2-methyl-4-[5-(4-phenylbutanoyl)thiophen-2-yl]butan-1-ol oxalate (Exemplification Compound No.1-1330)

The title compound was obtained according to a similar reaction to that described in Example 50 using (2R)-amino-2-methyl-4-[5-(4-phenylbut-1-ynyl)thiophen-2-yl]butan-1-ol obtained in Example 54.

Nuclear magnetic resonance spectrum (400 MHz, DMSO-$d_6$) δ ppm: 1.19 (3H, s), 1.82–1.98 (4H, m), 2.62 (2H, t, J=7.7 Hz), 2.85-2.97 (4H, m), 3.39 (1H, d, J=11.7 Hz), 3.45 (1H, d, J=11.7 Hz), 7.00 (1H, d, J=3.8 Hz), 7.15-7.33 (5H,m), 7.76 (1H, d, J=3.8 Hz)

Infrared absorption spectrum $v_{max}$ cm$^{-1}$ (KBr): 3410, 3210, 2941, 2653, 2576, 1665, 1641, 1530, 1452, 1325

EXAMPLE 56

(2R)-Amino-2-methyl-4-[5-(4-cyclohexylbut-1-ynyl)thiophen-2-yl]butan-1-ol (Exemplification Compound No.1-743)

The title compound was obtained according to a similar reaction to that described in Example 1.

Nuclear magnetic resonance spectrum (400 MHz, CH$_3$OD) δ ppm: 0.87–0.99 (2H, m), 1.08 (3H, s), 1.11–1.50 (6H, m), 1.62–1.81 (7H, m), 2.41 (2H, t, J=7.2 Hz), 2.74–2.88 (2h, m), 3.34 (1H, d, J=11.0 Hz), 3.37 (1H, d, J=11.0 Hz), 6.66 (1H, d, J=3.6 Hz), 6.87 (1H, d, J=3.6 Hz)

Infrared absorption spectrum $v_{max}$ cm$^{-1}$ (KBr): 3334, 3269, 3153, 2922, 2851, 1618, 1449, 1060, 804

EXAMPLE 57

(2R)-Amino-2-methyl-4-[5-(4-cyclohexylbutyl)thiophen-2-yl]butan-1-ol (Exemplification Compound No.1-71)

The title compound was obtained according to a similar reaction to that described in Example 11 using (2R)-amino-2-methyl-4-[5-(4-cyclohexylbut-1-ynyl)thiophen-2-yl]butan-1-ol obtained in Example 56.

Nuclear magnetic resonance spectrum (400 MHz, CH$_3$OD) δ ppm: 0.80–0.95 (2H, m), 1.08 (3H, s), 1.10–1.40 (8H, m), 1.54–1.81 (9H, m), 2.68–2.87 (4H, m), 3.34 (1H, d, J=10.9 Hz), 3.37 (1H, d, J=10.9 Hz), 6.53 (1H, d, J=3.2 Hz), 6.58 (1H, d, J=3.2 Hz)

Infrared absorption spectrum $v_{max}$ cm$^{-1}$ (KBr): 3333, 3269, 3170, 2923, 2850, 1619, 1461, 1447, 1059, 801

EXAMPLE 58

(2R)-Amino-2-methyl-4-[5-(4-cyclohexylbutanoyl)thiophen-2-yl]butan-1-ol (Exemplification Compound No.1-1 329)

The title compound was obtained according to a similar reaction to that described in Example 17 using (2R)-amino-2-methyl-4-[5-(4-cyclohexylbut-1-ynyl)thiophen-2-yl]butan-1-ol obtained in Example 56.

Nuclear magnetic resonance spectrum (400 MHz, CH$_3$OD) δ ppm: 0.83–0.97 (2H, m), 1.09 (3H, s), 1.10–1.33 (6H, m), 1.61–1.86 (9H, m), 2.82–3.00 (4H, m), 3.35 (1H, d, J=10.9 Hz), 3.39 (1H, d, J=10.9 Hz), 6.94 (1H, d, J=3.7 Hz), 7.69 (1H, d, J=3.7 Hz)

Infrared absorption spectrum $v_{max}$ cm$^{-1}$ (KBr): 3333, 3268, 3142, 2921, 2849, 1648, 1457, 1208, 1057, 923, 816

EXAMPLE 59

2-Amino-2-methyl-4-[5-(3-cyclohexylmethoxypropynyl)thiophen-2-yl]butan-1-ol maleate (Exemplification Compound No.1-1185)

The title compound was obtained according to a similar reaction to that described in Example 1.

Nuclear magnetic resonance spectrum (400 MHz, CH$_3$OD) δ ppm: 0.92–1.04 (2H, m), 1.13–1.37 (3H, m), 1.31 (3H, s), 1.53–1.82 (6H, m), 1.89–2.11 (2H, m), 2.82–2.96 (2H, m), 3.35 (2H, d, J=6.4 Hz), 3.51 (1H, d, J=11.5 Hz), 3.61 (1H, d, J=11.5 Hz), 4.87 (2H, s), 6.25 (2H, s), 6.78 (1H, d, J=3.6 Hz), 7.05 (1H, d, J=3.6 Hz)

Infrared absorption spectrum $v_{max}$ cm$^{-1}$ (KBr): 2924, 2852, 2218, 1577, 1496, 1386, 1356, 1195, 1089, 866

EXAMPLE 60

(2R)-Amino-2-methyl-4-[5-(4-cyclohexyloxybutyl)thiophen-2-yl]butan-1-ol maleate (Exemplification Compound No.1-400)

The title compound was obtained according to a similar reaction to that described in Example 11 using (2R)-amino-2-methyl-4-[5-(4-cyclohexylbut-1-yl)thiophen-2-yl]butan-1-ol in Example 31.

Nuclear magnetic resonance spectrum (400 MHz, CH$_3$OD) δ ppm: 1.15–1.35 (5H, m), 1.31 (3H, s), 1.50–1.80 (7H, m), 1.85–2.08 (4H, m), 2.73–2.92 (4H, m), 3.20–3.30 (1H, m), 3.45–3.55 (3H, m), 3.60 (1H, d, J=11.6 Hz), 6.25 (2H, s), 6.59(1H, d, J=3.3 Hz), 6.64 (1H, d, J=3.3 Hz)

Infrared absorption spectrum $v_{max}$ cm-$^1$ (KBr): 2931, 2856, 1577, 1490, 1471, 1459, 1388, 1357, 1108, 1081, 868

EXAMPLE 61

(2R)-Amino-2-methyl-4-{5-[4-(4-fluorophenoxy)butyl]thiophen-2-yl}butan-1-ol (Exemplification Compound No.1-463)

The title compound was obtained according to a similar reaction to that described in Example 11 using (2R)-amino-2-methyl-4-{5-[4-(4-fluorophenoxy)but-1-ynyl]thiophen-2-yl}butan-1-ol obtained in Example 45.

Nuclear magnetic resonance spectrum (400 MHz, CH$_3$OD) δ ppm: 1.08 (3H, s), 1.70–1.85 (6H, m), 2.73–2.88 (4H, m), 3.34 (1H, d, J=10.9 Hz), 3.38 (1H, d, J=10.9 Hz), 3.94 (2H, t, J=5.9 Hz), 6.58 (1H, d, J=3.7 Hz), 6.60 (1H, d, J=3.7 Hz), 6.83–6.90 (2H, m), 6.93–7.00 (2H, m)

Infrared absorption spectrum $v_{max}$ cm$^{-1}$ (KBr): 3333, 3268, 3162, 2940, 2865, 1509, 1474, 1244, 1220, 1060, 830, 763

EXAMPLE 62

(2R)-Amino-2-methyl-4-{5-[4-(4-methoxyphenoxy)butyl]thiophen-2-yl}butan-1-ol (Exemplification Compound No.1-479)

The title compound was obtained according to a similar reaction to that described in Example 26 using (4R)-methyl-4-{2-[4-(4-methoxyphenoxy)but-1-ynyl]}ethyloxazolidine obtained in Example 1 (h).

Nuclear magnetic resonance spectrum (400 MHz, CH$_3$OD) δ ppm: 1.08 (3H, s), 1.68–1.84 (6H, m), 2.73–2.87 (4H, m), 3.34 (1H, d, J=10.8 Hz), 3.38 (1H, d, J=10.8 Hz), 3.72 (3H, s), 3.91 (2H, t, J=6.0 Hz), 6.58 (1H, d, J=3.1 Hz), 6.60 (1H, d, J=3.1 Hz), 6.81 (4H, s)

Infrared absorption spectrum $v_{max}$ cm$^{-1}$ (KBr): 3335, 3273 3183, 2945, 2868, 1514, 1473, 1233, 1045, 825, 735

EXAMPLE 63
(2R)-Amino-2-methyl-4-[5-(4-benzyloxybut-1-ynyl)thiophen-2-yl]butan-1-ol oxalate (Exemplification Compound No.1-1266)

The title compound was obtained according to a similar reaction to that described in Example 1.

Nuclear magnetic resonance spectrum (400 MHz, CH$_3$OD) δ ppm: 1.31 (3H, s), 1.89–2.10 (2H, m), 2.70 (2H, t, J=6.8 Hz), 2.80–2.94 (2H, m), 3.52 (1H, d, J=11.6 Hz), 3.61 (1H, d, J=11.6 Hz), 3.64 (2H, t, J=6.8 Hz), 4.57 (2H, s), 6.74 (1H, d, J=3.6 Hz), 6.94 (1d, J=3.6 Hz), 7.23–7.39 (5H, m)

Infrared absorption spectrum $v_{max}$ cm$^{-1}$ (KBr): 3358, 3028, 2926, 2544, 1719, 1702, 1605, 1496, 1468, 1454, 1402, 1279, 1204, 1105, 806, 739, 720, 699, 500

Mass spectrum (FAB) m/z: 344 ((M +H)$^+$) (acid free form)

EXAMPLE 64
(2R)-Amino-2-methyl-4-[5-(4-benzyloxybutyl)thiophen-2-yl]butan-1-ol maleate (Exemplification Compound No.1-594)

The title compound was obtained according to a similar reaction to that described in Example 11 using (2R)-amino-2-methyl-4-[5-(4-benzyloxybut-1-ynyl)thiophen-2-yl]butan-1-ol obtained in Example 63.

Nuclear magnetic resonance spectrum (400 MHz, CH$_3$OD) δ ppm: 1.31 (3H, s), 1.59–1.76 (4H, m), 1.88–2.08 (2H, m), 2.76 (2H, t, J=7.2 Hz), 2.79–2.91 (2H, m), 3.49 (2H, t, J=6.4 Hz), 3.51 (1H, d, J=11.6 Hz), 3.60 (1H, d, J=111.6 Hz), 4.48 (2H, s), 6.25 (2H, s), 6.58 (1H, d, J=3.6 Hz), 6.64 (1H, d, J=3.6 Hz), 7.23–7.38 (5H, m)

Infrared absorption spectrum $v_{max}$ cm$^{-1}$ (KBr): 2935, 2862, 1579, 1496, 1386, 1363, 1195, 1104, 1077, 1012, 875, 866, 804, 737, 698, 569

Mass spectrum (FAB) m/z: 348 ((M+H)$^+$) (acid free form)

EXAMPLE 65
(2R)-Amino-2-methyl-4-{5-[3-(4-methylcyclohexyloxy)propynyl]thiophen-2-yl}butan-1-ol maleate (Exemplification Compound No.1-1050)

The title compound was obtained according to a similar reaction to that described in Example 1.

Nuclear magnetic resonance spectrum (400 MHz, CD$_3$OD) δ ppm: 0.89, 0.90 (total 3H, d, J=6.4 Hz), 1.31 (3H, s), 0.92–1.56, 1.70–2.12 (total 11H, m), 2.81–2.96 (2H, m), 3.40–3.49, 3.73–3.79 (total 1H, m), 3.52 (1H, d, J=11.2 Hz), 3.61 (1H, d, J=11.2 Hz), 4.36, 4.39 (total 2H, s), 6.25 (2H, s), 6.78 (1H, d, J=3.6 Hz), 7.04 (1H, d, J=3.6 Hz)

Infrared absorption spectrum $v_{max}$ cm$^{-1}$ (KBr): 2927, 2864, 2219, 1579, 1508, 1386, 1366, 1193, 1093, 1077, 876, 865, 807, 717, 568

Mass spectrum (FAB) m/z: 336 ((M+H)$^+$) (acid free form)

EXAMPLE 66
(4R)-Methyl-4-[2-(thiophen-2-yl)ethyl]oxazolidin-2-one (Exemplification Compound No.4-4)

EXAMPLE 66 (a)
(2R)-t-Butoxycarbonylamino-3-n-hexanoyloxy-2-methyl-1-propanol 2-t-Butoxycarbonylamino-2-methyl-1,3-propanediol (20.0 g, 97.4 mmol) was suspended in diisopropyl ether (200 ml), and n-hexanoic acid vinyl ester (16.3 ml, 0.10 mmol) and lipase [Immobilized lipase from Pseudomonas sp. (TOYOBO; 0.67 U/mg)] (0.8 g) were added thereto followed by stirring vigorously for 2 hours at room temperature. The reaction solution was filtered, and the filtrate was evaporated under reduced pressure. The obtained residue was purified by chromatography on a silica gel column (elution solvent; hexane:ethyl acetate=10:1–2:1) to afford the title compound (25.0 g, 85% yield) as a colorless oil.

The obtained (2R)-t-butoxycarbonylamino-3-n-hexanoyloxy-2-methyl-1-propanol was subjected to an optically active HPLC column for analytical separation (ChiralCel OF (Daisel), 0.46 cm×25 cm, elution solvent; n-hexane:2-propanol=70:30, flow rate; 0.5 ml/mm) to determine the optical purity.

The peaks of the former elution band (8.2 mm) and the latter one (10.5 mm) corresponded to the 2S form and 2R form, respectively. The optical purity of this reaction product was confirmed to be 85% ee.

$[α]_D^{25}$ −8.5 (c 1.86°, CHCl$_3$)

Nuclear magnetic resonance spectrum (400 MHz, CDCl$_3$) δ ppm: 4.86 (s, 1H), 4.25 (d, 1H, J=11.2 Hz), 4.19 (d, 1H, J=11.2 Hz), 3.86 (brs, 1H), 3.70–3.55 (m, 2H), 2.36 (t, 2H, J=7.4 Hz), 1.68–1.58 (m, 2H), 1.44 (s, 9H), 1.40–1.30 (m, 4H), 1.25 (s, 3H), 0.90 (t, 3H, J=7.0 Hz)

Infrared absorption spectrum $v_{max}$ cm$^{-1}$ (KBr): 3415, 3380, 2961, 2935, 2874, 1721, 1505, 1458, 1392, 1368, 1293, 1248, 1168, 1076

Mass spectrum (FAB) m/z: 304 ((M+H)$^+$)

EXAMPLE 66 (b)
(2S)-t-Butoxycarbonylamino-3-n-hexanoyloxy-2-methyl-1-propanal (2R)-t-Butoxycarbonylamino-3-n-hexanoyloxy-2-methyl-1-propanol (30.7 g, 0.10 mol) obtained in Example 66(a) was dissolved in dichloromethane (600 ml), and then molecular sieve 4 Å (220 g) and pyridinium chlorochromate (43.6 g, 0.20 mol) were added thereto in an ice bath followed by stirring for 2 hours at room temperature. The reaction solution was diluted with ether, and then the solution was filtered. The filtrate was evaporated in vacuo, and the residue was purified by chromatography on a silica gel column (elution solvent; n-hexane:ethl acetate=10:1–5:1) to give the title compound (28.8 g, 95% yield) as a colorless oil.

Nuclear magnetic resonance spectrum (400 MHz, CDCl$_3$) δ ppm: 9.45 (s, 1H), 5.26 (brs, 1H), 4.44 (d, 1H, J=11.2 Hz), 4.32 (d, 1H, J=11.2 Hz), 2.32 (t, 2H, J=7.6 Hz), 1.70–1.55 (m, 2H), 1.45 (s, 9H), 1.38 (s, 3H), 1.40–1.25 (m, 4H), 0.90 (t, 3H, J=7.0 Hz)

Infrared absorption spectrum $v_{max}$ cm$^{-1}$ (liquid film): 3367, 2961, 2935, 2874, 1742, 1707, 1509, 1458, 1392, 1369, 1290, 1274, 1254, 1166, 1100, 1078

Mass spectrum (FAB) m/z: 302 ((M+H)$^+$)

EXAMPLE 66 (c)
(2R)-t-Butoxycarbonylamino-1-n-hexanoyloxy-2-methyl-4-(thiophen-2-yl)-3-butene 2-Thienylmethyltriphenylphosphonium bromide (67.1 g, 0.15 mol) was suspended in tetrahydrofuran (750 ml), and potassium t-butoxide (17.2 g, 0.15 mol) was added thereto followed by stirring under a nitrogen atmosphere for 20 minutes at room temperature. A tetrahydrofuran (250 ml) solution of (2S)-t-butoxycarbonylamino-3-n-hexanoyloxy-2-methyl-1-propanal (23.0 g, 76.4 mmol) obtained in Example 66(b) was added dropwise to the reaction solution in an ice bath, and then the reaction mixture was stirred for 30 minutes in the ice bath. To the reaction solution was added water, and the resulting solution was extracted with ethyl acetate, and then the ethyl acetate layer was washed with a saturated aqueous sodium chloride solution. The ethyl acetate layer was dried over anhydrous sodium sulfate, and the solvent was evaporated under reduced pressure. The residue was purified by chromatography on a silica gel column (elution solvent; n-hexane:ethyl acetate=20:1) to afford the title compound (27.8 g, 96% yield) as a colorless oil.

Nuclear magnetic resonance spectrum (400 MHz, CDCl$_3$) δ ppm: 7.32–7.26, 7.16–7.14 (m, total 1H), 7.04–7.01, 7.01–6.93 (m, total 2H), 6.63 (d, 0.5 H, J=16.0 Hz), 6.60 (d, 0.5 H, J=13.6 Hz), 6.10 (d, 0.5 H, J=16.0 Hz), 5.58 (d, 0.5 H, J=13.6 Hz), 4.94, 4.93 (brs, total 1H), 4.40–4.10 (m, 2H), 2.34 (t, 2H, J=7.4 Hz), 1.70–1.55 (m, 2H), 1.57, 1.50, 1.44 (s, total 9H), 1.40–1.25 (m, 7H), 0.88 (t, 3H, J=7.0 Hz)

Infrared absorption spectrum $v_{max}$ cm$^{-1}$ (liquid film): 3370, 2961, 2933, 1725, 1495, 1456, 1391, 1367, 1247, 1167, 1109, 1100, 1072, 697

Mass spectrum (FAB) m/z: 381 (M$^+$)

EXAMPLE 66 (d)
(4R)-Methyl-4-[2-(thiophen-2-yl)ethenyl]oxazolidin-2-one (2R)-t-Butoxycarbonylamino-1-n-hexanoyloxy-2-methyl-4-(thiophen-2-yl)-3-butene (40.5 g, 0.11 mol) obtained in Example 66(c) was dissolved in the mixture of tetrahydrofuran (150 ml) and methanol (150 ml), and a 1N aqueous sodium hydroxide solution (530 ml) was added thereto in an ice bath followed by stirring for 30 minutes in the ice bath and subsequently for 1 hour at room temperature. After the reaction solution was concentrated in vacuo, water was added thereto, and the solution was extracted with dichloromethane, and then the dichloromethane layer was washed with a saturated aqueous sodium chloride solution. The dichloromethane layer was dried over anhydrous sodium sulfate, and the solvent was evaporated in vacuo to give a crude product (35.0 g). This crude product was dissolved in tetrahydrofuran (300 ml), and t-butoxy potassium (17.8 g, 0.16 mol) was added thereto in an ice bath followed by stirring for 10 minutes in the ice bath and subsequently for 40 minutes at room temperature. To the reaction solution was added water, and the resulting solution was extracted with ethyl acetate, and then the ethyl acetate layer was washed with the saturated aqueous sodium chloride solution. After the ethyl acetate layer was dried over anhydrous sodium sulfate, the solvent was evaporated under reduced pressure. The residue was purified by chromatography on a silica gel column (elution solvent; hexane:ethyl acetate=3:1–1:1) to afford the title compound (18.0 g, 81% yield) as a white solid.

Nuclear magnetic resonance spectrum (400 MHz, CDCl$_3$) δ ppm: 7.34 (d, 0.5H, J=5.1 Hz), 7.19 (d, 0.5H, J=5.0 Hz), 7.07–6.91 (m, 2H), 6.74 (d, 0.5H, J=16.0 Hz), 6.59 (d, 0.5H, J=12.5), 6.17 (brs, 1H), 6.06 (d, 0.5H, J=16.0 Hz), 5.65 (d, 0.5H, J=12.5 Hz), 4.41 (d, 0.5H, J=8.6 Hz), 4.31–4.16 (m, 1.5H), 1.60 (s, 1.5H), 1.55 (s, 1.5H)

Infrared absorption spectrum $v_{max}$ cm$^{-1}$ (KBr): 3275, 3110, 2974, 1752, 1391, 1376, 1281, 1169, 1039, 960, 704

Mass spectrum (FAB) m/z: 209 (M$^+$)

EXAMPLE 66 (e)
(4R)-Methyl-4-r2-(thiophen-2-yl)ethyl]oxazolidin-2-one (4R)-Methyl-4-[2-(thiophen-2-yl)ethenyl]oxazolidin-2-one (18.0 g, 86.0 mmol) obtained in Example 66(d) was dissolved in methanol (150 ml), and 10% palladium-charcoal (4.5 g) was added thereto followed by stirring for 10 hours at room temperature under a hydrogen atmosphere. The palladium-charcoal in the reaction solution was removed by filtration using Kiriyama funnel covered with a silica gel thin layer, and the filtrate was evaporated in vacuo. The obtained solid was washed with diethyl ether, and dried to give the title compound (16.5 g, 91% yield) as a white solid.

The obtained (4R)-methyl-4-[2-(thiophen-2-yl)ethyl]oxazolidin-2-one was subjected to an optically active HPLC column for analytical separation (ChiralCel OD-H (Daisel), 0.46 cm×25 cm, elution solvent; n-hexane:2-propanol=60:40, flow rate; 0.5 ml/min) to determine the optical purity.

The peaks of the former elution band (16.8 min) and the latter one (17.6 min) corresponded to the 2S form and 2R form, respectively. The optical purity of this reaction product was confirmed to be 85% ee.

[α]$_D^{25}$ +5.1 (c 2.4, CHCl$_3$)

Nuclear magnetic resonance spectrum (400 MHz, CDCl$_3$) δ ppm: 7.15 (d, 1H, J=5.2 Hz), 6.93 (dd, 1H, J=5.2, 3.6 Hz), 6.81 (d, 1H, J=3.6 Hz), 5.39 (brs, 1H), 4.19 (d, 1H, J=8.4 Hz), 4.08 (d, 1H, J=8.4 Hz), 3.00–2.84 (m, 2H), 2.08–1.92 (m, 2H), 1.42 (s, 3H)

Infrared absorption spectrum $v_{max}$ cm$^{-1}$ (KBr): 3283, 1770, 1399, 1244, 1043, 941, 846, 775, 706, 691

Mass spectrum (EI) m/z: 211 (M$^+$)

This optical purity 85% ee compound, (4R)-methyl-4-[2-(thiophen-2-yl)ethyl]oxazolidin-2-one (11 g) was dissolved in a mixture of ethyl acetate (25 ml) and n-hexane (5.0 ml) by heating, and the solution was left at room temperature for 2 hours. The precipitated white crystals were filtered off, and dried to give the title compound (4.0 g, optical purity 99% ee).

[α]=hd D$^{25}$ +7.8 (c 2.0°, CHCl$_3$)

EXAMPLE 67
(4R)-Methyl-4-[2-(thiophen-2-yl)ethyl]oxazolidin-2-one (Exemplification Compound No.4-4)

EXAMPLE 67 (a)
(2R)-t-Butoxycarbonylamino-1-n-hexanoyloxy-2-methyl-4-(thiophen-2-yl)butane (2R)-t-Butoxycarbonylamino-1-n-hexanoyloxy-2-methyl-4-(thiophen-2-yl)-3-butene (27.6 g, 72.4 mmol) obtained in Example 66(c) was dissolved in ethanol (450 ml), and 10% palladium-charcoal (14.0 g) was added thereto followed by stirring for 4 days at room temperature under a hydrogen atmosphere. After the palladium-charcoal in the reaction solution was filtered out through Celite, the filtrate was evaporated to dryness under reduced pressure. The residue was purified by chromatography on a silica gel column (elution solvent; hexane:ethyl acetate=20:1–10:1) to give the title compound (22.1 g, 80% yield) as a colorless oil.

Nuclear magnetic resonance spectrum (400 MHz, CDCl$_3$) δ ppm: : 7.02 (d, 1H, J=5.2 Hz), 6.91 (dd, 1H, J=5.2, 3.6 Hz), 6.80 (d, 1H, J=3.6 Hz), 4.53 (brs, 1H), 4.26–4.12 (m, 2H), 2.85 (t, 2H, J=8.4 Hz), 2.34 (t, 2H, J=7.6 Hz), 2.26–2.16 (m, 1H), 2.01–1.90 (m, 1H), 1.68–1.56 (m, 2H), 1.44 (s, 9H), 1.31 (s, 3H), 1.40–1.26 (m, 4H), 0.89 (t, 3H, J=7.6 Hz)

Infrared absorption spectrum $v_{max}$ cm$^{-1}$ (liquid film): 3371, 2961, 2933, 2872, 2864, 1721, 1502, 1466, 1455, 1392, 1367, 1246, 1168, 1074, 694

Mass spectrum (FAB) m/z: 384 ((M+H)$^+$)

EXAMPLE 67 (b)
(2R)-t-Butoxycarbonylamino-2-methyl-4-(thiophen-2-yl)-1-butanol (2R)-t-Butoxycarbonylamino-1-n-hexanoyloxy-2-methyl-4-(thiophen-2-yl)butane (22.0 g, 57.4 mmol) obtained in Example 67(a) was dissolved in a mixture solution of tetrahydrofuran (140 ml) and methanol (280 ml), and a 1N aqueous sodium hydroxide solution (280 ml) was added in an ice bath followed by stirring 30 minutes in an ice bath and subsequently for 1 hour at room temperature. The reaction solution was concentrated in vacuo, and water was added thereto, and after the resulting solution was extracted with dichloromethane, the dichloromethane layer was washed with a saturated aqueous sodium chloride solution. The dichloromethane layer was dried over anhydrous sodium sulfate, and the solvent was evaporated in vacuo to afford the title compound (15.5 g, 95% yield) as a white solid.

Nuclear magnetic resonance spectrum (400 MHz, CDCl$_3$) δ ppm: : 7.11 (d, 1H, J=5.2 Hz), 6.92 (dd, 1H, J=5.2, 3.6 Hz), 6.81 (d, 1H, J=3.6 Hz), 4.64 (brs, 1H), 4.08 (brs, 1H), 3.74–3.60 (m, 2H), 2.98–2.76 (m, 2H), 2.20–2.10 (m, 1H), 2.03–1.90 (m, 1H), 1.44 (s, 9H), 1.22 (s, 3H)

Infrared absorption spectrum $v_{max}$ cm$^{-1}$ (KBr): 3279, 3250, 3067, 2973, 2929, 2908, 2857, 1679, 1552, 1367, 1291, 1245, 1167, 1076, 1064, 1009, 861, 851, 701

Mass spectrum (FAB) m/z: 286 ((M+H)$^+$)

EXAMPLE 67 (c)
(4R)-Methyl-4-[2-(thiophen-2-yl)ethyl]oxazolidin-2-one (2R)-t-Butoxycarbonylamino-2-methyl-4-(thiophen-2-yl)-1-butanol (15.4 g, 53.9 mmol) obtained in Example 67(b) was dissolved in N,N-dimethylformamide (200 ml), and potassium t-butoxide (9.07 g, 80.8 mmol) was added thereto in an ice bath followed by stirring for 10 minutes in an ice bath and subsequently for 40 minutes at room temperature. To the reaction solution was added water, and then the solution was extracted with ethyl acetate, and after the ethyl acetate layer was washed with a saturated aqueous sodium chloride solution, dried over anhydrous sodium sulfate, and the solvent was evaporated in vacuo. The residue was purified by chromatography on a silica gel column (elution solvent; hexane:ethyl acetate=3:1–1:1) to afford the title compound (11.5 g, 100% yield) as a white solid. The data obtained from analytical instruments were in accord with that obtained in Example 66.

EXAMPLE 68
(4R)-[2-(benzo[b]thiophen-6-yl)ethyl]-4-methyloxazolidin-2-one (Exemplification Compound No.4-17)

EXAMPLE 68 (a)
(2R)-t-Butoxycarbonylamino-1-n-hexanoyloxy-2-methyl-4-(benzo[b]thiophen-6-yl)-3-butene (2R)-t-Butoxycarbonylamino-3-n-hexanoyloxy-2-methyl-1-propanal-(28.2 g, 93.6 mmol) obtained in Example 66(b) and 6-bromotriphenylphosphoniumbenzo[b] thiophene (45.8 g, 93.6 mmol) were suspended in tetrahydrofuran (700 ml), and potassium t-butoxide (11.6 g, 0.10 mol) were added thereto followed by stirring for 30 minutes at room temperature. To the resulting reaction solution was added water, and the solution was extracted with ethyl acetate, and then the ethyl acetate layer was washed with a saturated aqueous sodium chloride solution. The ethyl acetate layer was dried over anhydrous sodium sulfate, and the solvent was evaporated in vacuo. The residue was purified by chromatography on a silica gel column (elution solvent; hexane:ethyl acetate=10:1) to afford the title compound (28.0 g, 69% yield) as a colorless oil.

Nuclear magnetic resonance spectrum (400 MHz, CDCl$_3$) δ ppm: 7.82 (d, 1H, J=9.7 Hz), 7.75 (d, 1H, J=8.2 Hz), 7.44–7.39 (m, 1H), 7.32–7.26 (m, 2H), 6.74, 5.73 (d, total 1H, J=12.6 Hz), 6.61, 6.34 (d, total 1H, J=16.2 Hz), 4.87, 4.69 (br s, total 1H), 4.34–4.16, (m, 2H), 2.37–2.32 (m, 2H), 1.67–1.15 (m, 20H), 0.91–0.84 (m, 3H).

Infrared absorption spectrum $v_{max}$ cm$^{-1}$ (liquid film): 3440, 3373, 2961, 2932, 2872, 1724, 1597, 1498, 1457, 1390, 1367, 1247, 1167, 1099, 1073

Mass spectrum (FAB) m/z: 431 (M$^+$)

EXAMPLE 68 (b)
(2R)-t-Butoxycarbonylamino-1-n-hexanoyloxy-2-methyl-4-(benzo[b]thiophen-6-yl)butane (2R)-t-Butoxycarbonylamino-1-n-hexanoyloxy-2-methyl-4-(benzo[b]thiophen-6-yl)-3-butene (28.0 g, 64.9 mmol) obtained in Example 68(a) was dissolved in methanol (700 ml), and 10% palladium-charcoal (14.0 g) was added thereto followed by stirring for 6 days at room temperature under a hydrogen atmosphere. After the palladium-charcoal in the reaction solution was filtered out through Celite, the filtrate was evaporated under reduced pressure. The residue was purified by chromatography on a silica gel column (elution solvent; hexane:ethyl acetate=15:1–10:1) to give the title compound (24.30 g, 87% yield) as a colorless oil.

Nuclear magnetic resonance spectrum (400 MHz, CDCl$_3$) δ ppm: 7.73 (d, 1H, J=8.2. Hz), 7.69 (s, 1H), 7.36 (d, 1H, J=5.2 Hz), 7.28 (d, 1H, J=5.6 Hz), 7.19 (d, 1H, J=8.1 Hz), 4.56 (br s, 1H), 4.28 (d, 1H, J=11.0 Hz), 4.14 (d, 1H, J=11.0 Hz), 2.73 (t, 2H, J=8.7 Hz), 2.34 (t, 2H, J=7.5 Hz), 1.68–1.61 (m, 2H), 1.45 (s, 9H), 1.41–1.38 (m, 8H), 0.89 (t, 3H, J=6.7 Hz).

Infrared absorption spectrum $v_{max}$ cm$^{-1}$ (liquid film): 3371, 2960, 2933, 2870, 1720, 1604, 1501, 1466, 1392, 1367, 1248, 1167, 1074

Mass spectrum (FAB) m/z: 456 ((M+Na)$^+$)

EXAMPLE 68 (c)
(4R)-[2-(benzo[b]thiophen-6-yl)ethyl]-4-methyloxazolidin-2-one (2R)-t-Butoxycarbonylamino-1-n-hexanoyloxy-2-methyl-4-(benzo[b]thiophen-6-yl)butane (24.3 g, 56.0 mmol) obtained in Example 68(b) was dissolved in a mixture of tetarahydrofuran (220 ml) and methanol (110 ml), and a 1N aqueous sodium hydroxide solution (110 ml) was added thereto in an ice bath followed by stirring for 15 minutes in the ice bath and subsequently for 2 hours at room temperature. After the reaction solution was concentrated in vacuo, water was added thereto, and the solution was extracted with dichloromethane, and then the dichloromethane layer was washed with a saturated aqueous sodium chloride solution. The dichloromethane layer was dried over anhydrous sodium sulfate, and the solvent was evaporated in vacuo to give a crude product (18.8 g, 100% yield). This crude product was dissolved in dimethylformamide (380 ml), and potassium t-butoxide (9.43 g, 84.1 mmol) was added thereto in an ice bath followed by stirring for 5 minutes in the ice bath and subsequently for 1 hour at room temperature. To the reaction solution was added water, and the resulting solution was extracted with ethyl acetate, and then the ethyl acetate layer was washed with a saturated aqueous sodium chloride solution. After the ethyl acetate layer was dried over anhydrous sodium sulfate, the solvent was evaporated under reduced pressure. The residue was purified by chromatography on a silica gel column (elution solvent; hexane:ethyl acetate=3:2–2:1) to afford the title compound (13.8 g, 94% yield) as a white solid.

The obtained compound, (4R)-[2-(benzo[b]thiophen-6-yl)ethyl]-4-methyloxazolidin-2-one was subjected to an optically active HPLC column for analytical separation (ChiralCel AD (Daisel), 0.46 cm×25 cm, elution solvent; n-hexane:2-propanol=70:30, flow rate; 0.5 m/min) to determine the optical purity.

The peaks of the former elution band (15.9 min) and the latter one (17.6 min) corresponded to the 4S form and 4R form, respectively. The optical purity of this reaction product was confirmed to be 80% ee.

$[α]_D^{24}$ +2.3 (c 0.6, CHCl$_3$)

Nuclear magnetic resonance spectrum (400 MHz, CDCl$_3$) δ ppm: 7.73 (d, 1H, J=8.2 Hz), 7.68 (s, 1H), 7.38 (d, 1H, J=5.7 Hz), 7.29 (d, 1H, J=13.0 Hz), 7.18 (d, 1H, J=13.6 Hz), 5.91 (br s, 1H), 4.21 (d, 1H, J=8.7 Hz), 4.09 (d, 1H, J=8.7 Hz), 2.84–2.76 (m, 2H), 1.97 (t, J=8.5 Hz, 3H).

Infrared absorption spectrum $v_{max}$ cm$^{-1}$ (KBr): 3292, 2970, 2930, 1749, 1722, 1601, 1479, 1461, 1397, 1277, 1045

Mass spectrum (EI) m/z: 261 (M$^+$)

EXAMPLE 69

(2R)-t-Butoxycarbonylamino-3-n-hexanoyloxy-2-methyl-1-propanol 2-t-Butoxycarbonylamino-2-methyl-1,3-propanediol (200 mg, 0.97 mmol) was dissolved in diisopropylether (2 ml), and n-hexanoic acid vinyl ester (0.16 ml, 1.02 mmol) and lipase [Immnobilized lipase from *Pseudomonas sp.* =l (TOYOBO; 0.67 U/mg)] (20 mg) were added thereto followed by stirring 4 hours at room temperature. After the insoluble substances in the reaction mixture were removed by filtration, the filtrate was concentrated, and the residue was purified by flash chromatography on a silica gel column (elution solvent; n-hexane:ethyl acetate=10:1–7:3) to give the title compound (258 mg, 87% yield) as a colorless oil. The obtained compound, (2R)-t-butoxycarbonylamino-3-n-hexanoyloxy-2-methyl-1-propanol was subjected to an optically active HPLC column for analytical separation (ChiralCel OF (Daisel), 0.46 cmφ×25 cm, elution solvent; n-hexane:2-propanol=70:30, flow rate; 0.5 ml/min) to determine the optical purity.

The peaks of the former elution band (8.2 min) and the latter one (10.5 min) corresponded to the 2S form and 2R form, respectively. The optical purity in this reaction was confirmed to be 89% ee.

The absolute configuration of the title compound was determined by comparison of the specific rotation of the known compound, (2R)-t-butoxycarbonylamino-2-methyl-3-buten-1-ol (Tetrahedron Asymmetry 10 (1999) 4653–4661) which can be easily synthesized from the title compound as described in Reference example 1(a).

Nuclear magnetic resonance spectrum (400 MHz, CDCl$_3$) δ ppm: 4.89(1H,br.s), 4.24(1H,d,J=11.2 Hz), 4.19(1H,d,J=11.2 Hz), 3.66–3.54(2H,m), 2.36(2H,t,J=7.4 Hz), 1.69–1.57 (2H,m), 1.44(9H,s), 1.39–1.22(4H,m), 1.25(3H,s), 0.90(3H, t,J=6.6 Hz)

Infrared absorption spectrum $v_{max}$ cm$^{-1}$ (CHCl$_3$): 3411, 3380, 2961, 2934, 1722, 1504, 1459, 1392, 1368, 1292, 1248, 1168, 1077, 1015 Optical rotation $[\alpha]_D^{24}$: −1.1° (c=0.81, methanol)

EXAMPLE 70

(2R)-t-Butoxycarbonylamino-3-n-hexanoyloxy-2-ethyl-1-propanol

The title compound was obtained as a colorless oil (252 mg, 87% yield) according to a similar reaction to that described in Example 69 using 2-t-butoxycarbonylamino-2-ethyl-1,3-propanediol (200 mg, 0.91 mmol).

The obtained compound, (2R)-t-butoxycarbonylamino-3-n-hexanoyloxy-2-ethyl-1-propanol was subjected to an optically active HPLC column for analytical separation (ChiralCel OF (Daisel), 0.46 cmφ×25 cm, elution solvent; n-hexane:2-propanol=70:30, flow rate; 0.5 ml/min) to determine the optical purity.

The peaks of the former elution band (8.5 min) and the latter one (10.7 min) corresponded to the 2S form and 2R form, respectively. The optical purity in this reaction was confirmed to be 95% ee.

The absolute configuration of the title compound was determined by comparison of the specific rotation of the known compound, (+)-(R)-α-ethyl-α-vinylglycine (Helvetica Chimica Acta 69 (1986) 1365–1377) which can be easily synthesized from the-title compound as described in Reference example 5(f).

Nuclear magnetic resonance spectrum (400 MHz, CDCl$_3$) δ ppm: 4.78(1H,br.s), 4.28(1H,d,J=11.1 Hz), 4.13(1H,d,J=11.1 Hz), 3.72–3.57(2H,m), 2.35(2H,t,J=7.6 Hz), 1.83–1.54 (4H,m), 1.44(9H,s), 1.38–1.24(4H,m), 0.95–0.86(6H,m)

Infrared absorption spectrum $v_{max}$ cm$^{-1}$ (CHCl$_3$): 3371, 2966, 2935, 1722, 1503, 1460, 1368, 1249, 1168, 1086, 1028, 866, 781 Optical rotation $[\alpha]_D^{24}$: −2.4° (c=0.72, methanol)

The known and useful compounds, (−)-(R)-α-methyl-α-vinylglycine (Reference example 1), (+)-(S)-α-methyl-α-ethylglycine (Reference example 2), and (+)-(R)-α-ethyl-α-vinylglycine (Reference example 3) were prepared by using the compounds obtained in Example 69 or Example 70.

Reference Example 1

(−)-(R)-α-Methyl-α-vinylglycine

Reference Example 1(a)

(2R)-t-Butoxycarbonylamino-2-methyl-3-buten-1-ol

To the dichloromethane solution (18 ml) of (2R)-t-buthoxycarbonylamino-3-n-hexanoyloxy-2-methyl-1-propanol (1.5 g, 4.9 mmol) obatained in Example 69 was added molecular sieve 4 Å (10.5 g) thereto, and after stirring for 10 minutes at room temperature, pyridinium chlorochromate (2.1 g, 9.8 mmol) were added thereto followed by stirring for 1 hours.

To the reaction solution was added diethyl ether, and insoluble substances of the solution were filtered out by a silica gel short column (elution solvent:diethyl ether). The organic solvents of the filtrate were evaporated in vacuo, and the obtained residue (1.5 g) was used for the following reaction.

To a suspension of methyltriphenylphosphonium bromide (4.5 g, 12.5 mmol) in tetrahydrofuran (10 ml) was added potassium t-butoxide (1.3 g, 11.5 mmol) at 0° C. followed by stirring for 1 hour. To this reaction solution was added dropwise a tetrahydrofuran solution (10 ml) of the residue obtained in the previous reaction. After this reaction mixture was stirred for 30 minutes at 0° C., distilled water was added thereto followed by extraction with ethyl acetate. The ethyl acetate layer was washed with distilled water and subsequently with a saturated aqueous sodium chloride solution, and dried over magnesium sulfate. After the solvent was evaporated, the insoluble substances were filtered out by a silica gel short column (elution solvent: hexane:ethyl acetate=10:1). The filtrate was concentrated, and the obtained residue (1.2 g) was dissolved in methanol (20 ml), and then a 1N aqueous sodium hydroxide solution (20 ml) was added thereto followed by stirring for 30 minutes at room temperature. After, to this reaction solution was added diethyl ether, the solution was washed with distilled water and subsequently with the saturated aqueous sodium chloride solution, and dried over magnesium sulfate. The solvent was evaporated, and the residue was purified by preparative thin layer chromatography (elution solvent; hexane:ethyl acetate=1:1) to give the title compound (180 mg, 0.894 mmol, 18% yield).

Nuclear magnetic resonance spectrum (400 MHz, CDCl$_3$) δ ppm: 5.89(1H,ddd,J=11.0,6.6,1.5 Hz), 5.21(1H,d,J=1.5 Hz), 5.17(1H,d,J=6.6 Hz), 4.84(1H,br.s), 3.76(1H,br.s), 3.62 (2H,m), 1.44(9H,s), 1.32(3H,s)

Infrared absorption spectrum $v_{max}$ cm$^{-1}$ (CHCl$_3$): 3418, 3348, 2979, 1692, 1499, 1455, 1393, 1368, 1283, 1253, 1170, 1074, 918 Optical rotation $[\alpha]_D^{24}$: +10.4° (c=0.51, methanol)

Reference Example 1(b)
(2R)-t-Butoxycarbonylamino-2-methyl-3-butenal (2R)-t-Butoxycarbonylamino-2-methyl-3-buten-1-ol (180 mg, 0.894 mmol) obtained in Reference example 1(a) was dissolved in dichloromethane (5.0 ml), and molecular sieve 4 Å (2.0 g) and pyridinium chlorochromate (386 mg, 1.79 mmol) were added thereto in an ice bath followed by stirring for 1 hour at room temperature. To the reaction solution was added ether, and insoluble substances of the solution were filtered out, and then the filtrate was evaporated in vacuo. The residue was purified by flash chromatography on a silica gel column (elution solvent; n-hexane:ethyl acetate=10:1) to give the title compound (160 mg, 90% yield) as a colorless oil.

Nuclear magnetic resonance spectrum (400 MHz, $CDCl_3$) δ ppm: 9.26(1H,s), 5.83(1H,dd,J=17.5,10.6 Hz), 5.35(1H,d,J=10.6 Hz), 5.32(1H,d,J=17.5 Hz), 5.22(1H,br.s), 1.48(3H,s), 1.45(9H,s)

Infrared absorption spectrum $v_{max}$ $cm^{-1}$ ($CHCl_3$): 3350, 2980, 1737, 1707, 1505, 1455, 1369, 1279, 1256, 1168, 1069, 925, 867

Reference Example 1(c)
(2R)-t-Butoxycarbonylamino-2-methyl-3-butenoic acid (2R)-t-Butoxycarbonylamino-2-methyl-3-butenal (160 mg, 0.803 mmol) obtained in Reference example 1(b) was dissolved in a mixture of t-butanol (8.0 ml) and water (2.0 ml), and then 2-methyl-2-butene (0.38 ml, 3.61 mmol), sodium dihydrogenphosphate dihydrate (96 mg, 0.803 mmol), and sodium chlorite (254 mg, 2.81 mmol) were added thereto followed by stirring 1 hour at room temperature. To the reaction solution was added ethyl acetate, and the ethyl acetate layer was washed with a saturated aqueous sodium chloride solution. The ethyl acetate layer was dried over anhydrous magnesium sulfate, and the solvent was evaporated under reduced pressure. The residue was purified by flash chromatography on a silica gel column (elution solvent; n-hexane:ethyl acetate=20:1–1:1) to give the title compound (130 mg, 75% yield) as a colorless oil.

Nuclear magnetic resonance spectrum (400 MHz, $CDCl_3$) δ ppm: 5.07(1H,br.s), 5.68(1H,br.s), 5.12(1H,d,J=17.4 Hz), 5.05(1H,d,J=10.6 Hz), 1.48(3H,s), 1.40(9H,s)

Infrared absorption spectrum $v_{max}$ $cm^{-1}$ ($CHCl_3$): 3394, 2980, 1691, 1602, 1483, 1455, 1368, 1253, 1172, 1066, 756

Reference Example 1(d)
(−)-(R)-α-Methyl-α-vinylglycine hydrochloride (2R)-t-Butoxycarbonylamino-2-methyl-3-butenoic acid (120 mg, 0.557 mmol) obtained in Reference example 1(c) was dissolved in ethanol (1.5 ml), and a dioxane solution (1.5 ml) of 4N hydrochloric acid was added thereto followed by stirring 18 hours at room temperature. The reaction solution was concentrated in vacuo, and the residue was washed with ether, and dried to give the title compound (72 mg, 85% yield) as a white solid.

Nuclear magnetic resonance spectrum (400 MHz, $CDCl_3$) δ ppm: 6.07(1H,dd,J=17.6,11.0 Hz), 5.48(1H,d,J=11.1 Hz), 5.47(1H,d,J=17.6 Hz), 1.66(3H,s)

Infrared absorption spectrum $v_{max}$ $cm^{-1}$ (KBr): 3349, 3029, 1751, 1524, 1200, 954 Optical rotation $[\alpha]_D^{25}$: −18.7° (c=0.70, $H_2O$)

Reference Example 1(e)
(−)-(R)-α-methyl-α-vinylglycine (−)-(R)-α-methyl-α-vinylglycine hydrochloride (60 mg, 0.40 mmol) obtained in Reference example 1(d) was dissolved in ethanol (1.5 ml), and propylene oxide (1.5 ml) was added thereto followed by heating under reflux for 2 hours. The white solid in the reaction solution was filtered off to give the title compound (32 mg, 70 % yield) as a white solid.

Nuclear magnetic resonance spectrum (400 MHz, $CDCl_3$) δ ppm: 6.17(1H,dd,J=17.2,10.6 Hz), 5.56(1H,d,J=10.6 Hz), 5.54(1H,d,J=17.2 Hz), 1.43(3H,s)

Infrared absorption spectrum $v_{max}$ $cm^{-1}$ (KBr): 3600-2500, 1605, 1535, 1455, 1415, 1385, 1360, 1280, 1235, 1150, 1000, 940 Optical rotation $[\alpha]_D^{25}$: −27.6° (c=0.62, $H_2O$)

Reference Example 2
(+)-(S)-α-Methyl-α-ethynyl glycine

Reference Example 2(a)
3-t-Butoxycarbonyl-2,2-dimethyl-(4R)-n-hexanoyloxymethyl-4-methyloxazolidine (2R)-t-Butoxycarbonylamino-3-n-hexanoyloxy-2-methyl-i-propanol (10.1 g, 33.3 mmol) obtained in Example 69 was dissolved in dichloromethane (152 ml), and acetone dimethylacetal (16.4 ml, 133 mmol) and p-toluenesulfonic acid (172 mg, 1.00 mmol) were added thereto followed by stirring 12 hours at room temperature. The reaction solution was concentrated, and the residue was purified by flash chromatography on a silica gel column (elution solvent; n-hexane:ethyl acetate=10:1) to afford the title compound (5.72 g, 50% yield) as a colorless oil.

Nuclear magnetic resonance spectrum (400 MHz, $CDCl_3$) δ ppm: 4.29(1H,s), 4.18(1H,s), 3.99(1H,m), 3.64(1H,m), 2.28–2.34(2H,m), 1.26–1.25(24H,m), 0.89(3H,t) Optical rotation $[\alpha]_D^{25}$: +17.2° (c=1.50, $CHCl_3$)

Reference Example 2(b)
3-t-Butoxycarbonyl-2,2-dimethyl-(4S)-hydroxymethyl-4-methyloxazolidine 3-t-Butoxycarbonyl-2,2-dimethyl-(4R)-n-hexanoyloxymethyl-4-methyloxazolidine (13.7 g, 39.9 mmol) obtained in Reference example 2(a) was dissolved in dichloromethane (200 ml), and the hexane solution of 1.0M diisobutylaluminium hydride (99 ml, 99.7 mmol) was added dropwise thereto at −78° C. After, the reaction mixture was stirred for 30 minutes at −78° C., cooled down to room temperature, and 10 wt % aqueous potassium sodium tartrate solution (200 ml) was added thereto followed by stirring vigorously for 30 minutes. The reaction solution was extracted with diethyl ether, and after the ether layer was dried over anhydrous sodium sulfate, the solvent was evaporated in vacuo. The residue was purified by flash chromatography on a silica gel column (elution solvent; n-hexane:ethyl acetate=5:2) to afford the title compound (10.5 g, 100% yield) as a white crystalline solid.

Nuclear magnetic resonance spectrum (400 MHz, $CDCl_3$) δ ppm: 4.49(1H,br.s), 3.55–3.71(4H,m), 1.56(3H,s), 1.49 (12H,s), 1.42(3H,s) Optical rotation $[\alpha]_D^{25}$: −1.67° (c=1.45, $CHCl_3$)

Reference Example 2(c)
3-t-Butoxycarbonyl-2,2-dimethyl-(4R)-formyl-4-methyloxazolidine 3-t-Butoxycarbonyl-2,2-dimethyl-(4S)-hydroxymethyl-4-methyloxazolidine (9.79 g, 39.9 mmol) obtained in Reference example 2(b) was dissolved in dichloromethane (150 ml), and then pyridinium chlorochromate (13.0 g, 59.8 mmol) and molecular sieve 4 Å (65.0 g) were added thereto in an ice bath followed by stirring for 1 hour at room temperature. The reaction solution was diluted with ether, and then the solution was filtered by silica gel column. The filtrate was evaporated in vacuo, and the residue was purified by flash chromatography on a silica gel column (elution solvent; n-hexane:ethyl acetate=8:1) to give the title compound (8.07 g, 88% yield) as a white crystalline solid.

Nuclear magnetic resonance spectrum (400 MHz, CDCl$_3$) δ ppm: 9.40–9.48(1H,s), 3.91(1H,d,J=9.2 Hz), 3.67(1H,d, J=9.2 Hz), 1.14–1.66(18H,m) Optical rotation $[\alpha]_D^{25}$: +20.6° (c=1.25, CHCl$_3$)

Reference Example 2(d)
3-t-Butoxycarbonyl-2,2-dimethyl-(4S)-(2,2-dibromo) ethenyl-4-methyloxazolidine Triphenylphosphine (17.3 g, 65.8 mmol) was dissolved in dichloromethane (25 ml), and a solution of carbon tetrabromide (10.9 g, 32.9 mmol) in dichloromethane (15 ml) was added dropwise thereto in an ice bath followed by stirring for 5 minutes in the ice bath. To the reaction solution was added dropwise a dichloromethane (40 ml) solution of 3-t-butoxycarbonyl-2,2-dimethyl-(4S)-formyl-4-methyloxazolidine (4.00 g, 16.4 mmol) obtained in Reference example 2(c). After stirring for 14 hours at room temperature, insoluble substances of the reaction mixture were filtered out, the filtrate was concentrated under reduced pressure to give the crude title compound (4.70 g, 71.2% yield) as a colorless oil.

Reference Example 2(e)
3-t-Butoxycarbonyl-2,2-dimethyl-(4S)-ethynyl-4-methyloxazolidine 3-t-Butoxycarbonyl-2,2-dimethyl-(4S)-(2,2-dibromo) ethenyl-4-methyloxazolidine (4.70 g, 11.8 mmol) obtained in Reference example 2(d) was dissolved in tetrahydrofuran (94 ml), and n-butyllithium (1.6N hexane solution) was added dropwise with stirring at −78° C. followed by stirring for 3.5 hours at −78° C. To the reaction solution was added a saturated aqueous ammonium chloride solution, and the resulting solution was extracted with ethyl acetate. The ethyl acetate layer was dried over anhydrous sodium sulfate, evaporated in vacuo, and the residue was purified by flash chromatography on a silica gel column (elution solvent; n-hexane:ethyl acetate=15:1) to afford the title compound (2.21 g, 78% yield) as a white crystal.

Nuclear magnetic resonance spectrum (400 MHz, CDCl$_3$) δ ppm: 4.13(1H,d,J=8.4 Hz), 3.84(1H,d,J=8.4 Hz), 2.32(1H, s), 1.49–1.69(18H,m) Optical rotation $[\alpha]_D^{25}$: +65.6° (c=1.10, CHCl$_3$)

Reference Example 2(f)
(2S)-Amino-2-methyl-3-butyn-1-ol

To 3-t-butoxycarbonyl-2,2-dimethyl-(4S)-ethynyl-4-methyloxazolidine (350 mg, 1.46 mmol) obtained in Reference example 2(e) was added hydrochloric acid (10 ml), and the solution was stirred for 2 hours at room temperature, and then the reaction solution was concentrated to give the crude title compound (127 mg) as a yellow oil.

Reference Example 2(g)
(2S)-t-Butoxycarbonylamino-2-methyl-3-butyn-1-ol (2S)-Amino-2-methyl-3-butyn-1-ol (127 mg, 1.28 mmol) obtained in Reference example 2(f) was dissolved in a mixture of water (1 ml) and tetrahydrofuran (5 ml), and di-t-butyl dicarbonate (380 mg, 1.74 mmol) and anhydrous sodium carbonate (385 mg, 3.63 mmol) were added thereto followed by stirring for 14 hours at room temperature. To the reaction solution was added a saturated aqueous ammonium chloride solution (6 ml), and the resulting solution was extracted with ethyl acetate, and the ethyl acetate layer was dried over anhydrous sodium sulfate and concentrated under reduced pressure. The residue was purified by flash chromatography on a silica gel column (elution solvent; n-hexane:ethyl acetate=1:1) to give the title compound (154 mg, 53% yield) as a white crystal.

Nuclear magnetic resonance spectrum (400 MHz, CDCl$_3$) δ ppm: 5.00(1H,br.s), 3.78(1H,dd,J=6.0 and 11.2 Hz), 3.67 (1H,dd,J=7.9 and 11.2 Hz), 3.20(1H,br.s), 2.40(1H,s),1.55 (3H,s), 1.46(9H,s) Optical rotation $[\alpha]_D^{25}$: +1.89° (c=0.70, CHCl$_3$)

Reference Example 2(h)
(2S)-t-Butoxycarbonylamino-2-methyl-3-butynic acid (2S)-t-Butoxycarbonylamino-2-methyl-3-butyn-1-ol (1.20 g, 6.02 mmol) obtained in Reference example 2(g) was dissolved in acetone (30 ml), and Jones reagent (3.48 ml, 9.03 mmol) was added thereto followed by stirring for 2 hours in an ice bath. To this reaction solution was added more Jones reagent (3.48 ml, 9.03 mmol) followed by stirring for 14 hours at room temperature. To the resulting reaction solution were added 2-propanol (5 ml) and water (30 ml), and then the solution was extracted with ethyl acetate. The ethyl acetate layer was dried over anhydrous sodium sulfate, and then the solvent was evaporated in vacuo to give the crude title compound (1.38 g) as a yellow oil.

Reference Example 2(i)
(+)-(S)-α-Methyl-α-ethynylglycine hydrochloride (2S)-t-Butoxycarbonylamino-2-methyl-3-butynic acid (1.38 g, 6.02 mmol) obtained in Reference example 2(h) was dissolved in tetrahydrofuran (20 ml), and hydrochloric acid (10 ml) was added thereto followed by stirring for 5 hours at room temperature. The reaction solution was concentrated in vacuo, and water (20 ml) and ethyl acetate (10 ml) were added thereto, and then the water layer was concentrated to afford the crude title compound (0.24 g, 27% yield) as a yellow crystalline solid.

Reference Example 2(j)
(+)-(S)-α-Methyl-α-ethynylglycine

To (+)-(S)-α-Methyl-α-ethynylglycine hydrochloride (0.24 g, 6.02 mmol) obtained in Reference example 2(i) were added ethanol (9 ml) and propylene oxide (3 ml) followed by heating under reflux for 2 hours. The solid substance obtained by filtration of the reaction solution was washed with ether to afford the title compound (108 mg, 60% yield) as a white crystal.

Nuclear magnetic resonance spectrum (400 MHz, CDCl$_3$) δ ppm: 3.06(1H,s), 1.77(3H,s) Optical rotation $[\alpha]_D^{25}$: +41.7° (c=0.96, H$_2$O)

Reference Example 3
(+)-(R)-α-Ethyl-α-vinyl glycine

Reference Example 3(a)
(2S)-t-Butoxycarbonylamino-2-ethyl-3-n-hexanoyloxy-1-propanal (2R)-t-Butoxycarbonylamino-3-n-hexanoyloxy-2-ethyl-1-propanol (3 g, 9.45 mmol) was dissolved in dichloromethane (60 ml), and then molecular sieve 4 Å (20 g) and pyridinium chlorochromate (4.07 g, 18.9 mmol) were added thereto in an ice bath followed by stirring for 1 hour at room temperature. The reaction solution was diluted with ether, and after insoluble substances of the reaction mixture were filtered out, the filtrate was evaporated in vacuo, and then the residue was purified by flash chromatography on a silica gel column (elution solvent; n-hexane:ethyl acetate=10:1) to give the title compound (2.79 g, 94% yield) as a colorless oil.

Nuclear magnetic resonance spectrum (400 MHz, CDCl$_3$) δ ppm: 9.34(1H,s), 5.29(1H,br.s), 4.60(1H,d,J=11.5 Hz), 4.40(1H,d,J=11.5 Hz), 2.28(2H,t,J=7.5 Hz), 2.05–2.20(1H, m), 1.70–1.80(1H,m), 1.55–1.65(2H,m), 1.45(9H,s), 1.25–1.40(4H,m), 0.90(3H,t,J=7.0 Hz), 0.81(3H,t,J=7.5 Hz)

Infrared absorption spectrum $v_{max}$ cm$^{-1}$ (CHCl$_3$): 3418, 2979, 2934, 2873, 1737, 1710, 1496, 1369, 1251, 1160

Mass spectrum (FAB) m/z: 316 ((M+H)$^+$)

Reference Example 3(b)

(2R)-t-Butoxycarbonylamino-2-ethyl-3-buten-1-ol-n-hexanoic acid ester

Methyltriphenylphosphonium bromide (7.90 g, 22.0 mmol) was suspended in tetrahydrofuran (25 ml), and potassium t-butoxide (2.28 g, 20.3 mmol) was added thereto in an ice bath followed by stirring under a nitrogen atmosphere.

(2S)-t-Butoxycarbonylamino-2-ethyl-3-n-hexanoyloxy-1-propanal (2.79 g, 8.85 mmol) obtained in Reference example 3(a) was dissolved in tetrahydrofuran (25 ml), and this solution was added dropwise to the previous reaction solution followed by stirring for 15 minutes. To the resulting mixture solution was added water, and the solution was extracted, and after ethyl acetate layer was washed with a saturated aqueous sodium chloride solution, dried on anhydrous magnesium sulfate, and the solvent was evaporated. The residue was purified by flash chromatography on a silica gel column (elution solvent; n-hexane:ethyl acetate= 40:1–20:1) to give the title compound (1.30 g, 47% yield) as a colorless oil, Nuclear magnetic resonance spectrum (400 MHz, CDCl$_3$) δ ppm: 5.78(1H,dd,J=17.6,11.0 Hz), 5.22(1H,d,J=11.0 Hz), 5.12(1H,d,J=17.6 Hz), 4.62(1H,br.s), 4.29(2H,s), 2.31(2H,t, J=7.5 Hz), 1.83–1.95(1H,m), 1.55–1.75(3H,m), 1.44(9H,s), 1.25–1.35(4H,m), 0.83–0.93(6H,m)

Infrared absorption spectrum $v_{max}$ cm$^{-1}$ (CHCl$_3$): 3448, 2972, 2934, 2873, 1721, 1494, 1368, 1249, 1163

Mass spectrum (FAB) m/z: 314 ((M+H)$^+$)

Reference Example 3(c)

(2R)-t-Butoxycarbonylamino-2-ethyl-3-buten-1-ol (2R)-t-Butoxycarbonylamino-2-ethyl-3-buten-1-ol-n-hexanoic acid ester (1.30 g, 4.15 mmol) obtained in Reference example 3(b) was dissolved in methanol (20 ml), and a 1N aqueous sodium hydroxide solution (40 ml) was added thereto in an ice bath followed by stirring for 2 hours at room temperature. To the resulting mixture solution was added water, and the solution was extracted with ether, and after ether layer was washed with a saturated aqueous sodium chloride solution, dried on anhydrous magnesium sulfate, and then the solvent was evaporated in vacuo. The residue was purified by flash chromatography on a silica gel column (elution solvent; n-hexane:ethyl acetate=9:1–4:1) to give the title compound (0.85 g, 95% yield) as a white solid.

Nuclear magnetic resonance spectrum (400 MHz, CDCl$_3$) δ ppm: 5.77(1H,dd,J=17.0,10.7 Hz), 5.25(1H,d,J=10.7 Hz), 5.16(1H,d,J=17.0 Hz), 4.77(1H,br.s), 4.10(1H,br.s), 3.65–3.75(2H,m), 1.58–1.83(2H,m), 1.45(9H,s), 0.87(3H,t, J=7.5 Hz)

Infrared absorption spectrum $v_{max}$ cm$^{-1}$ (CHCl$_3$): 3448, 3275, 2987, 2969, 2935, 1685, 1541, 1277, 1170, 1053

Mass spectrum,(FAB) m/z: 216 ((M+H)$^+$) Optical rotation $[\alpha]_D^{24}$: +2.8° (c=1.03, methanol)

Reference Example 3(d)

(2R)-t-Butoxycarbonylamino-2-ethyl-3-butenal

The title compound was obtained as a white solid (0.63 g, 80% yield) according to a similar reaction to that described in Reference example 3(a) using (2R)-t-butoxycarbonylamino-2-ethyl-3-buten-1-ol (0.79 g, 3.67 mmol) obtained in Reference example 3(c).

Nuclear magnetic resonance spectrum (400 MHz, CDCl$_3$) δ ppm: 9.24( 1H,s),5.83(1H,dd,J=17.5,10.7 Hz), 5.39(1H,d, J=10.7 Hz), 5.31(1H,d,J=17.5 Hz), 5.29(1H,br.s), 1.85–2.15 (2H,m), 1.57(9H,s), 0.85(3H,t,J=7.5 Hz)

Infrared absorption spectrum $v_{max}$ cm$^{-1}$ (CHCl$_3$): 3343, 3416, 2980, 1712, 1489, 1369, 1249, 1162

Mass spectrum (FAB) m/z: 214 ((M+H)$^+$) Optical rotation $[\alpha]_D^{25}$: +69° (c=1.00, methanol)

Reference Example 3(e)

(2R)-t-Butoxycarbonylamino-2-ethyl-3-butenoic acid (2R)-t-Butoxycarbonylamino-2-ethyl-3-butenal (0.60 g, 2.81 mmol) obtained in Reference example 3(d) was dissolved in the mixture of t-butanol (8 ml) and water (2 ml), and 2-methyl-2-butene (1.34 ml, 12.7 mmol), sodium dihydrogenphosphate dihydrate (0.44 g, 2.81 mmol), and sodium chlorite (0.89 g, 9.85 mmol) were added thereto followed by stirring 1 hour at room temperature. To the reaction solution was added ethyl acetate, and the ethyl acetate layer was washed with a saturated aqueous sodium chloride solution. The ethyl acetate layer was dried over anhydrous magnesium sulfate, and the solvent was evaporated under reduced pressure. The residue was purified by flash chromatography on a silica gel column (elution solvent; n-hexane:ethyl acetate=20:1–1:1) to give the title compound (0.42 g, 65% yield) as a white solid.

Nuclear magnetic resonance spectrum (400 MHz, CDCl$_3$) δ ppm: 6.05(1H,dd,J=17.3,10.7 Hz), 5.25–5.35(3H,m), 1.95–2.20(2H,m), 1.44(9H,s), 0.90(3H,t,J=7.4 Hz)

Infrared absorption spectrum $v_{max}$ cm$^{-1}$ (CHCl$_3$): 3430, 2981, 1713, 1493, 1369, 1252, 1166

Mass spectrum (FAB) m/z: 230 ((M+H)$^+$) Optical rotation $[\alpha]_D^{25}$: +19.4° (c=1.00, methanol)

Reference Example 3(f)

(+)-(R)-α-Ethyl-α-vinylglycine (2R)-t-Butoxycarbonylamino-2-ethyl-3-butenoic acid (379 mg, 1.65 mmol) obtained in Reference example 3(e) was dissolved in ethanol (2 ml), and a dioxane solution (2 ml) of 4N hydrochloric acid was added thereto followed by stirring for 18 hours at room temperature. The reaction solution was concentrated under reduced pressure, and then the residue was washed with ether and dried. The obtained white solid was dissolved in ethanol (6 ml), and propylene oxide (2 ml) was added thereto followed by heating under reflux. The title compound (83 mg) was obtained as a white solid by filtering off the white solid in the reaction solution. After the filtrate was concentrated, the residue was dissolved in water, and the solution was filtered through Bond Elut HF (C$_{18}$), and then the filtrate was concentrated to give the title compound (61 mg, total amount 144 mg, 75% yield).

Nuclear magnetic resonance spectrum (400 MHz, CDCl$_3$) δ ppm: 6.08(1H,dd,J=17.7,11.1 Hz), 5.41(1H,d,J=11.1 Hz), 5.34(1H,d,J=17.7 Hz), 1.82–2.12(2H,m), 0.95(3H,t,J=7.6 Hz)

Infrared absorption spectrum $v_{max}$ cm$^{-1}$ (KBr): 3200–2400, 1623, 1605, 1511, 1369

Mass spectrum (FAB) m/z: 130 ((M+H)$^+$) Optical rotation $[\alpha]_D^{25}$: +20.6° (c=1.00, H$_2$O)

Reference Example 4

5-(4-Fluorophenyl)pent-1-yne

Sodium hydride (2.11 g, 48.4 mmol) was suspended in anhydrous tetrahydrofuran (60 ml), and diethylphosphonoacetic acid ethyl ester (10.84 g, 48.4 mmol) was added dropwise thereto in an ice bath followed by stirring for 10 minutes. To this mixture solution, a solution of 4-fluorobenzaldehyde (5.00 g, 40.3 mmol) in anhydrous tetrahydrofuran (60 ml) was added dropwise at the same temperature. The reaction solution was stirred for 3 hours, and poured into ice-cold water (150 ml), and then extracted with ethyl acetate. The organic layer was dried over magnesium sulfate, and the solvent was evaporated in vacuo, and then the residue was purified by flash chromatography on a silica gel column (elution solvent; hexane:ethyl acetate= 10:1–3:1) to give 4-fluorocinnamic acid ethyl ester (6.69 g, 86% yield) as a colorless oil.

This ester (6.52 g, 33.6 mmol) was dissolved in ethyl acetate (100 ml), and 5% rhodium/alumina (1.30 g) was added thereto followed by stirring under a hydrogen atmosphere for 8 hours at room temperature. The reaction mixture was filtered through Celite, and the filtrate was concentrated under reduced pressure, and then the residue was dissolved in anhydrous tetrahydrofuran (30 ml). This solution was added dropwise to a suspension of lithium aluminium hydride (1.26 g, 33.2 mmol) in anhydrous tetrahydrofuran (60 ml) in the ice bath. The reaction mixture was stirred for 30 minutes at the same temperature, and a saturated aqueous sodium sulfate solution was added thereto followed by stirring for 10 minutes at room temperature. The mixture was filtered through Celite, and the filtrate was extracted with ethyl acetate. The organic layer was washed with a saturated aqueous sodium chloride solution, and dried over anhydrous magnesium sulfate. The solvent was evaporated in vacuo, and the residue was purified by flash chromatography on a silica gel column (elution solvent; hexane-:ethyl acetate=5:1–1:1) to give 4-fluorophenylpropan-1-ol (4.86 g, 95% yield) as a colorless oil.

The obtained 4-fluorophenylpropan-1-ol (4.83 g, 31.3 mmol) was dissolved in dichloromethane (50 ml), and triethylamine (6.55 ml, 47.0 mmol) and methanesulfonyl chloride (2.91 ml, 37.6 mmol) were added thereto in the ice bath followed by stirring under a nitrogen atmosphere for 30 minutes. The reaction mixture was diluted with dichloromethane (50 ml), and washed with 10% hydrochloric acid and subsequently with a saturated aqueous sodium chloride solution, and then dried over magnesium sulfate. The solvent was evaporated in vacuo, and the residue was dissolved in acetone (100 ml), and then sodium iodide (9.39 g, 62.6 mmol) was added thereto followed by stirring under a nitrogen atmosphere for 2 hours at 50° C. The reaction mixture was diluted with ethyl acetate (250 ml), and washed with 10% aqueous sodium thiosulfate solution and subsequently with a saturated aqueous sodium chloride solution, and then dried over magnesium sulfate. The solvent was evaporated in vacuo, and the residue was purified by flash chromatography on a silica gel column (elution solvent; hexane:ethyl acetate=5:1–2:1) to afford 4-fluorophenyl-1-iodopropane (7.12 g, 86% yield) as a yellow oil.

To hexamethylphosphoramide (20 ml) was added a suspension (50 ml) of 18% sodium acetylide in xylene, and an anhydrous dimethylformamide (20 ml) solution of 4-fluorophenyl-1-iodopropane (7.00 g, 26.5 mmol) obtained above was added thereto in the ice bath. The reaction mixture was stirred for 2 hours at room temperature, and ice-cold water was carefully poured thereto in the ice bath, and then the mixture was extracted with ethyl acetate. The organic layer was washed with a saturated aqueous sodium chloride solution, and dried over magnesium sulfate. The solvent was evaporated under reduced pressure, and the residue was purified by flash chromatography on a silica gel column (elution solvent; hexane) to give the title compound (2.67 g, 62% yield) as a colorless oil.

Nuclear magnetic resonance spectrum (400 MHz, CDCl$_3$) δ ppm: 1.82 (2H, m), 1.99 (1H, t, J=2.6 Hz), 2.19 (2H, m), 2.71 (2H, t, J=7.5 Hz), 6.97 (2H, m), 7.14 (2H, m)

Mass spectrum (EI) m/z: 162 (M$^+$)

Reference Example 5

5-(4-Methoxyphenyl)pent-1-yne

The title compound was obtained using 3-(4-methoxyphenyl)-1-iodopropane and sodium acetylide according to a similar procedure to that described in Reference example 4.

Nuclear magnetic resonance spectrum (500 MHz, CDCl$_3$) δ ppm: 1.78–1.88 (2H, m), 1.98 (1H, t, J=2.6 Hz), 2.15–2.22 (2H, m), 2.67 (2H, t, J=7.5 Hz), 3.79 (3H, s), 6.83 (2H, d, J=8.6 Hz), 7.11 (2H, d, J=8.6 Hz)

Mass spectrum (EI) m/z: 174 (M$^+$)

Reference Example 6

5-Phenylpent-1-yne

The title compound was obtained using 3-phenyl-1-iodopropane and sodium acetylide according to a similar procedure to that described in Reference example 4.

Nuclear magnetic resonance spectrum (400 MHz, CDCl$_3$) δ ppm: 1.81–1.89 (2H, m), 1.99 (1H, t, J=2.8 Hz), 2.21 (2H, dt, J=2.8, 7.6 Hz), 2.74 (2H, t, J=7.6 Hz), 7.16–7.23 (3H, m), 7.26–7.32 (2H, m)

Mass spectrum (EI) m/z: 144 ($^+$)

Reference Example 7

5-Cyclohexylpent-1-yne

The title compound was obtained using 3-cyclohexyl-1-iodopropane and sodium acetylide according to a similar procedure to that described in Reference example 4.

Nuclear magnetic resonance spectrum (400 MHz, CDCl$_3$) δ ppm: 0.75–1.38 (13H, m), 1.48–1.59 (2H, m), 1.94 (1H, t, J=2.8 Hz), 2.16 (2H, dt, J=2.8, 7.2 Hz)

Mass spectrum (EI) m/z: 150 (M$^+$)

Reference Example 8

4-(4-Fluorophenyloxy)but-1-yne

4-Fluorophenol (5.00 g, 44.6 mmol), 3-butyn-1-ol (3.38 ml, 44.6 mmol), and triphenylphosphine (17.5 g, 66.9 mmol) were dissolved in tetrahydrofuran (100 ml), and diethyl azodicarboxylate (11.7 g, 66.9 mmol) was added thereto in an ice bath followed by stirring for 18 hours at room temperature. After the solvent was concentrated in vacuo, hexane (200 ml) and ethyl acetate (20 ml) were added thereto, and the resulting precipitate was filtered out, and then the filtrate was concentrated in vacuo. The obtained residue was purified by flash chromatography on a silica gel column (elution solvent; hexane:ethyl acetate=1:0) to afford the title compound.

Nuclear magnetic resonance spectrum (400 MHz, CDCl$_3$) δ ppm: 2.05 (1H, t, J=2.7 Hz), 2.63–2.70 (2H, m), 4.07 (2H, t, J=7.0 Hz), 6.82–6.90 (2H, m), 6.94–7.02 (2H, m)

Mass spectrum (EI) m/z: 164 (M$^+$)

Reference Example 9

3-(4-Methylphenyloxy)-1-propyne

The title compound was obtained using 4-methylphenol and propargyl alcohol according to a similar procedure to that described in Reference example 8.

Nucclear magnetic resonance spectrum (400 MHz, CDCl$_3$) δ ppm: 2.29 (3H, s), 2.50 (1H, t, J=2.4 Hz), 4.67 (2H, d, J=2.4 Hz), 6.88 (2H, d, J=8.4 Hz), 7.10 (2H, d, J=8.4 Hz)

Mass spectrum (EI) m/z: 146 (M$^+$)

Reference Example 10

3-[(4-Methylthio)phenyloxy]-1-propyne

The title compound was obtained using 4-(methylthio) phenol and propargyl alcohol according to a similar procedure to that described in Reference example 8.

Nuclear magnetic resonance spectrum (400 MHz, CDCl$_3$)
δ ppm: 2.45 (3H, s), 2.52 (1H, t, J=2.4 Hz), 4.68 (2H, d, J=2.4 Hz), 6.93 (2H, d, J=8.9 Hz), 7.27 (2H, d, J=8.9 Hz)

Mass spectrum (EI) m/z: 178 (M$^+$)

Reference Example 11

3-(3-Methoxyphenyloxy)-1-propyne

The title compound was obtained using 3-methoxyphenol and propargyl alcohol according to a similar procedure to that described in Reference example 8.

Nuclear magnetic resonance spectrum (400 MHz, CDCl$_3$)
δ ppm: 2.52 (1H, t, J=2.4 Hz), 3.79 (3H, s), 4.67 (2H, d, J=2.4 Hz), 6.53–6.60 (3H, m), 7.16–7.23 (1H, m)

Mass spectrum (EI) m/z: 162 (M$^+$)

Reference Example 12

3-(3,4-Dimethylphenyloxy)-1-propyne

The title compound was obtained using 3,4-dimethylphenol and propargyl alcohol according to a similar procedure to that described in Reference example 8.

Nuclear magnetic resonance spectrum (400 MHz, CDCl$_3$)
δ ppm: 2.20 (3H, s), 2.24 (3H, s), 2.49 (1H, t, J=2.4 Hz), 4.65 (2H, d, J=2.4 Hz), 6.72 (1H, dd, J=2.4, 8.0 Hz), 6.78 (1H, d, J=2.4 Hz), 7.04 (1H, d, J=8.0 Hz)

Mass spectrum (EI) m/z: 160 (M$^+$)

Reference Example 13

4-(4-Methylphenyloxy)but-1-yne

The title compound was obtained using 4-methylphenol and 3-butyn-1-ol according to a similar procedure to that described in Reference example 8.

Nuclear magnetic resonance spectrum (400 MHz, CDCl$_3$)
δ ppm: 2.03 (1H, t, J=2.8 Hz), 2.28 (3H, s), 2.66 (2H, dt, J=2.8, 7.2 Hz), 4.07 (2H, t, J=7.2 Hz), 6.81 (2H, d, J=8.8 Hz), 7.08 (2H, d, J=8.8 Hz)

Mass spectrum (EI) m/z: 160 (M$^+$)

Reference Example 14

4-Cyclohexyloxybut-1-yne

To anhydrous dichloromethane (950 ml) were added cyclohexanone (32 ml, 0.31 mol), 1, 3-propanediol (33.5 ml, 0.46 mol), triethyl orthoformate (51.5 ml, 0.31 mol), and zirconium chloride (1.44 g, 6.18 mmol) followed by stirring under a nitrogen atmosphere for 1 hour at room temperature. An ice-cold 1N aqueous sodium hydroxide solution (1.5 l) was added to the reaction mixture, and the reaction solution was extracted with dichloromethane, and then the dichloromethane layer was washed with water. The dichloromethane layer was dried over anhydrous sodium sulfate, and the solvent was evaporated under reduced pressure. The residue was purified by distillation under reduced pressure to give cyclohexanone trimethyl ketal (26.8 g, 55% yield). To the suspension of zirconiumchloride (24.9 g, 0.11 mol) in tetrahydrofuran (500 ml) was slowly added sodium borohydride (20.5 g, 0.54 mmol) under a nitrogen atmosphere followed by stirring for 20 minutes at room temperature. A solution of tetrahydrofuran (170 ml) including cyclohexanone trimethyl ketal (16.9 g, 0.11 mol) obtained above was added dropwise in a nitrogen atmosphere to the reaction solution in an ice bath. After the end of dropping, the reaction solution was stirred overnight at room temperature. To this reaction solution was added ice-cold 2N hydrochloric acid (600 ml) in the ice bath to stop the reaction, and tetrahydrofuran was evaporated in vacuo. The water layer residue was extracted with ethyl acetate, and the ethyl acetate layer was washed with a saturated aqueous sodium chloride solution. The ethyl acetate layer was dried over anhydrous sodium sulfate, and the solvent was evaporated in vacuo. The obtained residue was purified by chromatography on a silica gel column (elution solvent; hexane:ethyl acetate=10:1–5:2) to afford 3-cyclohexyloxypropan-1-ol (13.4 g, 78% yield).

The obtained 3-cyclohexyloxypropan-1-ol (11.5 g, 72.9 mmol) was dissolved in dichloromethane (240 ml), and then molecular sieve 4 Å (58 g) and pyridinium chlorochromate (23.8 g, 0.11 mol) were added thereto in the ice bath followed by stirring under a nitrogen atmosphere for 1 hour and 40 minutes. The reaction solution was diluted with ether, and then the solution was filtered through Celite. The Celite was washed with diethyl ether, and this filtrate was added to the previous filtrate. The total filtrate was evaporated in vacuo, and the residue was purified roughly by chromatography on a silica gel column (elution solvent; n-hexane:ethyl acetate=20:1–10:1) to give a crude 3-cyclohexyloxypropionaldehyde (8.6 g).

A dichloromethane solution (120 ml) of triphenylphosphine (57.7 g, 0.22 mol) in an ice bath were added dropwise to the dichloromethane solution (120 ml) including carbon tetrabromide (36.5 g, 0.11 mol) under a nitrogen atmosphere. After the end of dropping, the reaction mixture was stirred for 5 more minutes. To the reaction solution in the ice bath was added dropwise under a nitrogen atmosphere a dichloromethane solution (90 ml) of the crude 3-cyclohexyloxypropionaldehyde (8.6 g) obtained above, and after dropping, the reaction mixture was stirred for 25 more minutes. The reaction solution was diluted with dichloromethane, and washed with a saturated aqueous sodium hydrogencarbonate solution and then with a saturated aqueous sodium chloride solution. After the dichloromethane layer was dried over anhydrous sodium sulfate, the solvent was evaporated in vacuo. The residue was purified by chromatography on a silica gel column (elution solvent; hexane:ethyl acetate=100:1–33:1) to afford 4-cyclohexyloxy-1,1-dibromobut-1-ene (12.6 g, 55% yield, 2 processes).

To a tetrahydrofuran solution (130 ml) of 4-cyclohexyloxy-1,1-dibromobut-1-ene (12.6 g, 40.4 mmol) obtained above, was added dropwise under a nitrogen atmosphere at –78° C. the hexane solution of 1.5N n-butyllithium (54 ml, 81.0 mmol). After the end of dropping, the reaction solution was stirred for 1 hour, and then warmed up gradually to room temperature. After the reaction solution was stirred at room temperature for 50 minutes, water was added thereto in the ice bath to terminate the reaction. The resulting reaction solution was extracted with diethyl ether, and the diethyl ether layer was washed with the saturated aqueous sodium chloride solution. The diethyl ether layer was dried over anhydrous sodium sulfate, and the solvent was evaporated under reduced pressure. The residue was purified by chromatography on a silica gel column (elution solvent; hexane:ethyl acetate=100:1–50:1) to give the title compound (4.35 g, 71% yield).

Nuclear magnetic resonance spectrum (400 MHz, CDCl$_3$)
δ ppm: 1.13–1.36 (5H, m), 1.48–1.58 (1H, m), 1.67–1.81 (2H, m), 1.85–1.95 (2H, m) 1.97 (1H, t, J=2.8 Hz), 2.45 (2H, dt, J=2.8, 7.2 Hz), 3.23–3.32 (1H, m), 3.59 (2H, t, J=7.2 Hz)

Mass spectrum (EI) m/z: 153 (M+H)$^+$

Test Example 1

Determination of the Inhibitory Activity Against Host Versus Graft Reaction (HvGR) in the Rat.

(1) Two strains of rats (Lewis rats (male, 6 weeks old, Charles River Japan) and WKAH/Hkm (male, 7 weeks old, SLC Japan)) were used. Five rats (host) per group were used.

(2) Induction of HvGR

The spleen cells were isolated from the spleen of the rats and $1\times10^8$ cells were suspended in the RPMI640 medium (LIFE TECHNOLOGIES, Rockville Md. USA). One hundred microliter ($1\times10^7$ cells) of the spleen cell suspension whose cells were isolated from either WKAH/Hkm rats or Lewis rats were subcutaneously injected into the bilateral feet pad of the hindlimbs of the Lewis rat.

(3) Administration of the Compound

The compound was suspended in 0.5% tragacanth solution. The suspended compound was orally administered to rats in the drug-treated group (Lewis rats injected with spleen cells isolated from AH/Hkm rats, and treated with the compound) at a volume of 5 ml/kg. The treatment was started on the day of the spleen cell injection, once a day, for 4 successive days. Tragacanth solution (0.5%) was orally administered, instead of the suspension of the test compound, to the rats in the same strain group (Lewis rats injected with spleen cells which were isolated from the Lewis rats) and to the rats in the control group (Lewis rats injected spleen cells isolated from WKAH/Hkm rats, and not treated with the test compound).

(4) Determination Procedures for Inhibitory Activity against HvGR

The average weight of the popliteal lymph node of the same strain rats was subtracted from the weight of the popliteal lymph node of the individual rat (popliteal lymph gland weight due to HvGR). The inhibition rate of the popliteal lymph node weight due to HvGR of the individual rat treated with the test compound against the average weight of the control rats was calculated. The inhibitory activity of the test compound was expressed as an ID50 value (mg/kg) calculated from the dose-inhibition rate by the least square method.

As the results of the present experiment, the compound of the present invention showed an excellent inhibitory activity against HvGR in the rat.

TABLE 5

| Test Compounds | HvGR ID50 values (mg/kg) |
| --- | --- |
| Example 1 | 0.0843 |
| Example 11 | 0.0844 |
| Example 40 | 0.0683 |
| Example 43 | 0.0730 |
| Example 46 | 0.0454 |
| Reference Compound 1 | 0.354 |

In the above Table, the reference compound 1 is Example Compound 29 described in WO94/08943.

Test Example 2

Determination of the Inhibitory Activity of the Compounds of the Present Invention on Induction of Adjuvant Arthritis 1. Preparation of Adjuvant Heat-killed, *Mycobacterium butylricum* was suspended in mineral oil at a concentration of 2 mg/ml and sonicated with an ultrasonic apparatus.

2. Preparation of the Test Compound.

The test compound was suspended in 0.5% Tragacanth solution.

3. Induction of Adjuvant Arthritis

The adjuvant prepared as described in 1 was intradermally injected into the right hind paw of the female rats (usually Lewis rats were used) at a volume of 0.05 ml. Five rats per group were used. In one group of rats, adjuvant was not injected for the control group.

4. Administration of the Compound

The compound solution prepared as described in 2 was orally administered to rats from the injection day of the adjuvant, once daily for 21 days, at a dose of 5 ml/kg. Tragacanth solution (0.5%) was orally administered to one group of rats treated with adjuvant (the control group) and also to rats not treated with adjuvant.

5. Calculation Methods of Inhibitory Activity of the Compound

The volume of the right hind paw was determined with a plethymometer. The volume of the intact paw was subtracted from the individual volume, and the difference was used as the swelling volume. Then the inhibitory activity of the compound was calculated from the individual swelling volume of rats treated with the compound and that in the swelling volume of the control rats. The ID50 value of the compound was obtained from the doses treated and the average inhibitory rate of the group.

From the present experiment, the compound in the present invention showed a potent inhibitory activity.

TABLE 6

| Compound | ID50 value (mg/kg) |
| --- | --- |
| Test Example 1 | 0.0897 |
| Test Example 34 | 0.0470 |
| Reference Compound | 0.1666 |

In the above Table, the Test Example 1 is the Test Example 29 described in WO94/08943.

What is claimed is:

1. A compound of formula (La) or (Lb):

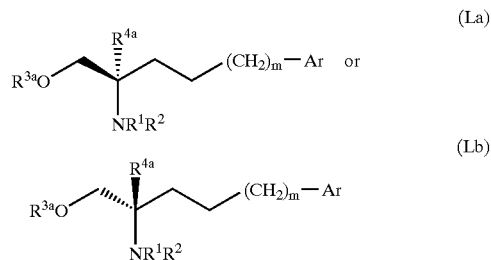

wherein:

$R^1$ and $R^2$ are the same or different and each represents a hydrogen atom or an amino protecting group;

$R^{3a}$ represents a hydrogen atom or a hydroxy protecting group or when $R^1$ is a hydrogen atom;

$R^2$ and $R^{3a}$ taken together form a group of formula —(C=O)—;

$R^{4a}$ represents a $C_1$–$C_{20}$ alkyl group, a $C_2$–$C_{20}$ alkyl group interrupted with a heteroatom(s), a $C_1$–$C_{20}$ alkyl group substituted with an aryl group(s) or a heteroaryl group(s), a $C_2$–$C_{20}$ alkynyl group, a $C_3$–$C_{20}$ alkynyl group interrupted with a heteroatom(s), a $C_2$–$C_{20}$ alkynyl group substituted with an aryl group(s) or a heteroaryl group(s), a $C_2$–$C_{20}$ alkenyl group, a $C_3$–$C_{20}$ alkenyl group interrupted with a heteroatom(s), a $C_2$–$C_{20}$ alkenyl group substituted with an aryl group(s) or a heteroaryl group(s), a $C_2$–$C_{20}$ alkyl group which is substituted with an aryl group(s) or a heteroaryl group(s) and interrupted with a heteroatom(s), or a cycloalkyl group;

m represent an integer from 0 to 4;

Ar represents an aryl group, a heteroaryl group, an aryl group substituted with 1 to 5 substituents selected from substituent group a, a heteroaryl group substituted with 1 to 5 substituents selected from substituent group a, with the proviso that when Ar is an aryl group, $R^1$ is not a hydrogen atom and $R^2$ and/or $R^{3a}$ do not represent a hydrogen atom;

wherein substituent group a represents a halogen atom, a lower alkyl group, a halogenated lower alkyl group, a lower alkoxy group, a lower alkylthio group, a carboxyl group, a lower alkoxycarbonyl group, a hydroxyl group, a lower aliphatic acyl group, an amino group, a lower mono-alkylamino group, a lower di-alkylamino group, a lower aliphatic acylamino group, a cyano group, and a nitro group.

2. A compound according to claim 1 wherein said compound has a formula (La).

3. A compound according to claim 1 or 2 wherein $R^1$ is a hydrogen atom.

4. A compound according to claim 1 or 2 wherein $R^2$ and $R^{3a}$ taken together form a group of formula —(C=O)—.

5. A compound according to claim 1 or 2 wherein $R^{3a}$ is a hydrogen atom.

6. A compound according to claim 1 or 2 wherein $R^{4a}$ is a $C_1$–$C_{10}$ alkyl group, a $C_2$–$C_{10}$ alkyl group interrupted with a heteroatom(s), a $C_1$–$C_{10}$ alkyl group substituted with an aryl group(s) or a heteroaryl group(s), a $C_2$–$C_{10}$ alkynyl group, a $C_3$–$C_{10}$ alkynyl group interrupted with a heteroatom(s), a $C_2$–$C_{10}$ alkynyl group substituted with an aryl group(s) or a heteroaryl group(s), a $C_2$–$C_{10}$ alkenyl group, a $C_3$–$C_{10}$ alkenyl group interrupted with a heteroatom(s), a $C_2$–$C_{10}$ alkenyl group substituted with an aryl group(s) or a heteroaryl group(s), a $C_2$–$C_{10}$ alkyl group which is substituted with an aryl group(s) or a heteroaryl group(s) and interrupted with a heteroatom(s), or a $C_5$–$C_{10}$ cycloalkyl group.

7. A compound according to claim 1 or 2 wherein $R^{4a}$ is a $C_1$–$C_{10}$ alkyl group, a $C_2$–$C_{10}$ alkyl group interrupted with a heteroatom(s), a $C_1$–$C_{10}$ alkyl group substituted with an aryl group(s) or a heteroaryl group(s), a $C_2$–$C_{10}$ alkynyl group, a $C_2$–$C_{10}$ alkenyl group, or a $C_5$–$C_{10}$ cycloalkyl group.

8. A compound according to claim 1 or 2 wherein $R^{4a}$ is a $C_1$–$C_{10}$ alkyl group.

9. A compound according to claim 1 or 2 wherein $R^{4a}$ is a $C_1$–$C_6$ alkyl group.

10. A compound according to claim 1 or 2 wherein $R^{4a}$ is a methyl group or an ethyl group.

11. A compound according to claim 1 or 2 wherein Ar is a phenyl, furyl, thienyl, benzothienyl group, or a phenyl, furyl, thienyl, or benzothienyl group, said groups optionally being substituted with 1 to 4 substituents selected from substituent group a.

12. A compound according to claim 1 or 2 wherein Ar is a thienyl group or a thienyl group substituted with 1 to 4 substituents selected from substituent group a.

13. A compound according to claim 1 or 2 wherein Ar is a benzothienyl group or a benzothienyl group substituted with 1 to 4 substituents selected from substituent group a.

14. A compound according to claim 1 or 2 wherein m is 0 or 1.

15. A compound according to claim 1 or 2 wherein substituent group a is a halogen atom, a hydroxyl group, a lower alkyl group, a halogenated lower alkyl group, a lower alkoxy group, a carboxyl group, a lower aliphatic acyl group, a lower aliphatic acylamino group, an amino group, a cyano group, or a nitro group.

16. A compound according to claim 1 or 2 wherein $R^1$ is a hydrogen atom;

$R^2$ and $R^{3a}$ taken together form a group of formula —(C=O)—;

$R^{3a}$ is a hydrogen atom;

$R^{4a}$ is a $C_1$–$C_{10}$ alkyl group, a $C_2$–$C_{10}$ alkyl group interrupted with a heteroatom(s), a $C_1$–$C_{10}$ alkyl group substituted with an aryl group(s) or a heteroaryl group(s), a $C_2$–$C_{10}$ alkynyl group, a $C_3$–$C_{10}$ alkynyl group interrupted with a heteroatom(s), a $C_2$–$C_{10}$ alkynyl group substituted with an aryl group(s) or a heteroaryl group(s), a $C_2$–$C_{10}$ alkenyl group, a $C_3$–$C_{10}$ alkenyl group interrupted with a heteroatom(s), a $C_2$–$C_{10}$ alkenyl group substituted with an aryl group(s) or a heteroaryl group(s), a $C_2$–$C_{10}$ alkyl group which is substituted with an aryl group(s) or a heteroaryl group(s) and interrupted with a heteroatom(s), or a $C_5$–$C_{10}$ cycloalkyl group;

m is 0 or 1;

Ar is a phenyl, furyl, thienyl, benzothienyl group, or a phenyl, furyl, thienyl, or benzothienyl group, said groups optionally being substituted with 1 to 4 substituents selected from substituent group a; and substituent group a is a halogen atom, a hydroxyl group, a lower alkyl group, a halogenated lower alkyl group, a lower alkoxy group, a carboxyl group, a lower aliphatic acyl group, a lower aliphatic acylamino group, an amino group, a cyano group, or a nitro group.

17. A compound according to claim 16 wherein $R^{4a}$ is a $C_1$–$C_{10}$ alkyl group, a $C_2$–$C_{10}$ alkyl group interrupted with a heteroatom(s), a $C_1$–$C_{10}$ alkyl group substituted with an aryl group(s) or a heteroaryl group(s), a $C_2$–$C_{10}$ alkynyl group, a $C_2$–$C_{10}$ alkenyl group, or a $C_5$–$C_{10}$ cycloalkyl group; and Ar is a thienyl group or a thienyl group substituted with 1 to 4 substituents selected from substituent group a.

18. A compound according to claim 16 wherein $R^{4a}$ is a $C_1$–$C_{10}$ alkyl group; and Ar is a benzothienyl group or a benzothienyl group substituted with 1 to 4 substituents selected from substituent group a.

19. A compound according to claim 16 wherein $R^{4a}$ is a $C_1$–$C_6$ alkyl group; and Ar is a benzothienyl group or a benzothienyl group substituted with 1 to 4 substituents selected from substituent group a.

20. A compound according to claim 18 wherein $R^{4a}$ is a methyl group or an ethyl group; and Ar is a benzothienyl group or a benzothienyl group substituted with 1 to 4 substituents selected from substituent group a.

21. A compound according to claim 18 wherein $R^1$ is a hydrogen atom;

$R^2$ and $R^{3a}$ taken together form a group of formula —(C=O)—;

$R^{3a}$ is a hydrogen atom;

$R^{4a}$ is a methyl group or an ethyl group;

Ar is a benzothienyl group or a benzothienyl group substituted with 1 to 4 substituents selected from substituent group a.

22. A process for the preparation of a compound of a formula (XLIVa) or (XLIVb)

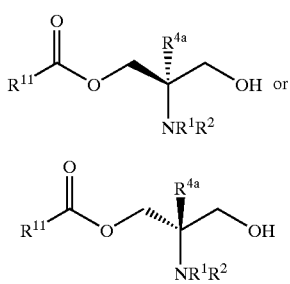

(XLIVa)

(XLIVb)

wherein:

R$^1$ and R$^2$ are the same or different and each represents a hydrogen atom or an amino protecting group; R$^{4a}$ represents a C$_1$–C$_{20}$ alkyl group, a C$_2$–C$_{20}$ alkyl group interrupted with a heteroatom(s), a C$_1$–C$_{20}$ alkyl group substituted with an aryl group(s) or a heteroaryl group(s), a C$_2$–C$_{20}$ alkynyl group, a C$_3$–C$_{10}$ alkynyl group interrupted with a heteroatom(s), a C$_2$–C$_{20}$ alkynyl group substituted with an aryl group(s) or a heteroaryl group(s), a C$_2$–C$_{20}$ alkenyl group, a C$_3$–C$_{20}$ alkenyl group interrupted with a heteroatom(s), a C$_2$–C$_{20}$ alkenyl group substituted with an aryl group(s) or a heteroaryl group(s), a C$_2$–C$_{20}$ alkyl group which is substituted with an aryl group(s) or a heteroaryl group(s) and interrupted with a heteroatom(s), or a cycloalkyl group; and R$^{11}$ has the same meaning as that indicated above for R$^{4a}$;

which process comprises the selective acylation of one hydroxyl group of a 2-substituted 2-amino-1,3-propanediol derivative of formula (XLII)

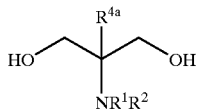

(XLII)

(wherein R$^1$, R$^2$ and R$^{4a}$ are as defined above)

with a carboxylic acid ester derivative of formula (XLIII)

R$^{11}$COOCH=CH$_2$ (XLIII)

(wherein R$^{11}$ is as defined above)

in the presence of a lipase to afford a 2-substituted 2-amino-1,3-propanediol mono-ester derivative of formula (XLIVa) or (XLIVb).

23. A process for preparation according to claim 22 wherein one of R$^1$ and R$^2$ is a hydrogen atom and the other one is an amino protecting group.

24. A process for preparation according to claim 22 or 23 wherein R$^{4a}$ is a C$_1$–C$_{10}$ alkyl group, a C$_2$–C$_{10}$ alkyl group interrupted with a heteroatom(s), a C$_1$–C$_{10}$ alkyl group substituted with an aryl group(s) or a heteroaryl group(s), a C$_2$–C$_{10}$ alkynyl group, a C$_3$–C$_{10}$ alkynyl group interrupted with a heteroatom(s), a C$_2$–C$_{10}$ alkynyl group substituted with an aryl group(s) or a heteroaryl group(s), a C$_2$–C$_{10}$ alkenyl group, a C$_3$–C$_{10}$ alkenyl group interrupted with a heteroatom(s), a C$_2$–C$_{10}$ alkenyl group substituted with an aryl group(s) or a heteroaryl group(s), a C$_2$–C$_{10}$ alkyl group which is substituted with an aryl group(s) or a heteroaryl group(s) and interrupted with a heteroatom(s), or a C$_5$–C$_{10}$ cycloalkyl group.

25. A process for preparation according to claim 22 or 23 wherein R$^{4a}$ is a C$_1$–C$_{10}$ alkyl group, a C$_2$–C$_{10}$ alkyl group interrupted with a heteroatom(s), a C$_1$–C$_{10}$ alkyl group substituted with an aryl group(s) or a heteroaryl group(s), a C$_2$–C$_{10}$ alkynyl group, a C$_2$–C$_{10}$ alkenyl group, or a C$_5$–C$_{10}$ cycloalkyl group.

26. A process for preparation according to claim 25 wherein R$^{11}$ is a C$_1$–C$_{20}$ alkyl group, or a C$_1$–C$_{20}$ alkyl group substituted with an aryl group(s) or a heteroaryl group(s).

27. A process for preparation according to claim 24 wherein R$^{11}$ is a C$_1$–C$_{20}$ alkyl group, or a C$_1$–C$_{20}$ alkyl group substituted with an aryl group(s) or a heteroaryl group(s).

28. A process for preparation according to claim 22 or 23 wherein R$^{11}$ is a C$_1$–C$_{20}$ alkyl group, or a C$_1$–C$_{20}$ alkyl group substituted with an aryl group(s) or a heteroaryl group(s).

* * * * *

UNITED STATES PATENT AND TRADEMARK OFFICE
CERTIFICATE OF CORRECTION

PATENT NO.        : 6,964,976 B2  
APPLICATION NO. : 10/718858  
DATED             : November 15, 2005  
INVENTOR(S)       : Nishi et al.

It is certified that error appears in the above-identified patent and that said Letters Patent is hereby corrected as shown below:

On the cover page,

[*] Notice: Subject to any disclaimer, the term of this patent is extended or adjusted under 35 USC 154(b) by 62days Delete the phrase "by 62 days" and insert -- by 94 days--

Signed and Sealed this

Twenty-second Day of May, 2007

JON W. DUDAS  
*Director of the United States Patent and Trademark Office*